(12) United States Patent
Kitamura et al.

(10) Patent No.: US 8,575,153 B2
(45) Date of Patent: Nov. 5, 2013

(54) PYRIDINE-3-CARBOXYAMIDE DERIVATIVE

(75) Inventors: Takahiro Kitamura, Fuji (JP); Hajime Yamada, Higashimurayama (JP); Shunji Takemura, Higashimurayama (JP); Masanori Ashikawa, Higashimurayama (JP); Tetsuya Ishikawa, Tokyo (JP); Yoshiharu Miyake, Higashimurayama (JP); Akiyasu Kouketsu, Higashimurayama (JP); Seiichi Sato, Higashimurayama (JP); Hiroyuki Ishiwata, Higashimurayama (JP); Yuichiro Tabunoki, Higashimurayama (JP); Manabu Shibasaki, Higashimurayama (JP); Takatoshi Ozawa, Tokyo (JP); Ryota Shigemi, Higashimurayama (JP); Takeshi Doi, Higashimurayama (JP); Masahiro Tamura, Higashimurayama (JP)

(73) Assignee: Kowa Company, Ltd., Aichi (JP)

( * ) Notice: Subject to any disclaimer, the term of this patent is extended or adjusted under 35 U.S.C. 154(b) by 117 days.

(21) Appl. No.: 13/131,561

(22) PCT Filed: Nov. 27, 2009

(86) PCT No.: PCT/JP2009/070363
§ 371 (c)(1),
(2), (4) Date: May 26, 2011

(87) PCT Pub. No.: WO2010/061971
PCT Pub. Date: Jun. 3, 2010

(65) Prior Publication Data
US 2011/0237590 A1   Sep. 29, 2011

(30) Foreign Application Priority Data

Nov. 28, 2008  (JP) ................................. 2008-305054
Dec. 25, 2008  (JP) ................................. 2008-330724
Jan. 28, 2009  (JP) ................................. 2009-016951

(51) Int. Cl.
*A61K 31/506* (2006.01)
*C07D 239/48* (2006.01)

(52) U.S. Cl.
USPC .............. 514/218; 544/60; 544/323; 546/257

(58) Field of Classification Search
USPC ............................ 514/256; 544/323; 546/257
See application file for complete search history.

(56) References Cited

U.S. PATENT DOCUMENTS

2005/0272753 A1   12/2005   Nagashima et al.

FOREIGN PATENT DOCUMENTS

| EP | 2 361 902 A1 | 8/2011 |
|---|---|---|
| WO | WO 2004/002964 A1 | 1/2004 |
| WO | WO 2004/002964 A1 * | 1/2004 |
| WO | WO 2004/065378 A1 | 8/2004 |
| WO | WO 2006/105023 A1 | 10/2006 |
| WO | WO 2007/062459 * | 6/2007 |
| WO | WO 2007/062459 A1 | 6/2007 |
| WO | WO 2007/077949 A1 | 7/2007 |
| WO | WO 2008/009458 A1 | 1/2008 |

OTHER PUBLICATIONS

Morissette, et al., Advanced Drug Delivery Reviews, 2004, 56, 275-300.*
Extended European Search Report for corresponding European Patent Application No. 09829208.9, dated May 24, 2012, 6pp.
International Search Report, dated Dec. 28, 2009, corresponding to PCT/JP2009/070363, 5 pages.
Nagashima, et al., "Identification of 4-benzylamino-2-[(4-morpholin-4-ylphenyl)amino]pyrimidine-5-carboxamide derivatives as potent and orally bioavailable STAT6 inhibitors", Bioorganic & Medicinal Chemistry, Jul. 1, 2008, vol. 16, Issue.13, pp. 6509-6521.

* cited by examiner

*Primary Examiner* — Susannah Chung
(74) *Attorney, Agent, or Firm* — Christie, Parker & Hale, LLP

(57) ABSTRACT

To provide a novel JAK3 inhibitor that is useful as a preventive and/or therapeutic agent for rejection and graft versus host disease (GvHD) in organ transplantation, rheumatoid arthritis, multiple sclerosis, systemic lupus erythematosus, Sjögren syndrome, Behcet's disease, type I diabetes mellitus, autoimmune thyroiditis, idiopathic thrombocytopenic purpura, ulcerative colitis, Crohn's disease, asthma, allergic rhinitis, atopic dermatitis, contact dermatitis, urticaria, eczema, psoriasis, allergic conjunctivitis, uveitis, cancer, leukemia and the like. The pyridine-3-carboxyamide derivative represented by the general formula (1):

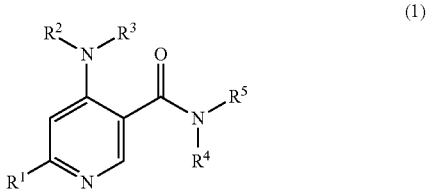

or its salt or a solvate thereof.

6 Claims, No Drawings

PYRIDINE-3-CARBOXYAMIDE DERIVATIVE

CROSS-REFERENCE TO RELATED APPLICATION

This application is a National Phase Patent Application and claims the priority of International Application Number PCT/JP2009/070363, filed on Nov. 27, 2009, which claims priority of Japanese Patent Application Number 2008-305054, filed on Nov. 28, 2008, Japanese Patent Application Number 2008-330724, filed on Dec. 25, 2008, and Japanese Patent Application Number 2009-016951, filed on Jan. 28, 2009.

FIELD OF THE INVENTION

The present invention relates to a novel compound useful as Janus tyrosine kinase 3 (JAK3) inhibitor, a method for preparing the same, a pharmaceutical composition comprising the compound or a pharmaceutically acceptable salt thereof, and the use thereof.

BACKGROUND OF THE INVENTION

Protein kinase JAK (Janus kinase) is a protein-tyrosine phosphorylation enzyme present in the cytoplasm that regulates functions involved in the growth and survival of cells in the lymphohematopoietic system. JAK is activated by stimulation via a cytokine receptor, and induces the phosphorylation of tyrosine residues of STAT (signal transducers actuators of transcription) protein. The phosphorylated STATs dimerize and translocate from the cytoplasm to the nucleus where they bind to specific DNA sequences leading to the transcriptional activation of genes (Gene, 285, 1-24, 2002).

The JAK family is known to be composed of four members: JAK1, JAK2, JAK 3 and Tyk2. While Jak1, Jak2 and Tyk2 are expressed relatively ubiquitously, the expression of Jak3 is localized. JAK3 is constantly expressed in NK cells, thymic cells, mast cells, platelet cells etc., whereas in T cells and B cells its expression is induced following the activation of the cells. JAK3 is specifically associated with the γc chain of the interleukin (IL)-2 receptor and is activated by each cytokine stimulation via each receptor of IL-2, IL-4, IL-7, IL-9, IL-13, IL-15 and IL-21 (Curr. Pharm. Design., 10, 1767-1784, 2004). It is demonstrated that JAK3 is also involved in IL-2 production from T cells and T cell activation by associating with the T cell receptor/CD3 complex (J. Immunol., 163, 5411-5417, 1999; J. Biol. Chem., 276, 25378-25385, 2001). Furthermore, in some patients with severe combined immunodeficiency disease (SCID), the reduced expression of the JAK3 protein due to JAK3 gene mutation can be noted, and in patients with X-linked severe combined immunodeficiency disease (XSCID), gene defect in the γc chain has been reported suggesting that the blockage of JAK3-related signal transduction may inhibit the immune system (Nature, 377, 65-68, 1995; Science 266, 1042-1045, 1994). Furthermore, it is reported that in JAK3-deficient mice, the onset of streptozotocin-induced autoimmune diabetes mellitus can be suppressed (Curr. Pharm. Design., 10, 1767-1784, 2004).

Since JAK3 is expressed in many lymphatic cells, involved in the activation and propagation of T cells, and has been implicated in autoimmune diseases of model animals, as described above, it is expected to provide a selective target for drug discovery and the development of an agent for specifically inhibiting JAK3 has been sought after.

On the other hand, a study on gene-deficient mice suggested that JAK3 is involved in degranulation and release of chemical mediators induced by IgE/antigen stimulation, JAK3 is also promising as a target for drug discovery intended to inhibit allergic reactions associated with mast cells (Biochem. Biophys. Res. Commun., 257, 807-813, 1999).

Accordingly, it is expected that inhibition of JAK3 could lead to the prevention and treatment of rejection and graft versus host disease (GvHD) in organ transplantation, rheumatoid arthritis, multiple sclerosis, systemic lupus erythematosus, Sjögren syndrome, Behcet's disease, type I diabetes mellitus, autoimmune thyroiditis, idiopathic thrombocytopenic purpura, ulcerative colitis, Crohn's disease, asthma, allergic rhinitis, atopic dermatitis, contact dermatitis, urticaria, eczema, psoriasis, allergic conjunctivitis, uveitis, cancer, leukemia and the like.

Under these circumstances, low molecular weight inhibitors for JAK3 intended for pharmaceuticals have been reported. For example, a pyrrolo-pyrimidine derivative (WO2000/142246; Bioorg. Med. Chem. Lett., 17, 1250-1253, 2007), a pyrrolo-pyridine derivative (WO2007/007919), an indolone derivative (Bioorg. Med. Chem. Lett., 13, 3105-3110, 2003), a purine derivative (WO2006/108103), a benzoxazole derivative (WO2008/031594 pamphlet), a quinazoline derivative (WO2000/010981), a quinoline derivative (WO2005/075429), a highly-fused ring compound (WO2007/145957; Bioorg. Med. Chem. Lett., 17, 326-31, 2007), a pyrimidine derivative (WO2008/009458; WO2006/133426) and the like.

Also, there is a report on a pyridine derivative having a JAK3 inhibitory activity (WO2007/062459), which describes the following the general formula:

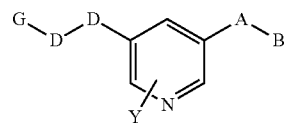

[see the description for definition of symbols]

However, the pyridine derivative described in this reference is different from the pyridine derivative of the present invention in the type and in the position of bonding of functional group, and the 50% inhibition concentration for the JAK3 inhibitory activity described in the Example is about 20 μM (see the description of the present invention on pages 49 to 50). There are no further reports on JAK3 inhibitors of the pyridine type, and thus pyridine derivatives having an excellent JAK3 inhibitory activity are still in great need.

DISCLOSURE OF THE INVENTION

The problem to be solved by the present invention is to provide a compound having an excellent JAK3-inhibitory activity and to provide a preventive and therapeutic agent for diseases associated with JAK3.

After intensive and extensive research to attain the above objective, the present inventors have found that a pyridine-3-carboxyamide derivative represented by the following the general formula (1) has an excellent JAK3-inhibitory activity and thereby have completed the present invention.

Thus, the present invention is:

[1] A pyridine-3-carboxyamide derivative represented by the general formula (1):

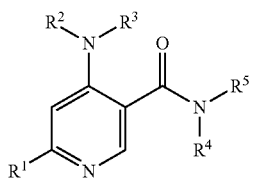

(1)

[wherein
$R^1$ is a group selected from one of the following formulas i to iv:

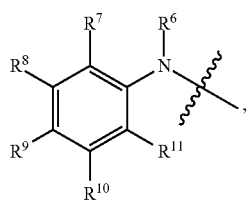

i

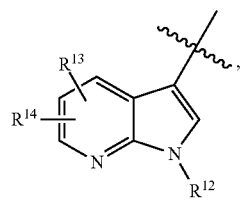

ii

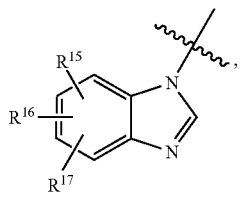

iii

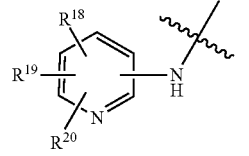

iv wherein
$R^6$ is selected from the group consisting of a hydrogen atom, a $C_{1-6}$ alkyl group and an optionally substituted acl group,
$R^7$, $R^8$, $R^9$, $R^{10}$ and $R^{11}$, which may be the same or different, are selected from the group consisting of a hydrogen atom, a halogen atom, an optionally substituted $C_{1-6}$ alkyl group, a cyano group, an optionally substituted $C_{3-8}$ cycloalkyl group, a $C_{1-6}$ alkoxycarbonyl group, an optionally substituted $C_{1-6}$ alkylcarbonyl group, a $C_{3-8}$ cycloalkylcarbonyl group, a carbamoyl group, a carboxyl group, a $C_{1-6}$ alkylthio group, a $C_{1-6}$ alkylsulfinyl group, a $C_{1-6}$ alkylsulfonyl group, a (5-11-membered heterocyclic)-sulfonyl group, an optionally substituted 5-11-membered heterocyclic group, an optionally substituted sulfamoyl group, —O—$R^{21}$ represents a hydrogen atom, an optionally substituted $C_{1-6}$ alkyl group or a piperazinyl group that may be substituted with a $C_{1-6}$ alkyl group), —$NR^{22}R^{23}$ (wherein $R^{22}$ and $R^{23}$, which may be the same or different, represent a hydrogen atom, an optionally substituted $C_{1-6}$ alkyl group, an optionally substituted $C_{1-6}$ alkylsulfonyl group, a $C_{2-6}$ alkenylsulfonyl group or an optionally substituted 5-11-membered heterocyclic group) and —$NR^{24}COR^{25}$ (wherein $R^{24}$ represents a hydrogen atom or a $C_{1-6}$ alkyl group and $R^{25}$ represents an amino group, a mono($C_{1-6}$ alkyl)amino group, a di($C_{1-6}$ alkyl)amino group or an optionally substituted 5-11-membered heterocyclic group),
$R^{12}$ represents a hydrogen atom or a sulfonyl group, and $R^{13}$, $R^{14}$, $R^{15}$, $R^{16}$, $R^{17}$, $R^{18}$, $R^{19}$ and $R^{20}$, which may be the same or different, represent a hydrogen atom, a halogen atom, a cyano group or a morpholino group,
$R^2$ represents a group selected from one of the following formulas v to x:

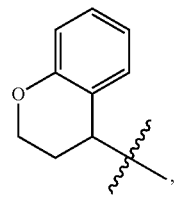

v

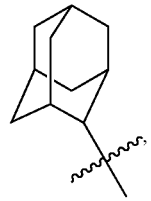

vi

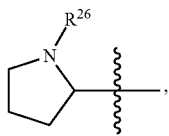

vii

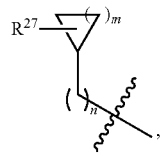

viii

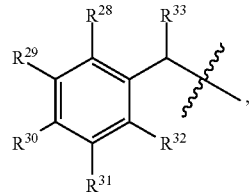

ix

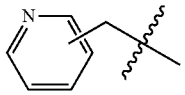

x $R^{26}$ represents a hydrogen atom, a $C_{1-6}$ alkyl group, a $C_{6-10}$ aryl $C_{1-6}$ alkyl group or a $C_{1-6}$ alkylcarbonyl group,
$R^{27}$ represents a hydrogen atom or a $C_{1-6}$ alkyl group,
$R^{28}$, $R^{29}$, $R^{30}$, $R^{31}$ and $R^{32}$, which may be the same or different, are selected from the group consisting of a hydrogen atom, a halogen atom, a C$_{1-6}$ alkyl group, a halo C$_{1-6}$ alkyl group, a C$_{1-6}$ alkoxy group, a carboxyl group, a C$_{1-6}$ alkoxycarbonyl group, a carbamoyl group, a nitro group, a piperazinyl group that may be substituted with a C$_{1-6}$ alkyl group, an amino group, a mono (C$_{1-6}$ alkyl)amino group, a di (C$_{1-6}$ alkyl)amino group, a C$_{1-6}$ alkylcarbonylamino group, —N(R$^{34}$)SO$_2$R$^{35}$ (wherein R$^{34}$ represents a hydrogen atom or a C$_{1-6}$ alkyl group and R$^{35}$ represents a C$_{1-6}$ alkyl group or a C$_{2-6}$ alkenyl group) and —SO$_2$NR$^{36}$R$^{37}$ (wherein R$^{36}$ and R$^{37}$, which may be the same or different, represent a hydrogen atom or a C$_{1-6}$ alkyl group), or R$^{28}$ and R$^{29}$ or R$^{29}$ and R$^{30}$ may together form a benzene ring, R$^{33}$ represents a hydrogen atom or a C$_{1-6}$ alkyl group, m represents an integer of 1 to 6, n represents 0 or 1, R$^3$ represents a hydrogen atom or a C$_{1-6}$ alkyl group, and R$^4$ and R$^5$, which may be the same or different, are selected from the group consisting of a hydrogen atom, a C$_{1-6}$ alkyl group, a C$_{1-6}$ alkoxy group, an amino group and a hydroxy group], or its salt or a solvate thereof.

[2] The pyridine-3-carboxyamide derivative according to the above [1], wherein R$^{28}$, R$^{29}$, R$^{30}$, R$^{31}$ and R$^{32}$, which may be the same or different, are selected from the group consisting of a hydrogen atom, a halogen atom, a C$_{1-6}$ alkyl group, a halo C$_{1-6}$ alkyl group, a C$_{1-6}$ alkoxy group, a carboxyl group, a C$_{1-6}$ alkoxycarbonyl group, a carbamoyl group, a nitro group, a piperazinyl group that may be substituted with a C$_{1-6}$ alkyl group, —N(R$^{34}$)SO$_2$R$^{35}$ (wherein R$^{34}$ and R$^{35}$ represent the same groups as described above) and —SO$_2$NR$^{36}$R$^{37}$ (wherein R$^{36}$ and R$^{37}$ represent the same groups as described above), or R$^{28}$ and R$^{29}$ or R$^{29}$ and R$^{30}$ may together form a benzene ring, or its salt or a solvate thereof.

[3] The pyridine-3-carboxyamide derivative according to the above [1] or [2], wherein the optionally substituted 5-11-membered heterocyclic group in R$^7$, R$^8$, R$^9$, R$^{10}$ and R$^{11}$ is selected from the group consisting of an optionally substituted morpholinyl group, an optionally substituted piperazinyl group, an optionally substituted piperidinyl group, an optionally substituted hexahydro-1H-1,4-diazepinyl group, an optionally substituted 1,1-dioxoisothiazolidinyl group, an optionally substituted oxolanyl group and an optionally substituted pyrrolidinyl group, or its salt or a solvate thereof.

[4] The pyridine-3-carboxyamide derivative according to the above [1] to [3], wherein the compound represented by the general formula (1) is, 4-(benzylamino)-6-({4-[(1-methylpiperidin-4-yl)oxy] phenyl}amino)pyridine-3-carboxyamide,
4-(benzylamino)-6-({4-[4-(2-hydroxyethyl)piperidino] phenyl}amino)pyridine-3-carboxyamide,
4-(benzylamino)-6-[(4-{4-[2-(diethylamino)ethyl] piperidino}phenyl)amino]pyridine-3-carboxyamide,
4-(benzylamino)-6-({4-[4-(2-cyanoethyl)piperidino] phenyl}amino)pyridine-3-carboxyamide,
6-[(4-aminophenyl)amino]-4-(benzylamino)pyridine-3-carboxyamide,
4-(benzylamino)-6-({4-[(2-morpholinoethyl)amino] phenyl}amino)pyridine-3-carboxyamide,
4-(benzylamino)-6-({4-[methyl(2-morpholinoethyl)amino] phenyl}amino)pyridine-3-carboxyamide,
4-(benzylamino)-6-[(4-morpholinophenyl)amino]pyridine-3-carboxyamide,
4-[(2-methoxybenzyl)amino]-6-[(4-morpholinophenyl) amino]pyridine-3-carboxyamide,
4-[(2-methylbenzyl)amino]-6-[(4-morpholinophenyl) amino]pyridine-3-carboxyamide,
4-[(3-methylbenzyl)amino]-6-[(4-morpholinophenyl) amino]pyridine-3-carboxyamide,
4-[(2-chlorobenzyl)amino]-6-[(4-morpholinophenyl)amino] pyridine-3-carboxyamide,
4-[(3-chlorobenzyl)amino]-6-[(4-morpholinophenyl)amino] pyridine-3-carboxyamide,
4-[(2,3-difluorobenzyl)amino]-6-[(4-morpholinophenyl) amino]pyridine-3-carboxyamide,
4-[(2,5-difluorobenzyl)amino]-6-[(4-morpholinophenyl) amino]pyridine-3-carboxyamide,
4-[(2,6-difluorobenzyl)amino]-6-[(4-morpholinophenyl) amino]pyridine-3-carboxyamide,
6-[(4-morpholinophenyl)amino]-4-{[3-fluoro-5-(trifluoromethyl)benzyl]amino}pyridine-3-carboxyamide,
4-[(5-fluoro-2-methoxybenzyl)amino]-6-[(4-morpholinophenyl)amino]pyridine-3-carboxyamide,
4-[(3-fluoro-2-methylbenzyl)amino]-6-[(4-morpholinophenyl)amino]pyridine-3-carboxyamide,
6-[(4-morpholinophenyl)amino]-4-[(3-nitrobenzyl)amino] pyridine-3-carboxyamide,
4-[(3-carbamoylbenzyl)amino]-6-[(4-morpholinophenyl) amino]pyridine-3-carboxyamide,
6-[(3-cyano-4-morpholinophenyl)amino]-4-[(3,5-difluorobenzyl)amino]pyridine-3-carboxyamide,
4-[(3,5-difluorobenzyl)amino]-6-[(3-methyl-4-morpholinophenyl)amino]pyridine-3-carboxyamide,
6-[(3-chloro-4-morpholinophenyl)amino]-4-[(3,5-difluorobenzyl)amino]pyridine-3-carboxyamide,
4-[(3,5-difluorobenzyl)amino]-6-[(3-methoxy-4-morpholinophenyl)amino]pyridine-3-carboxyamide,
4-[(3,5-difluorobenzyl)amino]-6-[(3-morpholinophenyl) amino]pyridine-3-carboxyamide,
4-(benzylamino)-6-({4-[(3S)-3-methylmorpholino] phenyl}amino) pyridine-3-carboxyamide,
4-[(2,3-difluorobenzyl)amino]-6-({4-[(3R,5S)-3,5-dimethylpiperazin-1-yl]phenyl}amino)pyridine-3-carboxyamide,
4-[(3,5-difluorobenzyl)amino]-6-({4-[(3R,5S)-3,5-dimethylpiperazin-1-yl]phenyl}amino)pyridine-3-carboxyamide,
4-[(2,5-difluorobenzyl)amino]-6-({4-[(3R,5S)-3,5-dimethylpiperazin-1-yl]phenyl}amino)pyridine-3-carboxyamide,
4-[(2,5-difluorobenzyl)amino]-6-({3-[(3R,5S)-3,5-dimethylpiperazin-1-yl]phenyl}amino)pyridine-3-carboxyamide,
4-(benzylamino)-6-{[4-(4-methylpiperazin-1-yl)phenyl] amino}pyridine-3-carboxyamide,
4-(benzylamino)-6-({4-[4-(propan-2-yl)piperazin-1-yl] phenyl}amino)pyridine-3-carboxyamide,
4-[(2-methoxybenzyl)amino]-6-({4-[4-(propan-2-yl)piperazin-1-yl]phenyl}amino)pyridine-3-carboxyamide,
4-[(2,3-difluorobenzyl)amino]-6-({4-[4-(propan-2-yl)piperazin-1-yl]phenyl}amino)pyridine-3-carboxyamide,
4-[(3,5-difluorobenzyl)amino]-6-({4-[4-(propan-2-yl)piperazin-1-yl]phenyl}amino)pyridine-3-carboxyamide,
4-[(3,5-difluorobenzyl)amino]-6-({3-[4-(propan-2-yl)piperazin-1-yl]phenyl}amino)pyridine-3-carboxyamide,
4-[(3,5-difluorobenzyl)amino]-6-{[4-({2-[(methylsulfonyl) amino]ethyl}amino)phenyl]amino}pyridine-3-carboxyamide,
4-[(3-nitrobenzyl)amino]-6-({4-[(methylsulfonyl)amino] phenyl}amino)pyridine-3-carboxyamide,
4-[(3,5-difluorobenzyl)amino]-6-({4-[(propylsulfonyl) amino]phenyl}amino)pyridine-3-carboxyamide, 4-(benzylamino)-6-({4-[(propan-2-ylsulfonyl)amino]phenyl}amino)pyridine-3-carboxamide,
4-[(3,5-difluorobenzyl)amino]-6-({3-[(methylsulfonyl)amino]phenyl}amino)pyridine-3-carboxamide,
4-[(3,5-difluorobenzyl)amino]-6-({3-[(propan-2-ylsulfonyl)amino]phenyl}amino)pyridine-3-carboxamide,
4-[(3,5-difluorobenzyl)amino]-6-({4-[4-(methylsulfonyl)piperidin-1-yl]phenyl}amino)pyridine-3-carboxamide,
4-[(2,6-difluorobenzyl)amino]-6-({4-[4-(methylsulfonyl)piperidin-1-yl]phenyl}amino)pyridine-3-carboxamide,
4-[(3,5-difluorobenzyl)amino]-6-({3-[4-(propan-2-ylsulfonyl)piperazin-1-yl]phenyl}amino)pyridine-3-carboxamide,
4-(benzylamino)-6-[(4-{4-[(2-hydroxy)carbamoyl]piperidino}phenyl)amino]pyridine-3-carboxamide,
4-[(2,3-difluorobenzyl)amino]-6-({4-[4-(2-hydroxyethyl)piperidino]phenyl}amino)pyridine-3-carboxamide,
6-({4-[4-(2-hydroxyethyl)piperidino]phenyl}amino)-4-[(3-nitrobenzyl)amino]pyridine-3-carboxamide,
4-[(2-methylbenzyl)amino]-6-{[4-(4-hydroxypiperidino)phenyl]amino}pyridine-3-carboxamide,
4-[(2-chlorobenzyl)amino]-6-{[4-(4-hydroxypiperidino)phenyl]amino}pyridine-3-carboxamide,
4-[(2,3-difluorobenzyl)amino]-6-{[4-(4-hydroxypiperidino)phenyl]amino}pyridine-3-carboxamide,
4-[(2,5-difluorobenzyl)amino]-6-{[4-(4-hydroxypiperidino)phenyl]amino}pyridine-3-carboxamide,
4-[(3,5-difluorobenzyl)amino]-6-{[4-(4-methoxypiperidino)phenyl]amino}pyridine-3-carboxamide,
4-[(3,5-difluorobenzyl)amino]-6-{[4-(4-hydroxypiperidino)phenyl]amino}pyridine-3-carboxamide,
4-[(3,5-difluorobenzyl)amino]-6-{[4-(4-oxopiperidino)phenyl]amino}pyridine-3-carboxamide,
6-{[4-(3-aminopropyl)phenyl]amino}-4-[(3,5-difluorobenzyl)amino]pyridine-3-carboxamide,
4-[(3,5-difluorobenzyl)amino]-6-[(4-{3-[(methanesulfonyl)amino]propyl}phenyl)amino]pyridine-3-carboxamide,
4-(benzylamino)-6-{[4-piperazin-1-yl]phenyl}amino) pyridine-3-carboxamide,
4-[(3,5-difluorobenzyl)amino]-6-{[4-(piperazin-1-yl)phenyl]amino}pyridine-3-carboxamide,
4-[(2,5-difluorobenzyl)amino]-6-{[4-(piperazin-1-yl)phenyl]amino}pyridine-3-carboxamide,
4-[(2,6-difluorobenzyl)amino]-6-{[4-(piperazin-1-yl)phenyl]amino}pyridine-3-carboxamide,
4-[(3-nitrobenzyl)amino]-6-{[4-(piperazin-1-yl)phenyl]amino}pyridine-3-carboxamide,
4-[(3,5-difluorobenzyl)amino]-6-{[3-(piperazin-1-yl)phenyl]amino}pyridine-3-carboxamide,
4-(benzylamino)-6-{[4-(1,4-diazepan-1-yl)phenyl]amino}pyridine-3-carboxamide,
4-[(3,5-difluorobenzyl)amino]-6-({4-[(2-methoxyethyl)amino]phenyl}amino)pyridine-3-carboxamide,
4-[(3,5-difluorobenzyl)amino]-6-({4-[(2-hydroxyethyl)amino]phenyl}amino)pyridine-3-carboxamide,
6-[(4-{4-[2-(diethylamino)ethyl]piperazin-1-yl}phenyl)amino]-4-[(3-nitrobenzyl)amino]pyridine-3-carboxamide,
4-(benzylamino)-6-[(4-{4-[2-(diethylamino)ethyl]piperazin-1-yl}phenyl)amino]pyridine-3-carboxamide,
6-[(4-{4-[2-(diethylamino)ethyl]piperazin-1-yl}phenyl)amino]-4-[(2,3-difluorobenzyl)amino]pyridine-3-carboxamide,
6-[(3-{4-[2-(diethylamino)ethyl]piperazin-1-yl}phenyl)amino]-4-[(3,5-difluorobenzyl)amino]pyridine-3-carboxamide,
6-({4-{4-(2-cyanoethyl)piperazin-1-yl]phenyl}amino)-4-[(3,5-difluorobenzyl)amino]pyridine-3-carboxamide,
4-(benzyl)-6-({4-[4-(2-cyanoethyl)piperazin-1-yl]phenyl}amino)pyridine-3-carboxamide,
6-({4-{4-(3-cyanopropyl)piperazin-1-yl]phenyl}amino)-4-[(3-nitrobenzylamino)pyridine-3-carboxamide,
4-(benzylamino)-6-{[4-(4-methyl-1,4-diazepan-1-yl)phenyl]amino}pyridine-3-carboxamide,
4-(benzylamino)-6-({4-[4-(2-hydroxyethyl)-1,4-diazepan-1-yl]phenyl}amino)pyridine-3-carboxamide,
6-({4-[4-(2-aminoethyl)piperazin-1-yl]phenyl}amino)-4-[(3,5-difluorobenzyl)amino]pyridine-3-carboxamide,
4-[(3,5-difluorobenzyl)amino]-6-{[4-(4-{2-[(methylsulfonyl)amino]ethyl}piperazin-1-yl)phenyl]amino}pyridine-3-carboxamide,
4-[(3,5-difluorobenzyl)amino]-6-[(4-{4-[2-(methylamino)ethyl]piperazin-1-yl}phenyl)amino]pyridine-3-carboxamide,
6-{[4-(4-acetylpiperazin-1-yl)phenyl]amino}-4-(benzylamino)pyridine-3-carboxamide,
6-{[4-(4-acetyl-1,4-diazepan-1-yl)phenyl]amino}-4-(benzylamino)pyridine-3-carboxamide,
4-(benzylamino)-6-{[4-(4-butanoylpiperazin-1-yl)phenyl]amino}pyridine-3-carboxamide,
4-(benzylamino)-6-({4-[4-(2-methylpropanoyl)piperazin-1-yl]phenyl}amino)pyridine-3-carboxamide,
4-(benzylamino)-6-({4-[4-(cyanoacetyl)piperazin-1-yl]phenyl}amino)pyridine-3-carboxamide,
6-({4-[4-(cyanoacetyl)piperazin-1-yl]phenyl}amino)-4-[(2,5-difluorobenzyl)amino]pyridine-3-carboxamide,
6-({4-[4-(cyanoacetyl)piperazin-1-yl]phenyl}amino)-4-[(2,6-difluorobenzyl)amino]pyridine-3-carboxamide,
6-({3-[4-(cyanoacetyl)piperazin-1-yl]phenyl}amino)-4-[(3,5-difluorobenzyl)amino]pyridine-3-carboxamide,
4-(benzylamino)-6-({4-[4-(cyanoacetyl)-1,4-diazepan-1-yl]phenyl}amino)pyridine-3-carboxamide,
4-(benzylamino)-6-({4-[4-(N,N-diethylglycyl)piperazin-1-yl]phenyl}amino)pyridine-3-carboxamide,
6-({4-[4-(N,N-diethylglycyl)piperazin-1-yl]phenyl}amino)-4-[(3-nitrobenzyl)amino]pyridine-3-carboxamide,
4-(benzylamino)-6-({4-[1-(N,N-diethylglycyl)piperidin-4-yl]phenyl}amino)pyridine-3-carboxamide,
4-(benzylamino)-6-({4-[(diethylcarbamoyl)amino]phenyl}amino)pyridine-3-carboxamide,
4-(benzylamino)-6-({4-[(4-diethylcarbamoyl)piperazin-1-yl]phenyl}amino)pyridine-3-carboxamide,
4-(benzylamino)-6-[(4-{[4-(propan-2-yl)carbamoyl]piperazin-1-yl}phenyl)amino]pyridine-3-carboxamide,
4-[(3-nitrobenzyl)amino]-6-[(4-{[4-(propan-2-yl)carbamoyl]piperazin-1-yl}phenyl)amino]pyridine-3-carboxamide,
4-(benzylamino)-6-({4-[4-(morpholinocarbonyl)piperazin-1-yl]phenyl}amino)pyridine-3-carboxamide,
4-(benzylamino)-6-{[4-(piperidin-4-ylamino)phenyl]amino}pyridine-3-carboxamide,
4-(benzylamino)-6-[(4-{[1-(diethylcarbamoyl)piperidin-4-yl]amino}phenyl)amino]pyridine-3-carboxamide,
4-(benzylamino)-6-[(4-{[1-(propan-2-ylcarbamoyl)piperidin-4-yl]amino}phenyl)amino]pyridine-3-carboxamide,
4-[(2,3-difluorobenzyl)amino]-6-({4-[4-(methylsulfonyl)piperazin-1-yl]phenyl}amino)pyridine-3-carboxamide,
4-[(3,5-difluorobenzyl)amino]-6-({4-[4-(methylsulfonyl)piperazin-1-yl]phenyl}amino)pyridine-3-carboxamide,
4-(benzylamino)-6-({4-[4-(methylsulfonyl)-1,4-diazepan-1-yl]phenyl}amino)pyridine-3-carboxamide,
4-(benzylamino)-6-({4-[bis(methylsulfonyl)amino]phenyl}amino)pyridine-3-carboxamide, 4-(benzylamino)-6-({4-[(methylsulfonyl)amino]
phenyl}amino)pyridine-3-carboxyamide,
4-[(3,5-difluorobenzyl)amino]-6-({4-[(propan-2-ylsulfonyl)
amino]phenyl}amino)pyridine-3-carboxyamide,
6-{[4-({[2-(diethylamino)ethyl]sulfonyl}amino)phenyl]
amino}-4-[(3,5-difluorobenzyl)amino]pyridine-3-carboxyamide,
6-[(4-{[(2-aminoethyl)sulfonyl]amino}phenyl)amino]-4-
[(3,5-difluorobenzyl)amino]pyridine-3-carboxyamide,
4-(benzylamino)-6-{[4-(1,1-dioxo-1,2-thiazolidin-2-yl)phenyl]amino}pyridine-3-carboxyamide,
4-(benzylamino)-6-({4-[(piperidin-4-ylcarbonyl)amino]
phenyl}amino)pyridine-3-carboxyamide,
4-[(3,5-difluorobenzyl)amino]-6-({4-[(piperidin-4-ylcarbamoyl)amino]phenyl}amino)pyridine-3-carboxyamide,
4-(benzylamino)-6-{[4-(L-prolylamino)phenyl]
amino}pyridine-3-carboxyamide,
4-[(3,5-difluorobenzyl)amino]-6-{[4-(L-prolylamino)phenyl]amino}pyridine-3-carboxyamide,
4-(benzylamino)-6-{[4-(morpholin-4-ylmethyl)phenyl]
amino}pyridine-3-carboxyamide,
6-[(4-acetylphenyl)amino]-4-[(3,5-difluorobenzyl)amino]
pyridine-3-carboxyamide,
4-[(3,5-difluorobenzyl)amino]-6-{[(4-trifluoroacetyl)phenyl]amino}pyridine-3-carboxyamide,
4-[(3,5-difluorobenzyl)amino]-6-({4-[(2-methoxyethyl)sulfamoyl]phenyl}amino)pyridine-3-carboxyamide,
6-[(4-carboxyphenyl)amino]-4-[(3,5-difluorobenzyl)amino]
pyridine-3-carboxyamide,
4-cyclohexylamino-6-[(4-morpholinophenyl)amino]pyridine-3-carboxyamide,
4-cyclohexylamino-6-({4-[4-(methylsulfonyl)piperazin-1-
yl]phenyl}amino)pyridine-3-carboxyamide,
4-cyclohexylamino-6-({4-[(methylsulfonyl)amino]
phenyl}amino)pyridine-3-carboxyamide,
4-cyclohexylamino-6-[(3,5-difluorophenyl)amino]pyridine-3-carboxyamide,
4-[(2-methylcyclohexyl)amino]-6-[(4-morpholinophenyl)
amino]pyridine-3-carboxyamide,
6-[(4-morpholinophenyl)amino]-4-(tricyclo [3.3.1.1$^{3,7}$]
deca-2-ylamino)pyridine-3-carboxyamide,
4-(3,4-dihydro-2H-1-benzopyran-4-ylamino)-6-[(4-morpholinophenyl)amino]pyridine-3-carboxyamide,
4-(3,4-dihydro-2H-1-benzopyran-4-ylamino)-6-({4-[4-(propan-2-ylsulfonyl)piperazin-1-yl]phenyl}amino)pyridine-3-carboxyamide,
6-[(4-morpholinophenyl)amino]-4-[(pyridin-3-ylmethyl)
amino]pyridine-3-carboxyamide,
4-[(pyridin-3-ylmethyl)amino]-6-({4-[4-(trifluoroacetyl)
piperazin-1-yl]phenyl}amino)pyridine-3-carboxyamide,
6-{[4-(piperazin-1-yl)phenyl]amino}-4-[(pyridin-3-ylmethyl)amino]pyridine-3-carboxyamide,
6-({4-[4-(propan-2-yl)piperazin-1-yl]phenyl}amino)-4-
[(pyridin-3-ylmethyl)amino]pyridine-3-carboxyamide,
4-{[(1-benzylpyrrolidin-2-yl)methyl]amino}-6-[(4-morpholinophenyl)amino]pyridine-3-carboxyamide,
6-[(4-morpholinophenyl)amino]-4-[(pyrrolidin-2-ylmethyl)
amino]pyridine-3-carboxyamide,
4-{[(1-methylpyrrolidin-2-yl)methyl]amino}-6-[(4-morpholinophenyl)amino]pyridine-3-carboxyamide,
4-{[(1-acetylpyrrolidin-2-yl)methyl]amino}-6-[(4-morpholinophenyl)amino]pyridine-3-carboxyamide,
4-[(cyclohexylmethyl)amino]-6-[(4-morpholinophenyl)
amino]pyridine-3-carboxyamide,
4-[(cyclopropylmethyl)amino]-6-[(4-morpholinophenyl)
amino]pyridine-3-carboxyamide,
6-[(4-morpholinophenyl)amino]-4-[(pyridin-2-ylmethyl)
amino]pyridine-3-carboxyamide,
6-(5-chloro-1H-benzimidazol-1-yl)-4-[(3,5-difluorobenzyl)
amino]pyridine-3-carboxyamide,
6-(6-chloro-1H-benzimidazol-1-yl)-4-[(3,5-difluorobenzyl)
amino]pyridine-3-carboxyamide,
6-(1H-benzimidazol-1-yl)-4-[(3,5-difluorobenzyl)amino]
pyridine-3-carboxyamide,
6-(6-cyano-1H-benzimidazol-1-yl)-4-[(3,5-difluorobenzyl)
amino]pyridine-3-carboxyamide,
6-(5-cyano-1H-benzimidazol-1-yl)-4-[(3,5-difluorobenzyl)
amino]pyridine-3-carboxyamide,
4-[(3,5-difluorobenzyl)amino]-6-(6-morpholino-1H-benzimidazol-1-yl)pyridine-3-carboxyamide,
4-[(3,5-difluorobenzyl)amino]-6-(5-morpholino-1H-benzimidazol-1-yl)pyridine-3-carboxyamide,
4-[(3,5-difluorobenzyl)amino]-6-{1-[(4-methylphenyl)sulfonyl]-1H-pyloro[2,3-b]pyridin-3-yl}pyridine-3-carboxyamide,
4-[(3,5-difluorobenzyl)amino]-6-(1H-pyloro[2,3-b]pyridin-3-yl)pyridine-3-carboxyamide,
4-benzylamino-6-(pyridin-4-ylamino)pyridine-3-carboxyamide, or
4-benzylamino-6-[(6-morpholinopyridin-3-yl)amino]pyridine-3-carboxyamide,
or its salt or a solvate thereof.

[5] A drug comprising, as an active ingredient, the pyridine-3-carboxyamide derivative according to the above [1] to [4] or its salt or a solvate thereof.

[6] The drug according to the above [5] which is a preventive and/or therapeutic agent for rejection and graft versus host disease (GvHD) in organ transplantation, rheumatoid arthritis, multiple sclerosis, systemic lupus erythematosus, Sjögren syndrome, Behcet's disease, type I diabetes mellitus, autoimmune thyroiditis, idiopathic thrombocytopenic purpura, ulcerative colitis, Crohn's disease, asthma, allergic rhinitis, atopic dermatitis, contact dermatitis, urticaria, eczema, psoriasis, allergic conjunctivitis, uveitis, cancer and leukemia.

[7] A JAK3 inhibitor comprising, as an active ingredient, the pyridine-3-carboxyamide derivative according to the above [1] to [4] or its salt or a solvate thereof.

[8] A pharmaceutical composition comprising the pyridine-3-carboxyamide derivative according to the above [1] to [4] or its salt or a solvate thereof and a pharmaceutically acceptable carrier.

[9] A method of preventing and/or treating rejection and graft versus host disease (GvHD) in organ transplantation, rheumatoid arthritis, multiple sclerosis, systemic lupus erythematosus, Sjögren syndrome, Behcet's disease, type I diabetes mellitus, autoimmune thyroiditis, idiopathic thrombocytopenic purpura, ulcerative colitis, Crohn's disease, asthma, allergic rhinitis, atopic dermatitis, contact dermatitis, urticaria, eczema, psoriasis, allergic conjunctivitis, uveitis, cancer and leukemia, said method comprising administering to patients in need thereof an effective amount of the pyridine-3-carboxyamide derivative according to the above [1] to [4] or its salt or a solvate thereof.

[10] The use of the pyridine-3-carboxyamide derivative according to the above [1] to [4] or its salt or a solvate thereof in the preparation of a pharmaceutical preparation for preventing and/or treating rejection and graft versus host disease (GvHD) in organ transplantation, rheumatoid arthritis, multiple sclerosis, systemic lupus erythematosus, Sjögren syndrome, Behcet's disease, type I diabetes mellitus, autoimmune thyroiditis, idiopathic thrombocytopenic purpura, ulcerative colitis, Crohn's disease, asthma, allergic rhinitis, atopic dermatitis, contact dermatitis, urticaria, eczema, psoriasis, allergic conjunctivitis, uveitis, cancer and leukemia.

EFFECT OF THE INVENTION

The pyridine-3-carboxyamide derivative according to the present invention or its salt or a solvate thereof has an excellent JAK3 inhibitory activity, and is useful as a preventive and therapeutic agent for diseases associated with JAK3 such as rejection and graft versus host disease (GvHD) in organ transplantation, rheumatoid arthritis, multiple sclerosis, systemic lupus erythematosus, Sjögren syndrome, Behcet's disease, type I diabetes mellitus, autoimmune thyroiditis, idiopathic thrombocytopenic purpura, ulcerative colitis, Crohn's disease, asthma, allergic rhinitis, atopic dermatitis, contact dermatitis, urticaria, eczema, psoriasis, allergic conjunctivitis, uveitis, cancer and leukemia.

MODE FOR CARRYING OUT THE INVENTION

The definition of terms used in the present invention is as described below.

As used herein "halogen" atom refers to a fluorine atom, a chlorine atom, a bromine atom, an iodine atom or the like.

As used herein "$C_{1-6}$ alkyl group" refers to a straight or branched alkyl group of 1-6 carbon atoms. Specifically there can be mentioned, for example, a methyl group, an ethyl group, a n-propyl group, an iso-propyl group, a n-butyl group, an isobutyl group, a sec-butyl group, a tert-butyl group, a n-pentyl group, an isopentyl group, a neopentyl group, a 2-methylbutyl group, a 1-methylbutyl group, a 1-ethylpropyl group, a 2,2-dimethylpropyl group, n-hexyl group, an isohexyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 1-ethylbutyl group, a 2-ethylbutyl group and the like.

As used herein, "$C_{3-8}$ cycloalkyl group" refers to a cyclic alkyl group of 3-8 carbon atoms. Specifically, for example, a cyclopropyl group, a cyclobutyl group, a cyclopentyl group, a cyclohexyl group, a cycloheptyl group, a cyclooctyl group and the like can be mentioned.

As used herein "$C_{2-6}$ alkenyl group" refers to a straight or branched alkenyl group of 2-6 carbon atoms having a carbon-carbon double bond at one or more positions on an alkyl chain. Specifically, there can be mentioned, for example, an ethenyl (vinyl) group, a prop-1-en-1-yl group, a prop-2-en-1-yl group, a prop-1-en-2-yl group, a but-1-en-1-yl group, a but-2-en-1-yl group, a but-3-en-1-yl group, a but-1-en-2-yl group, a but-3-en-2-yl group, a pent-1-en-1-yl group, a pent-2-en-1-yl group, a pent-3-en-1-yl group, a pent-4-en-1-yl group, a pent-1-en-2-yl group, a pent-4-en-2-yl group, a 3-methylbut-1-en-1-yl group, a 3-methylbut-2-en-1-yl group, a 3-methylbut-3-en-1-yl group, a hex-1-en-1-yl group, a hex-5-en-1-yl group, a 4-methylpent-3-en-1-yl group and the like.

As used herein "$C_{2-6}$ alkynyl group" refers to a straight or branched alkynyl group of 2-6 carbon atoms having a carbon-carbon triple bond at one or more positions on an alkyl chain. Specifically, there can be mentioned, for example, an ethynyl group, a prop-1-yn-1-yl group, a prop-2-yn-1-yl group, a but-1-yn-1-yl group, a but-3-yn-1-yl group, a 1-methylprop-2-yn-1-yl group, a pent-1-yn-1-yl group, a pent-4-yn-1-yl group, a hex-1-yn-1-yl group, a hex-5-yn-1-yl group and the like.

As used herein "haloalkyl" refers to an alkyl group substituted with one to a maximum number of the same or different halogen atoms. Thus, as "halo $C_{1-6}$ alkyl group", there can be specifically mentioned, for example, a monofluoro methyl group, a difluoromethyl group, a trifluoromethyl group, a monochloromethyl group, a monobromomethyl group, a monoiodomethyl group, a 2,2,2-trifluoroethyl group and the like.

As used herein "$C_{1-6}$ alkoxy group" refers to a group ($C_{1-6}$ alkyloxy group) in which the above "$C_{1-6}$ alkyl group" is bound via an oxygen atom. Specifically there can be mentioned, for example, a methoxy group, an ethoxy group, a n-propoxy group, an isopropoxy group, a n-butoxy group, an isobutoxy group, a sec-butoxy group, a tert-butoxy group, a n-pentoxy group, an isopentoxy group, a neopentoxy group, a 2-methylbutoxy group, a 1-methylbutoxy group, a 1-ethylpropoxy group, a 2,2-dimethylpropoxy group, a n-hexyloxy group, an isohexyloxy group, a 3-methylpentoxy group, a 2-methylpentoxy group, a 1-methylpentoxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 1-ethylbutoxy group, a 2-ethylbutoxy group and the like.

As used herein "$C_{1-6}$ alkoxycarbonyl group" refers to a group in which the above "$C_{1-6}$ alkoxy group" is bound via a carbonyl group. Specifically there can be mentioned, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentoxycarbonyl group, an isopentoxycarbonyl group, a neopentoxycarbonyl group, a 2-methylbutoxycarbonyl group, a 1-methylbutoxycarbonyl group, a 1-ethylpropoxycarbonyl group, a 2,2-dimethylpropoxycarbonyl group, a n-hexyloxycarbonyl group, an isohexyloxycarbonyl group, a 3-methylpentoxycarbonyl group, a 2-methylpentoxycarbonyl group, a 1-methylpentoxycarbonyl group, a 3,3-dimethylbutoxycarbonyl group, a 2,2-dimethylbutoxycarbonyl group, a 1,1-dimethylbutoxycarbonyl group, a 1,2-dimethylbutoxycarbonyl group, a 1,3-dimethylbutoxycarbonyl group, a 2,3-dimethylbutoxycarbonyl group, a 1-ethylbutoxycarbonyl group, a 2-ethylbutoxycarbonyl group and the like.

As used herein "$C_{6-10}$ aryl group" refers to a monocyclic or fused cyclic aryl group of 6-10 carbon atoms. Specifically, for example, a phenyl group, a naphthyl group, an azulenyl group and the like can be mentioned.

As used herein "$C_{1-6}$ alkylthio group" refers to a group in which the above "$C_{1-6}$ alkyl group" is bound via a sulfur atom. Specifically there can be mentioned, for example, a methylthio group, an ethylthio group, a n-propylthio group, an isopropylthio group, a n-butylthio group, an isobutylthio group, a sec-butylthio group, a tert-butylthio group, a n-pentylthio group, an isopentylthio group, a neopentylthio group, a 2-methylbutylthio group, a 1-methylbutylthio group, a 1-ethylpropylthio group, a 2,2-dimethylpropylthio group, a n-hexylthio group, an isohexylthio group, a 3-methylpentylthio group, a 2-methylpentylthio group, a 1-methylpentylthio group, a 3,3-dimethylbutylthio group, a 2,2-dimethylbutylthio group, a 1,1-dimethylbutylthio group, a 1,2-dimethylbutylthio group, a 1,3-dimethylbutylthio group, a 2,3-dimethylbutylthio group, a 1-ethylbutylthio group, a 2-ethylbutylthio group and the like.

As used herein "$C_{1-6}$ alkylsulfinyl group" refers to a group in which the above "$C_{1-6}$ alkyl group" is bound via a sulfinyl group (—S(O)—). Specifically there can be mentioned, for example, a methylsulfinyl group, an ethylsulfinyl group, a n-propylsulfinyl group, an isopropylsulfinyl group, a n-butylsulfinyl group, an isobutylsulfinyl group, a sec-butylsulfinyl group, a tert-butylsulfinyl group, a n-pentylsulfinyl group, an isopentylsulfinyl group, a neopentylsulfinyl group, a 2-methylbutylsulfinyl group, a 1-methylbutylsulfinyl group, a 1-ethylpropylsulfinyl group, a 2,2-dimethylpropylsulfinyl group, a n-hexylsulfinyl group, an isohexylsulfinyl group, a 3-methylpentylsulfinyl group, a 2-methylpentylsulfinyl group, a 1-methylpentylsulfinyl group, a 3,3-dimethylbutylsulfinyl group, a 2,2-dimethylbutylsulfinyl group, a 1,1-dimethylbutylsulfinyl group, a 1,2-dimethylbutylsulfinyl group, a 1,3-dimethylbutylsulfinyl group, a 2,3-dimethylbutylsulfinyl group, a 1-ethylbutylsulfinyl group, a 2-ethylbutylsulfinyl group and the like.

As used herein "sulfonyl group" refers to a "$C_{1-6}$ alkylsulfonyl group" in which an alkyl group is bound via sulfonyl (—$SO_2$—), a "$C_{2-6}$ alkenylsulfonyl group" in which an alkenyl group is bound via sulfonyl, a "halo $C_{1-6}$ alkylsulfonyl group" in which a haloalkyl group is bound via sulfonyl, a "$C_{6-10}$ arylsulfonyl group" in which an aryl group is bound via sulfonyl, an "alkylated $C_{6-10}$ arylsulfonyl group" in which an alkylated aryl group is bound via sulfonyl, a "halogenated $C_{6-10}$ arylsulfonyl group" in which an halogenated aryl group is bound via sulfonyl and the like.

As used herein "$C_{1-6}$ alkylsulfonyl group" refers specifically to, for example, a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a n-pentylsulfonyl group, an isopentylsulfonyl group, a neopentylsulfonyl group, a 2-methylbutylsulfonyl group, a 1-methylbutylsulfonyl group, a 1-ethylpropylsulfonyl group, a 2,2-dimethylpropylsulfonyl group, a n-hexylsulfonyl group, an isohexylsulfonyl group, a 3-methylpentylsulfonyl group, a 2-methylpentylsulfonyl group, a 1-methylpentylsulfonyl group, a 3,3-dimethylbutylsulfonyl group, a 2,2-dimethylbutylsulfonyl group, a 1,1-dimethylbutylsulfonyl group, a 1,2-dimethylbutylsulfonyl group, a 1,3-dimethylbutylsulfonyl group, a 2,3-dimethylbutylsulfonyl group, a 1-ethylbutylsulfonyl group, a 2-ethylbutylsulfonyl group and the like.

As used herein "$C_{2-6}$ alkenylsulfonyl group" refers specifically to, for example, a vinylsulfonyl group, a prop-1-en-1-ylsulfonyl group, a prop-2-en-1-ylsulfonyl group, a prop-1-en-2-ylsulfonyl group, a but-1-en-1-ylsulfonyl group, a but-2-en-1-ylsulfonyl group, a but-3-en-1-ylsulfonyl group, a but-1-en-2-ylsulfonyl group, a but-3-en-2-ylsulfonyl group, a pent-1-en-1-ylsulfonyl group, a pent-2-en-1-ylsulfonyl group, a pent-3-en-1-ylsulfonyl group, a pent-4-en-1-ylsulfonyl group, a pent-1-en-2-ylsulfonyl group, a pent-4-en-2-ylsulfonyl group, a 3-methylbut-1-en-1-ylsulfonyl group, a 3-methylbut-2-en-1-ylsulfonyl group, a 3-methylbut-3-en-1-ylsulfonyl group, a hex-1-en-1-ylsulfonyl group, a hex-5-en-1-ylsulfonyl group, a 4-methylpent-3-en-1-ylsulfonyl group and the like.

As used herein "$C_{1-6}$ haloalkylsulfonyl group" refers specifically to, for example, a monofluoromethylsulfonyl group, a difluoromethylsulfonyl group, a trifluoromethylsulfonyl group, a monochloromethylsulfonyl group, a monobromomethylsulfonyl group, a monoiodomethylsulfonyl group, a 2,2,2-trifluoroethylsulfonyl group and the like.

As used herein "$C_{6-10}$ arylsulfonyl group" refers specifically to, for example, a phenylsulfonyl group, a naphthylsulfonyl group, an azulenylsulfonyl group and the like.

As used herein "alkylated $C_{6-10}$ arylsulfonyl group" refers specifically to, for example, a toluenesulfonyl group, an ethylphenylsulfonyl group, a n-propylphenyl sulfonyl group, an isopropylphenylsulfonyl group, a n-butylphenylsulfonyl group, an isobutylphenylsulfonyl group, a sec-butylphenylsulfonyl group, a tert-butylphenylsulfonyl group, a n-pentylphenylsulfonyl group, an isopentylphenylsulfonyl group, a neopentylphenylsulfonyl group, a 2-methylbutylphenylsulfonyl group, a 1-methyl butylphenylsulfonyl group, a 1-ethylpropylphenylsulfonyl group, a 2,2-dimethylpropylphenylsulfonyl group, a n-hexylphenylsulfonyl group, an isohexylphenylsulfonyl group, a 3-methylpentylphenylsulfonyl group, a 2-methyl pentylphenylsulfonyl group, a 1-methylpentylphenyl sulfonyl group, a 3,3-dimethylbutylphenylsulfonyl group, a 2,2-dimethylbutylphenylsulfonyl group, a 1,1-dimethyl butylphenyl group, a 1,2-dimethylbutylphenyl group, a 1,3-dimethylbutylphenyl group, a 2,3-dimethylbutylphenyl sulfonyl group, a 1-ethylbutylphenylsulfonyl group, a 2-ethylbutylphenylsulfonyl group, a xylylsulfonyl group, a mesitylsulfonyl group, a cumenylsulfonyl group, a methyl naphthylsulfonyl group, a dimethylnaphthylsulfonyl group, a tert-butylnaphthylsulfonyl group, a methylazulenyl sulfonyl group, an ethylazulenylsulfonyl group, a n-propylazulenylsulfonyl group, an isopropylazulenyl sulfonyl group, a dimethylazulenylsulfonyl group, a trimethylazulenylsulfonyl group, a dimethylisopropyl azulenylsulfonyl group and the like.

As used herein "halogenated $C_{6-10}$ arylsulfonyl group" refers specifically to, for example, a 4-fluorophenylsulfonyl group, a 4-chlorophenylsulfonyl group, a 4-bromophenylsulfonyl group, a 4-iodophenyl sulfonyl group, a 3,4-difluorophenylsulfonyl group, a 3,4-dichlorophenylsulfonyl group, a 3,4,5-trifluoro phenylsulfonyl group and the like.

As used herein "5-11-membered heterocyclic group" refers to a 5-7-membered saturated or unsaturated heterocyclic ring containing 1-4 heteroatoms selected from nitrogen atoms, oxygen atoms and sulfur atoms in addition to carbon atoms as ring-constituting atoms, or a fused heterocyclic ring in which such a heterocyclic ring and a benzene ring have been fused. As a 5-7-membered saturated heterocyclic ring, there can be mentioned, for example, a pyrrolidinyl group (pyrrolidin-1-yl group etc.), a pyrazolidinyl group, an imidazolidinyl group, an oxazolidinyl group, a thiazolidinyl group, an oxolanyl group (an oxolan-4-yl group etc.), a morpholinyl group (a morpholino group etc.), a piperazinyl group (a piperazin-1-yl group etc.), a piperidinyl group (a piperidino group, a piperidin-3-yl group, a piperidin-4-yl group etc.), a hexahydro-1H-1,4-diazepinyl group (a hexahydro-1H-1,4-diazepin-1-yl group etc.), a 1,1-dioxoisothiazolidinyl group (a 1,1-dioxoisothiazolidin-2-yl group etc.) and the like. As a 5-7-membered unsaturated heterocyclic ring, there can be mentioned, for example, a furyl group, a thienyl group, a pyrrolyl group, an imidazolyl group, an oxazolyl group, a thiazolyl group, a pyrazolyl group (a pyrazol-1-yl group etc.), an isoxazolyl group, an isothiazolyl group, an oxadiazolyl group, a thiadiazolyl group, a 1,2,3-triazolyl group, a 1,2,4-triazolyl group, a tetrazolyl group, a pyridyl group, a pyrazinyl group, a pyrimidinyl group (a pyrimidin-2-yl group etc.), a pyridazinyl group and the like. As a fused heterocyclic ring, there can be mentioned, for example, a benzofuranyl group, an isobenzofuranyl group, a benzothiophenyl group, an indolyl group, an indolinyl group, an isoindolyl group, an indazolyl group, a benzoimidazolyl group, a benzoxazolyl group, a benzoisoxazolyl group, a benzothiazolyl group, a benzoisothiazolyl group, a benzotriazolyl group, a chromenyl group, a quinolyl group, an isoquinolyl group, a 1,2,3,4-tetrahydroquinolyl group, a 1,2,3,4-tetrahydroisoquinolyl group, a cinnolinyl group, a quinazolinyl group, a quinoxalinyl group, a phthalazinyl group, a naphthyridinyl group, a purinyl group, a pteridinyl group, a carbazolyl group, a carbolinyl group, an acridinyl group, a phenoxadinyl group, a phenothiazinyl group, a phenazinyl group and the like.

As used herein "acyl group" refers to a formyl group, an "alkylcarbonyl group" in which a linear or branched alkyl group is bound via carbonyl (C=O), a "cycloalkylcarbonyl group" in which a cyclic alkyl group is bound via carbonyl (C=O), an "arylcarbonyl group" in which an aryl group is bound via carbonyl (C=O), or a "heterocyclic carbonyl group" in which a saturated or unsaturated heterocyclic ring is bound via carbonyl (C=O). As "alkylcarbonyl group" there can be specifically mentioned, for example, a "$C_{1-6}$ alkylcarbonyl group" such as an acetyl group, a propionyl group, a butylyl group, an isobutylyl group, a valeryl group, an isovaleryl group and a pivaloyl group. As "cycloalkylcarbonyl group", there can be specifically mentioned, for example, a "$C_{3-8}$ cycloalkylcarbonyl group" such as a cyclopropylcarbonyl group, a cyclobutylcarbonyl group, a cyclopentylcarbonyl group and a cyclohexylcarbonyl group. As "arylcarbonyl group", there can be specifically mentioned, for example, a "$C_{6-10}$ arylcarbonyl group" such as a benzoyl group, a naphthoyl group and an azulenylcarbonyl group. As "heterocyclic carbonyl group", there can be mentioned a "5-14-membered heterocyclic carbonyl group" such as a pyrrolidinylcarbonyl group, an imidazolidinylcarbonyl group, an oxazolidinylcarbonyl group, a thiazolidinylcarbonyl group, an oxolanylcarbonyl group, a morpholinylcarbonyl group (morpholinocarbonyl group etc.), a piperazinylcarbonyl group, a piperidinylcarbonyl group, a hexahydro-1H-1,4-diazepinylcarbonyl group, a furoyl group, a thenoyl group, a pyrrolylcarbonyl group, a pyridylcarbonyl group (nicotinoyl group etc.), a pyrazinylcarbonyl group, a pyrimidinylcarbonyl group, a pyridazinylcarbonyl group, an imidazolylcarbonyl group, a pyrazolylcarbonyl group, a thiazolylcarbonyl group, an oxazolylcarbonyl group, an isoxazolylcarbonyl group, a thiadiazolylcarbonyl group, a 1,2,3-triazolylcarbonyl group, a 1,2,4-triazolylcarbonyl group, a tetrazolyl carbonyl group, a benzofuranylcarbonyl group, an isobenzofuranylcarbonyl group, a benzothiophenylcarbonyl group, an indolylcarbonyl group, an indolynylcarbonyl group, an isoindolylcarbonyl group, an indazolylcarbonyl group, a benzoimidazolylcarbonyl group, a benzoxazolyl carbonyl group, a benzoisoxazolylcarbonyl group, a benzothiazolylcarbonyl group, a benzoisothiazolylcarbonyl group, a benzotriazolylcarbonyl group, a chromenyl carbonyl group, a quinolylcarbonyl group, an isoquinolylcarbonyl group, a 1,2,3,4-tetrahydroquinolyl carbonyl group, a 1,2,3,4-tetrahydroisoquinolylcarbonyl group, a cinnolinylcarbonyl group, a quinazolinylcarbonyl group, a quinoxalinylcarbonyl group, a phthalazinyl carbonyl group, a naphthyridinylcarbonyl group, a purinylcarbonyl group, a pteridinylcarbonyl group, a carbazolylcarbonyl group, a carbolinylcarbonyl group, an acridinylcarbonyl group, a phenoxadinylcarbonyl group, a phenothiadinylcarbonyl group and a phenadinylcarbonyl group.

As used herein "acylamino group" refers to an "alkylcarbonylamino group", a "cycloalkylcarbonylamino group", an "arylcarbonylamino group" and a "heterocyclic carbonyl amino group" in which the above acyl group is bound via an amino group. Specifically there can be mentioned, for example, an acetylamino group, a cyclohexylcarbonylamino group, a benzoylamino group, a pyrrolidinylcarbonylamino group, an oxolanylcarbonylamino group, a morpholinocarbonylamino group, a piperazinylcarbonylamino group, a piperidinylcarbonyl amino group, a hexahydro-1H-1,4-diazepinylcarbonylamino group and the like.

As used herein "mono($C_{1-6}$ alkyl)amino group" refers to a group in which above "$C_{1-6}$ alkyl group" is bound via an amino group (—NH—). Specifically there can be mentioned, for example, a methylamino group, an ethylamino group, a n-propylamino group, an isopropyl amino group, a n-butylamino group, a sec-butylamino group, a tert-butylamino group, a n-pentylamino group, an isopentylamino group, a neopentylamino group, a 2-methyl butylamino group, a 1-methylbutylamino group, a 1-ethyl propylamino group, a 2,2-dimethylpropylamino group, a n-hexylamino group, an isohexylamino group, a 3-methyl pentylamino group, a 2-methylpentylamino group, 1-methylpentylamino group, a 3,3-dimethylbutylamino group, a 2,2-dimethylbutylamino group, a 1,1-dimethylbutylamino group, a 1,2-dimethylbutylamino group, a 1,3-dimethyl butylamino group, a 2,3-dimethylbutylamino group, a 1-ethylbutylamino group, a 2-ethylbutylamino group and the like.

As used herein "di ($C_{1-6}$ alkyl)amino group" refers to a group in which two "$C_{1-6}$ alkyl groups" described above are bound to one nitrogen atom. Specifically there can be mentioned, for example, a dimethylamino group, a methyl ethylamino group, a diethylamino group, a methyl-n-propyl amino group, an ethyl-n-propylamino group, a di-n-propylamino group, a methylisopropylamino group, an ethylisopropylamino group, a diisopropylamino group, a methyl-n-butylamino group, an ethyl-n-butylamino group, a n-propyl-n-butylamino group, a di-n-butylamino group, a di-sec-butylamino group, a di-tert-butylamino group, a dibenzylamino group, a dihexylamino group and the like.

As used herein, as "substituent group" in "optionally substituted $C_{1-6}$ alkyl group", "optionally substituted $C_{3-8}$ cycloalkyl group", "optionally substituted acyl group", "optionally substituted 5-11-membered heterocyclic group", "optionally substituted sulfamoyl group", "optionally substituted $C_{1-6}$ alkylsulfonyl group" and the like, there can be mentioned a halogen atom, an optionally substituted or unsubstituted $C_{1-6}$ alkyl group, an optionally substituted or unsubstituted $C_{1-6}$ alkenyl group, an optionally substituted or unsubstituted $C_{1-6}$ alkynyl group, a $C_{1-6}$ alkoxy group, a halo $C_{1-6}$ alkoxy group, a hydroxy group, a cyano group, an optionally substituted or unsubstituted $C_{6-10}$ aryl group, an optionally substituted or unsubstituted 5-11-membered heterocyclic group, a $C_{1-6}$ alkylsulfonyl group, an amino group, a mono($C_{1-6}$ alkyl)amino group, a di ($C_{1-6}$ alkyl)amino group, a $C_{1-6}$ alkylsulfonylamino group, a $C_{1-6}$ alkenylsulfonylamino group, an optionally substituted or unsubstituted acylamino group, a $C_{1-6}$ alkoxycarbonyl group, a (5-11-membered heterocyclic)-carbonyl group, an optionally substituted or unsubstituted carbamoyl group, an oxo group and the like. The number of substituents is not specifically limited and may be one to the maximum substitutable number can be permitted. When there are two or more substituents, they may be the same or different.

For groups that are not defined herein, commonly used definitions are used.

Preferred embodiments of the present invention include the following:

As the $C_{1-6}$ alkyl group in $R^3$ in the general formula (1), a $C_{1-4}$ alkyl group is preferred, and a methyl group is more preferred.

As the $C_{1-6}$ alkyl group in $R^4$ and $R^5$ in the general formula (1), a $C_{1-4}$ alkyl group is preferred, and a methyl group and an ethyl group are more preferred.

As the $C_{1-6}$ alkoxy group in $R^4$ and $R^5$ in the general formula (1), a $C_{1-4}$ alkoxy group is preferred, and a methoxy group is more preferred.

As the $C_{1-6}$ alkyl group in $R^6$ in the general formula (1), a $C_{1-4}$ alkyl group is preferred, and a methyl group is more preferred.

As the acyl group in $R^6$ in the general formula (1), a $C_{1-6}$ alkylcarbonyl group and a 5-7-membered heterocyclic carbonyl group are preferred, and an acetyl group and a morpholino carbonyl group are more preferred.

As the halogen atom in $R^7$, $R^8$, $R^9$, $R^{10}$ and $R^{11}$ in the general formula (1), a fluorine atom, a chlorine atom and a bromine atom are preferred, with a chlorine atom and a bromine atom being more preferred.

As the alkyl group in "an optionally substituted $C_{1-6}$ alkyl group" in $R^7$, $R^8$, $R^9$, $R^{10}$ and $R^{11}$ in the general formula (1), a $C_{1-4}$ alkyl group is preferred, and a methyl group, an ethyl group and a n-propyl group are more preferred. As the substituent of the alkyl group, a hydroxy group, an amino group, an azide group, a mono($C_{1-6}$ alkyl)amino group, a di ($C_{1-6}$ alkyl)amino group, a halogen atom, a $C_{1-6}$ alkylsulfonyloxy group, a $C_{1-6}$ alkylsulfonyl amino group and a 5-11-membered heterocyclic group are preferred, a hydroxy group, an amino group, an azide group, a di ($C_{1-4}$ alkyl)amino group, a halogen atom, a $C_{1-4}$ alkylsulfonyloxy group, a $C_{1-4}$ alkylsulfonylamino group, a 5-7-membered unsaturated heterocyclic group are more preferred, and a hydroxy group, an amino group, an azide group, a dimethylamino group, a methylsulfonyloxy group, a methylsulfonylamino group and a morpholino group are even more preferred.

As the $C_{3-8}$ cycloalkyl group in "an optionally substituted $C_{3-8}$ cycloalkyl group" in $R^7$, $R^8$, $R^9$, $R^{10}$ and $R^{11}$ in the general formula (1), a $C_{3-8}$ cycloalkyl group optionally substituted with a $C_{1-6}$ alkylsulfonylamino group is preferred, a cycloalkyl group optionally substituted with a $C_{1-6}$ alkylsulfonylamino group is more preferred, and a cyclohexyl group and a methylsulfonyl aminocyclohexyl group are most preferred.

As the $C_{1-6}$ alkoxycarbonyl group in $R^7$, $R^8$, $R^9$, $R^{10}$ and $R^{11}$ in the general formula (1), a $C_{1-4}$ alkoxycarbonyl group is preferred, and a methoxycarbonyl group and an ethoxycarbonyl group are more preferred.

As the optionally substituted acyl group in $R^7$, $R^8$, $R^9$, $R^{10}$ and $R^{11}$ in the general formula (1), a $C_{1-6}$ alkylcarbonyl group is preferred, and an acetyl group, an isobutylyl group, a cyclopropylcarbonyl group and a trifluoroacetyl group are more preferred.

As the $C_{1-6}$ alkylthio group in $R^7$, $R^8$, $R^9$, $R^{10}$ and $R^{11}$ in the general formula (1), a $C_{1-4}$ alkylthio group is preferred, and a methylthio group is more preferred.

As the $C_{1-6}$ alkylsulfinyl group in $R^7$, $R^8$, $R^9$, $R^{10}$ and $R^{11}$ in the general formula (1), a $C_{1-4}$ alkylsulfinyl group is preferred, and a methylsulfinyl group is more preferred.

As the $C_{1-6}$ alkylsulfonyl group in $R^7$, $R^8$, $R^9$, $R^{10}$ and $R^{11}$ in the general formula (1), a $C_{1-4}$ alkylsulfonyl group is preferred, and a methylsulfonyl group is more preferred.

As the (5-11-membered heterocyclic)-sulfonyl group in $R^7$, $R^8$, $R^9$, $R^{10}$ and $R^{11}$ in the general formula (1), a (5-7-membered saturated heterocyclic)-sulfonyl group is preferred, and a morpholylsulfonyl group is more preferred.

As the optionally substituted 5-11-membered heterocyclic group in $R^7$, $R^8$, $R^9$, $R^{10}$ and $R^{11}$ in the general formula (1), an optionally substituted 5-7-membered heterocyclic saturated group is preferred, and an optionally substituted morpholinyl group, an optionally substituted piperazinyl group, an optionally substituted piperidinyl group, an optionally substituted hexahydro-1H-1,4-diazepinyl group, an optionally substituted pyrrolidinyl group, a 1,1-dioxoisothiazolidinyl group, an oxolanyl group and an optionally substituted pyrrolidinyl group are more preferred. As the optionally substituted morpholinyl group, a morpholino group (4-morpholinyl group), a 3-methylmorpholino group and a 2,6-diethyl morpholino group are preferred. As the piperazinyl group, a 1-piperazinyl group is preferred. As the substituent group for the piperazinyl group, an optionally substituted $C_{1-6}$ alkyl group, an acyl group, an optionally substituted 5-11-membered heterocyclic group, an optionally substituted carbamoyl group, a $C_{1-6}$ alkylsulfonyl group and a $C_{1-6}$ alkoxycarbonyl group are preferred. As the substituent group for the piperidyl group, a piperidino group (1-piperidyl group) and a 4-piperidyl group are preferred. As the substituent group for the piperidyl group, an optionally substituted $C_{1-6}$ alkyl group, an acyl group, an optionally substituted carbamoyl group, a $C_{1-6}$ alkoxy group, a hydroxy group, an amino group, an oxo group, a 5-11-membered heterocyclic group, a $C_{1-6}$ alkoxycarbonyl group, a $C_{1-6}$ alkylsulfonyl group, a $C_{1-6}$ alkylsulfonylamino group and an optionally substituted $C_{1-6}$ alkylcarbonylamino group are preferred. As the hexahydro-1H-1,4-diazepinyl group, a hexahydro-1H-1,4-diazepin-1-yl group is preferred. As the substituent group for the hexahydro-1H-1,4-diazepinyl group, an optionally substituted $C_{1-6}$ alkyl group, an optionally substituted acyl group and a $C_{1-6}$ alkylsulfonyl group are preferred. As the oxolanyl group, a 4-oxolanyl group is preferred. As the pyrrolidinyl group, a pyrrolidin-1-yl group is preferred. As the substituent group for the pyrrolidinyl group, a $C_{1-6}$ alkyl group optionally substituted with a $C_{1-6}$ alkyl group is preferred.

As the optionally substituted sulfamoyl group in $R^7$, $R^8$, $R^9$, $R^{10}$ and $R^{11}$ in the general formula (1), an unsubstituted sulfamoyl group, a sulfamoyl group optionally substituted with a $C_{1-6}$ alkyl group and a sulfamoyl group optionally substituted with a ($C_{1-6}$ alkoxy) $C_{1-6}$ alkyl group are preferred, and a N-methylsulfamoyl group and a N-(2-methoxyethyl)sulfamoyl group are more preferred.

As the sulfonyl group in $R^{12}$ in the general formula (1), an alkylated $C_{6-10}$ arylsulfonyl group is preferred, and a toluenesulfonyl group is more preferred.

As the halogen atom in $R^{13}$, $R^{14}$, $R^{15}$, $R^{16}$, $R^{17}$, $R^{18}$, $R^{19}$ and $R^{20}$ in the general formula (1), a chlorine atom is preferred.

As the optionally substituted $C_{1-6}$ alkyl group in $R^{21}$ in the general formula (1), an optionally substituted $C_{1-4}$ alkyl group is preferred, and a methyl group, an ethyl group, a 2-methoxyethyl group, a 2-hydroxyethyl group, a morpholinoethyl group and a trifluoromethyl group are more preferred.

As the optionally substituted 5-11-membered heterocyclic group in $R^{21}$ in the general formula (1), a 5-7-membered saturated heterocyclic group optionally substituted with a $C_{1-6}$ alkyl group is preferred, and a 1-methylpiperidin-4-yl group is more preferred.

As the optionally substituted $C_{1-6}$ alkyl group in $R^{22}$ and $R^{23}$ in the general formula (1), an optionally substituted $C_{1-4}$ alkyl group is preferred, and an ethyl group and a n-propyl group are more preferred. As the substituent group for the alkyl group, a hydroxy group, an amino group, a cyano group, a $C_{1-6}$ alkoxy group, a $C_{1-6}$ acylamino group, a di$C_{1-6}$ alkylamino group, a $C_{1-6}$ alkylsulfonylamino group and a 5-7-membered saturated heterocyclic group are preferred, and a hydroxy group, an amino group, a cyano group, a methoxy group, a 2-trifluoroacetylamino group, a diethylamino group, a methylsulfonylamino group and a morpholino group are more preferred.

As the optionally substituted $C_{1-6}$ alkylsulfonyl group in $R^{22}$ and $R^{23}$ in the general formula (1), a $C_{1-4}$ alkylsulfonyl group is preferred, and a methanesulfonyl group, a n-propylsulfonyl group, an isopropylsulfonyl group are more preferred. As the substituent group for the alkylsulfonyl group, an amino group, a halogen atom and a di($C_{1-6}$ alkyl)amino group are preferred. As the di ($C_{1-6}$ alkyl)amino group, a di ($C_{1-4}$ alkyl)amino group is more preferred, and a diethylamino group is most preferred.

As the $C_{2-6}$ alkenylsulfonyl group in $R^{22}$ and $R^{23}$ in the general formula (1), a vinylsulfonyl group is preferred.

As the optionally substituted 5-11-membered heterocyclic group in $R^{22}$ and $R^{23}$ in the general formula (1), an optionally substituted 5-7-membered saturated heterocyclic group is preferred, and an optionally substituted 4-piperidinyl group is more preferred, and a piperidin-4-yl group, a 1-(diethylcarbamoyl)piperidin-4-yl group, a 1-(N-isopropylcarbamoyl)piperidin-4-yl group and a 1-(N-t-butoxycarbonyl)piperidin-4-yl group are more preferred.

In the general formula (1), $R^{24}$ is preferably a hydrogen atom.

As the optionally substituted $C_{1-6}$ alkyl group in $R^{25}$ in the general formula (1), an $C_{1-4}$ alkyl group is preferred, and a methyl group is preferred.

As the mono ($C_{1-6}$ alkyl)amino group in $R^{25}$ in the general formula (1), a mono($C_{1-4}$ alkyl)amino group is preferred, and an isopropylamino group is more preferred.

As the di ($C_{1-6}$ alkyl)amino group in $R^{25}$ in the general formula (1), a di($C_{1-4}$ alkyl)amino group is preferred, and a diethylamino group is more preferred.

As the optionally substituted 5-11-membered heterocyclic group in $R^{25}$ in the general formula (1), an optionally substituted piperidinyl group and an optionally substituted pyrrolidinyl group are preferred, and a piperidinyl group optionally substituted with a $C_{1-6}$ alkoxycarbonyl group is more preferred, a pyrrolidinyl group optionally substituted with a $C_{1-4}$ alkoxycarbonyl group is even more preferred, and a piperidin-3-yl group, a piperidin-4-yl group, a 1-(tert-butoxycarbonyl)piperidin-3-yl group, a 1-(tert-butoxycarbonyl)piperidin-4-yl group, a pyrrolidin-2-yl group and a 1-(tert-butoxycarbonyl)pyrrolidin-2-yl group are most preferred.

As the $C_{1-6}$ alkyl group in $R^{26}$ in the general formula (1), a $C_{1-4}$ alkyl group is preferred, and a methyl group is more preferred.

As the $C_{6-10}$ aryl alkyl group in $R^{26}$ in the general formula (1), a phenyl $C_{1-4}$ alkyl group is preferred, and a benzyl group is more preferred.

As the $C_{1-6}$ alkylcarbonyl group in $R^{26}$ in the general formula (1), a $C_{1-4}$ alkylcarbonyl group is preferred, and an acetyl group is more preferred.

As the $C_{1-6}$ alkyl group in $R^{27}$ in the general formula (1), a $C_{1-4}$ alkyl group is preferred, and a methyl group is more preferred.

As the halogen atom in $R^{28}$, $R^{29}$, $R^{30}$, $R^{31}$ and $R^{32}$ in the general formula (1), a fluorine atom and a chlorine atom are preferred.

As the $C_{1-6}$ alkyl group in $R^{28}$, $R^{29}$, $R^{30}$, $R^{31}$ and $R^{32}$ in the general formula (1), a $C_{1-4}$ alkyl group is more preferred, and a methyl group and an ethyl group are more preferred.

As the $C_{1-6}$ alkyl group in $R^{28}$, $R^{29}$, $R^{30}$, $R^{31}$ and $R^{32}$ in the general formula (1), a halo $C_{1-4}$ alkyl group is more preferred and a trifluoromethyl group is most preferred.

As the $C_{1-6}$ alkoxy group in $R^{28}$, $R^{29}$, $R^{30}$, $R^{31}$ and $R^{32}$ in the general formula (1), a $C_{1-4}$ alkoxy group is preferred and a methoxy group is more preferred.

As the halo alkoxycarbonyl group in $R^{28}$, $R^{29}$, $R^{30}$, $R^{31}$ and $R^{32}$ in the general formula (1), a $C_{1-4}$ alkoxy group is preferred and a methoxycarbonyl group and an ethoxycarbonyl group are more preferred.

As the piperazinyl group optionally substituted a $C_{1-6}$ alkyl group in $R^{28}$, $R^{29}$, $R^{30}$, $R^{31}$ and $R^{32}$ in the general formula (1), a piperazinyl group optionally substituted a $C_{1-4}$ alkyl group is preferred and a 4-methylpiperazinyl group is more preferred.

As the di ($C_{1-6}$ alkyl)amino group in $R^{28}$, $R^{29}$, $R^{30}$, $R^{31}$ and $R^{32}$ in the general formula (1), a di ($C_{1-4}$ alkyl)amino group is preferred and a dimethylamino group is more preferred.

As the acylamino group in $R^{28}$, $R^{29}$, $R^{30}$, $R^{31}$ and $R^{32}$ in the general formula (1), a $C_{1-6}$ alkylcarbonylamino group is preferred, a $C_{1-4}$ alkylcarbonylamino group is more preferred, and an acetylamino group is most preferred.

As the $C_{1-6}$ alkyl group in $R^{33}$ in the general formula (1), a $C_{1-4}$ alkyl group is preferred, and a methyl group is more preferred.

As the $C_{1-6}$ alkyl group in $R^{34}$ in the general formula (1), a $C_{1-4}$ alkyl group is preferred, and a methyl group is more preferred.

As the $C_{1-6}$ alkyl group in $R^{35}$ in the general formula (1), a $C_{1-4}$ alkyl group is preferred, and a methyl group is more preferred.

As the $C_{1-6}$ alkyl group in $R^{36}$ and $R^{37}$ in the general formula (1), a $C_{1-4}$ alkyl group is preferred, and a methyl group is more preferred.

As further preferred embodiments of the general formula (1), the following combinations may be mentioned.

A pyridine-3-carboxyamide derivative represented by the general formula (1) [wherein $R^{28}$, $R^{29}$, $R^{30}$, $R^{31}$ and $R^{32}$, which may be the same or different, are selected from the group consisting of a hydrogen atom, a halogen atom, a $C_{1-6}$ alkyl group, a halo $C_{1-6}$ alkyl group, a $C_{1-6}$ alkoxy group, a carbamoyl group and a nitro group, and $R^7$, $R^8$, $R^9$, $R^{10}$ and $R^{11}$, which may be the same or different, represent a hydrogen atom, a halogen atom, an optionally substituted $C_{1-6}$ alkyl group, a cyano group, an optionally substituted acyl group, a carboxyl group, an optionally substituted 5-11-membered heterocyclic group, an optionally substituted sulfamoyl group, O—$R^{21}$ (wherein, $R^{21}$ represents an optionally substituted $C_{1-6}$ alkyl group, or a piperazinyl group optionally substituted with a $C_{1-6}$ alkyl group), —N$R^{22}R^{23}$ (wherein, $R^{22}$ and $R^{23}$, which may be the same or different, represent a hydrogen atom, an optionally substituted $C_{1-6}$ alkyl group, an optionally substituted $C_{1-6}$ alkylsulfonyl group or an optionally substituted 5-11-membered heterocyclic group), —NHCOR$^{25}$ (wherein, $R^{25}$ represents an amino group, a ($C_{1-6}$ alkyl)amino group, a di($C_{1-6}$ alkyl)amino group or an optionally substituted 5-11-membered heterocyclic group), and $R^3$, $R^4$, $R^5$, $R^{20}$ and $R^{33}$ represent a hydrogen atom].

As preferred embodiments of the general formula (1), the following compounds may be mentioned.

4-(benzylamino)-6-({4-[(1-methylpiperidin-4-yl)oxy]phenyl}amino)pyridine-3-carboxyamide, 4-(benzylamino)-6-({4-[4-(2-hydroxyethyl)piperidino]phenyl}amino)pyridine-3-carboxyamide, 4-(benzylamino)-6-[(4-{4-[2-(diethylamino)ethyl]piperidino}phenyl)amino]pyridine-3-carboxyamide, 4-(benzylamino)-6-({4-[4-(2-cyanoethyl)piperidino]phenyl}amino)pyridine-3-carboxyamide, 6-[(4-aminophenyl)amino]-4-(benzylamino)pyridine-3-carboxyamide, 4-(benzylamino)-6-({4-[(2-morpholinoethyl)amino]phenyl}amino)pyridine-3-carboxyamide, 4-(benzylamino)-6-({4-[methyl(2-morpholinoethyl)amino]phenyl}amino)pyridine-3-carboxyamide, 4-(benzylamino)-6-[(4-morpholinophenyl)amino]pyridine-3-carboxyamide, 4-[(2-methoxybenzyl)amino]-6-[(4-morpholinophenyl)amino]pyridine-3-carboxyamide, 4-[(2-methylbenzyl)amino]-6-[(4-morpholinophenyl)amino]pyridine-3-carboxyamide, 4-[(3-methylbenzyl)amino]-6-[(4-morpholinophenyl)amino]pyridine-3-carboxyamide, 4-[(2-chlorobenzyl)amino]-6-[(4-morpholinophenyl)amino]pyridine-3-carboxyamide,
4-[(3-chlorobenzyl)amino]-6-[(4-morpholinophenyl)amino]pyridine-3-carboxyamide,
4-[(2,3-difluorobenzyl)amino]-6-[(4-morpholinophenyl)amino]pyridine-3-carboxyamide,
4-[(2,5-difluorobenzyl)amino]-6-[(4-morpholinophenyl)amino]pyridine-3-carboxyamide,
4-[(2,6-difluorobenzyl)amino]-6-[(4-morpholinophenyl)amino]pyridine-3-carboxyamide,
6-[(4-morpholinophenyl)amino]-4-{[3-fluoro-5-(trifluoromethyl)benzyl]amino}pyridine-3-carboxyamide,
4-[(5-fluoro-2-methoxybenzyl)amino]-6-[(4-morpholinophenyl)amino]pyridine-3-carboxyamide,
4-[(3-fluoro-2-methylbenzyl)amino]-6-[(4-morpholinophenyl)amino]pyridine-3-carboxyamide,
6-[(4-morpholinophenyl)amino]-4-[(3-nitrobenzyl)amino]pyridine-3-carboxyamide,
4-[(3-carbamoylbenzyl)amino]-6-[(4-morpholinophenyl)amino]pyridine-3-carboxyamide,
6-[(3-cyano-4-morpholinophenyl)amino]-4-[(3,5-difluorobenzyl)amino]pyridine-3-carboxyamide,
4-[(3,5-difluorobenzyl)amino]-6-[(3-methyl-4-morpholinophenyl)amino]pyridine-3-carboxyamide,
6-[(3-chloro-4-morpholinophenyl)amino]-4-[(3,5-difluorobenzyl)amino]pyridine-3-carboxyamide,
4-[(3,5-difluorobenzyl)amino]-6-[(3-methoxy-4-morpholinophenyl)amino]pyridine-3-carboxyamide,
4-[(3,5-difluorobenzyl)amino]-6-[(3-morpholinophenyl)amino]pyridine-3-carboxyamide,
4-(benzylamino)-6-({4-[(3S)-3-methylmorpholino]phenyl}amino)pyridine-3-carboxyamide,
4-[(2,3-difluorobenzyl)amino]-6-({4-[(3R,5S)-3,5-dimethylpiperazin-1-yl]phenyl}amino)pyridine-3-carboxyamide,
4-[(3,5-difluorobenzyl)amino]-6-({4-[(3R,5S)-3,5-dimethylpiperazin-1-yl]phenyl}amino)pyridine-3-carboxyamide,
4-[(2,5-difluorobenzyl)amino]-6-({4-[(3R,5S)-3,5-dimethylpiperazin-1-yl]phenyl}amino)pyridine-3-carboxyamide,
4-[(2,5-difluorobenzyl)amino]-6-({3-[(3R,5S)-3,5-dimethylpiperazin-1-yl]phenyl}amino)pyridine-3-carboxyamide,
4-(benzylamino)-6-{[4-(4-methylpiperazin-1-yl)phenyl]amino}pyridine-3-carboxyamide,
4-(benzylamino)-6-({4-[4-(propan-2-yl)piperazin-1-yl]phenyl}amino)pyridine-3-carboxyamide,
4-[(2-methoxybenzyl)amino]-6-({4-[4-(propan-2-yl)piperazin-1-yl]phenyl}amino)pyridine-3-carboxyamide,
4-[(2,3-difluorobenzyl)amino]-6-({4-[4-(propan-2-yl)piperazin-1-yl]phenyl}amino)pyridine-3-carboxyamide,
4-[(3,5-difluorobenzyl)amino]-6-({4-[4-(propan-2-yl)piperazin-1-yl]phenyl}amino)pyridine-3-carboxyamide,
4-[(3,5-difluorobenzyl)amino]-6-({3-[4-(propan-2-yl)piperazin-1-yl]phenyl}amino)pyridine-3-carboxyamide,
4-[(3,5-difluorobenzyl)amino]-6-{[4-({2-[(methylsulfonyl)amino]ethyl}amino)phenyl]amino}pyridine-3-carboxyamide,
4-[(3-nitrobenzyl)amino]-6-({4-[(methylsulfonyl)amino]phenyl}amino)pyridine-3-carboxyamide,
4-[(3,5-difluorobenzyl)amino]-6-({4-[(propylsulfonyl)amino]phenyl}amino)pyridine-3-carboxyamide,
4-(benzylamino)-6-({4-[(propan-2-ylsulfonyl)amino]phenyl}amino)pyridine-3-carboxyamide,
4-[(3,5-difluorobenzyl)amino]-6-({3-[(methylsulfonyl)amino]phenyl}amino)pyridine-3-carboxyamide,
4-[(3,5-difluorobenzyl)amino]-6-({3-[(propan-2-ylsulfonyl)amino]phenyl}amino)pyridine-3-carboxyamide,
4-[(3,5-difluorobenzyl)amino]-6-({4-[4-(methylsulfonyl)piperidin-1-yl]phenyl}amino)pyridine-3-carboxyamide,
4-[(2,6-difluorobenzyl)amino]-6-({4-[4-(methylsulfonyl)piperidin-1-yl]phenyl}amino)pyridine-3-carboxyamide,
4-[(3,5-difluorobenzyl)amino]-6-({3-[4-(propan-2-ylsulfonyl)piperazin-1-yl]phenyl}amino)pyridine-3-carboxyamide,
4-(benzylamino)-6-[(4-{4-[(2-hydroxy)carbamoyl]piperidino}phenyl)amino]pyridine-3-carboxyamide,
4-[(2,3-difluorobenzyl)amino]-6-({4-[4-(2-hydroxyethyl)piperidino]phenyl}amino)pyridine-3-carboxyamide,
6-({4-[4-(2-hydroxyethyl)piperidino]phenyl}amino)-4-[(3-nitrobenzyl)amino]pyridine-3-carboxyamide,
4-[(2-methylbenzyl)amino]-6-{[4-(4-hydroxypiperidino)phenyl]amino}pyridine-3-carboxyamide,
4-[(2-chlorobenzyl)amino]-6-{[4-(4-hydroxypiperidino)phenyl]amino}pyridine-3-carboxyamide,
4-[(2,3-difluorobenzyl)amino]-6-{[4-(4-hydroxypiperidino)phenyl]amino}pyridine-3-carboxyamide,
4-[(2,5-difluorobenzyl)amino]-6-{[4-(4-hydroxypiperidino)phenyl]amino}pyridine-3-carboxyamide,
4-[(3,5-difluorobenzyl)amino]-6-{[4-(4-methoxypiperidino)phenyl]amino}pyridine-3-carboxyamide,
4-[(3,5-difluorobenzyl)amino]-6-{[4-(4-hydroxypiperidino)phenyl]amino}pyridine-3-carboxyamide,
4-[(3,5-difluorobenzyl)amino]-6-{[4-(4-oxopiperidino)phenyl]amino}pyridine-3-carboxyamide,
6-{[4-(3-aminopropyl)phenyl]amino}-4-[(3,5-difluorobenzyl)amino]pyridine-3-carboxyamide,
4-[(3,5-difluorobenzyl)amino]-6-[(4-{3-[(methanesulfonyl)amino]propyl}phenyl)amino]pyridine-3-carboxyamide,
4-(benzylamino)-6-{[4-piperazin-1-yl]phenyl}amino) pyridine-3-carboxyamide,
4-[(3,5-difluorobenzyl)amino]-6-{[4-(piperazin-1-yl)phenyl]amino}pyridine-3-carboxyamide,
4-[(2,5-difluorobenzyl)amino]-6-{[4-(piperazin-1-yl)phenyl]amino}pyridine-3-carboxyamide,
4-[(2,6-difluorobenzyl)amino]-6-{[4-(piperazin-1-yl)phenyl]amino}pyridine-3-carboxyamide,
4-[(3-nitrobenzyl)amino]-6-{[4-(piperazin-1-yl)phenyl]amino}pyridine-3-carboxyamide,
4-[(3,5-difluorobenzyl)amino]-6-{[3-(piperazin-1-yl)phenyl]amino}pyridine-3-carboxyamide,
4-(benzylamino)-6-{[4-(1,4-diazepan-1-yl)phenyl]amino}pyridine-3-carboxyamide,
4-[(3,5-difluorobenzyl)amino]-6-({4-[(2-methoxyethyl)amino]phenyl}amino)pyridine-3-carboxyamide,
4-[(3,5-difluorobenzyl)amino]-6-({4-[(2-hydroxyethyl)amino]phenyl}amino)pyridine-3-carboxyamide,
6-[(4-{4-[2-(diethylamino)ethyl]piperazin-1-yl}phenyl)amino]-4-[(3-nitrobenzyl)amino]pyridine-3-carboxyamide,
4-(benzylamino)-6-[(4-{4-[2-(diethylamino)ethyl]piperazin-1-yl}phenyl)amino]pyridine-3-carboxyamide,
6-[(4-{4-[2-(diethylamino)ethyl]piperazin-1-yl}phenyl)amino]-4-[(2,3-difluorobenzyl)amino]pyridine-3-carboxyamide,
6-(3-{4-[2-(diethylamino)ethyl]piperazin-1-yl}phenyl)amino]-4-[(3,5-difluorobenzyl)amino]pyridine-3-carboxyamide,
6-({4-[4-(2-cyanoethyl)piperazin-1-yl]phenyl}amino)-4-[(3,5-difluorobenzyl)amino]pyridine-3-carboxyamide,
4-(benzyl)-6-({4-[4-(2-cyanoethyl)piperazin-1-yl]phenyl}amino)pyridine-3-carboxyamide, 6-({4-{4-(3-cyanopropyl)piperazin-1-yl]phenyl}amino)-4-[(3-nitrobenzylamino)pyridine-3-carboxamide,
4-(benzylamino)-6-{[4-(4-methyl-1,4-diazepan-1-yl)phenyl]amino}pyridine-3-carboxamide,
4-(benzylamino)-6-({4-[4-(2-hydroxyethyl)-1,4-diazepan-1-yl]phenyl}amino)pyridine-3-carboxamide,
6-({4-[4-(2-aminoethyl)piperazin-1-yl]phenyl}amino)-4-[(3,5-difluorobenzyl)amino]pyridine-3-carboxamide,
4-[(3,5-difluorobenzyl)amino]-6-{[4-(4-{2-[(methylsulfonyl)amino]ethyl}piperazin-1-yl)phenyl]amino}pyridine-3-carboxamide,
4-[(3,5-difluorobenzyl)amino]-6-[(4-{4-[2-(methylamino)ethyl]piperazin-1-yl}phenyl)amino]pyridine-3-carboxamide,
6-{[4-(4-acetylpiperazin-1-yl)phenyl]amino}-4-(benzylamino)pyridine-3-carboxamide,
6-{[4-(4-acetyl-1,4-diazepan-1-yl)phenyl]amino}-4-(benzylamino)pyridine-3-carboxamide,
4-(benzylamino)-6-{[4-(4-butanoylpiperazin-1-yl)phenyl]amino}pyridine-3-carboxamide,
4-(benzylamino)-6-({4-[4-(2-methylpropanoyl)piperazin-1-yl]phenyl}amino)pyridine-3-carboxamide,
4-(benzylamino)-6-({4-[4-(cyanoacetyl)piperazin-1-yl]phenyl}amino)pyridine-3-carboxamide,
6-({4-[4-(cyanoacetyl)piperazin-1-yl]phenyl}amino)-4-[(2,5-difluorobenzyl)amino]pyridine-3-carboxamide,
6-({4-[4-(cyanoacetyl)piperazin-1-yl]phenyl}amino)-4-[(2,6-difluorobenzyl)amino]pyridine-3-carboxamide,
6-({3-[4-(cyanoacetyl)piperazin-1-yl]phenyl}amino)-4-[(3,5-difluorobenzyl)amino]pyridine-3-carboxamide,
4-(benzylamino)-6-({4-[4-(cyanoacetyl)-1,4-diazepan-1-yl]phenyl}amino)pyridine-3-carboxamide,
4-(benzylamino)-6-({4-[4-(N,N-diethylglycyl)piperazin-1-yl]phenyl}amino)pyridine-3-carboxamide,
6-({4-[4-(N,N-diethylglycyl)piperazin-1-yl]phenyl}amino)-4-[(3-nitrobenzyl)amino]pyridine-3-carboxamide,
4-(benzylamino)-6-({4-[1-(N,N-diethylglycyl)piperidin-4-yl]phenyl}amino)pyridine-3-carboxamide,
4-(benzylamino)-6-({4-[(diethylcarbamoyl)amino]phenyl}amino)pyridine-3-carboxamide,
4-(benzylamino)-6-({4-[4-diethylcarbamoyl)piperazin-1-yl]phenyl}amino)pyridine-3-carboxamide,
4-(benzylamino)-6-[(4-{[4-(propan-2-yl)carbamoyl]piperazin-1-yl}phenyl)amino]pyridine-3-carboxamide,
4-[(3-nitrobenzyl)amino]-6-[(4-{[4-(propan-2-yl)carbamoyl]piperazin-1-yl}phenyl)amino]pyridine-3-carboxamide,
4-(benzylamino)-6-({4-[4-(morpholinocarbonyl)piperazin-1-yl]phenyl}amino)pyridine-3-carboxamide,
4-(benzylamino)-6-{[4-(piperidin-4-ylamino)phenyl]amino}pyridine-3-carboxamide,
4-(benzylamino)-6-[(4-{[1-(diethylcarbamoyl)piperidin-4-yl]amino}phenyl)amino]pyridine-3-carboxamide,
4-(benzylamino)-6-[(4-{[1-(propan-2-ylcarbamoyl)piperidin-4-yl]amino}phenyl)amino]pyridine-3-carboxamide,
4-[(2,3-difluorobenzyl)amino]-6-({4-[4-(methylsulfonyl)piperazin-1-yl]phenyl}amino)pyridine-3-carboxamide,
4-[(3,5-difluorobenzyl)amino]-6-({4-[4-(methylsulfonyl)piperazin-1-yl]phenyl}amino)pyridine-3-carboxamide,
4-(benzylamino)-6-({4-[4-(methylsulfonyl)-1,4-diazepan-1-yl]phenyl}amino)pyridine-3-carboxamide,
4-(benzylamino)-6-({4-[bis(methylsulfonyl)amino]phenyl}amino)pyridine-3-carboxamide,
4-(benzylamino)-6-({4-[(methylsulfonyl)amino]phenyl}amino)pyridine-3-carboxamide,
4-[(3,5-difluorobenzyl)amino]-6-({4-[(propan-2-ylsulfonyl)amino]phenyl}amino)pyridine-3-carboxamide,
6-{[4-({[2-(diethylamino)ethyl]sulfonyl}amino)phenyl]amino}-4-[(3,5-difluorobenzyl)amino]pyridine-3-carboxamide,
6-[(4-{[(2-aminoethyl)sulfonyl]amino}phenyl)amino]-4-[(3,5-difluorobenzyl)amino]pyridine-3-carboxamide,
4-(benzylamino)-6-{[4-(1,1-dioxo-1,2-thiazolidin-2-yl)phenyl]amino}pyridine-3-carboxamide,
4-(benzylamino)-6-({4-[(piperidin-4-ylcarbonyl)amino]phenyl}amino)pyridine-3-carboxamide,
4-[(3,5-difluorobenzyl)amino]-6-({4-[(piperidin-4-ylcarbonyl)amino]phenyl}amino)pyridine-3-carboxamide,
4-(benzylamino)-6-{[4-(L-prolylamino)phenyl]amino}pyridine-3-carboxamide,
4-[(3,5-difluorobenzyl)amino]-6-{[4-(L-prolylamino)phenyl]amino}pyridine-3-carboxamide,
4-(benzylamino)-6-{[4-(morpholin-4-ylmethyl)phenyl]amino}pyridine-3-carboxamide,
6-[(4-acetylphenyl)amino]-4-[(3,5-difluorobenzyl)amino]pyridine-3-carboxamide,
4-[(3,5-difluorobenzyl)amino]-6-{[(4-trifluoroacetyl)phenyl]amino}pyridine-3-carboxamide,
4-[(3,5-difluorobenzyl)amino]-6-({4-[(2-methoxyethyl)sulfamoyl]phenyl}amino)pyridine-3-carboxamide,
6-[(4-carboxyphenyl)amino]-4-[(3,5-difluorobenzyl)amino]pyridine-3-carboxamide,
4-cyclohexylamino-6-[(4-morpholinophenyl)amino]pyridine-3-carboxamide,
4-cyclohexylamino-6-({4-[4-(methylsulfonyl)piperazin-1-yl]phenyl}amino)pyridine-3-carboxamide,
4-cyclohexylamino-6-({4-[(methylsulfonyl)amino]phenyl}amino)pyridine-3-carboxamide,
4-cyclohexylamino-6-[(3,5-difluorophenyl)amino]pyridine-3-carboxamide,
4-[(2-methylcyclohexyl)amino]-6-[(4-morpholinophenyl)amino]pyridine-3-carboxamide,
6-[(4-morpholinophenyl)amino]-4-(tricyclo[3.3.1.1$^{3.7}$]deca-2-ylamino)pyridine-3-carboxamide,
4-(3,4-dihydro-2H-1-benzopyran-4-ylamino)-6-[(4-morpholinophenyl)amino]pyridine-3-carboxamide,
4-(3,4-dihydro-2H-1-benzopyran-4-ylamino)-6-({4-[4-(propan-2-ylsulfonyl)piperazin-1-yl]phenyl}amino) pyridine-3-carboxamide,
6-[(4-morpholinophenyl)amino]-4-[(pyridin-3-ylmethyl)amino]pyridine-3-carboxamide,
4-[(pyridin-3-ylmethyl)amino]-6-({4-[4-(trifluoroacetyl)piperazin-1-yl]phenyl}amino)pyridine-3-carboxamide,
6-{[4-(piperazin-1-yl)phenyl]amino}-4-[(pyridin-3-ylmethyl)amino]pyridine-3-carboxamide,
6-({4-[4-(propan-2-yl)piperazin-1-yl]phenyl}amino)-4-[(pyridin-3-ylmethyl)amino]pyridine-3-carboxamide,
4-{[(1-benzylpyrrolidin-2-yl)methyl]amino}-6-[(4-morpholinophenyl)amino]pyridine-3-carboxamide,
6-[(4-morpholinophenyl)amino]-4-[(pyrrolidin-2-ylmethyl)amino]pyridine-3-carboxamide,
4-{[(1-methylpyrrolidin-2-yl)methyl]amino}-6-[(4-morpholinophenyl)amino]pyridine-3-carboxamide,
4-{[(1-acetylpyrrolidin-2-yl)methyl]amino}-6-[(4-morpholinophenyl)amino]pyridine-3-carboxamide,
4-[(cyclohexylmethyl)amino]-6-[(4-morpholinophenyl)amino]pyridine-3-carboxamide,
4-[(cyclopropylmethyl)amino]-6-[(4-morpholinophenyl)amino]pyridine-3-carboxamide,
6-[(4-morpholinophenyl)amino]-4-[(pyridin-2-ylmethyl)amino]pyridine-3-carboxamide,
6-(5-chloro-1H-benzimidazol-1-yl)-4-[(3,5-difluorobenzyl)amino]pyridine-3-carboxamide, 6-(6-chloro-1H-benzimidazol-1-yl)-4-[(3,5-difluorobenzyl)amino]pyridine-3-carboxyamide, 6-(1H-benzimidazol-1-yl)-4-[(3,5-difluorobenzyl)amino]pyridine-3-carboxyamide, 6-(6-cyano-1H-benzimidazol-1-yl)-4-[(3,5-difluorobenzyl)amino]pyridine-3-carboxyamide, 6-(5-cyano-1H-benzimidazol-1-yl)-4-[(3,5-difluorobenzyl)amino]pyridine-3-carboxyamide, 4-[(3,5-difluorobenzyl)amino]-6-(6-morpholino-1H-benzimidazol-1-yl)pyridine-3-carboxyamide, 4-[(3,5-difluorobenzyl)amino]-6-(5-morpholino-1H-benzimidazol-1-yl)pyridine-3-carboxyamide, 4-[(3,5-difluorobenzyl)amino]-6-{1-[(4-methylphenyl) sulfonyl]-1H-pyloro[2,3-b]pyridin-3-yl}pyridine-3-carboxyamide, 4-[(3,5-difluorobenzyl)amino]-6-(1H-pyloro[2,3-b]pyridin-3-yl)pyridine-3-carboxyamide, 4-benzylamino-6-(pyridin-4-ylamino)pyridine-3-carboxyamide, or 4-benzylamino-6-[(6-morpholinopyridin-3-yl)amino]pyridine-3-carboxyamide.

Salts of the pyridine-3-carboxyamide derivative represented by the general formula (1) are not specifically limited as long as they are pharmaceutically acceptable salts. When the compound is handled as a basic compound, there can be mentioned a salt of inorganic acids such as hydrochloric acid, hydrobromic acid, hydriodic acid, sulfuric acid, nitric acid and phosphoric acid, and a salt of organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, p-toluenesulfonic acid, aspartic acid and glutamic acid. When the compound is handled as an acidic compound, there can be mentioned inorganic salts such as sodium, potassium, lithium, barium, calcium and magnesium salts, and organic salts such as pyridinium, picolinium and triethylammonium salts. Among them, salts of hydrochloric acid and methanesulfonic acid are preferred. As solvates of the pyridine-3-carboxyamide derivative represented by the general formula (1), a hydrate etc. may be mentioned.

When an asymmetric carbon atom is present in a pyridine-3-carboxyamide derivative represented by the general formula (1), the compound has optical isomers. The present invention encompasses all the optical isomers and racemic mixtures thereof.

A pyridine-3-carboxyamide derivative represented by the general formula (1) may be prepared by a variety of known methods, which include, but not limited to, the methods described below. In the present invention, the heating means is not specifically limited, and a variety of heating means such as heating with microwave radiation may be applied.

1. Method A

A method of preparing a compound in which $R^1$ is represented by formula i

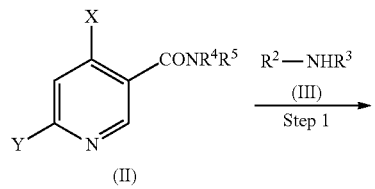

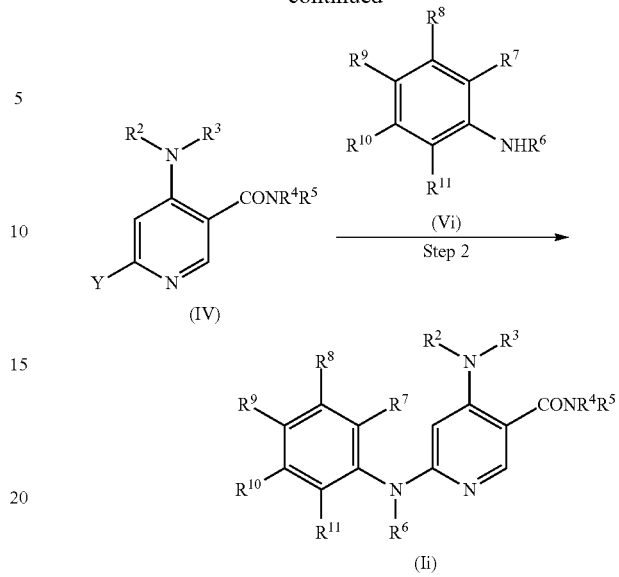

[wherein, $R^2$, $R^3$, $R^4$, $R^5$, $R^6$, $R^7$, $R^8$, $R^9$, $R^{10}$ and $R^{11}$ represent a group as defined above, and X and Y are a leaving group such as a halogen atom and a sulfonyloxy group].

Step 1 represents a process for preparing a compound (IV) from a pyridine derivative (II) and an amine derivative (III). In (II), X and Y represent fluorine, chlorine, bromine, iodine or a trifluoromethanesulfonyl group, with chlorine being specifically preferred. This reaction may be carried out without a solvent, or in an organic solvent including an alcohol such as methanol, ethanol and 2-propanol, an ether such as diethylether, tetrahydrofuran and 1,4-dioxane, an aromatic hydrocarbon such as benzene, toluene and xylene, a halogenated hydrocarbon such as dichloromethane, chloroform and 1,2-dichloroethane, N,N-dimethylformamide, N,N-dimethylacetamide, N-methylpyrrolidone, acetonitrile or ethyl acetate, and may preferably be carried out without a solvent or in an alcohol as the solvent. If desired, the reaction may be carried out in the presence of an organic base such as triethylamine, tributylamine, N,N-dimethylaniline, N,N-diisopropyl ethylamine, pyridine and N,N-dimethylaminopyridine, or an inorganic base such as potassium carbonate, sodium carbonate, sodium bicarbonate and sodium hydroxide. The feed ratio per mole of the compound (II) is 0.5-10 moles, preferably 0.5-2 moles, of the amine derivative (III). The reaction temperature is 0-300° C., preferably 0-150° C., and the reaction time is 1-24 hours, preferably 2-6 hours.

Step 2 represents a step for preparing the compound (II) from the compound (IV) and a compound (Vi) using a metal catalyst reaction or acid catalyst. A metal catalyst or a compound containing copper or palladium as a precursor thereof may be used. Metal copper, copper oxide (II), copper chloride (I) and copper iodide (I) in the case of a copper compound, and palladium acetate (II), tris(dibenzylidene acetone)bispalladium (0) etc. in the case of palladium are preferred. As needed, a base such as cesium carbonate and potassium phosphate can be used. When a palladium compound is used as a catalyst, a ligand such as diphenylphosphino ferrocene and 2,2'-bis(diphenylphosphino)-1,1'-binaphthyl and a base such as sodium t-butoxide and sodium hexamethyldisilazide may preferably added. When a copper compound is used as a metal catalyst, the reaction may preferably be carried out without a solvent or using a solvent such as N,N-dimethylformamide, N,N-dimethylacetamide, N-methylpyrrolidone, tetrahydrofuran and 1,4-dioxane at 0-30° C., preferably 50-150° C. When a palladium compound is used as a metal catalyst, the reaction may preferably carried out using 1,4-dioxane, toluene or xylene as a solvent at 0-300° C., preferably 50-150° C. For the use of a copper compound as a metal catalyst, reference may be made to, for example, Y.-J. Chen, H.-H. Chen, Org. Lett. 2006, 8, 5609-5612, and when a palladium compound is used, reference may be made to, for example, John F. Hartwig et al., J. Am. Chem. Soc. 1996, 118, 7217-7218.

When an acid catalyst is used, no solvent or a solvent such as diphenylether may be used, and as the acid catalyst an inorganic acid such as hydrochloric acid, sulfuric acid or an organic acid such as methanesulfonic acid and a benzenesulfonic acid may be used. The feed ratio per mole of the compound (IV) is 0.5-10 moles, preferably 0.5-3 moles, of the compound (Vi). The acid per mole of the compound (IV) is 0.1-10 moles, preferably 0.5-3 moles. The reaction temperature is 100-200° C., preferably 150-200° C., and the reaction time is 5 minutes to 8 hours, preferably 10 minutes to 2 hours. The compound (II) of the present invention may obtained by a standard method of work up after the reaction, and may be purified, as needed, using a standard method such as recrystallization and column chromatography.

2. Method B

A method of preparing a compound in which $R^1$ is represented by formula i

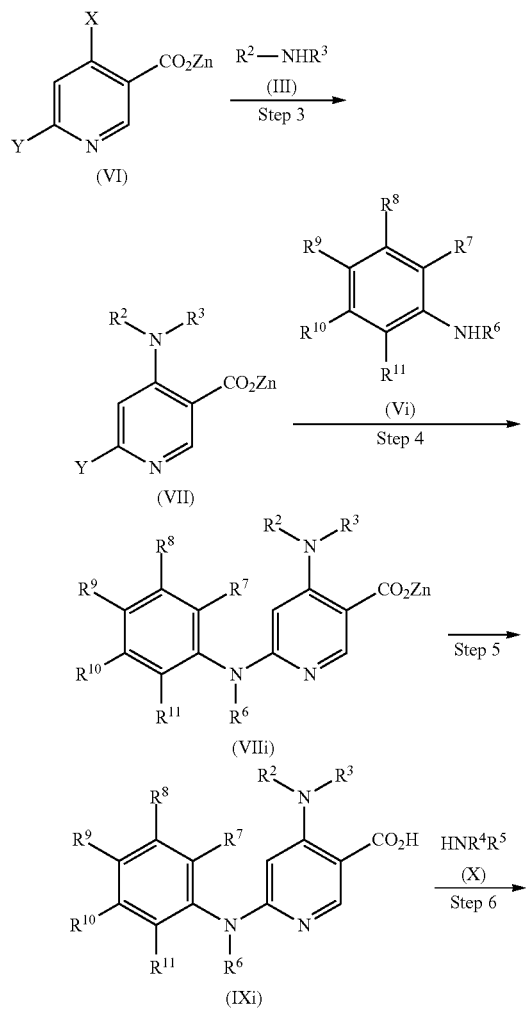

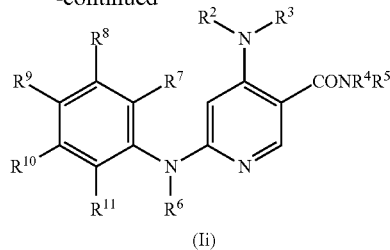

[wherein, $R^2$, $R^3$, $R^4$, $R^5$, $R^6$, $R^7$, $R^8$, $R^9$, $R^{10}$, $R^{11}$, X and Y represent a group as defined above, and Za represents an optionally substituted $C_{1-6}$ alkyl group, for example, a methyl group, an ethyl group, a benzyl group, etc.].

For step 3 and step 4, reaction conditions similar to those described in step 1 and step 2, respectively, of Method A can be applied.

Step 5 represents a process for preparing a compound (IXi) from a compound (VIIIi) in the presence of a catalyst. For example, a standard condition for ester hydrolysis can be applied. For example, a base such as lithium hydroxide, sodium hydroxide, potassium hydroxide and a mixed solvent such as water-methanol and water-ethanol can be used, and the reaction temperature is 0-200° C., preferably 0-100° C., and the reaction time is 0.5-24 hours, preferably 0.5-6 hours. When Za is a benzyl group, it can be removed by for example hydrolysis with a palladium catalyst in addition to the above reaction condition.

Step 6 is a process for preparing a compound (II) from a compound (IXi) and an amine (X). In this step, a standard condition for preparing an amide from a carboxylic acid can be applied. In this case, a method of using a carboxylic acid directly, or a preparation method that uses an acid halide, a mixed anhydride with pivalic acid, or a reactive derivative of a carboxylic acid such as p-nitrophenyl ester may be used. When a carboxylic acid is directly used, a condensation agent such as N,N'-dicyclohexylcarbodiimide, 1-(3-dimethylaminopropyl)-3-ethylcarbodiimide (WSC), dicarbonylimidazole, diethylphosphate cyanide and a diphenylphosphoryl azide can be used. When a reactive derivative of a carboxylic acid is used, coexistence of a base is preferred. As the base, an inorganic base such as sodium carbonate and sodium bicarbonate, or an organic base such as triethylamine, N,N-diisopropylethylamine and pyridine and a derivative thereof can be used. As the solvent, a hydrocarbon such as toluene, a halogenated hydrocarbon such as dichloromethane, chloroform and dichloroethane, or an ether such as tetrahydrofuran, 1,4-dioxane, dimethoxyethane, and ethyleneglycol methyl ether can be used. The reaction temperature may be carried out at −100-200° C., preferably 0-50° C.

3. Method C

A method of preparing a compound in which $R^1$ is represented by formula ii

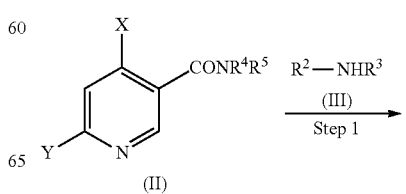

-continued

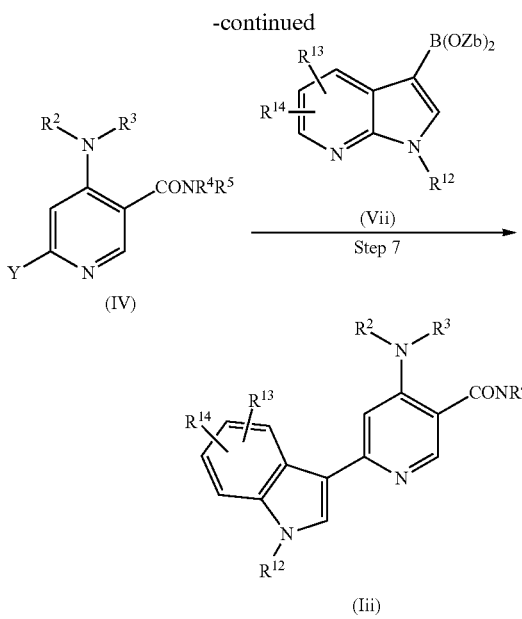

[wherein, $R^2$, $R^3$, $R^4$, $R^5$, $R^{12}$, $R^{13}$ and $R^{14}$ represent a group as defined above, and X and Y represent a leaving group such as a halogen atom and an sulfonyloxy group, $B(Zb)_2$ represents boronic acid or a boronic acid ester group, and Zb represents hydrogen, a lower alkyl group, an ethylene glycol residue, a pinacole residue, a propanediol residue or 2,2-dimethyl-1,3-propanediol residue].

Step 1 is identical to step 1 in Method A.

Step 7 represents a process for preparing a compound (Iii) by a cross coupling reaction using the compound (IV) and a boronic acid or a boronic acid ester (Vii) in the presence of a metal catalyst and a base. As the boronic acid ester, boronic acid dimethyl ester, boronic acid diethyl ester, boronic acid dipropyl ester, boronic acid pinacole ester, boronic acid propanediol ester, boronic acid 2,2-dimethyl-1,3-propanediol ester etc. can be used, with the use of boronic acid being preferred. As the base, an inorganic base or an organic base may be used. As the inorganic base, sodium hydride, potassium hydride, lithium carbonate, sodium carbonate, potassium carbonate, rubidium carbonate, cesium carbonate, magnesium carbonate, calcium carbonate, barium carbonate, lithium phosphate, sodium phosphate, potassium phosphate etc. can be used. As the organic base, sodium methoxide, sodium ethoxide, sodium phenoxide, potassium methoxide, potassium ethoxide, potassium phenoxide, lithium phenoxide, lithium tert-butoxide, sodium tert-butoxide, potassium tert-butoxide, triethylamine, N,N-diisopropylethylamine, tributylamine, tripropylamine, triisopropylamine, tricyclohexylamine, sodium acetate, potassium acetate etc. can be used. Among them, a carbonate and a phosphate are preferred, and sodium carbonate, potassium carbonate, cesium carbonate and potassium phosphate are more preferred. As the solvent, an aliphatic hydrocarbon such as pentane, hexane, heptane, octane, cyclohexane and methyl cyclohexane, an aromatic hydrocarbon such as benzene, toluene and xylene, an ether such as diethylether, diisopropylether, dimethoxyethane, tetrahydrofuran, dioxane and dioxolane, and acetonitrile, dimethylformamide, dimethyl sulfoxide, hexamethyl phosphoramide etc. can be used with an romatic hydrocarbon such as benzene, toluene and xylene, and an ether such as diethylether, dimethoxyethane, tetrahydrofuran and dioxane being preferred. The feed ratio per mole of the compound (IV) is 0.5-10 moles, preferably 0.5-3 moles, of boronic acid or the boronic acid ester compound (Vii). As the metal catalyst, a palladium compound such as palladium acetate (II) and tris(dibenzylidene acetone)bispalladium (0) can be used. The amount of the catalyst per mole of the compound (IV) is 0.001-0.5 mole, preferably 0.01-0.1 mole. The amount of the base per mole of the compound (IV) is 0.1-20 moles, preferably 1-5 moles. The reaction temperature is 0-200° C., preferably 50-120° C., and the reaction time is 5 minutes to 48 hours, preferably 10 minutes to 24 hours. The compound (Iii) of the present invention may obtained by a standard method of work up after the reaction, and may be purified, as needed, using a standard method such as recrystallization and column chromatography. As a reference for the coupling reaction using a palladium compound as in this process, Miyaura, N., Suzuki, A., Chem. Rev. 1995, 95, 2457-2483 can be mentioned.

4. Method D

A method of preparing a compound in which $R^1$ is represented by formula iii

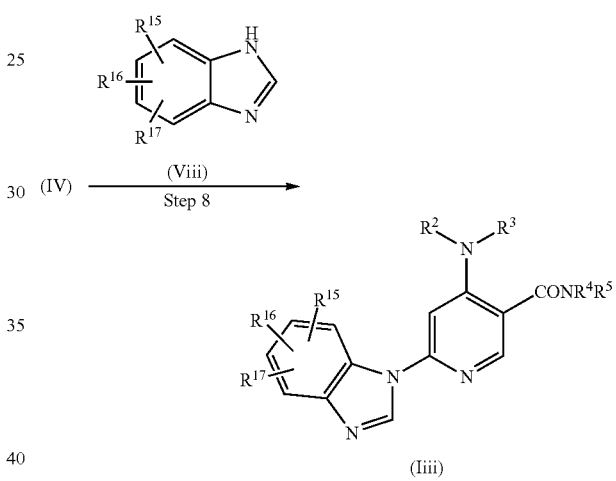

[wherein, $R^2$, $R^3$, $R^4$, $R^5$, $R^{15}$, $R^{16}$ and $R^{17}$ represent a group as defined above].

Step 8 represents a process for preparing a compound (Iiii) from the compound (IV) and a benzimidazole derivative (Viii) using a metal catalyst, an acid or a base. A metal catalyst or a compound containing copper or palladium as a precursor thereof may be used. Metal copper, copper oxide (II), copper chloride (I) and copper iodide (I) in the case of a copper compound and palladium acetate (II), tris(dibenzylidene acetone)bispalladium (0) etc. in the case of palladium are preferred, and, as needed, a base such as cesium carbonate and potassium phosphate may be added. When a palladium compound is used as a catalyst, a ligand such as diphenylphosphino ferrocene and 2,2'-bis(diphenylphosphino)-1,1'-binaphthyl, and a base such as sodium t-butoxide and sodium hexamethyldisilazide may preferably added. When a copper compound is used as the metal catalyst, the reaction may preferably be carried out without a solvent or with a solvent such as N,N-dimethylformamide, N,N-dimethylacetamide, N-methylpyrrolidone, tetrahydrofuran and 1,4-dioxane, and the reaction temperature is 0-300° C., preferably 50-150° C. When a palladium compound is used as the metal catalyst, the reaction may preferably carried out in a solvent such as toluene and xylene, and the reaction temperature is 0-300° C., preferably 50-150° C. For the use of a copper compound as the metal catalyst, reference may be made to, for example, Y.-J. Chen, H.-H. Chen, Org. Lett. 2006, 8, 5609-5612, and when a palladium compound is used, reference may be made to, for example, John F. Hartwig et al., J. Am. Chem. Soc. 1996, 118, 7217-7218.

A reaction under an acidic condition may be carried out without a solvent or in a solvent such as diphenylether. As the acid, hydrochloric acid, sulfuric acid, methanesulfonic acid, benzenesulfonic acid etc. may be used. The feed ratio per mole of the compound (IV) is 0.5-10 moles, preferably 0.5-3 moles, of the benzimidazole derivative (Viii), and the amount of the acid per mole of the compound (IV) is 0.1-10 moles, preferably 0.5-3 moles. The reaction temperature is 100-200° C., preferably 150-200° C., and the reaction time is 5 minutes to 8 hours, preferably 10 minutes to 2 hours.

In the case of a reaction under a basic condition, an inorganic base or organic base may be used. As the inorganic base, for example, sodium hydride, potassium hydride, lithium carbonate, sodium carbonate, potassium carbonate, rubidium carbonate, cesium carbonate, magnesium carbonate, calcium carbonate, barium carbonate, lithium phosphate, sodium phosphate, potassium phosphate, etc. can be used. As the organic base, sodium methoxide, sodium ethoxide, sodium phenoxide, potassium methoxide, potassium ethoxide, potassium phenoxide, lithium phenoxide, lithium tert-butoxide, sodium tert-butoxide, potassium tert-butoxide, triethylamine, N,N-diisopropylethylamine etc. can be used. Among them, sodium hydride, potassium hydride, a carbonate, triethylamine and N,N-diisopropylethylamine are preferred. As the solvent, an alcohol such as methanol, ethanol, 1-propanol and 2-propanol, an ether such as diethylether, tetrahydrofuran and 1,4-dioxane, an aromatic hydrocarbon such as benzene, toluene and xylene, an amide compound such as N,N-dimethylformamide, N,N-dimethylacetamide and N-methylpyrrolidone, dimethyl sulfoxide etc. can be used, and preferred solvents are an alcohol, an aromatic hydrocarbon, an amide compound and dimethyl sulfoxide. The feed ratio per mole of the compound (IV) is 0.5-10 moles, preferably 0.5-3 moles, of the compound (Viii), and the amount of the base per mole of the compound (IV) is 0.1-10 moles, preferably 0.5-3 moles. The reaction temperature is −20-200° C., preferably 60-200° C., and the reaction time is 5 minutes to 48 hours, preferably 3 hours to 24 hours. The compound (Iiii) may obtained by a standard method of work up after the reaction, and may be purified, as needed, using a standard method such as recrystallization and column chromatography.

5. Method E

A method of preparing a compound in which $R^1$ is represented by formula iii

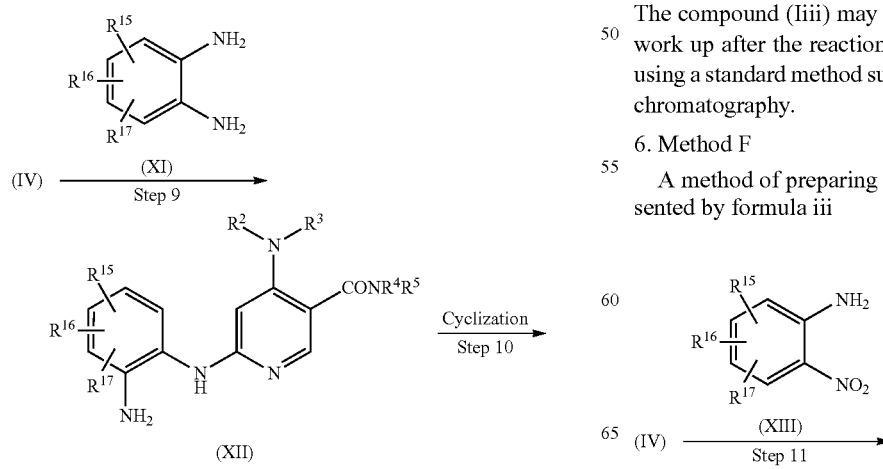

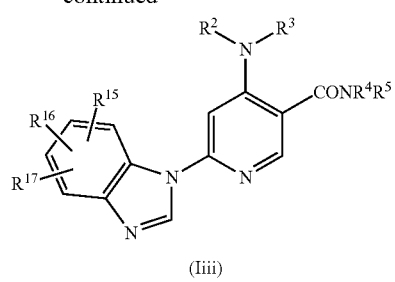

[wherein, $R^2$, $R^3$, $R^4$, $R^5$, $R^{15}$, $R^{16}$ and $R^{17}$ represent a group as defined above].

Step 9 represents a process for preparing a compound (XII) from the compound (IV) and an aniline derivative (XI), and may be carried out in a manner similar to step 2 in Method A or step 8 in Method D.

Step 10 represents a process for preparing a compound (Iiii) from the compound (XII). The reaction may be carried out using an acid catalyst and an orthocarboxylic acid ester. As the acid catalyst, for example, sulfuric acid, methanesulfonic acid, p-toluenesulfonic acid, boron trifluoride ether complex, aluminum chloride etc. can be used, methanesulfonic acid and p-toluenesulfonic acid are preferred, and p-toluenesulfonic acid is more preferred. As the orthocarboxylic acid ester, for example, methyl orthoformate, triethyl orthoformate, tri-n-propyl orthoformate, triisopropyl orthoformate, tri-n-butyl orthoformate etc. may be mentioned, with triethyl orthoformate being preferred. As the solvent, an alcohol such as methanol, ethanol, 1-propanol and 2-propanol, an ether such as diethylether, tetrahydrofuran and 1,4-dioxane, an aromatic hydrocarbon such as benzene, toluene and xylene can be used, and an alcohol such as methanol, ethanol, 1-propanol and 2-propanol is preferred. The amount of the acid catalyst base per mole of the compound (XII) is 0.005-1 mole, preferably 0.01-0.5 mole, and the amount of the orthocarboxylic acid ester per mole of the compound (XII) is 1-50 moles, preferably 1-10 moles. The reaction temperature is −20-200° C., preferably 0-100° C., and the reaction time is 0.5 to 48 hours, preferably 1 hour to 12 hours. The compound (Iiii) may obtained by a standard method of work up after the reaction, and may be purified, as needed, using a standard method such as recrystallization and column chromatography.

6. Method F

A method of preparing a compound in which $R^1$ is represented by formula iii

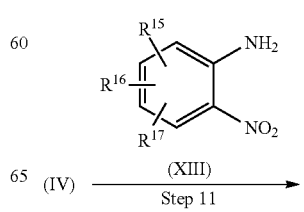

-continued

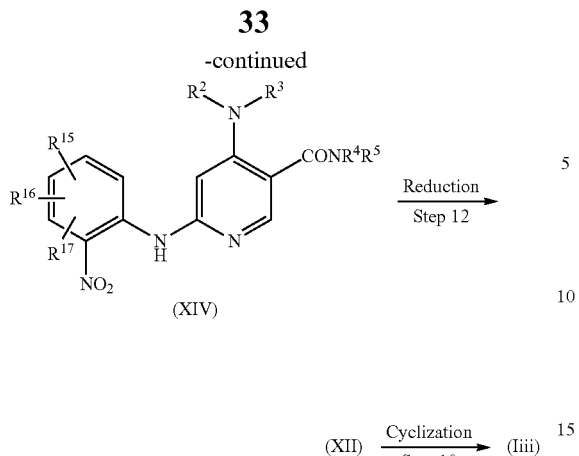

(XII) →(Cyclization Step 10)→ (Iiii)

[wherein, $R^2$, $R^3$, $R^4$, $R^5$, $R^{15}$, $R^{16}$ and $R^{17}$ are as defined above].

Step 11 represents a process for preparing a compound (XIV) from the compound (IV) obtained in step 1 in Method A and an aniline derivative (XIII), and may be carried out in a manner similar to step 2 in Method A or step 8 in Method D.

Step 12 represents a process for preparing the compound (XII) by reducing the nitro group of the compound (XIV) to an amino group. A reduction reaction that employs a catalytic hydrogenation reaction with a metal catalyst or a reduction reaction that employs a metal or a metal salt under an acidic condition may be applied. When a catalytic hydrogenation reaction with a metal catalyst is carried out, a solvent such as an organic acid such as water, acetic acid and propionic acid, an alcohol such as methanol, ethanol, 1-propanol and 2-propanol, an ether such as tetrahydrofuran, dioxane and diethyleneglycol dimethylether, and an ester such as methyl acetate and ethyl acetate may be used alone or in combination as appropriate. As the metal catalyst, there can be used palladium, palladium-black, palladium-carbon, palladium-barium sulfate, palladium hydroxide, palladium hydroxide-carbon, platinum, rhodium-alumina, platinum oxide, copper chromite, Raney Nickel and the like. As needed, an inorganic acid such as hydrochloric acid, sulfuric acid, nitric acid and phosphoric acid may be added to the reaction mixture. The weight ratio of the catalyst to the compound (XIV) is 0.0001-1 fold, preferably 0.03-0.5 fold, and the hydrogen pressure is 1-50 atm, preferably 1-3 atm. The reaction temperature is −20-200° C., preferably 20-100° C., and the reaction time is 10 minutes to 48 hours, preferably 30 minutes to 6 hours. As a reduction reaction with a metal or a metal salt under an acidic condition, there can be mentioned a method that employs zinc, iron, tin, tin chloride (II) etc., and its specific conditions are also described in such a reference as "Fourth Edition, Chemical Experiment Series, Vol. 15, Oxidation and Reduction (II)", edited by The Chemical Society of Japan (Maruzen, 1991).

The compound (XII) can be converted to the compound (Iiii) under the condition described in step 10 in Method E. The compound (Iiii) may obtained by a standard method of work up after the reaction, and may be purified, as needed, using a standard method such as recrystallization and column chromatography.

7. Method G

A method of preparing a compound in which $R^1$ is represented by formula iv

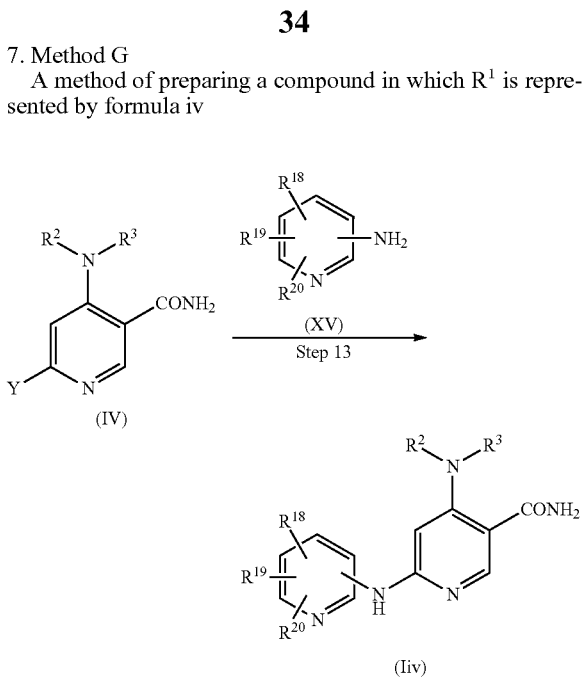

[wherein, $R^2$, $R^3$, $R^4$, $R^5$, $R^{18}$, $R^{19}$ and $R^{20}$ are as defined above].

Step 13 represents a process for preparing a compound (Iiv) from the compound (IV) and an aminopyridine derivative (XV), and may be carried out in a manner similar to step 2 in Method A or step 8 in Method D. The compound (Iiv) may obtained by a standard method of work up after the reaction, and may be purified, as needed, using a standard method such as recrystallization and column chromatography.

8. Method H

A method of preparing a compound in which $R^1$ is represented by formula iv

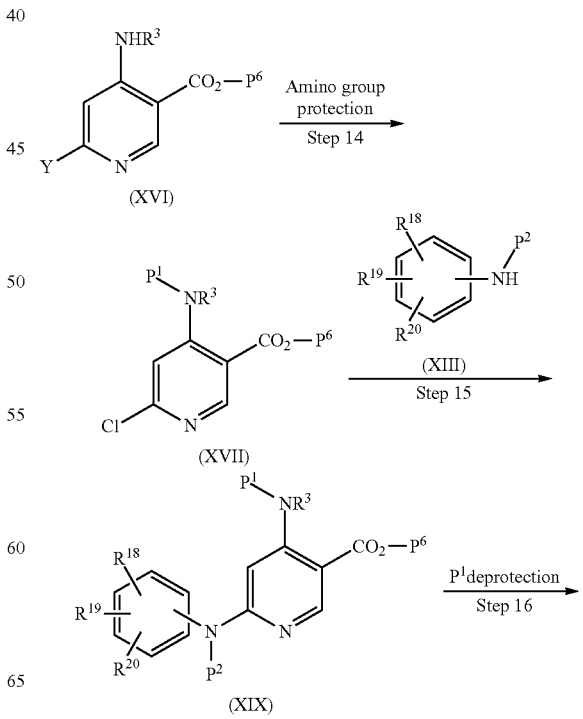

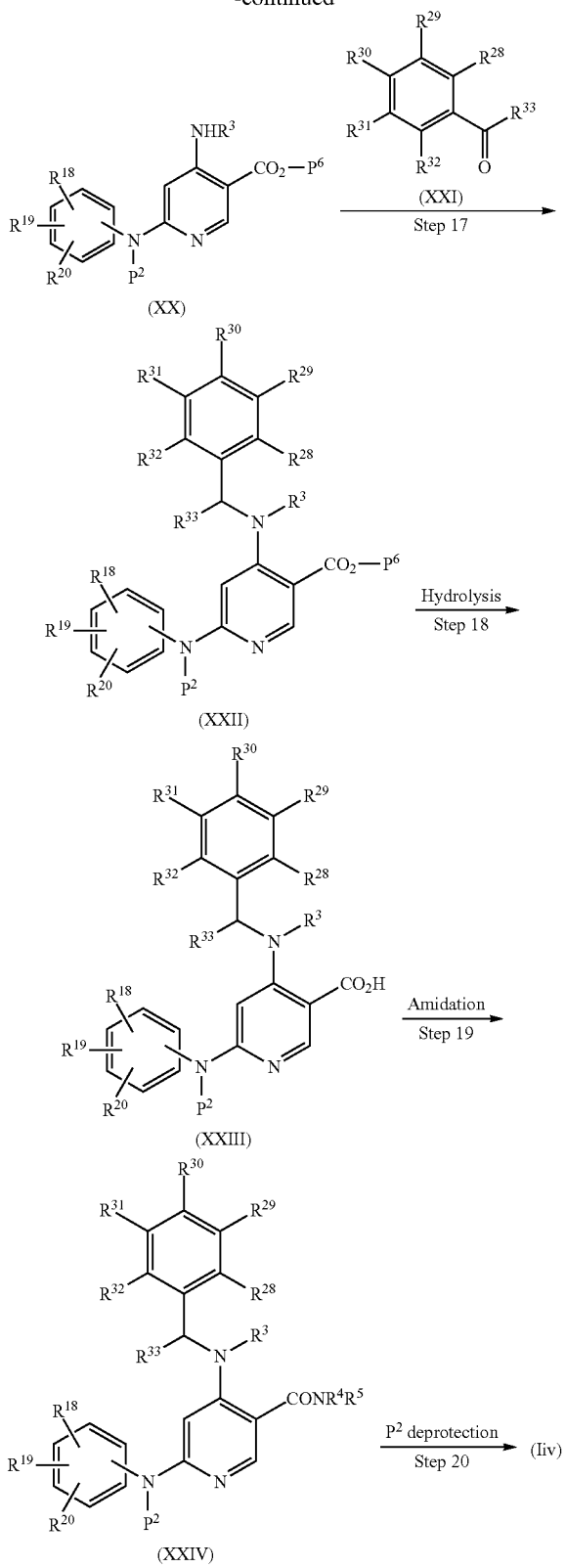

[wherein, $R^3$, $R^4$, $R^5$, $R^{18}$, $R^{19}$, $R^{20}$, $R^{28}$, $R^{29}$, $R^{30}$, $R^{31}$, $R^{32}$, $R^{33}$ and Y are as defined above, $P^0$ represents the protecting group of the carboxyl group, and $P^1$ and $P^2$ represent the protecting group of the amino group].

Step 14 represents a process for protecting the amino group of an available compound (XVI) (for example, Y=Cl, $P^0$=Et). $P^1$ is not specifically limited as long as it is a protecting group commonly used in the protection of the amino group. In selecting a protecting group, reference can be made to Protective Groups in Organic Synthesis, 2nd Ed., John Wiley & Sons Pub., 1990, pp. 309-385, etc., and for example a formyl group, an acetyl group, a trifluoroacetyl group, a tert-butylcarbamate group, preferably a trifluoroacetyl group can be used.

Step 15 represents a process for preparing a compound (XIX) from a compound (XVII) and an aminopyridine derivative (XVIII). The reaction may be carried out in a manner similar to step 2 in Method A or step 8 in Method D. See the above reference for the selection of a protecting group $P^2$ of the amino group of the compound (XVIII), and for example a benzyl group, a 4-methoxybenzyl group and a tert-butyl group, preferably a 4-methoxybenzyl group can be used.

Step 16 represents a process for preparing a compound (XX) by removing the protecting group $P^1$ of the amino group of the compound (XIX). A common condition for amino group protection may be applied, and when the protecting group is a trifluoroacetyl group, for example, an inorganic base or an organic base may be used to obtain the compound (XX). As the inorganic base, there can be used, for example, lithium hydroxide, sodium hydroxide, potassium hydroxide, calcium hydroxide, magnesium hydroxide, barium hydroxide, sodium carbonate, potassium carbonate, cesium carbonate, sodium bicarbonate, potassium bicarbonate, sodium acetate, potassium acetate, ammonia etc. As the organic base, there can be used, for example, trimethylamine, triethylamine, tripropylamine, tributylamine, pyridine, chloropyridine, lutidine, collidine, dimethylaminopyridine etc. In this reaction, water, solvents including, for example, an alcohol such as methanol, ethanol, 1-propanol and 2-propanol, an ether such as tetrahydrofuran, 1,4-dioxane, dimethoxyethane and ethyleneglycol dimethylether, and an amide compound such as dimethylformamide, dimethylacetamide, N-methylpyrrolidone, acetonitrile and dimethyl sulfoxide etc. may be used alone or in combination. The reaction temperature is −40-200° C., preferably 0-100° C., and the reaction time is 0.5 to 48 hours, preferably 0.5 to 6 hours.

Step 17 represents a process for preparing a compound (XXII) from the compound (XX) and a compound (XXI) by a reductive amination reaction. For this reaction, a reducing agent such as sodium borohydride, sodium cyanoborohydride and sodium triacetoxyborohydride can be used. As the solvent, for example, an ether such as diethylether, 1,4-dioxane and tetrahydrofuran, and an alcohol such as methanol, ethanol, 1-propanol and 2-propanol can be used. The feed ratio per mole of the compound (XX) is 0.5-10 moles, preferably 0.5-2 moles, of the compound (XXI). The amount of the reducing agent per mole of the compound (XX) is 0.5-10 moles, preferably 0.5-2 moles. The reaction temperature is −20-120° C., preferably 0-100° C., and the reaction time is 0.5 to 24 hours, preferably 0.5 to 12 hours. References for this reaction are R. F. Borch, M. D. Bernstein, H. D. Durst, J. Am Chem. Soc., 1971, 93, 2897-2904., Ahmed F. Abdel-Magid, Cynthia A. Maryanoff, Tetrahedron Lett., 1990, 31, 5595-5598 and the like. A reductive amination reaction with a tin catalyst using hydrosilane as a hydrogen source can also be applied. As the hydrosilane, there can be used, for example, triethylsilane, trimethylsilane, triphenylsilane, diethylsilane, dimethylsilane, diphenylsilane, phenylsilane etc., with phenylsilane being preferred. As the tin catalyst, there can be used, for example, tetraphenyltin, tetrabutyltin, tripropyltin chloride, tripentyltin chloride, triphenyltin chloride, tributyltin chloride, diphenyltin dichloride, dibutyltin dichloride, butyltin trichloride, phenyltin trichloride etc., with dibutyltin dichloride being preferred. As the solvent, there can be used an ether such as tetrahydrofuran, dioxane and diethyleneglycol dimethylether, and an aromatic hydrocarbon such as benzene, toluene and xylene, with tetrahydrofuran being preferred. The feed ratio relative to the compound (XX) is 0.5-10 moles, preferably 0.5-4 moles, of the aldehyde derivative (XXI). The weight ratio of the hydrosilane relative to the compound (XX) is 0.5-10 folds, preferably 1-5 folds. The amount of the tin catalyst per mole of the compound (XX) is 0.0001-10 moles, preferably 0.01-5 moles. The reaction temperature is −40-200° C., preferably 0-100° C., and the reaction time is 30 minutes to 120 hours, preferably 24 to 72 hours. References for this reaction are R. Apodaca, W. Xiao, Org. Lett., 2001, 3, 1745-1748., H. Kato, I. Shibata, S. Yasaka, S. Tsunoi, M. Yasuda, A. Baba, Chem. Commun. 2006, 4189-4191 and the like.

Step 18 represents a process for preparing a carboxylic acid derivative (XXIII) by deprotecting the protecting group $P^0$ of the carboxyl group of a compound (XXII). For this reaction, a common hydrolysis condition for esters may be applied. For example, as the base, lithium hydroxide, sodium hydroxide, potassium hydroxide etc. can be used, and, as the solvent, a mixed solvent such as water-methanol and water-ethanol can be used. The reaction temperature is 0-200° C., preferably 0-100° C., and the reaction time is 0.5 to 24 hours, preferably 0.5 to 6 hours. $P^0$s is not limited to the ethyl group, and another group such as a benzyl group can also be used. When $P^0$ is a benzyl group, it can be removed by hydrolysis etc. with a palladium catalyst in addition to the above reaction condition.

Step 19 represents a process for preparing an amide derivative (XXIV) from a carboxylic acid derivative (XXIII). For this reaction, a condition similar to that in step 6 in Method B can be applied.

Step 20 represents a process for preparing a compound (Iiv) by deprotecting the protecting group $P^2$ of the amino group of the amide derivative (XXIV). The reaction condition can be selected as appropriate depending on the protecting group used, and references described in connection with step 14 may be referred to. When $P^2$ is a 4-methoxybenzyl group, a deprotection reaction using trifluoroacetic acid as the acid catalyst may be carried out in dichloromethane or without a solvent. The reaction temperature is −78-150° C., preferably 0-100° C., and the reaction time is 0.5 to 48 hours, preferably 0.5 to 6 hours. The compound (Iiv) may obtained by a standard method of work up after the reaction, and may be purified, as needed, using a standard method such as recrystallization and column chromatography.

In the above Method H, the compounds (Vi), (Vii), (Viii), (XI), (XIII) or (XV) in stead of the compound (XVIII), a compound represented by the following formula:

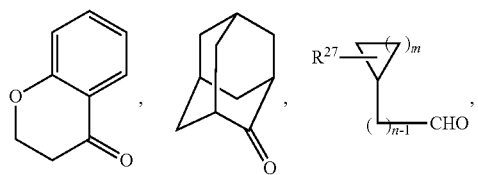

-continued

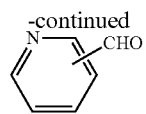

[wherein, $R^{27}$, m and n are as defined above], in stead of the compound (XXI) can be similarly reacted to prepare the compounds (II), (Iii), (Iiii) and (Iiv) of the present invention.

The compound (I) of the present invention having an alkylamino group, an amide group, an ureido group etc. as $R^7$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, $R^{28}$, $R^{29}$, $R^{30}$, $R^{31}$ and $R^{32}$ can be prepared by synthesizing it using the compound (II) or compound (VI) having these functional groups at the corresponding substituent positions, or by using the compound (I) of the present invention having an amide group at the corresponding substituent positions as the feed material and by applying a preparation method that is obvious or known to a person skilled in the art or a modification thereof.

In order to obtain the compound (I) of the present invention having an alkylamino group from the compound (I) of the present invention having an amino group, the desired amino group may be alkylated with a halogenated alkyl such as alkyl chloride, alkyl bromide and alkyl iodide, and an alkylating agent such as alkyl trifluoromethanesulfonate, alkyl methanesulfonate, alkyl benzenesulfonate and alkyl toluenesulfonate. In this reaction, as needed, an inorganic base such as sodium carbonate, sodium bicarbonate and sodium hydride, or an organic base such as triethylamine, N,N-diisopropylethylamine and pyridine or its derivative can be used. As the solvent, an ether such as tetrahydrofuran, 1,4-dioxane, dimethoxyethane and ethyleneglycol dimethylether, and an organic solvent such as N,N-dimethylformamide, N,N-dimethylacetamide, N-methylpyrrolidone and acetonitrile can be used, and the reaction temperature is about −50-200° C., preferably 0-100° C.

In order to obtain the compound (I) of the present invention having an amide group from the compound (I) of the present invention having an amino group, the condition described in step 6 in Method B can be applied to condense the desired amino group and carboxylic acid. As the carboxylic acid, carboxylic acid per se or a reactive derivative thereof such as an acid halide, a mixed acid anhydride with pivalic acid or p-nitrophenyl ester may be used in the reaction. Alternatively, the reactive derivative of carboxylic acid may be replaced with a reactive derivative of sulfonic acid such as a halogenated sulfonic acid and sulfonic acid anhydride to prepare the compound (I) of the present invention having a sulfonamide group.

In order to obtain the compound (I) of the present invention having an ureido group from the compound (I) of the present invention having an amino group, the reaction of a urea-forming agent such as an alkyl or arylisocyanate derivative with the desired amino group can be used. As the reaction solvent, there can be used a hydrocarbon such as toluene, a halogenated hydrocarbon such as dichloromethane, chloroform and dichloroethane, or an ether such as tetrahydrofuran, 1,4-dioxane, dimethoxyethane and ethyleneglycol dimethylether. The reaction temperature is 0-300° C., preferably 0-200° C., and the reaction time is 0.5 to 24 hours, preferably 0.5 to 6 hours.

Among the compounds (I) of the present invention, a compound having a carbonyl group at $R^7$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, $R^{28}$, $R^{29}$, $R^{30}$, $R^{31}$ and $R^{32}$ can be prepared by synthesizing it using the compound (II) or compound (VI) having these functional groups or by a common oxidation reaction using the compound (I) in which the carbonyl group in the substituent is a carbinol group as the raw material. Any method that does not affect the other functional groups carried by the compound (I) can be applied. For example, an oxidation reaction including the chromic acid oxidation using pyridinium chlorochromate, pyridinium dichlorochromate, chromic oxide, dichromic acid or the like, or the dimethylsulfoxide oxidation using dimethylsulfoxide-N,N-dicyclohexylcarbodiimide, dimethylsulfoxide-oxalyl chloride or the like can be applied ("Fourth Edition, Chemical Experiment Series, Vol. 21, Organic Synthesis Reaction III", edited by The Chemical Society of Japan, Maruzen, 1991, pp. 196-238).

Though the pyridine-3-carboxyamide derivative of the present invention represented by the general formula (1) may be obtained by a method described above, it can be purified, as needed, using a standard method such as recrystallization and column chromatography. Also, as needed, it may be converted to the desired salt or solvate described above by a standard method.

The pyridine-3-carboxyamide derivative represented by the general formula (1) thus obtained or its salt or a solvate thereof (sometimes collectively referred to hereinafter as "the compound represented by the general formula (1)") have an JAK3 inhibitory activity and are useful as preventive and therapeutic agents for diseases associated with JAK3, including, for example, rejection and graft versus host disease (GvHD) in organ transplantation, rheumatoid arthritis, multiple sclerosis, systemic lupus erythematosus, Sjögren syndrome, Behcet's disease, type I diabetes mellitus, autoimmune thyroiditis, idiopathic thrombocytopenic purpura, ulcerative colitis, Crohn's disease, asthma, allergic rhinitis, atopic dermatitis, contact dermatitis, urticaria, eczema, psoriasis, allergic conjunctivitis, uveitis, cancer and leukemia.

The pharmaceutical composition of the present invention, which comprises a pyridine-3-carboxyamide derivative represented by the general formula (1) or its salt or a solvate thereof, may be used alone, but may usually be used in combination with a pharmaceutically acceptable carrier, an additive and the like. The dosage form of the pharmaceutical composition is not specifically limited, and may be selected as appropriate depending on the purpose of treatment. For example, it may be an oral agent, an injection, a suppository, an ointment, an inhalant, an eye drop, a skin patch and the like. A pharmaceutical composition suitable for use in such a dosage form can be produced by a known method of pharmaceutical formulation.

When an oral solid preparation is to be prepared, an excipient, and, as needed, a binding agent, a disintegrant, a lubricant, a colorant, a corrigent, an odor-improving agent etc. may be added to a pyridine-3-carboxyamide derivative represented by the general formula (1), and then formulated into a tablet, a coated tablet, granules, a powder, a capsule and the like by a standard method. The additive may be any of the commonly used ones in the art. As the excipient, there can be mentioned for example, lactose, white sugar, sodium chloride, glucose, starch, calcium carbonate, kaolin, microcrystalline cellulose, silicic acid and the like. As the binding agent, there can be mentioned, for example, water, ethanol, propanol, simple syrup, a dextrose solution, a starch solution, a gelatin solution, carboxymethyl cellulose, hydroxypropyl cellulose, hydroxypropyl starch, methyl cellulose, ethyl cellulose, shellac, calcium phosphate, polyvinyl pyrrolidone and the like. As the disintegrant, there can be mentioned, for example, dry starch, sodium alginate, an agar powder, sodium bicarbonate, calcium carbonate, sodium lauryl sulfate, monoglyceride stearate, lactose and the like. As the lubricant, there can be mentioned, for example, purified talc, a stearate, borax, polyethylene glycol and the like. As the corrigent, there can be mentioned, for example, white sugar, orange peel, citric acid, tartaric acid and the like.

When an oral liquid preparation is to be prepared, a corrigent, a buffering agent, a stabilizing agent, an odor-improving agent etc. may be added to a pyridine-3-carboxyamide derivative represented by the general formula (1), and then formulated into an internal liquid, a syrup, an elixir and the like by a standard method. The corrigent may be any one described above. As the buffering agent, sodium citrate etc. may be mentioned, and as the stabilizing agent, tragacanth, gum arabic, gelatin etc. may be mentioned.

When an injection is to be prepared, a pH-modifying agent, a buffering agent, a stabilizing agent, an isotonic agent, a local anesthetic etc. may be added to a pyridine-3-carboxyamide derivative represented by the general formula (1), and then formulated into a subcutaneous, intramuscular and intravenous injection by a standard method. As the pH-modifying agent, sodium citrate, sodium acetate, sodium phosphate etc. may be mentioned. As the stabilizing agent, sodium pyrosulfite, EDTA, thioglycolic acid, thiolactic acid etc. may be mentioned. As the local anesthetic, procaine hydrochloride, lidocaine hydrochloride etc. may be mentioned. As the isotonic agent, sodium chloride, dextrose solution etc. may be mentioned.

When a suppository is to be prepared, a known carrier for suppository such as polyethylene glycol, lanolin, cacao butter, fatty acid triglyceride etc. and, as needed, a surfactant such as Tween (trade mark) may be added to a pyridine-3-carboxyamide derivative represented by the general formula (1), and then formulated by a standard method.

In addition to the above dosage forms, the pyridine-3-carboxyamide derivative represented by the general formula (1) may also be formulated into an inhalant, an eye drop or a nasal drop.

The dosage of the pyridine-3-carboxyamide derivative represented by the general formula (1) may vary depending on the age, body weight, dosage form and the number of administration etc. but for an adult usually 1-1000 mg of the pyridine-3-carboxyamide derivative represented by the general formula (1) per day may be administered orally or prenterally in one or a few divided doses.

EXAMPLES

The present invention will be further explained with reference to Examples and Preparation Examples, but it should be noted that the present invention is not limited to them in any way.

Example 1

Preparation of 4-(benzylamino)-6-chloropyridine-3-carboxyamide

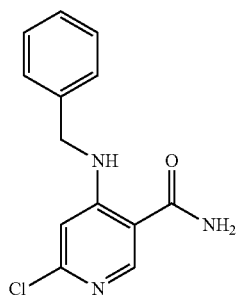 [SMILES: NC(=O)c1cnc(Cl)cc1NCc1ccccc1]

5.00 g of 4,6-dichloropyridine-3-carboxyamide synthesized according to the method described in US 2006/0217417 was dissolved in 50 mL of ethanol, to which 3.37 g of benzylamine and 4.40 g of N,N-diisopropylethylamine were added, and heated at reflux for 12 hours. After cooling, the solvent was evaporated, and 100 mL of water was added to the residue. After cooling with ice, the deposited crystals were filtered, washed with water and hexane, and air-dried. It was further dried under reduced pressure (100° C., 2 hours) to obtain the title compound (5.96 g, 87%) as light yellow needle crystals.

$^1$H-NMR (400 MHz, CDCl$_3$) δ: 4.42 (2H, d, J=5.6 Hz), 5.82 (2H, br), 6.53 (1H, s), 7.26-7.39 (5H, m), 8.28 (1H, s), 8.90 (1H, br).

Example 2

Preparation of 6-chloro-4-[(2-methoxybenzyl)amino] pyridine-3-carboxyamide

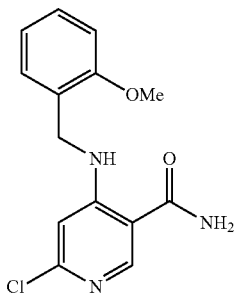 [SMILES: COc1ccccc1CNc1cc(Cl)ncc1C(N)=O]

From 4,6-dichloropyridine-3-carboxyamide and 2-methoxybenzylamine in a manner similar to Example 1, the title compound was obtained as a colorless crystalline powder (yield 71%).

$^1$H-NMR (400 MHz, CDCl$_3$) δ: 3.89 (3H, s), 4.40 (2H, d, J=6.1 Hz), 5.77 (2H, br), 6.60 (1H, s), 6.89-6.95 (2H, m), 7.21 (1H, dd, J=8.8, 1.5 Hz), 7.29 (1H, dd, J=7.6, 1.9 Hz), 8.25 (1H, s), 8.86 (1H, br).

Example 3

Preparation of 6-chloro-4-[(3-methoxybenzyl)amino] pyridine-3-carboxyamide

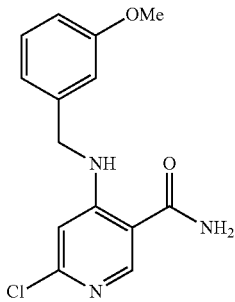 [SMILES: COc1cccc(CNc2cc(Cl)ncc2C(N)=O)c1]

From 4,6-dichloropyridine-3-carboxyamide and 3-methoxybenzylamine in a manner similar to Example 1, the title compound was obtained as a colorless crystalline powder (yield 99%).

$^1$H-NMR (400 MHz, CDCl$_3$) δ: 3.80 (3H, s), 4.39 (2H, d, J=5.6 Hz), 5.78 (2H, br), 6.52 (1H, s), 6.82-6.85 (2H, m), 6.88-6.91 (1H, m), 7.27-7.30 (1H, m), 8.28 (1H, s), 8.90 (1H, br).

Example 4

Preparation of 6-chloro-4-[(4-methoxybenzyl)amino] pyridine-3-carboxyamide

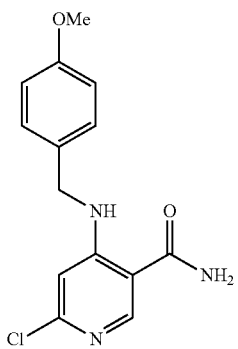 [SMILES: COc1ccc(CNc2cc(Cl)ncc2C(N)=O)cc1]

From 4,6-dichloropyridine-3-carboxyamide and 4-methoxybenzylamine in a manner similar to Example 1, the title compound was obtained as a slight yellow crystalline powder (yield 91%).

$^1$H-NMR (400 MHz, CDCl$_3$) δ: 3.81 (3H, s), 4.34 (2H, d, J=5.6 Hz), 6.54 (1H, s), 6.89 (2H, d, J=8.6 Hz), 7.23 (2H, d, J=8.6 Hz), 8.28 (1H, s), 8.90 (1H, br).

Example 5

Preparation of 6-chloro-4-[(2-methylbenzyl)amino] pyridine-3-carboxyamide

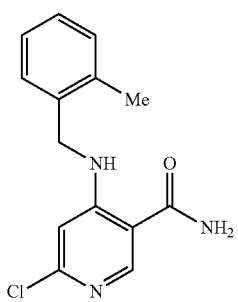 [SMILES: Cc1ccccc1CNc1cc(Cl)ncc1C(N)=O]

From 4,6-dichloropyridine-3-carboxyamide and 2-methylbenzylamine in a manner similar to Example 1, the title compound was obtained as colorless needle crystals (yield 63%).

¹H-NMR (400 MHz, CDCl₃) δ: 2.36 (3H, s), 4.35 (2H, d, J=5.6 Hz), 6.54 (1H, s), 7.15-7.25 (4H, m), 8.29 (1H, s), 8.75 (1H, br).

Example 6

Preparation of 6-chloro-4-[(3-methylbenzyl)amino]pyridine-3-carboxyamide

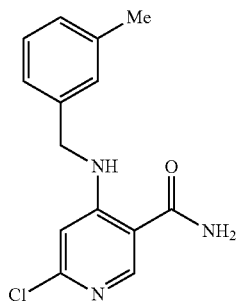 [SMILES: Cc1cccc(CNc2cc(Cl)ncc2C(N)=O)c1]

From 4,6-dichloropyridine-3-carboxyamide and 3-methylbenzylamine in a manner similar to Example 1, the title compound was obtained as colorless needle crystals (yield 75%).

¹H-NMR (400 MHz, CDCl₃) δ: 2.35 (3H, s), 4.37 (2H, d, J=5.6 Hz), 5.81 (2H, br), 6.54 (1H, s), 7.08-7.13 (3H, m), 7.22-7.27 (1H, m), 8.28 (1H, s), 8.87 (1H, br).

Example 7

Preparation of 6-chloro-4-[(4-methylbenzyl)amino]pyridine-3-carboxyamide

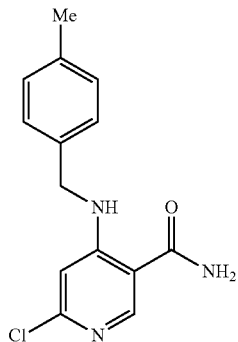 [SMILES: Cc1ccc(CNc2cc(Cl)ncc2C(N)=O)cc1]

From 4,6-dichloropyridine-3-carboxyamide and 4-methylbenzylamine in a manner similar to Example 1, the title compound was obtained as colorless needle crystals (yield 80%).

¹H-NMR (400 MHz, CDCl₃) δ: 2.35 (3H, s), 4.37 (2H, d, J=5.9 Hz), 5.84 (2H, br), 6.53 (1H, s), 7.16 (2H, d, J=8.5 Hz), 7.19 (2H, d, J=8.5 Hz), 8.29 (1H, s), 8.89 (1H, br).

Example 8

Preparation of 6-chloro-4-[(3-ethylbenzyl)amino]pyridine-3-carboxyamide

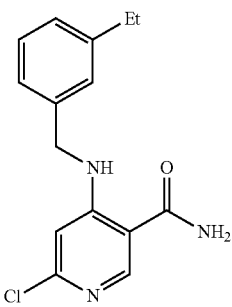 [SMILES: CCc1cccc(CNc2cc(Cl)ncc2C(N)=O)c1]

From 4,6-dichloropyridine-3-carboxyamide and 2-ethylbenzylamine in a manner similar to Example 1, the title compound was obtained as a reddish brown oil (yield 35%). MS: m/z 289 (M⁺).

Example 9

Preparation of 6-chloro-4-[(2-chlorobenzyl)amino]pyridine-3-carboxyamide

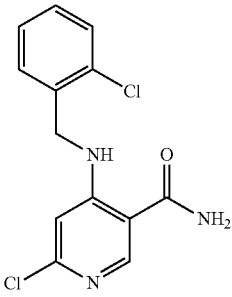 [SMILES: NC(=O)c1cnc(Cl)cc1NCc1ccccc1Cl]

From 4,6-dichloropyridine-3-carboxyamide and 2-chlorobenzylamine in a manner similar to Example 1, the title compound was obtained as colorless needle crystals (yield 35%).

¹H-NMR (400 MHz, CD₃OD) δ: 4.56 (2H, s), 6.62 (1H, s), 7.28-7.33 (2H, m), 7.36-7.40 (1H, m), 7.42-7.48 (1H, m), 8.37 (1H, s).

Example 10

Preparation of 6-chloro-4-[(3-chlorobenzyl)amino]pyridine-3-carboxyamide

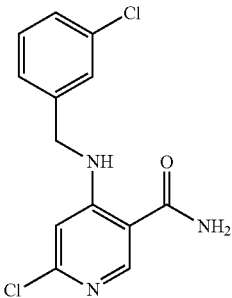

From 4,6-dichloropyridine-3-carboxyamide and 3-chlorobenzylamine in a manner similar to Example 1, the title compound was obtained as colorless needle crystals (yield 59%).

¹H-NMR (400 MHz, CD₃OD) δ: 4.48 (2H, s), 6.63 (1H, s), 7.26-7.38 (4H, m), 8.37 (1H, s).

Example 11

Preparation of 6-chloro-4-[(4-chlorobenzyl)amino]pyridine-3-carboxyamide

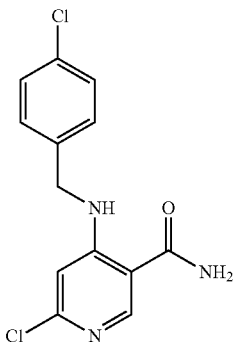 [SMILES: NC(=O)c1cnc(Cl)cc1NCc1ccc(Cl)cc1]

From 4,6-dichloropyridine-3-carboxyamide and 4-chlorobenzylamine in a manner similar to Example 1, the title compound was obtained as colorless needle crystals (yield 59%).

¹H-NMR (400 MHz, CD₃OD) δ: 4.86 (2H, s), 6.62 (1H, s), 7.34 (2H, d, J=8.8 Hz), 7.36 (2H, d, J=8.8 Hz), 8.37 (1H, s).

Example 12

Preparation of 6-chloro-4-[(2-fluorobenzyl)amino]pyridine-3-carboxyamide

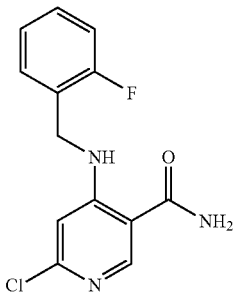 [SMILES: NC(=O)c1cnc(Cl)cc1NCc1ccccc1F]

From 4,6-dichloropyridine-3-carboxyamide and 2-fluorobenzylamine in a manner similar to Example 1, the title compound was obtained as a light yellow crystalline powder (yield 86%).

¹H-NMR (400 MHz, CDCl₃) δ: 4.48 (2H, d, J=5.8 Hz), 6.56 (1H, s), 7.07-7.15 (2H, m), 7.25-7.33 (2H, m), 8.29 (1H, s), 8.90 (1H, br).

Example 13

Preparation of 6-chloro-4-[(3-fluorobenzyl)amino]pyridine-3-carboxyamide

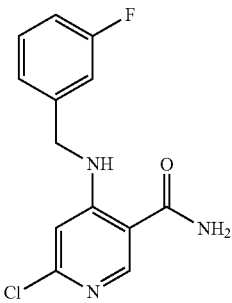 [SMILES: NC(=O)c1cnc(Cl)cc1NCc1cccc(F)c1]

From 4,6-dichloropyridine-3-carboxyamide and 3-fluorobenzylamine in a manner similar to Example 1, the title compound was obtained as a light yellow crystalline powder (yield 90%).

¹H-NMR (400 MHz, CDCl₃) δ: 4.43 (2H, d, J=5.8 Hz), 6.48 (1H, s), 6.97-7.02 (2H, m), 7.08-7.10 (1H, m), 7.30-7.36 (1H, m), 8.30 (1H, s), 8.96 (1H, br).

Example 14

Preparation of 6-chloro-4-[(4-fluorobenzyl)amino]pyridine-3-carboxyamide

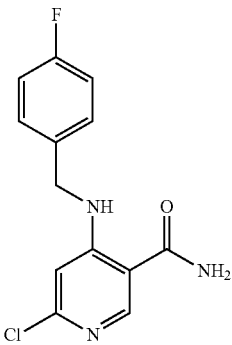 [SMILES: NC(=O)c1cnc(Cl)cc1NCc1ccc(F)cc1]

From 4,6-dichloropyridine-3-carboxyamide and 4-fluorobenzylamine in a manner similar to Example 1, the title compound was obtained as a light yellow crystalline powder (yield 81%).

¹H-NMR (400 MHz, CDCl₃) δ: 4.39 (2H, d, J=5.6 Hz), 6.50 (1H, s), 7.05 (2H, dddd, J=8.8, 8.8, 2.2, 2.2, Hz), 7.26-7.30 (2H, m), 8.29 (1H, s), 8.89 (1H, br).

Example 15

Preparation of 6-chloro-4-{[2-(trifluoromethyl)benzyl]amino}pyridine-3-carboxyamide

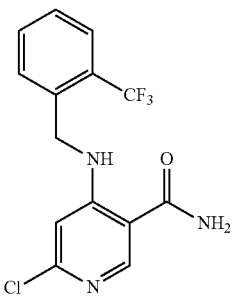 [SMILES: NC(=O)c1cnc(Cl)cc1NCc1ccccc1C(F)(F)F]

From 4,6-dichloropyridine-3-carboxyamide and 2-(trifluoromethyl)benzylamine in a manner similar to Example 1, the title compound was obtained as a white crystalline powder (yield 83%).

¹H-NMR (400 MHz, CD₃OD) δ: 4.66 (2H, s), 6.52 (1H, s), 7.49 (1H, dd, J=7.3, 7.3 Hz), 7.55 (1H, d, J=7.1 Hz), 7.61 (1H, dd, J=7.6, 7.6 Hz), 7.76 (1H, d, J=8.0 Hz), 8.39 (1H, s).

Example 16

Preparation of 6-chloro-4-{[3-(trifluoromethyl)benzyl]amino}pyridine-3-carboxyamide

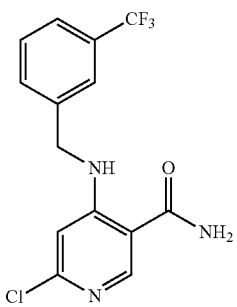

From 4,6-dichloropyridine-3-carboxyamide and 3-trifluoromethylbenzylamine in a manner similar to Example 1, the title compound was obtained as a light yellow crystalline powder (yield 80%).

¹H-NMR (400 MHz, CDCl₃+CD₃OD) δ: 4.49 (2H, d, J=5.9 Hz), 6.48 (1H, s), 7.50-7.52 (2H, m), 7.56-7.60 (2H, m), 8.33 (1H, s), 9.11 (1H, br).

Example 17

Preparation of 6-chloro-4-{[4-(trifluoromethyl)benzyl]amino}pyridine-3-carboxyamide

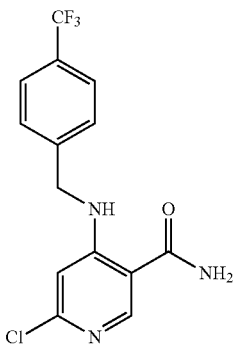 [SMILES: NC(=O)c1cnc(Cl)cc1NCc1ccc(C(F)(F)F)cc1]

From 4,6-dichloropyridine-3-carboxyamide and 4-trifluoromethylbenzylamine in a manner similar to Example 1, the title compound was obtained as a white crystalline powder (yield 94%).

¹H-NMR (400 MHz, CDCl₃) δ: 4.50 (2H, d, J=5.9 Hz), 6.47 (1H, s), 7.43 (2H, d, J=8.0 Hz), 7.63 (2H, d, J=8.0 Hz), 8.30 (1H, s), 9.02 (1H, brs).

Example 18

Preparation of 6-chloro-4-[(3,4-dichlorobenzyl)amino]pyridine-3-carboxyamide

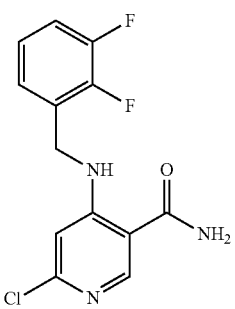 [SMILES: NC(=O)c1cnc(Cl)cc1NCc1cccc(F)c1F]

From 4,6-dichloropyridine-3-carboxyamide and 3,4-dichlorobenzylamine in a manner similar to Example 1, the title compound was obtained as a slight yellow crystalline powder (yield 70%).

¹H-NMR (400 MHz, CDCl₃+CD₃OD) δ: 4.39 (2H, d, J=5.9 Hz), 6.42 (1H, s), 7.15 (1H, dd, J=8.2, 2.3 Hz), 7.40 (1H, d, J=2.3 Hz), 7.44 (1H, d, J=8.2 Hz), 8.33 (1H, s), 9.15 (1H, br).

Example 19

Preparation of 6-chloro-4-[(2,3-difluorobenzyl)amino]pyridine-3-carboxyamide

From 4,6-dichloropyridine-3-carboxyamide and 2,3-difluorobenzylamine in a manner similar to Example 1, the title compound was obtained as a slight yellow crystalline powder (yield 78%).

$^1$H-NMR (400 MHz, DMSO-d6) δ: 4.61 (2H, d, J=6.3 Hz), 6.73 (1H, s), 7.12-7.23 (2H, m), 7.36 (1H, m), 8.13 (1H, br), 8.44 (1H, s), 9.18 (1H, dd, J=6.3, 6.3 Hz).

Example 20

Preparation of 6-chloro-4-[(3,5-difluorobenzyl)amino]pyridine-3-carboxyamide

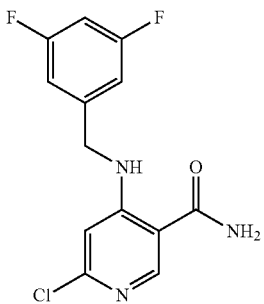 [SMILES: NC(=O)c1cnc(Cl)cc1NCc1cc(F)cc(F)c1]

From 4,6-dichloropyridine-3-carboxyamide and 3,5-difluorobenzylamine in a manner similar to Example 1, the title compound was obtained as colorless needle crystals (yield 87%).

$^1$H-NMR (400 MHz, CDCl$_3$) δ: 4.43 (2H, d, J=5.8 Hz), 5.86 (2H, br), 6.42 (1H, s), 6.75 (1H, dddd, J=7.7, 7.7, 2.3, 2.3 Hz), 6.80-6.87 (1H, m), 8.32 (1H, s), 9.02 (1H, br).

Example 21

Preparation of 6-chloro-4-[(2,4-difluorobenzyl)amino]pyridine-3-carboxyamide

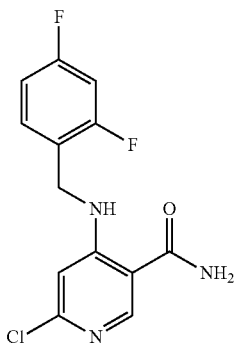 [SMILES: NC(=O)c1cnc(Cl)cc1NCc1ccc(F)cc1F]

From 4,6-dichloropyridine-3-carboxyamide and 2,4-difluorobenzylamine in a manner similar to Example 1, the title compound was obtained as a white crystalline powder (yield 81%).

$^1$H-NMR (400 MHz, CDCl$_3$) δ: 4.43 (2H, d, J=5.8 Hz), 6.54 (1H, s), 6.83-6.90 (2H, m), 7.21-7.29 (1H, m), 8.29 (1H, s), 8.88 (1H, brs).

Example 22

Preparation of 6-chloro-4-[(2,5-difluorobenzyl)amino]pyridine-3-carboxyamide

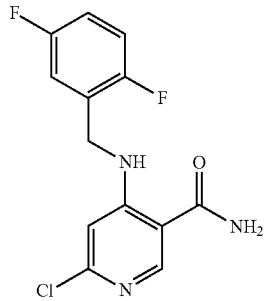 [SMILES: NC(=O)c1cnc(Cl)cc1NCc1cc(F)ccc1F]

From 4,6-dichloropyridine-3-carboxyamide and 2,5-difluorobenzylamine in a manner similar to Example 1, the title compound was obtained as a white crystalline powder (yield 74%).

$^1$H-NMR (400 MHz, CDCl$_3$) δ: 4.47 (2H, d, J=5.9 Hz), 6.50 (1H, s), 6.93-7.00 (2H, m), 7.03-7.10 (1H, m), 8.30 (1H, s), 8.96 (1H, brs).

Example 23

Preparation of 6-chloro-4-[(2,6-difluorobenzyl)amino]pyridine-3-carboxyamide

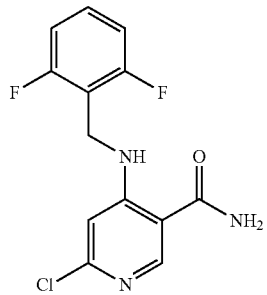 [SMILES: NC(=O)c1cnc(Cl)cc1NCc1c(F)cccc1F]

From 4,6-dichloropyridine-3-carboxyamide and 2,6-difluorobenzylamine in a manner similar to Example 1, the title compound was obtained as a white crystalline powder (yield 69%).

$^1$H-NMR (400 MHz, CDCl$_3$) δ: 4.47 (2H, d, J=6.1 Hz), 6.78 (1H, s), 6.94 (2H, dd, J=7.9, 7.9 Hz), 7.22-7.34 (1H, m), 8.25 (1H, s), 8.87 (1H, brs).

Example 24

Preparation of 6-chloro-4-[(3,4-difluorobenzyl)amino]pyridine-3-carboxyamide

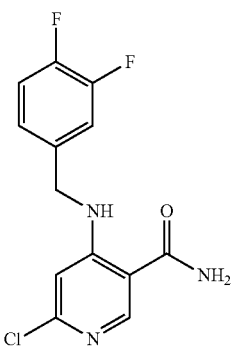 [SMILES: NC(=O)c1cnc(Cl)cc1NCc1ccc(F)c(F)c1]

From 4,6-dichloropyridine-3-carboxyamide and 3,4-difluorobenzylamine in a manner similar to Example 1, the title compound was obtained as a white crystalline powder (yield 88%).

¹H-NMR (400 MHz, CDCl₃) δ: 4.39 (2H, d, J=5.6 Hz), 6.46 (1H, s), 7.01-7.09 (1H, m), 7.09-7.20 (2H, m), 8.30 (1H, s), 8.96 (1H, brs).

Example 25

Preparation of 6-chloro-4-{[3-fluoro-5-(trifluoromethyl)benzyl]amino}pyridine-3-carboxyamide

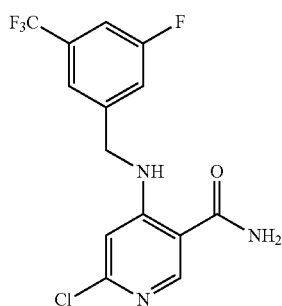 [SMILES: NC(=O)c1cnc(Cl)cc1NCc1cc(F)cc(C(F)(F)F)c1]

From 4,6-dichloropyridine-3-carboxyamide and 3-fluoro-5-(trifluoromethyl)benzylamine in a manner similar to Example 1, the title compound was obtained as a yellow crystalline powder (yield 80%).

¹H-NMR (400 MHz, CD₃OD) δ: 4.61 (2H, s), 6.63 (1H, s), 7.35-7.41 (2H, m), 7.52 (1H, s), 8.39 (1H, s).

Example 26

Preparation of 6-chloro-4-{[3,5-bis(trifluoromethyl)benzyl]amino}pyridine-3-carboxyamide

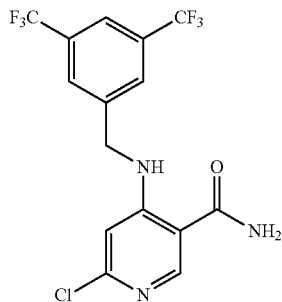 [SMILES: NC(=O)c1cnc(Cl)cc1NCc1cc(C(F)(F)F)cc(C(F)(F)F)c1]

From 4,6-dichloropyridine-3-carboxyamide and 3,5-bis(trifluoromethyl)benzylamine in a manner similar to Example 1, the title compound was obtained as a white crystalline powder (yield 90%).

¹H-NMR (400 MHz, CDCl₃) δ: 4.56 (2H, d, J=5.9 Hz), 6.44 (1H, s), 7.76 (2H, s), 7.84 (1H, s), 8.33 (1H, s), 9.11 (1H, brs).

Example 27

Preparation of 6-chloro-4-[(2-chloro-5-fluorobenzyl)amino]pyridine-3-carboxyamide

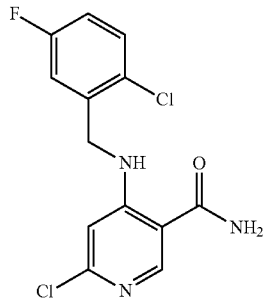

From 4,6-dichloropyridine-3-carboxyamide and 2-chloro-5-fluorobenzylamine in a manner similar to Example 1, the title compound was obtained as a light yellow crystalline powder (yield 39%).

¹H-NMR (400 MHz, CDCl₃) δ: 4.50 (2H, d, J=6.1 Hz), 6.42 (1H, s), 6.94-7.01 (2H, m), 7.38 (1H, dd, J=4.9, 8.6 Hz), 8.32 (1H, s), 9.03 (1H, br).

Example 28

Preparation of 6-chloro-4-[(5-fluoro-2-methoxybenzyl)amino]pyridine-3-carboxyamide

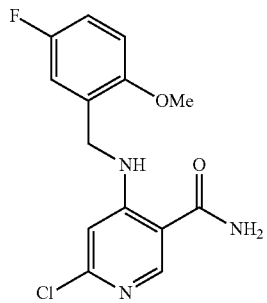 [SMILES: COc1ccc(F)cc1CNc1cc(Cl)ncc1C(N)=O]

From 4,6-dichloropyridine-3-carboxyamide and 5-fluoro-2-methoxybenzylamine in a manner similar to Example 1, the title compound was obtained as slight yellow needle crystals (yield 96%).

¹H-NMR (400 MHz, CD₃OD) δ: 3.88 (3H, s), 4.42 (2H, s), 6.67 (1H, s), 6.97-7.03 (3H, m), 8.34 (1H, s).

Example 29

Preparation of 6-chloro-4-[(3-fluoro-2-methylbenzyl)amino]pyridine-3-carboxyamide

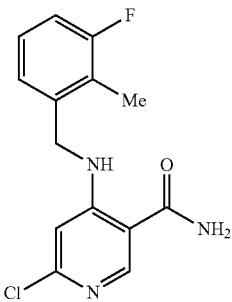 [SMILES: Cc1c(F)cccc1CNc1cc(Cl)ncc1C(N)=O]

From 4,6-dichloropyridine-3-carboxamide and 3-fluoro-2-methylbenzylamine in a manner similar to Example 1, the title compound was obtained as slight yellow prism crystals (yield 98%).

$^1$H-NMR (400 MHz, CDCl$_3$+CD$_3$OD) δ: 2.26 (3H, d, J=2.0 Hz), 4.36 (2H, d, J=5.4 Hz), 6.97-7.05 (2H, m), 7.15 (1H, ddd, J=5.6, 7.8, 7.8 Hz), 8.92 (1H, brt, J=5.4 Hz).

Example 30

Preparation of 6-chloro-4-[(2-chloro-6-fluorobenzyl)amino]pyridine-3-carboxamide

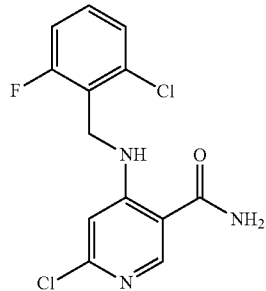

From 4,6-dichloropyridine-3-carboxamide and 2-chloro-6-fluorobenzylamine in a manner similar to Example 1, the title compound was obtained as a slight yellow amorphous substance (yield 85%).

$^1$H-NMR (400 MHz, CD$_3$OD) δ: 4.60 (2H, brs), 6.94 (1H, s), 7.17 (1H, dd, J=8.8, 8.8 Hz), 7.29-7.46 (2H, m), 8.36 (1H, s).

Example 31

Preparation of 6-chloro-4-[(3-nitrobenzyl)amino]pyridine-3-carboxamide

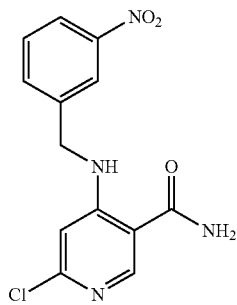 [SMILES: NC(=O)c1cnc(Cl)cc1NCc1cccc([N+](=O)[O-])c1]

From 4,6-dichloropyridine-3-carboxamide and 3-nitrobenzylamine in a manner similar to Example 1, the title compound was obtained as a light yellow crystalline powder (yield 90%).

$^1$H-NMR (400 MHz, DMSO-d6) δ: 4.66 (2H, d, J=6.1 Hz), 6.66 (1H, s), 7.57 (1H, brs), 7.66 (1H, dd, J=7.8 Hz), 7.79 (1H, d, J=7.8 Hz), 8.08-8.16 (2H, m), 8.20 (1H, s), 8.29 (1H, s), 8.93 (1H, brt, J=6.1 Hz).

Example 32

Preparation of 6-chloro-4-{[3-(dimethylamino)benzyl]amino}pyridine-3-carboxamide

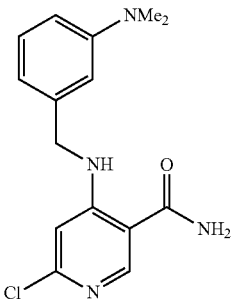 [SMILES: CN(C)c1cccc(CNc2cc(Cl)ncc2C(N)=O)c1]

From 4,6-dichloropyridine-3-carboxamide and 3-(dimethylamino)benzylamine in a manner similar to Example 1, the title compound was obtained as a white powder (yield 69%).

$^1$H-NMR (270 MHz, CDCl$_3$) δ: 2.95 (6H, s), 4.36 (2H, d, J=5.9 Hz), 6.57 (1H, s), 6.63-6.69 (3H, m), 7.20 (1H, d, J=7.6 Hz), 8.26 (1H, s), 8.84 (1H, br s).

Example 33

Preparation of 6-chloro-4-[(3-sulfamoylbenzyl)amino]pyridine-3-carboxamide

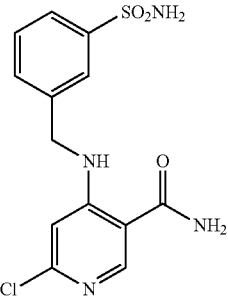 [SMILES: NC(=O)c1cnc(Cl)cc1NCc1cccc(S(N)(=O)=O)c1]

From 4,6-dichloropyridine-3-carboxamide and 3-sulfamoylbenzylamine in a manner similar to Example 1, the title compound was obtained as a light brown powder (yield 49%).

$^1$H-NMR (400 MHz, CD$_3$OD) δ: 4.58 (2H, s), 6.64 (1H, s), 7.50-7.62 (2H, m), 7.83 (1H, d, J=7.8 Hz), 7.90 (1H, s), 8.38 (1H, br).

Example 34

Preparation of 6-chloro-4-({3-[(methylsulfonyl)amino]benzyl}amino)pyridine-3-carboxamide

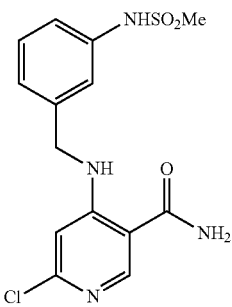

From 4,6-dichloropyridine-3-carboxyamide and 3-[(methylsulfonyl)amino]benzylamine in a manner similar to Example 1, the title compound was obtained as a white solid (yield 28%).

$^1$H-NMR (400 MHz, DMSO-d6) δ: 2.95 (3H, s), 4.46 (2H, br), 6.61 (1H, s), 7.01 (1H, d, J=7.8 Hz), 7.09 (1H, d, J=7.8 Hz), 7.14 (1H, s), 7.30 (1H, dd, J=7.8, 7.8 Hz), 7.53 (1H, br), 8.11 (1H, br), 8.42 (1H, br), 9.17 (1H, br).

Example 35

Preparation of 6-chloro-4-({3-[methyl(methylsulfonyl)amino]benzyl}amino)pyridine-3-carboxyamide

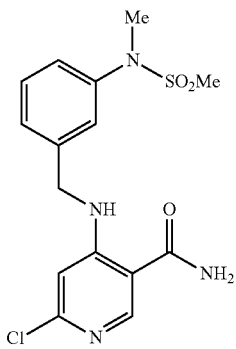 [SMILES: CN(c1cccc(CNc2cc(Cl)ncc2C(N)=O)c1)S(C)(=O)=O]

From 4,6-dichloropyridine-3-carboxyamide and 3-[methyl(methylsulfonyl)amino]benzylamine in a manner similar to Example 1, the title compound was obtained as a slight yellow amorphous substance (yield 76%).

$^1$H-NMR (400 MHz, CDCl$_3$) δ: 2.84 (3H, s), 3.32 (3H, s), 4.43 (2H, s), 6.50 (1H, s), 7.25-7.45 (4H, m), 8.31 (1H, s), 8.96 (1H, br).

Example 36

Preparation of 6-chloro-4-({2-[methyl(methylsulfonyl)amino]benzyl}amino)pyridine-3-carboxyamide

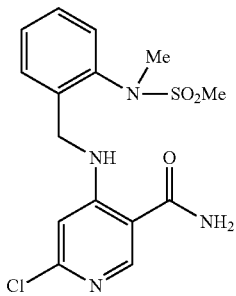 [SMILES: CN(c1ccccc1CNc1cc(Cl)ncc1C(N)=O)S(C)(=O)=O]

From 4,6-dichloropyridine-3-carboxyamide and 2-[methyl(methylsulfonyl)amino]benzylamine in a manner similar to Example 1, the title compound was obtained as a light brown solid (yield 72%).

$^1$H-NMR (400 MHz, DMSO-d6) δ: 3.11 (3H, s), 3.21 (3H, s), 4.56 (1H, brs), 4.63 (1H, brs), 6.54 (1H, s), 7.31 (01H, dd, J=7.3, 2.2 Hz), 7.33-7.42 (2H, m), 7.53 (1H, brs), 7.57 (1H, dd, J=7.3, 1.7 Hz), 8.11 (1H, brs), 8.42 (1H, s), 9.18 (1H, t, J=6.0 Hz).

Example 37

Preparation of 6-chloro-4-{[3-(methylsulfamoyl)benzyl]amino}pyridine-3-carboxyamide

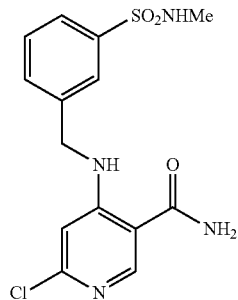

From 4,6-dichloropyridine-3-carboxyamide and 3-(methylsulfamoyl)benzylamine in a manner similar to Example 1, the title compound was obtained as a slight yellow amorphous substance (yield 66%).

$^1$H-NMR (400 MHz, DMSO-d6) δ: 2.38 (3H, br), 4.62 (2H, d, J=6.2 Hz), 6.62 (1H, s), 7.46 (1H, s), 7.52-7.70 (4H, m), 7.73 (1H, s), 8.13 (1H, brs), 8.43 (1H, s), 9.76 (1H, t, J=6.2 Hz).

Example 38

Preparation of 6-chloro-4-{[3-(dimethylsulfamoyl)benzyl]amino}pyridine-3-carboxyamide

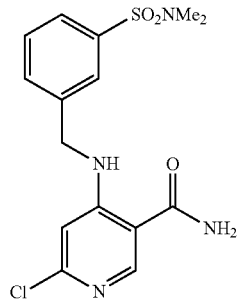

From 4,6-dichloropyridine-3-carboxyamide and [3-(dimethylsulfamoyl)benzyl]amine in a manner similar to Example 1, the title compound was obtained as a slight yellow amorphous substance (yield 18%).

$^1$H-NMR (400 MHz, DMSO-d6) δ: 2.55 (6H, s), 4.64 (2H, d, J=6.3 Hz), 6.63 (1H, s), 7.55-7.68 (4H, m), 7.71 (1H, s), 8.12 (1H, brs), 8.41 (1H, s), 9.25 (1H, t, J=6.3 Hz).

Example 39

Preparation of 6-chloro-4-{[3-(4-methylpiperazin-1-yl)benzyl]amino}pyridine-3-carboxyamide

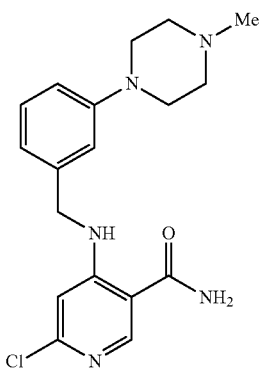 [SMILES: CN1CCN(c2cccc(CNc3cc(Cl)ncc3C(N)=O)c2)CC1]

From 4,6-dichloropyridine-3-carboxyamide and 3-(4-methylpiperazin-1-yl)benzylamine in a manner similar to Example 1, the title compound was obtained as a slight yellow amorphous substance (yield 79%).

$^1$H-NMR (400 MHz, CDCl$_3$) δ: 2.34 (3H, s), 2.58-2.63 (4H, m), 3.18-3.24 (4H, m), 4.41 (2H, s), 6.65 (1H, s), 6.84 (1H, d, J=7.7 Hz), 6.90 (1H, d, J=7.7 Hz), 6.97 (1H, s), 7.23 (1H, dd, J=7.7, 7.7 Hz), 8.35 (1H, s).

Example 40

Preparation of 4-[(3-ethoxycarbonylbenzyl)amino]-6-chloropyridine-3-carboxyamide

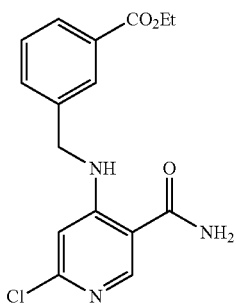 [SMILES: CCOC(=O)c1cccc(CNc2cc(Cl)ncc2C(N)=O)c1]

From 4,6-dichloropyridine-3-carboxyamide and 3-(ethoxycarbonyl)benzylamine in a manner similar to Example 1, the title compound was obtained as a light brown solid (yield 30%).

$^1$H-NMR (400 MHz, DMSO-d6) δ: 1.31 (3H, t, J=7.1 Hz), 4.31 (2H, q, J=7.1 Hz), 4.58 (2H, d, J=6.1 Hz), 6.64 (1H, s), 7.48-7.63 (3H, m), 7.87 (1H, d, J=8.1 Hz), 7.93 (1H, s), 8.12 (1H, s), 8.42 (1H, s), 9.22 (1H, t, J=7.7 Hz).

Example 41

Preparation of 6-chloro-4-{[(1S)-1-phenylethyl]amino}pyridine-3-carboxyamide

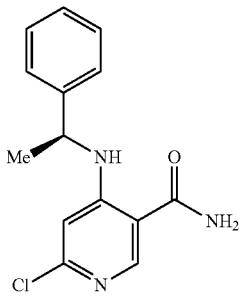 [SMILES: C[C@H](Nc1cc(Cl)ncc1C(N)=O)c1ccccc1]

From 4,6-dichloropyridine-3-carboxyamide and (S)-(−)-1-phenethylamine in a manner similar to Example 1, the title compound was obtained as colorless needle crystals (yield 88%).

$^1$H-NMR (400 MHz, CDCl$_3$) δ: 1.59 (3H, d, J=6.8 Hz), 4.53 (1H, quint, J=6.8 Hz), 5.86 (2H, br), 6.33 (1H, s), 7.25-7.38 (5H, m), 8.26 (1H, s), 8.91 (1H, brd, J=5.4 Hz).

Example 42

Preparation of 6-chloro-4-{[(1R)-1-phenylethyl]amino}pyridine-3-carboxyamide

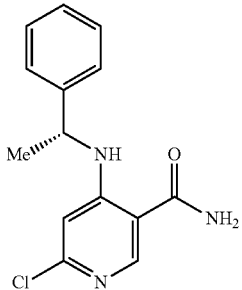 [SMILES: C[C@@H](Nc1cc(Cl)ncc1C(N)=O)c1ccccc1]

From 4,6-dichloropyridine-3-carboxyamide and (R)-(+)-1-phenethylamine in a manner similar to Example 1, the title compound was obtained as colorless needle crystals (yield 92%).

$^1$H-NMR (400 MHz, CDCl$_3$) δ: 1.58 (3H, d, J=6.8 Hz), 4.53 (1H, quint, J=6.8 Hz), 5.81 (2H, br), 6.34 (1H, s), 7.25-7.38 (5H, m), 8.25 (1H, s), 8.91 (1H, brd, J=6.4 Hz).

Example 43

Preparation of 4-[benzyl(methyl)amino]-6-chloropyridine-3-carboxyamide

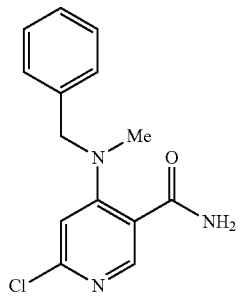 [SMILES: CN(Cc1ccccc1)c1cc(Cl)ncc1C(N)=O]

From 4,6-dichloropyridine-3-carboxyamide and N-benzylamine in a manner similar to Example 1, the title compound was obtained as a white crystalline powder (yield 87%).

¹H-NMR (400 MHz, CDCl₃+CD₃OD) δ: 2.93 (3H, s), 4.51 (2H, s), 6.70 (1H, s), 7.13-7.19 (2H, m), 7.27-7.38 (3H, m), 8.26 (1H, s).

Example 44

Preparation of 6-chloro-4-[(naphthalen-1-ylmethyl)amino]pyridine-3-carboxyamide

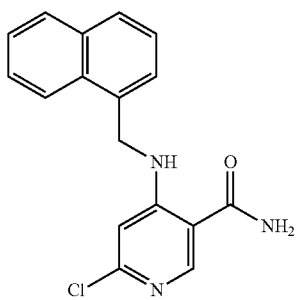 [SMILES: NC(=O)c1cnc(Cl)cc1NCc1cccc2ccccc12]

From 4,6-dichloropyridine-3-carboxyamide and 1-naphthalenemethylamine in a manner similar to Example 1, the title compound was obtained as a colorless crystalline powder (yield 88%).

¹H-NMR (400 MHz, DMSO-d6) δ: 4.93 (2H, d, J=5.4 Hz), 6.79 (1H, s), 7.45-7.62 (4H, m), 7.88-8.12 (3H, m), 8.45 (1H, s), 9.18 (1H, br).

Example 45

Preparation of 6-chloro-4-[(naphthalen-2-ylmethyl)amino]pyridine-3-carboxyamide

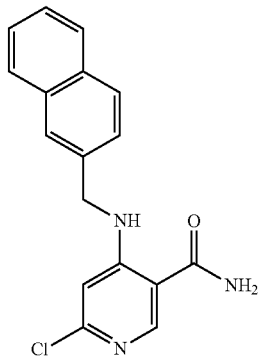 [SMILES: NC(=O)c1cnc(Cl)cc1NCc1ccc2ccccc2c1]

From 4,6-dichloropyridine-3-carboxyamide and 2-naphthalenemethylamine in a manner similar to Example 1, the title compound was obtained as a colorless crystalline powder (yield 85%).

¹H-NMR (400 MHz, DMSO-d6) δ: 4.65 (2H, d, J=5.9 Hz), 6.68 (1H, s), 7.47-7.56 (4 m), 7.83-7.93 (3H, m), 8.44 (1H, s), 9.28 (1H, br).

Example 46

Preparation of 4-(benzylamino)-6-(phenylamino)pyridine-3-carboxyamide

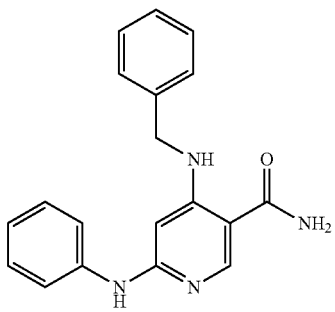 [SMILES: NC(=O)c1cnc(Nc2ccccc2)cc1NCc1ccccc1]

To 25 mg of 4-(benzylamino)-6-chloropyridine-3-carboxyamide suspended in 0.2 mL of diphenylether, 18 mg of aniline and 9 mg of methanesulfonic acid were added and stirred at 180° C. for 30 minutes. After cooling, the reaction mixture was dissolved in chloroform, washed with saturated aqueous sodium bicarbonate, and dried on anhydrous sodium sulfate. The solvent was evaporated and the residue was purified by silica gel column chromatography (chloroform:methanol=40:1-10:1) to obtain 30 mg (99%) of the title compound as a slight yellow crystalline powder.

¹H-NMR (400 MHz, CDCl₃) δ: 4.35 (2H, d, J=5.6 Hz), 5.91 (1H, s), 6.63 (2H, br), 6.95-7.07 (3H, m), 7.20-7.37 (7H, m), 8.22 (1H, s), 8.94 (1H, brt, J=5.6 Hz).

IR (ATR): 1636, 1612, 1597, 1574, 1549, 1411, 1303, 1256 cm⁻¹.

Example 47

Preparation of 4-(benzylamino)-6-[(2-methoxyphenyl)amino]pyridine-3-carboxyamide

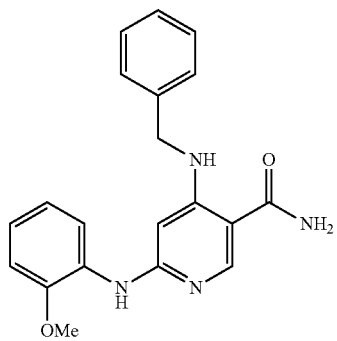 [SMILES: COc1ccccc1Nc1cc(NCc2ccccc2)c(C(N)=O)cn1]

From 4-(benzylamino)-6-chloropyridine-3-carboxyamide (the compound of Example 1) and 2-methoxyaniline in a manner similar to Example 46, the title compound was obtained as a light brown crystalline powder (yield 87%).

¹H-NMR (400 MHz, CDCl₃) δ: 3.83 (3H, s), 4.37 (2H, d, J=5.6 Hz), 5.73 (2H, br), 5.95 (1H, s), 6.77-6.82 (1H, m), 6.82-6.91 (2H, m), 6.93-6.99 (1H, m), 7.27-7.39 (6H, m), 8.26 (1H, s), 8.88 (1H, brt, J=5.6 Hz).

IR (ATR): 1649, 1618, 1594, 1571, 1525, 1507, 1454, 1409, 1311, 1292, 1245, 1027 cm$^{-1}$.

Example 48

Preparation of 4-(benzylamino)-6-[(3-methoxyphenyl)amino]pyridine-3-carboxyamide

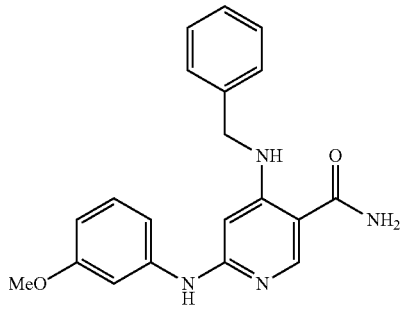 [SMILES: COc1cccc(Nc2cc(NCc3ccccc3)c(C(N)=O)cn2)c1]

From 4-(benzylamino)-6-chloropyridine-3-carboxyamide (the compound of Example 1) and 3-methoxyaniline in a manner similar to Example 46, the title compound was obtained as slight yellow needle crystals (yield 78%).

$^1$H-NMR (400 MHz, CDCl$_3$) δ: 3.72 (3H, s), 4.35 (2H, d, J=5.6 Hz), 5.64 (2H, br), 5.98 (1H, s), 6.55-6.62 (2H, m), 6.67-6.72 (2H, m), 7.12 (1H, dd, J=8.2, 8.2 Hz), 7.25-7.37 (5H, m), 8.22 (1H, s), 8.91 (1H, brt, J=5.6 Hz).

IR (ATR): 1634, 1598, 1578, 1493, 1415, 1303, 1249, 1233, 1160 cm$^{-1}$.

Example 49

Preparation of 4-(benzylamino)-6-[(4-methoxyphenyl)amino]pyridine-3-carboxyamide

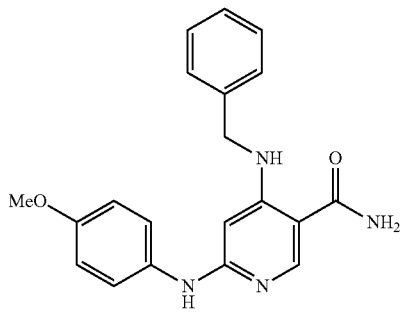 [SMILES: COc1ccc(Nc2cc(NCc3ccccc3)c(C(N)=O)cn2)cc1]

From 4-(benzylamino)-6-chloropyridine-3-carboxyamide (the compound of Example 1) and 4-methoxyaniline in a manner similar to Example 46, the title compound was obtained as slight yellow needle crystals (yield 90%).

$^1$H-NMR (400 MHz, CDCl$_3$) δ: 3.81 (3H, s), 4.30 (2H, d, J=5.8 Hz), 5.56 (2H, br), 5.70 (1H, s), 6.43 (1H, brs), 6.79 (2H, d, J=9.0 Hz), 6.92 (2H, d, J=9.0 Hz), 7.23-7.36 (5H, m), 8.19 (1H, s), 8.89 (1H, brt, J=5.8 Hz).

IR (ATR): 1638, 1604, 1576, 1511, 1418, 1258, 1237 cm$^{-1}$.

Example 50

Preparation of 4-(benzylamino)-6-[(4-hydroxyphenyl)amino]pyridine-3-carboxyamide

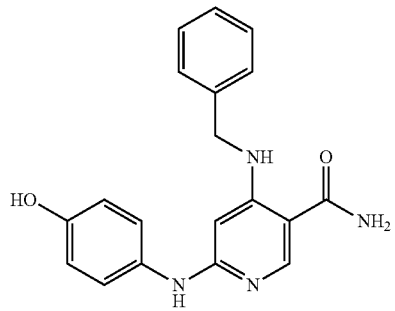 [SMILES: NC(=O)c1cnc(Nc2ccc(O)cc2)cc1NCc1ccccc1]

From 4-(benzylamino)-6-chloropyridine-3-carboxyamide (the compound of Example 1) and 4-hydroxyaniline in a manner similar to Example 46, the title compound was obtained as a purple crystalline powder (yield 12%).

$^1$H-NMR (400 MHz, CDCl$_3$) δ: 4.31 (2H, s), 5.69 (1H, s), 6.60-6.66 (3H, m), 6.70 (2H, d, J=9.0 Hz), 6.89 (2H, d, J=9.0 Hz), 7.24-7.35 (2H, m), 8.19 (1H, s).

IR (ATR): 1630, 1508, 1411, 1251, 834, 738 cm$^{-1}$.

Example 51

Preparation of 4-(benzylamino)-6-{4-[2-(morpholino) ethoxy]phenyl}amino)pyridine-3-carboxyamide

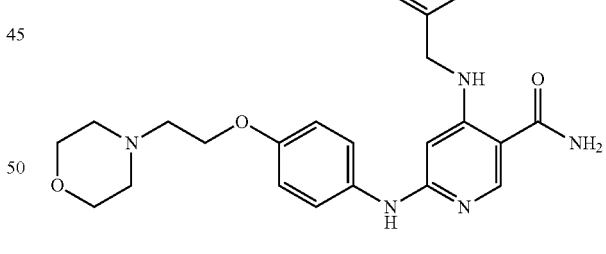

From 4-(benzylamino)-6-chloropyridine-3-carboxyamide (the compound of Example 1) and 4-[2-(morpholino)ethoxy] aniline in a manner similar to Example 46, the title compound was obtained as a colorless crystalline powder (yield 79%).

$^1$H-NMR (400 MHz, CDCl$_3$) δ: 2.58-2.61 (4H, m), 2.82 (2H, t, J=5.9 Hz), 3.74-3.77 (4H, m), 4.10 (2H, t, J=5.9 Hz), 4.30 (2H, d, J=5.6 Hz), 5.55 (1H, br), 5.71 (1H, s), 6.79 (2H, d, J=8.8 Hz), 6.93 (2H, d, J=8.8 Hz), 7.24-7.36 (5H, m), 8.19 (1H, s), 8.87 (1H, br).

IR (ATR): 1632, 1608, 1510, 1406, 1291, 1238 cm$^{-1}$.

Example 52

Preparation of 4-(benzylamino)-6-({4-[(1-methylpiperidin-4-yl)oxy]phenyl}amino)pyridine-3-carboxyamide

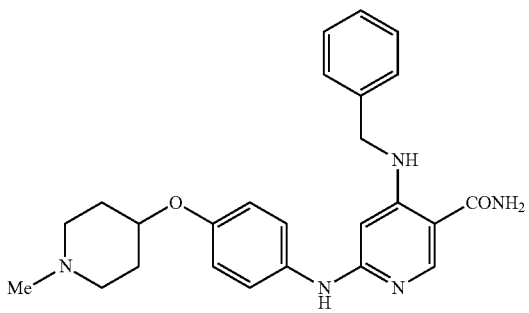 [SMILES: CN1CCC(Oc2ccc(Nc3cc(NCc4ccccc4)c(C(N)=O)cn3)cc2)CC1]

From 4-(benzylamino)-6-chloropyridine-3-carboxyamide (the compound of Example 1) and 4-[(1-methylpiperidin-4-yl)oxy]aniline in a manner similar to Example 46, the title compound was obtained as a light brown crystalline powder (yield 44%).

$^1$H-NMR (400 MHz, CDCl$_3$) δ: 1.80-1.90 (2H, m), 1.96-2.06 (2H, m), 2.28-2.32 (2H, m), 2.32 (3H, s), 2.60-2.76 (2H, m), 4.31 (2H, d, J=5.9 Hz), 5.54 (1H, br), 5.72 (1H, s), 6.79 (2H, d, J=9.0 Hz), 6.91 (2H, d, J=9.0 Hz), 7.30-7.40 (5H, m), 8.19 (1H, s), 8.87 (1H, br).

IR (ATR): 1712, 1413, 1387, 1254, 1214, 850 cm$^{-1}$.

Example 53

Preparation of 4-(benzylamino)-6-[(4-cyclohexylphenyl)amino]pyridine-3-carboxyamide

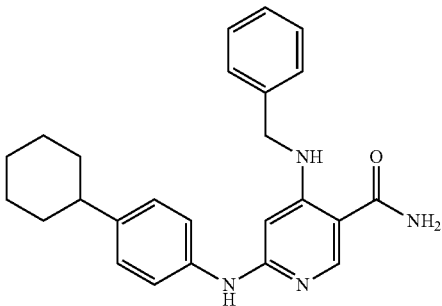 [SMILES: NC(=O)c1cnc(Nc2ccc(C3CCCCC3)cc2)cc1NCc1ccccc1]

From 4-(benzylamino)-6-chloropyridine-3-carboxyamide (the compound of Example 1) and 4-cyclohexylaniline in a manner similar to Example 46, the title compound was obtained as a slight yellow crystalline powder (yield 81%).

$^1$H-NMR (400 MHz, CDCl$_3$) δ: 1.21-1.32 (1H, m), 1.33-1.47 (4H, m), 1.72-1.80 (1H, m), 1.81-1.91 (4H, m), 2.43-2.51 (1H, m), 4.33 (2H, d, J=5.9 Hz), 5.56 (2H, br), 5.87 (1H, s), 6.48 (1H, brs), 6.90 (2H, d, J=8.5 Hz), 7.06 (2H, d, J=8.5 Hz), 7.27-7.37 (5H, m), 8.20 (1H, s), 8.89 (1H, brt, J=5.9 Hz).

IR (ATR): 1639, 1597, 1571, 1547, 1410, 1305, 1255 cm$^{-1}$.

Example 54

Preparation of 4-(benzylamino)-6-[(4-bromophenyl)amino]pyridine-3-carboxyamide

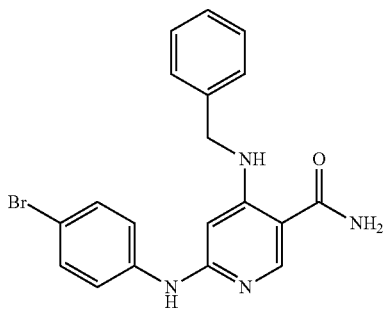 [SMILES: NC(=O)c1cnc(Nc2ccc(Br)cc2)cc1NCc1ccccc1]

From 4-(benzylamino)-6-chloropyridine-3-carboxyamide (the compound of Example 1) and 4-bromoaniline in a manner similar to Example 46, the title compound was obtained as colorless needle crystals (yield 84%).

$^1$H-NMR (400 MHz, CDCl$_3$) δ: 4.37 (2H, d, J=5.6 Hz), 5.58 (2H, br), 5.82 (1H, s), 6.45 (1H, brs), 6.87 (2H, d, J=8.8 Hz), 7.27-7.39 (7H, m), 8.22 (1H, s), 8.95 (1H, brt, J=5.6 Hz).

IR (ATR): 1639, 1612, 1603, 1570, 1548, 1500, 1417, 1396, 1303 cm$^{-1}$.

Example 55

Preparation of 4-(benzylamino)-6-[(4-cyanophenyl)amino]pyridine-3-carboxyamide

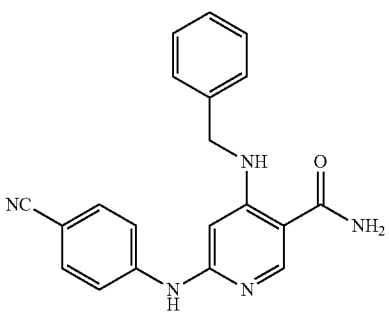 [SMILES: N#Cc1ccc(Nc2cc(NCc3ccccc3)c(C(N)=O)cn2)cc1]

20 mg of 4-(benzylamino)-6-[(4-bromophenyl)amino]pyridine-3-carboxyamide (the compound of Example 54) was dissolved in 0.4 mL of 1-methyl-2-pyrrolidinone, to which 5 mg of copper cyanide (I) was added, and stirred at 180° C. for 3 hours. After cooling, a 30% aqueous solution of ethylenediamine was added to the reaction mixture, extracted with chloroform, the extract was washed with water, and dried on anhydrous sodium sulfate. The solvent was evaporated and the residue was purified by silica gel thin layer chromatography (chloroform:methanol=10:1) to obtain 2.3 mg (13%) of the title compound as a light brown solid.

$^1$H-NMR (400 MHz, CDCl$_3$) δ: 4.43 (2H, d, J=5.9 Hz), 5.70 (2H, br), 5.92 (1H, s), 6.96 (1H, brs), 7.09 (2H, d, J=8.6 Hz), 7.27-7.64 (7H, m), 8.25 (1H, s), 9.01 (1H, brt, J=5.9 Hz).

IR (ATR): 2220, 1653, 1625, 1600, 1507, 1498, 1406, 1312, 1250, 1175 cm$^{-1}$.

Example 56

Preparation of 4-(benzylamino)-6-{[4-piperidino)phenyl])amino}pyridine-3-carboxyamide

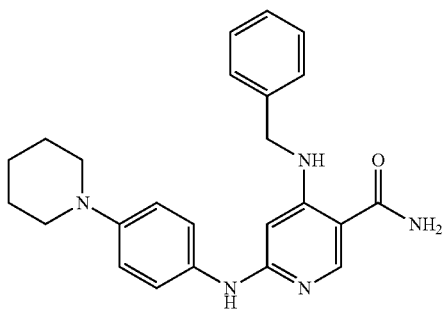

From 4-(benzylamino)-6-chloropyridine-3-carboxyamide (the compound of Example 1) and 4-(piperidino)aniline in a manner similar to Example 46, the title compound was obtained as a slight yellow crystalline powder (yield 68%).

¹H-NMR (400 MHz, CDCl$_3$) δ: 1.55-1.63 (2H, m), 1.70-1.77 (4H, m), 3.10-3.15 (4H, m), 4.29 (2H, d, J=5.6 Hz), 5.54 (2H, br), 5.74 (1H, s), 6.39 (1H, s), 6.83 (2H, d, J=9.0 Hz), 6.90 (2H, d, J=9.0 Hz), 7.24-7.36 (5H, m), 8.18 (1H, s), 8.85 (1H, brt, J=5.6 Hz).

IR (ATR): 1635, 1597, 1570, 1545, 1513, 1408, 1297, 1254, 1235, 1214 cm$^{-1}$.

Example 57

Preparation of 4-(benzylamino)-6-({4-[4-(2-hydroxyethyl)piperidino]phenyl}amino)pyridine-3-carboxyamide

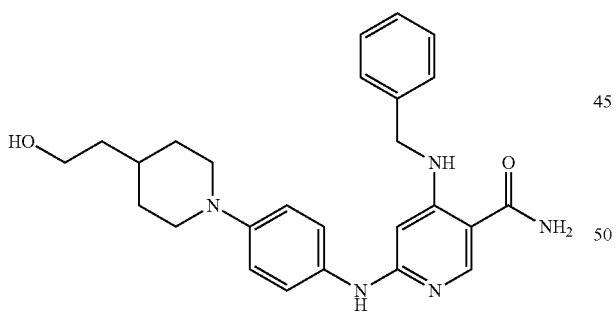

From 4-(benzylamino)-6-chloropyridine-3-carboxyamide (the compound of Example 1) and 4-[4-(2-hydroxyethyl)piperidino]aniline in a manner similar to Example 46, the title compound was obtained as slight brown needle crystals (yield 49%).

¹H-NMR (400 MHz, CDCl$_3$+CD$_3$OD) δ: 1.35-1.48 (2H, m), 1.54-1.62 (2H, m), 1.81-1.88 (2H, m), 2.65-2.73 (2H, m), 3.58-3.65 (2H, m), 3.72 (2H, d, J=6.3 Hz), 4.28 (2H, d, J=5.4 Hz), 5.74 (1H, s), 6.84 (2H, d, J=9.0 Hz), 6.88 (2H, d, J=9.0 Hz), 7.22-7.27 (2H, m), 7.27-7.36 (4H, m), 8.14 (1H, s), 8.90 (1H, brt, J=5.4 Hz).

IR (ATR): 3306, 1642, 1620, 1566, 1511, 1416, 1408, 1292 cm$^{-1}$.

Example 58

Preparation of 4-(benzylamino)-6-({4-[4-(2-methylsulfonyloxyethyl)piperidino]phenyl}amino)pyridine-3-carboxyamide

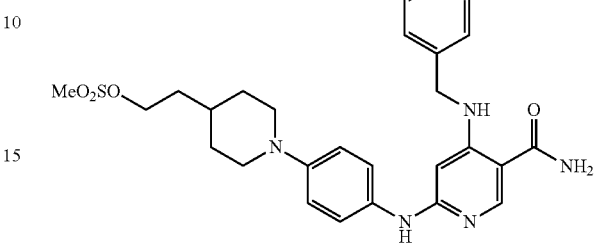

60 mg of 4-(benzylamino)-6-({4-[4-(2-hydroxyethyl)piperidin-1-yl]phenyl}amino)pyridine-3-carboxyamide (the compound of Example 57), 18 mg of triethylamine and 2 mg of 4-dimethylaminopyridine were dissolved in 5 mL of tetrahydrofuran, to which 18 mg of methanesulfonyl chloride was added under ice cooling, and stirred at the same temperature for 2 hours. Saturated aqueous sodium bicarbonate was added to the reaction mixture, extracted with chloroform, the extract was washed with water, and dried on anhydrous sodium sulfate. The solvent was evaporated and the residue was purified by silica gel thin layer chromatography (chloroform:methanol=5:1) to obtain 44 mg (62%) of the title compound as a light brown crystalline powder.

¹H-NMR (400 MHz, CDCl$_3$) δ: 1.34-1.50 (2H, m), 1.56-1.70 (1H, m), 1.76 (2H, q, J=6.5 Hz), 1.82-1.89 (2H, m), 2.65-2.73 (2H, m), 3.03 (3H, s), 3.58-3.66 (2H, m), 4.29 (2H, d, J=5.6 Hz), 5.66 (2H, br), 5.74 (1H, s), 6.69 (1H, brs), 6.81 (2H, d, J=9.0 Hz), 6.90 (2H, d, J=9.0 Hz), 7.23-7.35 (5H, m), 8.19 (1H, s), 8.89 (1H, brt, J=5.6 Hz).

Example 59

Preparation of 4-(benzylamino)-6-[(4-{4-[2-(diethylamino)ethyl]piperidino}phenyl)amino]pyridine-3-carboxyamide

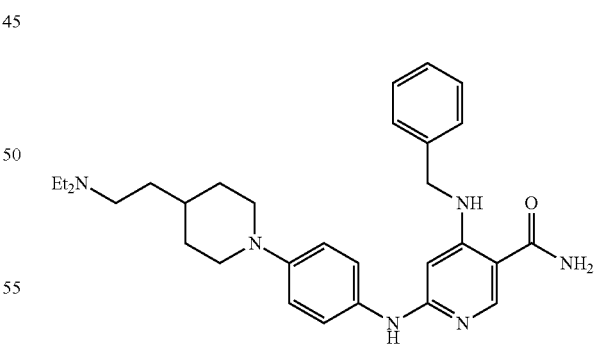

20 mg of 4-(benzylamino)-6-({4-[4-(2-methylsulfonyloxyethyl)piperidino]phenyl}amino)pyridine-3-carboxyamide (the compound of Example 58) was dissolved in 1 mL of ethanol, to which 0.5 mL of diethylamine was added, and stirred in a sealed tube at 100° C. for 3 hours. After cooling, the solvent was evaporated and the residue was purified by silica gel thin layer chromatography (chloroform:ammonia methanol=10:1) to obtain 13 mg (68%) of the title compound as a slight brown crystalline powder.

¹H-NMR (400 MHz, CDCl₃) δ: 1.04 (6H, t, J=7.1 Hz), 1.35-1.50 (2H, m), 1.68-1.87 (4H, m), 2.43-2.53 (2H, m), 2.55 (4H, q, J=7.1 Hz), 2.64-2.72 (2H, m), 3.58-3.64 (2H, m), 4.29 (2H, d, J=5.6 Hz), 5.57 (2H, br), 5.74 (1H, s), 6.43 (1H, brs), 6.82 (2H, d, J=9.0 Hz), 6.89 (2H, d, J=9.0 Hz), 7.24-7.35 (5H, m), 8.18 (1H, s), 8.85 (1H, brt, J=5.6 Hz).

IR (ATR): 1606, 1571, 1513, 1410, 1306, 1246, 1211 cm⁻¹.

Example 60

Preparation of 4-(benzylamino)-6-({4-[4-(2-cyanoethyl)piperidino]phenyl}amino)pyridine-3-carboxyamide

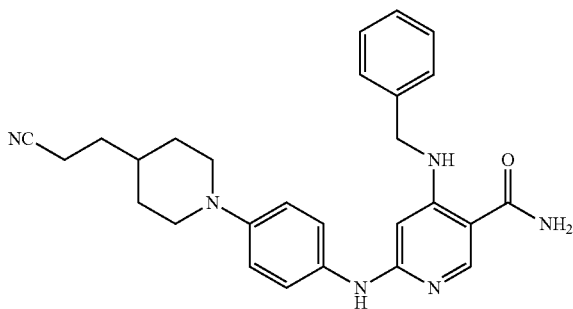 [SMILES: N#CCCC1CCN(c2ccc(Nc3cc(NCc4ccccc4)c(C(N)=O)cn3)cc2)CC1]

20 mg of 4-(benzylamino)-6-({4-[4-(2-methylsulfonyloxyethyl)piperidino]phenyl}amino)pyridine-3-carboxyamide (the compound of Example 58) was dissolved in 0.5 mL of N,N-dimethylformamide, to which 3 mg of sodium cyanide and 9 mg of sodium iodide were added, and stirred overnight at 120° C. After cooling, the solvent was evaporated, water was added to the residue, and extracted with chloroform. The extract was washed with water and dried on anhydrous sodium sulfate. The solvent was evaporated and the residue was purified by silica gel thin layer chromatography (chloroform:methanol=8:1) to obtain 6 mg (29%) of the title compound as a light yellow crystalline powder.

¹H-NMR (400 MHz, CDCl₃) δ: 1.35-1.46 (2H, m), 1.57-1.66 (1H, m), 1.68 (2H, q, J=7.1 Hz), 1.80-1.89 (2H, m), 2.43 (2H, q, J=7.1 Hz), 2.66-2.75 (2H, m), 3.60-3.67 (2H, m), 4.30 (2H, d, J=5.6 Hz), 5.62 (2H, br), 5.75 (1H, s), 6.64 (1H, brs), 6.82 (2H, d, J=8.9 Hz), 6.91 (2H, d, J=8.9 Hz), 7.24-7.36 (5H, m), 8.20 (1H, s), 8.89 (1H, brt, J=5.6 Hz).

IR (ATR): 2246, 1650, 1618, 1569, 1513, 1408, 1306, 1295, 1256, 1239 cm⁻¹.

Example 61

Preparation of 4-(benzylamino)-6-({4-[4-(2-methoxyethyl)piperidino]phenyl}amino)pyridine-3-carboxyamide

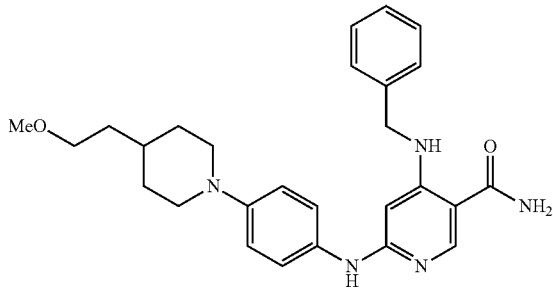

From 4-(benzylamino)-6-chloropyridine-3-carboxyamide (the compound of Example 1) and 4-[4-(2-methoxyethyl) piperidino]aniline in a manner similar to Example 46, the title compound was obtained as a light purple crystalline powder (yield 73%).

¹H-NMR (400 MHz, CDCl₃) δ: 1.36-1.44 (2H, m), 1.56-1.70 (3H, m), 1.81-1.85 (2H, m), 2.65-2.72 (2H, m), 3.36 (3H, s), 3.47 (2H, t, J=6.3 Hz), 3.60-3.63 (2H, m), 4.29 (2H, d, J=5.6 Hz), 5.74 (1H, s), 6.42 (1H, s), 6.82 (2H, d, J=9.0 Hz), 6.89 (2H, d, J=9.0 Hz), 7.24-7.35 (5H, m), 8.18 (1H, s), 8.85 (1H, br).

IR (ATR): 1621, 1606, 1516, 1407, 1298, 738 cm⁻¹.

Example 62

Preparation of 4-(benzylamino)-6-{[4-(4-{2-[(4-methoxybenzyl)oxy]ethyl}piperidino)phenyl]amino}pyridine-3-carboxyamide

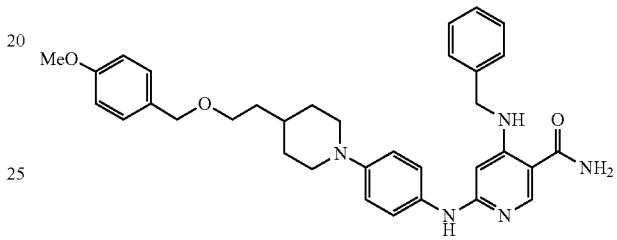

From 4-(benzylamino)-6-chloropyridine-3-carboxyamide (the compound of Example 1) and 4-(4-{2-[(4-methoxybenzyl)oxy]ethyl}piperidino)aniline in a manner similar to Example 46, the title compound was obtained as a light yellow crystalline powder (yield 42%).

¹H-NMR (400 MHz, CDCl₃) δ: 1.32-1.44 (2H, m), 1.57-1.63 (3H, m), 1.71-1.84 (2H, m), 2.63-2.71 (2H, m), 3.50-3.55 (2H, m), 3.57-3.63 (2H, m), 3.81 (3H, s), 4.29 (2H, d, J=6.6 Hz), 4.45 (2H, s), 5.56 (1H, s), 5.74 (2H, br), 6.43 (1H, brs), 6.82 (2H, d, J=8.7 Hz), 6.89 (2H, d, J=8.7 Hz), 6.90 (2H, d, J=8.7 Hz), 7.24-7.35 (7H, m), 8.19 (1H, s), 8.87 (1H, brt, J=5.6 Hz).

IR (ATR): 1657, 1613, 1588, 1540, 1514, 1404, 1302, 1288, 1257, 1242 cm⁻¹.

Example 63

Preparation of 4-(benzylamino)-6-[(4-{4-[2-(benzyloxy)ethyl]piperidino}phenyl)amino]pyridine-3-carboxyamide

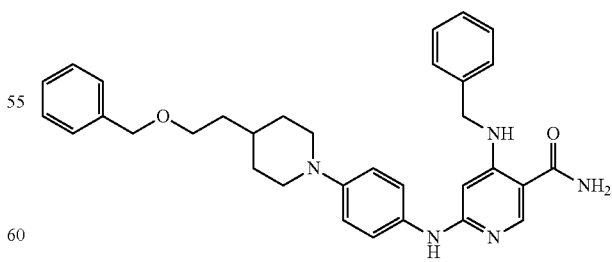

From 4-(benzylamino)-6-chloropyridine-3-carboxyamide (the compound of Example 1) and 4-{4-[2-(benzyloxy)ethyl] piperidino}aniline in a manner similar to Example 46, the title compound was obtained as a white crystalline powder (yield 58%).

¹H-NMR (400 MHz, CDCl₃) δ: 1.30-1.45 (2H, m), 1.55-1.70 (1H, m), 1.81 (2H, d, J=13.9 Hz), 2.62-2.74 (2H, m), 3.54-3.61 (4H, m), 4.29 (2H, d, J=5.6 Hz), 4.53 (2H, s), 5.55 (2H, s), 5.74 (1H, s), 6.40 (1H, s), 6.81 (2H, d, J=9.0 Hz), 6.90 (2H, d, J=8.8 Hz), 7.24-7.36 (10H, m), 8.18 (1H, s), 8.85 (1H, t, J=5.5 Hz).

IR (ATR): 3379, 3186, 1637, 1608, 1513, 1410, 1294, 1259, 1121 cm⁻¹.

Example 64

Preparation of 4-(benzylamino)-6-[(4-{4-[2-(1H-pyrazol-1-yl)ethyl]piperidino}phenyl)amino]pyridine-3-carboxyamide

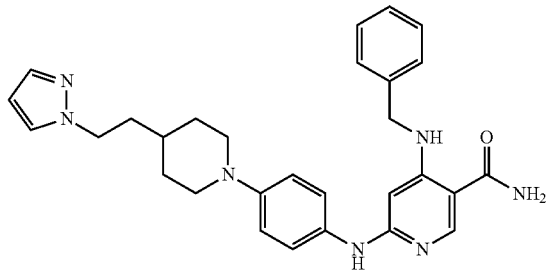 [SMILES: NC(=O)c1cnc(Nc2ccc(N3CCC(CCn4cccn4)CC3)cc2)cc1NCc1ccccc1]

From 4-(benzylamino)-6-chloropyridine-3-carboxyamide (the compound of Example 1) and 4-{4-[2-(1H-pyrazol-1-yl)ethyl]piperidino}aniline in a manner similar to Example 46, the title compound was obtained as a white crystalline powder (yield 65%).

¹H-NMR (400 MHz, CD₃OD) δ: 1.37-1.45 (3H, m), 1.81-1.87 (4H, m), 2.58-2.64 (2H, t, J=11.5 Hz), 3.58 (2H, d, J=12.4 Hz), 4.23-4.26 (2H, t, J=7.8 Hz), 4.33 (2H, s), 5.76 (1H, s), 6.29 (1H, m), 6.88 (2H, d, J=9.0 Hz), 6.98 (2H, d, J=8.8 Hz), 7.21-7.34 (5H, m), 7.48 (1H, s), 7.65 (1H, s), 8.21 (1H, s).

IR (ATR): 1624, 1593, 1512, 1408, 1292, 1257, 1231 cm⁻¹

Example 65

Preparation of 6-[(4-aminophenyl)amino]-4-(benzylamino)pyridine-3-carboxyamide

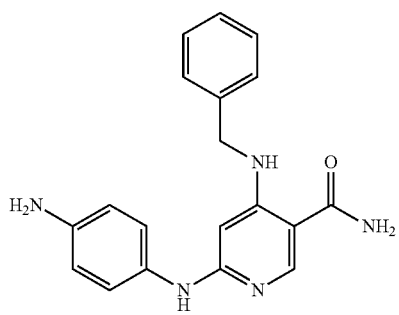 [SMILES: NC(=O)c1cnc(Nc2ccc(N)cc2)cc1NCc1ccccc1]

From 4-(benzylamino)-6-chloropyridine-3-carboxyamide (the compound of Example 1) and 1,4-phenylenediamine in a manner similar to Example 46, the title compound was obtained as slight yellow needle crystals (yield 91%).

¹H-NMR (400 MHz, CDCl₃) δ: 3.63 (2H, br), 4.28 (2H, d, J=5.6 Hz), 5.52 (2H, br), 5.68 (1H, s), 6.31 (1H, brs), 6.59 (2H, d, J=8.8 Hz), 6.82 (2H, d, J=8.8 Hz), 7.23-7.36 (5H, m), 8.18 (1H, s), 8.85 (1H, brt, J=5.6 Hz).

IR (ATR): 1633, 1608, 1572, 1550, 1514, 1408, 1304, 1252 cm⁻¹.

Example 66

Preparation of 6-[(4-aminophenyl)amino]-4-[(2,3-difluorobenzyl)amino]pyridine-3-carboxyamide

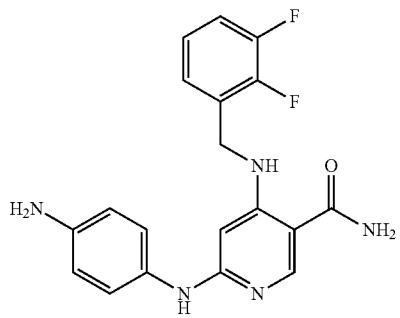 [SMILES: NC(=O)c1cnc(Nc2ccc(N)cc2)cc1NCc1cccc(F)c1F]

From 6-chloro-4-[(2,3-difluorobenzyl)amino]pyridine-3-carboxyamide (the compound of Example 19) and 1,4-phenylenediamine in a manner similar to Example 46, the title compound was obtained as a light brown crystalline powder (yield 91%).

¹H-NMR (400 MHz, CDCl₃) δ: 3.66 (2H, br), 4.35 (2H, d, J=5.9 Hz), 5.58 (2H, br), 5.60 (1H, s), 6.36 (1H, brs), 6.62 (2H, d, J=8.5 Hz), 6.85 (2H, d, J=8.5 Hz), 6.99-7.12 (3H, m), 8.18 (1H, s), 8.87 (1H, br).

Example 67

Preparation of 6-[(4-aminophenyl)amino]-4-[(3,5-difluorobenzyl)amino]pyridine-3-carboxyamide

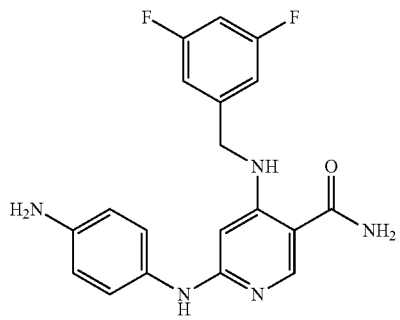 [SMILES: NC(=O)c1cnc(Nc2ccc(N)cc2)cc1NCc1cc(F)cc(F)c1]

From 6-chloro-4-[(3,5-difluorobenzyl)amino]pyridine-3-carboxyamide (the compound of Example 20) and 1,4-phenylenediamine in a manner similar to Example 46, the title compound was obtained as a light purple crystalline powder (yield 88%).

¹H-NMR (400 MHz, CDCl₃) δ: 4.24 (2H, q, J=5.4 Hz), 5.50 (1H, s), 6.61 (2H, d, J=8.9 Hz), 6.69-6.76 (3H, m), 6.78 (2H, d, J=8.9 Hz), 8.16 (1H, s), 8.96 (1H, br).

Example 68

Preparation of 6-[(4-aminophenyl)amino]-4-[(3-nitrobenzyl)amino]pyridine-3-carboxyamide

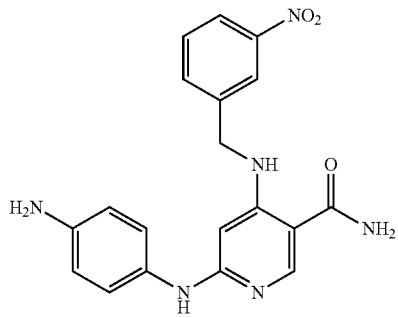 [SMILES: NC(=O)c1cnc(Nc2ccc(N)cc2)cc1NCc1cccc([N+](=O)[O-])c1]

From 6-chloro-4-[(3-nitrobenzyl)amino]pyridine-3-carboxyamide (the compound of Example 31) and 1,4-phenylenediamine in a manner similar to Example 46, the title compound was obtained as a light red crystalline powder (yield 59%).

¹H-NMR (400 MHz, CDCl₃) δ: 3.64 (2H, brs), 4.37 (2H, d, J=5.8 Hz), 5.43 (1H, s), 5.55 (2H, brs), 6.30 (1H, brs), 6.52 (2H, d, J=8.3 Hz), 6.75 (2H, d, J=8.3 Hz), 7.49 (1H, t, J=7.9 Hz), 7.60 (1H, d, J=7.6 Hz), 8.03 (1H, s), 8.13 (1H, d, J=8.8 Hz), 8.19 (1H, s), 9.03 (1H, s).

Example 69

Preparation of 6-[(2-aminophenyl)amino]-4-(3,5-difluorobenzyl)amino]pyridine-3-carboxyamide

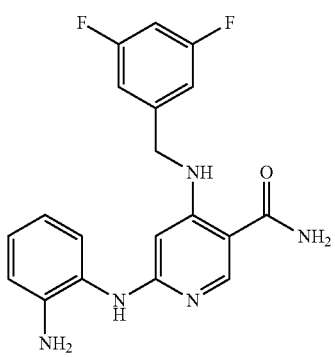 [SMILES: NC(=O)c1cnc(Nc2ccccc2N)cc1NCc1cc(F)cc(F)c1]

From 6-chloro-4-[(3,5-difluorobenzyl)amino]pyridine-3-carboxyamide (the compound of Example 20) and 1,2-phenylenediamine in a manner similar to Example 46, the title compound was obtained as a light brown powder (yield 17%).

¹H-NMR (270 MHz, DMSO-d6) δ: 4.31 (2H, d, J=5.8 Hz), 5.52 (1H, s), 6.42 (1H, t, J=7.6 Hz), 6.66-6.72 (1H, m), 6.79-6.94 (4H, m), 7.02-7.16 (1H, m), 7.85 (1H, s), 8.30 (1H, s), 9.06 (1H, t, J=5.8 Hz).

Example 70

Preparation of 4-(benzylamino)-6-({4-[(2-morpholinoethyl)amino]phenyl}amino)pyridine-3-carboxyamide

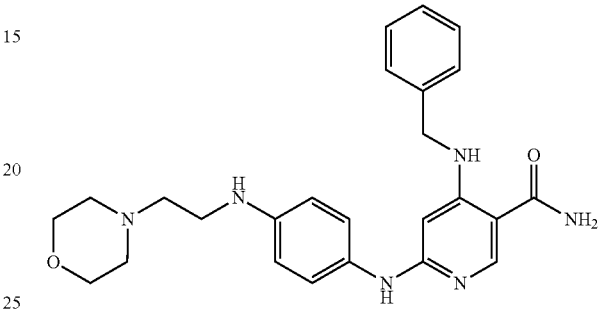

From 4-(benzylamino)-6-chloropyridine-3-carboxyamide (the compound of Example 1) and 4-[2-(morpholinoethyl)amino]aniline in a manner similar to Example 46, the title compound was obtained as a slight brown solid (yield 55%).

¹H-NMR (400 MHz, CDCl₃) δ: 2.45-2.54 (4H, m), 2.64-2.67 (2H, t, J=5.9 Hz), 3.16-3.19 (2H, t, J=5.9 Hz), 3.73-3.75 (4H, t, J=4.5 Hz), 4.27 (2H, d, J=5.6 Hz), 5.54 (2H, s), 5.68 (1H, s), 6.36 (1H, s), 6.54 (2H, d, J=8.8 Hz), 6.86 (2H, d, J=8.8 Hz), 7.24-7.35 (6H, m), 8.18 (1H, s), 8.85 (1H, t, J=5.6 Hz).

IR (ATR): 3187, 1654, 1614, 1571, 1518, 1409, 1268, 1114 cm⁻¹.

Example 71

Preparation of 4-(benzylamino)-6-({4-[methyl(2-morpholinoethyl)amino]phenyl}amino)pyridine-3-carboxyamide

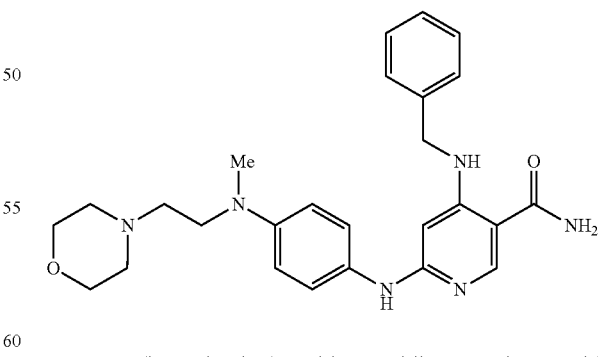

From 4-(benzylamino)-6-chloropyridine-3-carboxyamide (the compound of Example 1) and 4-[methyl(2-morpholinoethyl)amino]aniline in a manner similar to Example 46, the title compound was obtained as a slight brown solid (yield 66%).

¹H-NMR (400 MHz, CDCl₃) δ: 2.46-2.58 (6H, m), 2.96 (1H, s), 3.46-3.50 (2H, t, J=5.6 Hz), 3.72-3.74 (4H, t, J=4.6

Hz), 4.28 (2H, d, J=5.6 Hz), 5.54 (2H, s), 5.68 (1H, s), 6.36 (1H, s), 6.60 (2H, d, J=9.0 Hz), 6.89 (2H, d, J=8.8 Hz), 7.22-7.35 (5H, m), 8.18 (1H, s), 8.85 (1H, t, J=5.4 Hz).

IR (ATR): 3190, 1608, 1517, 1408, 1295, 1260, 1116 cm$^{-1}$.

Example 72

Preparation of 4-(benzylamino)-6-{(4-morpholinophenyl)amino]pyridine-3-carboxyamide

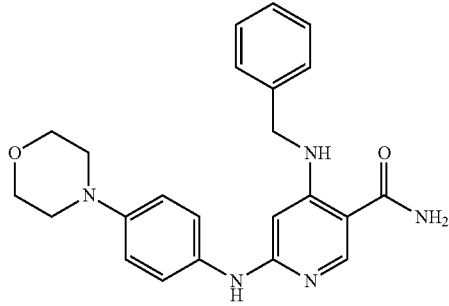 [SMILES: NC(=O)c1cnc(Nc2ccc(N3CCOCC3)cc2)cc1NCc1ccccc1]

From 4-(benzylamino)-6-chloropyridine-3-carboxyamide (the compound of Example 1) and 4-morpholinoaniline in a manner similar to Example 46, the title compound was obtained as slight yellow needle crystals (yield 84%).

m.p. 240-242° C. (dec.)

$^1$H-NMR (400 MHz, CDCl$_3$) δ: 3.11-3.15 (4H, m), 3.87-3.91 (4H, m), 4.31 (2H, d, J=5.6 Hz), 5.54 (2H, br), 5.75 (1H, s), 6.39 (1H, brs), 6.80 (2H, d, J=9.0 Hz), 6.93 (2H, d, J=9.0 Hz), 7.24-7.36 (5H, m), 8.19 (1H, s), 8.86 (1H, brt, J=5.6 Hz).

IR (ATR): 1637, 1578, 1548, 1514, 1407, 1297, 1269, 1235, 1225, 1121 cm$^{-1}$.

Example 73

Preparation of 4-[(2-methoxybenzyl)amino]-6-[(4-morpholinophenyl)amino]pyridine-3-carboxyamide

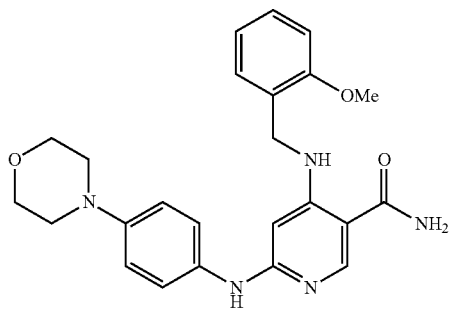 [SMILES: COc1ccccc1CNc1cc(Nc2ccc(N3CCOCC3)cc2)ncc1C(N)=O]

From 6-chloro-4-[(2-methoxybenzyl)amino]pyridine-3-carboxyamide (the compound of Example 2) and 4-morpholinoaniline in a manner similar to Example 46, the title compound was obtained as a slight yellow crystalline powder (yield 72%).

$^1$H-NMR (400 MHz, CDCl$_3$) δ: 3.10-3.15 (4H, m), 3.78 (3H, s), 3.86-3.89 (4H, m), 4.29 (2H, d, J=5.8 Hz), 5.67 (2H, br), 5.79 (1H, s), 6.66 (1H, brs), 6.82 (2H, d, J=8.8 Hz), 6.84-6.93 (2H, m), 7.02 (2H, d, J=8.8 Hz), 7.18 (1H, dd, J=7.3, 1.4 Hz), 7.23-7.27 (1H, m), 8.19 (1H, s), 8.79 (1H, brt, J=5.8 Hz).

Example 74

Preparation of 4-[(3-methoxybenzyl)amino]-6-[(4-morpholinophenyl)amino]pyridine-3-carboxyamide

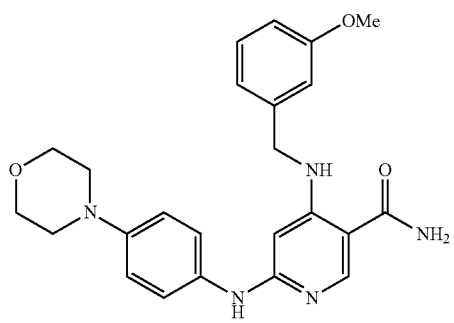 [SMILES: COc1cccc(CNc2cc(Nc3ccc(N4CCOCC4)cc3)ncc2C(N)=O)c1]

From 6-chloro-4-[(3-methoxybenzyl)amino]pyridine-3-carboxyamide (the compound of Example 3) and 4-morpholinoaniline in a manner similar to Example 46, the title compound was obtained as a colorless crystalline powder (yield 81%).

$^1$H-NMR (400 MHz, CDCl$_3$) δ: 3.12-3.15 (4H, m), 3.78 (3H, s), 3.86-3.90 (4H, m), 4.29 (2H, d, J=5.6 Hz), 5.54 (2H, br), 5.75 (1H, s), 6.40 (1H, brs), 6.78-6.88 (5H, m), 6.91 (2H, d, J=9.0 Hz), 7.24 (1H, dd, J=7.8, 7.8 Hz), 8.19 (1H, s), 8.87 (1H, brt, J=5.6 Hz).

IR (ATR): 1651, 1636, 1596, 1513, 1408, 1298, 1252, 1233, 1226, 1119 cm$^{-1}$.

Example 75

Preparation of 4-[(4-methoxybenzyl)amino]-6-[(4-morpholinophenyl)amino]pyridine-3-carboxyamide

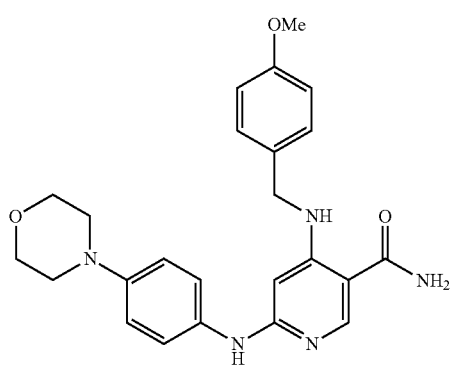 [SMILES: COc1ccc(CNc2cc(Nc3ccc(N4CCOCC4)cc3)ncc2C(N)=O)cc1]

From 6-chloro-4-[(4-methoxybenzyl)amino]pyridine-3-carboxyamide (the compound of Example 4) and 4-morpholinoaniline in a manner similar to Example 46, the title compound was obtained as a light brown crystalline powder (yield 70%).

$^1$H-NMR (400 MHz, CDCl$_3$) δ: 3.12-3.15 (4H, m), 3.81 (3H, s), 3.86-3.90 (4H, m), 4.22 (2H, d, J=5.4 Hz), 5.60 (2H, br), 5.77 (1H, s), 6.56 (1H, brs), 6.83 (2H, d, J=8.8 Hz), 6.86

(2H, d, J=8.8 Hz), 6.98 (2H, d, J=8.8 Hz), 7.17 (2H, d, J=8.8 Hz), 8.19 (1H, s), 8.79 (1H, brt, J=5.4 Hz).

IR (ATR): 1636, 1599, 1570, 1547, 1512, 1407, 1296, 1268, 1237, 1224, 1121 cm$^{-1}$.

Example 76

Preparation of 4-[(2-methylbenzyl)amino]-6-[(4-morpholinophenyl)amino]pyridine-3-carboxyamide

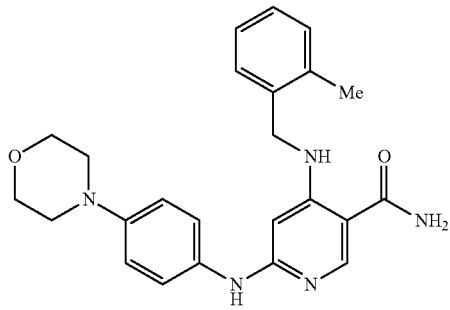 [SMILES: Cc1ccccc1CNc1cc(Nc2ccc(N3CCOCC3)cc2)ncc1C(N)=O]

From 6-chloro-4-[(2-methylbenzyl)amino]pyridine-3-carboxyamide (the compound of Example 5) and 4-morpholinoaniline in a manner similar to Example 46, the title compound was obtained as a light yellow crystalline powder (yield 90%).

$^1$H-NMR (400 MHz, CDCl$_3$) δ: 2.27 (3H, s), 3.12-3.15 (4H, m), 3.86-3.90 (4H, m), 4.24 (2H, d, J=5.4 Hz), 5.51 (2H, br), 5.71 (1H, s), 6.42 (1H, brs), 6.82 (2H, d, J=9.0 Hz), 7.01 (2H, d, J=9.0 Hz), 7.13-7.24 (4H, m), 8.19 (1H, s), 8.73 (1H, brt, J=5.4 Hz).

IR (ATR): 1635, 1608, 1596, 1570, 1549, 1515, 1406, 1297, 1267, 1236, 1224 cm$^{-1}$.

Example 77

Preparation of 4-[(3-methylbenzyl)amino]-6-[(4-morpholinophenyl)amino]pyridine-3-carboxyamide

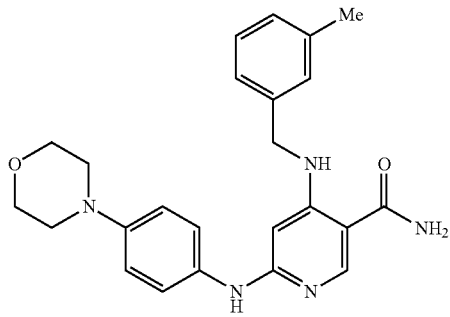 [SMILES: Cc1cccc(CNc2cc(Nc3ccc(N4CCOCC4)cc3)ncc2C(N)=O)c1]

From 6-chloro-4-[(3-methylbenzyl)amino]pyridine-3-carboxyamide (the compound of Example 6) and 4-morpholinoaniline in a manner similar to Example 46, the title compound was obtained as a light yellow crystalline powder (yield 85%).

$^1$H-NMR (400 MHz, CDCl$_3$) δ: 2.34 (3H, s), 3.11-3.15 (4H, m), 3.86-3.90 (4H, m), 4.26 (2H, d, J=5.6 Hz), 5.54 (2H, br), 5.77 (1H, s), 6.43 (1H, brs), 6.81 (2H, d, J=9.0 Hz), 6.96 (2H, d, J=9.0 Hz), 7.03-7.10 (3H, m), 7.19-7.24 (1H, m), 8.20 (1H, s), 8.85 (1H, brt, J=5.6 Hz).

IR (ATR): 1636, 1598, 1570, 1548, 1514, 1408, 1296, 1267, 1232, 1224, 1120 cm$^{-1}$.

Example 78

Preparation of 4-[(4-methylbenzyl)amino]-6-[(4-morpholinophenyl)amino]pyridine-3-carboxyamide

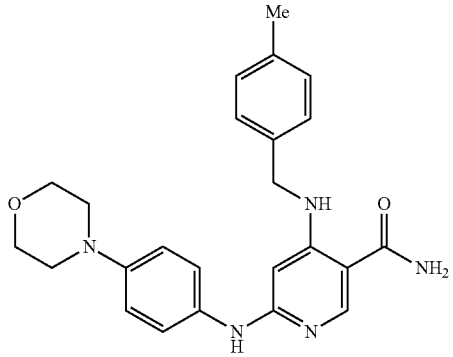 [SMILES: Cc1ccc(CNc2cc(Nc3ccc(N4CCOCC4)cc3)ncc2C(N)=O)cc1]

From 6-chloro-4-[(4-methylbenzyl)amino]pyridine-3-carboxyamide (the compound of Example 7) and 4-morpholinoaniline in a manner similar to Example 46, the title compound was obtained as a light yellow crystalline powder (yield 61%).

$^1$H-NMR (400 MHz, CDCl$_3$) δ: 2.35 (3H, s), 3.12-3.15 (4H, m), 3.87-3.90 (4H, m), 4.25 (2H, d, J=5.6 Hz), 5.61 (2H, br), 5.77 (1H, s), 6.56 (1H, brs), 6.81 (2H, d, J=9.0 Hz), 6.97 (2H, d, J=9.0 Hz), 7.14 (2H, d, J=8.8 Hz), 7.15 (2H, d, J=8.8 Hz), 8.18 (1H, s), 8.82 (1H, brt, J=5.6 Hz).

IR (ATR): 1635, 1598, 1571, 1548, 1515, 1407, 1296, 1268, 1235, 1222, 1221 cm$^{-1}$.

Example 79

Preparation of 4-[(3-ethylbenzyl)amino]-6-[(4-morpholinophenyl)amino]pyridine-3-carboxyamide

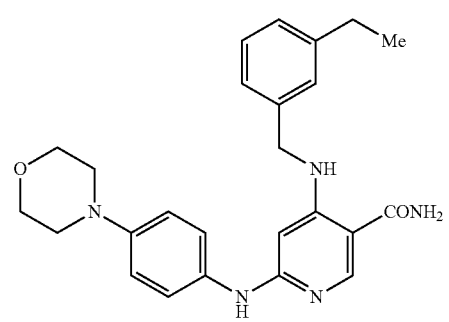 [SMILES: CCc1cccc(CNc2cc(Nc3ccc(N4CCOCC4)cc3)ncc2C(N)=O)c1]

From 6-chloro-4-[(3-ethylbenzyl)amino]pyridine-3-carboxyamide (the compound of Example 8) and 4-morpholinoaniline in a manner similar to Example 46, the title compound was obtained as a light brown solid (yield 31%).

$^1$H-NMR (270 MHz, CDCl$_3$) δ: 1.21 (3H, t, J=7.6 Hz), 2.63 (2H, q, J=7.6 Hz), 3.09-3.15 (4H, m), 3.84-3.91 (4H, m), 4.27 (2H, d, J=5.6 Hz), 5.68 (2H, brs), 5.78 (1H, s), 6.71-6.77 (1H, m), 6.79 (2H, d, J=8.9 Hz), 6.96 (2H, d, J=8.9 Hz), 7.03-7.16 (3H, m), 8.20 (1H, s), 8.82-8.90 (1H, m).

Example 80

Preparation of 4-[(2-chlorobenzyl)amino]-6-[(4-morpholinophenyl)amino]pyridine-3-carboxyamide

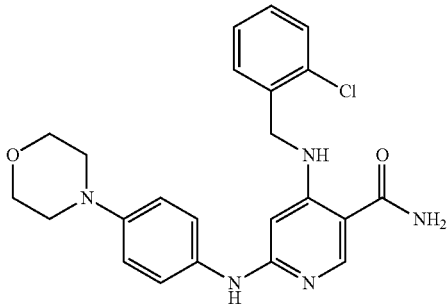 [SMILES: NC(=O)c1cnc(Nc2ccc(N3CCOCC3)cc2)cc1NCc1ccccc1Cl]

From 6-chloro-4-[(2-chlorobenzyl)amino]pyridine-3-carboxyamide (the compound of Example 9) and 4-morpholinoaniline in a manner similar to Example 46, the title compound was obtained as a slight yellow crystalline powder (yield 78%).

$^1$H-NMR (400 MHz, CDCl$_3$) δ: 3.10-3.14 (4H, m), 3.86-3.90 (4H, m), 4.40 (2H, d, J=5.9 Hz), 5.58 (2H, br), 5.64 (1H, s), 6.42 (1H, brs), 6.81 (2H, d, J=9.0 Hz), 6.97 (2H, d, J=9.0 Hz), 7.19-7.25 (2H, m), 7.27-7.31 (1H, m), 7.34-7.37 (1H, m), 8.21 (1H, s), 8.92 (1H, brt, J=5.9 Hz).

IR (ATR): 1623, 1600, 1570, 1548, 1515, 1405, 1296, 1269, 1237, 1225, 1124, 1117 cm$^{-1}$.

Example 81

Preparation of 4-[(3-chlorobenzyl)amino]-6-[(4-morpholinophenyl)amino]pyridine-3-carboxyamide

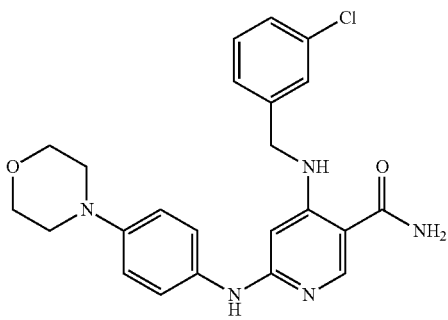 [SMILES: NC(=O)c1cnc(Nc2ccc(N3CCOCC3)cc2)cc1NCc1cccc(Cl)c1]

From 6-chloro-4-[(3-chlorobenzyl)amino]pyridine-3-carboxyamide (the compound of Example 10) and 4-morpholinoaniline in a manner similar to Example 46, the title compound was obtained as a slight yellow crystalline powder (yield 81%).

$^1$H-NMR (400 MHz, CDCl$_3$) δ: 3.12-3.16 (4H, m), 3.86-3.90 (4H, m), 4.29 (2H, d, J=5.6 Hz), 5.56 (2H, br), 5.66 (1H, s), 6.42 (1H, brs), 6.81 (2H, d, J=9.0 Hz), 6.89 (2H, d, J=9.0 Hz), 7.13-7.17 (1H, m), 7.23-7.28 (3H, m), 8.20 (1H, s), 8.94 (1H, brt, J=5.6 Hz).

IR (ATR): 1637, 1600, 1571, 1514, 1408, 1297, 1269, 1234, 1225, 1118 cm$^{-1}$.

Example 82

Preparation of 4-[(4-chlorobenzyl)amino]-6-[(4-morpholinophenyl)amino]pyridine-3-carboxyamide

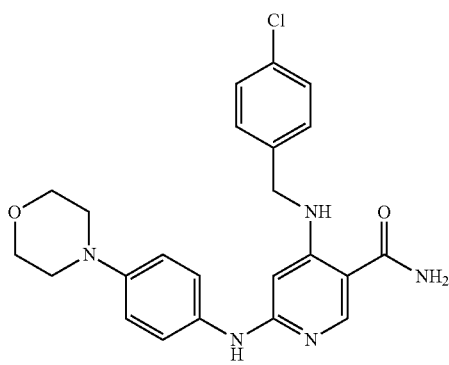 [SMILES: NC(=O)c1cnc(Nc2ccc(N3CCOCC3)cc2)cc1NCc1ccc(Cl)cc1]

From 6-chloro-4-[(4-chlorobenzyl)amino]pyridine-3-carboxyamide (the compound of Example 11) and 4-morpholinoaniline in a manner similar to Example 46, the title compound was obtained as a slight yellow crystalline powder (yield 89%).

$^1$H-NMR (400 MHz, CDCl$_3$) δ: 3.13-3.16 (4H, m), 3.87-3.91 (4H, m), 4.28 (2H, d, J=5.9 Hz), 5.56 (2H, br), 5.62 (1H, s), 6.39 (1H, brs), 6.79 (2H, d, J=9.0 Hz), 6.90 (2H, d, J=9.0 Hz), 7.17 (2H, d, J=8.8 Hz), 7.29 (2H, d, J=8.8 Hz), 8.19 (1H, s), 8.89 (1H, brt, J=5.9 Hz).

IR (ATR): 1635, 1599, 1571, 1548, 1515, 1411, 1405, 1297, 1270, 1237, 1224, 1117 cm$^{-1}$.

Example 83

Preparation of 4-[(2-fluorobenzyl)amino]-6-[(4-morpholinophenyl)amino]pyridine-3-carboxyamide

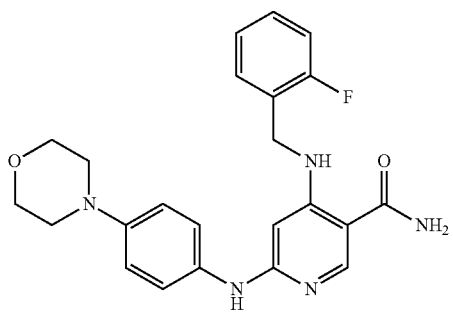 [SMILES: NC(=O)c1cnc(Nc2ccc(N3CCOCC3)cc2)cc1NCc1ccccc1F]

From 6-chloro-4-[(2-fluorobenzyl)amino]pyridine-3-carboxyamide (the compound of Example 12) and 4-morpholinoaniline in a manner similar to Example 46, the title compound was obtained as a slight yellow crystalline powder (yield 79%).

$^1$H-NMR (400 MHz, DMSO-d6) δ: 3.00-3.02 (4H, m), 3.71-3.74 (4H, m), 4.40 (2H, d, J=6.0 Hz), 5.75 (1H, s), 6.82 (2H, d, J=8.8 Hz), 7.17-7.37 (6H, m), 8.35 (1H, s), 8.63 (1H, s), 8.98 (1H, t, J=6.0 Hz).

IR (ATR): 1659, 1620, 1517, 1411, 1225, 1113, 929, 762 cm$^{-1}$.

Example 84

Preparation of 4-[(3-fluorobenzyl)amino]-6-[(4-morpholinophenyl)amino]pyridine-3-carboxyamide

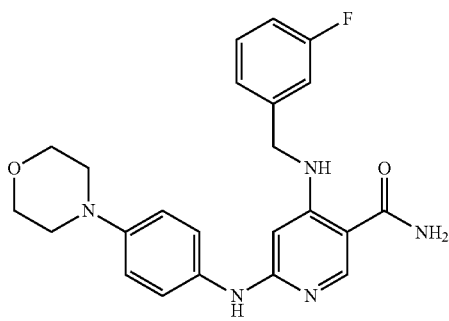 [SMILES: NC(=O)c1cnc(Nc2ccc(N3CCOCC3)cc2)cc1NCc1cccc(F)c1]

From 6-chloro-4-[(3-fluorobenzyl)amino]pyridine-3-carboxyamide (the compound of Example 13) and 4-morpholinoaniline in a manner similar to Example 46, the title compound was obtained as a slight yellow crystalline powder (yield 22%).

$^1$H-NMR (400 MHz, DMSO-d6) δ: 2.99-3.02 (4H, m), 3.71-3.74 (4H, m), 4.38 (2H, d, J=5.8 Hz), 5.71 (1H, s), 6.80 (2H, d, J=9.0 Hz), 7.08-7.15 (2H, m), 7.22 (2H, d, J=9.0 Hz), 7.37-7.44 (1H, m), 8.34 (1H, s), 8.60 (1H, s), 9.03 (1H, t, J=5.8 Hz).

IR (ATR): 1637, 1598, 1514, 1407, 1297, 1120, 923, 788 cm$^{-1}$.

Example 85

Preparation of 4-[(4-fluorobenzyl)amino]-6-[(4-morpholinophenyl)amino]pyridine-3-carboxyamide

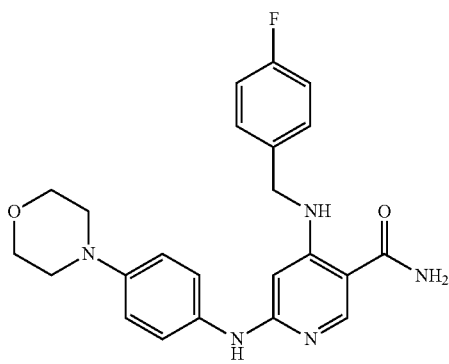 [SMILES: NC(=O)c1cnc(Nc2ccc(N3CCOCC3)cc2)cc1NCc1ccc(F)cc1]

From 6-chloro-4-[(4-fluorobenzyl)amino]pyridine-3-carboxyamide (the compound of Example 14) and 4-morpholinoaniline in a manner similar to Example 46, the title compound was obtained as a slight yellow crystalline powder (yield 16%).

$^1$H-NMR (400 MHz, DMSO-d6) δ: 2.99-3.02 (4H, m), 3.71-3.74 (4H, m), 4.32 (2H, d, J=5.9 Hz), 5.74 (1H, s), 6.82 (2H, d, J=8.8 Hz), 7.19 (2H, dddd, J=8.8, 8.8, 2.0, 2.0 Hz), 7.26 (2H, d, J=8.8 Hz), 7.31-7.35 (2H, m), 8.33 (1H, s), 8.60 (1H, s), 8.97 (1H, t, J=5.9 Hz).

Example 86

Preparation of 6-[(4-morpholinophenyl)amino]-4-{[2-(trifluoromethyl)benzyl]amino}pyridine-3-carboxyamide

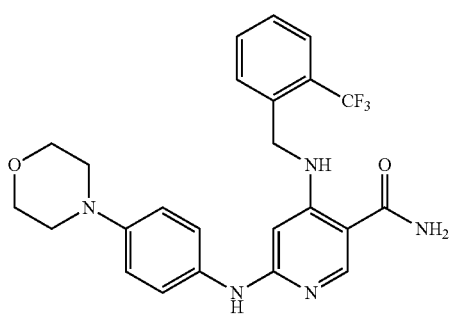 [SMILES: NC(=O)c1cnc(Nc2ccc(N3CCOCC3)cc2)cc1NCc1ccccc1C(F)(F)F]

From 6-chloro-4-{[2-(trifluoromethyl)benzyl]amino}pyridine-3-carboxyamide (the compound of Example 15) and 4-morpholinoaniline in a manner similar to Example 46, the title compound was obtained as a white crystalline powder (yield 51%).

$^1$H-NMR (400 MHz, DMSO-d6) δ: 2.97-3.02 (4H, m), 3.70-3.75 (4H, m), 4.54 (2H, d, J=6.0 Hz), 5.59 (1H, s), 6.77 (2H, d, J=9.3 Hz), 7.18 (2H, d, J=8.6 Hz), 7.46-7.53 (2H, m), 7.66 (1H, dd, J=8.2, 8.2 Hz), 7.78 (1H, d, J=8.3 Hz), 8.36 (1H, s), 8.59 (1H, s), 9.07 (1H, t, J=6.0 Hz).

Example 87

Preparation of 6-[(4-morpholinophenyl)amino]-4-{[3-(trifluoromethyl)benzyl]amino}pyridine-3-carboxyamide

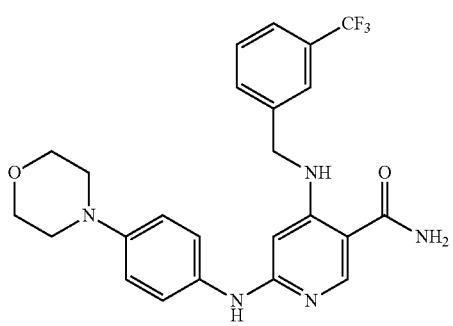 [SMILES: NC(=O)c1cnc(Nc2ccc(N3CCOCC3)cc2)cc1NCc1cccc(C(F)(F)F)c1]

From 6-chloro-4-{[3-(trifluoromethyl)benzyl]amino}pyridine-3-carboxyamide (the compound of Example 16) and 4-morpholinoaniline in a manner similar to Example 46, the title compound was obtained as a light purple crystalline powder (yield 65%).

$^1$H-NMR (400 MHz, CDCl$_3$+CD$_3$OD) δ: 3.10-3.13 (4H, m), 3.86-3.89 (4H, m), 4.36 (2H, d, J=5.6 Hz), 5.66 (1H, s), 6.76 (2H, d, J=9.0 Hz), 6.89 (2H, d, J=9.0 Hz), 7.45-7.56 (4H, m), 8.19 (1H, s), 8.99 (1H, br).

IR (ATR): 1637, 1515, 1409, 1329, 1298, 1172 cm$^{-1}$.

Example 88

Preparation of 6-[(4-morpholinophenyl)amino]-4-{[4-(trifluoromethyl)benzyl]amino}pyridine-3-carboxyamide

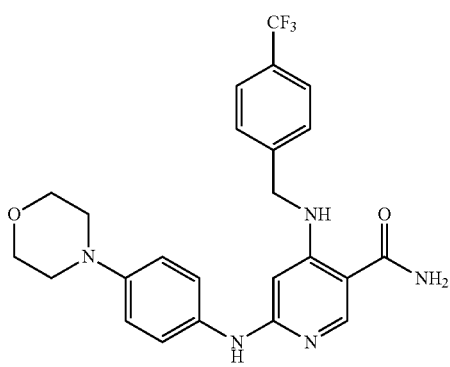 [SMILES: NC(=O)c1cnc(Nc2ccc(N3CCOCC3)cc2)cc1NCc1ccc(C(F)(F)F)cc1]

From 6-chloro-4-{[4-(trifluoromethyl)benzyl]amino}pyridine-3-carboxyamide (the compound of Example 17) and 4-morpholinoaniline in a manner similar to Example 46, the title compound was obtained as a white crystalline powder (yield 80%).

$^1$H-NMR (400 MHz, DMSO-d6) δ: 2.97-3.03 (4H, m), 3.70-3.75 (4H, m), 4.48 (2H, d, J=6.3 Hz), 5.64 (1H, s), 6.77 (2H, d, J=9.0 Hz), 7.19 (2H, d, J=9.0 Hz), 7.50 (2H, d, J=8.5 Hz), 7.74 (2H, d, J=8.5 Hz), 8.35 (1H, s), 8.59 (1H, s), 9.10 (1H, t, J=6.1 Hz).

Example 89

Preparation of 4-[(3,4-dichlorobenzyl)amino]-6-[(4-morpholinophenyl)amino]pyridine-3-carboxyamide

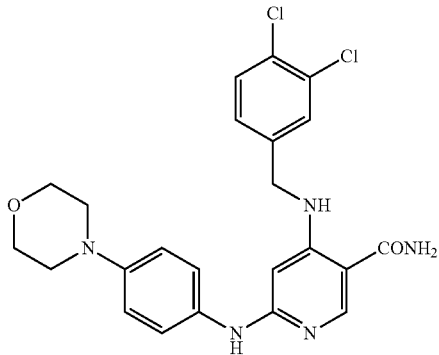 [SMILES: NC(=O)c1cnc(Nc2ccc(N3CCOCC3)cc2)cc1NCc1ccc(Cl)c(Cl)c1]

From 6-chloro-4-[(3,4-dichlorobenzyl)amino]pyridine-3-carboxyamide (the compound of Example 18) and 4-morpholinoaniline in a manner similar to Example 46, the title compound was obtained as a light brown crystalline powder (yield 46%).

$^1$H-NMR (400 MHz, CDCl$_3$+CD$_3$OD) δ: 3.05-3.25 (4H, m), 3.80-3.90 (4H, m), 4.46 (2H, d, J=5.9 Hz), 5.70 (1H, s), 6.81 (2H, d, J=9.0 Hz), 7.09 (1H, m), 7.20 (1H, m), 7.26 (2H, d, J=9.0 Hz), 7.36 (1H, m), 8.35 (1H, s), 8.62 (1H, s), 9.02 (1H, br).

IR (ATR): 1637, 1602, 1515, 1410, 1296, 1227 cm$^{-1}$.

Example 90

Preparation of 4-[(2,3-difluorobenzyl)amino]-6-[(4-morpholinophenyl)amino]pyridine-3-carboxyamide

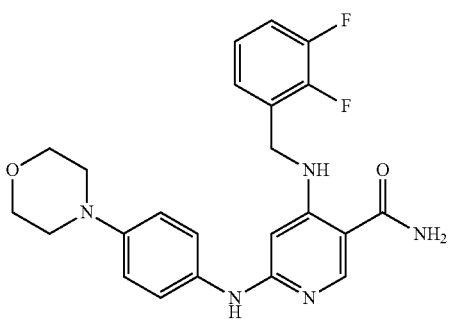 [SMILES: NC(=O)c1cnc(Nc2ccc(N3CCOCC3)cc2)cc1NCc1cccc(F)c1F]

From 6-chloro-4-[(2,3-difluorobenzyl)amino]pyridine-3-carboxyamide (the compound of Example 19) and 4-morpholinoaniline in a manner similar to Example 46, the title compound was obtained as a light purple crystalline powder (yield 42%).

$^1$H-NMR (400 MHz, DMSO-d6) δ: 2.99-3.02 (4H, m), 3.72-3.74 (4H, m), 4.46 (2H, s), 5.57 (1H, s), 6.78 (2H, d, J=10.0 Hz), 6.87 (2H, d, J=10.0 Hz), 7.09 (1H, d, J=6.6 Hz), 7.35-7.43 (2H, m), 8.18 (1H, d, s), 8.96 (1H, br).

IR (ATR): 1637, 1597, 1514, 1408, 1297, 783 cm$^{-1}$.

Example 91

Preparation of 4-[(3,5-difluorobenzyl)amino]-6-[(4-morpholinophenyl)amino]pyridine-3-carboxyamide

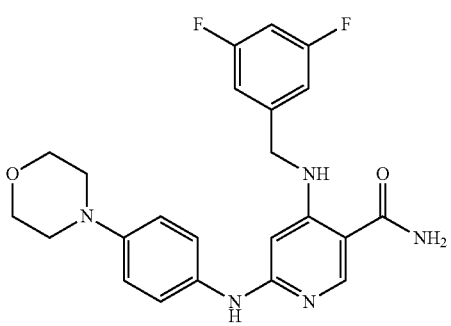 [SMILES: NC(=O)c1cnc(Nc2ccc(N3CCOCC3)cc2)cc1NCc1cc(F)cc(F)c1]

From 6-chloro-4-[(3,5-difluorobenzyl)amino]pyridine-3-carboxyamide (the compound of Example 20) and 4-morpholinoaniline in a manner similar to Example 46, the title compound was obtained as slight yellow needle crystals (yield 87%).

m.p. 248-249° C. (dec.)

$^1$H-NMR (400 MHz, CDCl$_3$) δ: 3.12-3.17 (4H, m), 3.86-3.91 (4H, m), 4.28 (2H, d, J=6.1 Hz), 5.55 (2H, br), 5.59 (1H, s), 6.37 (1H, brs), 6.73 (1H, dddd, J=8.9, 8.9, 2.2, 2.2 Hz), 6.77-6.80 (2H, m), 6.81 (2H, d, J=9.0 Hz), 6.88 (2H, d, J=9.0 Hz), 8.20 (1H, s), 8.97 (1H, brt, J=6.1 Hz).

IR (ATR): 1644, 1626, 1599, 1576, 1568, 1542, 1516, 1409, 1310, 1288, 1275, 1257, 1241, 1118 cm$^{-1}$.

Example 92

Preparation of 4-[(2,4-difluorobenzyl)amino]-6-[(4-morpholinophenyl)amino]pyridine-3-carboxyamide

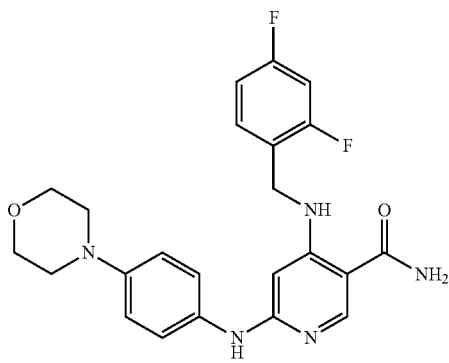 [SMILES: NC(=O)c1cnc(Nc2ccc(N3CCOCC3)cc2)cc1NCc1ccc(F)cc1F]

From 6-chloro-4-[(2,4-difluorobenzyl)amino]pyridine-3-carboxyamide (the compound of Example 21) and 4-morpholinoaniline in a manner similar to Example 46, the title compound was obtained as a white crystalline powder (yield 48%).

$^1$H-NMR (400 MHz, DMSO-d6) δ: 2.98-3.03 (4H, m), 3.70-3.76 (4H, m), 4.37 (2H, d, J=5.9 Hz), 5.73 (1H, s), 6.83 (2H, d, J=8.8 Hz), 7.05-7.12 (1H, m), 7.26-7.36 (2H, m), 7.29 (2H, d, J=8.8 Hz), 8.34 (1H, s), 8.63 (1H, s), 8.96 (1H, t, J=5.9 Hz).

Example 93

Preparation of 4-[(2,5-difluorobenzyl)amino]-6-[(4-morpholinophenyl)amino]pyridine-3-carboxyamide

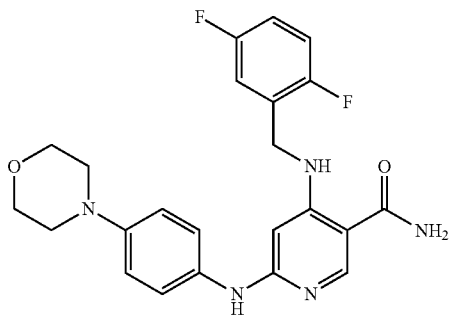 [SMILES: NC(=O)c1cnc(Nc2ccc(N3CCOCC3)cc2)cc1NCc1cc(F)ccc1F]

From 6-chloro-4-[(2,5-difluorobenzyl)amino]pyridine-3-carboxyamide (the compound of Example 22) and 4-morpholinoaniline in a manner similar to Example 46, the title compound was obtained as a white crystalline powder (yield 29%).

$^1$H-NMR (400 MHz, DMSO-d6) δ: 2.98-3.04 (4H, m), 3.70-3.76 (4H, m), 4.40 (2H, d, J=6.1 Hz), 5.71 (1H, s), 6.82 (2H, d, J=9.0 Hz), 7.02-7.08 (1H, m), 7.15-7.22 (1H, m), 7.25-7.34 (1H, m), 7.28 (2H, d, J=9.0 Hz), 8.35 (1H, s), 8.64 (1H, s), 8.99 (1H, t, J=6.1 Hz).

Example 94

Preparation of 4-[(2,6-difluorobenzyl)amino]-6-[(4-morpholinophenyl)amino]pyridine-3-carboxyamide

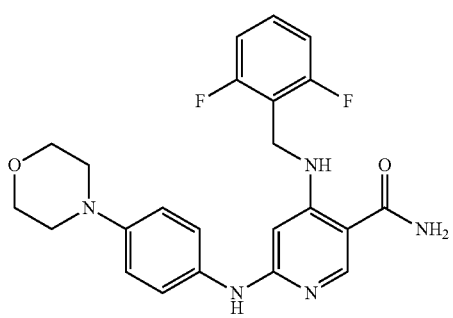

From 6-chloro-4-[(2,6-difluorobenzyl)amino]pyridine-3-carboxyamide (the compound of Example 23) and 4-morpholinoaniline in a manner similar to Example 46, the title compound was obtained as a brown crystalline powder (yield 62%).

$^1$H-NMR (400 MHz, DMSO-d6) δ: 3.02-3.06 (4H, m), 3.71-3.86 (4H, m), 4.35 (2H, d, J=6.1 Hz), 5.94 (1H, s), 6.89 (2H, d, J=9.0 Hz), 7.14 (2H, dd, J=7.9, 7.9 Hz), 7.33 (2H, d, J=9.0 Hz), 7.40-7.48 (1H, m), 8.32 (1H, s), 8.69 (1H, s), 8.96 (1H, t, J=6.1 Hz).

Example 95

Preparation of 4-[(3,4-difluorobenzyl)amino]-6-[(4-morpholinophenyl)amino]pyridine-3-carboxyamide

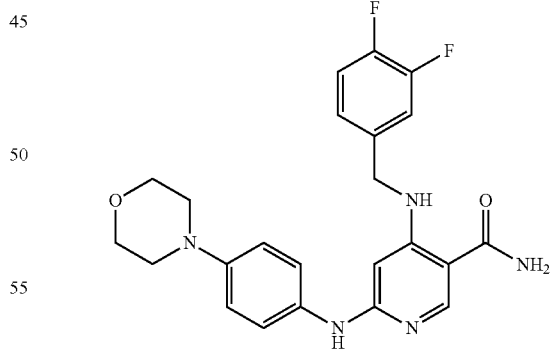

From 6-chloro-4-[(3,4-difluorobenzyl)amino]pyridine-3-carboxyamide (the compound of Example 24) and 4-morpholinoaniline in a manner similar to Example 46, the title compound was obtained as a white crystalline powder (yield 81%).

$^1$H-NMR (400 MHz, DMSO-d6) δ: 2.99-3.04 (4H, m), 3.70-3.76 (4H, m), 4.34 (2H, d, J=5.9 Hz), 5.69 (1H, s), 6.81 (2H, d, J=9.0 Hz), 7.10-7.16 (1H, m), 7.24 (2H, d, J=9.0 Hz), 7.33 (1H, ddd, J=9.5, 8.0, 2.2 Hz), 7.43 (1H, ddd, J=10.7, 8.4, 8.4 Hz), 8.34 (1H, s), 8.60 (1H, s), 9.01 (1H, t, J=5.9 Hz).

Example 96

Preparation of 6-[(4-morpholinophenyl)amino]-4-{[3-fluoro-5-(trifluoromethyl)benzyl]amino}pyridine-3-carboxyamide

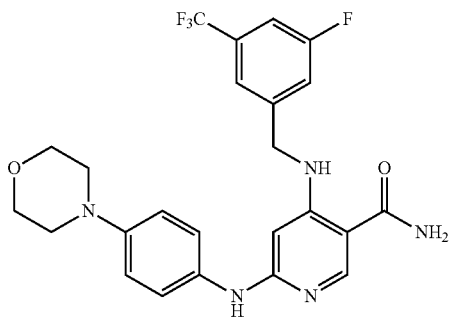 [SMILES: NC(=O)c1cnc(Nc2ccc(N3CCOCC3)cc2)cc1NCc1cc(F)cc(C(F)(F)F)c1]

From 6-chloro-4-{(3-fluoro-5-(trifluoromethyl)benzyl]amino}pyridine-3-carboxyamide (the compound of Example 25) and 4-morpholinoaniline in a manner similar to Example 46, the title compound was obtained as a white crystalline powder (yield 70%).

$^1$H-NMR (400 MHz, DMSO-d6) δ: 2.97-3.02 (4H, m), 3.70-3.75 (4H, m), 4.48 (2H, d, J=6.3 Hz), 5.65 (1H, s), 6.78 (2H, d, J=9.0 Hz), 7.19 (2H, d, J=9.0 Hz), 7.42 (1H, d, J=9.3 Hz), 7.51 (1H, s), 7.60 (1H, d, J=8.6 Hz), 8.35 (1H, s), 8.60 (1H, s), 9.08 (1H, t, J=6.3 Hz).

Example 97

Preparation of 4-{[3,5-bis(trifluoromethyl)benzyl]amino}-6-[(4-morpholinophenyl)amino]pyridine-3-carboxyamide

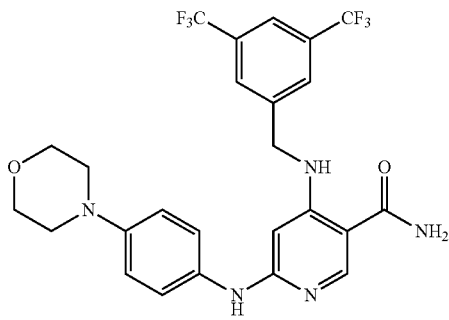

From 6-chloro-4-[(3,5-bis(trifluoromethyl)benzyl]amino}pyridine-3-carboxyamide (the compound of Example 26) and 4-morpholinoaniline in a manner similar to Example 46, the title compound was obtained as a white crystalline powder (yield 55%).

$^1$H-NMR (400 MHz, DMSO-d6) δ: 2.96-3.01 (4H, m), 3.70-3.75 (4H, m), 4.58 (2H, d, J=5.6 Hz), 5.64 (1H, s), 6.76 (2H, d, J=9.0 Hz), 7.18 (2H, d, J=9.0 Hz), 7.95 (2H, s), 8.05 (1H, s), 8.36 (1H, s), 8.61 (1H, s), 9.12 (1H, t, J=5.6 Hz).

Example 98

Preparation of 4-[(2-chloro-5-fluorobenzyl)amino]-6-[(4-morpholinophenyl)amino]pyridine-3-carboxyamide

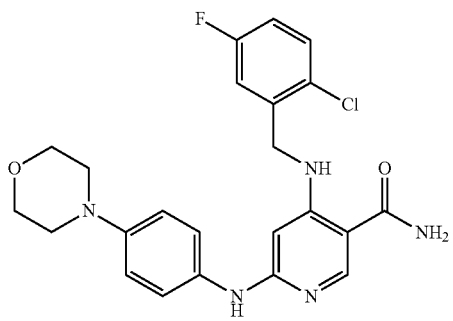 [SMILES: NC(=O)c1cnc(Nc2ccc(N3CCOCC3)cc2)cc1NCc1cc(F)ccc1Cl]

From 6-chloro-4-[(2-chloro-5-fluorobenzyl)amino]pyridine-3-carboxyamide (the compound of Example 27) and 4-morpholinoaniline in a manner similar to Example 46, the title compound was obtained as a slight yellow crystalline powder (yield 82%).

$^1$H-NMR (400 MHz, DMSO-d6) δ: 2.99-3.02 (4H, m), 3.71-3.74 (4H, m), 4.41 (2H, d, J=6.1 Hz), 5.61 (1H, s), 6.81 (2H, d, J=8.8 Hz), 7.04 (1H, dd, J=9.5, 3.0 Hz), 7.21 (1H, ddd, J=8.8, 8.8, 3.0 Hz), 7.27 (2H, d, J=8.8 Hz), 7.56 (1H, dd, J=8.8, 5.1 Hz), 8.36 (1H, s), 8.64 (1H, s), 9.04 (1H, t, J=6.1 Hz).

IR (ATR): 1635, 1599, 1513, 1402, 1296, 1237, 1116, 922 cm$^{-1}$.

Example 99

Preparation of 4-[(5-fluoro-2-methoxybenzyl)amino]-6-[(4-morpholinophenyl)amino]pyridine-3-carboxyamide

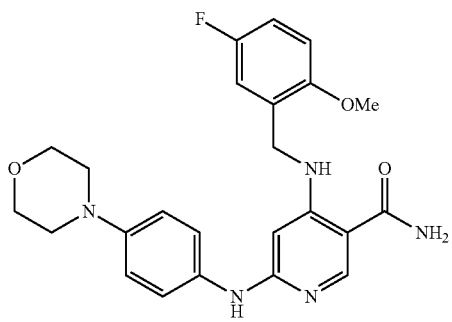 [SMILES: COc1ccc(F)cc1CNc1cc(Nc2ccc(N3CCOCC3)cc2)ncc1C(N)=O]

From 6-chloro-4-[(5-fluoro-2-methoxybenzyl)amino]pyridine-3-carboxyamide (the compound of Example 28) and 4-morpholinoaniline in a manner similar to Example 46, the title compound was obtained as slight yellow prism crystals (yield 91%).

m.p. 210-212° C.

$^1$H-NMR (400 MHz, CDCl$_3$) δ: 3.11-3.15 (4H, m), 3.76 (3H, s), 3.86-3.89 (4H, m), 4.26 (2H, d, J=6.1 Hz), 5.58 (2H,

Example 100

Preparation of 4-[(3-fluoro-2-methylbenzyl)amino]-6-[(4-morpholinophenyl)amino]pyridine-3-carboxyamide

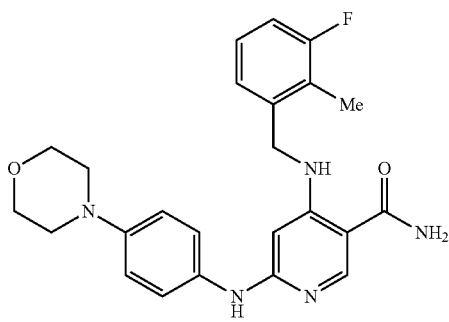 [SMILES: Cc1c(F)cccc1CNc1cc(Nc2ccc(N3CCOCC3)cc2)ncc1C(N)=O]

From 6-chloro-4-[(3-fluoro-2-methylbenzyl)amino]pyridine-3-carboxyamide (the compound of Example 29) and 4-morpholinoaniline in a manner similar to Example 46, the title compound was obtained as white needle crystals (yield 95%).

m.p. 229-230° C.

$^1$H-NMR (270 MHz, DMSO-d6) δ: 2.19 (3H, d, J=1.6 Hz), 2.97-3.04 (4H, m), 3.69-3.76 (4H, m), 4.33 (2H, d, J=5.6 Hz), 5.67 (1H, s), 6.81 (2H, d, J=8.9 Hz), 7.02-7.12 (2H, m), 7.16-7.23 (1H, m), 7.27 (2H, d, J=8.9 Hz), 8.35 (1H, s), 8.61 (1H, brs), 8.94 (1H, brt, J=5.6 Hz).

IR (ATR): 1637, 1598, 1572, 1514, 1467, 1407, 1298, 1267, 1240, 1122 cm$^{-1}$.

MS: m/z 435(M$^+$, base peak).

Example 101

Preparation of 4-[(2-chloro-6-fluorobenzyl)amino]-6-[(4-morpholinophenyl)amino]pyridine-3-carboxyamide

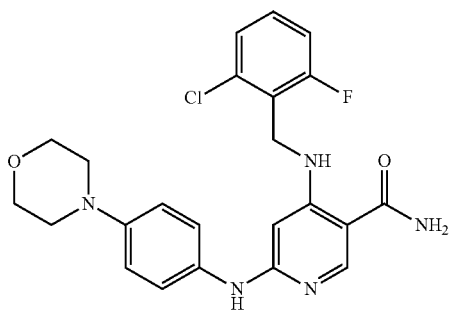 [SMILES: NC(=O)c1cnc(Nc2ccc(N3CCOCC3)cc2)cc1NCc1c(F)cccc1Cl]

From 6-chloro-4-[(2-chloro-6-fluorobenzyl)amino]pyridine-3-carboxyamide (the compound of Example 30) and 4-morpholinoaniline in a manner similar to Example 46, the title compound was obtained as a white solid (yield 29%).

$^1$H-NMR (400 MHz, DMSO-d6) δ: 2.96-3.06 (4H, m), 3.70-3.76 (4H, m), 4.42 (2H, d, J=5.9 Hz), 5.66 (1H, s), 6.81 (2H, d, J=8.8 Hz), 7.24-7.38 (6H, m), 7.47-7.52 (1H, m), 8.35 (1H, s), 8.63 (1H, s), 9.03 (1H, br).

Example 102

Preparation of 6-[(4-morpholinophenyl)amino]-4-[(3-nitrobenzyl)amino]pyridine-3-carboxyamide

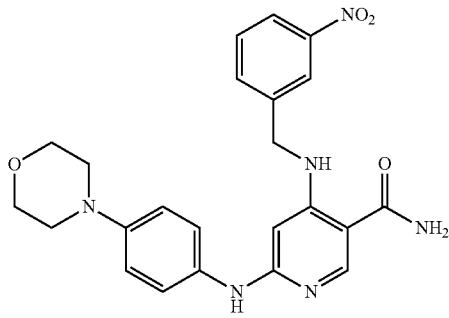

From 6-chloro-4-[(3-nitrobenzyl)amino]pyridine-3-carboxyamide (the compound of Example 31) and 4-morpholinoaniline in a manner similar to Example 46, the title compound was obtained as a light yellow solid (yield 49%).

$^1$H-NMR (270 MHz, DMSO-d6) δ: 2.96-3.02 (4H, m), 3.69-3.76 (4H, m), 4.52 (2H, d, J=5.9 Hz), 5.65 (1H, s), 6.76 (2H, d, J=9.0 Hz), 7.17 (2H, d, J=9.0 Hz), 7.63-7.78 (2H, m), 8.14 (2H, s), 8.33 (1H, d, J=7.9 Hz), 8.57 (1H, s), 9.13 (1H, s).

Example 103

Preparation of 4-[(3-aminobenzyl)amino]-6-[(4-morpholinophenyl)amino]pyridine-3-carboxyamide

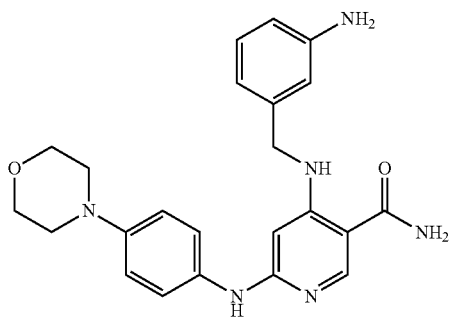 [SMILES: NC(=O)c1cnc(Nc2ccc(N3CCOCC3)cc2)cc1NCc1cccc([N+](=O)[O-])c1]

21 mg of 6-[(4-morpholinophenyl)amino]-4-[(3-nitrobenzyl)amino]pyridine-3-carboxyamide (the compound of Example 102) was dissolved in 1 mL of acetic acid, to which 21 mg of 10% palladium carbon was added, and stirred in a hydrogen atmosphere at room temperature for 4 hours. The 10% palladium carbon was filtered off, and the solvent was evaporated to obtain 19.5 mg (100%) of the title compound as a light gray solid.

$^1$H-NMR (270 MHz, DMSO-d6) δ: 2.98-3.04 (4H, m), 3.69-3.76 (4H, m), 4.17 (2H, d, J=5.3 Hz), 5.07 (2H, br s), 5.77 (1H, s), 6.39-6.52 (3H, m), 6.82 (2H, d, J=8.9 Hz), 6.98

(2H, dd, J=7.6, 7.6 Hz), 7.25 (2H, d, J=8.9 Hz), 8.32 (1H, s), 8.60 (1H, s), 8.86-8.93 (1H, m).

Example 104

Preparation of 4-{[3-(acetylamino)benzyl]amino}-6-[(4-morpholinophenyl)amino]pyridine-3-carboxyamide and 4-{[3-(acetylamino)benzyl]amino}-6-[acetyl(4-morpholinophenyl)amino]pyridine-3-carboxyamide

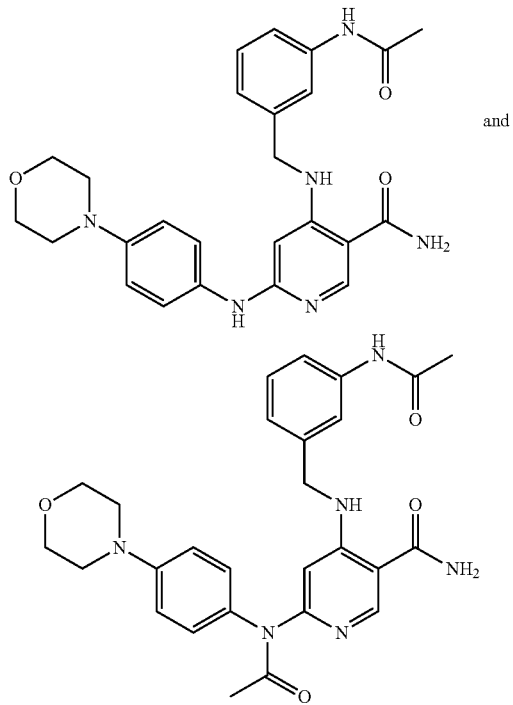

22 mg of 4-[(3-aminobenzyl)amino]-6-[(4-morpholinophenyl)amino]pyridine-3-carboxyamide (the compound of Example 103) was dissolved in 0.5 mL of pyridine, to which 5.4 mg of acetic anhydride was added, and stirred at room temperature for 4 hours. To the reaction mixture, water was added, stirred, and the solvent was evaporated. The residue was purified by silica gel thin layer chromatography (chloroform: methanol=10:1) to obtain 2.6 mg (11%) of 4-{[3-(acetylamino)benzyl]amino}-6-[(4-morpholinophenyl)amino]pyridine-3-carboxyamide (Example 104-1) as a white solid. Furthermore, 11.6 mg (44%) of 4-{[3-(acetylamino)benzyl]amino}-6-[acetyl(4-morpholinophenyl)amino]pyridine-3-carboxyamide (Example 104-2) was obtained as a yellowish brown oil.

4-{[3-(acetylamino)benzyl]amino}-6-[(4-morpholinophenyl)amino]pyridine-3-carboxyamide Example 104-1

¹H-NMR (270 MHz, DMSO-d6) δ: 2.02 (3H, s), 2.97-3.03 (4H, m), 3.70-3.75 (4H, m), 4.32 (2H, d, J=4.9 Hz), 5.71 (1H, s), 6.78 (2H, d, J=8.9 Hz), 6.94 (1H, d, J=7.8 Hz), 7.19 (2H, d, J=8.9 Hz), 7.27 (1H, dd, J=7.8, 7.8 Hz), 7.45 (1H, s), 7.56 (1H, d, J=7.8 Hz), 8.34 (1H, s), 8.59 (1H, s), 8.97-9.05 (1H, m), 9.96 (1H, s).

4-{[3-(acetylamino)benzyl]amino}-6-[acetyl(4-morpholinophenyl)amino]pyridine-3-carboxyamide Example 104-2

¹H-NMR (270 MHz, CD₃OD) δ: 1.99 (3H, s), 2.09 (3H, s), 3.09-3.17 (4H, m), 3.80-3.84 (4H, m), 4.43 (2H, s), 6.51 (1H, s), 6.88 (2H, d, J=8.9 Hz), 6.99 (1H, d, J=7.9 Hz), 7.06 (2H, d, J=8.9 Hz), 7.23 (1H, t, J=7.9 Hz), 7.40 (1H, s), 7.52 (1H, d, J=7.9 Hz), 8.44 (1H, s).

Example 105

Preparation of 4-{[3-(dimethylamino)benzyl]amino}-6-[(4-morpholinophenyl)amino]pyridine-3-carboxyamide

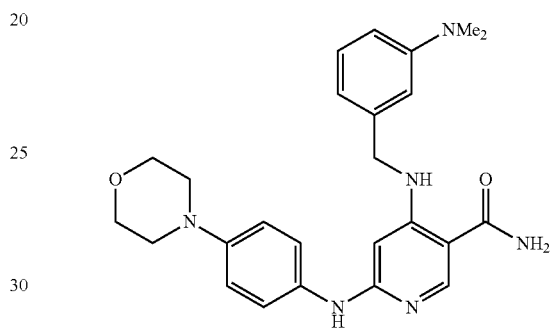

From 6-chloro-4-{[3-(dimethylamino)benzyl]amino}pyridine-3-carboxyamide (the compound of Example 32) and 4-morpholinoaniline in a manner similar to Example 46, the title compound was obtained as a white solid (yield 51%).

¹H-NMR (400 MHz, DMSO-d6) δ: 2.98-3.04 (4H, m), 3.29-3.48 (6H, brs), 3.69-3.76 (4H, m), 4.17 (2H, d, J=5.3 Hz), 5.07 (2H, br s), 5.77 (1H, s), 6.39-6.52 (3H, m), 6.82 (2H, d, J=8.9 Hz), 6.98 (2H, dd, J=7.6, 7.6 Hz), 7.25 (2H, d, J=8.9 Hz), 8.32 (1H, s), 8.60 (1H, s), 8.86-8.93 (1H, m).

Example 106

Preparation of 6-[(4-morpholinophenyl)amino]-4-[(3-sulfamoylbenzyl)amino]pyridine-3-carboxyamide

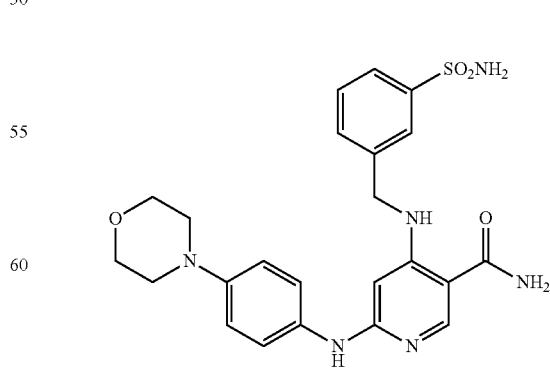

From 6-chloro-4-[(3-sulfamoylbenzyl)amino]pyridine-3-carboxyamide (the compound of Example 33) and 4-morpholinoaniline in a manner similar to Example 46, the title compound was obtained as a brown solid (yield 49%).

¹H-NMR (400 MHz, DMSO-d6) δ: 3.09-3.15 (4H, m), 3.72-3.78 (4H, m), 4.55 (2H, d, J=5.4 Hz), 5.73 (1H, s), 6.91 (2H, d, J=8.6 Hz), 6.96 (2H, d, J=8.6 Hz), 7.08 (1H, s), 7.21 (1H, s), 7.41 (1H, s), 7.44 (1H, d, J=7.6 Hz), 7.57 (1H, dd, J=7.6, 7.6 Hz), 7.74 (1H, s), 7.78 (1H, d, J=7.6 Hz), 8.23 (1H, s), 9.74 (1H, brs).

Example 107

Preparation of 4-({3-[(methylsulfonyl)amino]benzyl}amino)-6-[(4-morpholinophenyl)amino]pyridine-3-carboxyamide

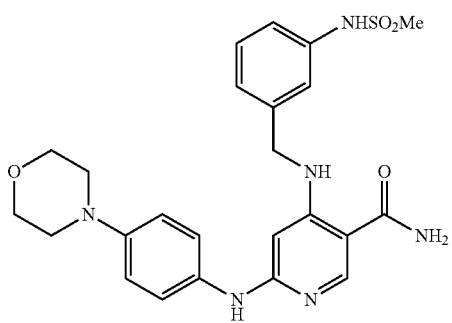

From 6-chloro-4-({3-[(methylsulfonyl)amino]benzyl}amino)pyridine-3-carboxyamide (the compound of Example 34) and 4-morpholinoaniline in a manner similar to Example 46, the title compound was obtained as a light pink solid (yield 29%).

¹H-NMR (400 MHz, DMSO-d6) δ: 2.98 (3H, s), 3.09-3.14 (4H, m), 3.72-3.78 (4H, m), 4.45 (2H, d, J=5.8 Hz), 5.72 (1H, s), 6.90-7.00 (5H, m), 7.16-7.19 (2H, m), 7.33 (1H, dd, J=7.8, 7.8 Hz), 8.16 (1H, s), 8.20 (1H, brs), 9.82 (1H, s).

Example 108

Preparation of 4-({3-[methyl(methylsulfonyl)amino]benzyl}amino)-6-[(4-morpholinophenyl)amino]pyridine-3-carboxyamide

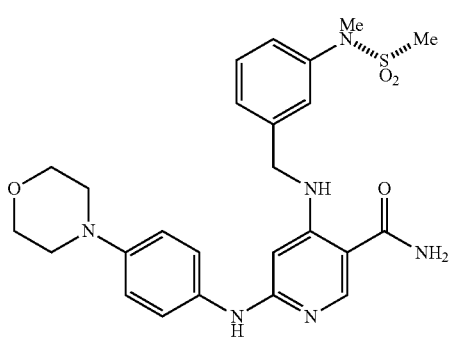

From 6-chloro-4-({3-[methyl(methylsulfonyl)amino]benzyl}amino)pyridine-3-carboxyamide (the compound of Example 35) and 4-morpholinoaniline in a manner similar to Example 46, the title compound was obtained as a yellowish brown amorphous substance (yield 12%).

¹H-NMR (400 MHz, DMSO-d6) δ: 2.92 (3H, s), 3.00-3.15 (4H, m), 3.21 (3H, s), 3.68-3.82 (4H, m), 4.41 (2H, br), 5.77 (1H, s), 6.03 (1H, brs), 6.85-7.05 (4H, m), 7.05-7.25 (1H, m), 7.30-7.45 (3H, m), 8.32 (1H, s), 8.55 (1H, brs), 8.96 (1H, brs).

Example 109

Preparation of 4-({2-[methyl(methylsulfonyl)amino]benzyl}amino)-6-[(4-morpholinophenyl)amino]pyridine-3-carboxyamide

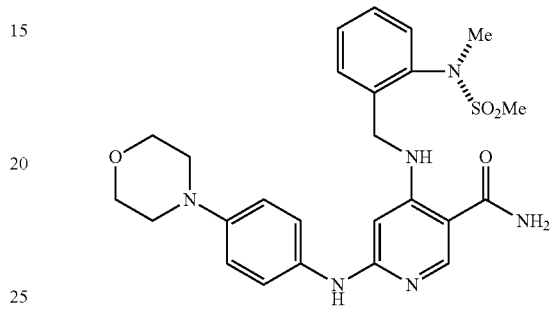

From 6-chloro-4-({2-[methyl(methylsulfonyl)amino]benzyl}amino)pyridine-3-carboxyamide (the compound of Example 36) and 4-morpholinoaniline in a manner similar to Example 46, the title compound was obtained as a light brown solid (yield 73%).

¹H-NMR (400 MHz, DMSO-d6) δ: 2.98-3.03 (4H, m), 3.07 (3H, s), 3.12 (3H, s), 3.70-3.75 (4H, m), 4.38 (1H, brs), 4.48 (1H, brs), 5.70 (1H, s), 6.80 (2H, d, J=9.0 Hz), 7.24 (2H, d, J=9.0 Hz), 7.33-7.43 (3H, m), 7.53-7.58 (1H, m), 8.34 (1H, s), 8.59 (1H, s), 8.97 (1H, t, J=5.7 Hz).

Example 110

Preparation of 4-{[3-(methylsulfamoyl)benzyl]amino}-6-[(4-morpholinophenyl)amino]pyridine-3-carboxyamide

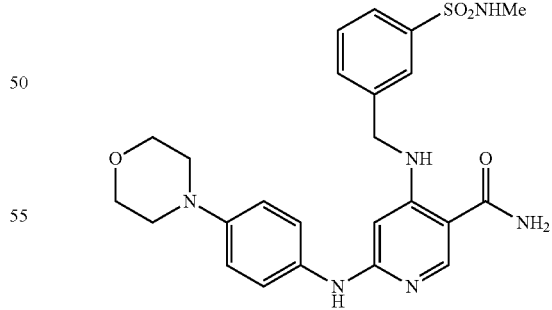

From 6-chloro-4-{[3-(methylsulfamoyl)benzyl]amino}pyridine-3-carboxyamide (the compound of Example 37) and 4-morpholinoaniline in a manner similar to Example 46, the title compound was obtained as a light pink amorphous substance (yield 30%).

¹H-NMR (400 MHz, DMSO-d6) δ: 2.38 (3H, d, J=4.9 Hz), 3.10-3.14 (4H, m), 3.72-3.77 (4H, m), 4.58 (2H, d, J=5.6 Hz), 5.71 (1H, s), 6.91 (2H, d, J=9.3 Hz), 6.95 (2H, d, J=9.3 Hz), 7.48-7.54 (2H, m), 7.59-7.74 (4H, m), 8.25 (1H, s), 9.69 (1H, br), 9.76 (1H, br).

Example 111

Preparation of 4-{[3-(dimethylsulfamoyl)benzyl]amino}-6-[(4-morpholinophenyl)amino]pyridine-3-carboxyamide

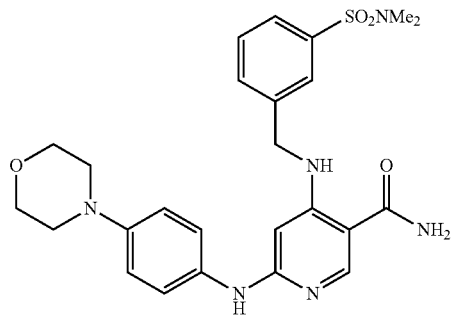

From 6-chloro-4-{[3-(dimethylsulfamoyl)benzyl]amino}pyridine-3-carboxyamide (the compound of Example 38) and 4-morpholinoaniline in a manner similar to Example 46, the title compound was obtained as a light pink amorphous substance (yield 79%).

$^1$H-NMR (400 MHz, DMSO-d6) δ: 2.56 (6H, brs), 3.08-3.14 (4H, m), 3.71-3.79 (4H, m), 4.59 (2H, d, J=5.4 Hz), 5.69 (1H, s), 6.91 (2H, d, J=7.7 Hz), 6.99 (2H, d, J=7.7 Hz), 7.58 (1H, d, J=6.4 Hz), 7.62-7.72 (3H, m), 8.10-8.24 (1H, br), 8.16 (1H, s), 9.67 (1H, brs).

Example 112

Preparation of 4-{[3-(4-methylpiperazin-1-yl)benzyl]amino}-6-[(4-morpholinophenyl)amino]pyridine-3-carboxyamide

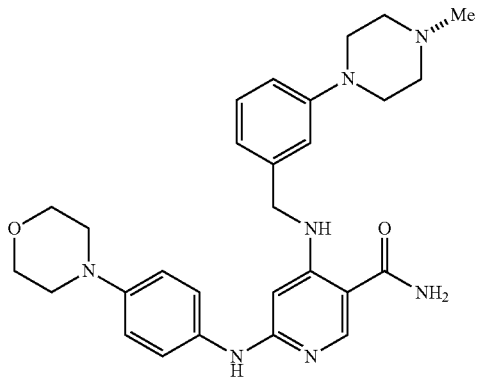

From 6-chloro-4-{[3-(4-methylpiperazin-1-yl)benzyl]amino}pyridine-3-carboxyamide (the compound of Example 39) and 4-morpholinoaniline in a manner similar to Example 46, the title compound was obtained as a light pink amorphous substance (yield 79%).

$^1$H-NMR (400 MHz, DMSO-d6) δ: 2.32 (3H, s), 2.80-2.87 (2H, m), 2.96-3.18 (6H, m), 3.44-3.60 (2H, m), 3.72-3.84 (6H, m), 4.37 (2H, d, J=5.6 Hz), 5.84 (1H, s), 6.74 (1H, d, J=7.7 Hz), 6.92-7.00 (4H, m), 7.05 (2H, d, J=9.0 Hz), 7.25 (1H, dd, J=7.7, 7.7 Hz), 7.64 (1H, br), 8.16 (1H, s), 8.23 (1H, br), 9.69 (1H, br).

Example 113

Preparation of 4-{[3-ethoxycarbonyl)benzyl]amino}-6-[(4-morpholinophenyl)amino]pyridine-3-carboxyamide

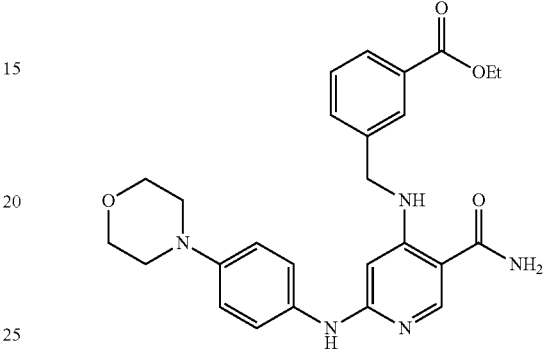

From 4-[(3-ethoxycarbonylbenzyl)amino]-6-chloropyridine-3-carboxyamide (the compound of Example 40) and 4-morpholinoaniline in a manner similar to Example 46, the title compound was obtained as a gray solid (yield 91%).

$^1$H-NMR (400 MHz, DMSO-d6) δ: 1.31 (3H, t, J=7.1 Hz), 2.97-3.01 (4H, m), 3.70-3.75 (4H, m), 4.31 (2H, q, J=7.1 Hz), 4.44 (2H, d, J=6.1 Hz), 5.69 (1H, s), 6.77 (2H, d, J=9.0 Hz), 7.18 (2H, d, J=9.0 Hz), 7.50-7.59 (2H, m), 7.87 (1H, d, J=7.1 Hz), 7.90 (1H, s), 8.34 (1H, s), 8.58 (1H, s), 9.07 (1H, t, J=6.1 Hz).

Example 114

Preparation of 4-{(3-carboxybenzyl)amino}-6-[(4-morpholinophenyl)amino]pyridine-3-carboxyamide

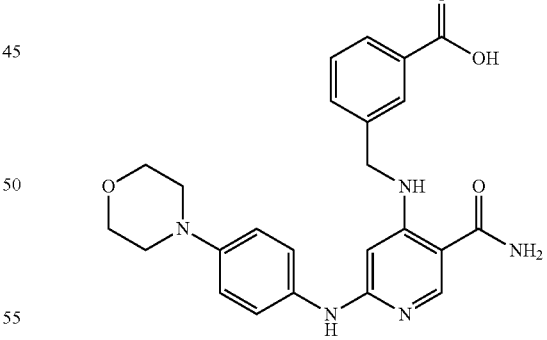

240 mg of 4-{[3-ethoxycarbonyl)benzyl]amino}-6-[(4-morpholinophenyl)amino]pyridine-3-carboxyamide (the compound of Example 113) was dissolved in 10 mL of methanol, to which 10 mL of 4 mol/L sodium hydroxide in water was added at room temperature, and stirred at the same temperature for 4 hours. Under ice cooling, 1 mol/L hydrochloric acid in water was added to the reaction mixture to neutralize it, extracted with chloroform, the extract was washed with water, and dried on anhydrous sodium sulfate. The solvent was evaporated to obtain 29 mg (14%) of the title compound as a light brown solid.

¹H-NMR (400 MHz, DMSO-d6) δ: 2.97-3.02 (4H, m), 3.70-3.76 (4H, m), 4.43 (2H, d, J=5.8 Hz), 5.70 (1H, s), 6.77 (2H, d, J=9.0 Hz), 7.16 (2H, d, J=9.0 Hz), 7.47-7.56 (2H, m), 7.86 (1H, d, J=7.3 Hz), 7.88 (1H, s), 8.34 (1H, s), 8.59 (1H, s), 9.09 (1H, t, J=5.6 Hz), 13.00 (1H, s).

Example 115

Preparation of 4-[(3-carbamoylbenzyl)amino]-6-[(4-morpholinophenyl)amino]pyridine-3-carboxyamide

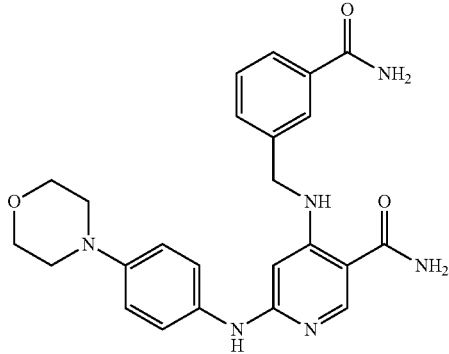 [SMILES: NC(=O)c1cccc(CNc2cc(Nc3ccc(N4CCOCC4)cc3)ncc2C(N)=O)c1]

From 4,6-dichloropyridine-3-carboxyamide and 3-aminomethylbenzamide in a manner similar to Example 1, 4-[(3-carbamoylbenzyl)amino]-6-chloropyridine-3-carboxyamide was obtained as a light brown solid (yield 65%).

¹H NMR (400 MHz, DMSO-d6) δ: 4.53 (2H, d, J=5.9 Hz), 6.62 (1H, s), 7.37 (1H, brs), 7.41-7.49 (2H, m), 7.53 (1H, brs), 7.77 (1H, d, J=7.1 Hz), 7.84 (1H, s), 7.98 (1H, s), 8.12 (1H, brs), 8.43 (1H, s), 9.20 (1H, t, J=5.9 Hz).

From 4-[(3-carbonylbenzyl)amino]-6-chloropyridine-3-carboxyamide and 4-morpholinoaniline in a manner similar to Example 46, the title compound was obtained as a gray solid (yield 60%).

¹H-NMR (400 MHz, DMSO-d6) δ: 2.97-3.03 (4H, m), 3.70-3.76 (4H, m), 4.40 (2H, d, J=6.1 Hz), 5.71 (1H, s), 6.77 (2H, d, J=9.0 Hz), 7.15 (2H, d, J=9.0 Hz), 7.38-7.47 (3H, m), 7.79 (1H, d, J=6.6 Hz), 7.84 (1H, s), 7.99 (1H, s), 8.34 (1H, s), 8.60 (1H, s), 9.07 (1H, t, J=6.1 Hz).

Example 116

Preparation of 6-[(4-morpholinophenyl)amino]-4-{[(1S)-1-phenylethyl]amino}pyridine-3-carboxyamide

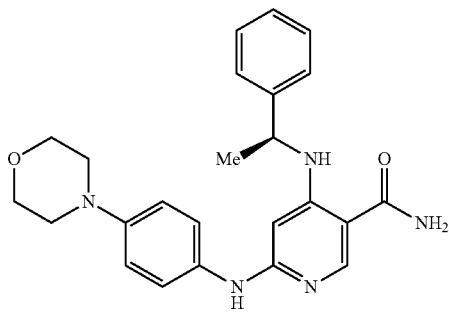 [SMILES: C[C@H](Nc1cc(Nc2ccc(N3CCOCC3)cc2)ncc1C(N)=O)c1ccccc1]

From 6-chloro-4-{[(1S)-1-phenylethyl]amino}pyridine-3-carboxyamide (the compound of Example 41) and 4-morpholinoaniline in a manner similar to Example 46, the title compound was obtained as a light brown crystalline powder (yield 79%).

¹H-NMR (400 MHz, CDCl₃) δ: 1.53 (3H, d, J=6.6 Hz), 3.11-3.15 (4H, m), 3.88-3.92 (4H, m), 4.31-4.39 (1H, m), 5.59 (1H, s), 5.60 (2H, br), 6.46 (1H, brs), 6.74 (4H, s), 7.21-7.36 (5H, m), 8.17 (1H, s), 8.82 (1H, brd, J=5.4 Hz).

IR (ATR): 1649, 1612, 1570, 1514, 1449, 1410, 1296, 1264, 1227, 1117 cm⁻¹.

Example 117

Preparation of 6-[(4-morpholinophenyl)amino]-4-{[(1R)-1-phenylethyl]amino}pyridine-3-carboxyamide

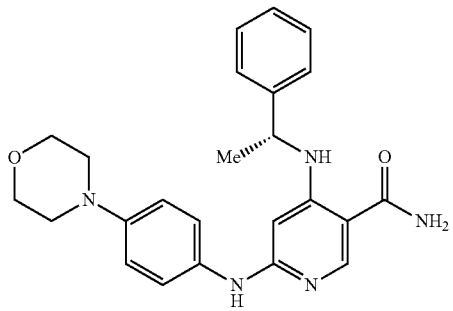 [SMILES: C[C@@H](Nc1cc(Nc2ccc(N3CCOCC3)cc2)ncc1C(N)=O)c1ccccc1]

From 6-chloro-4-{[(1R)-1-phenylethyl]amino}pyridine-3-carboxyamide (the compound of Example 42) and 4-morpholinoaniline in a manner similar to Example 46, the title compound was obtained as a light brown crystalline powder (yield 87%).

¹H-NMR (400 MHz, CDCl₃) δ: 1.53 (3H, d, J=6.8 Hz), 3.11-3.15 (4H, m), 3.88-3.92 (4H, m), 4.31-4.39 (1H, m), 5.59 (1H, s), 5.60 (2H, br), 6.44 (1H, brs), 6.74 (4H, s), 7.21-7.36 (5H, m), 8.17 (1H, s), 8.81 (1H, brd, J=5.4 Hz).

IR (ATR): 1649, 1612, 1570, 1514, 1449, 1410, 1296, 1264, 1226, 1117 cm⁻¹.

Example 118

Preparation of 4-[benzyl(methyl)amino]-6-[(4-morpholinophenyl)amino]pyridine-3-carboxyamide

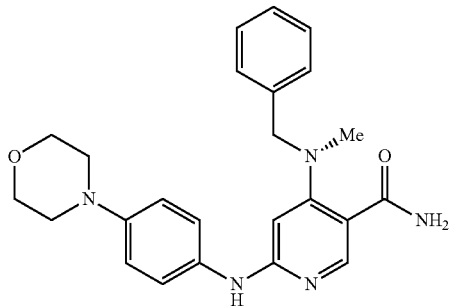

From 4-[benzyl(methyl)amino]-6-chloropyridine-3-carboxyamide (the compound of Example 43) and 4-morpholinoaniline in a manner similar to Example 46, the title compound was obtained as a light brown crystalline powder (yield 47%).

m.p. 203-204° C.

$^1$H-NMR (400 MHz, CDCl$_3$) δ: 2.68 (3H, s), 3.19-3.26 (4H, m), 3.85-3.89 (4H, m), 4.19 (2H, s), 5.68 (1H, br), 6.17 (1H, s), 6.78 (1H, br), 6.88 (2H, d, J=8.9 Hz), 7.08 (2H, d, J=8.9 Hz), 7.12-7.17 (2H, m), 7.78-7.35 (3H, m), 7.59 (1H, br), 8.65 (1H, s).

IR (ATR): 1597, 1561, 1512, 1384, 1296, 1231, 1116 cm$^{-1}$.

MS: m/z 417 (M$^+$), 399 (base peak).

Example 119

Preparation of 6-[(4-morpholinophenyl)amino]-4-[(naphthalen-1-ylmethyl)amino]pyridine-3-carboxyamide

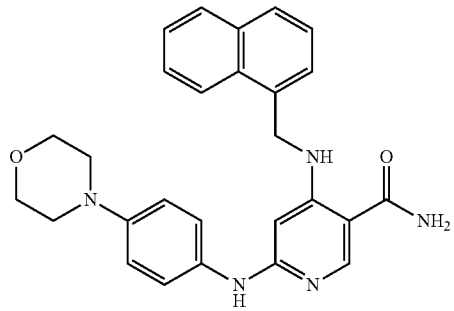 [SMILES: NC(=O)c1cnc(Nc2ccc(N3CCOCC3)cc2)cc1NCc1cccc2ccccc12]

From 6-chloro-4-[(naphthalen-1-ylmethyl)amino]pyridine-3-carboxyamide (the compound of Example 44) and 4-morpholinoaniline in a manner similar to Example 46, the title compound was obtained as a light purple crystalline powder (yield 64%).

$^1$H-NMR (400 MHz, CDCl$_3$+CD$_3$OD) δ: 2.99-3.01 (4H, m), 3.84-3.86 (4H, m), 4.74 (2H, d, J=3.2 Hz), 5.80 (1H, s), 6.60 (2H, d, J=9.0 Hz), 6.86 (2H, d, J=9.0 Hz), 7.47-7.52 (4H, m), 7.81-7.88 (3H, m), 8.18 (1H, s), 8.92 (1H, br).

IR (ATR): 1640, 1611, 1587, 1514, 1400, 1263 cm$^{-1}$.

Example 120

Preparation of 6-[(4-morpholinophenyl)amino]-4-[(naphthalen-2-ylmethyl)amino]pyridine-3-carboxyamide

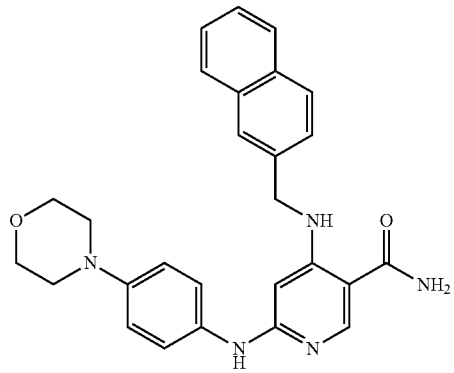 [SMILES: NC(=O)c1cnc(Nc2ccc(N3CCOCC3)cc2)cc1NCc1ccc2ccccc2c1]

From 6-chloro-4-[(naphthalen-2-ylmethyl)amino]pyridine-3-carboxyamide (the compound of Example 45) and 4-morpholinoaniline in a manner similar to Example 46, the title compound was obtained as a light purple crystalline powder (yield 86%).

$^1$H-NMR (400 MHz, CDCl$_3$) δ: 3.00-3.02 (4H, m), 3.84-3.87 (4H, m), 4.50 (2H, d, J=5.6 Hz), 5.59 (1H, br), 5.75 (1H, s), 6.46 (2H, d, J=9.0 Hz), 6.74 (2H, d, J=9.0 Hz), 7.41 (1H, d, J=8.5 Hz), 7.45-7.50 (4H, m), 7.68 (1H, s), 7.78-7.87 (3H, m), 8.20 (1H, s), 9.00 (1H, br).

IR (ATR): 1603, 1515, 1412, 11298, 1236, 1121 cm$^{-1}$.

Example 121

Preparation of 6-[(2-cyano-4-morpholinophenyl)amino]-4-[(3,5-difluorobenzyl)amino]pyridine-3-carboxyamide

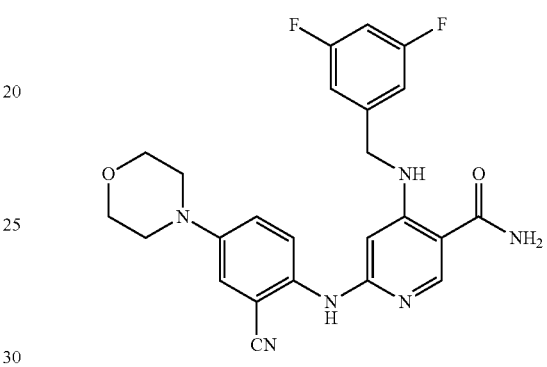

From 6-chloro-4-[(3,5-difluorobenzyl)amino]pyridine-3-carboxyamide (the compound of Example 20) and 2-cyano-4-morpholinoaniline in a manner similar to Example 46, the title compound was obtained as orange needle crystals (yield 28%).

m.p. 186-188° C. (dec.)

$^1$H-NMR (400 MHz, CDCl$_3$+CD$_3$OD) δ: 3.18-3.23 (4H, m), 3.88-3.93 (4H, m), 4.45 (2H, s), 5.97 (1H, s), 6.71 (1H, dddd, J=9.0, 9.0, 2.4, 2.4 Hz), 6.87-6.91 (2H, m), 7.07 (1H, d, J=2.5 Hz), 7.33 (1H, dd, J=9.2, 2.5 Hz), 7.40 (1H, d, J=9.2 Hz), 9.39 (1H, s).

IR (ATR): 1676, 1654, 1606, 1530, 1491, 1443, 1317, 1252, 1231, 1111, 811 cm$^{-1}$.

MS: m/z 464 (M$^+$, base peak).

Example 122

Preparation of 4-[(3,5-difluorobenzyl)amino]-6-[(2-methyl-4-morpholinophenyl)amino]pyridine-3-carboxyamide

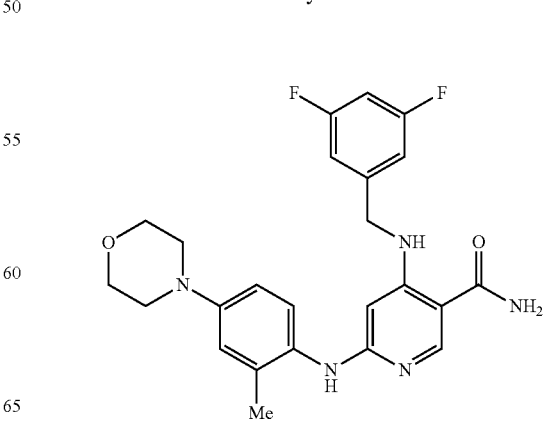

From 6-chloro-4-[(3,5-difluorobenzyl)amino]pyridine-3-carboxyamide (the compound of Example 20) and 2-methyl-4-morpholinoaniline in a manner similar to Example 46, the title compound was obtained as white needle crystals (yield 73%).

m.p. 216-217° C. (dec.)

¹H-NMR (400 MHz, CDCl₃) δ: 2.01 (3H, s), 3.14-3.18 (4H, m), 3.86-3.90 (4H, m), 4.19 (2H, d, J=5.9 Hz), 5.19 (1H, s), 5.68 (2H, br), 6.29 (1H, brs), 6.63-6.76 (5H, m), 6.87 (1H, d, J=8.6 Hz), 8.19 (1H, s), 8.94 (1H, d, J=5.9 Hz).

IR (ATR): 1625, 1596, 1565, 1523, 1508, 1450, 1411, 1314, 1261, 1238, 1122 cm⁻¹.

MS: m/z 453 (M⁺, base peak).

Example 123

Preparation of 6-[(2-chloro-4-morpholinophenyl)amino]-4-[(3,5-difluorobenzyl)amino]pyridine-3-carboxyamide

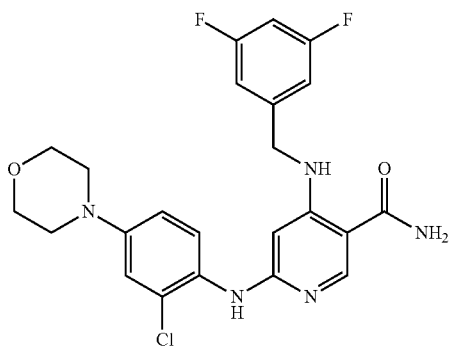 [SMILES: NC(=O)c1cnc(Nc2ccc(N3CCOCC3)cc2Cl)cc1NCc1cc(F)cc(F)c1]

From 6-chloro-4-[(3,5-difluorobenzyl)amino]pyridine-3-carboxyamide (the compound of Example 20) and 2-chloro-4-morpholinoaniline in a manner similar to Example 46, the title compound was obtained as brown needle crystals (yield 34%).

m.p. 217-220° C. (dec.)

¹H-NMR (400 MHz, CDCl₃+CD₃OD) δ: 3.10-3.19 (4H, m), 4.26-4.33 (4H, m), 4.29 (2H, d, J=5.6 Hz), 5.50 (1H, s), 6.67 (1H, dd, J=8.8, 2.9 Hz), 6.69-6.81 (3H, m), 6.91 (1H, d, J=2.9 Hz), 6.99 (1H, d, J=8.8 Hz), 8.22 (1H, s), 9.01 (1H, br).

IR (ATR): 1645, 1623, 1595, 1569, 1522, 1508, 1448, 1404, 1299, 1226, 1116 cm⁻¹.

MS: m/z 475, 473 (M⁺), 438 (base peak).

Example 124

Preparation of 4-[(3,5-difluorobenzyl)amino]-6-[(2-methoxy-4-morpholinophenyl)amino]-pyridine-3-carboxyamide

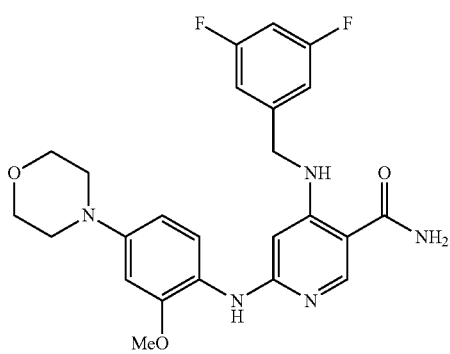 [SMILES: COc1cc(N2CCOCC2)ccc1Nc1cc(NCc2cc(F)cc(F)c2)c(C(N)=O)cn1]

From 6-chloro-4-[(3,5-difluorobenzyl)amino]pyridine-3-carboxyamide (the compound of Example 20) and 2-methoxy-4-morpholinoaniline in a manner similar to Example 46, the title compound was obtained as a light brown crystalline powder (yield 78%).

m.p. 190-191° C. (dec.)

¹H-NMR (400 MHz, CDCl₃) δ: 3.12-3.16 (4H, m), 3.79 (3H, s), 3.86-3.90 (4H, m), 4.31 (2H, d, J=5.8 Hz), 5.59 (2H, br), 5.65 (1H, s), 6.37 (1H, dd, J=8.7, 2.4 Hz), 6.48 (1H, d, J=2.4 Hz), 6.54 (1H, brs), 6.72 (1H, dddd, J=8.7, 8.7, 2.3, 2.3 Hz), 6.78-6.85 (2H, m), 7.00 (1H, d, J=8.7 Hz), 8.22 (1H, s), 8.95 (1H, brt, J=5.8 Hz).

IR (ATR): 1656, 1617, 1597, 1567, 1546, 1518, 1449, 1441, 1302, 1248, 1201, 1119, 973 cm⁻¹.

MS: m/z 469 (M⁺, base peak).

Example 125

Preparation of 6-[(3-cyano-4-morpholinophenyl)amino]-4-[(3,5-difluorobenzyl)amino]pyridine-3-carboxyamide

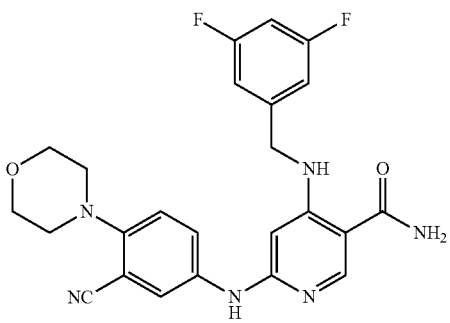 [SMILES: N#Cc1cc(Nc2cc(NCc3cc(F)cc(F)c3)c(C(N)=O)cn2)ccc1N1CCOCC1]

From 6-chloro-4-[(3,5-difluorobenzyl)amino]pyridine-3-carboxyamide (the compound of Example 20) and 3-cyano-4-morpholinoaniline in a manner similar to Example 46, the title compound was obtained as light brown needle crystals (yield 50%).

m.p. 213.5-214.1° C. (dec.)

¹H-NMR (400 MHz, CDCl₃) δ: 3.14-3.18 (4H, m), 3.89-3.93 (4H, m), 4.34 (2H, d, J=5.4 Hz), 5.58 (1H, s), 6.74 (1H, dddd, J=8.8, 8.8, 2.2, 2.2 Hz), 6.78-6.84 (2H, m), 6.89 (1H, d, J=8.8 Hz), 7.17 (1H, dd, J=8.8, 2.7 Hz), 7.46 (1H, d, J=2.7 Hz), 8.22 (1H, s), 9.03 (1H, d, J=5.4 Hz).

IR (ATR): 1647, 1606, 1569, 1544, 1500, 1415, 1307, 1251, 1227, 1129 cm⁻¹.

MS: m/z 464 (M⁺).

Example 126

Preparation of 4-[(3,5-difluorobenzyl)amino]-6-[(3-methyl-4-morpholinophenyl)amino]-pyridine-3-carboxyamide

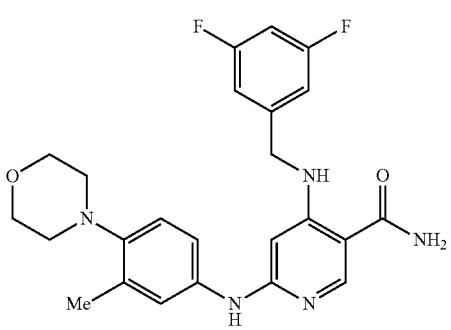 [SMILES: Cc1cc(Nc2cc(NCc3cc(F)cc(F)c3)c(C(N)=O)cn2)ccc1N1CCOCC1]

From 6-chloro-4-[(3,5-difluorobenzyl)amino]pyridine-3-carboxyamide (the compound of Example 20) and 3-methyl-4-morpholinoaniline in a manner similar to Example 46, the title compound was obtained as white needle crystals (yield 77%).

m.p. 223-224° C. (dec.)

$^1$H-NMR (400 MHz, CDCl$_3$) δ: 2.23 (3H, s), 2.87-2.93 (4H, m), 3.85-3.89 (4H, m), 4.30 (2H, d, J=5.8 Hz), 5.70 (1H, s), 6.70-6.82 (4H, m), 6.86-6.91 (2H, m), 8.91 (1H, s), 9.01 (1H, d, J=5.8 Hz).

IR (ATR): 1649, 1607, 1573, 1548, 1504, 1414, 1307, 1253, 1223, 1114, 1106 cm$^{-1}$.

MS: m/z 453 (M$^+$, base peak).

Example 127

Preparation of 6-[(3-chloro-4-morpholinophenyl)amino]-4-[(3,5-difluorobenzyl)amino]pyridine-3-carboxyamide

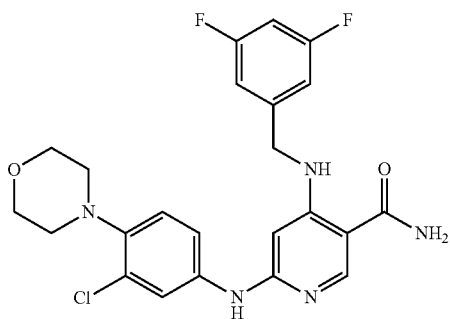 [SMILES: NC(=O)c1cnc(Nc2ccc(N3CCOCC3)c(Cl)c2)cc1NCc1cc(F)cc(F)c1]

From 6-chloro-4-[(3,5-difluorobenzyl)amino]pyridine-3-carboxyamide (the compound of Example 20) and 3-chloro-4-morpholinoaniline in a manner similar to Example 46, the title compound was obtained as light pink needle crystals (yield 78%).

m.p. 222-223° C. (dec.)

$^1$H-NMR (400 MHz, DMSO-d6) δ: 2.85-2.91 (4H, m), 3.69-3.75 (4H, m), 4.43 (2H, d, J=5.9 Hz), 5.71 (1H, s), 6.96-7.05 (3H, m), 7.14 (1H, dddd, J=9.4, 9.4, 2.3, 2.3 Hz), 7.19 (1H, s), 7.25 (1H, dd, J=8.6, 2.3 Hz), 7.83 (1H, br), 7.86 (1H, d, J=2.3 Hz), 8.40 (1H, s), 8.95 (1H, brs), 9.05 (1H, brt, J=5.9 Hz).

IR (ATR): 1645, 1603, 1566, 1541, 1500, 1416, 1306, 1249, 1228, 1109 cm$^{-1}$.

MS: m/z 473, 475 (M$^+$).

Example 128

Preparation of 4-[(3,5-difluorobenzyl)amino]-6-[(3-methoxy-4-morpholinophenyl)amino]pyridine-3-carboxyamide

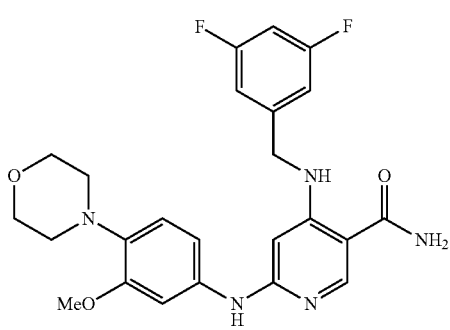 [SMILES: COc1cc(Nc2cc(NCc3cc(F)cc(F)c3)c(C(N)=O)cn2)ccc1N1CCOCC1]

From 6-chloro-4-[(3,5-difluorobenzyl)amino]pyridine-3-carboxyamide (the compound of Example 20) and 3-methoxy-4-morpholinoaniline in a manner similar to Example 46, the title compound was obtained as light purple needle crystals (yield 78%).

m.p. 229.6-230.0° C. (dec.)

$^1$H-NMR (400 MHz, CDCl$_3$) δ: 3.03-3.07 (4H, m), 3.76 (3H, s), 3.88-3.92 (4H, m), 4.29 (2H, d, J=5.9 Hz), 5.78 (1H, s), 6.50 (1H, dd, J=8.3, 2.4 Hz), 6.65 (1H, d, J=2.4 Hz), 6.72 (1H, dddd, J=8.9, 8.9, 2.3, 2.3 Hz), 6.75-6.81 (4H, m), 8.20 (1H, s), 9.00 (1H, brt, J=5.9 Hz).

IR (ATR): 1644, 1608, 1592, 1572, 1544, 1508, 1439, 1413, 1304, 1221, 1110 cm$^{-1}$.

MS: m/z 469 (M$^+$, base peak).

Example 129

Preparation of 4-(benzylamino)-6-[methyl(4-morpholinophenyl)amino]pyridine-3-carboxyamide

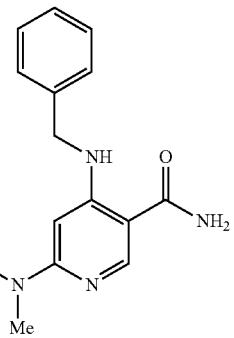

From 4-(benzylamino)-6-chloropyridine-3-carboxyamide (the compound of Example 1) and methyl-4-morpholinoaniline in a manner similar to Example 46, the title compound was obtained as a slight brown crystalline powder (yield 77%).

m.p. 226-227° C. (dec.)

$^1$H-NMR (400 MHz, CDCl$_3$) δ: 3.88-3.92 (4H, m), 3.16-3.21 (4H, m), 3.36 (3H, s), 4.15 (2H, d, J=5.4 Hz), 5.74 (1H, s), 5.57 (2H, br), 6.84 (2H, d, J=8.8 Hz), 6.98 (2H, d, J=8.8 Hz), 7.13-7.15 (2H, m), 7.19-7.28 (3H, m), 8.26 (1H, s), 8.65 (1H, brt, J=5.4 Hz).

IR (ATR): 1636, 1594, 1561, 1512, 1422, 1387, 1309, 1229, 1120 cm$^{-1}$.

MS: m/z 417 (M$^+$, base peak)

Example 130

Preparation of 4-(benzylamino)-6-[(3-morpholinophenyl)amino]pyridine-3-carboxyamide

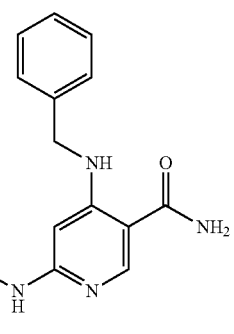

From 4-(benzylamino)-6-chloropyridine-3-carboxamide (the compound of Example 1) and 3-morpholinoaniline in a manner similar to Example 46, the title compound was obtained as a light brown crystalline powder (yield 62%).

$^1$H-NMR (400 MHz, CDCl$_3$) δ: 3.07-3.10 (4H, m), 3.80-3.84 (4H, m), 4.34 (2H, d, J=5.8 Hz), 5.61 (2H, br), 5.96 (1H, s), 6.49 (1H, dd, J=8.0, 2.0 Hz), 6.62 (1H, dd, J=8.0, 2.0 Hz), 6.65 (1H, brs), 6.68 (1H, dd, J=2.0, 2.0 Hz), 7.11 (1H, dd, J=8.0, 8.0 Hz), 8.22 (1H, s), 8.91 (1H, brt, J=5.8 Hz).

IR (ATR): 1659, 1620, 1598, 1572, 1495, 1450, 1414, 1302, 1245 cm$^{-1}$.

Example 131

Preparation of 4-[(3,5-difluorobenzyl)amino]-6-[(3-morpholinophenyl)amino]pyridine-3-carboxyamide

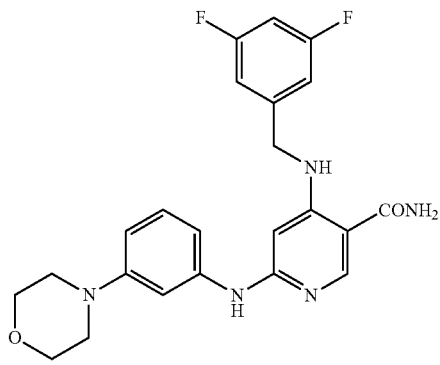 [SMILES: NC(=O)c1cnc(Nc2cccc(N3CCOCC3)c2)cc1NCc1cc(F)cc(F)c1]

From 6-chloro-4-[(3,5-difluorobenzyl)amino]pyridine-3-carboxyamide (the compound of Example 20) and 3-morpholinoaniline in a manner similar to Example 46, the title compound was obtained as light brown needle crystals (yield 65%).

m.p. 197-198° C. (dec.)

$^1$H-NMR (400 MHz, CDCl$_3$) δ: 3.08-3.13 (4H, m), 3.82-3.86 (4H, m), 4.31 (2H, d, J=5.9 Hz), 5.82 (1H, s), 6.46 (1H, dd, J=8.8, 1.9 Hz), 6.63-6.83 (2H, m), 6.72 (1H, dddd, J=8.8, 8.8, 2.3, 2.3 Hz), 6.76-6.83 (2H, m), 7.12 (1H, dd, J=8.8, 8.0 Hz), 8.01 (1H, s), 9.01 (1H, brt, J=5.9 Hz).

IR (ATR): 1622, 1595, 1578, 1503, 1444, 1468, 1319, 1287, 1263, 1236, 1200, 1115 cm$^{-1}$.

MS: m/z 440 (M$^+$).

Example 132

Preparation of 4-[(3,5-difluorobenzyl)amino]-6-[(4-fluoro-3-morpholinophenyl)amino]pyridine-3-carboxyamide

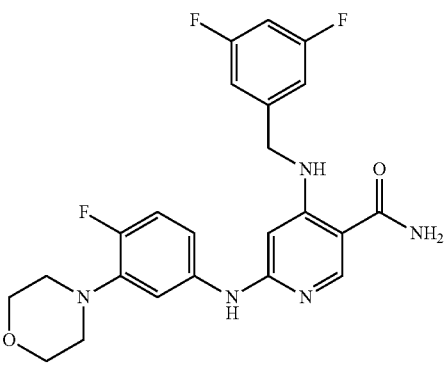 [SMILES: NC(=O)c1cnc(Nc2ccc(F)c(N3CCOCC3)c2)cc1NCc1cc(F)cc(F)c1]

From 6-chloro-4-[(3,5-difluorobenzyl)amino]pyridine-3-carboxyamide (the compound of Example 20) and 4-fluoro-3-morpholinoaniline in a manner similar to Example 46, the title compound was obtained as white needle crystals (yield 57%).

m.p. 214.7-215.2° C.

$^1$H-NMR (400 MHz, CDCl$_3$) δ: 2.98-3.02 (4H, m), 3.83-3.87 (4H, m), 4.31 (2H, d, J=6.0 Hz), 5.65 (1H, s), 6.57 (1H, dddd, J=8.8, 3.6, 2.7 Hz), 6.53 (1H, br), 6.67-6.83 (4H, m), 6.91 (1H, dd, J=12.2, 8.8 Hz), 8.21 (1H, m), 9.00 (1H, brt, J=6.0 Hz).

IR (ATR): 1608, 1585, 1550, 1508, 1417, 1299, 1262, 1250, 1237, 1213, 1114, 991 cm$^{-1}$.

MS: m/z 457 (M$^+$, base peak).

Example 133

Preparation of 4-(benzylamino)-6-[(2-morpholinophenyl)amino]pyridine-3-carboxyamide

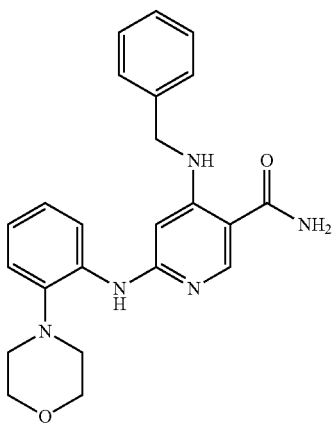 [SMILES: NC(=O)c1cnc(Nc2ccccc2N2CCOCC2)cc1NCc1ccccc1]

From 4-(benzylamino)-6-chloropyridine-3-carboxyamide (the compound of Example 1) and 2-morpholinoaniline in a manner similar to Example 46, the title compound was obtained as a slight yellow crystalline powder (yield 88%).

$^1$H-NMR (400 MHz, CDCl$_3$) δ: 2.83-2.87 (4H, m), 3.80-3.84 (4H, m), 4.40 (2H, d, J=5.6 Hz), 5.66 (2H, br), 5.99 (1H, s), 6.92 (1H, ddd, J=7.7, 7.7, 1.7 Hz), 6.98 (1H, ddd, J=7.7, 7.7, 1.7 Hz), 7.08 (1H, dd, J=7.7, 1.7 Hz), 7.13 (1H, dd, J=7.7, 1.7 Hz), 7.23 (1H, brs), 8.26 (1H, s), 8.95 (1H, brt, J=5.6 Hz).

IR (ATR): 1653, 1618, 1594, 1570, 1518, 1452, 1409, 1302, 1227, 1114 cm$^{-1}$.

Example 134

Preparation of 4-(benzylamino)-6-({4-[(3S)-3-methylmorpholino]phenyl}amino)pyridine-3-carboxyamide

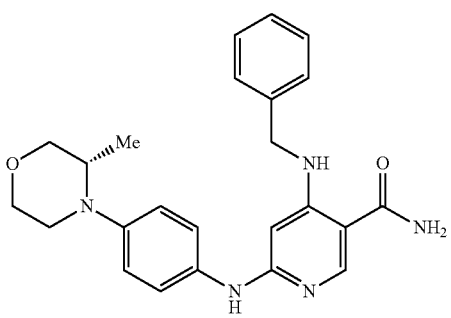 [SMILES: C[C@H]1COCCN1c1ccc(Nc2cc(NCc3ccccc3)c(C(N)=O)cn2)cc1]

From 4-(benzylamino)-6-chloropyridine-3-carboxyamide (the compound of Example 1) and 4-[(3S)-3-methylmorpholino]aniline in a manner similar to Example 46, the title compound was obtained as a brown solid (yield 11%).

$^1$H-NMR (270 MHz, CDCl$_3$) δ: 1.06 (3H, d, J=6.3 Hz), 2.98-3.19 (2H, m), 3.60-3.69 (2H, m), 3.69-3.81 (2H, m), 3.88 (1H, dd, J=11.0, 2.8 Hz), 3.97 (1H, td, J=7.4, 3.5 Hz), 4.30 (2H, d, J=5.6 Hz), 5.67 (2H, br s), 5.74 (1H, s), 6.65 (1H, br s), 6.78 (2H, d, J=8.9 Hz), 6.92 (2H, d, J=8.9 Hz), 7.22-7.37 (5H, m), 8.20 (1H, s), 8.86-8.93 (1H, m).

Example 135

Preparation of 4-[(3,5-difluorobenzyl)amino]-6-({4-[(2R,6S)-2,6-dimethylmorpholino]phenyl}amino)pyridine-3-carboxyamide

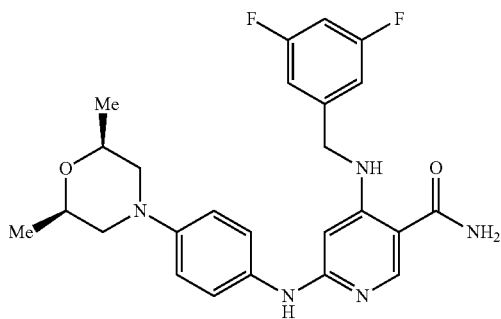 [SMILES: C[C@@H]1CN(c2ccc(Nc3cc(NCc4cc(F)cc(F)c4)c(C(N)=O)cn3)cc2)C[C@H](C)O1]

From 6-chloro-4-[(3,5-difluorobenzyl)amino]pyridine-3-carboxyamide (the compound of Example 20) and 4-[(2R,6S)-2,6-dimethylmorpholino]aniline in a manner similar to Example 46, the title compound was obtained as a white solid (yield 94%).

$^1$H-NMR (400 MHz, CDCl$_3$) δ: 1.28 (6H, d, J=6.4 Hz), 2.42 (4H, dd, J=11.1, 11.1 Hz), 3.42 (2H, d, J=11.1 Hz), 3.78-3.87 (2H, m), 4.26 (2H, d, J=5.8 Hz), 5.58 (1H, s), 6.73 (1H, dddd, J=2.3, 2.3, 8.8, 8.8 Hz), 6.74-6.80 (2H, m), 6.80 (2H, d, J=8.8 Hz), 6.87 (2H, d, J=8.8 Hz), 8.18 (1H, s), 8.98 (1H, brt, J=5.8 Hz).

IR (ATR): 1605, 1570, 1515, 1451, 1410, 1348, 1314, 1294, 1241, 1175, 1118, 1086 cm$^{-1}$.

MS: m/z 467 (M$^+$, base peak).

Example 136

Preparation of 4-(benzylamino)-6-({4-[(3R,5S)-3,5-dimethylpiperazin-1-yl]phenyl}amino)pyridine-3-carboxyamide

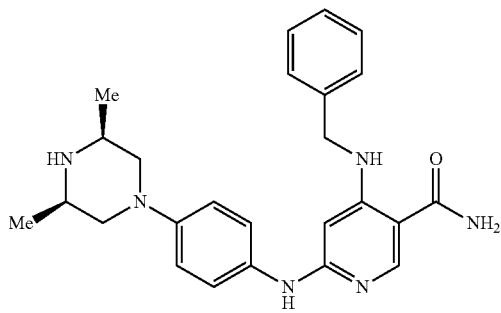 [SMILES: C[C@@H]1CN(c2ccc(Nc3cc(NCc4ccccc4)c(C(N)=O)cn3)cc2)C[C@H](C)N1]

From 4-(benzylamino)-6-chloropyridine-3-carboxyamide (the compound of Example 1) and 4-[(3R,5S)-3,5-dimethylpiperazin-1-yl]aniline in a manner similar to Example 46, the title compound was obtained as a light brown solid (yield 81%).

$^1$H-NMR (270 MHz, CDCl$_3$) δ: 1.16 (6H, d, J=6.3 Hz), 2.29 (2H, t, J=10.9 Hz), 3.01-3.12 (2H, m), 3.46 (2H, d, J=10.9 Hz), 4.29 (2H, d, J=5.3 Hz), 5.57 (2H, br s), 5.74 (1H, s), 6.44 (1H, s), 6.81 (2H, d, J=8.8 Hz), 6.92 (2H, d, J=8.8 Hz), 7.20-7.36 (5H, m), 8.18 (1H, s), 8.84 (1H, br s).

IR (ATR): 1652, 1618, 1583, 1544, 1513, 1409, 1284, 1252, 1192 cm$^{-1}$.

Example 137

Preparation of 4-[(2-methoxybenzyl)amino]-6-({4-[(3R,5S)-3,5-dimethylpiperazin-1-yl]phenyl}amino)pyridine-3-carboxyamide

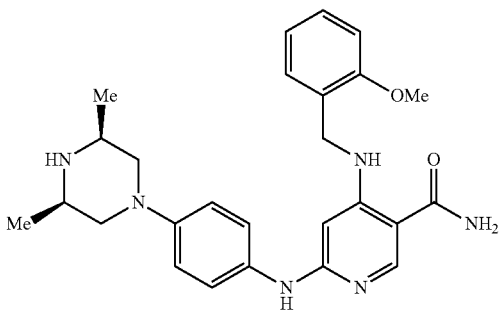 [SMILES: COc1ccccc1CNc1cc(Nc2ccc(N3C[C@@H](C)N[C@@H](C)C3)cc2)ncc1C(N)=O]

From 6-chloro-4-[(2-methoxybenzyl)amino]pyridine-3-carboxyamide (the compound of Example 2) and 4-[(3R,5S)-3,5-dimethylpiperazin-1-yl]aniline in a manner similar to Example 46, the title compound was obtained as a light brown amorphous substance (yield 29%).

$^1$H-NMR (400 MHz, CDCl$_3$) δ: 1.15 (6H, d, J=6.4 Hz), 2.28 (2H, dd, J=11.0, 11.0 Hz), 3.00-3.10 (2H, m), 3.46 (2H, dd, J=12.2, 2.7 Hz), 3.78 (3H, s), 4.28 (2H, d, J=5.9 Hz), 5.58 (2H, brs), 5.79 (1H, s), 6.47 (1H, s), 6.83 (2H, d, J=9.0 Hz), 6.86-6.93 (2H, m), 7.01 (2H, d, J=9.0 Hz), 7.18 (1H, dd, J=7.6, 1.5 Hz), 7.19-7.29 (1H, m), 8.17 (1H, s), 8.75 (1H, t, J=5.9 Hz).

Example 138

Preparation of 4-[(2-methylbenzyl)amino]-6-({4-[(3R,5S)-3,5-dimethylpiperazin-1-yl]phenyl}amino)pyridine-3-carboxyamide

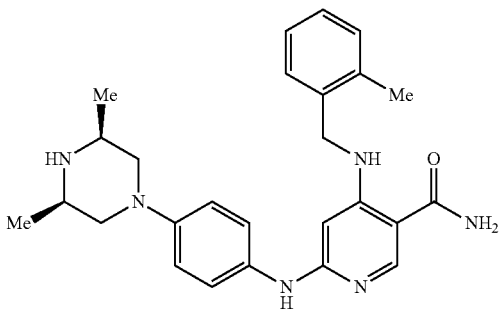 [SMILES: Cc1ccccc1CNc1cc(Nc2ccc(N3C[C@@H](C)N[C@@H](C)C3)cc2)ncc1C(N)=O]

From 6-chloro-4-[(2-methylbenzyl)amino]pyridine-3-carboxyamide (the compound of Example 5) and 4-[(3R,5S)-3,5-dimethylpiperazin-1-yl]aniline in a manner similar to Example 46, the title compound was obtained as a white crystalline powder (yield 45%).

¹H-NMR (400 MHz, DMSO-d6) δ: 1.01 (6H, d, J=6.4 Hz), 2.04 (2H, dd, J=10.9, 10.9 Hz), 2.29 (3H, s), 2.79-2.89 (2H, m), 3.39 (2H, d, J=11.0 Hz), 4.28 (2H, d, J=5.6 Hz), 5.74 (1H, s), 6.80 (2H, d, J=9.0 Hz), 7.13-7.23 (4H, m), 7.25-7.30 (2H, m), 8.34 (1H, s), 8.58 (1H, s), 8.87 (1H, t, J=5.7 Hz).

Example 139

Preparation of 4-[(2-chlorobenzyl)amino]-6-({4-[(3R,5S)-3,5-dimethylpiperazin-1-yl]phenyl}amino)pyridine-3-carboxyamide

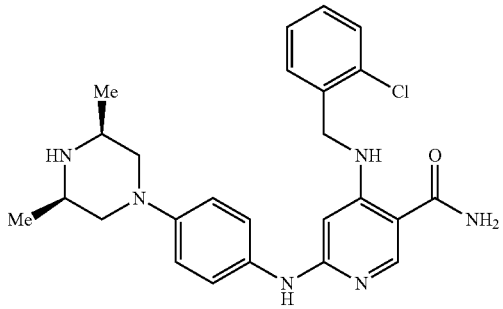 [SMILES: C[C@@H]1CN(c2ccc(Nc3cc(NCc4ccccc4Cl)c(C(N)=O)cn3)cc2)C[C@H](C)N1]

From 6-chloro-4-[(2-chlorobenzyl)amino]pyridine-3-carboxyamide (the compound of Example 9) and 4-[(3R,5S)-3,5-dimethylpiperazin-1-yl]aniline in a manner similar to Example 46, the title compound was obtained as a white crystalline powder (yield 65%).

¹H-NMR (400 MHz, DMSO-d6) δ: 1.01 (6H, d, J=6.4 Hz), 2.04 (2H, dd, J=10.7, 10.7 Hz), 2.79-2.88 (2H, m), 3.38 (2H, dd, J=10.8, 2.8 Hz), 4.41 (2H, d, J=6.1 Hz), 5.65 (1H, s), 6.78 (2H, d, J=9.0 Hz), 7.24 (2H, d, J=9.0 Hz), 7.28-7.36 (3H, m), 7.46-7.51 (1H, m), 8.35 (1H, s), 8.58 (1H, s), 9.03 (1H, t, J=6.1 Hz).

Example 140

Preparation of 4-[(2,3-difluorobenzyl)amino]-6-({4-[(3R,5S)-3,5-dimethylpiperazin-1-yl]phenyl}amino)pyridine-3-carboxyamide

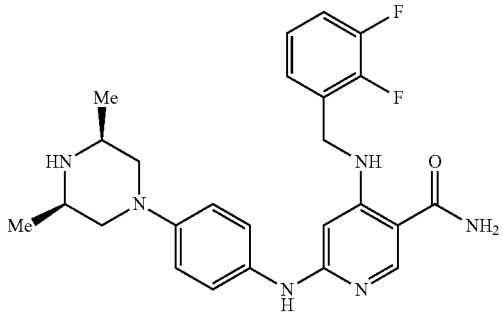 [SMILES: C[C@@H]1CN(c2ccc(Nc3cc(NCc4cccc(F)c4F)c(C(N)=O)cn3)cc2)C[C@H](C)N1]

From 6-chloro-4-[(2,3-difluorobenzyl)amino]pyridine-3-carboxyamide (the compound of Example 19) and 4-[(3R,5S)-3,5-dimethylpiperazin-1-yl]aniline in a manner similar to Example 46, the title compound was obtained as a white crystalline powder (yield 66%).

¹H-NMR (400 MHz, DMSO-d6) δ: 1.01 (6H, d, J=6.4 Hz), 2.04 (2H, dd, J=10.9, 10.9 Hz), 2.79-2.88 (2H, m), 3.39 (2H, dd, J=10.8, 2.6 Hz), 4.45 (2H, d, J=5.8 Hz), 5.68 (1H, s), 6.78 (2H, d, J=9.0 Hz), 7.09 (1H, dd, J=6.8, 6.8 Hz), 7.17-7.23 (3H, m), 7.36 (1H, ddd, J=8.3, 8.3, 8.3 Hz), 8.35 (1H, s), 8.57 (1H, s), 9.02 (1H, t, J=5.8 Hz).

Example 141

Preparation of 4-[(3,5-difluorobenzyl)amino]-6-({4-[(3R,5S)-3,5-dimethylpiperazin-1-yl]phenyl}amino)pyridine-3-carboxyamide

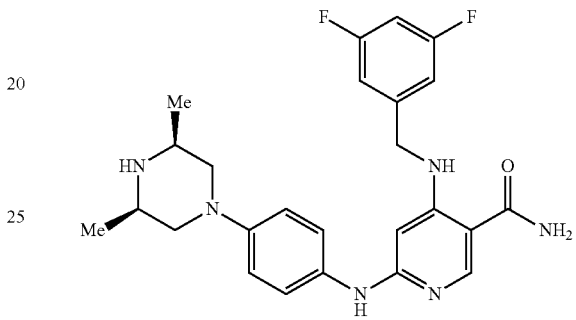

From 6-chloro-4-[(3,5-difluorobenzyl)amino]pyridine-3-carboxyamide (the compound of Example 20) and 4-[(3R,5S)-3,5-dimethylpiperazin-1-yl]aniline in a manner similar to Example 46, the title compound was obtained as a slight brown crystalline powder (yield 79%).

¹H-NMR (400 MHz, CDCl₃) δ: 1.16 (6H, d, J=6.4 Hz), 2.25-2.32 (2H, m), 3.01-3.11 (2H, m), 3.46-3.51 (2H, m), 4.27 (2H, d, J=5.8 Hz), 5.58 (3H, brs), 6.40 (1H, brs), 6.70-6.80 (3H, m), 6.82 (2H, d, J=9.0 Hz), 6.86 (2H, d, J=9.0 Hz), 8.19 (1H, s), 8.95 (1H, brt, J=5.8 Hz).

IR (ATR): 1661, 1616, 1609, 1594, 1558, 1514, 1494, 1402, 1252, 1315, 1253, 1243, 1112 cm⁻¹.

Example 142

Preparation of 4-[(2,5-difluorobenzyl)amino]-6-({4-[(3R,5S)-3,5-dimethylpiperazin-1-yl]phenyl}amino)pyridine-3-carboxyamide

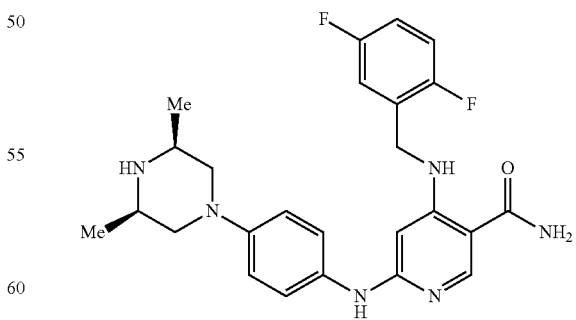

From 6-chloro-4-[(2,5-difluorobenzyl)amino]pyridine-3-carboxyamide (the compound of Example 22) and 4-[(3R,5S)-3,5-dimethylpiperazin-1-yl]aniline in a manner similar to Example 46, the title compound was obtained as a white crystalline powder (yield 72%).

¹H-NMR (400 MHz, DMSO-d6) δ: 1.01 (6H, d, J=6.3 Hz), 2.05 (2H, dd, J=10.7, 10.7 Hz), 2.79-2.89 (2H, m), 3.39 (2H, dd, J=10.7, 2.7 Hz), 4.40 (2H, d, J=6.1 Hz), 5.71 (1H, s), 6.80 (2H, d, J=9.0 Hz), 7.02-7.08 (1H, m), 7.15-7.22 (1H, m), 7.23-7.33 (3H, m), 8.35 (1H, s), 8.60 (1H, s), 8.99 (1H, t, J=6.1 Hz).

Example 143

Preparation of 4-[(2,6-difluorobenzyl)amino]-6-({4-[(3R,5S)-3,5-dimethylpiperazin-1-yl]phenyl}amino)pyridine-3-carboxyamide

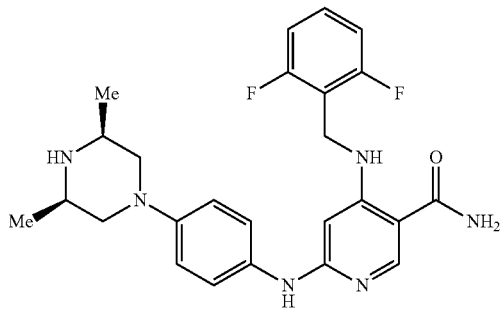 [SMILES: C[C@@H]1CN(c2ccc(Nc3cc(NCc4c(F)cccc4F)c(C(N)=O)cn3)cc2)C[C@H](C)N1]

From 6-chloro-4-[(2,6-difluorobenzyl)amino]pyridine-3-carboxyamide (the compound of Example 23) and 4-[(3R,5S)-3,5-dimethylpiperazin-1-yl]aniline in a manner similar to Example 46, the title compound was obtained as light pink needle crystals (yield 57%).

m.p. 218-219° C.
¹H-NMR (400 MHz, CDCl₃+CD₃OD) δ: 1.16 (6H, d, J=6.4 Hz), 2.33 (2H, t, J=11.1 Hz), 3.03-3.13 (2H, m), 3.52 (2H, dd, J=12.2, 2.4 Hz), 4.32 (2H, d, J=6.0 Hz), 5.97 (1H, s), 6.82-6.90 (2H, m), 6.96 (2H, d, J=8.8 Hz), 7.15 (2H, d, J=8.8 Hz), 7.12-7.26 (1H, m), 8.14 (1H, s), 8.78 (1H, brt, J=6.0 Hz).
IR (ATR): 1633, 1608, 1570, 1543, 1515, 1470, 1413, 1300, 1289, 1251, 1234, 1189 cm⁻¹.
MS: m/z 466 (M⁺), 396 (base peak).

Example 144

Preparation of 4-[(3,5-difluorobenzyl)amino]-6-({3-[(3R,5S)-3,5-dimethylpiperazin-1-yl]phenyl}amino)pyridine-3-carboxyamide

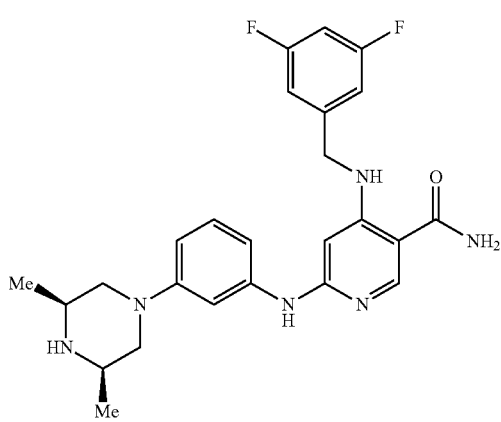 [SMILES: C[C@@H]1CN(c2cccc(Nc3cc(NCc4cc(F)cc(F)c4)c(C(N)=O)cn3)c2)C[C@H](C)N1]

From 6-chloro-4-[(3,5-difluorobenzyl)amino]pyridine-3-carboxyamide (the compound of Example 20) and 3-[(3R,5S)-3,5-dimethylpiperazin-1-yl]aniline in a manner similar to Example 46, the title compound was obtained as a light brown solid (yield 23%).

m.p. 222-224° C. (dec.)
¹H-NMR (270 MHz, DMSO-d6) δ: 1.02 (6H, d, J=6.3 Hz), 2.11 (2H, t, J=11.1 Hz), 2.80-2.91 (2H, m), 3.17 (1H, d, J=4.9 Hz), 3.44 (2H, d, J=11.1 Hz), 4.41 (2H, d, J=5.9 Hz), 5.77 (1H, s), 6.48 (1H, d, J=6.9 Hz), 6.88-7.18 (6H, m), 8.38 (1H, s), 8.70 (1H, s), 9.03 (1H, t, J=6.1 Hz).

Example 145

Preparation of 4-(benzylamino)-6-{[4-(4-methylpiperazin-1-yl)phenyl]amino}pyridine-3-carboxyamide

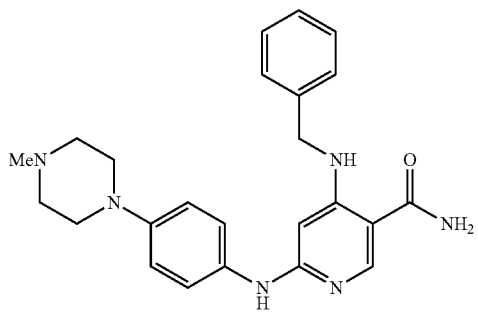 [SMILES: CN1CCN(c2ccc(Nc3cc(NCc4ccccc4)c(C(N)=O)cn3)cc2)CC1]

From 4-(benzylamino)-6-chloropyridine-3-carboxyamide (the compound of Example 1) and 4-(4-methylpiperazin-1-yl)aniline in a manner similar to Example 46, the title compound was obtained as a light brown crystalline powder (yield 63%).

¹H-NMR (400 MHz, CDCl₃) δ: 2.37 (3H, s), 2.58-2.62 (4H, m), 3.17-3.21 (4H, m), 4.30 (2H, d, J=5.6 Hz), 5.54 (2H, br), 5.74 (1H, s), 6.43 (1H, brs), 6.82 (2H, d, J=9.0 Hz), 6.91 (2H, d, J=9.0 Hz), 7.23-7.36 (5H, m), 8.19 (1H, s), 8.87 (1H, brt, J=5.6 Hz).
IR (ATR): 1649, 1618, 1569, 1514, 1452, 1408, 1307, 1291, 1237 cm⁻¹.

Example 146

Preparation of 4-(benzylamino)-6-({4-[4-(propan-2-yl)piperazin-1-yl]phenyl}amino)pyridine-3-carboxyamide

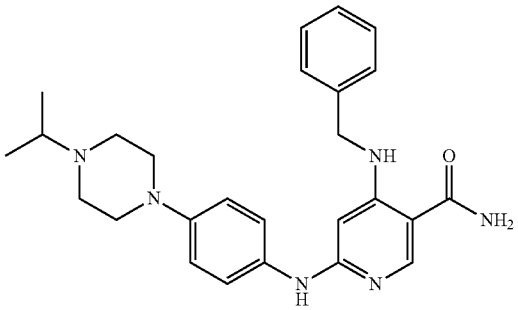 [SMILES: CC(C)N1CCN(c2ccc(Nc3cc(NCc4ccccc4)c(C(N)=O)cn3)cc2)CC1]

From 4-(benzylamino)-6-chloropyridine-3-carboxyamide (the compound of Example 1) and 4-[4-(propan-2-yl)piperazin-1-yl]aniline in a manner similar to Example 46, the title compound was obtained as a white crystalline powder (yield 45%).

¹H-NMR (400 MHz, CDCl₃) δ: 1.13 (6H, d, J=6.6 Hz), 2.68-2.79 (5H, m), 3.18-3.21 (4H, t, J=4.9 Hz), 4.30 (2H, d, J=5.6 Hz), 5.52 (2H, s), 5.74 (1H, s), 6.37 (1H, s), 6.81 (2H, d, J=9.0 Hz), 6.90 (2H, d, J=8.8 Hz), 7.24-7.35 (5H, m), 8.18 (1H, s), 8.86 (1H, t, J=5.9 Hz).

IR (ATR): 3320, 2967, 2818, 1635, 1599, 1570, 1546, 1514, 1410, 1297, 1233 cm⁻¹.

Example 147

Preparation of 4-[(2-methoxybenzyl)amino]-6-({4-[4-(propan-2-yl)piperazin-1-yl]phenyl}amino)pyridine-3-carboxyamide

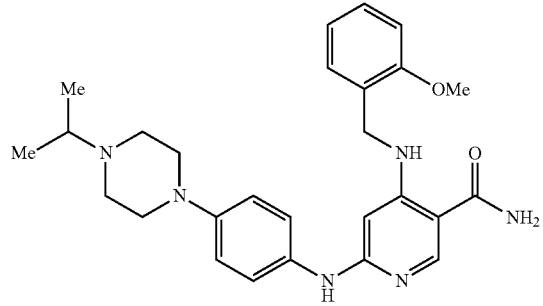 [SMILES: COc1ccccc1CNc1cc(Nc2ccc(N3CCN(C(C)C)CC3)cc2)ncc1C(N)=O]

From 6-chloro-4-[(2-methoxybenzyl)amino]pyridine-3-carboxyamide (the compound of Example 2) and 4-[4-(propan-2-yl)piperazin-1-yl]aniline in a manner similar to Example 46, the title compound was obtained as a light brown crystalline powder (yield 41%).

¹H-NMR (400 MHz, DMSO-d6) δ: 1.00 (6H, d, J=6.4 Hz), 2.53-2.59 (4H, m), 2.66 (1H, hept, J=6.5 Hz), 2.90-3.05 (4H, m), 3.80 (3H, s), 4.27 (2H, d, J=5.8 Hz), 5.73 (1H, s), 6.79 (2H, d, J=9.0 Hz), 6.92 (1H, dd, J=7.4, 7.4 Hz), 7.03 (1H, d, J=8.0 Hz), 7.09 (1H, d, J=7.1 Hz), 7.23-7.30 (3H, m), 8.33 (1H, s), 8.57 (1H, s), 8.90 (1H, t, J=5.7 Hz).

Example 148

Preparation of 4-[(2-methylbenzyl)amino]-6-({4-[4-(propan-2-yl)piperazin-1-yl]phenyl}amino)pyridine-3-carboxyamide

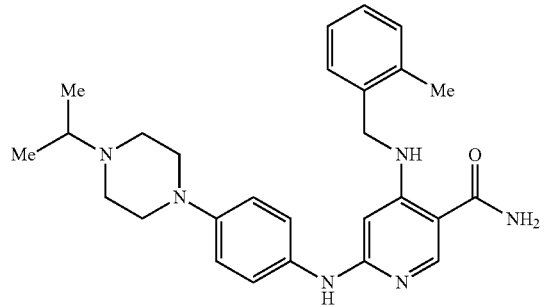 [SMILES: CC(C)N1CCN(c2ccc(Nc3cc(NCc4ccccc4Cl)c(C(N)=O)cn3)cc2)CC1]

From 6-chloro-4-[(2-methylbenzyl)amino]pyridine-3-carboxyamide (the compound of Example 5) and 4-[4-(propan-2-yl)piperazin-1-yl]aniline in a manner similar to Example 46, the title compound was obtained as a white crystalline powder (yield 67%).

¹H-NMR (400 MHz, DMSO-d6) δ: 1.00 (6H, d, J=6.4 Hz), 2.29 (3H, s), 2.53-2.60 (4H, m), 2.66 (1H, hept, J=6.5 Hz), 2.99-3.05 (4H, m), 4.28 (2H, d, J=5.7 Hz), 5.74 (1H, s), 6.81 (2H, d, J=9.0 Hz), 7.14-7.23 (4H, m), 7.27 (2H, d, J=9.0 Hz), 8.34 (1H, s), 8.59 (1H, s), 8.88 (1H, t, J=5.7 Hz).

Example 149

Preparation of 4-[(2-chlorobenzyl)amino]-6-({4-[4-(propan-2-yl)piperazin-1-yl]phenyl}amino)pyridine-3-carboxyamide

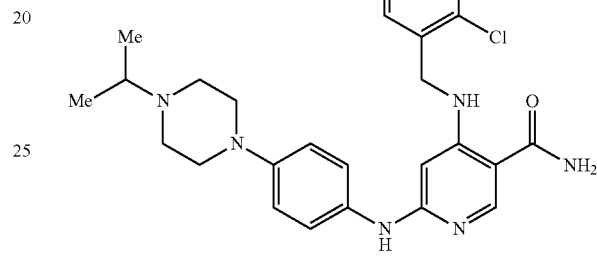

From 6-chloro-4-[(2-chlorobenzyl)amino]pyridine-3-carboxyamide (the compound of Example 9) and 4-[4-(propan-2-yl)piperazin-1-yl]aniline in a manner similar to Example 46, the title compound was obtained as a white crystalline powder (yield 61%).

¹H-NMR (400 MHz, DMSO-d6) δ: 1.00 (6H, d, J=6.4 Hz), 2.53-2.59 (4H, m), 2.65 (1H, hept, J=6.6 Hz), 2.93-3.05 (4H, m), 4.42 (2H, d, J=6.1 Hz), 5.65 (1H, s), 6.79 (2H, d, J=8.8 Hz), 7.23 (2H, d, J=9.0 Hz), 7.28-7.36 (3H, m), 7.46-7.52 (1H, m), 8.35 (1H, s), 8.60 (1H, s), 9.04 (1H, t, J=6.1 Hz).

Example 150

Preparation of 4-[(2,3-difluorobenzyl)amino]-6-({4-[4-(propan-2-yl)piperazin-1-yl]phenyl}amino)pyridine-3-carboxyamide

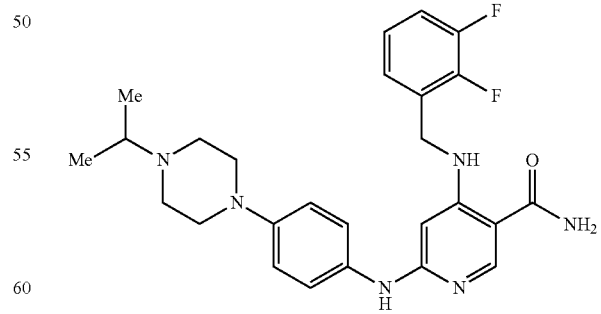

From 6-chloro-4-[(2,3-difluorobenzyl)amino]pyridine-3-carboxyamide (the compound of Example 19) and 4-[4-(propan-2-yl)piperazin-1-yl]aniline in a manner similar to Example 46, the title compound was obtained as a light brown crystalline powder (yield 30%).

¹H-NMR (400 MHz, DMSO-d6) δ: 1.01 (6H, d, J=6.3 Hz), 2.52-2.60 (4H, m), 2.62-2.71 (1H, m), 2.98-3.07 (4H, m), 4.46 (2H, d, J=5.8 Hz), 5.69 (1H, s), 6.79 (2H, d, J=9.0 Hz), 7.09 (1H, dd, J=6.8, 6.8 Hz), 7.16-7.26 (3H, m), 7.36 (1H, ddd, J=8.6, 8.6, 8.6 Hz), 8.34 (1H, s), 8.59 (1H, s), 9.02 (1H, t, J=5.8 Hz).

Example 151

Preparation of 4-[(3,5-difluorobenzyl)amino]-6-({4-[4-(propan-2-yl)piperazin-1-yl]phenyl}amino)pyridine-3-carboxyamide

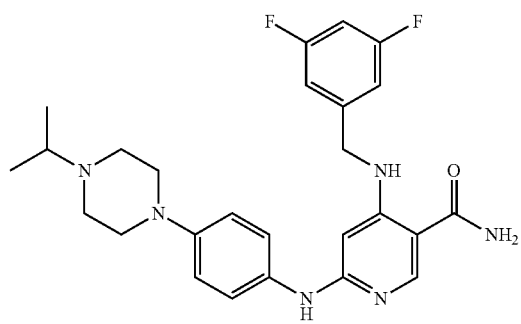 [SMILES: CC(C)N1CCN(c2ccc(Nc3cc(NCc4cc(F)cc(F)c4)c(C(N)=O)cn3)cc2)CC1]

From 6-chloro-4-[(3,5-difluorobenzyl)amino]pyridine-3-carboxyamide (the compound of Example 20) and 4-[4-(propan-2-yl)piperazin-1-yl]aniline in a manner similar to Example 46, the title compound was obtained as white needle crystals (yield 67%).

¹H-NMR (400 MHz, CDCl₃) δ: 1.11 (6H, d, J=6.6 Hz), 2.68-2.78 (5H, m), 3.16-3.22 (4H, m), 4.27 (2H, d, J=5.9 Hz), 5.59 (2H, br), 5.60 (1H, s), 6.43 (1H, brs), 6.69-6.80 (3H, m), 6.82 (2H, d, J=9.0 Hz), 6.87 (2H, d, J=9.0 Hz), 8.19 (1H, s), 8.95 (1H, br).

IR (ATR): 1623, 1597, 1569, 1516, 1452, 1410, 1351, 1311, 1237, 1116 cm⁻¹.

MS: m/z 480 (M⁺, base peak).

Example 152

Preparation of 4-[(2,5-difluorobenzyl)amino]-6-({4-[4-(propan-2-yl)piperazin-1-yl]phenyl}amino)pyridine-3-carboxyamide

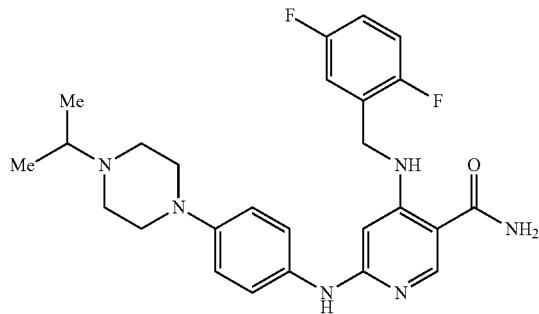 [SMILES: CC(C)N1CCN(c2ccc(Nc3cc(NCc4cc(F)ccc4F)c(C(N)=O)cn3)cc2)CC1]

From 6-chloro-4-[(2,5-difluorobenzyl)amino]pyridine-3-carboxyamide (the compound of Example 22) and 4-[4-(propan-2-yl)piperazin-1-yl]aniline in a manner similar to Example 46, the title compound was obtained as a white crystalline powder (yield 65%).

¹H-NMR (400 MHz, DMSO-d6) δ: 1.00 (6H, d, J=6.6 Hz), 2.54-2.60 (4H, m), 2.66 (1H, hept, J=6.5 Hz), 2.99-3.05 (4H, m), 4.40 (2H, d, J=5.8 Hz), 5.71 (1H, s), 6.80 (2H, d, J=8.8 Hz), 7.02-7.08 (1H, m), 7.15-7.22 (1H, m), 7.25 (2H, d, J=9.0 Hz), 7.26-7.34 (1H, m), 8.35 (1H, s), 8.61 (1H, s), 8.99 (1H, t, J=6.0 Hz).

Example 153

Preparation of 4-[(2,6-difluorobenzyl)amino]-6-({4-[4-(propan-2-yl)piperazin-1-yl]phenyl}amino)pyridine-3-carboxyamide

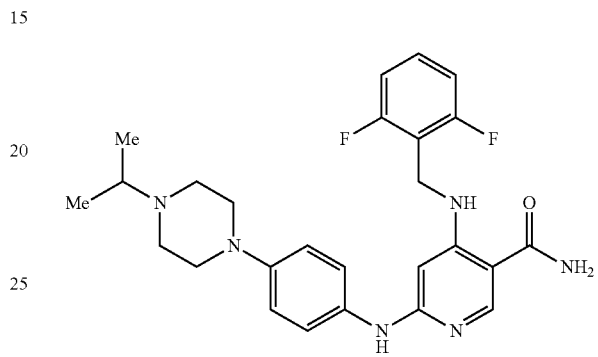

From 6-chloro-4-[(2,6-difluorobenzyl)amino]pyridine-3-carboxyamide (the compound of Example 23) and 4-[4-(propan-2-yl)piperazin-1-yl]aniline in a manner similar to Example 46, the title compound was obtained as light brown needle crystals (yield 54%).

m.p. 229-231° C. (dec.)

¹H-NMR (400 MHz, CDCl₃) δ: 1.11 (6H, d, J=6.3 Hz), 2.70-2.79 (3H, m), 3.22-3.26 (4H, m), 4.33 (2H, d, J=5.8 Hz), 5.96 (1H, s), 6.54 (1H, brs), 6.81-6.88 (2H, m), 6.96 (2H, d, J=8.8 Hz), 7.15 (2H, d, J=8.8 Hz), 7.17-7.26 (1H, m), 8.16 (1H, s), 8.78 (1H, brt, J=5.8 Hz).

IR (ATR): 1650, 1603, 1572, 1470, 1407, 1365, 1313, 1266, 1231, 1038 cm⁻¹.

Example 154

Preparation of 4-[(3-nitrobenzyl)amino]-6-({4-[4-(propan-2-yl)piperazin-1-yl]phenyl}amino)pyridine-3-carboxyamide

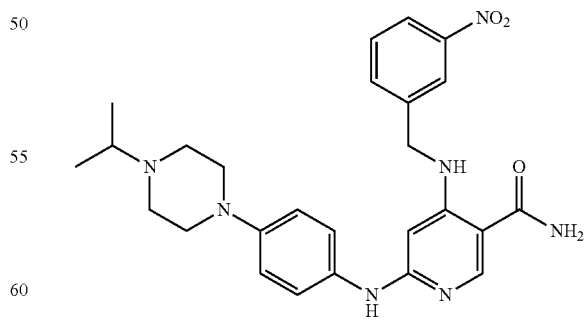

From 6-chloro-4-[(3-nitrobenzyl)amino]pyridine-3-carboxyamide (the compound of Example 31) and 4-[4-(propan-2-yl)piperazin-1-yl]aniline in a manner similar to Example 46, the title compound was obtained as a yellow crystalline powder (yield 51%).

¹H-NMR (400 MHz, CDCl₃) δ: 1.11 (6H, d, J=6.6 Hz), 2.70-2.75 (5H, m), 3.16-3.19 (4H, m), 4.40 (2H, d, J=5.9 Hz), 5.58 (1H, s), 6.40 (1H, br), 6.77 (2H, d, J=9.0 Hz), 6.86 (2H, d, J=9.0 Hz), 7.50 (1H, dd, J=7.8, 7.8 Hz), 7.60 (1H, d, J=7.8 Hz), 8.11 (1H, s), 8.15 (1H, d, J=7.8 Hz), 8.20 (1H, s), 9.03 (1H, br).

IR (ATR): 1605, 1528, 1514, 1408, 1347, 1237 cm⁻¹.

Example 155

Preparation of 4-[(3,5-difluorobenzyl)amino]-6-({3-[4-(propan-2-yl)piperazin-1-yl]phenyl}amino)pyridine-3-carboxyamide

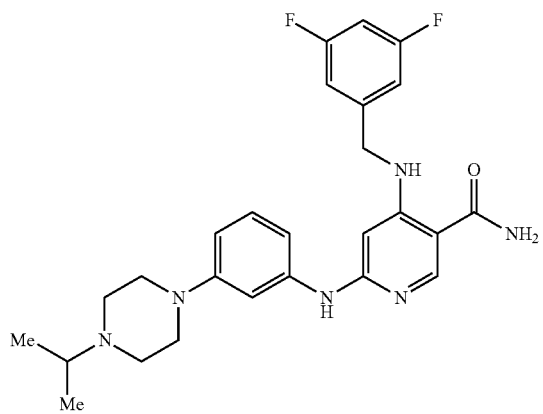 [SMILES: CC(C)N1CCN(c2cccc(Nc3cc(NCc4cc(F)cc(F)c4)c(C(N)=O)cn3)c2)CC1]

From 6-chloro-4-[(3,5-difluorobenzyl)amino]pyridine-3-carboxyamide (the compound of Example 20) and 3-[4-(propan-2-yl)piperazin-1-yl]aniline in a manner similar to Example 46, the title compound was obtained as a light brown crystalline powder (yield 81%).

m.p. 203-205° C.

¹H-NMR (400 MHz, CDCl₃) δ: 1.10 (6H, d, J=6.6 Hz), 2.64-2.76 (5H, m), 3.15-3.19 (4H, m), 4.32 (2H, d, J=5.8 Hz), 5.60 (2H, br), 5.84 (1H, s), 6.43-6.47 (1H, m), 6.54 (1H, brs), 6.64-6.68 (2H, m), 6.64-6.74 (1H, m), 6.76-6.83 (2H, m), 7.10 (1H, dd, J=8.4, 8.4 Hz), 8.23 (1H, s), 8.97 (1H, brt, J=5.8 Hz).

IR (ATR): 1651, 1597, 1575, 1552, 1496, 1406, 1383, 1303, 1235, 1116, 999 cm⁻¹.

Example 156

Preparation of 4-(benzylamino)-6-[(4-{[3-(diethylamino)propyl]amino}phenyl)amino]pyridine-3-carboxyamide

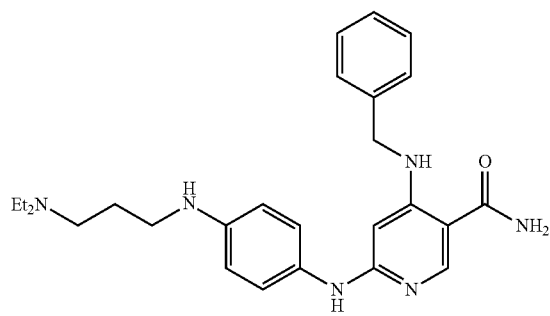

From 4-(benzylamino)-6-chloropyridine-3-carboxyamide (the compound of Example 1) and 4-([3-(diethylamino)propyl]amino}aniline in a manner similar to Example 46, the title compound was obtained as a light purple crystalline powder (yield 56%).

¹H-NMR (400 MHz, CDCl₃) δ: 1.06 (6H, dd, J=6.1, 6.1 Hz), 1.76-1.83 (2H, m), 2.52-2.60 (6H, m), 3.18 (2H, dd, J=6.3, 6.3 Hz), 4.26 (2H, d, J=5.6 Hz), 5.66 (1H, s), 6.37 (1H, s), 6.49 (2H, d, J=8.8 Hz), 6.84 (2H, d, J=8.8 Hz), 7.23-7.33 (5H, m), 8.16 (1H, s), 8.82 (1H, br).

Example 157

Preparation of 4-[(3,5-difluorobenzyl)amino]-6-{[4-({2-[(methylsulfonyl)amino]ethyl}amino)phenyl]amino}pyridine-3-carboxyamide

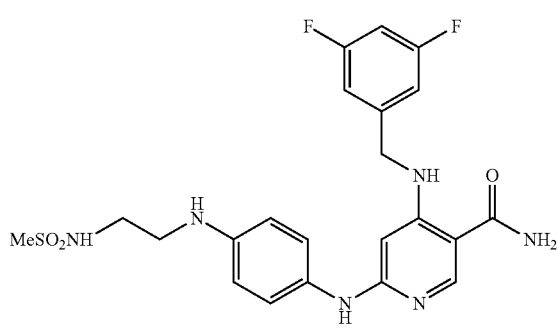

From 6-chloro-4-[(3,5-difluorobenzyl)amino]pyridine-3-carboxyamide (the compound of Example 20) and 4-({2-[(methylsulfonyl)amino]ethyl}amino)aniline in a manner similar to Example 46, the title compound was obtained as a light pink crystalline powder (yield 55%).

m.p. 205.7-206.2° C.

¹H-NMR (400 MHz, DMSO-d6) δ: 2.90 (3H, s), 3.06-3.15 (4H, m), 4.36 (2H, d, J=5.9 Hz), 5.36 (1H, brt, J=5.4 Hz), 5.58 (1H, s), 6.47 (2H, d, J=8.6 Hz), 6.94-7.04 (5H, m), 7.07-7.16 (2H, m), 8.31 (1H, s), 8.38 (1H, brs), 9.04 (1H, brt, J=5.9 Hz).

IR (ATR): 1640, 1605, 1519, 1415, 1304, 1252, 1153, 1116, 987 cm⁻¹.

Example 158

Preparation of 6-{[4-(acetylamino)phenyl]amino}-4-(benzylamino)pyridine-3-carboxyamide

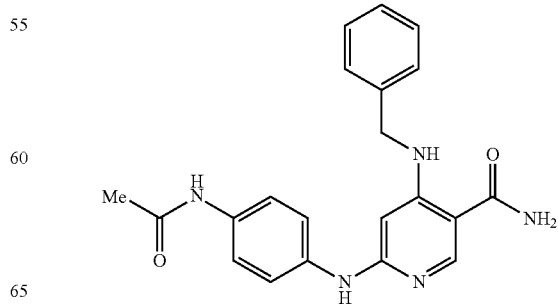

From 4-(benzylamino)-6-chloropyridine-3-carboxyamide (the compound of Example 1) and 4-acetylaminoaniline in a manner similar to Example 46, the title compound was obtained as a slight yellow crystalline powder (yield 67%).

1H-NMR (400 MHz, CDCl3) δ: 2.11 (3H, s), 4.36 (2H, s), 5.85 (1H, s), 7.06 (2H, d, J=8.8 Hz), 7.23-7.38 (5H, m), 7.40 (2H, d, J=8.8 Hz), 8.25 (1H, s).

IR (ATR): 1639, 1607, 1583, 1553, 1513, 1417, 1401, 1301, 1253 cm$^{-1}$.

Example 159

Preparation of 4-[(3,5-difluorobenzyl)amino]-6-({4-[(methylsulfonyl)amino]phenyl}amino)pyridine-3-carboxyamide

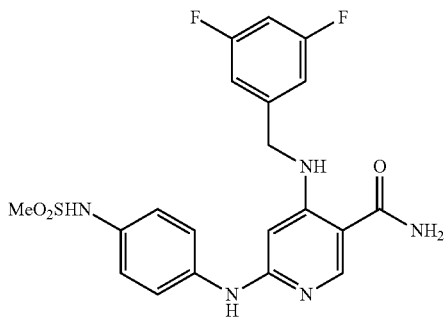

From 6-chloro-4-[(3,5-difluorobenzyl)amino]pyridine-3-carboxyamide (the compound of Example 20) and 4-[(methylsulfonyl)amino]aniline in a manner similar to Example 46, the title compound was obtained as slight purple needle crystals (yield 86%).

m.p. 236-238° C. (dec.)

1H-NMR (400 MHz, CD3OD) δ: 2.92 (3H, s), 4.41 (2H, s), 5.76 (1H, s), 6.84 (1H, dddd, J=2.2, 2.2, 9.0, 9.0 Hz), 6.88-6.95 (2H, m), 7.13 (2H, d, J=9.0 Hz), 7.19 (2H, d, J=9.0 Hz), 8.37 (1H, s).

IR (ATR): 1639, 1606, 1579, 1552, 1513, 1417, 1396, 1309, 1148, 1115, 985 cm$^{-1}$.

MS: m/z 448 (M$^+$+1), 136 (base peak).

Example 160

Preparation of 4-[(3-nitrobenzyl)amino]-6-({4-[(methylsulfonyl)amino]phenyl}amino)pyridine-3-carboxyamide

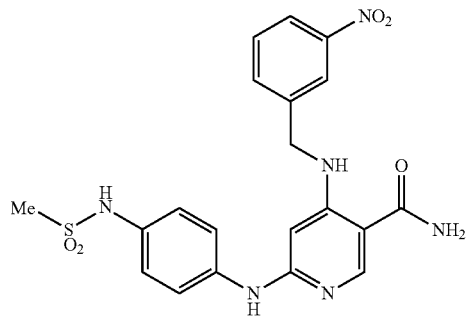 [SMILES: CS(=O)(=O)Nc1ccc(Nc2cc(NCc3cccc([N+](=O)[O-])c3)c(C(N)=O)cn2)cc1]

From 6-chloro-4-[(3-nitrobenzyl)amino]pyridine-3-carboxyamide (the compound of Example 31) and 4-[(methylsulfonyl)amino]aniline in a manner similar to Example 46, the title compound was obtained as a light yellow crystalline powder (yield 29%).

1H-NMR (400 MHz, CD3OD) δ: 2.90 (3H, s), 4.56 (2H, s), 5.76 (1H, s), 7.11 (2H, d, J=9.0 Hz), 7.18 (2H, d, J=9.0 Hz), 7.63 (1H, t, J=12.0 Hz), 7.77 (1H, d, J=12.0 Hz), 8.15 (1H, d, J=9.0 Hz), 8.19 (1H, s), 8.29 (1H, s).

Example 161

Preparation of 4-(benzylamino)-6-({4-[(propylsulfonyl)amino]phenyl}amino)pyridine-3-carboxyamide

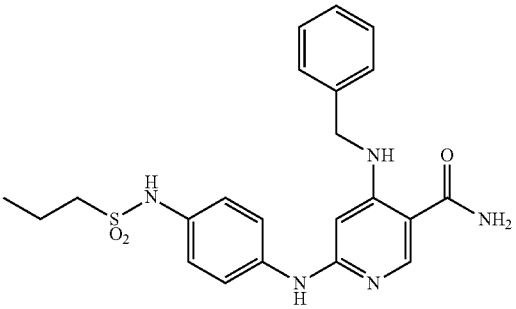 [SMILES: CCCS(=O)(=O)Nc1ccc(Nc2cc(NCc3ccccc3)c(C(N)=O)cn2)cc1]

39 mg of 4-(benzylamino)-6-{(4-aminophenyl)amino}pyridine-3-carboxyamide (the compound of Example 65), 83 mg of 1-propanesulfonyl chloride and 67 mg of triethylamine in 1.5 mL of dichloromethane were stirred at room temperature for 1 hour. Under ice cooling, ammonia water was added to the reaction mixture, and stirred for 5 minutes. The reaction mixture was extracted with chloroform, and the extract was dried on anhydrous sodium sulfate. The solvent was evaporated and the residue was purified by silica gel column chromatography (chloroform:ammonia methanol=10:1) to obtain 12 mg (19%) of the title compound as a light brown crystalline powder.

1H-NMR (400 MHz, DMSO-d6) δ: 0.93 (3H, t, J=7.4 Hz), 1.63-1.73 (2H, m), 2.97-3.01 (2H, m), 4.39 (2H, d, J=5.9 Hz), 5.82 (1H, s), 7.09 (2H, d, J=8.8 Hz), 7.24-7.38 (8H, m), 7.93 (1H, br), 8.31 (1H, s), 9.16 (1H, br), 9.26 (1H, br), 9.39 (1H, brs).

IR (ATR): 1653, 1621, 1598, 1568, 1533, 1511, 1468, 1415, 1311, 1300, 1222, 1139 cm$^{-1}$.

MS: m/z 439 (M$^+$), 332 (base peak).

Example 162

Preparation of 4-[(3,5-difluorobenzyl)amino]-6-({4-[(propylsulfonyl)amino]phenyl}amino)pyridine-3-carboxyamide

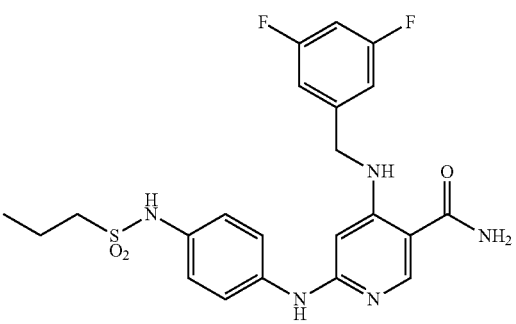 [SMILES: CCCS(=O)(=O)Nc1ccc(Nc2cc(NCc3cc(F)cc(F)c3)c(C(N)=O)cn2)cc1]

From 6-[(4-aminophenyl)amino]-4-[(3,5-difluorobenzyl)amino]pyridine-3-carboxyamide (the compound of Example 67) and 1-propanesulfonyl chloride in a manner similar to Example 161, the title compound was obtained as a light brown crystalline powder (yield 78%).

$^1$H-NMR (400 MHz, DMSO-d6) δ: 0.93 (3H, t, J=7.4 Hz), 1.62-1.73 (2H, m), 2.96 (2H, t, J=7.7 Hz), 4.42 (2H, d, J=6.1 Hz), 5.75 (1H, s), 6.97-7.03 (3H, m), 7.06 (2H, d, J=8.8 Hz), 7.08-7.16 (1H, m), 7.40 (2H, d, J=8.8 Hz), 7.80 (1H, br), 8.37 (1H, s), 8.85 (1H, s), 9.05 (1H, brt, J=6.1 Hz), 9.44 (1H, s).

IR (ATR): 1632, 1600, 1575, 1556, 1513, 1415, 1311, 1253, 1137, 1117 cm$^{-1}$.

MS (EI): m/z 475 (M$^+$), 368 (base peak).

Example 163

Preparation of 4-(benzylamino)-6-({4-[(propan-2-ylsulfonyl)amino]phenyl}amino)pyridine-3-carboxyamide

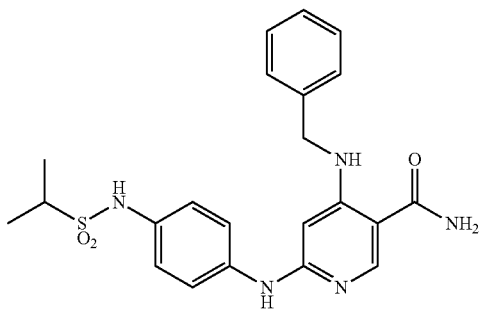 [SMILES: CC(C)S(=O)(=O)Nc1ccc(Nc2cc(NCc3ccccc3)c(C(N)=O)cn2)cc1]

From 6-[(4-aminophenyl)amino]-4-(benzylamino) pyridine-3-carboxyamide (the compound of Example 65) and 2-propanesulfonyl chloride in a manner similar to Example 161, the title compound was obtained as a light brown crystalline powder (yield 34%).

$^1$H-NMR (400 MHz, CDCl$_3$) δ: 1.40 (6H, d, J=7.1 Hz), 3.26 (1H, octet, J=7.1 Hz), 4.35 (2H, s), 5.81 (1H, s), 6.93 (2H, d, J=8.8 Hz), 7.10 (2H, d, J=8.8 Hz), 7.22-7.39 (5H, m), 8.19 (1H, s).

IR (ATR): 1664, 1627, 1609, 1572, 1537, 1511, 1466, 1412, 1303, 1224, 1131 cm$^{-1}$.

MS: m/z 440 (M$^+$+1), 91 (base peak).

Example 164

Preparation of 4-[(3,5-difluorobenzyl)amino]-6-({3-[(methylsulfonyl)amino]phenyl}amino)pyridine-3-carboxyamide

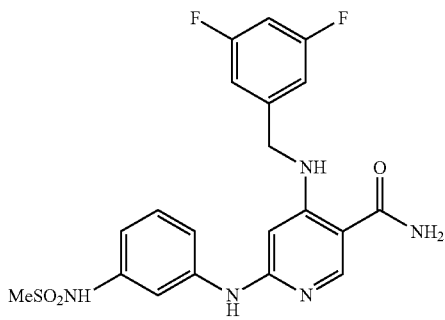

From 6-chloro-4-[(3,5-difluorobenzyl)amino]pyridine-3-carboxyamide (the compound of Example 20) and 3-[(methylsulfonyl)amino]aniline in a manner similar to Example 46, the title compound was obtained as a light brown crystalline powder (yield 57%).

m.p. 172-173° C.

$^1$H-NMR (400 MHz, DMSO-d6) δ: 2.96 (3H, s), 4.43 (2H, d, J=6.1 Hz), 5.82 (1H, s), 6.70 (1H, dd, J=8.0, 1.9 Hz), 6.96-7.04 (2H, m), 7.06-7.15 (3H, m), 7.32 (1H, dd, J=8.0, 1.9 Hz), 7.39 (1H, dd, J=1.9, 1.9 Hz), 7.82 (1H, br), 8.38 (1H, s), 8.94 (1H, brs), 9.03 (1H, brt, J=6.1 Hz), 9.62 (1H, s).

IR (ATR): 1648, 1597, 1554, 1495, 1413, 1389, 1311, 1302, 1248, 1237, 1147, 1120 cm$^{-1}$.

MS: m/z 447 (M$^+$), 368 (base peak).

Example 165

Preparation of 4-[(3,5-difluorobenzyl)amino]-6-({3-[(propan-2-ylsulfonyl)amino]phenyl}amino)pyridine-3-carboxyamide

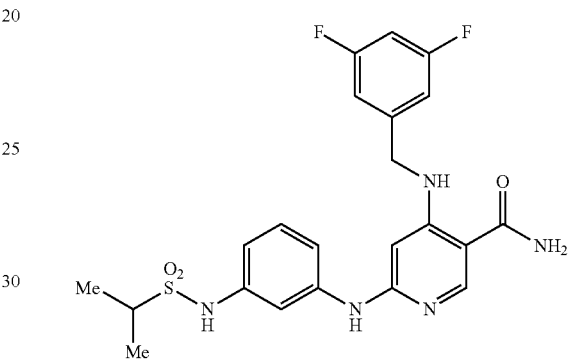

From 6-chloro-4-[(3,5-difluorobenzyl)amino]pyridine-3-carboxyamide (the compound of Example 20) and 3-[(propan-2-ylsulfonyl)amino]aniline in a manner similar to Example 46, the title compound was obtained as light brown needle crystals (yield 67%).

m.p. 248-249° C. (dec.)

$^1$H-NMR (400 MHz, DMSO-d6) δ: 1.22 (6H, d, J=6.8 Hz), 3.22 (1H, quint, J=6.8 Hz), 4.42 (2H, d, J=6.1 Hz), 5.82 (1H, s), 6.71 (1H, dd, J=7.8, 1.9 Hz), 6.95-7.03 (2H, m), 7.06-7.16 (3H, m), 7.33 (1H, dd, J=7.8, 1.9 Hz), 7.39 (1H, dd, J=1.9, 1.9 Hz), 7.83 (1H, br), 8.37 (1H, s), 8.93 (1H, s), 9.03 (1H, brt, J=6.1 Hz), 9.64 (1H, s).

Example 166

Preparation of 4-[(2-methoxybenzyl)amino]-6-({4-[4-(propan-2-ylsulfonyl)piperazin-1-yl]phenyl}amino) pyridine-3-carboxyamide

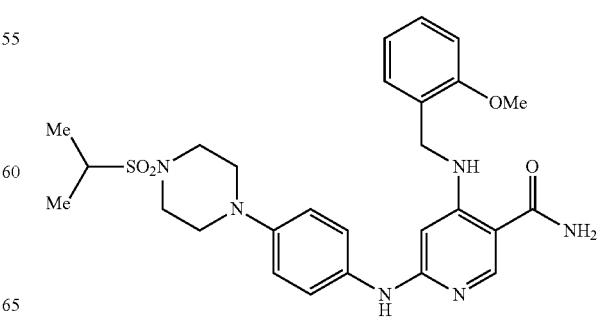

From 6-chloro-4-[(2-methoxybenzyl)amino]pyridine-3-carboxamide (the compound of Example 2) and 4-[4-(propan-2-ylsulfonyl)piperazin-1-yl]aniline in a manner similar to Example 46, the title compound was obtained as a light brown crystalline powder (yield 25%).

¹H-NMR (400 MHz, DMSO-d6) δ: 1.25 (6H, d, J=6.8 Hz), 3.04-3.10 (4H, m), 3.34-3.43 (5H, m), 3.81 (3H, s), 4.28 (2H, d, J=5.4 Hz), 5.75 (1H, s), 6.85 (2H, d, J=9.0 Hz), 6.92 (1H, dd, J=7.3, 7.3 Hz), 7.04 (1H, d, J=8.3 Hz), 7.16 (1H, d, J=7.1 Hz), 7.25-7.34 (3H, m), 8.33 (1H, s), 8.67 (1H, s), 8.93 (1H, brs).

Example 167

Preparation of 4-[(2-methylbenzyl)amino]-6-({4-[4-(propan-2-ylsulfonyl)piperazin-1-yl]phenyl}amino) pyridine-3-carboxamide

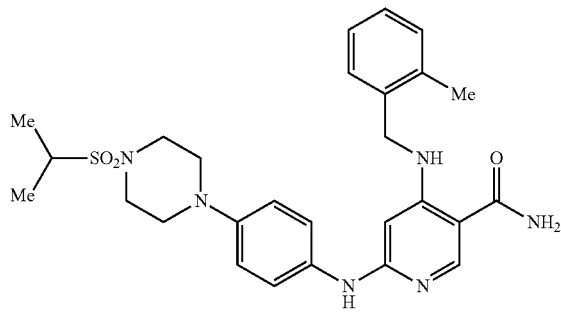

From 6-chloro-4-[(2-methylbenzyl)amino]pyridine-3-carboxamide (the compound of Example 5) and 4-[4-(propan-2-ylsulfonyl)piperazin-1-yl]aniline in a manner similar to Example 46, the title compound was obtained as a light brown crystalline powder (yield 75%).

¹H-NMR (400 MHz, DMSO-d6) δ: 1.25 (6H, d, J=6.6 Hz), 2.30 (3H, s), 3.04-3.12 (4H, m), 3.34-3.43 (5H, m), 4.29 (2H, d, J=5.1 Hz), 5.76 (1H, s), 6.86 (2H, d, J=9.0 Hz), 7.14-7.24 (4H, m), 7.33 (2H, d, J=9.0 Hz), 8.35 (1H, s), 8.67 (1H, s), 8.89 (1H, t, J=5.1 Hz).

Example 168

Preparation of 4-[(2-chlorobenzyl)amino]-6-({4-[4-(propan-2-ylsulfonyl)piperazin-1-yl]phenyl}amino) pyridine-3-carboxamide

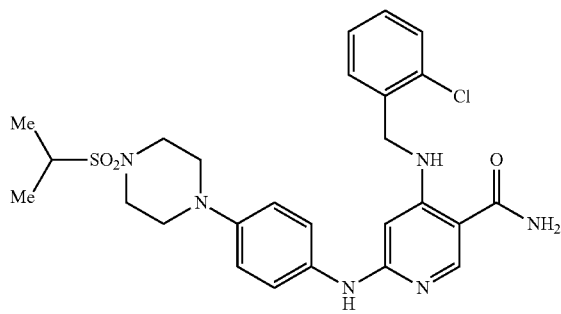

From 6-chloro-4-[(2-chlorobenzyl)amino]pyridine-3-carboxamide (the compound of Example 9) and 4-[4-(propan-2-ylsulfonyl)piperazin-1-yl]aniline in a manner similar to Example 46, the title compound was obtained as a light brown crystalline powder (yield 80%).

¹H-NMR (400 MHz, DMSO-d6) δ: 1.25 (6H, d, J=6.8 Hz), 3.03-3.10 (4H, m), 3.35-3.43 (5H, m), 4.42 (2H, d, J=5.6 Hz), 5.67 (1H, s), 6.84 (2H, d, J=9.0 Hz), 7.26-7.37 (5H, m), 7.47-7.52 (1H, m), 8.36 (1H, s), 8.67 (1H, s), 9.04 (1H, t, J=5.6 Hz).

Example 169

Preparation of 4-[(2,3-difluorobenzyl)amino]-6-({4-[4-(propan-2-ylsulfonyl)piperazin-1-yl]phenyl}amino) pyridine-3-carboxamide

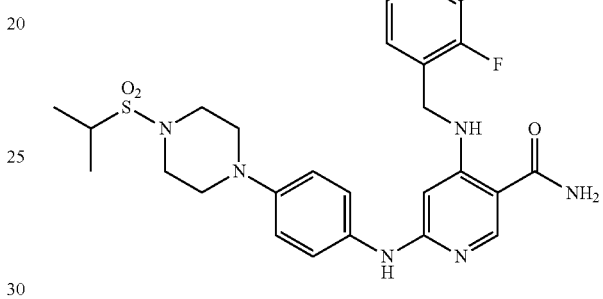

From 6-chloro-4-[(2,3-difluorobenzyl)amino]pyridine-3-carboxamide (the compound of Example 19) and 4-[4-(propan-2-ylsulfonyl)piperazin-1-yl]aniline in a manner similar to Example 46, the title compound was obtained as a light brown crystalline powder (yield 71%).

¹H-NMR (400 MHz, DMSO-d6) δ: 1.25 (6H, d, J=6.8 Hz), 3.04-3.10 (4H, m), 3.35-3.43 (5H, m), 4.47 (2H, d, J=5.9 Hz), 5.71 (1H, s), 6.85 (2H, d, J=9.0 Hz), 7.10 (1H, dd, J=7.0, 7.0 Hz), 7.16-7.24 (1H, m), 7.29 (2H, d, J=9.0 Hz), 7.36 (1H, ddd, J=8.4, 8.4, 8.4 Hz), 8.35 (1H, s), 8.66 (1H, s), 9.03 (1H, t, J=5.9 Hz).

Example 170

Preparation of 4-[(3,5-difluorobenzyl)amino]-6-({4-[4-(propan-2-ylsulfonyl)piperazin-1-yl]phenyl}amino) pyridine-3-carboxamide

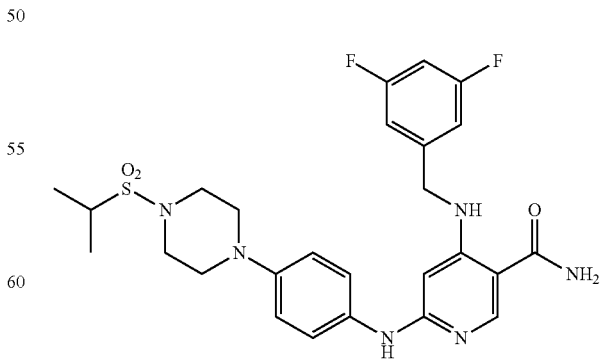

From 6-chloro-4-[(3,5-difluorobenzyl)amino]pyridine-3-carboxamide (the compound of Example 20) and 4-[4-(propan-2-ylsulfonyl)piperazin-1-yl]aniline in a manner similar to Example 46, the title compound was obtained as light brown prism crystals (yield 99%).

m.p. 239-242° C. (dec.)

$^1$H-NMR (400 MHz, CDCl$_3$) δ: 1.39 (6H, d, J=6.8 Hz), 3.17-3.29 (5H, m), 3.52-3.56 (4H, m), 4.28 (2H, d, J=5.8 Hz), 6.58 (2H, br), 6.49 (1H, s), 6.40 (1H, brs), 6.70-6.80 (3H, m), 6.82 (2H, d, J=9.0 Hz), 6.89 (2H, d, J=9.0 Hz), 8.20 (1H, s), 8.98 (1H, brt, J=5.8 Hz).

IR (ATR): 3415, 3337, 1621, 1612, 1592, 1577, 1531, 1514, 1400, 1298, 1266, 1233, 1137, 1117, 958 cm$^{-1}$.

MS: m/z 544 (M$^+$), 438 (base peak).

Example 171

Preparation of 4-[(2,5-difluorobenzyl)amino]-6-({4-[4-(propan-2-ylsulfonyl)piperazin-1-yl]phenyl}amino) pyridine-3-carboxyamide

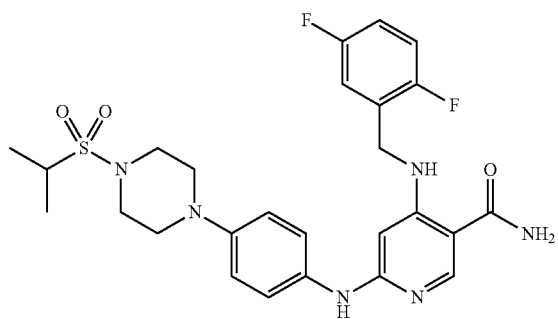 [SMILES: CC(C)S(=O)(=O)N1CCN(c2ccc(Nc3cc(NCc4cc(F)ccc4F)c(C(N)=O)cn3)cc2)CC1]

From 6-chloro-4-[(2,5-difluorobenzyl)amino]pyridine-3-carboxyamide (the compound of Example 22) and 4-[4-(propan-2-ylsulfonyl)piperazin-1-yl]aniline in a manner similar to Example 46, the title compound was obtained as a purple solid (yield 23%).

$^1$H-NMR (400 MHz, DMSO-d6) δ: 1.26 (6H, d, J=6.8 Hz), 3.18-3.25 (4H, m), 3.36-3.48 (5H, m), 4.49 (2H, d, J=5.8 Hz), 5.72 (1H, s), 6.99 (2H, d, J=9.0 Hz), 7.06 (2H, d, J=9.0 Hz), 7.07-7.13 (1H, m), 7.19-7.34 (2H, m), 7.68 (1H, brs), 8.17 (1H, s), 8.24 (1H, brs), 9.64 (1H, brs), 9.68 (1H, brs).

Example 172

Preparation of 4-[(2,6-difluorobenzyl)amino]-6-({4-[4-(propan-2-ylsulfonyl)piperazin-1-yl]phenyl}amino) pyridine-3-carboxyamide

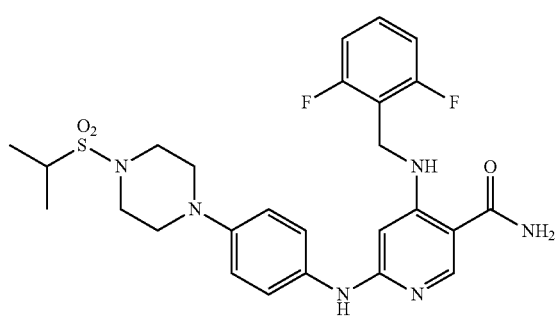 [SMILES: CC(C)S(=O)(=O)N1CCN(c2ccc(Nc3cc(NCc4c(F)cccc4F)c(C(N)=O)cn3)cc2)CC1]

From 6-chloro-4-[(2,6-difluorobenzyl)amino]pyridine-3-carboxyamide (the compound of Example 23) and 4-[4-(pro-pan-2-ylsulfonyl)piperazin-1-yl]aniline in a manner similar to Example 46, the title compound was obtained as a brown solid (yield 33%).

$^1$H-NMR (400 MHz, DMSO-d6) δ: 1.25 (6H, d, J=6.8 Hz), 3.08-3.13 (4H, m), 3.35-3.44 (5H, m), 4.35 (2H, d, J=5.8 Hz), 5.95 (1H, s), 6.91 (2H, d, J=9.0 Hz), 7.14 (2H, dd, J=8.1, 8.1 Hz), 7.35 (2H, d, J=9.0 Hz), 7.39-7.48 (1H, m), 8.32 (1H, s), 8.72 (1H, s), 8.96 (1H, t, J=5.8 Hz).

Example 173

Preparation of 4-{[3-fluoro-5-(trifluoromethyl)benzyl]amino}-6-({4-[4-(propan-2-ylsulfonyl)piperazin-1-yl]phenyl}amino)pyridine-3-carboxyamide

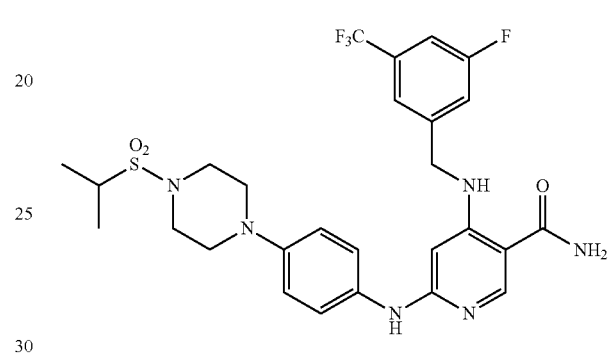

From 6-chloro-4-{[3-fluoro-5-(trifluoromethyl)benzyl]amino}pyridine-3-carboxyamide (the compound of Example 25) and 4-[4-(propan-2-ylsulfonyl)piperazin-1-yl]aniline in a manner similar to Example 46, the title compound was obtained as a light brown solid (yield 30%).

$^1$H-NMR (400 MHz, DMSO-d6) δ: 1.26 (6H, d, J=6.8 Hz), 3.15-3.22 (4H, m), 3.36-3.46 (5H, m), 4.58 (2H, d, J=6.1 Hz), 5.68 (1H, s), 6.93 (2H, d, J=9.0 Hz), 7.00 (2H, d, J=9.0 Hz), 7.42 (1H, d, J=9.3 Hz), 7.50 (1H, s), 7.66 (1H, d, J=8.8 Hz), 7.68 (1H, brs), 8.20 (1H, s), 8.25 (1H, brs), 9.69 (1H, brs), 9.73 (1H, brs).

Example 174

Preparation of 4-[(3,5-difluorobenzyl)amino]-6-({3-[4-(propan-2-ylsulfonyl)piperazin-1-yl]phenyl}amino) pyridine-3-carboxyamide

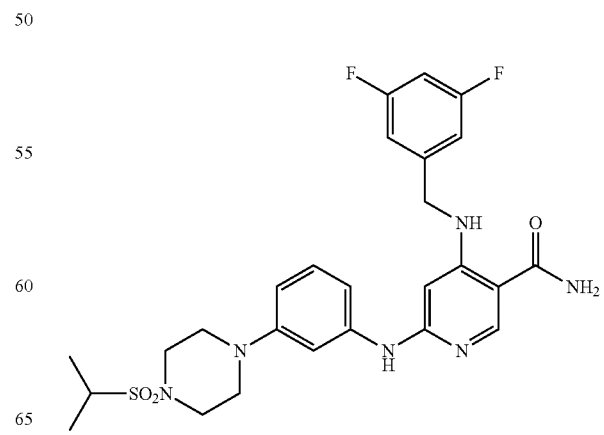

From 6-chloro-4-[(3,5-difluorobenzyl)amino]pyridine-3-carboxyamide (the compound of Example 20) and 3-[4-(propan-2-ylsulfonyl)piperazin-1-yl]aniline in a manner similar to Example 46, the title compound was obtained as light brown needle crystals (yield 71%).

m.p. 213-214° C. (dec.)

¹H-NMR (400 MHz, CDCl₃) δ: 1.38 (6H, d, J=6.8 Hz), 3.16-3.27 (5H, m), 3.47-3.51 (4H, m), 4.32 (2H, d, J=5.8 Hz), 5.63 (2H, br), 5.87 (1H, s), 6.52 (1H, dd, J=8.2, 2.0 Hz), 6.56 (1H, brs), 6.64 (1H, dd, J=8.2, 2.0 Hz), 6.70 (1H, dd, J=2.0, 2.0 Hz), 6.72-6.76 (1H, m), 6.77-6.84 (2H, m), 7.12 (1H, dd, J=8.2, 8.2 Hz), 8.24 (1H, s), 8.99 (1H, brt, J=5.8 Hz).

IR (ATR): 1661, 1621, 1596, 1578, 1513, 1496, 1395, 1310, 1138, 1118, 965 cm⁻¹.

Example 175

Preparation of 4-(benzylamino)-6-{[4-(4-ethoxycarbonylpiperidino)phenyl]amino}pyridine-3-carboxyamide

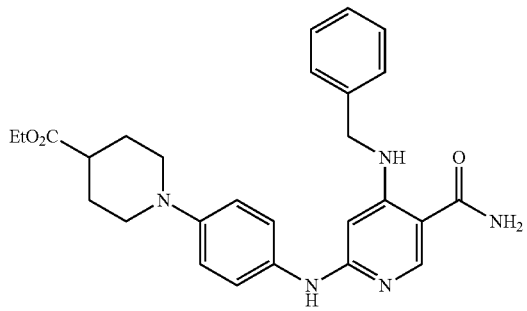 [SMILES: CCOC(=O)C1CCN(c2ccc(Nc3cc(NCc4ccccc4)c(C(N)=O)cn3)cc2)CC1]

From 4-(benzylamino)-6-chloropyridine-3-carboxyamide (the compound of Example 1) and 4-(4-ethoxycarbonylpiperidino)aniline in a manner similar to Example 46, the title compound was obtained as a slight yellow crystalline powder (yield 96%).

¹H-NMR (400 MHz, CDCl₃) δ: 1.28 (3H, t, J=7.1 Hz), 1.84-1.96 (2H, m), 2.01-2.10 (2H, m), 2.40-2.49 (2H, m), 2.74-2.84 (2H, m), 3.55-3.63 (2H, m), 4.17 (2H, d, J=5.6 Hz), 5.59 (2H, br), 5.75 (1H, s), 6.47 (1H, brs), 6.82 (2H, d, J=9.0 Hz), 6.91 (2H, d, J=9.0 Hz), 7.24-7.35 (5H, m), 8.18 (1H, s), 8.85 (1H, brt, J=5.6 Hz).

IR (ATR): 1655, 1615, 1600, 1572, 1543, 1512, 1408, 1293, 1259, 1201, 1172 cm⁻¹.

Example 176

Preparation of 4-(benzylamino)-6-[(4-{4-[(2-hydroxyethyl) carbamoyl]piperidino}phenyl)amino]pyridine-3-carboxyamide

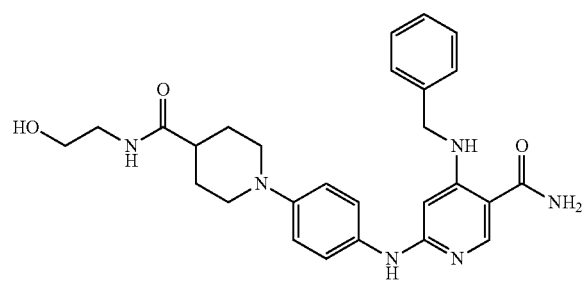 [SMILES: NC(=O)c1cnc(Nc2ccc(N3CCC(C(=O)NCCO)CC3)cc2)cc1NCc1ccccc1]

20 mg of 4-(benzylamino)-6-{[4-(4-ethoxycarbonylpiperidino)phenyl]amino}pyridine-3-carboxyamide (Example 175) and 50 mg of ethanolamine were stirred at 150° C. for 2 hours. After cooling, the reaction mixture was purified by silica gel thin layer chromatography (chloroform:methanol=5:1) to obtain 20 mg (89%) of the title compound as a slight yellow crystalline powder.

¹H-NMR (400 MHz, DMSO-d6) δ: 1.60-1.78 (4H, m), 2.18-2.28 (1H, m), 2.52-2.61 (2H, m), 3.08-3.15 (2H, m), 3.35-3.42 (2H, m), 3.54-3.61 (2H, m), 4.33 (2H, d, J=5.6 Hz), 4.64 (1H, t, J=5.5 Hz), 5.76 (1H, s), 6.81 (2H, d, J=9.0 Hz), 7.00 (1H, br), 7.22 (2H, d, J=9.0 Hz), 7.24-7.39 (5H, m), 7.71 (1H, br), 8.33 (1H, s), 8.57 (1H, brs), 8.99 (1H, brt, J=5.6 Hz).

IR (ATR): 1637, 1604, 1571, 1548, 1514, 1410, 1300, 1262, 1207 cm⁻¹.

Example 177

Preparation of 4-(benzylamino)-6-[(4-{4-[bis(2-hydroxyethyl)carbamoyl]piperidino}phenyl)amino]pyridine-3-carboxyamide

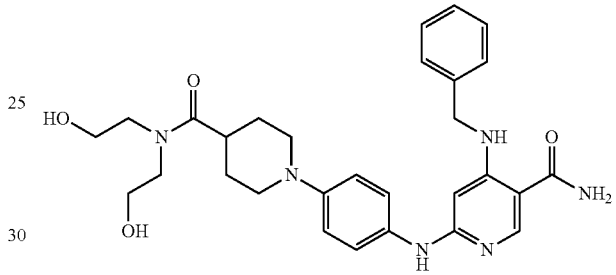

From 4-(benzylamino)-6-{[4-(4-ethoxycarbonylpiperidino)phenyl]amino}pyridine-3-carboxyamide (the compound of Example 175) and diethanolamine in a manner similar to Example 176, the title compound was obtained as a slight yellow crystalline powder (yield 98%).

¹H-NMR (400 MHz, DMSO-d6) δ: 1.65-1.73 (4H, m), 2.53-2.70 (2H, m), 2.70-2.82 (1H, m), 3.29-3.35 (2H, m), 3.41-3.49 (4H, m), 3.49-3.62 (4H, m), 4.34 (2H, d, J=5.6 Hz), 4.66 (1H, t, J=5.4 Hz), 4.81 (1H, t, J=5.4 Hz), 5.76 (1H, s), 6.81 (2H, d, J=9.0 Hz), 7.00 (1H, br), 7.21 (2H, d, J=9.0 Hz), 7.24-7.33 (3H, m), 7.33-7.39 (2H, m), 7.71 (1H, br), 8.33 (1H, s), 8.58 (1H, brs), 8.99 (1H, brt, J=5.6 Hz).

IR (ATR): 3316, 1652, 1621, 1557, 1515, 1433, 1409, 1389, 1057 cm⁻¹.

Example 178

Preparation of 4-[(2,3-difluorobenzyl)amino]-6-({4-{4-(2-hydroxyethyl)piperidino]phenyl}amino)pyridine-3-carboxyamide

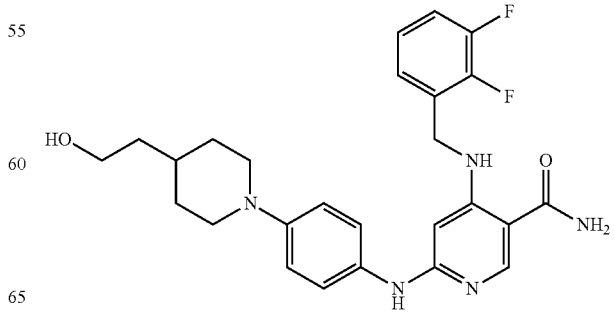

From 6-chloro-4-[(2,3-difluorobenzyl)amino]pyridine-3-carboxamide (the compound of Example 19) and 4-[4-(2-hydroxyethyl)piperidino]aniline in a manner similar to Example 46, the title compound was obtained as a light brown crystalline powder (yield 43%).

$^1$H-NMR (400 MHz, CDCl$_3$+CD$_3$OD) δ: 1.38-1.46 (2H, m), 1.54-1.62 (3H, m), 1.80-1.88 (2H, m), 3.60-3.75 (4H, m), 4.36 (2H, s), 5.69 (1H, s), 6.88 (2H, d, J=9.0 Hz), 6.93 (2H, d, J=9.0 Hz), 7.00-7.14 (3H, m), 8.17 (1H, s).

IR (ATR): 3250, 1619, 1515, 1484, 1410, 1243 cm$^{-1}$.

Example 179

Preparation of 4-[(3,5-difluorobenzyl)amino]-6-({4-[4-[bis(2-hydroxyethyl)piperidino]phenyl}amino)pyridine-3-carboxamide

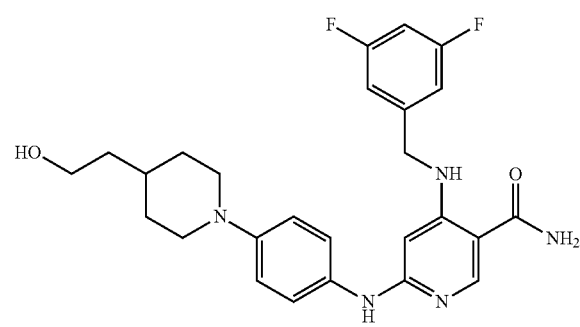 [SMILES: NC(=O)c1cnc(Nc2ccc(N3CCC(CCO)CC3)cc2)cc1NCc1cc(F)cc(F)c1]

From 6-chloro-4-[(3,5-difluorobenzyl)amino]pyridine-3-carboxamide (the compound of Example 20) and 4-[4-(2-hydroxyethyl)piperidino]aniline in a manner similar to Example 46, the title compound was obtained as a light brown crystalline powder (yield 35%).

$^1$H-NMR (400 MHz, CDCl$_3$+CD$_3$OD) δ: 1.35-1.46 (2H, m), 1.55-1.63 (3H, m), 1.80-1.88 (2H, m), 2.65-2.73 (2H, m), 3.60-3.65 (2H, m), 3.73 (2H, t, J=6.6 Hz), 4.26 (2H, brs), 5.59 (1H, s), 6.70-6.80 (3H, m), 6.84 (4H, s), 8.17 (1H, s).

IR (ATR): 1625, 1602, 1572, 1549, 1514, 1411, 1311, 1298, 1259, 1118 cm$^{-1}$.

MS: m/z 482 (M$^+$+1), 55(base peak).

Example 180

Preparation of 6-({4-[4-(2-hydroxyethyl)piperidino]phenyl}amino)-4-[(3-nitrobenzyl)amino]pyridine-3-carboxamide

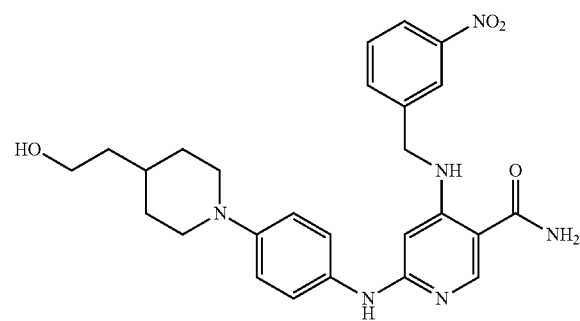 [SMILES: NC(=O)c1cnc(Nc2ccc(N3CCC(CCO)CC3)cc2)cc1NCc1cccc([N+](=O)[O-])c1]

From 6-chloro-4-[(3-nitrobenzyl)amino]pyridine-3-carboxamide (the compound of Example 31) and 4-[4-(2-hydroxyethyl)piperidino]aniline in a manner similar to Example 46, the title compound was obtained as a slight yellow crystalline powder (yield 42%).

$^1$H-NMR (400 MHz, CD$_3$OD) δ: 1.32-140 (2H, m), 1.50-1.56 (3H, m), 1.84 (2H, d, J=12.2 Hz), 2.64 (2H, t, J=10.9 Hz), 3.55 (2H, d, J=12.4 Hz), 3.64 (2H, t, J=6.5 Hz), 4.47 (2H, s), 5.61 (1H, s), 6.81 (2H, d, J=9.0 Hz), 6.90 (2H, d, J=9.0 Hz), 7.58 (1H, t, J=7.8 Hz), 7.66 (2H, d, J=7.8 Hz), 8.13-8.15 (2H, m), 8.25 (1H, s).

Example 181

Preparation of 4-[(3,5-difluorobenzyl)amino]-6-({3-[4-(2-hydroxyethyl)piperidino]phenyl}amino)pyridine-3-carboxamide

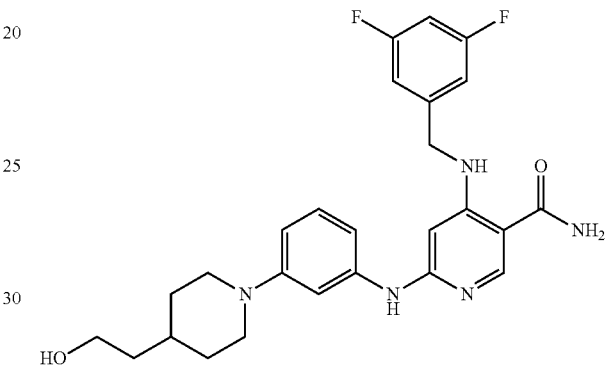

From 6-chloro-4-[(3,5-difluorobenzyl)amino]pyridine-3-carboxamide (the compound of Example 20) and 3-[4-(2-hydroxyethyl)piperidino]aniline in a manner similar to Example 46, the title compound was obtained as a light yellow amorphous substance (yield 71%).

$^1$H-NMR (400 MHz, CDCl$_3$) δ: 1.29-1.42 (2H, m), 1.53-1.63 (3H, m), 1.75-1.83 (2H, m), 2.62-2.70 (2H, m), 3.58-3.65 (2H, m), 3.74 (2H, t, J=6.5 Hz), 4.31 (2H, d, J=6.1 Hz), 5.67 (2H, br), 5.84 (1H, s), 6.38-6.46 (1H, m), 6.64-6.74 (4H, m), 6.76-6.83 (2H, m), 7.09 (1H, dd, J=7.8, 7.8 Hz), 8.24 (1H, s), 8.99 (1H, brt, J=6.1 Hz).

IR (ATR): 1649, 1621, 1596, 1572, 1493, 1409, 1314, 1250, 1117 cm$^{-1}$.

Example 182

Preparation of 6-{[3-cyano-4-(4-morpholinopiperidino) phenyl]amino}-4-[(3,5-difluorobenzyl)amino]pyridine-3-carboxamide

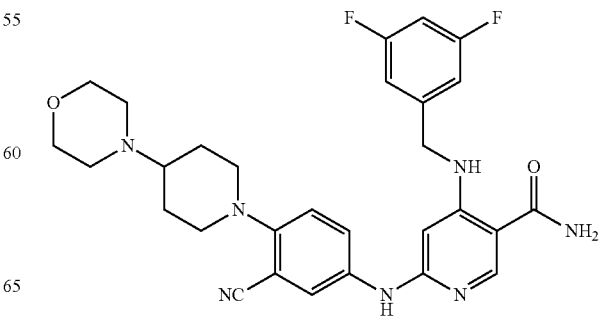

From 6-chloro-4-[(3,5-difluorobenzyl)amino]pyridine-3-carboxyamide (the compound of Example 20) and 3-cyano-4-(4-morpholinopiperidino)aniline in a manner similar to Example 46, the title compound was obtained as reddish brown needle crystals (yield 40%).

m.p. 211-213° C. (dec.)

$^1$H-NMR (400 MHz, CDCl$_3$) δ: 1.77-1.82 (2H, m), 1.87-2.21 (2H, m), 2.32-2.41 (1H, m), 2.58-2.62 (4H, m), 2.77-2.83 (2H, m), 3.57-3.61 (2H, m), 3.73-3.77 (4H, m), 4.32 (2H, d, J=5.8 Hz), 5.55 (1H, s), 5.80 (2H, br), 6.73 (1H, dddd, J=8.8, 8.8, 2.3, 2.3 Hz), 6.76-6.84 (3H, m), 6.86 (1H, d, J=2.7 Hz), 7.10 (1H, dd, J=8.8, 2.7 Hz), 7.43 (1H, d, J=2.7 Hz), 8.23 (1H, s), 9.00 (1H, brt, J=5.8 Hz).

IR (ATR): 1658, 1619, 1594, 1495, 1467, 1440, 1386, 1317, 1217, 1114 cm$^{-1}$.

MS: m/z 547 (M$^+$), 460 (base peak).

Example 183

Preparation of 4-[(3,5-difluorobenzyl)amino]-6-{[4-(2-methoxyethoxy)phenyl]amino}pyridine-3-carboxyamide

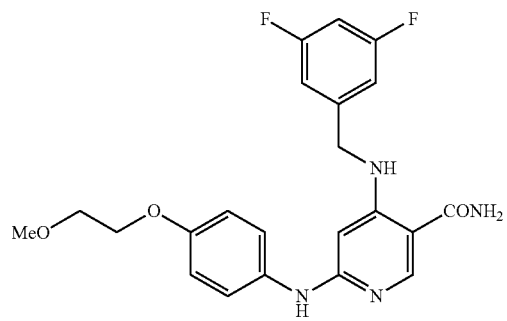 [SMILES: COCCOc1ccc(Nc2cc(NCc3cc(F)cc(F)c3)c(C(N)=O)cn2)cc1]

From 6-chloro-4-[(3,5-difluorobenzyl)amino]pyridine-3-carboxyamide (the compound of Example 20) and 4-(2-methoxyethoxy)aniline in a manner similar to Example 46, the title compound was obtained as a light pink crystalline powder (yield 18%).

m.p. 172.7-173.4° C.

$^1$H-NMR (270 MHz, CDCl$_3$) δ: 3.47 (3H, s), 3.75-3.79 (2H, m), 4.09-4.14 (2H, m), 4.25-4.29 (2H, m), 5.55 (1H, s), 5.55 (1H, br s), 6.39 (1H, brs), 6.70-6.79 (3H, m), 6.83 (2H, d, J=9.2 Hz), 6.91 (2H, d, J=9.2 Hz), 8.20 (1H, s), 8.97 (1H, brs).

Example 184

Preparation of 4-[(3,5-difluorobenzyl)amino]-6-{[4-(2-hydroxyethoxy)phenyl]amino}pyridine-3-carboxyamide

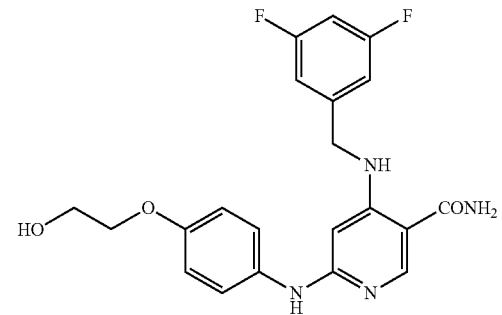 [SMILES: NC(=O)c1cnc(Nc2ccc(OCCO)cc2)cc1NCc1cc(F)cc(F)c1]

From 6-chloro-4-[(3,5-difluorobenzyl)amino]pyridine-3-carboxyamide (the compound of Example 20) and 4-(2-hydroxyethoxy)aniline in a manner similar to Example 46, the title compound was obtained as a white solid (yield 1%).

$^1$H-NMR (270 MHz, DMSO-d6) δ: 3.98-4.06 (2H, m), 4.22-4.28 (2H, m), 4.73 (2H, d, J=5.9 Hz), 5.18 (1H, t, J=5.6 Hz), 5.99 (1H, s), 7.12 (2H, d, J=9.2 Hz), 7.25-7.53 (4H, m), 7.59 (2H, d, J=9.2 Hz), 8.68 (1H, s), 8.98 (1H, s), 9.37 (1H, t, J=6.1 Hz)

Example 185

Preparation of 4-[(2-methylbenzyl)amino]-6-{[4-(4-hydroxypiperidino)phenyl]amino}pyridine-3-carboxyamide

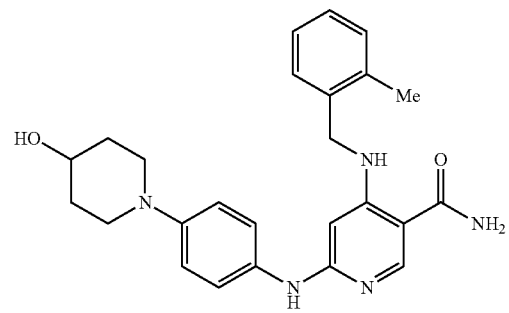 [SMILES: Cc1ccccc1CNc1cc(Nc2ccc(N3CCC(O)CC3)cc2)ncc1C(N)=O]

From 6-chloro-4-[(2-methylbenzyl)amino]pyridine-3-carboxyamide (the compound of Example 5) and 4-(4-hydroxypiperidino)aniline in a manner similar to Example 46, the title compound was obtained as a white crystalline powder (yield 34%).

$^1$H-NMR (400 MHz, DMSO-d6) δ: 1.42-1.53 (2H, m), 1.76-1.86 (2H, m), 2.29 (3H, s), 2.69-2.77 (2H, m), 3.35-3.45 (2H, m), 3.54-3.63 (1H, m), 4.28 (2H, d, J=5.4 Hz), 4.65 (1H, d, J=4.1 Hz), 5.74 (1H, s), 6.81 (2H, d, J=9.0 Hz), 7.14-7.28 (6H, m), 8.33 (1H, s), 8.58 (1H, s), 8.88 (1H, t, J=5.4 Hz).

Example 186

Preparation of 4-[(2-chlorobenzyl)amino]-6-{[4-(4-hydroxypiperidino)phenyl]amino}pyridine-3-carboxyamide

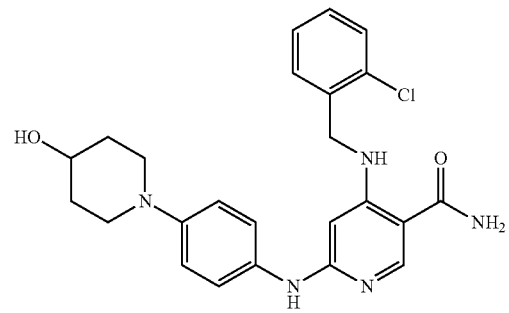 [SMILES: NC(=O)c1cnc(Nc2ccc(N3CCC(O)CC3)cc2)cc1NCc1ccccc1Cl]

From 6-chloro-4-[(2-chlorobenzyl)amino]pyridine-3-carboxyamide (the compound of Example 9) and 4-(4-hydroxypiperidino)aniline in a manner similar to Example 46, the title compound was obtained as a light brown crystalline powder (yield 44%).

¹H-NMR (400 MHz, DMSO-d6) δ: 1.42-1.54 (2H, m), 1.76-1.85 (2H, m), 2.68-2.78 (2H, m), 3.35-3.44 (2H, m), 3.53-3.63 (1H, m), 4.42 (2H, d, J=5.8 Hz), 4.65 (1H, d, J=4.2 Hz), 5.65 (1H, s), 6.79 (2H, d, J=9.0 Hz), 7.21 (2H, d, J=9.0 Hz), 7.27-7.36 (3H, m), 7.46-7.52 (1H, m), 8.35 (1H, s), 8.58 (1H, s), 9.03 (1H, t, J=5.8 Hz).

Example 187

Preparation of 4-[(2,3-difluorobenzyl)amino]-6-{[4-(4-hydroxypiperidino)phenyl]amino}pyridine-3-carboxyamide

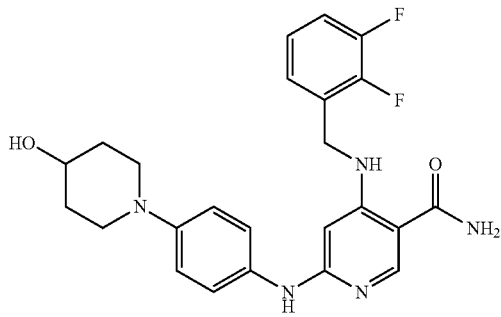 [SMILES: NC(=O)c1cnc(Nc2ccc(N3CCC(O)CC3)cc2)cc1NCc1cccc(F)c1F]

From 6-chloro-4-[(2,3-difluorobenzyl)amino]pyridine-3-carboxyamide (the compound of Example 19) and 4-(4-hydroxypiperidino)aniline in a manner similar to Example 46, the title compound was obtained as a light brown solid (yield 57%).

¹H-NMR (270 MHz, DMSO-d6) δ: 1.40-1.54 (2H, m), 1.75-1.86 (2H, m), 2.67-2.79 (2H, m), 3.35-3.44 (2H, m), 3.52-3.65 (1H, m), 4.45 (2H, d, J=6.3 Hz), 4.66 (1H, d, J=4.3 Hz), 5.68 (1H, s), 6.79 (2H, d, J=8.9 Hz), 7.07-7.13 (1H, m), 7.14-7.23 (3H, m), 7.32-7.39 (1H, m), 8.34 (1H, s), 8.57 (1H, s), 9.02 (1H, br s).

Example 188

Preparation of 4-[(2,5-difluorobenzyl)amino]-6-[(4-(4-hydroxypiperidino)phenyl]amino}pyridine-3-carboxyamide

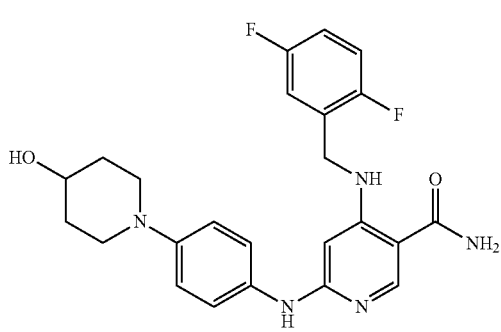 [SMILES: NC(=O)c1cnc(Nc2ccc(N3CCC(O)CC3)cc2)cc1NCc1cc(F)ccc1F]

From 6-chloro-4-[(2,5-difluorobenzyl)amino]pyridine-3-carboxyamide (the compound of Example 22) and 4-(4-hydroxypiperidino)aniline in a manner similar to Example 46, the title compound was obtained as a brown crystalline powder (yield 46%).

¹H-NMR (270 MHz, DMSO-d6) δ: 1.42-1.53 (2H, m), 1.76-1.85 (2H, m), 2.69-2.78 (2H, m), 3.36-3.44 (2H, m), 3.54-3.63 (1H, m), 4.40 (2H, d, J=5.6 Hz), 4.66 (1H, d, J=4.2 Hz), 5.70 (1H, s), 6.81 (2H, d, J=9.0 Hz), 7.02-7.08 (1H, m), 7.14-7.33 (4H, m), 8.34 (1H, s), 8.60 (1H, s), 9.00 (1H, t, J=5.6 Hz).

Example 189

Preparation of 6-{[3-cyano-4-(4-hydroxypiperidino)phenyl]amino}-4-[(3,5-difluorobenzyl)amino]pyridine-3-carboxyamide

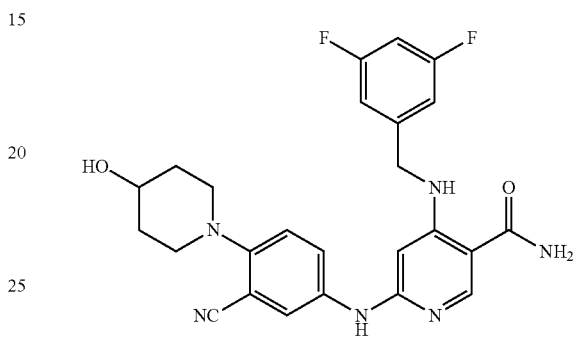

From 6-chloro-4-[(3,5-difluorobenzyl)amino]pyridine-3-carboxyamide (the compound of Example 20) and 3-cyano-4-(4-hydroxypiperidino)aniline in a manner similar to Example 46, the title compound was obtained as light brown needle crystals (yield 51%).

m.p. 173-176° C. (dec.)

¹H-NMR (400 MHz, CDCl₃+CD₃OD) δ: 1.75-1.85 (2H, m), 2.02-2.11 (2H, m), 2.92-2.99 (2H, m), 3.83-3.91 (2H, m), 4.33 (2H, d, J=4.6 Hz), 5.56 (1H, s), 6.74 (1H, dddd, J=8.8, 8.8, 2.2, 2.2 Hz), 6.77-6.83 (2H, m), 6.89 (1H, d, J=8.8 Hz), 7.11 (1H, dd, J=8.8, 2.7 Hz), 7.40 (1H, d, J=2.7 Hz), 8.21 (1H, s), 9.02 (1H, brt, J=4.6 Hz).

IR (ATR): 1647, 1603, 1546, 1503, 1463, 1417, 1344, 1309, 1219, 1117, 1077 cm⁻¹.

MS: m/z 478 (M⁺, base peak).

Example 190

Preparation of 4-[(3,5-difluorobenzyl)amino]-6-{[4-(4-methoxypiperidino)phenyl]amino}pyridine-3-carboxyamide

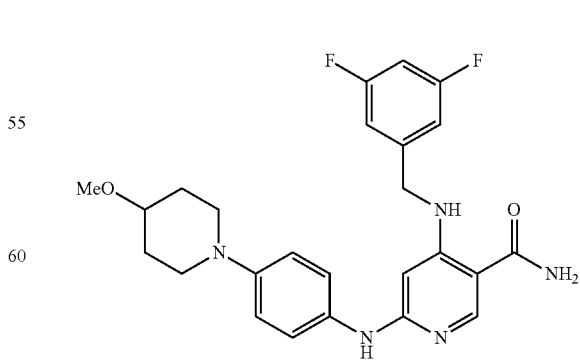

From 6-chloro-4-[(3,5-difluorobenzyl)amino]pyridine-3-carboxyamide (the compound of Example 20) and 4-(4-methoxypiperidino)aniline in a manner similar to Example 46, the title compound was obtained as slight yellow needle crystals (yield 64%).

m.p. 202.9-203.3° C. (dec.)

$^1$H-NMR (400 MHz, CDCl$_3$+CD$_3$OD) δ: 1.68-1.78 (2H, m), 2.00-2.08 (2H, m), 2.88-2.98 (2H, m), 3.05-3.42 (1H, m), 3.40 (3H, s), 3.46-3.53 (2H, m), 4.27 (2H, d, J=5.8 Hz), 5.59 (1H, s), 6.70-6.81 (3H, m), 6.84 (2H, d, J=8.8 Hz), 6.85 (2H, d, J=8.8 Hz), 8.18 (1H, s), 8.96 (1H, brt, J=5.8 Hz).

IR (ATR): 1629, 1603, 1515, 1415, 1312, 1298, 1259, 1233, 1196, 1115, 1096 cm$^{-1}$.

MS: m/z 468(M$^+$, base peak).

Example 191

Preparation of 4-[(3,5-difluorobenzyl)amino]-6-{[4-(4-hydroxypiperidino)phenyl]amino}pyridine-3-carboxamide

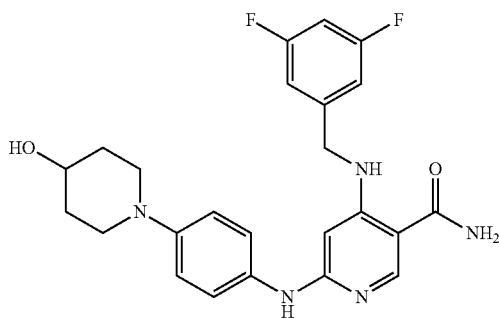 [SMILES: NC(=O)c1cnc(Nc2ccc(N3CCC(O)CC3)cc2)cc1NCc1cc(F)cc(F)c1]

From 6-chloro-4-[(3,5-difluorobenzyl)amino]pyridine-3-carboxamide (the compound of Example 20) and 4-(4-hydroxypiperidino)aniline in a manner similar to Example 46, the title compound was obtained as slight yellow needle crystals (yield 61%).

m.p. 238-240° C. (dec.)

$^1$H-NMR (400 MHz, DMSO-d6) δ: 1.42-1.53 (2H, m), 1.77-1.85 (2H, m), 2.69-2.77 (2H, m), 3.35-3.45 (2H, m), 3.54-3.63 (1H, m), 4.39 (2H, d, J=6.1 Hz), 4.66 (1H, d, J=4.2 Hz), 5.64 (1H, s), 6.79 (2H, d, J=9.0 Hz), 6.95-7.02 (2H, m), 7.08 (1H, br), 7.11-7.18 (3H, m), 7.74 (1H, br), 8.34 (1H, s), 8.56 (1H, s), 9.04 (1H, brt, J=6.1 Hz).

IR (ATR): IR (ATR): 1645, 1610, 1570, 1561, 1443, 1408, 1311, 1299, 1225, 1215, 1118 cm$^{-1}$.

MS: m/z 454 (M$^+$+1), 154 (base peak).

Example 192

Preparation of 4-[(3,5-difluorobenzyl)amino]-6-{[4-(4-oxopiperidino)phenyl]amino}pyridine-3-carboxamide

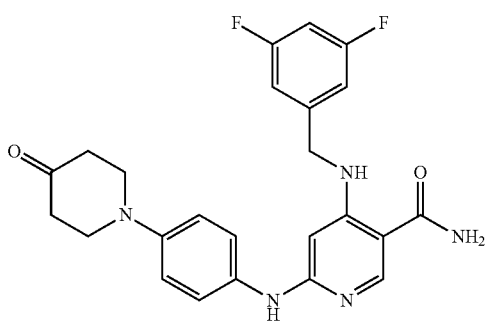 [SMILES: NC(=O)c1cnc(Nc2ccc(N3CCC(=O)CC3)cc2)cc1NCc1cc(F)cc(F)c1]

120 mg of 4-[(3,5-difluorobenzyl)amino]-6-{[4-(4-hydroxypiperidino)phenyl]amino}pyridine-3-carboxamide (the compound of Example 191) was dissolved in 1.5 mL of N,N-dimethylformamide, to which 78 mg of 4-methylmorpholine N-oxide, 120 mg of molecular sieve 4A powder and 2.8 mg of tetrapropylammonium perruthenate were added, and stirred at room temperature for 30 minutes. Water was added to the reaction mixture, extracted with ethyl acetate, and the extract was washed with saturated saline. After drying on anhydrous sodium sulfate, the solvent was evaporated, and the residue was purified by silica gel column chromatography (chloroform:methanol=20:1), recrystallized in methanol-ether-hexane to obtain 12 mg (10%) of the title compound as a light brown crystalline powder.

m.p. 223-226° C. (dec.)

$^1$H-NMR (270 MHz, CDCl$_3$+CD$_3$OD) δ: 2.59 (4H, t, J=6.1 Hz), 3.59 (4H, t, J=6.1 Hz), 4.28 (2H, s), 5.60 (1H, s), 6.70-6.82 (3H, m), 6.88 (4H, s), 8.18 (1H, s).

IR (ATR): 1711, 1597, 1513, 1461, 1406, 1309, 1293, 1256, 1213, 1117, 988 cm$^{-1}$.

MS: m/z 451 (M$^+$, base peak).

Example 193

Preparation of 4-[(3,5-difluorobenzyl)amino]-6-{[4-(tetrahydro-2H-pyran-4-yl)phenyl]amino}pyridine-3-carboxamide

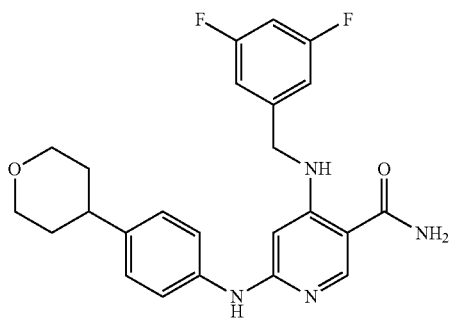

29 mg of 6-chloro-4-[(3,5-difluorobenzyl)amino]pyridine-3-carboxamide (the compound of Example 20) and 35 mg of 4-(tetrahydro-2H-pyran-4-yl)aniline were dissolved in 0.35 mL of 1,4-dioxane, to which 8.0 mg of [1,1'-bis(diphenylphosphino)ferrocene]dichloropalladium (II) complex with dichloromethane, 17 mg of 1,1'-bis (diphenylphosphino)ferrocene and 12 mg of sodium tert-butoxide were added, and stirred using a microwave reaction apparatus under an argon atmosphere at 100° C. for 1 hour. After cooling, the solvent was evaporated and the residue was purified by silica gel thin layer chromatography (chloroform:methanol=20:1) to obtain 7 mg (16%) of the title compound as a white crystalline powder.

m.p. 228-237° C.

$^1$H-NMR (400 MHz, CDCl$_3$) δ: 1.55-1.70 (4H, m), 3.35-3.46 (3H, m), 3.90-3.97 (2H, m), 4.42 (2H, d, J=5.8 Hz), 5.74 (1H, s), 7.00 (2H, d, J=6.4 Hz), 7.06 (2H, d, J=8.5 Hz), 7.15 (1H, t, J=9.5 Hz), 7.30 (2H, d, J=8.5 Hz), 8.37 (1H, s), 8.79 (1H, s), 9.05 (1H, t, J=5.6 Hz).

Example 194

Preparation of 4-[(3,5-difluorobenzyl)amino]-6-({4-[(2S)-2-(methoxymethyl)pyrrolidin-1-yl]phenyl}amino)pyridine-3-carboxyamide

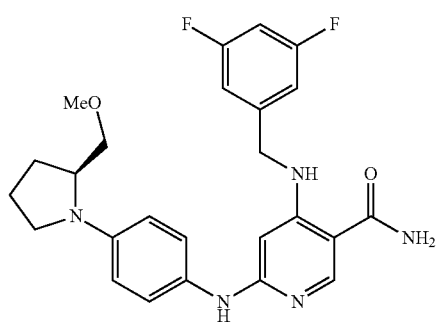 [SMILES: COC[C@@H]1CCCN1c1ccc(Nc2cc(NCc3cc(F)cc(F)c3)c(C(N)=O)cn2)cc1]

From 6-chloro-4-[(3,5-difluorobenzyl)amino]pyridine-3-carboxyamide (the compound of Example 20) and 4-[(2S)-2-(methoxymethyl)pyrrolidin-1-yl]aniline in a manner similar to Example 46, the title compound was obtained as a light yellow crystalline powder (yield 32%).

m.p. 215-216° C.

$^1$H-NMR (270 MHz, CDCl$_3$) δ: 1.96-2.10 (4H, m), 3.05-3.16 (1H, m), 3.21 (1H, t, J=8.9 Hz), 3.40 (3H, s), 3.41-3.57 (2H, m), 3.80-3.89 (1H, m), 4.25 (2H, d, J=5.9 Hz), 5.51-5.62 (1H, m), 5.52 (1H, s), 6.34 (1H, br s), 6.54 (2H, d, J=8.9 Hz), 6.69-6.80 (3H, m), 6.84 (2H, d, J=8.9 Hz), 8.18 (1H, s), 8.92 (1H, brs).

Example 195

Preparation of 4-[(3,5-difluorobenzyl)amino]-6-({4-[(2R)-2-(methoxymethyl)pyrrolidin-1-yl]phenyl}amino)pyridine-3-carboxyamide

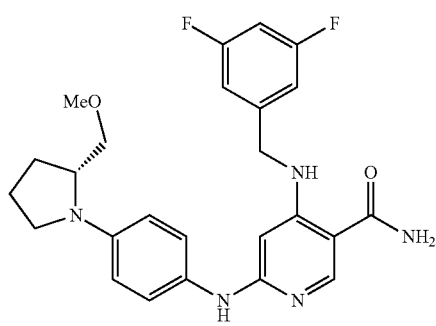 [SMILES: COC[C@H]1CCCN1c1ccc(Nc2cc(NCc3cc(F)cc(F)c3)c(C(N)=O)cn2)cc1]

From 6-chloro-4-[(3,5-difluorobenzyl)amino]pyridine-3-carboxyamide (the compound of Example 20) and 4-[(2R)-2-(methoxymethyl)pyrrolidin-1-yl]aniline in a manner similar to Example 46, the title compound was obtained as a light brown crystalline powder (yield 66%).

m.p. 214-215° C.

$^1$H-NMR (270 MHz, CDCl$_3$) δ: 1.96-2.10 (4H, m), 3.05-3.16 (1H, m), 3.21 (1H, t, J=9.1 Hz), 3.41 (3H, s), 3.41-3.57 (2H, m), 3.80-3.89 (1H, m), 4.25 (2H, d, J=5.9 Hz), 5.51-5.62 (1H, m), 5.52 (1H, s), 6.35 (1H, br s), 6.54 (2H, d, J=8.9 Hz), 6.66-6.80 (3H, m), 6.84 (2H, d, J=8.9 Hz), 8.18 (1H, s), 8.93 (1H, brs).

Example 196

Preparation of 4-[(3,5-difluorobenzyl)amino]-6-[(4-{trans-4-[(methylsulfonyl)amino]cyclohexyl}phenyl)amino]pyridine-3-carboxyamide

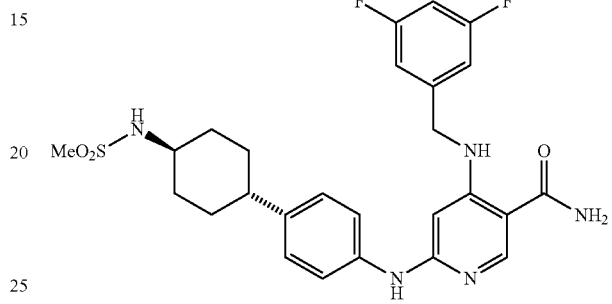

From 6-chloro-4-[(3,5-difluorobenzyl)amino]pyridine-3-carboxyamide (the compound of Example 20) and 4-{trans-4-[(methylsulfonyl)amino]cyclohexyl}aniline in a manner similar to Example 46, the title compound was obtained as a light yellow solid (yield).

$^1$H-NMR (400 MHz, CDCl$_3$) δ: 1.65-1.86 (6H, m), 1.98-2.01 (2H, m), 2.66-2.74 (1H, m), 3.02 (3H, s), 3.81-3.86 (1H, m), 4.63 (1H, d, J=6.3 Hz), 7.38 (2H, d, J=8.8 Hz), 8.18 (2H, d, J=8.8 Hz).

Example 197

Preparation of 4-[(3,5-difluorobenzyl)amino]-6-[(4-{cis-4-[(methylsulfonyl)amino]cyclohexyl]phenyl)amino]pyridine-3-carboxyamide

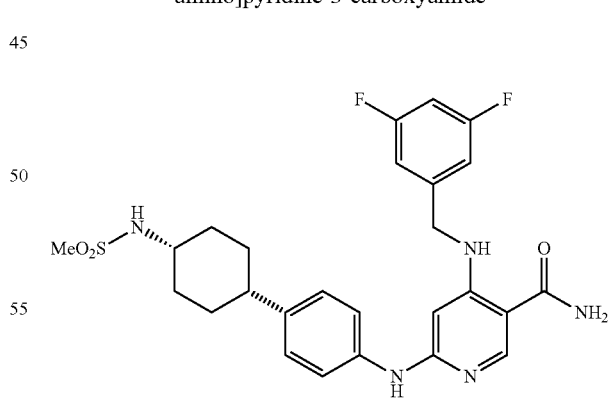

From 6-chloro-4-[(3,5-difluorobenzyl)amino]pyridine-3-carboxyamide (the compound of Example 20) and 4-{cis-4-[(methylsulfonyl)amino]cyclohexyl}aniline in a manner similar to Example 46, the title compound was obtained as a light yellow solid (yield 53%).

$^1$H-NMR (400 MHz, CD$_3$OD) δ: 1.66-1.84 (6H, m), 1.93-1.96 (2H, m), 2.50-2.56 (1H, m), 2.97 (3H, s), 3.68-3.70 (1H, m), 4.39 (2H, s), 5.75 (1H, s), 6.82-6.90 (3H, m), 7.03 (2H, d, J=8.6 Hz), 7.14 (2H, d, J=8.6 Hz), 8.27 (1H, s).

Example 198

Preparation of 4-[(3,5-difluorobenzyl)amino]-6-{[4-(3-hydroxypropyl)phenyl]amino}pyridine-3-carboxyamide

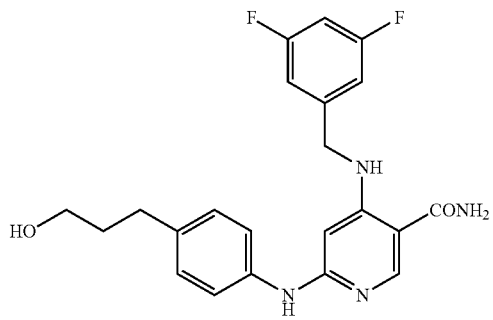 [SMILES: NC(=O)c1cnc(Nc2ccc(CCCO)cc2)cc1NCc1cc(F)cc(F)c1]

From 6-chloro-4-[(3,5-difluorobenzyl)amino]pyridine-3-carboxyamide (the compound of Example 20) and 4-(3-hydroxypropyl)aniline in a manner similar to Example 46, the title compound was obtained as a slight yellow crystalline powder (yield 95%).
m.p. 219-223° C. (dec.)
$^1$H-NMR (400 MHz, CDCl$_3$) δ: 1.78-1.86 (2H, m), 2.01-2.66 (2H, m), 3.57 (2H, t, J=6.6 Hz), 4.38 (2H, s), 5.74 (1H, s), 6.82-6.92 (3H, m), 7.01 (2H, d, J=8.6 Hz), 7.07 (2H, d, J=8.6 Hz), 8.27 (1H, s).
IR (ATR): 1667, 1619, 1593, 1564, 1522, 1411, 1314, 1115, 1014 cm$^{-1}$.

Example 199

Preparation of 4-[(3,5-difluorobenzyl)amino]-6-{[4-(3-methanesulfonyloxypropyl)phenyl]amino}pyridine-3-carboxyamide

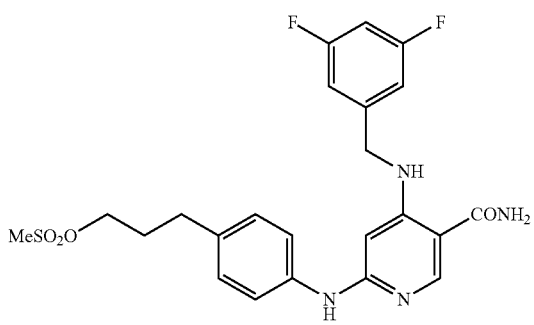

200 mg of 4-[(3,5-difluorobenzyl)amino]-6-{[4-(3-hydroxypropyl)phenyl]amino}pyridine-3-carboxyamide (the compound of Example 198) was suspended in 2 mL of pyridine, to which 278 mg of methanesulfonyl acid chloride was added under ice cooling, and stirred at the same temperature for 30 minutes. Water was added thereto, and the crystals that deposited were filtered, washed with water, and air-dried. By recrystallizing from methanol-ether, 223 mg (94%) of the title compound was obtained as slight yellow crystalline powder.

$^1$H-NMR (400 MHz, CD$_3$OD) δ: 1.97-2.09 (2H, m), 2.70 (2H, t, J=7.6 Hz), 3.05 (3H, s), 4.23 (2H, t, J=6.3 Hz), 4.39 (2H, s), 5.75 (1H, s), 6.80-6.92 (3H, m), 7.04 (2H, d, J=8.8 Hz), 7.09 (2H, d, J=8.8 Hz), 8.27 (1H, s).

Example 200

Preparation of 6-{[4-(3-azidopropyl)phenyl]amino}-4-[(3,5-difluorobenzyl)amino]pyridine-3-carboxyamide

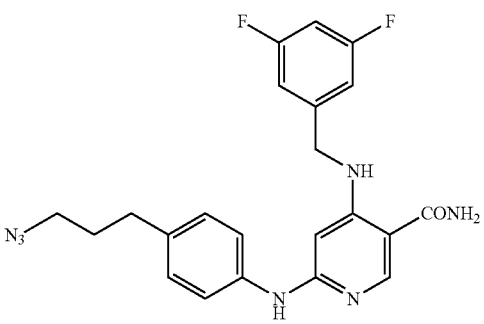 [SMILES: [N-]=[N+]=NCCCc1ccc(Nc2cc(NCc3cc(F)cc(F)c3)c(C(N)=O)cn2)cc1]

268 mg of 4-[(3,5-difluorobenzyl)amino]-6-{[4-(3-methanesulfonyloxypropyl)phenyl]amino}pyridine-3-carboxyamide (the compound of Example 199) was dissolved in 1.5 mL of N,N-dimethylformamide, to which 71 mg of sodium azide was added and stirred at 80° C. for 30 minutes. After cooling, hexane was added to the reaction mixture, and the deposit was filtered. The filtered product was dissolved in chloroform, washed with water and saturated saline, and dried on anhydrous sodium sulfate. By evaporating the solvent, 229 mg (94%) of the title compound was obtained as a slight yellow crystalline powder.
$^1$H-NMR (400 MHz, CD$_3$OD) δ: 1.88-1.95 (2H, m), 2.68 (2H, t, J=7.6 Hz), 3.31 (2H, t, J=6.8 Hz), 4.31 (2H, d, J=5.9 Hz), 5.67 (2H, br), 5.72 (1H, s), 6.65 (1H, brs), 6.71-6.83 (3H, m), 6.90 (2H, d, J=8.6 Hz), 7.06 (2H, d, J=8.6 Hz), 8.22 (1H, s), 8.97 (1H, brt, J=5.9 Hz).

Example 201

Preparation of 6-{[4-(3-aminopropyl)phenyl]amino}-4-[(3,5-difluorobenzyl)amino]pyridine-3-carboxyamide

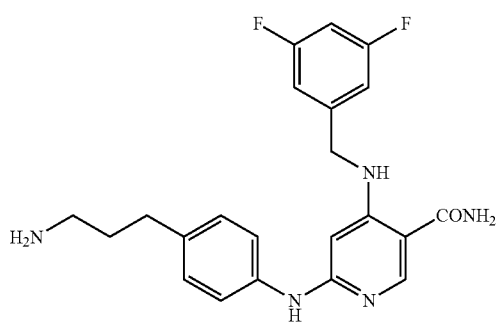 [SMILES: NCCCc1ccc(Nc2cc(NCc3cc(F)cc(F)c3)c(C(N)=O)cn2)cc1]

229 mg of 6-{[4-(3-azidopropyl)phenyl]amino}-4-[(3,5-difluorobenzyl)amino]pyridine-3-carboxyamide (the compound of Example 200) was dissolved in 30 mL of ethanol, to which 46 mg of 10% palladium carbon was added, and stirred under a hydrogen atmosphere at room temperature for 1 hour. The 10% palladium carbon was filtered off, the solvent was evaporated, and the residue was purified by silica gel column chromatography (chloroform:methanol=10:1 to chloroform: ammonia methanol=10:1) to obtain 161 mg (75%) of the title compound as a white crystalline powder.

m.p. 180-181° C.

$^1$H-NMR (400 MHz, CDCl$_3$) δ: 1.72-1.81 (2H, m), 2.60-2.66 (2H, m), 2.72-2.77 (2H, m), 4.30 (2H, t, J=5.9 Hz), 5.64 (2H, br), 5.71 (1H, s), 5.67 (1H, brs), 6.70-6.83 (3H, m), 6.88 (2H, d, J=8.5 Hz), 7.07 (2H, d, J=8.5 Hz), 8.21 (1H, s), 8.98 (1H, brt, J=5.9 Hz).

IR (ATR): 1637, 1596, 1567, 1544, 1515, 1405, 1301, 1255, 1116 cm$^{-1}$.

MS: m/z 412 (M$^+$).

Example 202

Preparation of 4-[(3,5-difluorobenzyl)amino]-6-[(4-{3-[(methanesulfonyl)amino]propyl}phenyl)amino]pyridine-3-carboxyamide

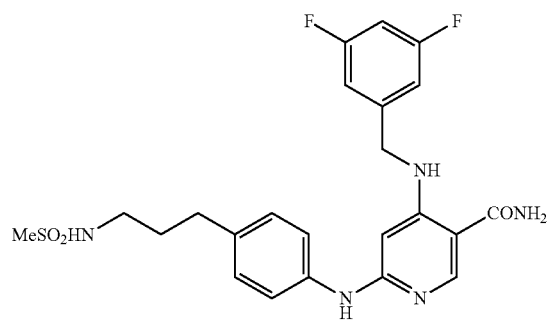

65 mg of 6-{[4-(3-aminopropyl)phenyl]amino}-4-[(3,5-difluorobenzyl)amino]pyridine-3-carboxyamide (the compound of Example 201) was dissolved in 1.5 mL of tetrahydrofuran, to which 32 mg of triethylamine and 27 mg of methanesulfonyl acid chloride were added under ice cooling, and stirred at room temperature for 1 hour. Ammonia water was added to the reaction mixture, extracted with chloroform, the extract was washed with saturated saline, and dried on anhydrous sodium sulfate. The solvent was evaporated, and the residue was purified by silica gel column chromatography (chloroform:methanol=20:1) to obtain 52 mg (67%) of the title compound as a white crystalline powder.

m.p. 181-182° C. (dec.)

$^1$H-NMR (400 MHz, CD$_3$OD) δ: 1.80-1.97 (2H, m), 2.65 (2H, t, J=7.7 Hz), 2.91 (3H, s), 3.07 (2H, t, J=7.0 Hz), 4.38 (2H, s), 5.75 (1H, s), 6.82-6.93 (3H, m), 7.03 (2H, d, J=8.5 Hz), 7.08 (2H, d, J=8.5 Hz), 8.27 (1H, s).

IR (ATR): 1637, 1601, 1573, 1547, 1515, 1413, 1306, 1257, 1148, 1117 cm$^{-1}$.

MS: m/z 490 (M$^+$).

Example 203

Preparation of 6-{[4-(methylsulfanyl)phenyl]amino}-4-[(3-nitrobenzyl)amino]pyridine-3-carboxyamide

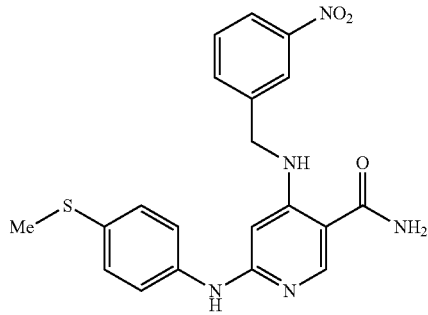 [SMILES: CSc1ccc(Nc2cc(NCc3cccc([N+](=O)[O-])c3)c(C(N)=O)cn2)cc1]

From 6-chloro-4-[(3-nitrobenzyl)amino]pyridine-3-carboxyamide (the compound of Example 31) and 4-methylsulfinylaniline in a manner similar to Example 46, the title compound was obtained as a white crystalline powder (yield 76%).

$^1$H-NMR (400 MHz, CD$_3$OD) δ: 2.43 (3H, s), 4.54 (2H, s), 5.76 (1H, s), 7.08 (2H, d, J=8.8 Hz), 7.13 (2H, d, J=8.8 Hz), 7.60 (1H, t, J=7.9 Hz), 7.72 (2H, d, J=7.6 Hz), 8.15-8.19 (2H, m), 8.28 (1H, s).

Example 204

Preparation of 6-{[4-(methylsulfinyl)phenyl]amino}-4-[(3-nitrobenzyl)amino]pyridine-3-carboxyamide and 6-{[4-(methylsulfonyl)phenyl]amino}-4-[(3-nitrobenzyl)amino]pyridine-3-carboxyamide

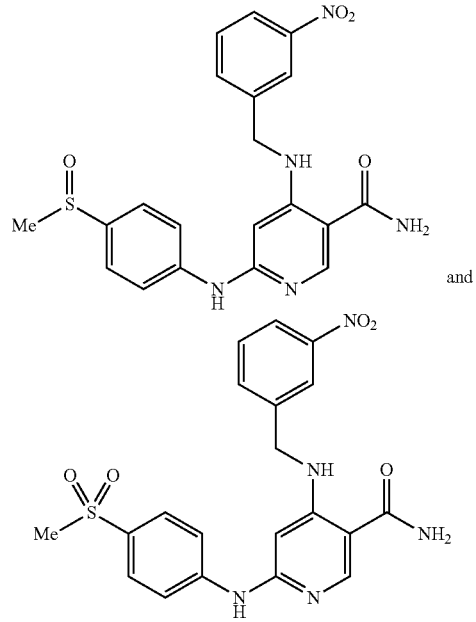

and 50 mg of 6-{[4-(methylsulfanyl)phenyl]amino}-4-[(3-nitrobenzyl)amino]pyridine-3-carboxyamide (the compound of Example 203) was dissolved in 3 mL of methylene chloride, to which 32 mg of 3-chloroperbenzoic acid was added, and stirred at room temperature for 1.5 hours. The reaction mixture was washed with saturated sodium bicarbonate and dried on anhydrous sodium sulfate. The solvent was evaporated, and the residue was purified by silica gel thin layer chromatography (chloroform:methanol=10:1) to obtain 10.1 mg (10%) of 6-{[4-(methylsulfinyl)phenyl]amino}-4-[(3-nitrobenzyl)amino]pyridine-3-carboxyamide (Example 204-1) as a light yellow crystalline powder and 20.1 mg (39%) of 6-{[4-(methylsulfonyl)phenyl]amino}-4-[(3-nitrobenzyl)amino]pyridine-3-carboxyamide (Example 204-2) as a white crystalline powder.

6-{[4-(methylsulfinyl)phenyl]amino}-4-[(3-nitrobenzyl)amino]pyridine-3-carboxyamide Example 204-1

$^1$H-NMR (400 MHz, CD$_3$OD) δ: 2.77 (3H, s), 4.59 (2H, s), 5.91 (1H, s), 7.54 (2H, d, J=9.0 Hz), 7.13 (2H, d, J=9.0 Hz), 7.61 (1H, t, J=7.8 Hz), 7.77 (2H, d, J=7.6 Hz), 8.16 (2H, d, J=7.8 Hz), 8.23 (1H, s), 8.38 (1H, s).

6-{[4-(methylsulfonyl)phenyl]amino}-4-[(3-nitrobenzyl)amino]pyridine-3-carboxyamide Example 204-2

$^1$H-NMR (400 MHz, CD$_3$OD) δ: 3.06 (3H, s), 4.60 (2H, s), 5.94 (1H, s), 7.62 (1H, t, J=8.1 Hz), 7.63 (2H, d, J=8.0 Hz), 7.72 (2H, d, J=9.0 Hz), 7.78 (1H, d, J=8.3 Hz), 8.15 (1H, d, J=8.1 Hz), 8.24 (1H, s), 8.41 (1H, s).

Example 205

Preparation of 6-({4-[4-(N,N-diethylglycyl)piperazin-1-yl]phenyl}amino)-4-[(2,3-difluorobenzyl)amino]pyridine-3-carboxyamide

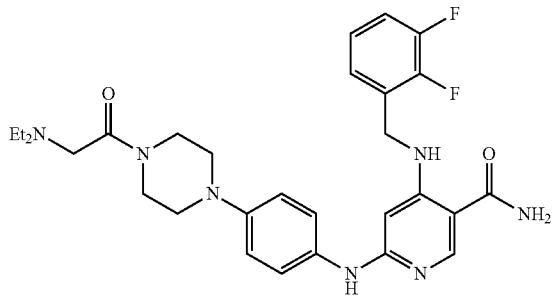

From 6-chloro-4-[(2,3-difluorobenzyl)amino]pyridine-3-carboxyamide (the compound of Example 19) and 4-(N,N-diethylaminoglycyl)piperazin-1-yl]aniline in a manner similar to Example 46, the title compound was obtained as a light brown crystalline powder (yield 46%).

$^1$H-NMR (400 MHz, CDCl$_3$) δ: 1.05 (6H, dd, J=7.1, 7.1 Hz), 2.56-2.61 (4H, m), 3.10-3.18 (4H, m), 3.31 (2H, s), 3.75-3.80 (2H, m), 3.82-3.88 (2H, m), 4.38 (2H, d, J=5.9 Hz), 5.67 (1H, s), 6.84 (2H, d, J=8.8 Hz), 6.96 (2H, d, J=8.8 Hz), 7.02-7.12 (3H, m), 8.20 (1H, s), 8.90 (1H, br).

IR (ATR): 1619, 1571, 1513, 1408, 1277, 1228 cm$^{-1}$.

Example 206

Preparation of 4-(benzylamino)-6-({4-[4-(trifluoroacetyl)piperazin-1-yl]phenyl}amino)pyridine-3-carboxyamide

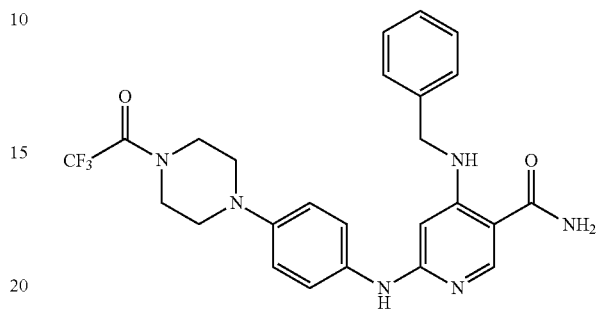

From 4-(benzylamino)-6-chloropyridine-3-carboxyamide (the compound of Example 1) and 4-[4-(trifluoroacetyl)piperazin-1-yl]aniline in a manner similar to Example 46, the title compound was obtained as slight brown prism crystals (yield 90%).

$^1$H-NMR (400 MHz, CDCl$_3$) δ: 3.16-3.21 (4H, m), 3.76-3.81 (2H, m), 3.84-3.89 (2H, m), 4.32 (2H, d, J=5.6 Hz), 5.55 (2H, br), 5.76 (1H, s), 6.44 (1H, brs), 6.82 (2H, d, J=9.0 Hz), 6.96 (2H, d, J=9.0 Hz), 7.25-7.36 (5H, m), 8.20 (1H, s), 8.89 (1H, brt, J=5.6 Hz).

IR (ATR): 1681, 1667, 1624, 1590, 1514, 1408, 1227, 1205, 1192, 1180, 1142, 1025 cm$^{-1}$.

Example 207

Preparation of 4-[(2,3-difluorobenzyl)amino]-6-({4-[4-(trifluoroacetyl)piperazin-1-yl]phenyl}amino)pyridine-3-carboxyamide

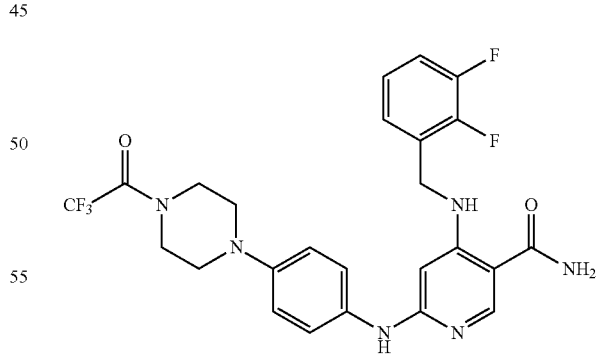

From 6-chloro-4-[(2,3-difluorobenzyl)amino]pyridine-3-carboxyamide (the compound of Example 19) and 4-[4-(trifluoroacetyl)piperazin-1-yl]aniline in a manner similar to Example 46, the title compound was obtained as a light yellow crystalline powder (yield 52%).

$^1$H-NMR (400 MHz, CDCl$_3$) δ: 3.18-3.24 (4H, m), 3.77-3.82 (2H, m), 3.85-3.89 (2H, m), 4.38 (2H, d, J=6.1 Hz), 5.61

(2H, br), 5.66 (1H, s), 6.51 (1H, brs), 6.85 (2H, d, J=9.0 Hz), 6.99 (2H, d, J=9.0 Hz), 7.01-7.12 (3H, m), 8.20 (1H, s), 8.93 (1H, brt, J=6.1 Hz).

Example 208

Preparation of 4-[(3,5-difluorobenzyl)amino]-6-({4-[4-(trifluoroacetyl)piperazin-1-yl]phenyl}amino)pyridine-3-carboxyamide

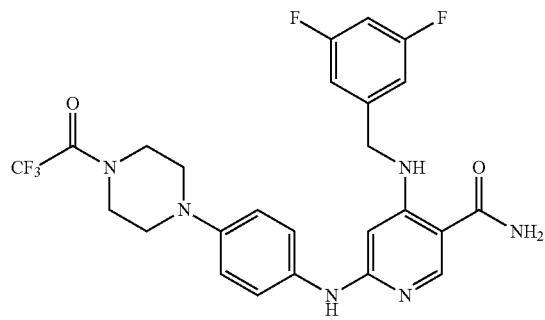 [SMILES: NC(=O)c1cnc(Nc2ccc(N3CCN(C(=O)C(F)(F)F)CC3)cc2)cc1NCc1cc(F)cc(F)c1]

From 6-chloro-4-[(3,5-difluorobenzyl)amino]pyridine-3-carboxyamide (the compound of Example 20) and 4-[4-(trifluoroacetyl)piperazin-1-yl]aniline in a manner similar to Example 46, the title compound was obtained as a light brown solid (yield 91%).

¹H-NMR (400 MHz, CDCl₃+CD₃OD) δ: 3.18-3.24 (4H, m), 3.76-3.82 (2H, m), 3.84-3.89 (2H, m), 4.28 (2H, d, J=5.6 Hz), 5.59 (1H, s), 6.71-6.80 (3H, m), 6.83 (2H, d, J=9.0 Hz), 6.88 (2H, d, J=9.0 Hz), 8.19 (1H, s), 9.03 (1H, brt, J=5.6 Hz).

Example 209

Preparation of 4-[(2,5-difluorobenzyl)amino]-6-({4-[4-(trifluoroacetyl)piperazin-1-yl]phenyl}amino)pyridine-3-carboxyamide

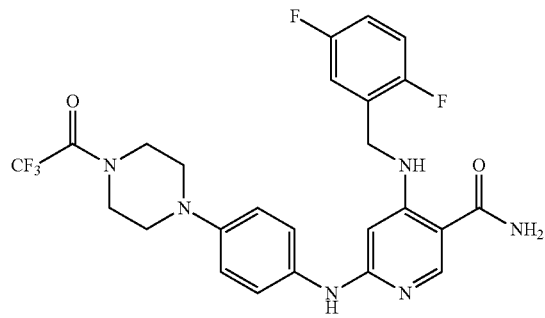 [SMILES: NC(=O)c1cnc(Nc2ccc(N3CCN(C(=O)C(F)(F)F)CC3)cc2)cc1NCc1cc(F)ccc1F]

From 6-chloro-4-[(2,5-difluorobenzyl)amino]pyridine-3-carboxyamide (the compound of Example 22) and 4-[4-(trifluoroacetyl)piperazin-1-yl]aniline in a manner similar to Example 46, the title compound was obtained as a light brown solid.

Example 210

Preparation of 4-[(2,6-difluorobenzyl)amino]-6-({4-[4-(trifluoroacetyl)piperazin-1-yl]phenyl}amino)pyridine-3-carboxyamide

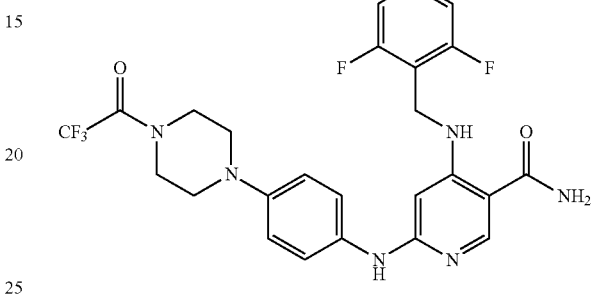

From 6-chloro-4-[(2,6-difluorobenzyl)amino]pyridine-3-carboxyamide (the compound of Example 23) and 4-[4-(trifluoroacetyl)piperazin-1-yl]aniline in a manner similar to Example 46, the title compound was obtained as a light brown solid.

Example 211

Preparation of 4-[(3-nitrobenzyl)amino]-6-({4-[4-(trifluoroacetyl)piperazin-1-yl]phenyl}amino)pyridine-3-carboxyamide

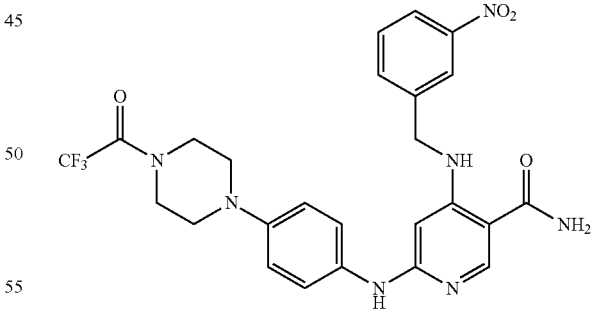

From 6-chloro-4-[(3-nitrobenzyl)amino]pyridine-3-carboxyamide (the compound of Example 31) and 4-[4-(trifluoroacetyl)piperazin-1-yl]aniline in a manner similar to Example 46, the title compound was obtained as a light yellow crystalline powder (yield 84%).

¹H-NMR (400 MHz, CD₃OD) δ: 3.14-3.20 (4H, m), 3.78-3.86 (4H, m), 4.49 (2H, s), 5.60 (1H, s), 6.83 (2H, d, J=8.5

Hz), 6.94 (2H, d, J=8.5 Hz), 7.58 (1H, dd, J=9.8, 9.8 Hz), 7.67-7.70 (1H, m), 8.11-8.17 (2H, m), 8.25 (1H, s).

Example 212

Preparation of 4-[(3,5-difluorobenzyl)amino]-6-({3-[4-(trifluoroacetyl)piperazin-1-yl]phenyl}amino)pyridine-3-carboxyamide

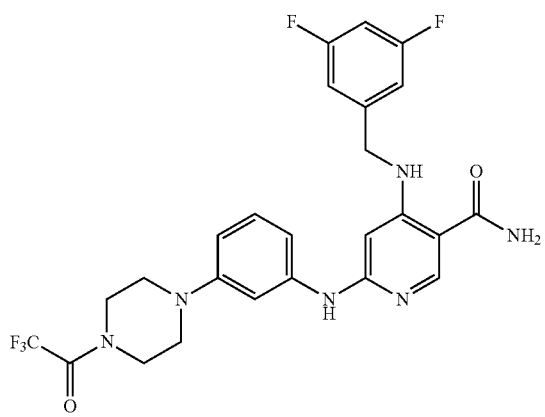 [SMILES: NC(=O)c1cnc(Nc2cccc(N3CCN(C(=O)C(F)(F)F)CC3)c2)cc1NCc1cc(F)cc(F)c1]

From 6-chloro-4-[(3,5-difluorobenzyl)amino]pyridine-3-carboxyamide (the compound of Example 20) and 3-[4-(trifluoroacetyl)piperazin-1-yl]aniline in a manner similar to Example 46, the title compound was obtained as a light brown crystalline powder (yield 89%).

¹H-NMR (400 MHz, CDCl₃) δ: 3.17-3.21 (4H, m), 3.72-3.77 (2H, m), 3.80-3.85 (2H, m), 4.33 (2H, d, J=5.7 Hz), 5.61 (2H, br), 5.77 (1H, s), 6.51-6.56 (1H, m), 6.64 (1H, dd, J=8.0, 2.0 Hz), 6.68-6.76 (2H, m), 6.78-6.82 (2H, m), 7.14 (1H, dd, J=8.0, 8.0 Hz), 8.24 (1H, s), 9.01 (1H, brt, J=5.7 Hz).

Example 213

Preparation of 4-(benzylamino)-6-{[4-(4-trifluoroacetyl-1,4-diazepan-1-yl)phenyl]amino}pyridine-3-carboxyamide

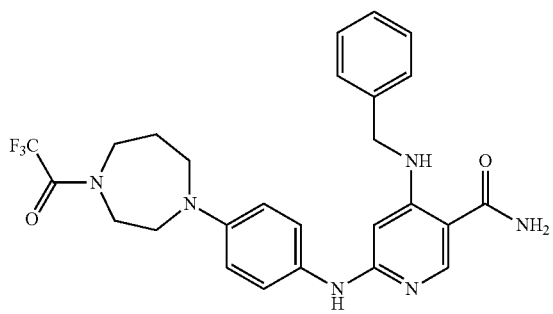 [SMILES: NC(=O)c1cnc(Nc2ccc(N3CCCN(C(=O)C(F)(F)F)CC3)cc2)cc1NCc1ccccc1]

From 4-(benzylamino)-6-chloropyridine-3-carboxyamide (the compound of Example 1) and 4-(4-trifluoroacetyl-1,4-diazepan-1-yl)aniline in a manner similar to Example 46, the title compound was obtained as a light gray amorphous substance (yield 84%).

¹H-NMR (400 MHz, CDCl₃) δ: 1.99-2.07 (1H, m), 2.09-2.18 (1H, m), 3.47-3.52 (1H, m), 3.56-3.64 (4H, m), 3.66-3.72 (1H, m), 3.73-3.75 (1H, m), 3.84-3.88 (1H, m), 4.29-4.34 (2H, m), 5.62 (1H, br), 5.64-5.68 (1H, m), 6.56-6.64 (3H, m), 6.88-6.94 (2H, m), 7.23-7.35 (6H, m), 8.19 (1H, s), 8.89 (1H, br).

Example 214

Preparation of 4-[(3,5-difluorobenzyl)amino]-6-({4-[4-(trifluoroacetyl)-1,4-diazepan-1-yl]phenyl}amino)pyridine-3-carboxyamide

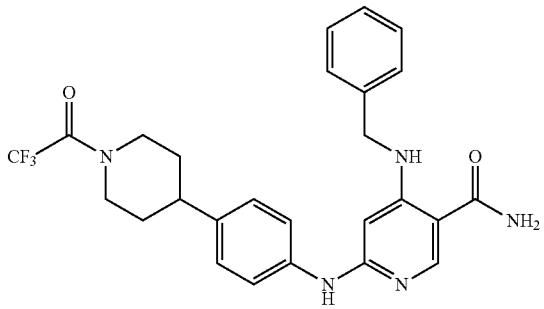 [SMILES: NC(=O)c1cnc(Nc2ccc(C3CCN(C(=O)C(F)(F)F)CC3)cc2)cc1NCc1ccccc1]

From 6-chloro-4-[(3,5-difluorobenzyl)amino]pyridine-3-carboxyamide (the compound of Example 20) and 4-(4-trifluoroacetyl-1,4-diazepan-1-yl)aniline in a manner similar to Example 46, the title compound was obtained as light brown needle crystals (yield 98%).

Example 215

Preparation of 4-(benzylamino)-6-({4-[1-(trifluoroacetyl)piperidin-4-yl]phenyl}amino)pyridine-3-carboxyamide From 4-(benzylamino)-6-chloropyridine-3-carboxyamide (the compound of Example 1) and 4-[1-(trifluoroacetyl)piperidin-4-yl]aniline in a manner similar to Example 46, the title compound was obtained (yield 75%).

¹H-NMR (400 MHz, CDCl₃) δ: 1.66 (2H, q, J=12.4 Hz), 1.99 (2H, d, J=12.2 Hz), 2.78 (1H, t, J=12.1 Hz), 2.87 (2H, t, J=12.4 Hz), 3.25 (1H, t, J=12.1 Hz), 4.15 (1H, d, J=14.4 Hz), 4.36 (2H, d, J=5.9 Hz), 4.71 (1H, d, J=13.4 Hz), 5.56 (2H, brs), 5.87 (1H, s), 6.49 (1H, s), 6.96 (2H, d, J=8.3 Hz), 7.04 (2H, d, J=8.3 Hz), 7.27-7.38 (5H, m), 8.21 (1H, s), 8.91 (1H, brs).

Example 216

Preparation of 4-[(3,5-difluorobenzyl)amino]-6-({4-[1-(trifluoroacetyl)piperidin-4-yl]phenyl}amino)pyridine-3-carboxyamide

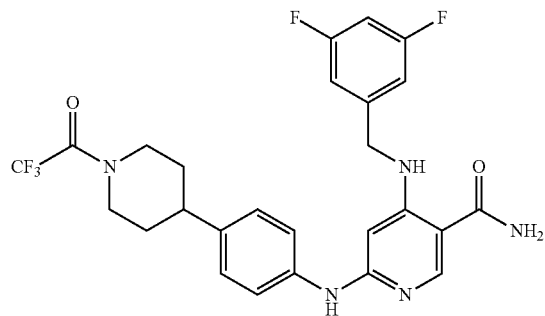 [SMILES: NC(=O)c1cnc(Nc2ccc(C3CCN(C(=O)C(F)(F)F)CC3)cc2)cc1NCc1cc(F)cc(F)c1]

From 6-chloro-4-[(3,5-difluorobenzyl)amino]pyridine-3-carboxyamide (the compound of Example 20) and 4-[1-(trifluoroacetyl)piperidin-4-yl]aniline in a manner similar to Example 46, the title compound was obtained as a slight brown crystalline powder (yield 86%).

$^1$H-NMR (400 MHz, CDCl$_3$) δ: 1.63-1.76 (2H, m), 1.95-2.10 (2H, m), 2.76-2.93 (2H, m), 3.22-3.31 (1H, m), 4.10-4.19 (1H, m), 4.31 (2H, d, J=5.8 Hz), 4.66-4.75 (1H, m), 5.72 (1H, s), 5.77 (2H, br), 6.68 (1H, br), 6.72-6.83 (3H, m), 6.93 (2H, d, J=8.5 Hz), 7.06 (2H, d, J=8.5 Hz), 8.22 (1H, s), 9.01 (1H, brt, J=5.8 Hz).

Example 217

Preparation of 4-[(3,5-difluorobenzyl)amino]-6-[(4-{[4-[(trifluoroacetyl)amino]piperidino}phenyl)amino]pyridine-3-carboxyamide

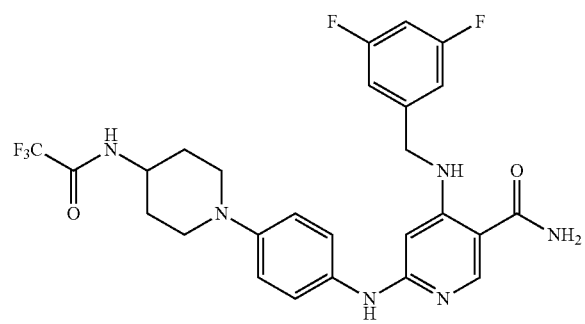 [SMILES: NC(=O)c1cnc(Nc2ccc(N3CCC(NC(=O)C(F)(F)F)CC3)cc2)cc1NCc1cc(F)cc(F)c1]

From 6-chloro-4-[(3,5-difluorobenzyl)amino]pyridine-3-carboxyamide (the compound of Example 20) and 4-{4-[(trifluoroacetyl)amino]piperidino}aniline in a manner similar to Example 46, the title compound was obtained as a light brown amorphous substance (yield 36%).

$^1$H-NMR (400 MHz, CDCl$_3$) δ: 1.31-1.45 (2H, m), 1.92-2.03 (2H, m), 2.80-2.91 (1H, m), 3.20-3.30 (1H, m), 4.03-4.13 (1H, m), 4.38 (2H, d, J=5.8 Hz), 4.60-4.68 (1H, m), 4.73-4.83 (1H, m), 5.72 (2H, brs), 5.79 (1H, s), 6.75 (1H, dddd, J=8.2, 8.2, 2.3, 2.3 Hz), 6.79-6.86 (2H, m), 6.91-6.98 (2H, m), 7.08 (2H, d, J=9.3 Hz), 7.20 (1H, brs), 8.25 (1H, s), 9.09 (1H, brt, J=5.8 Hz).

Example 218

Preparation of 4-[(3,5-difluorobenzyl)amino]-6-{[(4-{2-[(trifluoroacetyl)amino]ethyl}amino)phenyl]amino}pyridine-3-carboxyamide

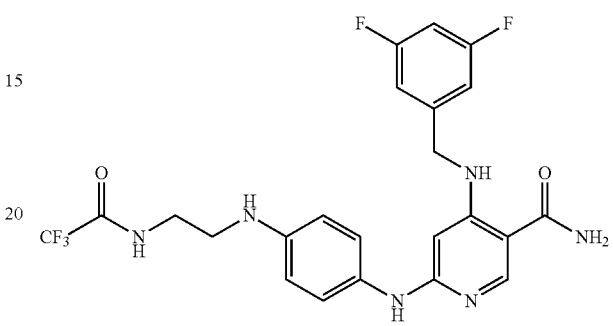

From 6-chloro-4-[(3,5-difluorobenzylamino)pyridine-3-carboxyamide (the compound of Example 20) and 4-{2-[(trifluoroacetyl)amino]ethyl}amino)aniline in a manner similar to Example 46, the title compound was obtained as a light yellow solid (yield 16%).

$^1$H-NMR (400 MHz, DMSO-d6) δ: 3.12-3.18 (2H, m), 3.41-3.47 (2H, m), 4.36 (2H, d, J=5.8 Hz), 5.46 (1H, br), 5.58 (1H, s), 6.48 (2H, d, J=8.8 Hz), 6.93-6.99 (2H, m), 7.00 (2H, d, J=8.8 Hz), 7.09-7.15 (1H, m), 8.31 (1H, brs), 8.39 (1H, brs), 9.04 (1H, brt, J=5.8 Hz), 9.48 (1H, br).

Example 219

Preparation of 4-(benzylamino)-6-{[4-piperazin-1-yl]phenyl}amino)pyridine-3-carboxyamide

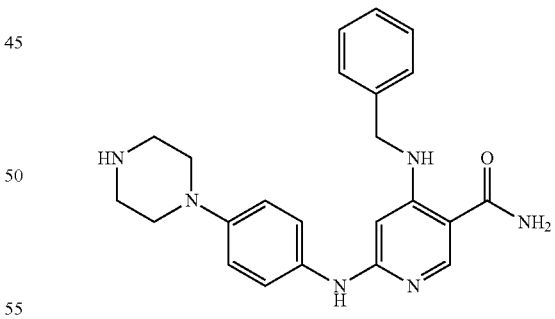

205 mg of 4-(benzylamino)-6-({4-[4-(trifluoroacetyl)piperazin-1-yl]phenyl}amino)pyridine-3-carboxyamide (the compound of Example 206) was dissolved in 10 mL of methanol, to which 2.5 mL of 0.2 mol/L barium hydroxide in water was added, and stirred at 50° C. for 30 minutes. After cooling, the solvent was evaporated, water was added to the residue and extracted with chloroform, and dried on anhydrous sodium sulfate. The solvent was evaporated, and the residue was purified by silica gel column chromatography (chloroform:methanol=20:1) to obtain 25 mg (76%) of the title compound as light brown prism crystals.

$^1$H-NMR (400 MHz, CDCl$_3$) δ: 3.05-3.09 (4H, m), 3.11-3.15 (4H, m), 4.30 (2H, d, J=5.8 Hz), 5.55 (2H, br), 5.74 (1H, s), 6.42 (1H, brs), 6.82 (2H, d, J=9.0 Hz), 6.92 (2H, d, J=9.0 Hz), 7.24-7.36 (5H, m), 8.21 (1H, s), 8.89 (1H, brt, J=5.8 Hz).

IR (ATR): 1613, 1603, 1585, 1568, 1541, 1514, 1408, 1292, 1272, 1254, 1236 cm$^{-1}$.

Example 220

Preparation of 4-[(2,3-difluorobenzyl)amino]-6-{[4-(piperazin-1-yl)phenyl]amino}pyridine-3-carboxyamide

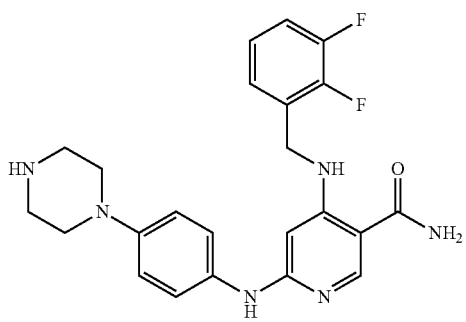 [SMILES: NC(=O)c1cnc(Nc2ccc(N3CCNCC3)cc2)cc1NCc1cccc(F)c1F]

From 4-[(2,3-difluorobenzyl)amino]-6-({4-[4-(trifluoroacetyl)piperazin-1-yl]phenyl}amino)pyridine-3-carboxyamide (the compound of Example 207) in a manner similar to Example 219, the title compound was obtained as a light yellow crystalline powder (yield 89%).

$^1$H-NMR (400 MHz, CDCl$_3$) δ: 3.03-3.09 (4H, m), 3.11-3.16 (4H, m), 4.37 (2H, d, J=5.4 Hz), 5.68 (1H, s), 6.85 (2H, d, J=8.8 Hz), 6.94 (2H, d, J=8.8 Hz), 7.01-7.14 (3H, m), 8.17 (1H, s), 8.92 (1H, br).

Example 221

Preparation of 4-[(3,5-difluorobenzyl)amino]-6-{[4-(piperazin-1-yl)phenyl]amino}pyridine-3-carboxyamide

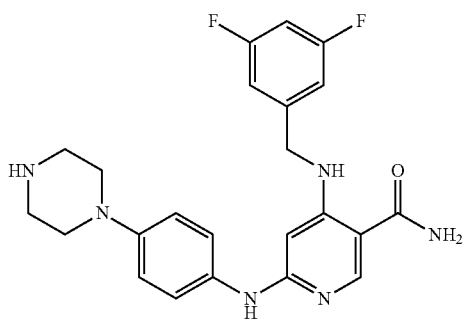 [SMILES: NC(=O)c1cnc(Nc2ccc(N3CCNCC3)cc2)cc1NCc1cc(F)cc(F)c1]

From 4-[(3,5-difluorobenzyl)amino]-6-({4-[4-(trifluoroacetyl)piperazin-1-yl]phenyl}amino)pyridine-3-carboxyamide (the compound of Example 208) in a manner similar to Example 219, the title compound was obtained as a white solid (yield 89%).

$^1$H-NMR (400 MHz, CDCl$_3$) δ: 3.03-3.08 (4H, m), 3.10-3.15 (4H, m), 4.27 (2H, d, J=5.6 Hz), 5.59 (1H, s), 6.70-6.80 (3H, m), 6.82 (2H, d, J=9.0 Hz), 6.86 (2H, d, J=9.0 Hz), 8.18 (1H, s), 8.99 (1H, br).

IR (ATR): 1639, 1600, 1571, 1548, 1515, 1408, 1312, 1299, 1259, 1226, 1116 cm$^{-1}$.

Example 222

Preparation of 4-[(2,5-difluorobenzyl)amino]-6-{[4-(piperazin-1-yl)phenyl]amino}pyridine-3-carboxyamide

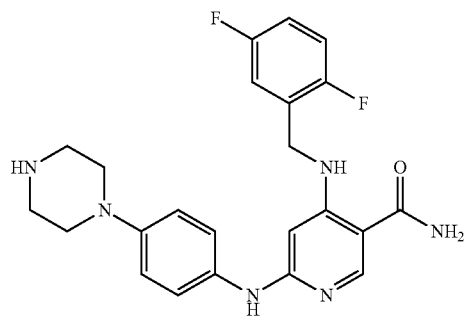 [SMILES: NC(=O)c1cnc(Nc2ccc(N3CCNCC3)cc2)cc1NCc1cc(F)ccc1F]

From 4-[(2,5-difluorobenzyl)amino]-6-({4-[4-(trifluoroacetyl)piperazin-1-yl]phenyl}amino)pyridine-3-carboxyamide (the compound of Example 209) in a manner similar to Example 219, the title compound was obtained as a light brown solid (yield 40%).

$^1$H-NMR (400 MHz, CDCl$_3$) δ: 3.03-3.08 (4H, m), 3.10-3.15 (4H, m), 4.32-4.33 (2H, d, J=5.8 Hz), 5.56 (2H, brs), 5.68 (1H, s), 6.40 (1H, s), 6.85 (2H, d, J=8.8 Hz), 6.89-7.03 (5H, m), 8.20 (1H, s), 8.89 (1H, t, J=5.8 Hz).

Example 223

Preparation of 4-[(2,6-difluorobenzyl)amino]-6-{[4-(piperazin-1-yl)phenyl]amino}pyridine-3-carboxyamide

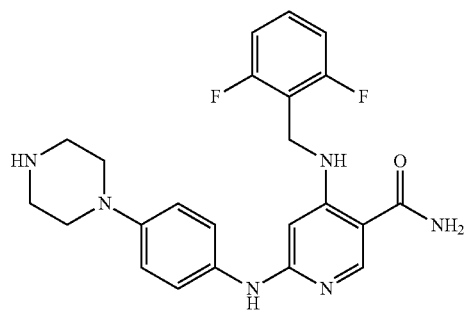 [SMILES: NC(=O)c1cnc(Nc2ccc(N3CCNCC3)cc2)cc1NCc1c(F)cccc1F]

From 4-[(2,6-difluorobenzyl)amino]-6-({4-[4-(trifluoroacetyl)piperazin-1-yl]phenyl}amino)pyridine-3-carboxyamide (the compound of Example 210) in a manner similar to Example 219, the title compound was obtained as a light brown solid (yield 34%).

$^1$H-NMR (400 MHz, CDCl$_3$) δ: 3.04-3.09 (4H, m), 3.14-3.19 (4H, m), 4.33 (2H, d, J=5.9 Hz), 5.49 (2H, brs), 5.97 (1H, s), 6.42 (1H, s), 6.86 (2H, dd, J=7.9, 7.9 Hz), 6.96 (2H, d,

Example 224

Preparation of 4-[(3-nitrobenzyl)amino]-6-{[4-(piperazin-1-yl)phenyl]amino}pyridine-3-carboxamide

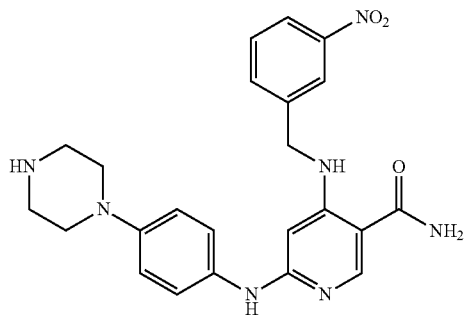 [SMILES: NC(=O)c1cnc(Nc2ccc(N3CCNCC3)cc2)cc1NCc1cccc([N+](=O)[O-])c1]

From 4-[(3-nitrobenzyl)amino]-6-({4-[4-(trifluoro) piperazin-1-yl]phenyl}amino)pyridine-3-carboxyamide (the compound of Example 211) in a manner similar to Example 219, the title compound was obtained as a yellow crystalline powder (yield 94%).

$^1$H-NMR (400 MHz, CD$_3$OD) δ: 2.98-3.02 (4H, m), 3.05-3.10 (4H, m), 4.48 (2H, s), 5.61 (1H, s), 6.80 (2H, d, J=8.8 Hz), 6.92 (2H, d, J=8.8 Hz), 7.59 (1H, dd, J=7.8, 7.8 Hz), 7.66-7.70 (1H, m), 8.12-8.17 (2H, m), 8.25 (1H, s).

IR (ATR): 1659, 1610, 1560, 1513, 1410, 1383, 1345, 1319, 1264, 1250, 1239 cm$^{-1}$.

Example 225

Preparation of 4-[(3,5-difluorobenzyl)amino]-6-{[3-(piperazin-1-yl)phenyl]amino}pyridine-3-carboxamide

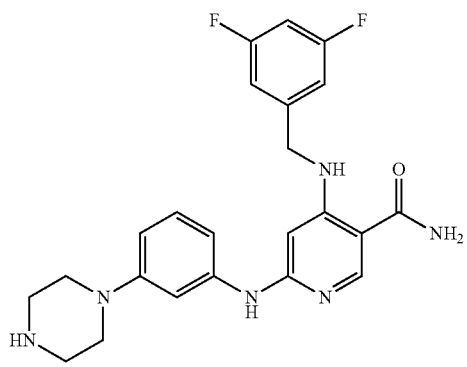 [SMILES: NC(=O)c1cnc(Nc2cccc(N3CCNCC3)c2)cc1NCc1cc(F)cc(F)c1]

From 4-[(3,5-difluorobenzyl)amino]-6-({3-[4-(trifluoroacetylamino)piperazin-1-yl]phenyl}amino) pyridine-3-carboxyamide (the compound of Example 212) in a manner similar to Example 219, the title compound was obtained as slight yellow prism crystals (yield 96%).

$^1$H-NMR (400 MHz, DMSO-d6) δ: 2.26 (1H, br), 2.78-2.83 (4H, m), 2.95-2.99 (4H, m), 4.42 (2H, d, J=6.1 Hz), 5.78 (1H, s), 6.67 (1H, dd, J=8.0, 2.0 Hz), 6.83 (1H, dd, J=8.0, 2.0 Hz), 6.97-7.04 (3H, m), 7.05-7.17 (3H, m), 7.81 (1H, br), 8.39 (1H, s), 8.72 (1H, brs), 9.04 (1H, brt, J=6.1 Hz).

IR (ATR): 1624, 1578, 1554, 1441, 1410, 1291, 1264, 1217 cm$^{-1}$.

Example 226

Preparation of 4-(benzylamino)-6-{[4-(1,4-diazepan-1-yl)phenyl]amino}pyridine-3-carboxamide

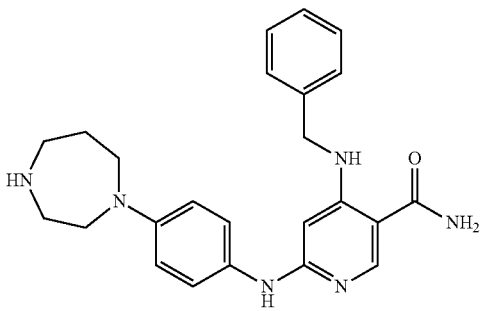 [SMILES: NC(=O)c1cnc(Nc2ccc(N3CCCNCC3)cc2)cc1NCc1ccccc1]

386 mg of 4-(benzylamino)-6-{[4-(4-trifluoroacetyl-1,4-diazepan-1-yl)phenyl]amino}pyridine-3-carboxamide (the compound of Example 213) was dissolved in a mixture of 10 mL of methanol and 10 mL of tetrahydrofuran, to which 2 mL of 2 mol/L sodium hydroxide in water was added at room temperature and stirred for 1 hour. The reaction mixture was concentrated, the residue was dissolved in chloroform, washed with water and saturated saline, and dried on anhydrous sodium sulfate. The solvent was evaporated, and the residue was crystallized from chloroform-methanol-diethylether to obtain 260 mg (83%) of the title compound as light brown needle crystals.

m.p. 201-202° C.

$^1$H-NMR (400 MHz, CDCl$_3$+CD$_3$OD) δ: 1.88-1.95 (2H, m), 2.83-2.87 (2H, m), 3.02-3.08 (2H, m), 3.53-3.61 (4H, m), 4.28 (2H, d, J=5.6 Hz), 5.58 (2H, br), 5.67 (1H, s), 6.37 (1H, brs), 6.58 (2H, d, J=9.0 Hz), 6.88 (2H, d, J=9.0 Hz), 7.22-7.34 (6H, m), 8.17 (1H, s), 8.83 (1H, brt, J=56 Hz).

IR (ATR): 1653, 1612, 1557, 1516, 1404, 1357, 1320, 1272, 1193, 1181, 1033 cm$^{-1}$.

Example 227

Preparation of 6-{[4-(1,4-diazepan-1-yl)phenyl]amino}-4-[(3,5-difluorobenzyl)amino]pyridine-3-carboxamide

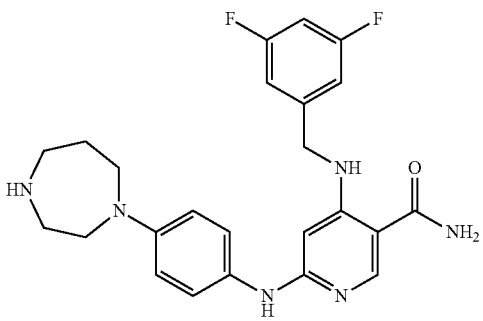 [SMILES: NC(=O)c1cnc(Nc2ccc(N3CCCNCC3)cc2)cc1NCc1cc(F)cc(F)c1]

From 4-[(3,5-difluorobenzyl)amino]-6-({4-[4-(trifluoroacetyl)-1,4-diazepan-1-yl]phenyl}amino) pyridine-3-carboxyamide (the compound of Example 214) in a manner similar to Example 226, the title compound was obtained as a light yellow solid (yield 90%).

¹H-NMR (270 MHz, CDCl₃+CD₃OD) δ: 1.80-1.97 (2H, m), 2.82-2.88 (2H, m), 3.01-3.06 (2H, m), 3.53-3.61 (4H, m), 4.25 (2H, d, J=5.9 Hz), 5.52 (1H, s), 6.58 (2H, d, J=9.2 Hz), 6.66-6.83 (5H, m), 8.16 (1H, s), 8.96 (1H, brt, J=5.9 Hz).

Example 228

Preparation of 4-(benzylamino)-6-{[4-(piperidin-4-yl)phenyl]amino}pyridine-3-carboxyamide

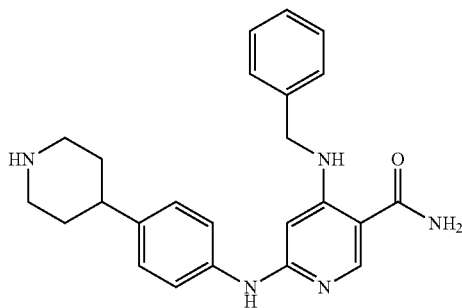 [SMILES: NC(=O)c1cnc(Nc2ccc(C3CCNCC3)cc2)cc1NCc1ccccc1]

From 4-(benzylamino)-6-({4-[1-(trifluoroacetyl)piperidin-4-yl]phenyl}amino)pyridine-3-carboxyamide (the compound of Example 215) in a manner similar to Example 226, the title compound was obtained as a slight yellow crystalline powder (yield 42%).

¹H-NMR (400 MHz, CD₃OD) δ: 1.66 (2H, q, J=12.4 Hz), 1.83 (2H, d, J=12.2 Hz), 2.64 (1H, t, J=12.1 Hz), 2.76 (2H, t, J=12.4 Hz), 3.17 (2H, d, J=12.0 Hz), 4.36 (2H, s), 5.87 (1H, s), 7.05 (2H, d, J=8.6 Hz), 7.10 (2H, d, J=8.6 Hz), 7.27-7.38 (5H, m), 8.25 (1H, s).

Example 229

Preparation of 4-[(3,5-difluorobenzyl)amino]-6-{[4-(piperidin-4-yl)phenyl]amino}pyridine-3-carboxyamide

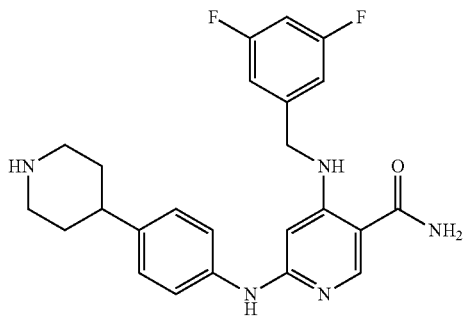

From 4-[(3,5-difluorobenzyl)amino]-6-({4-[1-(trifluoroacetyl)piperidin-4-yl]phenyl}amino)pyridine-3-carboxyamide (the compound of Example 216) in a manner similar to Example 226, the title compound was obtained as a slight brown crystalline powder (yield 93%).

¹H-NMR (400 MHz, DMSO-d6) δ: 1.39-1.52 (2H, m), 1.61-1.68 (2H, m), 2.32-2.58 (3H, m), 2.95-3.05 (2H, m), 4.42 (2H, d, J=6.1 Hz), 5.75 (1H, s), 6.98-7.03 (3H, m), 7.08 (2H, d, J=8.6 Hz), 7.14 (1H, dddd, J=9.2, 9.2, 2.3, 2.3 Hz), 7.28 (2H, d, J=8.6 Hz), 7.99 (1H, br), 8.37 (1H, s), 8.77 (1H, s), 9.05 (1H, brt, J=6.1 Hz).

Example 230

Preparation of 6-{[4-(4-aminopiperidino)phenyl]amino}-4-[(3,5-difluorobenzyl)amino]pyridine-3-carboxyamide

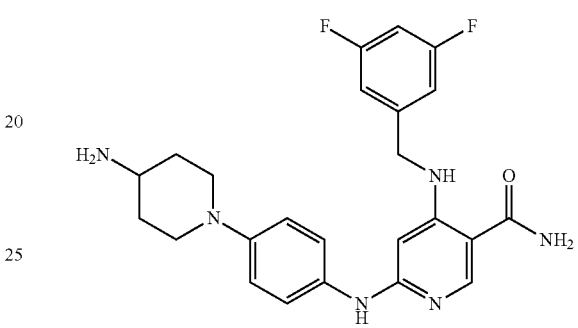

From 4-[(3,5-difluorobenzyl)amino]-6-[(4-{4-[(trifluoroacetyl)amino]piperidino}phenyl)amino]pyridine-3-carboxyamide (the compound of Example 217) in a manner similar to Example 226, the title compound was obtained as a white solid (yield 81%).

¹H-NMR (400 MHz, CDCl₃+CD₃OD) δ: 1.27-1.39 (2H, m), 1.79-1.87 (2H, m), 2.68-2.78 (2H, m), 3.06-3.14 (2H, m), 4.38 (2H, d, J=5.9 Hz), 4.56-4.66 (1H, m), 5.81 (1H, s), 6.72-6.79 (1H, m), 6.81-6.88 (2H, m), 6.98 (2H, d, J=8.8 Hz), 7.04 (2H, d, J=8.8 Hz), 8.25 (1H, s), 9.08 (1H, brt, J=5.9 Hz).

Example 231

Preparation of 6-({4-[(2-aminoethyl)amino]phenyl}amino)-4-[(3,5-difluorobenzyl)amino]pyridine-3-carboxyamide

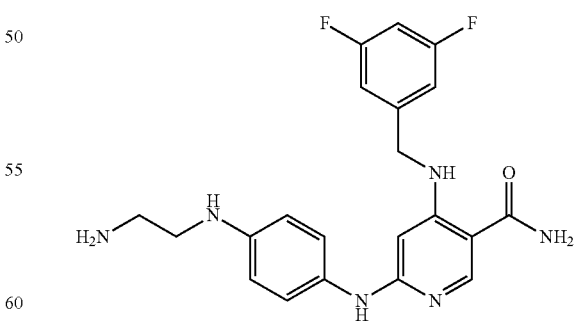

From 4-[(3,5-difluorobenzyl)amino]-6-{[(4-{2-[(trifluoroacetyl)amino]ethyl}amino)phenyl]amino}pyridine-3-carboxyamide (the compound of Example 218) in a manner similar to Example 226, the title compound was obtained as a light yellow solid (yield 74%).

¹H-NMR (400 MHz, CD₃OD) δ: 2.90 (2H, t, J=6.1 Hz), 3.22 (2H, t, J=6.1 Hz), 4.32 (2H, s), 5.54 (1H, s), 6.59 (2H, J=8.8 Hz), 6.79-6.88 (5H, m), 8.22 (1H, s).

Example 232

Preparation of 4-(benzylamino)-6-({4-[(3-cyanopropyl)amino]phenyl}amino)pyridine-3-carboxyamide

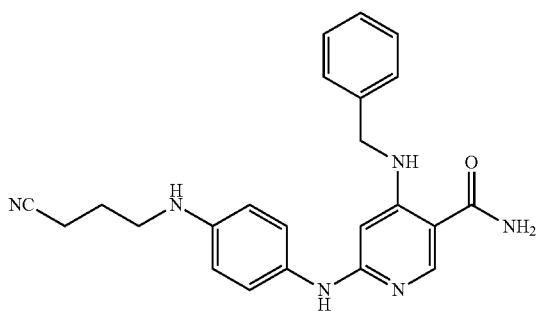 [SMILES: N#CCCCNc1ccc(Nc2cc(NCc3ccccc3)c(C(N)=O)cn2)cc1]

99 mg of 6-[(4-aminophenyl)amino]-4-(benzylamino)pyridine-3-carboxyamide (the compound of Example 65) and 44 mg of 4-bromobutyronitrile were added to 0.2 mL of N,N-dimethylformamide, and stirred at 70° C. for 1.5 hour. To the reaction mixture, saturated sodium bicarbonate in water was added, extracted with ethyl acetate, the extract was washed with saturated saline, and dried on anhydrous sodium sulfate. The solvent was evaporated, and the residue was purified by silica gel thin layer chromatography (chloroform:methanol=5:1) to obtain 59 mg (50%) of the title compound as a light brown powder.

¹H-NMR (400 MHz, CDCl₃) δ: 1.96-2.02 (2H, m), 2.51 (2H, dd, J=7.1, 7.1 Hz), 3.32 (2H, dd, J=6.6, 6.6 Hz), 4.29 (2H, d, J=5.6 Hz), 5.67 (1H, s), 6.52 (2H, d, J=9.0 Hz), 6.86 (2H, d, J=9.0 Hz), 7.24-7.35 (5H, m), 8.20 (1H, s), 8.88 (1H, br).

IR (ATR): 2359, 1610, 1516, 1411, 1355, 1259 cm⁻¹.

Example 233

Preparation of 4-[(3,5-difluorobenzyl)amino]-6-({4-[(2-methoxyethyl)amino]phenyl}amino)pyridine-3-carboxyamide

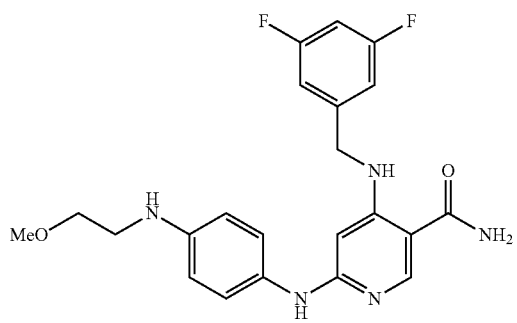 [SMILES: COCCNc1ccc(Nc2cc(NCc3cc(F)cc(F)c3)c(C(N)=O)cn2)cc1]

37 mg of 6-[(4-aminophenyl)amino]-4-[(3,5-difluorobenzyl)amino]pyridine-3-carboxyamide (the compound of Example 67) and 14 mg of 2-bromoethyl methylether were dissolved in 0.3 mL of N,N-dimethylformamide, and stirred using a microwave reaction apparatus under an argon atmosphere at 120° C. for 20 minutes. After cooling, water was added to the reaction mixture, extracted with ethyl acetate, the extract was washed with saturated saline, and dried on anhydrous sodium sulfate. The solvent was evaporated, and the residue was purified by silica gel thin layer chromatography (chloroform:methanol=20:1, developed twice) to obtain 13 mg (yield: 29%) of the title compound as a light yellow solid.

¹H-NMR (270 MHz, CD₃OD) δ: 3.26 (2H, t, J=5.6 Hz), 3.39 (3H, s), 3.57 (2H, t, J=5.6 Hz), 4.32 (2H, s), 5.55 (1H, s), 6.57 (1H, s), 6.60 (1H, s), 6.80-6.87 (5H, m), 8.21 (1H, s).

Example 234

Preparation of 4-[(3,5-difluorobenzyl)amino]-6-({4-[(2-hydroxyethyl)amino]phenyl}amino)pyridine-3-carboxyamide

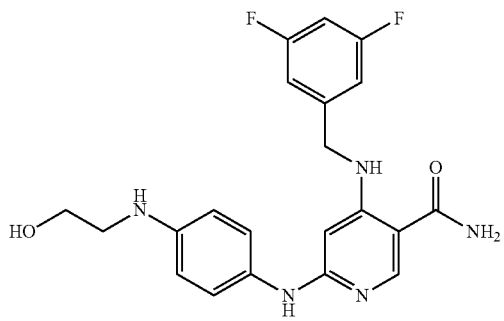 [SMILES: NC(=O)c1cnc(Nc2ccc(NCCO)cc2)cc1NCc1cc(F)cc(F)c1]

From 6-[(4-aminophenyl)amino]-4-[(3,5-difluorobenzyl)amino]pyridine-3-carboxyamide (the compound of Example 67) and 2-bromoethanol in a manner similar to Example 233, the title compound was obtained as a light brown solid (yield 20%).

¹H-NMR (270 MHz, CD₃OD) δ: 3.21 (2H, t, J=5.8 Hz), 3.73 (3H, t, J=5.8 Hz), 4.32 (2H, s), 5.54 (1H, s), 6.56 (1H, s), 6.60 (1H, s), 6.78-6.87 (5H, m), 8.21 (1H, s).

Example 235

Preparation of 6-[(4-{4-[2-(diethylamino)ethyl]piperazin-1-yl}phenyl)amino]-4-[(3-nitrobenzyl)amino]pyridine-3-carboxyamide

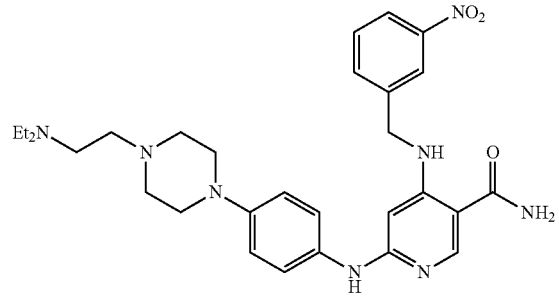

40 mg of 4-[(3-nitrobenzyl)amino]-6-{[4-(piperazin-1-yl)phenyl]amino}pyridine-3-carboxyamide (the compound of Example 224) was dissolved in 0.3 mL of N,N-dimethylformamide, to which 18.5 mg of 2-chloro-N,N-diethylethylamine hydrochloride and 25 mg of potassium carbonate were added, and stirred at room temperature for 3 hours. Water was added to the reaction mixture, extracted with chloroform, the extract was washed with saturated saline, and dried on anhydrous sodium sulfate. The solvent was evaporated, and the residue was purified by silica gel thin layer chromatography (chloroform:ammonia methanol=10:1) to obtain 43 mg (88%) of the title compound as an orange crystalline powder. m.p. 165-166° C.

$^1$H-NMR (400 MHz, CDCl$_3$) δ: 1.05 (6H, t, J=7.2 Hz), 2.52-2.68 (12H, m), 3.14-3.19 (4H, m), 4.39 (2H, d, J=5.6 Hz), 5.58 (1H, s), 5.69 (2H, br), 6.58 (1H, brs), 6.75 (2H, d, J=8.8 Hz), 6.86 (2H, d, J=8.8 Hz), 7.49 (1H, dd, J=7.9, 7.9 Hz), 7.59 (1H, brd, J=7.9 Hz), 8.10 (1H, brs), 8.14 (1H, brd, J=7.9 Hz), 8.20 (1H, s), 9.03 (1H, brt, J=5.6 Hz).

IR (ATR): 1639, 1602, 1571, 1550, 1528, 1515, 1408, 1346, 1299, 1238 cm$^{-1}$.

MS: m/z 547 (M$^+$+1), 86 (base peak).

Example 236

Preparation of 4-(benzylamino)-6-[(4-{4-[2-(diethylamino) ethyl]piperazin-1-yl}phenyl)amino]pyridine-3-carboxyamide

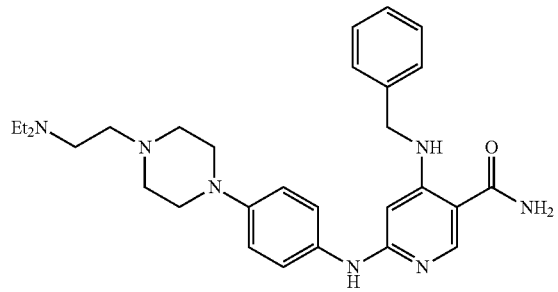

From 4-(benzylamino)-6-{[4-piperazin-1-yl]phenyl}amino)pyridine-3-carboxyamide (the compound of Example 219) and 2-chloro-N,N-diethylethylamine hydrochloride in a manner similar to Example 235, the title compound was obtained as a white powder (yield 68%).

$^1$H-NMR (400 MHz, CDCl$_3$) δ: 1.05-1.08 (6H, t, J=7.1 Hz), 2.56-2.69 (12H, m), 3.09-3.12 (4H, t, J=4.9 Hz), 3.17-3.19 (4H, t, J=4.9 Hz), 4.30 (2H, d, J=5.6 Hz), 5.53 (2H, s), 5.73 (1H, s), 6.36 (1H, s), 6.80 (2H, d, J=8.8 Hz), 6.91 (2H, d, J=8.8 Hz), 7.24-7.35 (5H, m), 8.18 (1H, s), 8.86 (1H, t, J=5.2 Hz).

IR (ATR): 3334, 2821, 1620, 1570, 1514, 1410, 1295, 1233, 1027 cm$^{-1}$.

Example 237

Preparation of 6-[(4-{4-[2-(diethylamino)ethyl]piperazin-1-yl}phenyl)amino]-4-[(2,3-difluorobenzyl)amino]pyridine-3-carboxyamide

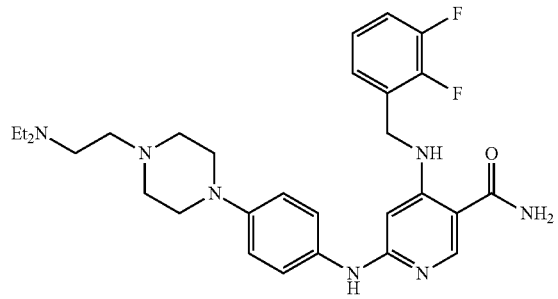

120 mg of 4-[(2,3-difluorobenzyl)amino]-6-{[4-(piperazin-1-yl)phenyl]amino}pyridine-3-carboxyamide (the compound of Example 220), 72 mg of 2-bromoethyl-N,N-diethylamine.hydrobromide and 72 mg of potassium carbonate were added to 2 mL of N,N-diethylformamide, and stirred at 70° C. for 1.5 hour. The solvent was evaporated, and the residue was dissolved in chloroform, washed with saturated saline, and dried on anhydrous sodium sulfate. The solvent was evaporated, and the residue was purified by silica gel thin layer chromatography (chloroform:ammonia methanol=10:1) to obtain 74 mg (60%) of the title compound as a light brown powder.

$^1$H-NMR (400 MHz, CDCl$_3$) δ: 1.05 (6H, dd, J=7.1, 7.1 Hz), 2.50-2.70 (12H, m), 3.18-3.21 (2H, m), 4.37 (2H, d, J=5.9 Hz), 5.68 (1H, s), 6.84 (2H, d, J=9.0 Hz), 6.94 (2H, d, J=9.0 Hz), 7.02-7.10 (3H, m), 8.18 (1H, s), 8.88 (1H, br).

IR (ATR): 1654, 1619, 1514, 1408, 1233, 820 cm$^{-1}$.

Example 238

Preparation of 6-[(4-{4-[2-(diethylamino)ethyl]piperazin-1-yl}phenyl)amino]-4-[(3,5-difluorobenzyl)amino]pyridine-3-carboxyamide

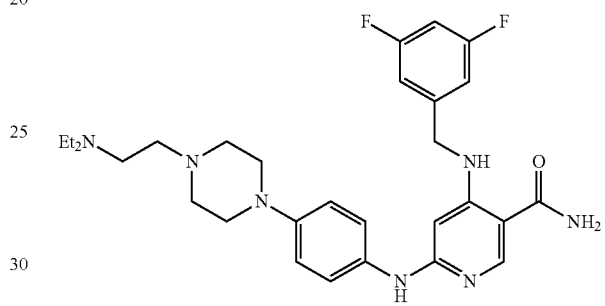

From 4-[(3,5-difluorobenzyl)amino]-6-{[4-(piperazin-1-yl)phenyl]amino}pyridine-3-carboxyamide (the compound of Example 221) and 2-bromoethyl-N,N-diethylamine.hydrobromide in a manner similar to Example 237, the title compound was obtained as a light brown solid (yield 40%).

$^1$H-NMR (400 MHz, CDCl$_3$) δ: 1.05 (6H, t, J=7.2 Hz), 2.52-2.69 (8H, m), 2.58 (4H, q, J=7.2 Hz), 3.17-3.21 (4H, m), 4.27 (2H, d, J=6.1 Hz), 5.59 (3H, brs), 6.43 (1H, brs), 6.73 (1H, dddd, J=8.8, 8.8, 2.3, 2.3 Hz), 6.76-6.79 (2H, m), 6.82 (2H, d, J=8.8 Hz), 6.86 (2H, d, J=8.8 Hz), 8.19 (1H, s), 8.95 (1H, brt, J=6.1 Hz).

IR (ATR): 1642, 1601, 1571, 1515, 1457, 1409, 1298, 1236, 1117 cm$^{-1}$.

MS: m/z 537 (M$^+$), 86 (base peak).

Example 239

Preparation of 6-[(3-{4-[2-(diethylamino)ethyl]piperazin-1-yl}phenyl)amino]-4-[(3,5-difluorobenzyl)amino]pyridine-3-carboxyamide

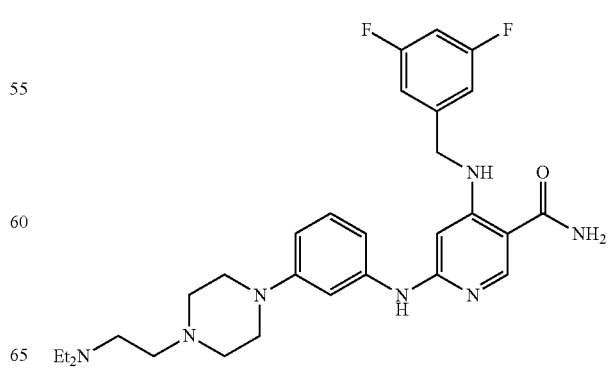

From 4-[(3,5-difluorobenzyl)amino]-6-{[3-(piperazin-1-yl)phenyl]amino}pyridine-3-carboxyamide (the compound of Example 225) and 2-bromoethyl-N,N-diethylamine.hydrobromide in a manner similar to Example 237, the title compound was obtained as a light yellow amorphous substance (yield 45%).

$^1$H-NMR (400 MHz, CDCl$_3$) δ: 1.06 (6H, t, J=7.2 Hz), 2.51-2.67 (12H, m), 3.13-3.18 (4H, m), 4.31 (2H, d, J=6.0 Hz), 5.78 (2H, br), 5.83 (1H, s), 6.41-6.45 (1H, m), 6.62-6.66 (2H, m), 6.68-6.74 (1H, m), 6.76-6.83 (2H, m), 6.92 (1H, brs), 7.07-7.12 (1H, m), 8.24 (1H, s), 8.97 (1H, brt, J=6.0 Hz).

IR (ATR): 1654, 1612, 1597, 1573, 1494, 1458, 1408, 1302, 1234, 1117 cm$^{-1}$.

Example 240

Preparation of 6-({4-[4-(2-cyanoethyl)piperazin-1-yl]phenyl}amino)-4-[(3,5-difluorobenzyl)amino]pyridine-3-carboxyamide

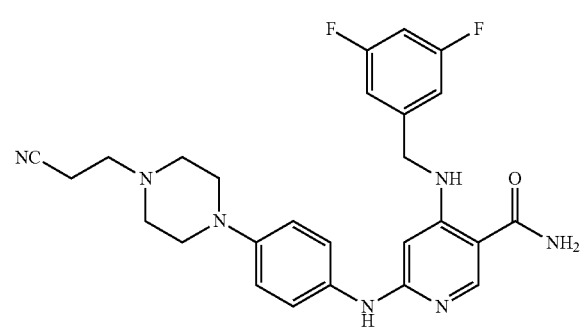 [SMILES: N#CCCN1CCN(c2ccc(Nc3cc(NCc4cc(F)cc(F)c4)c(C(N)=O)cn3)cc2)CC1]

60 mg of 4-[(3,5-difluorobenzyl)amino]-6-{[4-(piperazin-1-yl)phenyl]amino}pyridine-3-carboxyamide (the compound of Example 221) was dissolved in 0.6 mL of N,N-dimethylformamide, to which 45 mg of 3-bromopropionitrile and 57 mg of potassium carbonate were added, and stirred at 80° C. for 4 hours. After cooling, the solvent was evaporated, the residue was dissolved in chloroform, and the insoluble substances were filtered off. Chloroform was evaporated and the residue was purified by silica gel thin layer chromatography (chloroform:methanol=5:1) to obtain 52 mg (77%) of the title compound as a light yellow crystalline powder.

m.p. 192-194° C. (dec.)

$^1$H-NMR (400 MHz, CDCl$_3$) δ: 2.57 (2H, t, J=7.0 Hz), 2.67-2.71 (4H, m), 2.78 (2H, t, J=7.0 Hz), 3.17-3.22 (2H, m), 4.27 (2H, d, J=5.9 Hz), 5.58 (2H, br), 5.59 (1H, s), 6.41 (1H, brs), 6.69-6.80 (3H, m), 6.82 (2H, d, J=9.0 Hz), 6.87 (2H, d, J=9.0 Hz), 8.20 (1H, s), 8.97 (1H, brt, J=5.6 Hz).

IR (ATR): 1635, 1599, 1571, 1549, 1514, 1409, 1297, 1258, 1236, 1222, 1114 cm$^{-1}$.

Example 241

Preparation of 4-(benzyl)-6-({4-[4-(2-cyanoethyl)piperazin-1-yl]phenyl}amino)pyridine-3-carboxyamide

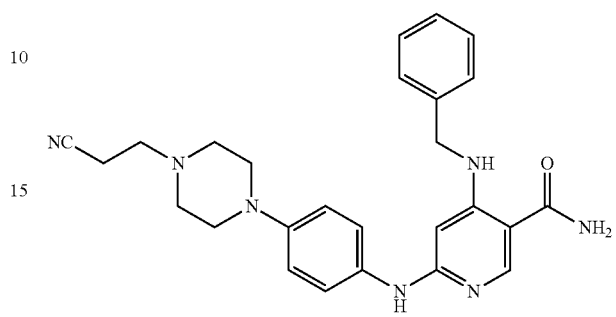

From 4-(benzylamino)-6-{[4-piperazin-1-yl]phenyl}amino)pyridine-3-carboxyamide (the compound of Example 219) in a manner similar to Example 240, the title compound was obtained as a slight yellow solid (yield 26%).

$^1$H-NMR (400 MHz, CDCl$_3$) δ: 2.55-2.59 (2H, t, J=7.0 Hz), 2.68-2.71 (4H, t, J=4.8 Hz), 2.76-2.79 (2H, t, J=7.2 Hz), 3.17-3.20 (4H, t, J=5.0 Hz), 4.30 (2H, d, J=5.2 Hz), 5.58 (2H, s), 5.74 (1H, s), 6.47 (1H, s), 6.80 (2H, d, J=8.8 Hz), 6.92 (2H, d, J=8.8 Hz), 7.25-7.35 (5H, m), 8.20 (1H, s), 8.88 (1H, brt, J=5.2 Hz).

IR (ATR): 3314, 1649, 1617, 1514, 1408, 1296, 1235 cm$^{-1}$.

Example 242

Preparation of 6-({4-[4-(3-cyanopropyl)piperazin-1-yl]phenyl}amino)-4-[(3-nitrobenzyl)amino]pyridine-3-carboxyamide

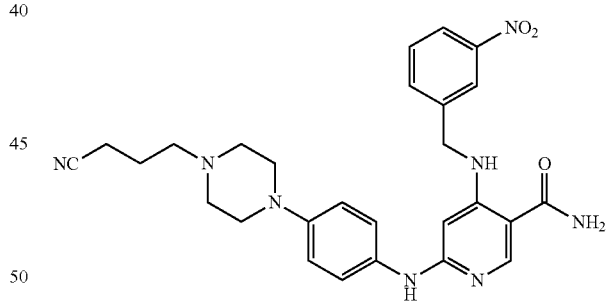

From 4-[(3-nitrobenzyl)amino]-6-{[4-(piperazin-1-yl)phenyl]amino}pyridine-3-carboxyamide (the compound of Example 224) and 4-bromobutyronitrile in a manner similar to Example 240, the title compound was obtained as an orange crystalline powder (yield 59%).

m.p. 190-191° C. (dec.)

$^1$H-NMR (400 MHz, CDCl$_3$) δ: 1.84-1.93 (2H, m), 2.48 (2H, t, J=7.1 Hz), 2.54 (2H, t, J=6.7 Hz), 2.60-2.64 (4H, m), 3.13-3.17 (4H, m), 4.40 (2H, d, J=5.9 Hz), 5.57 (1H, s), 6.75 (2H, d, J=9.0 Hz), 6.85 (2H, d, J=9.0 Hz), 7.51 (1H, dd, J=7.8, 7.8 Hz), 7.61 (1H, brd, J=7.8 Hz), 8.09 (1H, brs), 8.14 (1H, brd, J=7.8 Hz), 8.19 (1H, s), 9.05 (1H, br).

IR (ATR): 1656, 1617, 1561, 1528, 1516, 1407, 1348, 1315, 1278, 1239, 1143 cm$^{-1}$.

MS (FAB): m/z 515 (M$^+$+1), 136 (base peak).

Example 243

Preparation of 4-(benzylamino)-6-({4-[4-(pyrimidin-2-yl)piperazin-1-yl]phenyl}amino)pyridine-3-carboxamide

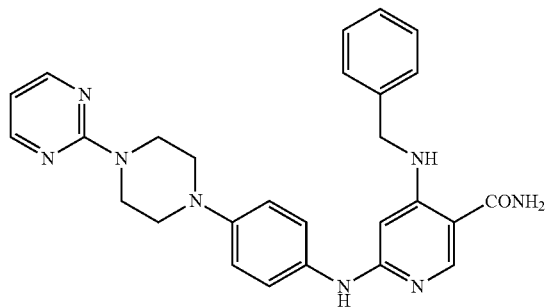 [SMILES: NC(=O)c1cnc(Nc2ccc(N3CCN(c4ncccn4)CC3)cc2)cc1NCc1ccccc1]

20 mg of 4-(benzylamino)-6-{4-[piperazin-1-yl]phenyl}amino)pyridine-3-carboxamide (the compound of Example 219) was dissolved in 1 mL of ethanol and 2 mL of tetrahydrofuran, to which 6.8 mg of 2-chloropyrimidine and 12.8 mg of diisopropylethylamine were added, and stirred at 80° C. for 6 hours. After cooling, saturated sodium bicarbonate in water was added to the reaction mixture, extracted with chloroform-methanol (10:1), and the extract was dried on anhydrous sodium sulfate. The solvent was evaporated and the residue was purified by silica gel thin layer chromatography (chloroform:methanol=10:1) to obtain 12 mg (50%) of the title compound as a white solid.

$^1$H-NMR (400 MHz, CDCl$_3$) δ: 3.21-3.23 (4H, t, J=5.1 Hz), 3.99-4.02 (4H, t, J=5.3 Hz), 4.31 (2H, d, J=5.6 Hz), 5.53 (2H, s), 5.76 (1H, s), 6.46 (1H, s), 6.52-6.54 (1H, t, J=4.6 Hz), 6.85 (2H, d, J=8.8 Hz), 6.94 (2H, d, J=8.8 Hz), 7.20-7.37 (5H, m), 8.19 (1H, s), 8.35 (2H, d, J=4.6 Hz), 8.86 (1H, brt, J=5.6 Hz).

IR (ATR): 3328, 1715, 1654, 1619, 1585, 1510, 1446, 1408, 1363, 1244, 1041 cm$^{-1}$.

Example 244

Preparation of 4-(benzylamino)-6-{[4-(4-methyl-1,4-diazepan-1-yl)phenyl]amino}pyridine-3-carboxamide

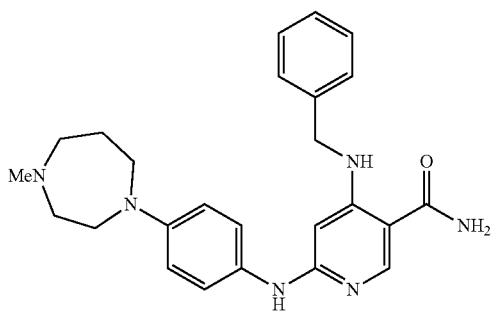 [SMILES: CN1CCCN(c2ccc(Nc3cc(NCc4ccccc4)c(C(N)=O)cn3)cc2)CC1]

25 mg of 4-(benzylamino)-6-{[4-(1,4-diazepan-1-yl)phenyl]amino}pyridine-3-carboxamide (the compound of Example 226) was dissolved in 0.3 mL of N,N-dimethylformamide, to which, under ice cooling, 10 mg of potassium carbonate and 4.3 mg of iodomethane were added, and stirred at the same temperature for 30 minutes and at room temperature for further 30 minutes. To the reaction mixture, chloroform was added, and the insoluble substances were filtered off. The solvent was evaporated and the residue was purified by silica gel thin layer chromatography (chloroform:ammonia methanol=10:1) to obtain 9 mg (35%) of the title compound as a light brown solid.

$^1$H-NMR (400 MHz, CDCl$_3$) δ: 1.99-2.06 (2H, m), 2.40 (3H, s), 2.56-2.61 (2H, m), 2.70-2.74 (2H, m), 3.46-3.51 (2H, m), 3.55-3.59 (2H, m), 4.28 (2H, d, J=5.6 Hz), 5.57 (2H, br), 5.68 (1H, s), 6.40 (1H, brs), 6.57 (2H, d, J=9.0 Hz), 6.88 (2H, d, J=9.0 Hz), 7.23-7.34 (6H, m), 8.17 (1H, s), 8.83 (1H, br).

IR (ATR): 1609, 1568, 1546, 1515, 1412, 1356, 1304, 1260, 1201 cm$^{-1}$.

MS: m/z 431 (M$^+$+1), 176 (base peak).

Example 245

Preparation of 4-(benzylamino)-6-({4-[4-(2-hydroxyethyl)-1,4-diazepan-1-yl]phenyl}amino)pyridine-3-carboxyamide

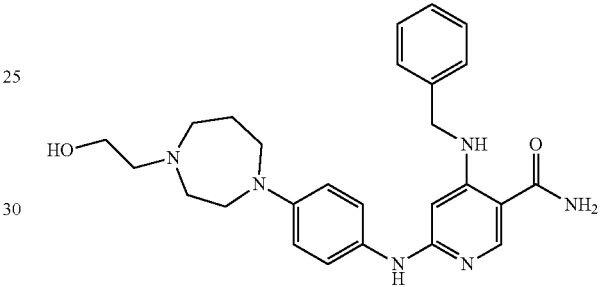

From 4-(benzylamino)-6-{[4-(1,4-diazepan-1-yl)phenyl]amino}pyridine-3-carboxamide (the compound of Example 226) and 2-bromoethanol in a manner similar to Example 244, the title compound was obtained as light yellow needle crystals (yield 90%).

m.p. 165-167° C.

$^1$H-NMR (400 MHz, CDCl$_3$) δ: 1.86-2.10 (2H, m), 2.66-2.73 (4H, m), 2.85-2.89 (2H, m), 3.49-3.59 (6H, m), 4.27 (2H, d, J=5.4 Hz), 5.68 (1H, s), 6.58 (2H, d, J=9.0 Hz), 6.88 (2H, d, J=9.0 Hz), 7.20-7.36 (6H, m), 8.14 (1H, s), 8.80-8.90 (1H, m).

MS (FAB): m/z 461 (M$^+$+1), 136 (base peak).

Example 246

Preparation of 4-[(3,5-difluorobenzyl)amino]-6-({4-[4-(propan-2-yl)-1,4-diazepan-1-yl]phenyl}amino)pyridine-3-carboxamide

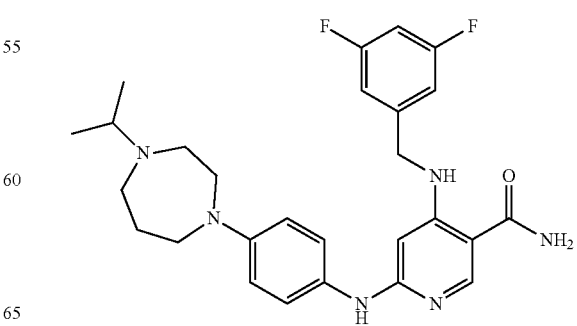

60 mg of 6-{[4-(1,4-diazepan-1-yl)phenyl]amino}-4-[(3,5-difluorobenzyl)amino]pyridine-3-carboxyamide (the compound of Example 227) was suspended in 1.5 mL of chloroform, to which 0.2 mL of acetone, 4.1 mg of acetic acid and 58 mg of sodium triacetoxyborohydride were added, and stirred at room temperature for 4 hours. To the reaction mixture, saturated sodium bicarbonate in water was added, extracted with chloroform, and the extract was dried on anhydrous sodium sulfate. The solvent was evaporated, and the residue was purified by silica gel thin layer chromatography (chloroform:ammonia methanol=20:1), recrystallized from methanol-ether to obtain 37 mg (53%) of the title compound as a white crystalline powder.

m.p. 167-168° C.

$^1$H-NMR (400 MHz, CDCl$_3$) δ: 1.02 (6H, d, J=6.3 Hz), 1.87-1.96 (2H, m), 2.54-2.61 (2H, m), 2.74-2.79 (2H, m), 2.94 (1H, sept, J=6.3 Hz), 3.47-3.55 (4H, m), 4.24 (2H, d, J=5.8 Hz), 5.53 (1H, s), 5.81 (2H, br), 6.57 (2H, d, J=9.0 Hz), 6.66-6.84 (6H, m), 8.17 (1H, s), 8.93 (1H, brt, J=5.8 Hz).

IR (ATR): 1653, 1619, 1566, 1517, 1403, 1350, 1310, 1256, 1116 cm$^{-1}$.

MS: m/z 495 (M$^+$+1).

Example 247

Preparation of 6-[(4-{4-[2-(tert-butoxycarbonyl)aminoethyl]piperazin-1-yl}phenyl)amino]-4-[(3,5-difluorobenzyl)amino]pyridine-3-carboxyamide

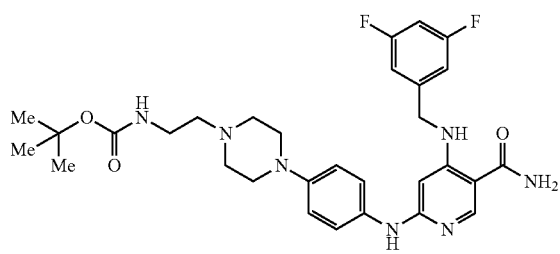 [SMILES: CC(C)(C)OC(=O)NCCN1CCN(c2ccc(Nc3cc(NCc4cc(F)cc(F)c4)c(C(N)=O)cn3)cc2)CC1]

20 mg of 4-[(3,5-difluorobenzyl)amino]-6-{[4-(piperazin-1-yl)phenyl]amino}pyridine-3-carboxyamide (the compound of Example 221) was dissolved in 0.5 mL of chloroform, to which 1.4 mg of acetic acid, 15 mg of sodium triacetoxyborohydride and 8.7 mg of N-Boc-2-aminoacetaldehyde were added, and stirred overnight at room temperature. The reaction mixture was washed with water and saturated saline, and dried on anhydrous sodium sulfate. The solvent was evaporated, and the residue was purified by silica gel thin layer chromatography (chloroform:methanol=5:1) to obtain 19 mg (71%) of the title compound as a light yellow solid.

$^1$H-NMR (400 MHz, DMSO-d6) δ: 1.39 (9H, s), 2.99-3.40 (12H, m), 4.40 (2H, t, J=5.8 Hz), 5.67 (1H, s), 6.83 (2H, d, J=8.8 Hz), 6.99 (2H, d, J=8.8 Hz), 7.14 (1H, dddd, J=9.3, 9.3, 2.4, 2.4 Hz), 7.18-7.25 (2H, m), 8.34 (1H, s), 8.68 (1H, brs), 9.08 (1H, brt, J=5.8 Hz).

Example 248

Preparation of 6-({4-{4-(2-aminoethyl)piperazin-1-yl]phenyl}amino]-4-[(3,5-difluorobenzyl)amino]pyridine-3-carboxyamide

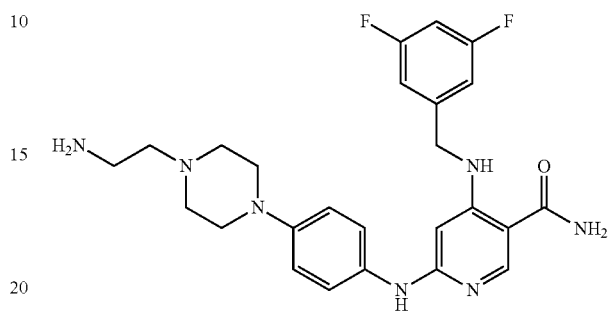

18 mg of 6-[(4-{4-[2-(tert-butoxycarbonyl)aminoethyl]piperazin-1-yl}phenyl)amino]-4-[(3,5-difluorobenzyl)amino]pyridine-3-carboxyamide (the compound of Example 247) was dissolved in 0.5 mL of chloroform, to which, under ice cooling, 0.5 mL of 4 mol/L hydrochloric acid-ethyl acetate was added, and stirred at room temperature for 2 hours. The solvent was evaporated and the residue was purified by silica gel thin layer chromatography (chloroform: ammonia methanol=10:1) to obtain 15 mg (95%) of the title compound as a slight yellow crystalline powder.

m.p. 190-194° C. (dec.)

$^1$H-NMR (400 MHz, CD$_3$OD) δ: 2.42 (3H, s), 2.57 (2H, t, J=6.8 Hz), 2.62-2.68 (4H, m), 2.74 (2H, t, J=6.8 Hz), 3.13-3.18 (4H, m), 4.34 (2H, s), 5.63 (1H, s), 6.81-6.89 (5H, m), 6.95 (2H, d, J=8.9 Hz), 8.25 (1H, s).

IR (ATR): 1603, 1572, 1547, 1515, 1453, 1410, 1298, 1235, 1116 cm$^{-1}$.

MS (FAB): m/z 496(M+H)$^+$.

Example 249

Preparation of 4-[(3,5-difluorobenzyl)amino]-6-{[4-(4-{2-[(methylsulfonyl)amino]ethyl}piperazin-1-yl)phenyl]amino}pyridine-3-carboxyamide

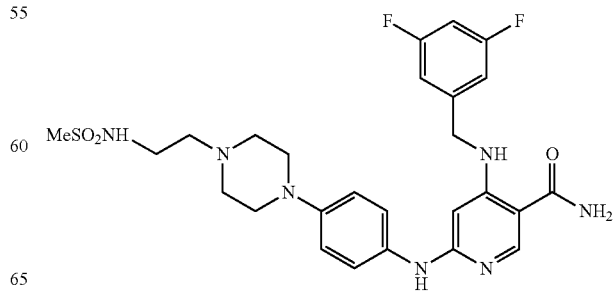

60 mg of 6-({4-[4-(2-aminoethyl)piperazin-1-yl]phenyl}amino)-4-[(3,5-difluorobenzyl)amino]pyridine-3-carboxyamide (the compound of Example 248) was suspended in 6 mL of chloroform, to which, under ice cooling, 20 mg of pyridine and 17 mg of methanesulfonyl chloride were added, and stirred at the same temperature for 20 minutes. To the reaction mixture, ammonia water was added, extracted with chloroform, the extract was washed with saturated saline, and dried on anhydrous sodium sulfate. The solvent was evaporated, and the residue was purified by silica gel thin layer chromatography (chloroform:methanol=5:1), recrystallized from chloroform-methanol-ether to obtain 40 mg (57%) of the title compound as a slight yellow crystalline powder.

m.p. 216-219° C. (dec.)

$^1$H-NMR (400 MHz, CDCl$_3$+CD$_3$OD) δ: 2.61-2.69 (6H, m), 3.00 (3H, s), 3.16-3.21 (4H, m), 3.26 (2H, t, J=5.7 Hz), 4.27 (2H, d, J=5.7 Hz), 5.59 (1H, s), 6.70-6.80 (3H, m), 6.82 (2H, d, J=9.0 Hz), 6.86 (2H, d, J=9.0 Hz), 8.17 (1H, s), 9.00 (1H, brt, J=5.7 Hz).

IR (ATR): 1626, 1602, 1572, 1515, 1411, 1312, 1301, 1259, 1239, 1146, 1118 cm$^{-1}$.

MS: m/z 559 (M$^+$).

Example 250

Preparation of 6-({4-[4-(2-chloroethyl)piperazin-1-yl]phenyl}amino)-4-[(3,5-difluorobenzyl)amino]pyridine-3-carboxyamide

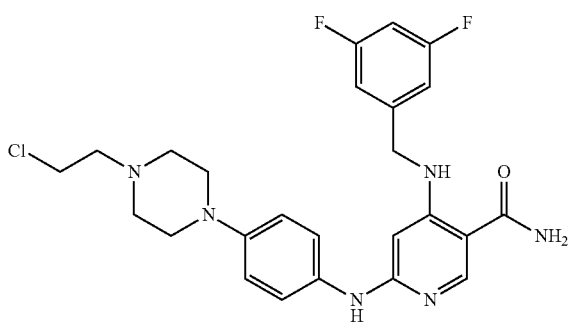 [SMILES: NC(=O)c1cnc(Nc2ccc(N3CCN(CCCl)CC3)cc2)cc1NCc1cc(F)cc(F)c1]

From 4-[(3,5-difluorobenzyl)amino]-6-{[4-(piperazin-1-yl)phenyl]amino}pyridine-3-carboxyamide (the compound of Example 221) and 1-bromo-2-chloroethane in a manner similar to Example 244, the title compound was obtained as a slight yellow solid (yield 31%).

$^1$H-NMR (400 MHz, CDCl$_3$+CD$_3$OD) δ: 2.69-2.75 (4H, m), 2.82 (2H, t, J=6.9 Hz), 3.17-3.23 (4H, m), 3.66 (2H, t, J=6.9 Hz), 4.27 (2H, d, J=5.6 Hz), 5.59 (1H, s), 6.69-6.87 (7H, m), 8.16 (1H, s), 9.01 (1H, brt, J=5.6 Hz).

Example 251

Preparation of 4-[(3,5-difluorobenzyl)amino]-6-[(4-{4-[2-(methylamino)ethyl]piperazin-1-yl}phenyl)amino]pyridine-3-carboxyamide

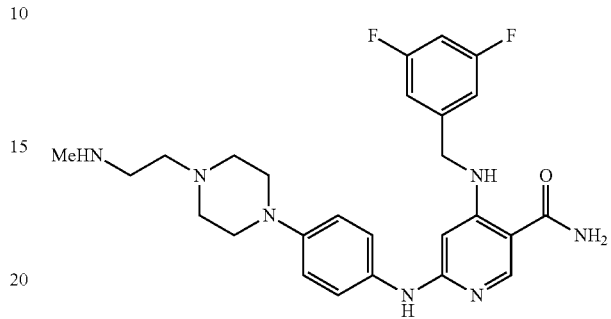

42 mg of 6-({4-[4-(2-chloroethyl)piperazin-1-yl]phenyl}amino)-4-[(3,5-difluorobenzyl)amino]pyridine-3-carboxyamide (the compound of Example 250) was dissolved in a 30% methylamine-ethanol solution, to which 23 mg of potassium carbonate was added, and stirred at 80° C. for 8 hours. After cooling, water was added to the reaction mixture, extracted with chloroform, the extract was washed with saturated saline, and dried on anhydrous sodium sulfate. The solvent was evaporated and the residue was purified by silica gel thin layer chromatography (chloroform:ammonia methanol=10:1), and crystallized by adding ether to obtain 8 mg (15%) of the title compound as a slight yellow solid.

m.p. 113-120° C. (dec.)

$^1$H-NMR (400 MHz, CD$_3$OD) δ: 2.42 (3H, s), 2.57 (2H, t, J=6.8 Hz), 2.62-2.68 (4H, m), 2.74 (2H, t, J=6.8 Hz), 3.13-3.18 (4H, m), 4.34 (2H, s), 5.63 (1H, s), 6.81-6.89 (5H, m), 6.95 (2H, d, J=8.9 Hz), 8.25 (1H, s).

IR (ATR): 1603, 1572, 1547, 1515, 1453, 1410, 1298, 1235, 1116 cm$^{-1}$.

MS: m/z 496(M+H)$^+$

Example 252

Preparation of 6-[(4-{4-[3-(tert-butoxycarbonyl)aminopropyl]piperazin-1-yl}phenyl)amino]-4-[(3,5-difluorobenzyl)amino]pyridine-3-carboxyamide

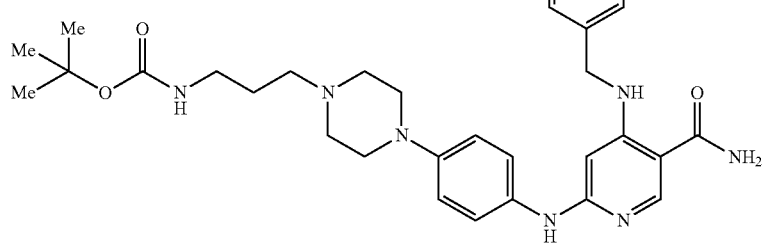

From 4-[(3,5-difluorobenzyl)amino]-6-{[4-(piperazin-1-yl)phenyl]amino}pyridine-3-carboxamide (the compound of Example 221) and 3-(Boc-amino)propylbromide in a manner similar to Example 244, the title compound was obtained as light yellow solid (yield 87%).

$^1$H-NMR (400 MHz, CDCl$_3$+CD$_3$OD) δ: 1.44 (9H, s), 1.68-1.77 (2H, m), 2.48 (2H, t, J=6.8 Hz), 2.60-2.66 (4H, m), 3.16-3.26 (6H, m), 4.27 (2H, d, J=5.6 Hz), 5.53 (1H, s), 6.69-6.86 (3H, m), 6.82 (2H, d, J=9.0 Hz), 6.86 (2H, d, J=9.0 Hz), 8.18 (1H, s), 8.98 (1H, brt, J=5.6 Hz).

Example 253

Preparation of 6-({4-[4-(3-aminopropyl)piperazin-1-yl]phenyl}amino)-4-[(3,5-difluorobenzyl)amino]pyridine-3-carboxyamide

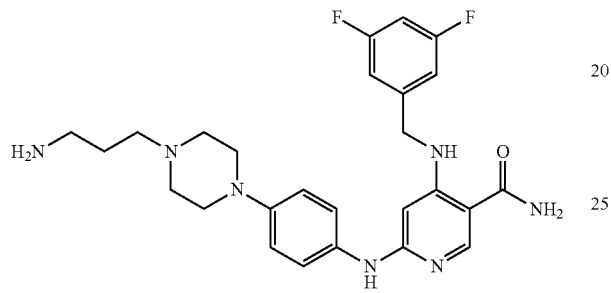

From 6-[(4-{4-[3-(tert-butoxycarbonyl)aminopropyl]piperazin-1-yl}phenyl)amino]-4-[(3,5-difluorobenzyl)amino]pyridine-3-carboxyamide (the compound of Example 252) in a manner similar to Example 248, the title compound was obtained as a slight brown crystalline powder (yield 79%).

m.p. 192-194° C. (dec.)

$^1$H-NMR (400 MHz, CDCl$_3$) δ: 1.68-1.75 (2H, m), 2.48 (2H, t, J=7.4 Hz), 2.61-2.66 (4H, m), 2.79 (2H, d, J=6.8 Hz), 3.16-3.22 (4H, m), 4.26 (2H, d, J=5.6 Hz), 5.59 (1H, s), 5.75 (2H, br), 6.60 (1H, brs), 6.69-6.80 (3H, m), 6.82 (2H, d, J=9.0 Hz), 6.86 (2H, d, J=9.0 Hz), 8.19 (1H, s), 8.96 (1H, brt, J=5.6 Hz).

IR (ATR): 1624, 1602, 1571, 1549, 1514, 1410, 1312, 1299, 1237, 1117 cm$^{-1}$.

MS: m/z 495 (M$^+$).

Example 254

Preparation of 4-(benzylamino)-6-[(4-{4-[(2-ethoxycarbonyl)ethyl]piperazin-1-yl}phenyl)amino]pyridine-3-carboxyamide

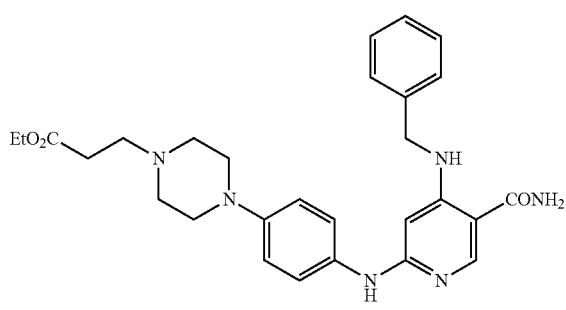 [SMILES: CCOC(=O)CCN1CCN(c2ccc(Nc3cc(NCc4ccccc4)c(C(N)=O)cn3)cc2)CC1]

From 4-(benzylamino)-6-{[4-piperazin-1-yl]phenyl}amino)pyridine-3-carboxyamide (the compound of Example 219) and 3-bromopropionic acid ethylester in a manner similar to Example 244, the title compound was obtained as a white solid (yield 72%).

$^1$H-NMR (400 MHz, CDCl$_3$) δ: 1.26-1.29 (3H, t, J=7.0 Hz), 2.53-2.57 (2H, t, J=7.2 Hz), 2.64-2.67 (4H, t, J=5.0 Hz), 2.76-2.80 (2H, t, J=7.4 Hz), 3.15-3.18 (4H, t, J=5.0 Hz), 4.14-4.19 (2H, q, J=7.2 Hz), 4.30 (2H, d, J=5.2 Hz), 5.52 (2H, s), 5.73 (1H, s), 6.37 (1H, s), 6.80 (2H, d, J=8.8 Hz), 6.91 (2H, d, J=8.8 Hz), 7.25-7.35 (5H, m), 8.18 (1H, s), 8.86 (1H, brt, J=6.0 Hz).

IR (ATR): 3178, 2819, 1732, 1606, 1514, 1411, 1297, 1236 cm$^{-1}$.

Example 255

Preparation of 6-{[4-(4-acetylpiperazin-1-yl)phenyl]amino}-4-(benzylamino)pyridine-3-carboxyamide and 6-{acetyl[4-(4-acetylpiperazin-1-yl)phenyl]amino}-4-(benzylamino)pyridine-3-carboxyamide

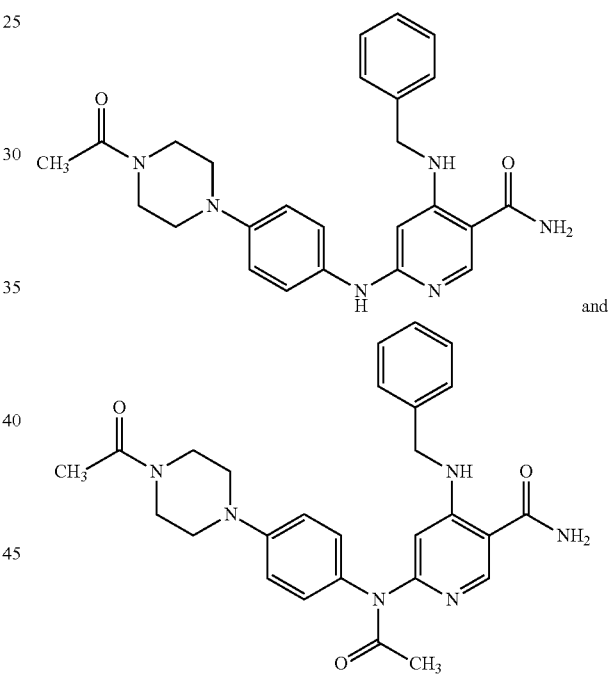

30 mg of 4-(benzylamino)-6-{[4-piperazin-1-yl]phenyl}amino)pyridine-3-carboxyamide (the compound of Example 219) was dissolved in 5 mL of methylene chloride, to which 20 mg of acetic anhydride was added at room temperature, and stirred at the same temperature for 30 minutes. To the reaction mixture, saturated sodium bicarbonate in water was added and stirred for 30 minutes, the organic layer was washed with water, and dried on anhydrous sodium sulfate. The solvent was evaporated and the residue was purified by silica gel thin layer chromatography (chloroform:methanol=10:1) to obtain 19 mg (57%) of 6-{[4-(4-acetylpiperazin-1-yl)phenyl]amino}-4-(benzylamino)pyridine-3-carboxyamide (Example 255-1) as a slight yellow crystalline powder, and 14 mg (39%) of 6-{acetyl[4-(4-acetylpiperazin-1-yl)phenyl]amino}-4-(benzylamino)pyridine-3-carboxyamide (Example 255-2) as a slight yellow crystalline powder.

6-{[4-(4-acetylpiperazin-1-yl)phenyl]amino}-4-(benzylamino)pyridine-3-carboxyamide Example 255-1

$^1$H-NMR (400 MHz, CDCl$_3$) δ: 2.16 (3H, s), 3.09-3.16 (4H, m), 3.62-3.66 (2H, m), 3.77-3.82 (2H, m), 4.31 (2H, d, J=5.8 Hz), 5.58 (2H, br), 5.75 (1H, s), 6.51 (1H, brs), 6.81 (2H, d, J=9.0 Hz), 6.94 (2H, d, J=9.0 Hz), 7.24-7.36 (5H, m), 8.19 (1H, s), 8.88 (1H, brt, J=5.8 Hz).
IR (ATR): 1652, 1647, 1622, 1569, 1517, 1444, 1409, 1231 cm$^{-1}$.

6-{acetyl[4-(4-acetylpiperazin-1-yl)phenyl]amino}-4-(benzylamino)pyridine-3-carboxyamide Example 255-2

$^1$H-NMR (400 MHz, CDCl$_3$) δ: 2.02 (3H, s), 2.14 (3H, s), 3.15-3.23 (4H, m), 3.60-3.64 (2H, m), 3.75-3.89 (2H, m), 4.40 (2H, d, J=5.6 Hz), 5.77 (2H, br), 6.72 (1H, s), 6.89 (2H, d, J=8.8 Hz), 7.09 (2H, d, J=8.8 Hz), 7.24-7.36 (5H, m), 8.33 (1H, s), 8.93 (1H, brt, J=5.6 Hz).
IR (ATR): 1731, 1677, 1649, 1570, 1515, 1374, 1267, 1234 cm$^{-1}$.

Example 256

Preparation of 6-{[4-(4-acetyl-1,4-diazepan-1-yl)phenyl]amino}-4-(benzylamino)pyridine-3-carboxyamide

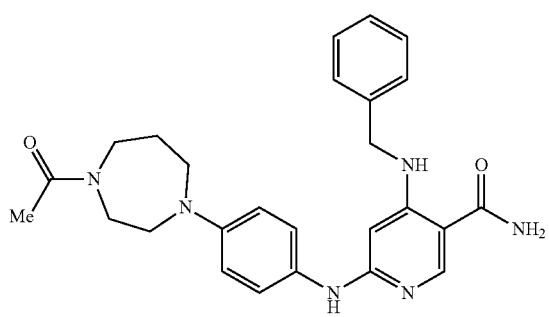 [SMILES: CC(=O)N1CCCN(c2ccc(Nc3cc(NCc4ccccc4)c(C(N)=O)cn3)cc2)CC1]

25 mg of 4-(benzylamino)-6-{[4-(1,4-diazepan-1-yl)phenyl]amino}pyridine-3-carboxyamide (the compound of Example 226) was dissolved in 1.5 mL of dichloromethane, to which, under ice cooling, 15.1 mg of acetic anhydride was added, and stirred for 30 minutes. To the reaction mixture 1.5 mL of ammonia water was added, extracted with chloroform, the extract was washed with saturated saline, and dried on anhydrous sodium sulfate. The solvent was evaporated, and the residue was purified by silica gel thin layer chromatography (chloroform:methanol=10:1), recrystallized from chloroform-methanol-diethylether to obtain 20 mg (73%) of the title compound as light brown needle crystals.
m.p. 224-227° C.
$^1$H-NMR (400 MHz, CDCl$_3$) δ: 1.97-2.12 (5H, m), 3.36-3.41 (1H, m), 3.44-3.49 (1H, m), 3.53-3.68 (5H, m), 3.75-3.79 (1H, m), 4.29 (2H, d, J=5.4 Hz), 5.62 (2H, br), 5.63-5.68 (1H, m), 6.50 (1H, brs), 6.56-6.61 (2H, m), 6.90 (2H, d, J=8.8 Hz), 7.22-7.35 (6H, m), 8.21 (1H, s), 8.89 (1H, br).
IR (ATR): 1671, 1618, 1567, 1515, 1410, 1390, 1361, 1333, 1258, 1218, 1181 cm$^{-1}$.
MS: m/z 459 (M$^+$+1), 154 (base peak).

Example 257

Preparation of 4-(benzylamino)-6-({4-[4-(ethoxycarbonyl) piperazin-1-yl]phenyl}amino)pyridine-3-carboxyamide

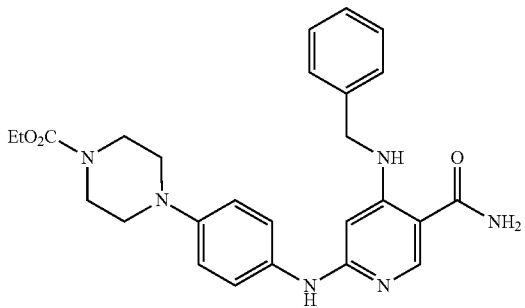 [SMILES: CCOC(=O)N1CCN(c2ccc(Nc3cc(NCc4ccccc4)c(C(N)=O)cn3)cc2)CC1]

20 mg of 4-(benzylamino)-6-{[4-piperazin-1-yl]phenyl}amino)pyridine-3-carboxyamide (the compound of Example 219) was dissolved in 3 mL of dichloromethane, to which 6.5 mg of ethyl chlorocarbonate and 7.9 mg of pyridine were added, and stirred overnight at room temperature. To the reaction mixture, saturated sodium bicarbonate in water was added, extracted with chloroform-methanol (10:1), and dried on anhydrous sodium sulfate. The solvent was evaporated, and the residue was purified by silica gel thin layer chromatography (chloroform:methanol=10:1) to obtain 17 mg (73%) of the title compound as a white solid.
$^1$H-NMR (400 MHz, CDCl$_3$) δ: 1.28-1.31 (3H, t, J=7.0 Hz), 2.53-2.57 (2H, t, J=7.2 Hz), 3.09-3.12 (4H, t, J=4.9 Hz), 3.64-3.67 (4H, t, J=5.0 Hz), 4.16-4.21 (2H, q, J=7.2 Hz), 4.31 (2H, d, J=5.6 Hz), 5.58 (2H, s), 5.75 (1H, s), 6.50 (1H, s), 6.81 (2H, d, J=8.8 Hz), 6.93 (2H, d, J=8.8 Hz), 7.25-7.35 (5H, m), 8.21 (1H, s), 8.89 (1H, brt, J=5.5 Hz).
IR (ATR): 1654, 1619, 1570, 1513, 1465, 1437, 1409, 1247, 1041 cm$^{-1}$.

Example 258

Preparation of 4-(benzylamino)-6-{[4-(4-butanoylpiperazin-1-yl)phenyl]amino}pyridine-3-carboxyamide

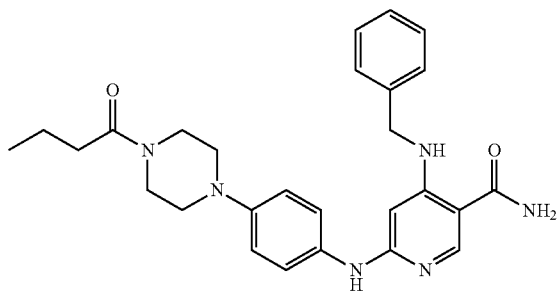 [SMILES: CCCC(=O)N1CCN(c2ccc(Nc3cc(NCc4ccccc4)c(C(N)=O)cn3)cc2)CC1]

35 mg of butanoic acid was dissolved in 0.5 mL of 1,4-dioxane, to which 46 mg of N-hydroxysuccinimide and 82 mg of N,N'-dicyclohexylcarbodiimide were added, and stirred at room temperature for 1 hour. The deposit was filtered off, and the solvent was evaporated to obtain 94 mg of butanoic acid 2,5-dioxopyrrolidin-1-yl ester crude product. The crude product was used in the next reaction without further purification.

30 mg of 4-(benzylamino)-6-{[4-piperazin-1-yl]phenyl}amino)pyridine-3-carboxyamide (the compound of Example 219) was dissolved in 4 mL of ethanol, to which 21 mg of butanoic acid 2,5-dioxopyrrolidin-1-yl ester and 15 mg of triethylamine were added, and stirred at room temperature for 2 days. The solvent was evaporated, and the residue was dissolved in chloroform, washed with saturated sodium bicarbonate in water and saturated saline, and dried on anhydrous sodium sulfate. The solvent was evaporated, and the residue was purified by silica gel thin layer chromatography (chloroform:methanol=7:1) to obtain 27 mg (77%) the title compound as a light yellow solid.

m.p. 233.5-235.2° C. (dec.)

$^1$H-NMR (400 MHz, CDCl$_3$) δ: 1.00 (3H, t, J=7.4 Hz), 1.66-1.76 (2H, m), 2.37 (2H, t, J=7.7 Hz), 3.09-3.16 (4H, m), 3.63-3.67 (2H, m), 3.76-3.82 (2H, m), 4.31 (2H, d, J=5.5 Hz), 5.58 (2H, br), 5.75 (1H, s), 6.48 (1H, brs), 6.81 (2H, d, J=8.8 Hz), 6.94 (2H, d, J=8.8 Hz), 7.24-7.36 (5H, m), 8.20 (1H, s), 8.89 (1H, brt, J=5.5 Hz).

IR (ATR): 1653, 1619, 1556, 1518, 1409, 1226, 1158, 1027 cm$^{-1}$.

MS: m/z 472 (M$^+$, base peak).

Example 259

Preparation of 4-(benzylamino)-6-({4-[4-(2-methylpropanoyl)piperazin-1-yl]phenyl}amino)pyridine-3-carboxyamide

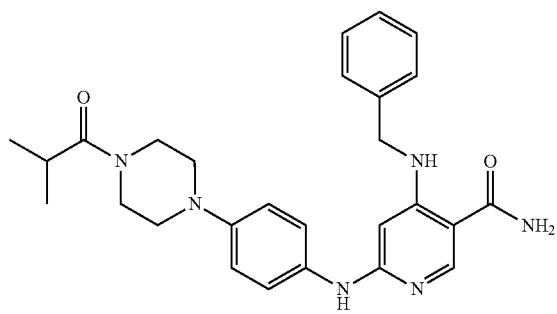 [SMILES: CC(C)C(=O)N1CCN(c2ccc(Nc3cc(NCc4ccccc4)c(C(N)=O)cn3)cc2)CC1]

From 2-methylpropionic acid and N-hydroxysuccinimide in a manner similar to Example 258, 2-methylpropionic acid 2,5-dioxopyrrolidin-1-yl ester was obtained. From 4-(benzylamino)-6-{[4-piperazin-1-yl]phenyl}amino)pyridine-3-carboxyamide (the compound of Example 219) and 2-methylpropionic acid 2,5-dioxopyrrolidin-1-yl ester, the title compound was obtained as a white crystalline powder (yield 76%).

m.p. 218-220° C. (dec.)

$^1$H-NMR (400 MHz, CDCl$_3$+CD$_3$OD) δ: 1.17 (6H, d, J=6.6 Hz), 2.86 (1H, sept, J=6.6 Hz), 3.09-3.18 (4H, m), 3.68-3.72 (2H, m), 3.78-3.82 (2H, m), 4.30 (2H, s), 5.75 (1H, s), 6.81 (2H, d, J=8.8 Hz), 6.92 (2H, d, J=8.8 Hz), 7.24-7.36 (6H, m), 8.17 (1H, s), 8.92 (1H, br).

IR (ATR): 1613, 1570, 1516, 1407, 1234, 1157, 1206 cm$^{-1}$.

MS: m/z 472 (M$^+$, base peak).

Example 260

Preparation of 6-({4-[4-(2-methylpropanoyl)piperazin-1-yl]phenyl}amino)-4-[(3-nitrobenzyl)amino]pyridine-3-carboxyamide

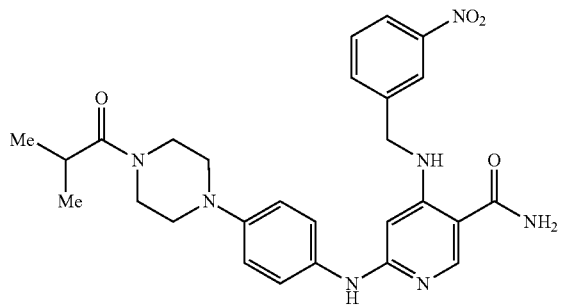 [SMILES: CC(C)C(=O)N1CCN(c2ccc(Nc3cc(NCc4cccc([N+](=O)[O-])c4)c(C(N)=O)cn3)cc2)CC1]

From 4-[(3-nitrobenzyl)amino]-6-{[4-(piperazin-1-yl)phenyl]amino}pyridine-3-carboxyamide (the compound of Example 224) and 2-methylpropionic acid 2,5-dioxopyrrolidin-1-yl ester (an intermediate compound of Example 259) in a manner similar to Example 258, the title compound was obtained as a light yellow crystalline powder (yield 89%).

$^1$H-NMR (400 MHz, CDCl$_3$) δ: 1.18 (6H, d, J=6.8 Hz), 2.86 (1H, sep, J=6.8 Hz), 3.08-3.16 (4H, m), 3.65-3.73 (2H, m), 3.78-3.83 (2H, m), 4.42 (2H, d, J=5.6 Hz), 5.57 (1H, s), 5.58 (2H, br), 6.38 (1H, brs), 6.76 (2H, d, J=8.9 Hz), 6.87 (2H, d, J=8.9 Hz), 7.51 (1H, dd, J=7.9, 7.9 Hz), 7.61-7.65 (1H, m), 8.07-8.09 (1H, m), 8.13-8.17 (1H, m), 8.21 (1H, s), 9.06 (1H, brt, J=5.6 Hz).

IR (ATR): 1663, 1619, 1574, 1524, 1513, 1440, 1407, 1347, 1295, 1228 cm$^{-1}$.

Example 261

Preparation of 4-(benzylamino)-6-({4-[4-(phenylacetyl)piperazin-1-yl]phenyl}amino)pyridine-3-carboxyamide

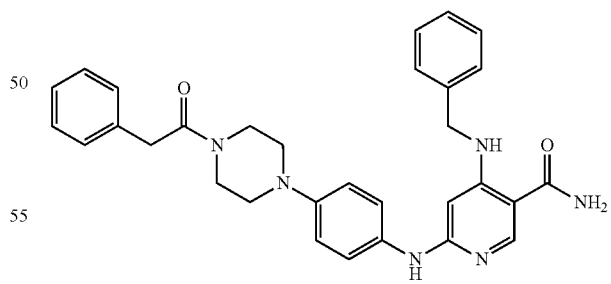

From phenylacetic acid and N-hydroxysuccinimide in a manner similar to Example 258, phenylacetic acid 2,5-dioxopyrrolidin-1-yl ester was obtained. From 4-(benzylamino)-6-{[4-piperazin-1-yl]phenyl}amino)pyridine-3-carboxyamide (the compound of Example 219) and phenylacetic acid 2,5-dioxopyrrolidin-1-yl ester, the title compound was obtained as slight yellow needle crystals (yield 76%).

m.p. 248-250° C. (dec.)

¹H-NMR (400 MHz, DMSO-d6) δ: 2.91-3.02 (4H, m), 3.59-3.64 (4H, m), 3.76 (2H, s), 4.35 (2H, d, J=5.6 Hz), 5.75 (1H, s), 6.81 (2H, brd, J=9.0 Hz), 7.16-7.38 (13H, m), 7.80 (1H, br), 8.12 (1H, s), 8.79 (1H, brs), 9.11 (1H, brs).

IR (ATR): 1672, 1617, 1569, 1542, 1514, 1406, 1306, 1227, 1151, 1034 cm⁻¹.

MS: m/z 520 (M⁺, base peak).

Example 262

Preparation of 4-(benzylamino)-6-({4-[4-(cyanoacetyl)piperazin-1-yl]phenyl}amino)pyridine-3-carboxyamide

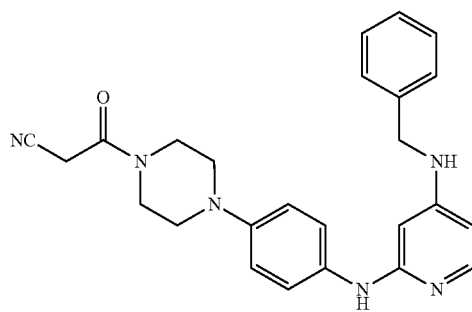

From cyanoacetic acid and N-hydroxysuccinimide in a manner similar to Example 258, cyanoacetic acid 2,5-dioxopyrrolidin-1-yl ester was obtained. From 4-(benzylamino)-6-{[4-piperazin-1-yl]phenyl}amino)pyridine-3-carboxyamide (the compound of Example 219) and cyanoacetic acid 2,5-dioxopyrrolidin-1-yl ester, the title compound was obtained as slight yellow needle crystals (yield 86%).

¹H-NMR (400 MHz, CDCl₃) δ: 3.13-3.17 (2H, m), 3.18-3.23 (2H, m), 3.54 (2H, s), 3.64-3.68 (2H, m), 3.80-3.84 (2H, m), 4.32 (2H, d, J=5.6 Hz), 5.56 (2H, br), 5.76 (1H, s), 6.43 (1H, brs), 6.81 (2H, d, J=9.0 Hz), 6.96 (2H, d, J=9.0 Hz), 7.25-7.37 (5H, m), 8.20 (1H, s), 8.88 (1H, brt, J=5.6 Hz).

IR (ATR): 2260, 1647, 1633, 1614, 1574, 1531, 1514, 1450, 1411, 1231, 1213, 1035 cm⁻¹.

Example 263

Preparation of 6-({4-[4-(cyanoacetyl)piperazin-1-yl]phenyl}amino)-4-[(2,3-difluorobenzyl)amino]pyridine-3-carboxyamide

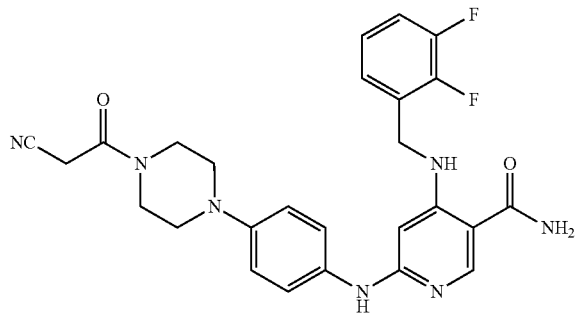 [SMILES: N#CCC(=O)N1CCN(c2ccc(Nc3cc(NCc4cccc(F)c4F)c(C(N)=O)cn3)cc2)CC1]

From cyanoacetic acid and N-hydroxysuccinimide in a manner similar to Example 258, cyanoacetic acid 2,5-dioxopyrrolidin-1-yl ester was obtained. From 4-[(2,3-difluorobenzyl)amino]-6-{[4-(piperazin-1-yl)phenyl]amino}pyridine-3-carboxyamide (the compound of Example 220) and cyanoacetic acid 2,5-dioxo-pyrrolidin-1-yl ester, the title compound was obtained as a yellow crystalline powder (yield 33%).

¹H-NMR (400 MHz, CDCl₃+CD₃OD) δ: 3.16-3.20 (2H, m), 3.20-3.26 (2H, m), 3.62-3.70 (2H, m), 3.78-3.84 (2H, m), 4.37 (2H, s), 5.67 (1H, s), 6.85 (2H, d, J=8.8 Hz), 6.95 (2H, d, J=8.8 Hz), 7.04-7.14 (3H, m), 8.18 (1H, s), 8.96 (1H, br).

IR (ATR): 2360, 1649, 1624, 1556, 1322, 1274 cm⁻¹

Example 264

Preparation of 6-({4-[4-(cyanoacetyl)piperazin-1-yl]phenyl}amino)-4-[(3,5-difluorobenzyl)amino]pyridine-3-carboxyamide

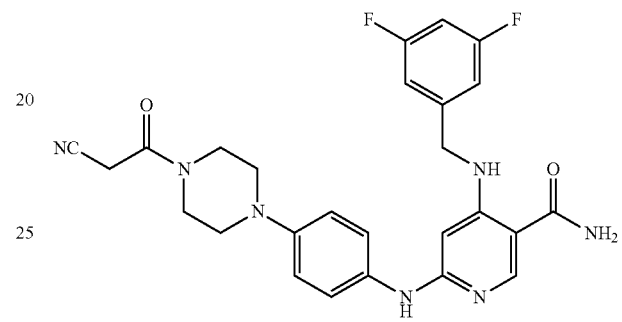

From cyanoacetic acid and N-hydroxysuccinimide in a manner similar to Example 258, cyanoacetic acid 2,5-dioxopyrrolidin-1-yl ester was obtained. From 4-[(3,5-difluorobenzyl)amino]-6-{[4-(piperazin-1-yl)phenyl]amino}pyridine-3-carboxyamide (the compound of Example 221) and cyanoacetic acid 2,5-dioxopyrrolidin-1-yl ester, the title compound was obtained as a light brown crystalline powder (yield 56%).

¹H-NMR (400 MHz, DMSO-d6) δ: 2.99-3.04 (2H, m), 3.04-3.09 (2H, m), 3.47-3.51 (2H, m), 3.58-3.62 (2H, m), 4.10 (2H, s), 4.40 (2H, d, J=5.8 Hz), 5.67 (1H, s), 6.83 (2H, d, J=9.0 Hz), 6.95-7.02 (2H, m), 7.04 (1H, br), 7.10-7.18 (1H, m), 7.23 (2H, d, J=9.0 Hz), 7.95 (1H, br), 8.35 (1H, s), 8.63 (1H, s), 9.04 (1H, brt, J=5.8 Hz).

IR (ATR): 1624, 1609, 1595, 1517, 1444, 1408, 1307, 1297, 1238, 1117 cm⁻¹.

MS (FAB): m/z 506 (M⁺+1), 136 (base peak).

Example 265

Preparation of 6-({4-[4-(cyanoacetyl)piperazin-1-yl]phenyl}amino)-4-[(2,5-difluorobenzyl)amino]pyridine-3-carboxyamide

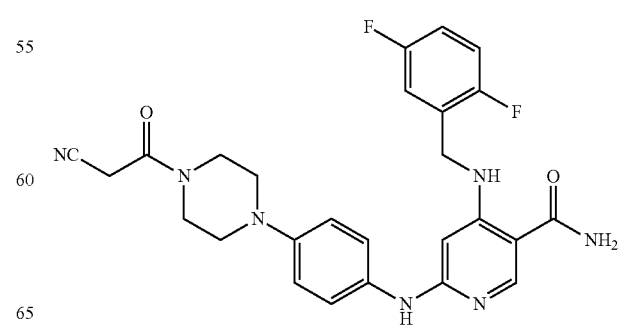

From cyanoacetic acid and N-hydroxysuccinimide in a manner similar to Example 258, cyanoacetic acid 2,5-dioxopyrrolidin-1-yl ester was obtained. From 4-[(2,5-difluorobenzyl)amino]-6-{[4-(piperazin-1-yl)phenyl]amino}pyridine-3-carboxyamide (the compound of Example 222) and cyanoacetic acid 2,5-dioxo-pyrrolidin-1-yl ester, the title compound was obtained as a light yellow solid (yield 46%).

$^1$H-NMR (400 MHz, CDCl$_3$): 3.13-3.24 (4H, m), 3.55 (2H, s), 3.63-3.68 (2H, m), 3.79-3.85 (2H, m), 4.34 (2H, d, J=5.9 Hz), 5.58 (2H, brs), 5.70 (1H, s), 6.50 (1H, s), 6.86 (2H, d, J=8.8 Hz), 6.90-7.03 (3H, m), 7.05 (2H, d, J=8.8 Hz), 8.21 (1H, s), 8.92 (1H, t, J=5.9 Hz).

Example 266

Preparation of 6-({4-[4-(cyanoacetyl)piperazin-1-yl]phenyl}amino)-4-[(2,6-difluorobenzyl)amino]pyridine-3-carboxyamide

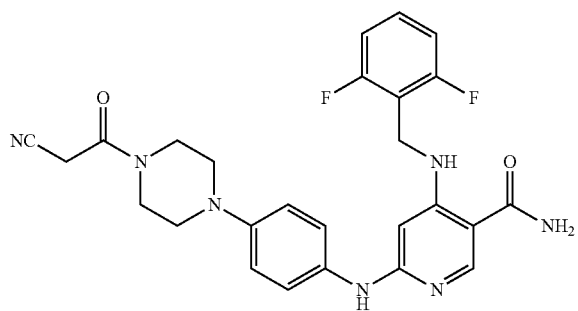 [SMILES: N#CCC(=O)N1CCN(c2ccc(Nc3cc(NCc4c(F)cccc4F)c(C(N)=O)cn3)cc2)CC1]

From cyanoacetic acid and N-hydroxysuccinimide in a manner similar to Example 258, cyanoacetic acid 2,5-dioxopyrrolidin-1-yl ester was obtained. From 4-[(2,6-difluorobenzyl)amino]-6-{[4-(piperazin-1-yl)phenyl]amino}pyridine-3-carboxyamide (the compound of Example 223) and cyanoacetic acid 2,5-dioxo-pyrrolidin-1-yl ester, the title compound was obtained as a light yellow solid (yield 45%).

$^1$H-NMR (400 MHz, CDCl$_3$): 3.16-3.30 (4H, m), 3.55 (2H, s), 3.64-3.70 (2H, m), 3.80-3.86 (2H, m), 4.35 (2H, d, J=6.1 Hz), 5.61 (2H, brs), 5.99 (1H, s), 6.78 (1H, brs), 6.87 (2H, dd, J=7.9, 7.9 Hz), 6.96 (2H, d, J=9.0 Hz), 7.21 (2H, d, J=9.0 Hz), 7.23-7.29 (1H, m), 8.20 (1H, s), 8.88 (1H, t, J=6.1 Hz).

Example 267

Preparation of 6-({3-[4-(cyanoacetyl)piperazin-1-yl]phenyl}amino)-4-[(3,5-difluorodibenzyl)amino]pyridine-3-carboxyamide

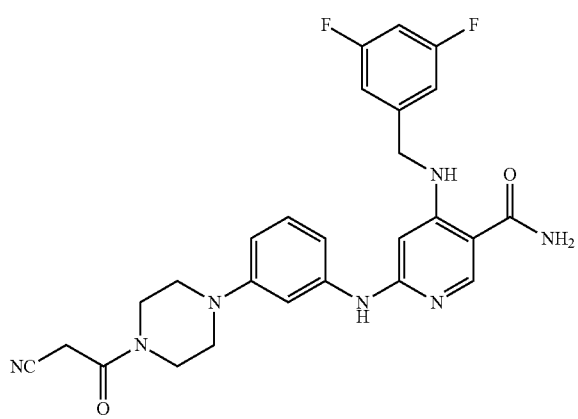 [SMILES: N#CCC(=O)N1CCN(c2cccc(Nc3cc(NCc4cc(F)cc(F)c4)c(C(N)=O)cn3)c2)CC1]

From cyanoacetic acid and N-hydroxysuccinimide in a manner similar to Example 258, cyanoacetic acid 2,5-dioxopyrrolidin-1-yl ester was obtained. From 4-[(3,5-difluorobenzyl)amino]-6-{[3-(piperazin-1-yl)phenyl]amino}pyridine-3-carboxyamide (the compound of Example 225) and cyanoacetic acid 2,5-dioxo-pyrrolidin-1-yl ester, the title compound was obtained as a light yellow crystalline powder (yield 41%).

$^1$H-NMR (400 MHz, CDCl$_3$) δ: 3.11-3.16 (2H, m), 3.19-3.23 (2H, m), 3.54 (2H, s), 3.59-3.63 (2H, m), 3.75-3.79 (2H, m), 4.33 (2H, d, J=6.0 Hz), 5.67 (2H, br), 5.78 (1H, s), 6.53 (1H, dd, J=8.1, 1.5 Hz), 6.65 (1H, dd, J=8.1, 2.0 Hz), 6.69-6.83 (5H, m), 7.14 (1H, dd, J=8.1, 8.1 Hz), 8.24 (1H, s), 9.03 (1H, brt, J=6.0 Hz).

IR (ATR): 1649, 1623, 1596, 1573, 1494, 1446, 1408, 1308, 1234, 1117 cm$^{-1}$.

Example 268

Preparation of 4-(benzylamino)-6-({4-[4-(cyanoacetyl)-1,4-diazepan-1-yl]phenyl}amino)pyridine-3-carboxyamide

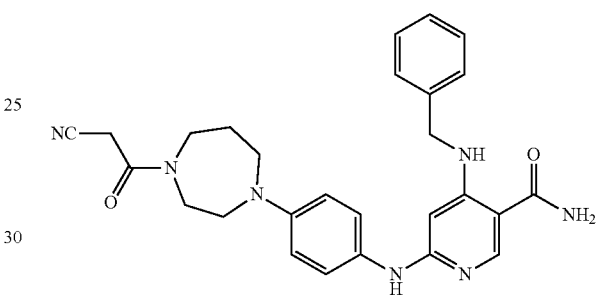

From cyanoacetic acid and N-hydroxysuccinimide in a manner similar to Example 258, cyanoacetic acid 2,5-dioxopyrrolidin-1-yl ester was obtained. From 4-(benzylamino)-6-({4-(1,4-diazepan-1-yl)phenyl}amino)pyridine-3-carboxyamide (the compound of Example 226) and cyanoacetic acid 2,5-dioxo-pyrrolidin-1-ylester, the title compound was obtained as light brown needle crystals (yield 31%).

$^1$H-NMR (400 MHz, CDCl$_3$) δ: 1.99-2.07 (2H, m), 3.20-3.65 (8H, m), 3.73-3.82 (2H, m), 4.27-4.32 (2H, m), 5.65-5.69 (1H, m), 5.78 (2H, br), 6.54-6.59 (2H, m), 6.80-6.93 (3H, m), 7.23-7.35 (5H, m), 8.21 (1H, s), 8.89-8.95 (1H, m).

IR (ATR): 1650, 1613, 1567, 1515, 1453, 1407, 1360, 1310, 1255, 1218, 1182 cm$^{-1}$.

MS: m/z 484 (M$^+$+1), 136 (base peak).

Example 269

Preparation of 4-(benzylamino)-6-({4-[4-(chloroacetyl)piperazin-1-yl]phenyl}amino)pyridine-3-carboxyamide

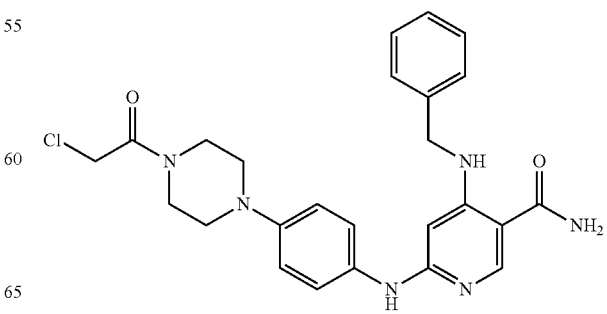

25 mg of 4-(benzylamino)-6-({4-piperazin-1-yl}phenyl)amino)pyridine-3-carboxyamide (the compound of Example 219) was dissolved in 4 mL of methylene chloride, to which 21 mg of chloroacetic acid anhydride was added and stirred at room temperature for 20 minutes. To the reaction mixture, 0.5 mL of a 28% ammonia water was added, stirred, the organic layer was separated, washed with water, and dried on anhydrous sodium sulfate. The solvent was evaporated, and the residue was purified by silica gel thin layer chromatography (chloroform:methanol=10:1) to obtain 25 mg (84%) of the title compound as a slight yellow crystalline powder.

$^1$H-NMR (400 MHz, CDCl$_3$) δ: 3.11-3.16 (2H, m), 3.16-3.23 (2H, m), 3.68-3.73 (2H, m), 3.78-3.84 (2H, m), 4.31 (2H, d, J=5.8 Hz), 5.75 (2H, br), 5.76 (1H, s), 6.79 (1H, brs), 6.80 (2H, d, J=8.8 Hz), 6.94 (2H, d, J=8.8 Hz), 7.24-7.36 (5H, m), 8.21 (1H, s), 8.90 (1H, brt, J=5.8 Hz).

Example 270

Preparation of 6-({4-[4-(chloroacetyl)piperazin-1-yl]phenyl}amino)-4-[(3,5-difluorobenzyl)aminopyridine-3-carboxyamide

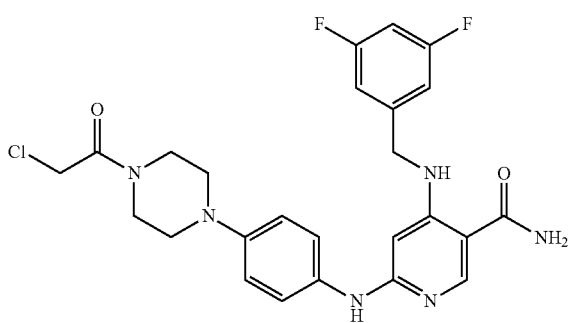 [SMILES: NC(=O)c1cnc(Nc2ccc(N3CCN(C(=O)CCl)CC3)cc2)cc1NCc1cc(F)cc(F)c1]

From 4-[(3,5-difluorobenzyl)amino]-6-{[4-(piperazin-1-yl)phenyl]amino}pyridine-3-carboxyamide (the compound of Example 221) in a manner similar to Example 269, the title compound was obtained as a light brown crystalline powder (yield 100%).

Example 271

Preparation of 6-({4-[4-(chloroacetyl)piperazin-1-yl]phenyl}amino)-4-[(3-nitrobenzyl)amino]pyridine-3-carboxyamide

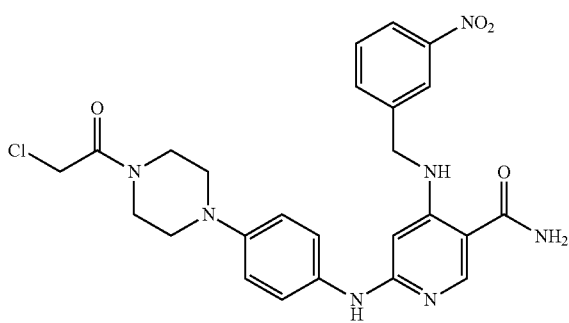 [SMILES: NC(=O)c1cnc(Nc2ccc(N3CCN(C(=O)CCl)CC3)cc2)cc1NCc1cccc([N+](=O)[O-])c1]

From 4-[(3-nitrobenzyl)amino]-6-{[4-(piperazin-1-yl)phenyl]amino}pyridine-3-carboxyamide (the compound of Example 224) in a manner similar to Example 269, the title compound was obtained as a light orange amorphous substance (yield 100%).

$^1$H-NMR (400 MHz, CDCl$_3$) δ: 3.12-3.21 (4H, m), 3.70-3.75 (2H, m), 3.78-3.83 (2H, m), 4.15 (2H, s), 4.41 (2H, d, J=5.4 Hz), 5.56 (1H, s), 6.75 (2H, d, J=8.8 Hz), 6.86 (2H, d, J=8.8 Hz), 7.52 (1H, dd, J=7.9, 7.9 Hz), 7.63 (1H, brd, J=7.9 Hz), 8.07 (1H, brs), 8.14 (1H, brd, J=7.9 Hz), 8.19 (1H, s), 9.11 (1H, t, J=5.4 Hz).

Example 272

Preparation of 4-(benzylamino)-6-({4-[1-(chloroacetyl)piperazin-1-yl]phenyl}amino)pyridine-3-carboxyamide

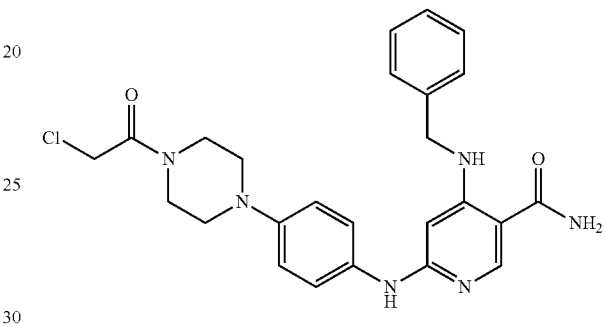

From 4-(benzylamino)-6-{[4-(piperidin-4-yl)phenyl]amino}pyridine-3-carboxyamide (the compound of Example 228) in a manner similar to Example 269, the title compound was obtained as a slight yellow oil (yield 43%).

$^1$H-NMR (400 MHz, CDCl$_3$) δ: 1.53-1.71 (2H, m), 1.91 (2H, d, J=13.0 Hz), 2.72 (2H, t, J=12.2 Hz), 3.24 (1H, t, J=13.0 Hz), 3.71 (1H, q, J=6.8 Hz), 4.01 (2H, d, J=11.7 Hz), 4.33 (2H, d, J=4.9 Hz), 4.74 (1H, d, J=13.2 Hz), 5.86-5.92 (3H, m), 6.86 (1H, s), 6.93 (2H, d, J=7.8 Hz), 7.03 (2H, d, J=7.8 Hz), 7.27-7.34 (5H, m), 8.24 (1H, s), 8.93 (1H, brs).

Example 273

Preparation of 6-({4-[4-(chloroacetyl)aminopiperidino]phenyl}amino)-4-[(3,5-difluorobenzyl)amino]pyridine-3-carboxyamide

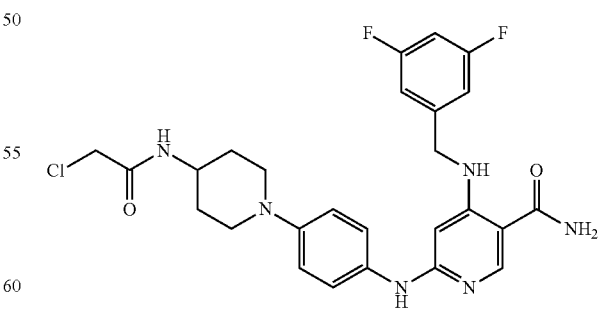

From 6-{[4-(4-aminopiperidino)phenyl]amino}-4-[(3,5-difluorobenzyl)amino]pyridine-3-carboxyamide (the compound of Example 230) in a manner similar to Example 269, the title compound was obtained as a reddish brown amorphous substance (yield 45%).

$^1$H-NMR (400 MHz, CDCl$_3$): 1.21-1.49 (2H, m), 1.87-2.03 (2H, m), 2.63-2.76 (1H, m), 3.19-3.30 (1H, m), 3.87-3.95 (1H, m), 4.00 (1H, d, J=12.2 Hz), 4.04 (1H, d, J=12.2 Hz), 4.38 (2H, d, J=5.8 Hz), 4.62-4.78 (2H, m), 5.78 (1H, s), 5.82 (2H, br), 6.75 (1H, dddd, J=8.7, 8.7, 2.2, 2.2 Hz), 6.80-6.87 (2H, m), 6.91-6.98 (2H, m), 7.03 (1H, brs), 7.06-7.13 (2H, m), 8.28 (1H, s), 9.07 (1H, brt, J=5.8 Hz).

Example 274

Preparation of 4-(benzylamino)-6-({4-[4-(N,N-diethylglycyl)piperazin-1-yl]phenyl}amino)pyridine-3-carboxyamide

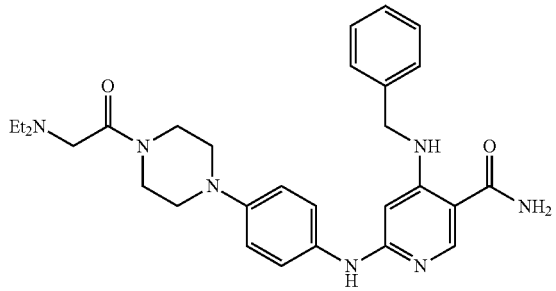

25 mg of 4-(benzylamino)-6-({4-[4-(chloroacetyl)piperazin-1-yl]phenyl}amino)pyridine-3-carboxyamide (the compound of Example 269) was dissolved in 2 mL of acetonitrile, to which 0.1 mL of diethylamine and 15 mg of potassium carbonate were added, and stirred at 80° C. for 1 hour. After cooling, the insoluble substances were filtered off, the solvent was evaporated, and the residue was purified by silica gel thin layer chromatography (chloroform:ammonia methanol=10:1) to obtain 16 mg (59%) of the title compound as a light brown crystalline powder.

$^1$H-NMR (400 MHz, CDCl$_3$) δ: 1.05 (6H, t, J=7.1 Hz), 2.58 (4H, q, J=7.1 Hz), 3.08-3.16 (4H, m), 3.30 (2H, s), 3.75-3.80 (2H, m), 3.83-3.88 (2H, m), 4.30 (2H, d, J=5.6 Hz), 5.68 (2H, br), 5.76 (1H, s), 6.62 (1H, brs), 6.82 (2H, d, J=9.0 Hz), 6.93 (2H, d, J=9.0 Hz), 7.24-7.36 (5H, m), 8.19 (1H, s), 8.87 (1H, brt, J=5.6 Hz).

IR (ATR): 1619, 1570, 1513, 1453, 1408, 1308, 1281, 1229 cm$^{-1}$.

Example 275

Preparation of 6-({4-[4-(N,N-diethylglycyl)piperazin-1-yl]phenyl}amino)-4-[(3,5-difluorobenzyl)amino]pyridine-3-carboxyamide

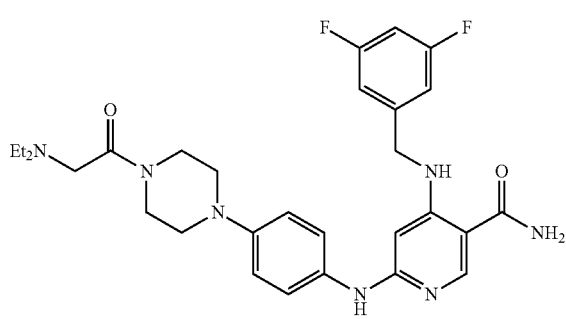

From 6-({4-[4-(chloroacetyl)piperazin-1-yl]phenyl}amino)-4-[(3,5-difluorobenzyl)amino]pyridine-3-carboxyamide (the compound of Example 270) in a manner similar to Example 274, the title compound was obtained as a light brown crystalline powder (yield 76%).

$^1$H-NMR (400 MHz, CDCl$_3$) δ: 1.06 (6H, t, J=7.2 Hz), 2.59 (4H, q, J=7.2 Hz), 3.11-3.18 (4H, m), 3.21 (2H, s), 3.75-3.80 (2H, m), 3.83-3.87 (2H, m), 4.28 (2H, d, J=5.8 Hz), 5.59 (1H, s), 5.64 (1H, brs), 6.52 (1H, brs), 6.73 (1H, dddd, J=2.2, 2.2, 8.8, 8.8 Hz), 6.78 (2H, brd, J=5.8 Hz), 6.82 (2H, dd, J=2.2, 6.6 Hz), 6.89 (2H, dd, J=2.2, 6.6 Hz), 8.20 (1H, s), 8.98 (1H, t, J=5.8 Hz).

IR (ATR): 1625, 1600, 1571, 1514, 1459, 1410, 1311, 1298, 1228, 1116 cm$^{-1}$.

MS: m/z 551 (M$^+$), 86 (base peak).

Example 276

Preparation of 6-({4-[4-(N,N-diethylglycyl)piperazin-1-yl]phenyl}amino)-4-[(3-nitrobenzyl)amino]pyridine-3-carboxyamide

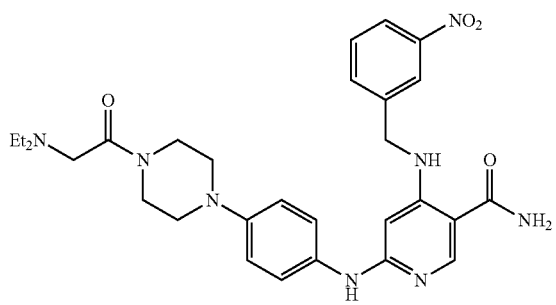

From 6-({4-[4-(chloroacetyl)piperazin-1-yl]phenyl}amino)-4-[(3-nitrobenzyl)amino]pyridine-3-carboxyamide (the compound of Example 271) in a manner similar to Example 274, the title compound was obtained as a light brown crystalline powder (yield 83%).

m.p. 190-191° C. (dec.)

$^1$H-NMR (400 MHz, CDCl$_3$) δ: 1.02-1.12 (6H, m), 2.50-2.65 (4H, m), 3.06-3.15 (4H, m), 3.31 (2H, s), 3.76-3.88 (4H, m), 4.41 (2H, brd, J=5.6 Hz), 5.58 (1H, s), 5.64 (2H, br), 6.48 (1H, brs), 6.76 (2H, d, J=8.8 Hz), 6.88 (2H, d, J=8.8 Hz), 7.51 (1H, dd, J=7.9, 7.9 Hz), 7.62 (1H, brd, J=7.9 Hz), 8.08 (1H, brs), 8.14 (1H, brd, J=7.9 Hz), 8.21 (1H, s), 9.04 (1H, br).

IR (ATR): 1628, 1566, 1517, 1433, 1405, 1346, 1316, 1287, 1230, 1155 cm$^{-1}$.

MS: m/z 561 (M$^+$+1).

Example 277

Preparation of 4-(benzylamino)-6-({4-[1-(N,N-diethylglycyl)piperidin-4-yl]phenyl}amino)pyridine-3-carboxyamide

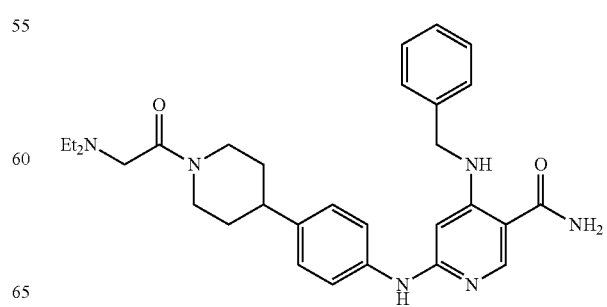

From 4-(benzylamino)-6-({4-[1-(chloroacetyl)piperidin-4-yl]phenyl}amino)pyridine-3-carboxyamide (the compound of Example 272) in a manner similar to Example 274, the title compound was obtained as a white crystalline powder (yield 45%).

$^1$H-NMR (400 MHz, CDCl$_3$) δ: 1.07 (6H, t, J=7.2 Hz), 1.53-1.71 (2H, m), 1.90 (2H, d, J=13.0 Hz), 2.55-2.68 (6H, m), 3.07 (1H, t, J=13.0 Hz), 3.26 (1H, d, J=13.6 Hz), 3.40 (1H, d, J=13.6 Hz), 4.35 (2H, d, J=5.2 Hz), 4.75 (1H, d, J=13.6 Hz), 5.71 (2H, brs), 5.86 (1H, s), 6.80 (1H, brs), 6.93 (2H, d, J=8.5 Hz), 7.03 (2H, d, J=8.6 Hz), 7.27-7.38 (5H, m), 8.23 (1H, s), 8.94 (1H, brs).

Example 278

Preparation of 6-({4-[4-(N,N-diethylglycyl)aminopiperidino]phenyl}amino)-4-[(3,5-difluorobenzyl)amino]pyridine-3-carboxyamide

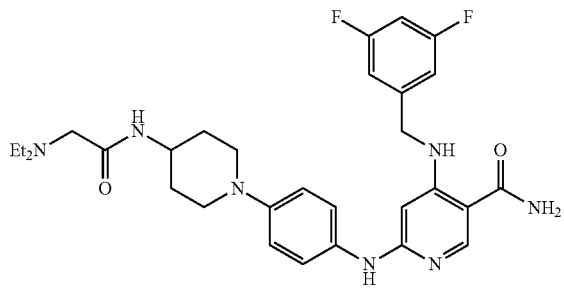

From 6-({4-[4-(chloroacetyl)aminopiperidino]phenyl}amino)-4-[(3,5-difluorobenzyl)amino]pyridine-3-carboxyamide (the compound of Example 230) in a manner similar to Example 274, the title compound was obtained as a white solid (yield 60%).

$^1$H-NMR (400 MHz, CDCl$_3$) δ: 0.93 (6H, t, J=7.1 Hz), 1.20-1.43 (2H, m), 1.81-1.92 (2H, m), 2.38-2.52 (4H, m), 2.56-2.66 (1H, m), 3.02-3.10 (1H, m), 3.10 (1H, d, J=13.3 Hz), 3.24 (1H, d, J=13.3 Hz), 4.26-4.34 (1H, m), 4.38 (2H, d, J=5.6 Hz), 4.64-4.76 (2H, m), 5.64 (2H, br), 5.77 (1H, s), 6.59 (1H, brs), 6.72-6.79 (1H, m), 6.80-6.88 (2H, m), 6.96 (2H, d, J=8.5 Hz), 7.04-7.14 (2H, m), 8.27 (1H, s), 9.06 (1H, brt, J=5.6 Hz).

Example 279

Preparation of 4-(benzylamino)-6-({4-[(diethylcarbamoyl)amino]phenyl}amino)pyridine-3-carboxyamide

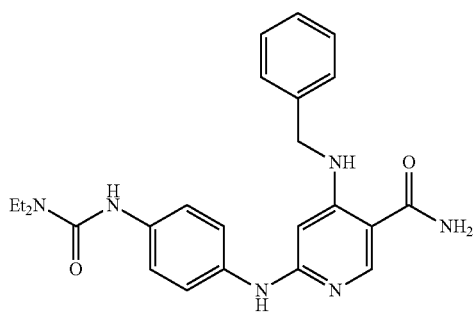

10 mg of 6-[(4-aminophenyl)amino]-4-(benzylamino)pyridine-3-carboxyamide (the compound of Example 65) was dissolved in 0.5 mL of methylene chloride and 0.2 mL of tetrahydrofuran, to which 33 mg of triethylamine and 41 mg of N,N-diethylcarbamoyl chloride were added, and stirred at room temperature for 3 days. To the reaction mixture, water was added, extracted with chloroform, the extract was washed with saturated saline, and dried on anhydrous sodium sulfate. The solvent was evaporated, and the residue was purified by silica gel thin layer chromatography (chloroform:methanol=5:1, developed twice) to obtain 9 mg (69%) of the title compound as a light brown crystalline powder.

$^1$H-NMR (400 MHz, CDCl$_3$+CD$_3$OD) δ: 1.24 (6H, t, J=7.1 Hz), 3.39 (4H, q, J=7.1 Hz), 4.30 (2H, s), 5.82 (1H, s), 6.35 (1H, br), 6.94 (2H, d, J=8.8 Hz), 7.24-7.38 (7H, m), 8.17 (1H, s), 8.95 (1H, br).

IR (ATR): 1635, 1604, 1583, 1554, 1512, 1497, 1409, 1300, 1260, 1233 cm$^{-1}$.

MS: m/z 433 (M$^+$+1), 154 (base peak).

Example 280

Preparation of 4-(benzylamino)-6-({4-[(propan-2-ylcarbamoyl)amino]phenyl}amino)pyridine-3-carboxyamide

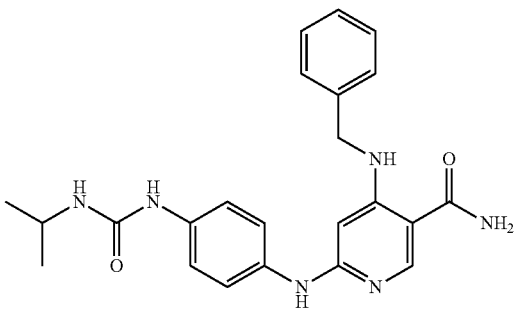 [SMILES: CC(C)NC(=O)Nc1ccc(Nc2cc(NCc3ccccc3)c(C(N)=O)cn2)cc1]

10 mg of 6-[(4-aminophenyl)amino]-4-(benzylamino)pyridine-3-carboxyamide (the compound of Example 65) was dissolved in 0.5 mL of tetrahydrofuran, and, under ice cooling, 7.6 mg of isopropyl isocyanate was added, and stirred at room temperature for 24 hours. To the reaction mixture, water was added, extracted with chloroform, the extract was washed with saturated saline, and dried on anhydrous sodium sulfate. The solvent was evaporated, and the residue was washed with methanol-ether to obtain 15 mg (80%) of the title compound as a light pink crystalline powder.

$^1$H-NMR (400 MHz, CD$_3$OD) δ: 1.18 (6H, d, J=6.6 Hz), 3.89 (1H, sept, J=6.6 Hz), 4.34 (2H, s), 5.81 (1H, s), 7.00 (2H, d, J=8.8 Hz), 7.22 (2H, d, J=8.8 Hz), 7.25-7.38 (6H, m), 8.24 (1H, s).

IR (ATR): 1637, 1600, 1551, 1511, 1421, 1405, 1303, 1227, 1174 cm$^{-1}$.

MS: m/z 419 (M$^+$), 136 (base peak).

Example 281

Preparation of 4-[(3-nitrobenzyl)amino]-6-({4-[(4-diethylcarbamoyl)piperazin-1-yl]phenyl}amino)pyridine-3-carboxyamide

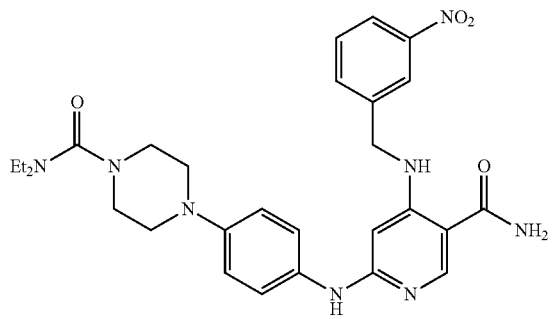

50 mg of 4-[(3-nitrobenzyl)amino]-6-{[4-(piperazin-1-yl)phenyl]amino}pyridine-3-carboxyamide (the compound of Example 224) was suspended in a mixed solvent of 2.5 mL of methylene chloride and 2.5 mL of tetrahydrofuran, to which, under ice cooling, 26 mg of pyridine and 18 mg of N,N-diethylcarbamoyl chloride were added, and stirred at room temperature for 24 hours. The solvent was evaporated and the residue was purified by silica gel column chromatography (chloroform:methanol=20:1) to obtain 31 mg (51%) of the title compound as a yellow solid.

$^1$H-NMR (400 MHz, DMSO-d6) δ: 1.07 (6H, dd, J=6.8, 6.8 Hz), 2.98-3.60 (4H, m), 3.12-3.24 (8H, m), 4.52 (2H, br), 5.66 (1H, s), 6.78 (2H, d, J=8.5 Hz), 7.16 (2H, d, J=8.5 Hz), 7.64-7.76 (2H, m), 8.14 (2H, br), 8.34 (1H, s), 8.63 (1H, br), 9.17 (1H, br).

IR (ATR): 1627, 1600, 1521, 1415, 1344, 1232 cm$^{-1}$.

Example 282

Preparation of 4-(benzylamino)-6-({4-[(4-diethylcarbamoyl)piperazin-1-yl]phenyl}amino)pyridine-3-carboxyamide

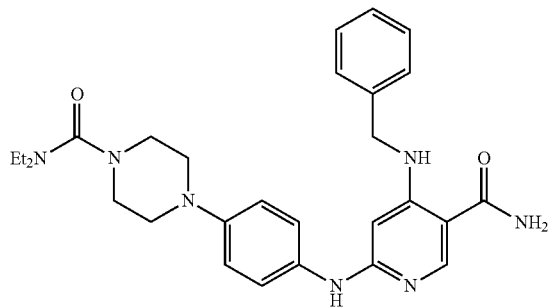

From 4-(benzylamino)-6-{[4-piperazin-1-yl]phenyl}amino)pyridine-3-carboxyamide (the compound of Example 219) and N,N-diethylcarbamoyl chloride in a manner similar to Example 281, the title compound was obtained as a slight yellow powder (yield 52%).

$^1$H-NMR (400 MHz, CDCl$_3$) δ: 1.14-1.17 (6H, t, J=6.5 Hz), 2.53-2.57 (2H, t, J=7.2 Hz), 3.14-3.16 (4H, t, J=5.0 Hz), 3.23-3.28 (4H, q, J=6.6 Hz), 3.38-3.40 (4H, t, J=5.0 Hz), 4.30 (2H, d, J=5.6 Hz), 5.55 (2H, s), 5.74 (1H, s), 6.48 (1H, s), 6.81 (2H, d, J=8.8 Hz), 6.93 (2H, d, J=8.8 Hz), 7.26-7.35 (5H, m), 8.19 (1H, s), 8.87 (1H, t, J=5.7 Hz).

IR (ATR): 3298, 1662, 1614, 1561, 1514, 1410, 1307, 1273, 1253, 1229, 1063 cm$^{-1}$.

Example 283

Preparation of 4-(benzylamino)-6-[(4-{[(4-(propan-2-yl)carbamoyl]piperazin-1-yl}phenyl)amino]pyridine-3-carboxyamide

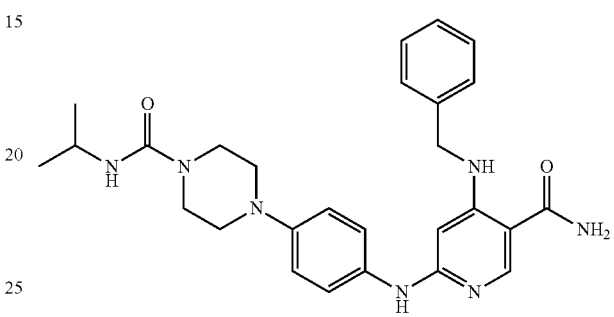

20 mg of 4-(benzylamino)-6-{[4-piperazin-1-yl]phenyl}amino)pyridine-3-carboxyamide (the compound of Example 219) was dissolved in 1 mL of tetrahydrofuran, to which 5.1 mg of isopropyl isocyanate was added, and stirred at room temperature for 2 hours. The solvent was evaporated, and the residue was purified by silica gel chromatography (chloroform:ammonia methanol=10:1) and washed with ethanol and ether to obtain 12 mg (49%) of the title compound as a white powder.

$^1$H-NMR (400 MHz, CDCl$_3$) δ: 1.18 (6H, d, J=6.6 Hz), 3.13-3.15 (4H, t, J=5.1 Hz), 3.51-3.54 (4H, t, J=5.0 Hz), 3.92-4.06 (1H, m), 4.30 (2H, d, J=5.4 Hz), 5.52 (2H, s), 5.75 (1H, s), 6.80 (2H, d, J=8.8 Hz), 6.92 (2H, d, J=9.0 Hz), 7.20-7.37 (5H, m), 8.17 (1H, s), 8.89 (1H, t, J=5.7 Hz).

IR (ATR): 3319, 2973, 1632, 1603, 1513, 1409, 1256, 1223, 1004 cm$^{-1}$.

Example 284

Preparation of 4-[(3-nitrobenzyl)amino]-6-[(4-{[4-(propan-2-yl)carbamoyl]piperazin-1-yl}phenyl)amino]pyridine-3-carboxyamide

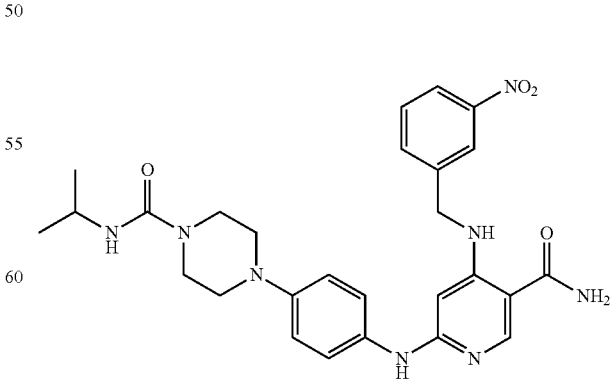

From 4-[(3-nitrobenzyl)amino]-6-{[4-(piperazin-1-yl)phenyl]amino}pyridine-3-carboxyamide (the compound of Example 224) and isopropyl isocyanate in a manner similar to Example 283, the title compound was obtained as a light orange powder (yield 81%).

$^1$H-NMR (400 MHz, DMSO-d6) δ: 1.06 (6H, d, J=6.6 Hz), 2.94-2.97 (4H, m), 3.39-3.41 (4H, m), 3.77 (1H, m), 4.52 (2H, d, J=5.9 Hz), 5.66 (1H, s), 6.79 (2H, d, J=9.0 Hz), 7.17 (2H, d, J=9.0 Hz), 7.67 (1H, m), 7.75 (1H, d, J=7.6 Hz), 8.14-8.16 (2H, m), 8.35 (1H, s), 8.58 (1H, s), 9.13 (1H, br).

IR (ATR): 1630, 1602, 1523, 1512, 1347, 1232 cm$^{-1}$.

Example 285

Preparation of 4-(benzylamino)-6-({4-[4-(morpholinocarbonyl)piperazin-1-yl]phenyl}amino)pyridine-3-carboxyamide and N-[4-(benzylamino)-5-carbamoylpyridine-2-yl]-N-{4-[4-(morpholinocarbonyl)piperazin-1-yl]phenyl}morpholinocarboxyamide

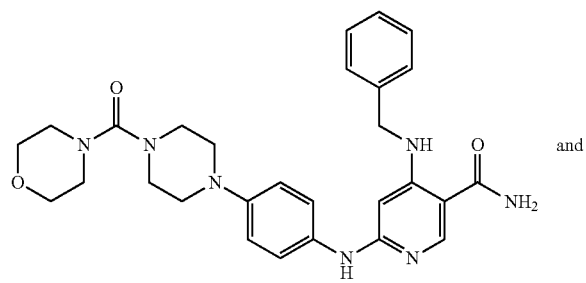

and

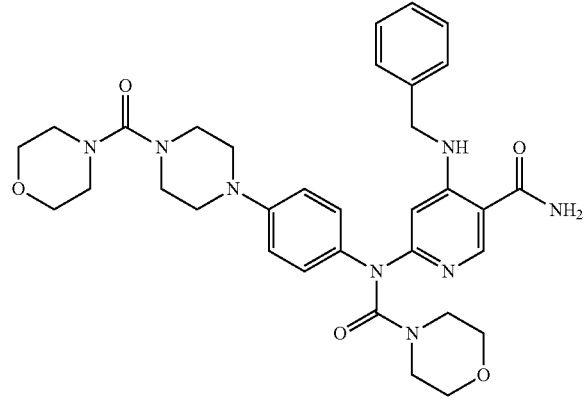

20 mg of 4-(benzylamino)-6-{[4-piperazin-1-yl]phenyl}amino)pyridine-3-carboxyamide (Example 219) was dissolved in 1 mL of dichloromethane and 1 mL of tetrahydrofuran, to which 11.2 mg of morpholino-4-carbonyl chloride and 4 mg of pyridine were added, and stirred overnight at room temperature. To the reaction mixture, water was added, extracted with chloroform-methanol (10:1), and the extract was dried on anhydrous sodium sulfate. The solvent was evaporated, and the residue was purified by silica gel thin layer chromatography (chloroform:ammonia methanol=10:1) to obtain 5.5 mg (19%) of 4-(benzylamino)-6-({4-[4-(morpholinocarbonyl)piperazin-1-yl]phenyl}amino)pyridine-3-carboxyamide (Example 285-1) as a slight yellow crystalline powder and 10 mg (32%) of N-[4-(benzylamino)-5-carbamoylpyridine-2-yl]-N-{4-[4-(morpholinocarbonyl)piperazin-1-yl]phenyl}morpholinocarboxyamide (Example 285-2) as a slight yellow crystalline powder.

4-(benzylamino)-6-({4-[4-(morpholinocarbonyl)piperazin-1-yl]phenyl}amino)pyridine-3-carboxyamide

Example 285-1

$^1$H-NMR (400 MHz, CDCl$_3$) δ: 3.13-3.15 (4H, t, J=5.0 Hz), 3.31-3.33 (4H, t, J=4.6 Hz), 3.44-3.46 (4H, t, J=5.0 Hz), 3.70-3.73 (4H, t, J=4.8 Hz), 4.30 (2H, d, J=5.8 Hz), 5.67 (2H, s), 5.75 (1H, s), 6.81 (2H, d, J=9.0 Hz), 6.93 (2H, d, J=8.8 Hz), 6.98 (1H, s), 7.22-7.37 (5H, m), 8.20 (1H, s), 8.94 (1H, t, J=5.6 Hz).

IR (ATR): 1618, 1513, 1416, 1231, 1113, 1029 cm$^{-1}$.

N-[4-(benzylamino)-5-carbamoylpyridine-2-yl]-N-{4-[4-(morpholinocarbonyl)piperazin-1-yl]phenyl}morpholinocarboxyamide

Example 285-2

$^1$H-NMR (400 MHz, CDCl$_3$) δ: 3.17-3.19 (4H, t, J=5.0 Hz), 3.31-3.34 (4H, t, J=4.6 Hz), 3.38-3.41 (4H, t, J=4.6 Hz), 3.43-3.46 (4H, t, J=5.0 Hz), 3.53-3.55 (4H, t, J=4.8 Hz), 3.70-3.72 (4H, t, J=4.8 Hz), 4.23 (2H, d, J=5.6 Hz), 5.75 (3H, brs), 6.83 (2H, d, J=9.0 Hz), 6.97 (2H, d, J=9.0 Hz), 7.15-7.17 (2H, m), 7.22-7.37 (5H, m), 8.31 (1H, s), 8.84 (1H, t, J=5.4 Hz).

IR (ATR): 1656, 1618, 1569, 1405, 1230, 1113, 1028 cm$^{-1}$

Example 286

Preparation of 4-(benzyl)-6-({4-[1-(propan-2-ylcarbamoyl)piperidin-4-yl]phenyl}amino)pyridine-3-carboxyamide

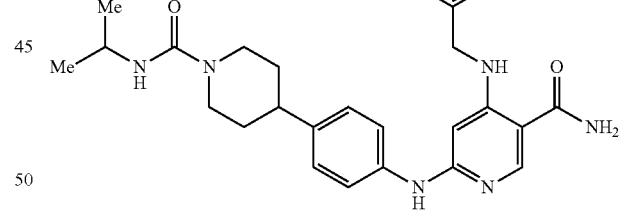

From 4-(benzylamino)-6-{[4-(piperidin-4-yl)phenyl]amino}pyridine-3-carboxyamide (the compound of Example 228) and isopropyl isocyanate in a manner similar to Example 283, the title compound was obtained as a white crystalline powder (yield 43%).

$^1$H-NMR (400 MHz, CDCl$_3$) δ: 1.18 (6H, d, J=6.4 Hz), 1.58-1.68 (2H, dq, J=12.4, 3.9 Hz), 1.84 (2H, d, J=13.4 Hz), 2.57-2.67 (1H, m), 2.81-2.91 (2H, dt, J=10.8, 2.2 Hz), 3.96-4.12 (3H, m), 4.28 (1H, d, J=7.3 Hz), 4.35 (2H, d, J=5.8 Hz), 5.66 (2H, s), 5.86 (1H, s), 6.69 (1H, s), 6.92 (2H, d, J=8.4 Hz), 7.05 (2H, d, J=8.4 Hz), 7.24-7.37 (5H, m), 8.22 (1H, s), 8.93 (1H, t, J=5.5 Hz).

IR (ATR): 3329, 2971, 1621, 1606, 1571, 1514, 1407, 1306, 1234, 730 cm$^{-1}$.

Example 287

Preparation of 4-(benzylamino)-6-{[4-(1-morpholinocarbonylpiperidin-4-yl)phenyl]amino}pyridine-3-carboxyamide

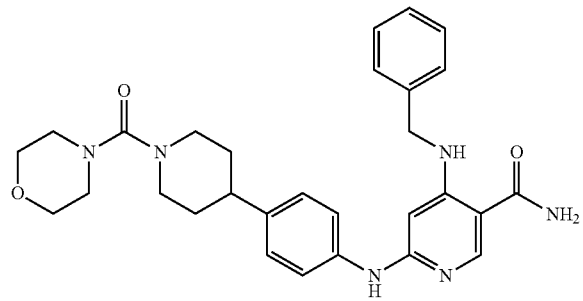 [SMILES: NC(=O)c1cnc(Nc2ccc(C3CCN(C(=O)N4CCOCC4)CC3)cc2)cc1NCc1ccccc1]

From 4-(benzylamino)-6-{[4-(piperidin-4-yl)phenyl]amino}pyridine-3-carboxyamide (the compound of Example 228) and morpholino-4-carbonyl chloride in a manner similar to Example 285, the title compound was obtained as a white crystalline powder (yield 33%).

$^1$H-NMR (400 MHz, CDCl$_3$) δ: 1.55-1.90 (4H, m), 2.55-2.70 (1H, m), 2.86-2.95 (2H, m), 3.28-3.31 (4H, t, J=4.8 Hz), 3.70-3.72 (4H, t, J=4.8 Hz), 3.85 (2H, d, J=13.2 Hz), 4.35 (2H, d, J=5.6 Hz), 5.63 (2H, s), 5.87 (1H, s), 6.83 (1H, s), 6.95 (2H, d, J=8.5 Hz), 7.07 (2H, d, J=8.5 Hz), 7.26-7.37 (5H, m), 8.21 (1H, s), 8.95 (1H, m).

IR (ATR): 3334, 2922, 2853, 1608, 1570, 1513, 1412, 1305, 1227, 1114, 754 cm$^{-1}$.

Example 288

Preparation of 4-(benzylamino)-6-({4-(1-(tert-butoxycarbonyl)piperidin-4-ylamino]phenyl}amino)pyridine-3-carboxyamide

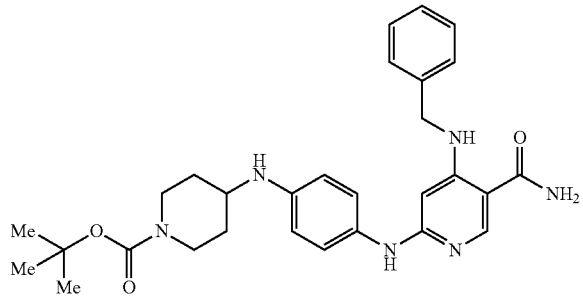 [SMILES: CC(C)(C)OC(=O)N1CCC(Nc2ccc(Nc3cc(NCc4ccccc4)c(C(N)=O)cn3)cc2)CC1]

30 mg of 6-[(4-aminophenyl)amino]-4-(benzylamino)pyridine-3-carboxyamide (Example 65) was dissolved in 2 mL of toluene and 2 mL of tetrahydrofuran, to which 54 mg of 1-Boc-4-piperidone and 38 mg of sodium triacetoxyborohydride were added, and stirred at room temperature for 19 hours. To the reaction mixture, water was added, extracted with chloroform, and dried on anhydrous sodium sulfate. The solvent was evaporated, and the residue was purified by silica gel thin layer chromatography (chloroform:methanol=5:1) to obtain 28 mg (60%) of the title compound as a light brown crystalline powder.

$^1$H-NMR (400 MHz, CDCl$_3$) δ: 1.28-1.39 (2H, m), 1.47 (9H, s), 2.01-2.08 (3H, m), 2.88-2.98 (2H, m), 3.35-3.43 (1H, m), 4.06 (2H, br), 4.28 (2H, d, J=5.6 Hz), 5.63 (2H, br), 5.67 (1H, s), 6.50 (2H, d, J=8.8 Hz), 6.54 (1H, br), 6.84 (2H, d, J=8.8 Hz), 7.22-7.33 (5H, m), 8.18 (1H, s), 8.85 (1H, brt, J=5.6 Hz).

Example 289

Preparation of 4-(benzylamino)-6-{[4-(piperidin-4-ylamino)phenyl]amino}pyridine-3-carboxyamide

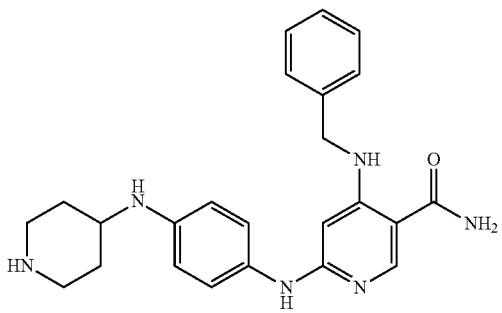 [SMILES: NC(=O)c1cnc(Nc2ccc(NC3CCNCC3)cc2)cc1NCc1ccccc1]

From 4-(benzylamino)-6-({4-[1-(tert-butoxycarbonyl)piperidin-4-ylamino]phenyl}amino)pyridine-3-carboxyamide (the compound of Example 288) in a manner similar to Example 248, the title compound was obtained as a light yellow crystalline powder (yield 90%).

m.p. 169-172° C. (dec.)

$^1$H-NMR (400 MHz, CDCl$_3$+CD$_3$OD) δ: 1.30-1.41 (2H, m), 2.06-2.13 (2H, m), 2.69-2.77 (2H, m), 3.10-3.18 (2H, m), 3.30-3.39 (1H, m), 4.26 (2H, s), 5.67 (1H, s), 6.52 (2H, d, J=8.8 Hz), 6.82 (2H, d, J=8.8 Hz), 7.22-7.34 (5H, m), 8.14 (1H, s), 8.86 (1H, br).

IR (ATR): 1651, 1616, 1565, 1518, 1406, 1300, 1258, 1148 cm$^{-1}$.

MS: m/z 416 (M$^+$).

Example 290

Preparation of 4-(benzylamino)-6-[(4-{[1-(diethylcarbamoyl)piperidin-4-yl]amino}phenyl)amino]pyridine-3-carboxyamide

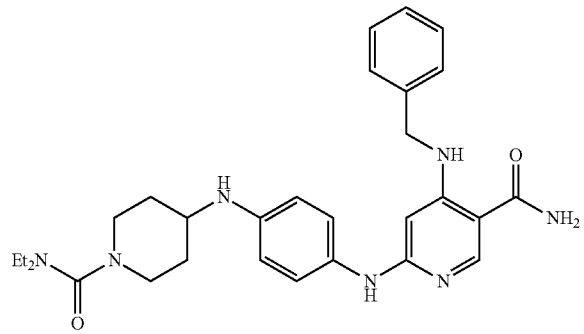

From 4-(benzylamino)-6-{[4-(piperidin-4-ylamino)phenyl]amino}pyridine-3-carboxyamide (the compound of Example 289) in a manner similar to Example 281, the title compound was obtained as light brown prism crystals (yield 34%).

¹H-NMR (400 MHz, CDCl₃) δ: 1.13 (6H, t, J=7.2 Hz), 1.36-1.48 (2H, m), 2.04-2.11 (2H, m), 2.88-2.96 (2H, m), 3.21 (4H, q, J=7.2 Hz), 3.37-3.45 (1H, m), 3.60-3.67 (2H, m), 4.28 (2H, d, J=5.6 Hz), 5.60 (2H, br), 5.67 (1H, s), 6.50 (2H, d, J=8.8 Hz), 6.73 (1H, brs), 6.85 (2H, d, J=8.8 Hz), 7.20-7.55 (5H, m), 8.18 (1H, s), 8.88 (1H, t, J=5.6 Hz).

IR (ATR): 1622, 1567, 1518, 1410, 1300, 1254, 1134 cm⁻¹.

MS: m/z 515 (M⁺, base peak).

Example 291

Preparation of 4-(benzylamino)-6-[(4-{[1-(propan-2-ylcarbamoyl)piperidin-4-yl]amino}phenyl)amino]pyridine-3-carboxyamide

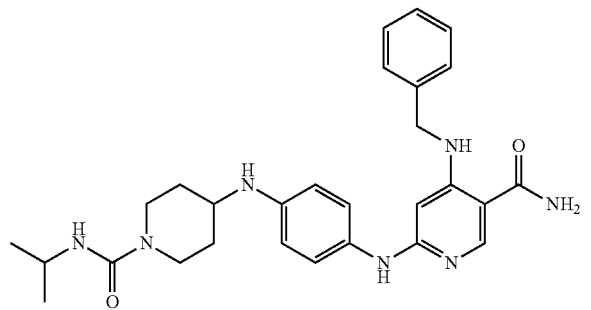 [SMILES: CC(C)NC(=O)N1CCC(Nc2ccc(Nc3cc(NCc4ccccc4)c(C(N)=O)cn3)cc2)CC1]

From 4-(benzylamino)-6-{[4-(piperidin-4-ylamino)phenyl]amino}pyridine-3-carboxyamide (the compound of Example 289) in a manner similar to Example 283, the title compound was obtained as a light brown crystalline powder (yield 34%).

m.p. 166-167° C.

¹H-NMR (400 MHz, CDCl₃) δ: 1.16 (6H, d, J=6.6 Hz), 1.31-1.43 (2H, m), 2.02-2.10 (2H, m), 2.92-3.00 (2H, m), 3.10 (1H, br), 3.36-3.45 (1H, m), 3.88-4.04 (3H, m), 4.27 (2H, d, J=5.6 Hz), 5.67 (1H, s), 5.78 (2H, br), 6.49 (2H, d, J=8.8 Hz), 6.84 (2H, d, J=8.8 Hz), 7.04 (1H, brs), 7.22-7.53 (5H, m), 8.18 (1H, s), 8.89 (1H, brt, J=5.6 Hz).

IR (ATR): 1613, 1571, 1514, 1408, 1300, 1258, 1230 cm⁻¹.

MS: m/z 502 (M⁺+1, base peak).

Example 292

Preparation of 4-[(2,3-difluorobenzyl)amino]-6-({4-[4-(methylsulfonyl)piperazin-1-yl]phenyl}amino)pyridine-3-carboxyamide

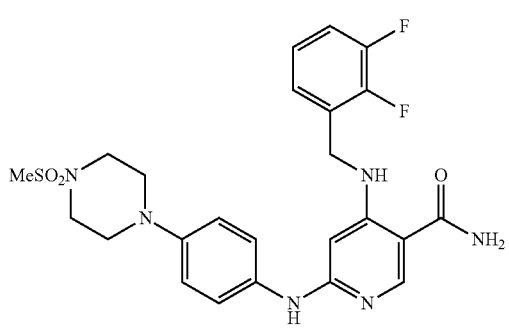

To a suspension of 60 mg of 4-[(2,3-difluorobenzyl)amino]-6-([4-(piperazin-1-yl)phenyl]amino)pyridine-3-carboxyamide (the compound of Example 220) in 2 mL of methylene chloride, under ice cooling, 20 mg of pyridine and 28 mg of methanesulfonyl chloride were added, and stirred at room temperature for 30 minutes. To the reaction mixture, saturated sodium bicarbonate in water was added, extracted with chloroform:methanol (5:1), washed with saturated saline, and dried on anhydrous sodium sulfate. The solvent was evaporated, the residue was purified by silica gel thin layer chromatography (chloroform:ammonia methanol=10:1) to obtain 47 mg (65%) of the title compound as a brown powder.

¹H-NMR (400 MHz, DMSO-d6) δ: 2.90 (3H, s), 4.47 (2H, d, J=6.1 Hz), 7.07 (2H, d, J=8.8 Hz), 7.10 (1H, m), 7.20 (1H, m), 7.35 (1H, m), 7.45 (2H, d, J=8.8 Hz), 8.32 (1H, s), 8.38 (1H, s), 8.88 (1H, s), 9.03 (1H, br), 9.35 (1H, br).

IR (ATR): 1664, 1536, 1409, 1305, 1142, 752 cm⁻¹

Example 293

Preparation of 4-[(3,5-difluorobenzyl)amino]-6-({4-[4-(methylsulfonyl)piperazin-1-yl]phenyl}amino)pyridine-3-carboxyamide

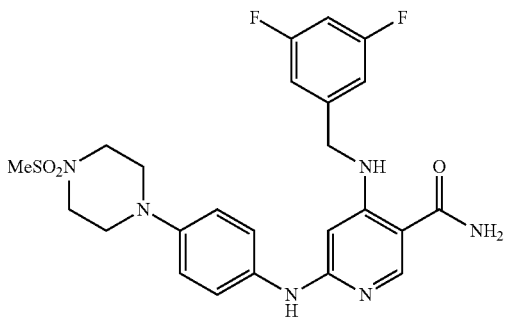

From 4-[(3,5-difluorobenzyl)amino]-6-{[4-(piperazin-1-yl)phenyl]amino}pyridine-3-carboxyamide (the compound of Example 221) in a manner similar to Example 292, the title compound was obtained as slight yellow needle crystals (yield 88%).

¹H-NMR (400 MHz, DMSO-d6) δ: 2.91 (3H, s), 3.10-3.14 (4H, m), 3.21-3.26 (4H, m), 4.39 (2H, d, J=5.8 Hz), 5.66 (1H, s), 6.83 (2H, d, J=8.8 Hz), 6.94-7.02 (2H, m), 7.04 (1H, br), 7.09-7.16 (1H, m), 7.23 (2H, d, J=8.8 Hz), 7.73 (1H, br), 8.34 (1H, s), 8.62 (1H, s), 9.03 (1H, t, J=5.8 Hz).

IR (ATR): 1611, 1595, 1518, 1407, 1324, 1295, 1278, 1242, 1159, 1116 cm⁻¹.

MS: m/z 516 (M⁺, base peak).

Example 294

Preparation of 4-(benzylamino)-6-({4-[1-(methylsulfonyl)piperidin-4-yl]phenyl}amino)pyridine-3-carboxyamide

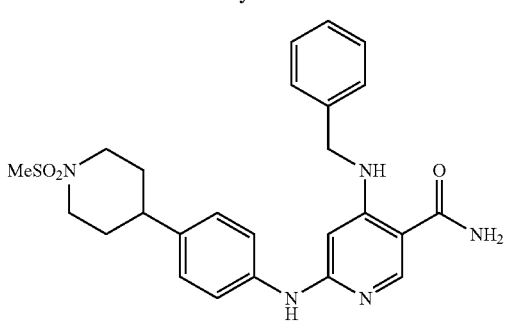

From 4-(benzylamino)-6-{[4-(piperidin-4-yl)phenyl]amino}pyridine-3-carboxamide (the compound of Example 228) in a manner similar to Example 292, the title compound was obtained as a slight yellow crystalline powder (yield 44%).

¹H-NMR (400 MHz, CDCl₃) δ: 1.80-1.87 (2H, m), 1.96 (2H, d, J=10.6 Hz), 2.57 (1H, t, J=12.0 Hz), 2.80 (2H, t, J=12.0 Hz), 2.83 (3H, s), 3.96 (2H, d, J=12.0 Hz), 4.36 (2H, s), 5.56 (2H, brs), 5.87 (1H, s), 6.46 (1H, brs), 6.96 (2H, d, J=8.6 Hz), 7.05 (2H, d, J=8.5 Hz), 7.27-7.38 (5H, m), 8.21 (1H, s), 8.91 (1H, brs).

Example 295

Preparation of 4-[(3,5-difluorobenzyl)amino]-6-({4-[1-(methylsulfonyl)piperidin-4-yl]phenyl}amino)pyridine-3-carboxyamide

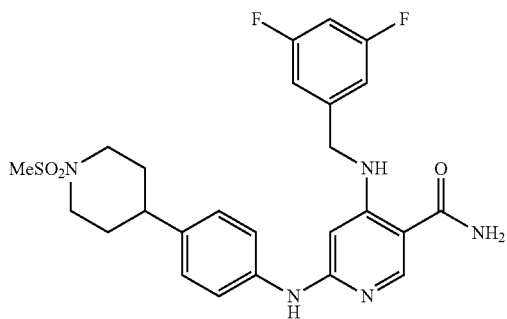

From 4-[(3,5-difluorobenzyl)amino]-6-{[4-(piperidin-4-yl)phenyl]amino}pyridine-3-carboxyamide (the compound of Example 229) in a manner similar to Example 292, the title compound was obtained as light yellow needle crystals (yield 58%).

m.p. 269-270° C.

¹H-NMR (400 MHz, DMSO-d₆) δ: 1.57-1.69 (2H, m), 1.80-1.86 (2H, m), 2.28-2.58 (1H, m), 2.75-2.84 (2H, m), 2.89 (3H, s), 3.62-3.69 (2H, m), 4.41 (2H, d, J=6.0 Hz), 5.75 (1H, s), 6.96-7.04 (2H, m), 7.12 (2H, d, J=8.6 Hz), 7.15 (1H, dddd, J=9.5, 9.5, 2.2, 2.2 Hz), 7.32 (2H, d, J=8.6 Hz), 7.79 (1H, br), 8.37 (1H, s), 8.81 (1H, brs), 9.05 (1H, brt, J=6.0 Hz).

IR (ATR): 1630, 1600, 1572, 1413, 1325, 1311, 1261, 1250, 1148, 1118 cm⁻.

MS: m/z 516 (M⁺), 136 (base peak).

Example 296

Preparation of 4-[(3,5-difluorobenzyl)amino]-6-({4-[1-(propan-2-ylsulfonyl)piperidin-4-yl]phenyl}amino) pyridine-3-carboxyamide

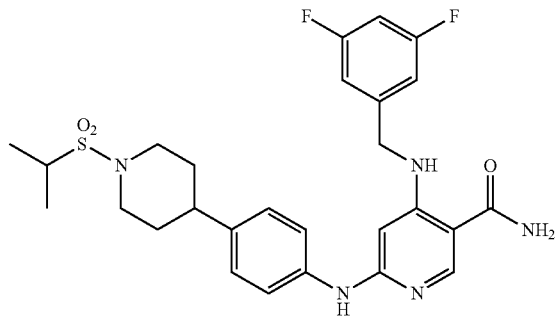 [SMILES: CC(C)S(=O)(=O)N1CCC(c2ccc(Nc3cc(NCc4cc(F)cc(F)c4)c(C(N)=O)cn3)cc2)CC1]

From 4-[(3,5-difluorobenzyl)amino]-6-{[4-(piperidin-4-yl)phenyl]amino}pyridine-3-carboxyamide (the compound of Example 229) and 2-propanesulfonyl chloride in a manner similar to Example 292, the title compound was obtained as a slight yellow crystalline powder (yield 58%).

m.p. 142-144° C. (dec.)

¹H-NMR (400 MHz, CD₃OD) δ: 1.33 (6H, d, J=6.8 Hz), 1.63-1.76 (2H, m), 1.82-1.90 (2H, m), 2.61-2.73 (1H, m), 2.98-3.11 (2H, m), 3.29-3.36 (1H, m), 3.72-3.93 (2H, m), 4.39 (2H, s), 5.75 (1H, s), 6.84-6.95 (3H, m), 7.02-7.07 (2H, m), 7.08-7.12 (2H, m), 8.27 (1H, s).

IR (ATR): 1625, 1599, 1573, 1547, 1516, 1411, 1310, 1251, 1136, 1117, 946 cm⁻¹.

MS: m/z 544(M⁺+1), 136 (base peak).

Example 297

Preparation of 4-[(3,5-difluorobenzyl)amino]-6-[(4-{4-[(methanesulfonyl)amino]piperidino}phenyl)amino]pyridine-3-carboxyamide

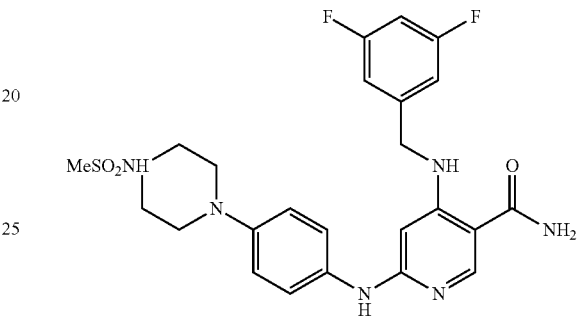

From 6-{[4-(4-aminopiperidino)phenyl]amino}-4-[(3,5-difluorobenzyl)amino]pyridine-3-carboxyamide (the compound of Example 230) in a manner similar to Example 292, the title compound was obtained as white amorphous crystals (yield 100%).

¹H-NMR (400 MHz, CDCl₃) δ: 1.45-1.57 (2H, m), 1.89-1.95 (2H, m), 2.75-2.84 (2H, m), 2.79 (3H, s), 3.84-3.90 (2H, m), 4.39 (2H, d, J=5.9 Hz), 4.58-4.66 (1H, m), 5.79 (1H, s), 5.79 (2H, br), 6.75 (1H, dddd, J=8.9, 8.9, 2.3, 2.3 Hz), 6.81-6.88 (2H, m), 6.96 (2H, d, J=8.6 Hz), 6.98 (1H, brs), 7.09 (2H, d, J=8.6 Hz), 8.28 (1H, s), 9.06 (1H, brt, J=5.9 Hz).

IR (ATR): 1689, 1656, 1621, 1598, 1594, 1510, 1406, 1317, 1194, 1154, 1118 cm⁻¹.

Example 298

Preparation of 4-(benzylamino)-6-({4-[4-(methylsulfonyl)-1,4-diazepan-1-yl]phenyl}amino)pyridine-3-carboxyamide

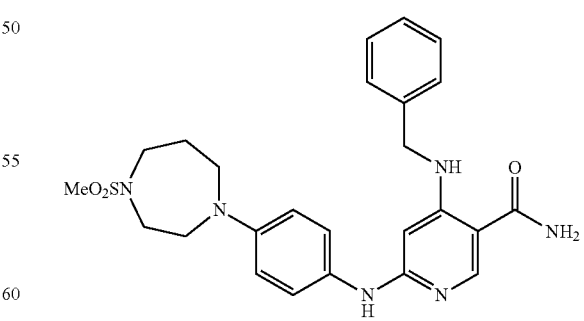

From 4-(benzylamino)-6-{[4-(1,4-diazepan-1-yl)phenyl]amino}pyridine-3-carboxyamide (the compound of Example 226) in a manner similar to Example 292, the title compound was obtained as a light yellow needle crystals (yield 76%).

m.p. 198.2-199.2° C.

¹H-NMR (400 MHz, CDCl₃+CD₃OD) δ: 2.03-2.11 (2H, m), 2.76 (3H, s), 3.24-3.31 (2H, m), 3.50-3.54 (2H, m), 3.64-3.70 (4H, m), 4.28 (2H, d, J=3.7 Hz), 5.67 (1H, s), 6.57 (2H, d, J=9.0 Hz), 6.89 (2H, d, J=9.0 Hz), 7.22-7.35 (5H, m), 8.16 (1H, s), 8.88 (1H, br).

IR (ATR): 1623, 1602, 1566, 1542, 1412, 1321, 1305, 1260, 1214, 1140 cm⁻¹.

MS: m/z 495 (M⁺+H), 154 (base peak).

Example 299

Preparation of 4-[(3,5-difluorobenzyl)amino]-6-({4-[4-(propan-2-ylsulfonyl)-1,4-diazepan-1-yl]phenyl}amino) pyridine-3-carboxamide

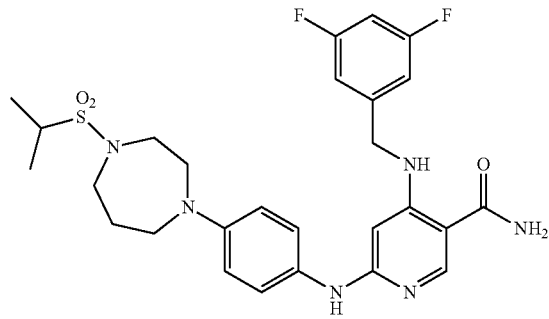 [SMILES: CC(C)S(=O)(=O)N1CCCN(c2ccc(Nc3cc(NCc4cc(F)cc(F)c4)c(C(N)=O)cn3)cc2)CC1]

From 6-{[4-(1,4-diazepan-1-yl)phenyl]amino}-4-[(3,5-difluorobenzyl)amino]pyridine-3-carboxamide (the compound of Example 227) and 2-propanesulfonyl chloride in a manner similar to Example 292, the title compound was obtained as white needle crystals (yield 75%).

m.p. 197-198° C. (dec.)

¹H-NMR (400 MHz, CDCl₃) δ: 1.33 (6H, d, J=6.8 Hz), 1.96-2.14 (2H, m), 3.18-3.31 (3H, m), 3.51-3.56 (2H, m), 3.63-3.73 (4H, m), 4.27 (2H, d, J=6.1 Hz), 5.53 (1H, s), 5.63 (2H, br), 6.41 (1H, brs), 6.58 (2H, d, J=9.0 Hz), 6.72 (1H, dddd, J=8.8, 8.8, 2.4, 2.4 Hz), 6.75-6.80 (2H, m), 6.83 (2H, d, J=9.0 Hz), 8.19 (1H, s), 8.97 (1H, brt, J=6.1 Hz).

IR (ATR): 1631, 1608, 1565, 1519, 1413, 1400, 1316, 1301, 1262, 1126, 1113 cm⁻¹.

Example 300

Preparation of 4-(benzylamino)-6-({4-[bis(methylsulfonyl)amino]phenyl}amino)pyridine-3-carboxamide

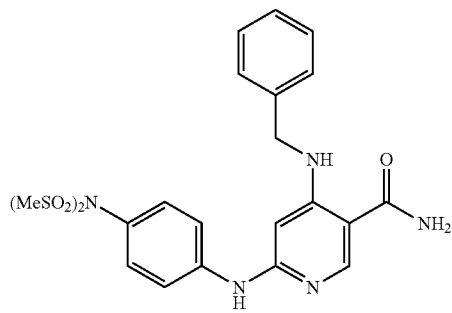

To 30 mg of 6-[(4-aminophenyl)amino]-4-(benzylamino)pyridine-3-carboxamide (the compound of Example 65) dissolved in 5 mL of methylene chloride, under ice cooling, 18 mg of triethylamine and 15 mg of methanesulfonyl chloride were added, and stirred at room temperature for 30 minutes. Furthermore, 18 mg of triethylamine and 15 mg of methanesulfonyl chloride were added, and stirred at room temperature for 1 hour. To the reaction mixture, ammonia water was added, the methylene chloride layer was separated, washed with water, and dried on anhydrous sodium sulfate. The solvent was evaporated, and the residue was purified by silica gel column chromatography (chloroform:methanol=30:1) to obtain 40 mg (92%) of the title compound as a light brown crystalline powder.

¹H-NMR (400 MHz, CDCl₃) δ: 3.60 (6H, s), 4.41 (2H, q, J=5.6 Hz), 5.63 (2H, br), 5.92 (1H, s), 6.71 (1H, brs), 7.10 (2H, d, J=8.8 Hz), 7.15 (2H, d, J=8.8 Hz), 7.29-7.40 (5H, m), 8.24 (1H, s), 8.97 (1H, brt, J=5.6 Hz).

IR (ATR): 1655, 1622, 1599, 1574, 1507, 1415, 1360, 1323, 1153 cm⁻¹.

Example 301

Preparation of 4-(benzylamino)-6-({4-[(methylsulfonyl)amino]phenyl}amino)pyridine-3-carboxamide

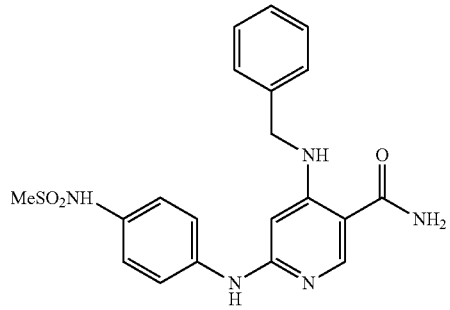

30 mg of 4-(benzylamino)-6-({4-[bis(methylsulfonyl)amino]phenyl}amino)pyridine-3-carboxamide (the compound of Example 300) was dissolved in 3 mL of methanol, to which 1 mL of 4 mol/L sodium hydroxide in water was added at room temperature, and stirred at 50° C. for 10 minutes. Under ice cooling, 2 mol/L hydrochloric acid in water was added to acidify the solution, extracted with chloroform, the extract was washed with water, and dried on anhydrous sodium sulfate. The solvent was evaporated to obtain 25 mg (99%) of the title compound as a slight yellow crystalline powder.

¹H-NMR (400 MHz, CD₃OD) δ: 2.91 (3H, s), 4.35-4.38 (2H, m), 5.83 (1H, s), 7.11 (4H, s), 7.25-7.88 (5H, m), 8.27 (1H, s).

IR (ATR): 1643, 1602, 1571, 1510, 1412, 1307, 1253, 1221, 1147 cm⁻¹.

Example 302

Preparation of 4-[(3,5-difluorobenzyl)amino]-6-({4-[(propan-2-ylsulfonyl)amino]phenyl}amino)pyridine-3-carboxyamide

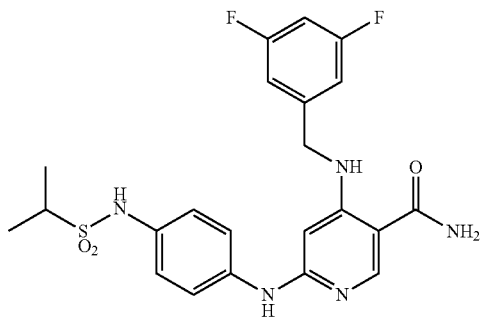 [SMILES: CC(C)S(=O)(=O)Nc1ccc(Nc2cc(NCc3cc(F)cc(F)c3)c(C(N)=O)cn2)cc1]

From 6-[(4-aminophenyl)amino]-4-[(3,5-difluorobenzyl)amino]pyridine-3-carboxyamide (the compound of Example 67) and 2-propanesulfonyl chloride in a manner similar to Example 292, the title compound was obtained as a light brown crystalline powder (yield 43%).

$^1$H-NMR (400 MHz, DMSO-d6) δ: 1.23 (6H, d, J=6.8 Hz), 3.13 (1H, sept, J=6.8 Hz), 4.42 (2H, d, J=5.8 Hz), 5.74 (1H, s), 6.97-7.04 (2H, m), 7.08 (2H, d, J=9.0 Hz), 7.12 (1H, dddd, J=9.3, 9.3, 2.1, 2.1 Hz), 7.39 (2H, brd, J=9.0 Hz), 7.80 (1H, br), 8.37 (1H, s), 8.84 (1H, s), 9.05 (1H, brt, J=5.8 Hz), 9.45 (1H, s).

IR (ATR): 1633, 1598, 1575, 1554, 1512, 1462, 1415, 1309, 1253, 1223, 1135, 1117 cm$^{-1}$.

MS: m/z 476 (M$^+$+1), 93 (base peak).

Example 303

Preparation of 4-[(3,5-difluorobenzyl)amino]-6-({4-[(vinylsulfonyl)amino]phenyl}amino)pyridine-3-carboxyamide

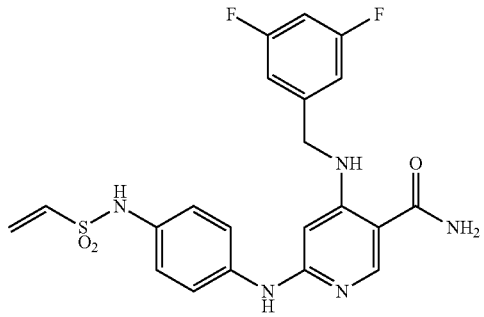 [SMILES: C=CS(=O)(=O)Nc1ccc(Nc2cc(NCc3cc(F)cc(F)c3)c(C(N)=O)cn2)cc1]

100 mg of 6-[(4-aminophenyl)amino]-4-[(3,5-difluorobenzyl)amino]pyridine-3-carboxyamide (the compound of Example 67) was dissolved in 3 mL of tetrahydrofuran, to which 190 μl of triethylamine and 40 μl of chloroethanesulfonyl chloride were added, and stirred at room temperature for 5 hours. To the reaction mixture, chloroform was added, washed with water, and dried on anhydrous sodium sulfate. The solvent was evaporated to obtain 100 mg of the mixture of the title compound and the feed material (the title compound:feed material=20:1) as a brown solid. Without further purification, this was used as it was in the next reaction.

Example 304

Preparation of 6-{[4-({[2-(diethylamino)ethyl]sulfonyl}amino)phenyl]amino}-4-[(3,5-difluorobenzyl)amino]pyridine-3-carboxyamide

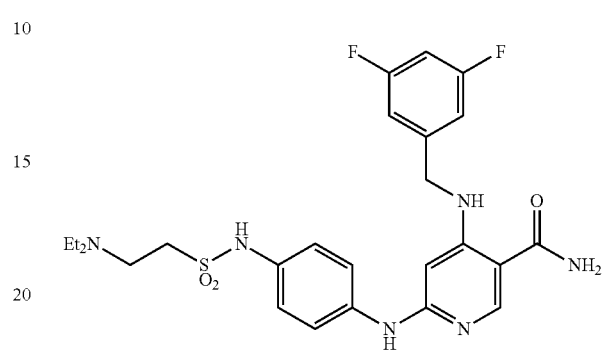

89 mg of 4-[(3,5-difluorobenzyl)amino]-6-({4-[(vinylsulfonyl)amino]phenyl}amino)pyridine-3-carboxyamide (the compound of Example 303) was dissolved in 1 mL of methanol, to which 0.28 mL of diethylamine was added, and stirred using a microwave reaction apparatus in an argon atmosphere at 120° C. for 30 minutes. The solvent was evaporated, and the residue was purified by silica gel column chromatography (chloroform:ammonia methanol=10:1), and solidified in acetone-ether to obtain 41 mg (yield 29%: 2 steps) of the title compound as a white powder.

$^1$H-NMR (270 MHz, CD$_3$OD) δ: 0.93-1.04 (6H, br m), 1.11-1.22 (2H, br m), 2.40-2.55 (4H, m), 2.87-2.91 (2H, br m), 3.12-3.23 (4H, m), 3.53-3.64 (2H, br m), 4.35-4.44 (2H, m), 5.76 (1H, s), 6.75-6.95 (3H, m), 7.06-7.24 (4H, m), 8.29 (1H, s).

Example 305

Preparation of 6-[(4-{[(2-aminoethyl)sulfonyl]amino}phenyl)amino]-4-[(3,5-difluorobenzyl)amino]pyridine-3-carboxyamide

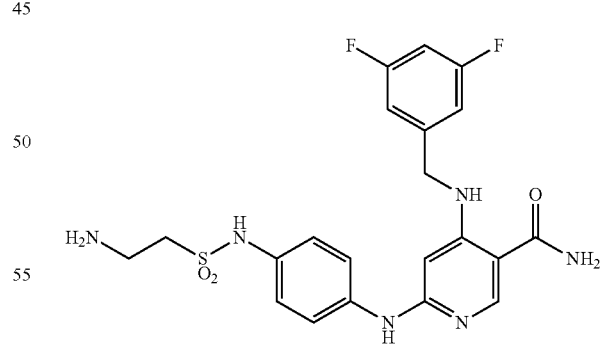

From 4-[(3,5-difluorobenzyl)amino]-6-({4-[(vinylsulfonyl)amino]phenyl}amino)pyridine-3-carboxyamide (the compound of Example 303) and a saturated ammonia methanol solution in a manner similar to Example 304, the title compound (yield 22%: 2 steps) was obtained as a white solid.

$^1$H-NMR (270 MHz, DMSO-d6) δ: 2.86 (2H, t, J=6.6 Hz), 3.05 (3H, t, J=6.6 Hz), 4.41 (2H, s), 5.74 (1H, s), 6.95-7.14 (5H, m), 7.35-7.43 (2H, m), 8.36 (1H, s), 8.87 (1H, s), 9.04 (1H, s).

Example 306

Preparation of 4-(benzylamino)-6-({4-[(3-chloropropylsulfonyl)amino]phenyl}amino)pyridine-3-carboxamide

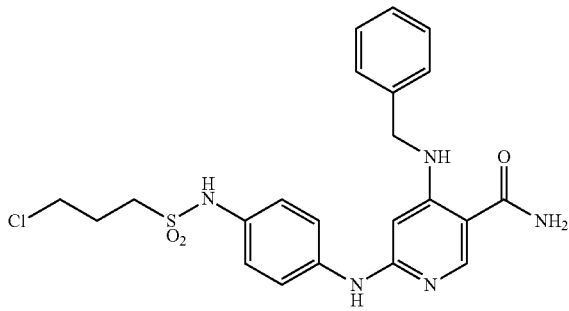 [SMILES: NC(=O)c1cnc(Nc2ccc(NS(=O)(=O)CCCCl)cc2)cc1NCc1ccccc1]

10 mg of 6-[(4-aminophenyl)amino]-4-(benzylamino) pyridine-3-carboxyamide (the compound of Example 65) was dissolved in 0.5 mL of methylene chloride, to which 8 mg of 3-chloropropane sulfonyl acid chloride and 6 mg of triethylamine were added, and stirred at room temperature for 3 hours. Furthermore, 8 mg of 3-chloropropane sulfonyl acid chloride and 6 mg of triethylamine were added, and stirred at room temperature twice for every 1 hour, and stirred for 1 hour. To the reaction mixture, under ice cooling, ammonia water was added, stirred for 5 minutes, the reaction mixture was extracted with chloroform, the extract was washed with saturated saline, and dried on anhydrous sodium sulfate. The solvent was evaporated, and the residue was purified by silica gel thin layer chromatography (chloroform:ammonia methanol=10:1). The recovered product (18 mg) was dissolved in methanol, to which 2 mol/L sodium hydroxide in water was added, and stirred for 30 minutes. 2 mol/L hydrochloric acid was added thereto to neutralize the solution, extracted with chloroform, the extract was washed with saturated saline, and then dried on anhydrous sodium sulfate. The solvent was evaporated to obtain 12 mg (84%) of the title compound as a brown crystalline powder.

$^1$H-NMR (400 MHz, CDCl$_3$) δ: 2.10-2.50 (2H, m), 3.23 (2H, t, J=7.4 Hz), 3.66 (2H, t, J=6.1 Hz), 4.34 (2H, br), 5.83 (1H, s), 6.95 (2H, br, J=8.9 Hz), 7.09 (2H, br, J=8.9 Hz), 7.20-7.40 (5H, m), 8.18 (1H, s).

Example 307

Preparation of 4-(benzylamino)-6-{[4-(1,1-dioxo-1,2-thiazolidin-2-yl)phenyl]amino}pyridine-3-carboxyamide

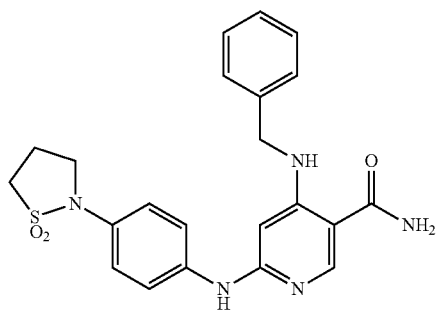 [SMILES: NC(=O)c1cnc(Nc2ccc(N3CCCS3(=O)=O)cc2)cc1NCc1ccccc1]

12 mg of 4-(benzylamino)-6-({4-[(3-chloropropylsulfonyl)amino]phenyl}amino)pyridine-3-carboxyamide (the compound of Example 306) was dissolved in 1 mL of acetonitrile, to which 0.2 mL of diethylamine and 7 mg of potassium carbonate were added, and stirred at 80° C. for 1 hour. After cooling, water was added to the reaction mixture, extracted with chloroform, the extract was washed with saturated saline, and dried on anhydrous sodium sulfate. The solvent was evaporated, and the residue was purified by silica gel column chromatography (chloroform:methanol=10:1) to obtain 12 mg (100%) of the title compound as a brown crystalline powder.

$^1$H-NMR (400 MHz, CDCl$_3$) δ: 2.50-2.58 (2H, m), 3.40 (2H, t, J=7.6 Hz), 3.75 (2H, t, J=6.3 Hz), 4.34 (2H, brd, J=5.4 Hz), 5.83 (1H, s), 6.97 (2H, d, J=8.9 Hz), 7.14 (2H, d, J=8.9 Hz), 7.24-7.38 (5H, m), 8.18 (1H, s).

IR (ATR): 1662, 1621, 1578, 1513, 1471, 1408, 1356, 1297, 1249, 1137 cm$^{-1}$.

MS: m/z 438 (M$^+$+1), 136 (base peak).

Example 308

Preparation of 4-(benzylamino)-6-[(4-{[1-(tert-butoxycarbonyl)pyridin-3-ylcarbonyl]amino}phenyl)amino]pyridine-3-carboxyamide

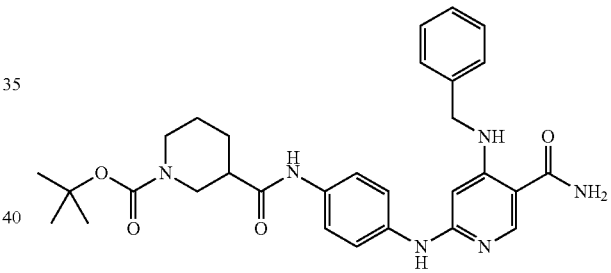

30 mg of 6-[(4-aminophenyl)amino]-4-(benzylamino) pyridine-3-carboxyamide (the compound of Example 65) was dissolved in 2 mL of methylene chloride, to which 25 mg of 1-(tert-butoxycarbonyl)-3-piperidine carboxylic acid, 21 mg of 1-ethyl-3-(3-dimethylaminopropyl)carbodiimide hydrochloride and 13 mg of N,N-dimethylaminopyridine were added, and stirred overnight at room temperature. The reaction mixture was washed with water, and dried on anhydrous sodium sulfate. The solvent was evaporated, and the residue was purified by silica gel thin layer chromatography (chloroform:methanol) to obtain 38 mg (78%) of the title compound as a light pink crystalline powder.

$^1$H-NMR (270 MHz, CDCl$_3$) δ: 1.48 (11H, s), 1.88-1.95 (1H, m), 2.45-2.55 (1H, m), 3.18-3.31 (1H, m), 3.49-3.89 (4H, m), 4.33 (2H, d, J=5.4 Hz), 5.59 (2H, d, J=2.4 Hz), 5.84 (1H, s), 6.83-6.94 (3H, m), 7.22-7.47 (9H, m), 8.91 (1H, s), 8.94 (1H, t, J=4.6 Hz).

IR (ATR): 1638, 1605, 1514, 1414, 1303, 1246, 1169, 1149 cm$^{-1}$.

MS: m/z 544(M$^+$), 444, 333, 262 (base peak).

Example 309

Preparation of 4-(benzylamino)-6-[(4-{[1-(tert-butoxycarbonyl)piperidin-4-ylcarbonyl]amino}phenyl)amino]pyridine-3-carboxyamide

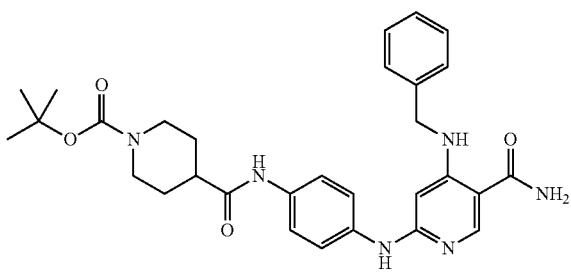 [SMILES: CC(C)(C)OC(=O)N1CCC(C(=O)Nc2ccc(Nc3cc(NCc4ccccc4)c(C(N)=O)cn3)cc2)CC1]

From 6-[(4-aminophenyl)amino]-4-(benzylamino) pyridine-3-carboxyamide (the compound of Example 65) and 1-(tert-butoxycarbonyl)-4-piperidine carboxylic acid in a manner similar to Example 308, the title compound was obtained as a light pink crystalline powder (yield 57%).

$^1$H-NMR (270 MHz, CDCl$_3$+CD$_3$OD) δ: 1.47 (9H, s), 1.71-1.91 (4H, m), 2.39-2.48 (1H, m), 3.80 (2H, brt, J=11.6 Hz), 4.16 (2H, brd, J=13.8 Hz), 4.32 (2H, s), 5.84 (1H, s), 6.94 (2H, d, J=8.9 Hz), 7.22-7.45 (7H, m), 8.17 (1H, s).

IR (ATR): 1653, 1605, 1515, 1414, 1243, 1168 cm$^{-1}$.

MS: m/z 544 (M$^+$), 333 (base peak).

Example 310

Preparation of 6-[(4-{[1-(tert-butoxycarbonyl)piperidin-4-ylcarbonyl]amino}phenyl)amino]-4-[(3,5-difluorobenzyl)amino]pyridine-3-carboxyamide

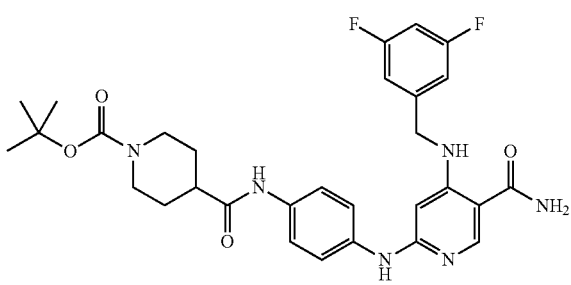 [SMILES: CC(C)(C)OC(=O)N1CCC(C(=O)Nc2ccc(Nc3cc(NCc4cc(F)cc(F)c4)c(C(N)=O)cn3)cc2)CC1]

From 6-[(4-aminophenyl)amino]-4-[(3,5-difluorobenzyl)amino]pyridine-3-carboxyamide (the compound of Example 67) and 1-(tert-butoxycarbonyl)-4-piperidine carboxylic acid in a manner similar to Example 308, the title compound was obtained as a slight brown crystalline powder (yield 78%).

$^1$H-NMR (400 MHz, DMSO-d6) δ: 1.39 (9H, s), 1.40-1.52 (2H, m), 1.68-1.78 (2H, m), 2.40-2.60 (1H, m), 2.72 (2H, br), 3.94-4.02 (2H, m), 4.40 (2H, d, J=6.1 Hz), 5.72 (1H, s), 6.99 (2H, m), 7.07 (1H, br), 7.11 (1H, dddd, J=9.3, 9.3, 2.2, 2.2 Hz), 7.34 (2H, d, J=9.0 Hz), 7.42 (2H, d, J=9.0 Hz), 7.78 (1H, br), 8.36 (1H, s), 8.78 (1H, s), 9.03 (1H, brt, J=6.1 Hz), 9.75 (1H, s).

Example 311

Preparation of 4-(benzylamino)-6-({4-[1-(tert-butoxycarbonyl)-L-prolylamino]phenyl}amino)pyridine-3-carboxyamide

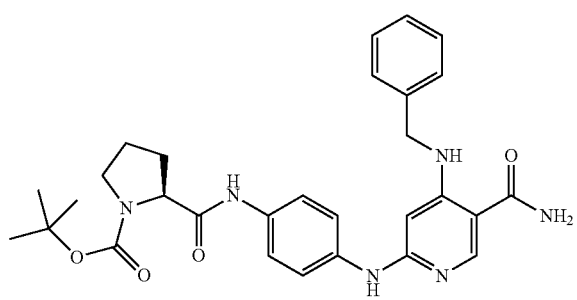 [SMILES: CC(C)(C)OC(=O)N1CCC[C@H]1C(=O)Nc1ccc(Nc2cc(NCc3ccccc3)c(C(N)=O)cn2)cc1]

From 6-[(4-aminophenyl)amino]-4-(benzylamino) pyridine-3-carboxyamide (the compound of Example 65) and N-tert-butoxycarbonyl-L-proline in a manner similar to Example 308, the title compound was obtained as a light pink crystalline powder (yield 71%).

$^1$H-NMR (270 MHz, CDCl$_3$) δ: 1.51 (11H, s), 1.95 (2H, brs), 3.44 (2H, br), 4.32 (2H, d, J=5.9 Hz), 4.45 (1H, brs), 5.59 (2H, s), 5.82 (1H, s), 6.72 (1H, s), 6.92 (2H, d, J=8.4 Hz), 7.21-7.41 (9H, m), 8.91 (1H, s), 8.93 (1H, t, J=5.7 Hz).

IR (ATR): 1649, 1607, 1513, 1405, 1304, 1252, 1160 cm$^{-1}$.

MS: m/z 530(M$^+$), 333 (base peak).

Example 312

Preparation of 6-({4-[1-(tert-butoxycarbonyl)-L-prolylamino]phenyl}amino)-4-[(3,5-difluoro)benzylamino]pyridine-3-carboxyamide

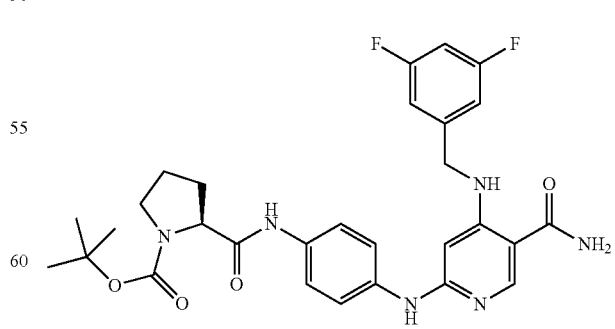

From 6-[(4-aminophenyl)amino]-4-[(3,5-difluorobenzyl)amino]pyridine-3-carboxyamide (the compound of Example 67) and N-tert-butoxycarbonyl-L-proline in a manner similar to Example 308, the title compound was obtained as a light brown crystalline powder with a yield of 90%.

Example 313

Preparation of 4-(benzylamino)-6-({4-[(piperidin-3-ylcarbonyl)amino]phenyl}amino)pyridine-3-carboxamide hydrochloride

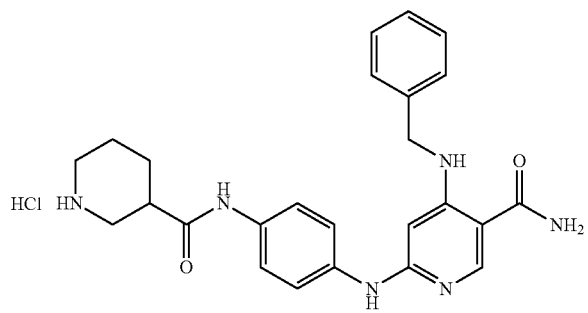 [SMILES: Cl ; NC(=O)c1cnc(Nc2ccc(NC(=O)C3CCCNC3)cc2)cc1NCc1ccccc1]

25.9 mg of 4-(benzylamino)-6-[(4-{[1-(tert-butoxycarbonyl)piperidin-3-ylcarbonyl]amino}phenyl)amino]pyridine-3-carboxamide (the compound of Example 308) was dissolved in 1 mL of methanol, to which 1 mL of 4 mol/L hydrochloric acid-ethyl acetate was added, and stirred at room temperature for 30 minutes. The solvent was evaporated, ether was added to the residue, the deposited crystals were filtered to obtain 20.7 mg (91%) of the title compound as a light brown crystalline powder.

$^1$H-NMR (400 MHz, DMSO-d6, 115° C.) δ: 1.87-2.09 (4H, m), 2.90-3.34 (5H, m), 4.41 (2H, s), 5.90 (1H, s), 7.09-7.61 (11H, m), 8.32 (1H, s), 9.51 (1H, br), 10.06 (1H, s).

IR (ATR): 1672, 1590, 1560, 1511, 1408, 1246 cm$^{-1}$.

Example 314

Preparation of 4-(benzylamino)-6-({4-[piperidin-4-ylcarbonyl]amino]phenyl}amino)pyridine-3-carboxamide hydrochloride

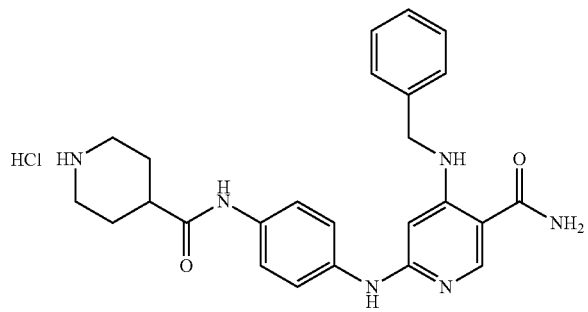 [SMILES: Cl ; NC(=O)c1cnc(Nc2ccc(NC(=O)C3CCNCC3)cc2)cc1NCc1ccccc1]

From 4-(benzylamino)-6-[(4-{[1-(tert-butoxycarbonyl)piperidin-4-ylcarbonyl]amino}phenyl)amino]pyridine-3-carboxamide (the compound of Example 309) in a manner similar to Example 313, the title compound was obtained as a light brown crystalline powder (yield 98%).

$^1$H-NMR (400 MHz, DMSO-d6, 115° C.) δ: 1.89-1.99 (4H, m), 2.68-3.24 (5H, m), 4.41 (2H, s), 5.89 (1H, s), 7.08-7.58 (11H, m), 8.30 (1H, s), 9.49 (1H, br), 9.82 (1H, s).

IR (ATR): 1681, 1655, 1561, 1509, 1411, 146 cm$^{-1}$.

Example 315

Preparation of 4-[(3,5-difluorobenzyl)amino]-6-({4-[(piperidin-4-ylcarbonyl)amino]phenyl}amino)pyridine-3-carboxamide hydrochloride

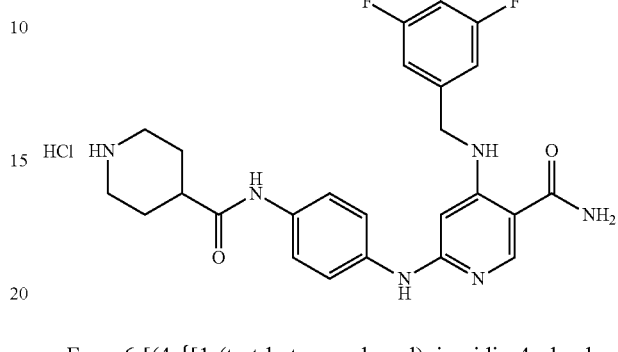

From 6-[(4-{[1-(tert-butoxycarbonyl)piperidin-4-ylcarbonyl]amino}phenyl)amino]-4-[(3,5-difluorobenzyl)amino] pyridine-3-carboxamide (the compound of Example 310) in a manner similar to Example 313, a crude product was obtained. This was recrystallized from methanol to obtain the title compound as a light brown crystalline powder (yield 62%).

m.p. 328-334° C. (dec.)

$^1$H-NMR (400 MHz, DMSO-d6) δ: 1.79-1.92 (2H, m), 1.93-2.01 (2H, m), 2.65-2.75 (1H, m), 2.85-2.97 (2H, m), 3.26-3.40 (2H, m), 4.50 (2H, d, J=5.9 Hz), 5.79 (1H, s), 6.95-7.10 (2H, m), 7.07 (1H, d, J=8.8 Hz), 7.12-7.19 (1H, m), 7.66 (2H, d, J=8.8 Hz), 8.29 (1H, s), 8.83 (1H, br), 9.16 (1H, br), 9.75 (1H, brs), 9.98 (1H, brs), 10.39 (1H, s), 12.86 (1H, br).

IR (ATR): 1682, 1673, 1654, 1626, 1597, 1550, 1518, 1448, 1414, 1356, 1318, 1245, 1118 cm$^{-1}$.

MS: m/z 480 (M$^+$, base peak).

Example 316

Preparation of 4-(benzylamino)-6-({4-(L-prolylamino) phenyl]amino}pyridine-3-carboxamide hydrochloride

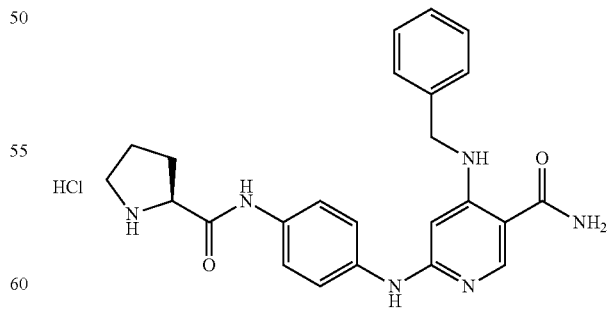

From 4-(benzylamino)-6-({4-[1-(tert-butoxycarbonyl)-L-prolylamino]phenyl}amino)pyridine-3-carboxamide (the compound of Example 311) in a manner similar to Example 313, the title compound was obtained as a light brown crystalline powder (yield 94%).

¹H-NMR (400 MHz, DMSO-d6, 115° C.) δ: 1.94-2.07 (2H, m), 3.23-3.38 (5H, m), 4.42 (2H, s), 5.92 (1H, s), 7.17-7.60 (11H, m), 8.32 (1H, s), 9.42 (1H, br), 10.59 (1H, s).

IR (ATR): 1694, 1671, 1651, 1563, 1537, 1514, 1413, 1249 cm⁻¹.

Example 317

Preparation of 4-[(3,5-difluorobenzyl)amino]-6-{[4-(L-prolylamino)phenyl]amino}pyridine-3-carboxyamide hydrochloride

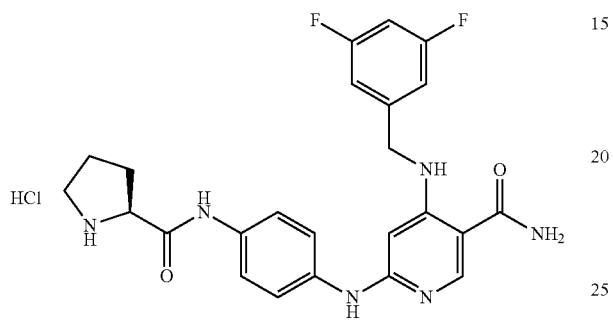

From 6-({4-[1-(tert-butoxycarbonyl)-L-prolylamino]phenyl}amino)-4-[(3,5-difluoro)benzylamino]pyridine-3-carboxyamide (the compound of Example 312) in a manner similar to Example 313, the title compound was obtained as a light brown crystalline powder (yield 97%).

m.p. 209-215° C. (dec.)

¹H-NMR (400 MHz, DMSO d₆) δ: 1.90-1.99 (3H, m), 2.39-2.44 (1H, m), 3.21-3.28 (2H, m), 4.38-4.47 (1H, m), 4.51 (2H, d, J=6.2 Hz), 5.82 (1H, s), 6.97-7.03 (2H, m), 7.10-7.20 (3H, m), 7.64-7.71 (3H, m), 8.31 (1H, s), 8.68 (1H, br), 9.77 (1H, br), 10.03 (2H, br), 11.10 (1H, s), 12.91 (1H, br).

IR (ATR): 1675, 1655, 1627, 1596, 1560, 1539, 1516, 1408, 1317, 1251, 1119, 847 cm⁻¹.

Example 318

Preparation of 4-(benzylamino)-6-{[4-(morpholinomethyl)phenyl]amino}pyridine-3-carboxyamide

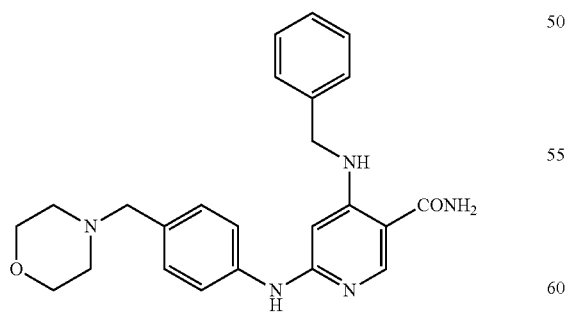

20 mg of 4-(benzylamino)-6-chloropyridine-3-carboxyamide (the compound of Example 1), 3.1 mg of [1,1'-bis(diphenylphosphino)ferrocene]dichloropalladium (II).methylene chloride adduct, 6.3 mg of 1,1'-bis(diphenylphosphino)ferrocene and 7.3 mg of sodium tert-butoxide were added to 1 mL of 1,4-dioxane, to which 18 mg of 4-(morpholinomethyl)aniline was added in an argon atmosphere, and stirred at 100° C. for 3 hours. The solvent was evaporated, and the residue was purified by silica gel thin layer chromatography (chloroform:ammonia methanol=10:1) to obtain 9 mg (28%) of the title compound as a light yellow powder.

¹H-NMR (400 MHz, CDCl₃) δ: 2.40-2.50 (4H, m), 3.45 (2H, s), 3.70-3.76 (4H, m), 4.35 (2H, d, J=5.6 Hz), 5.89 (1H, s), 6.53 (1H, br), 6.96 (2H, d, J=8.3 Hz), 7.18 (2H, d, J=8.3 Hz), 7.25-7.36 (5H, m), 8.21 (1H, s), 8.91 (1H, br).

IR (ATR): 1633, 1599, 1572, 1410, 1304, 1115 cm⁻¹.

Example 319

Preparation of 4-(benzylamino)-6-[(4-ethoxycarbonylphenyl)amino]pyridine-3-carboxyamide

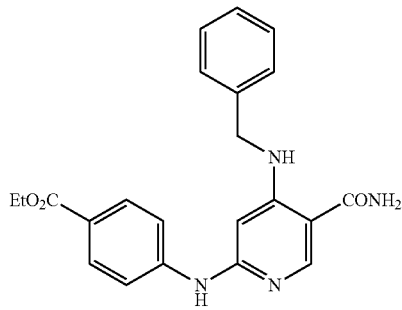 [SMILES: CCOC(=O)c1ccc(Nc2cc(NCc3ccccc3)c(C(N)=O)cn2)cc1]

From 4-(benzylamino)-6-chloropyridine-3-carboxyamide (the compound of Example 1) and 4-aminobenzoic acid ethylester in a manner similar to Example 318, the title compound was obtained as a slight yellow crystalline powder (yield 29%).

¹H-NMR (400 MHz, CDCl₃) δ: 1.40 (3H, t, J=7.2 Hz), 4.36 (2H, q, J=7.2 Hz), 4.41 (2H, d, J=5.6 Hz), 5.66 (2H, br), 5.99 (1H, s), 6.81 (1H, brs), 7.04 (2H, d, J=8.8 Hz), 7.29-7.41 (5H, m), 7.88 (2H, d, J=8.8 Hz), 8.26 (1H, s), 8.97 (1H, brt, J=5.6 Hz).

IR (ATR): 1709, 1638, 1595, 1572, 1546, 1416, 1271, 1255, 1177, 1105 cm⁻¹.

Example 320

Preparation of 4-[(3,5-difluorobenzyl)amino]-6-{[4-(trifluoromethyl)phenyl]amino}pyridine-3-carboxyamide

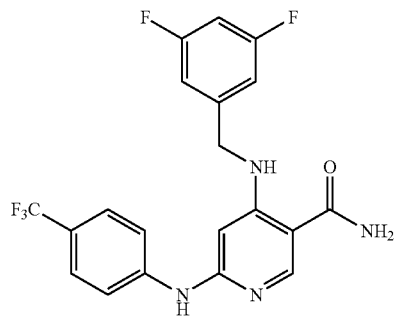 [SMILES: NC(=O)c1cnc(Nc2ccc(C(F)(F)F)cc2)cc1NCc1cc(F)cc(F)c1]

From 6-chloro-4-[(3,5-difluorobenzyl)amino]pyridine-3-carboxyamide (the compound of Example 20) and 4-trifluoromethylaniline in a manner similar to Example 193, the title compound was obtained as a light brown crystalline powder (yield 27%).

m.p. 207-211° C. (dec.)

$^1$H-NMR (270 MHz, DMSO-d6) δ: 4.46 (2H, d, J=5.6 Hz), 5.86 (1H, s), 6.99-7.17 (4H, m), 7.53 (2H, d, J=8.6 Hz), 7.74 (2H, d, J=8.6 Hz), 8.44 (1H, s), 9.07 (1H, br s), 9.32 (1H, s).

Example 321

Preparation of 4-[(3,5-difluorobenzyl)amino]-6-[(4-ethoxycarbonylphenyl)amino]pyridine-3-carboxyamide

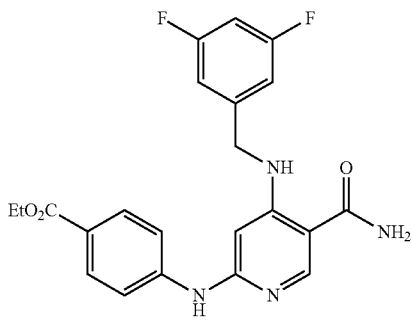 [SMILES: CCOC(=O)c1ccc(Nc2cc(NCc3cc(F)cc(F)c3)c(C(N)=O)cn2)cc1]

From 6-chloro-4-[(3,5-difluorobenzyl)amino]pyridine-3-carboxyamide (the compound of Example 20) and 4-aminobenzoic acid ethylester in a manner similar to Example 193, the title compound was obtained as a light brown crystalline powder (yield 46%).

m.p. 211-212° C.

$^1$H-NMR (270 MHz, DMSO-d6) δ: 1.30 (3H, t, J=7.1 Hz), 4.25 (2H, q, J=7.1 Hz), 4.46 (2H, d, J=6.6 Hz), 5.89 (1H, s), 6.99-7.19 (3H, m), 7.66 (2H, d, J=8.9 Hz), 7.81 (2H, d, J=8.9 Hz), 8.45 (1H, s), 9.07 (1H, br s), 9.36 (1H, br s).

Example 322

Preparation of 6-[(4-carbamoylphenyl)amino]-4-[(3,5-difluorobenzyl)amino]pyridine-3-carboxyamide

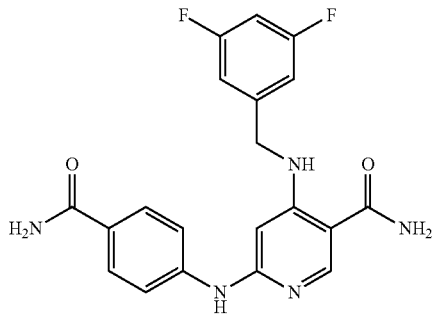

From 6-chloro-4-[(3,5-difluorobenzyl)amino]pyridine-3-carboxyamide (the compound of Example 20) and 4-aminobenzamide in a manner similar to Example 193, the title compound was obtained as a white crystalline powder (yield 43%).

m.p. 249-252° C.

$^1$H-NMR (270 MHz, DMSO-d6) δ: 4.45 (2H, d, J=5.9 Hz), 5.85 (1H, s), 6.98-7.18 (5H, m), 7.58 (2H, d, J=8.6 Hz), 7.73 (1H, br s), 7.74 (3H, d, J=8.6 Hz), 8.43 (1H, s), 9.05 (1H, t, J=6.1 Hz), 9.17 (1H, s).

Example 323

Preparation of 6-[(4-acetylphenyl)amino]-4-[(3,5-difluorobenzyl)amino]pyridine-3-carboxyamide

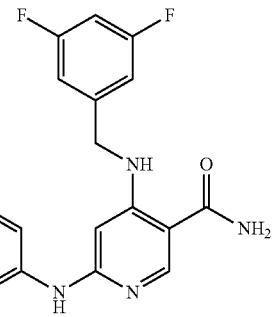

From 6-chloro-4-[(3,5-difluorobenzyl)amino]pyridine-3-carboxyamide (the compound of Example 20) and 4'-aminoacetophenone in a manner similar to Example 193, the title compound was obtained as a white crystalline powder (yield 36%).

m.p. 207-214° C. (dec.)

$^1$H-NMR (400 MHz, DMSO-d6) δ: 2.48 (3H, s), 4.46 (2H, d, J=6.4 Hz), 5.90 (1H, s), 6.96 (2H, d, J=6.4 Hz), 7.03 (1H, t, J=9.3 Hz), 7.66 (2H, d, J=9.0 Hz), 7.83 (2H, d, J=9.0 Hz), 8.31 (1H, s), 8.45 (1H, s), 9.08 (1H, t, J=6.0 Hz), 9.37 (1H, s).

Example 324

Preparation of 4-[(3,5-difluorobenzyl)amino]-6-{[4-(2-methylpropanoyl)phenyl]amino}pyridine-3-carboxyamide

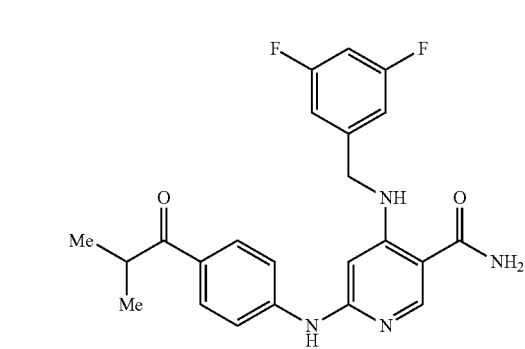 [SMILES: CC(C)C(=O)c1ccc(Nc2cc(NCc3cc(F)cc(F)c3)c(C(N)=O)cn2)cc1]

From 6-chloro-4-[(3,5-difluorobenzyl)amino]pyridine-3-carboxyamide (the compound of Example 20) and 4-(2-methylpropanoyl)aniline in a manner similar to Example 193, the title compound was obtained as a white crystalline powder (yield 37%).

m.p. 218-220° C.

$^1$H-NMR (400 MHz, DMSO-d6) δ: 1.09 (6H, d, J=6.8 Hz), 3.58 (1H, quint, J=6.8 Hz), 4.46 (2H, d, J=6.1 Hz), 5.90 (1H, s), 7.00-7.18 (3H, m), 7.66 (2H, d, J=9.2 Hz), 7.85 (2H, d, J=9.2 Hz), 8.45 (1H, s), 9.08 (1H, t, J=6.1 Hz), 9.37 (1H, brs).

Example 325

Preparation of 6-{[4-(cyclopropylcarbonyl)phenyl]amino}-4-[(3,5-difluorobenzyl)amino]pyridine-3-carboxyamide

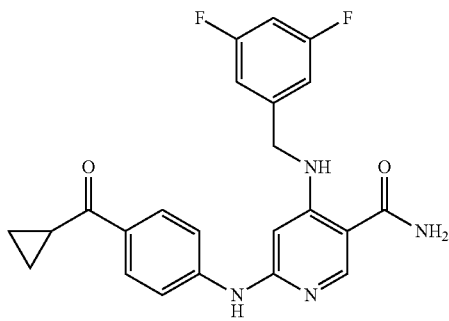 [SMILES: NC(=O)c1cnc(Nc2ccc(C(=O)C3CC3)cc2)cc1NCc1cc(F)cc(F)c1]

From 6-chloro-4-[(3,5-difluorobenzyl)amino]pyridine-3-carboxyamide (the compound of Example 20) and 4-(cyclopropylcarbonyl)aniline in a manner similar to Example 193, the title compound was obtained as a light yellow solid (yield 25%).

m.p. 183-193° C. (dec.)

$^1$H-NMR (270 MHz, CDCl$_3$) δ: 1.00-1.07 (2H, m), 1.20-1.26 (2H, m), 2.55-2.69 (1H, m), 4.39 (2H, d, J=6.3 Hz), 5.60-5.74 (1H, m), 5.90 (1H, s), 6.72-6.90 (4H, m), 7.13 (2H, d, J=8.6 Hz), 7.93 (2H, d, J=8.6 Hz), 8.29 (1H, s), 9.05 (1H, brs).

Example 326

Preparation of 4-[(3,5-difluorobenzyl)amino]-6-{[(4-trifluoroacetyl)phenyl]amino}pyridine-3-carboxyamide

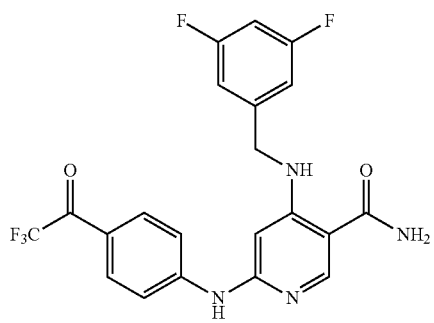 [SMILES: NC(=O)c1cnc(Nc2ccc(C(=O)C(F)(F)F)cc2)cc1NCc1cc(F)cc(F)c1]

From 6-chloro-4-[(3,5-difluorobenzyl)amino]pyridine-3-carboxyamide (the compound of Example 20) and 4-(trifluoroacetyl)aniline in a manner similar to Example 193, the title compound was obtained as a light yellow crystalline powder (yield 10%).

m.p. 212-213° C.

$^1$H-NMR (270 MHz, CD$_3$OD) δ: 4.45 (2H, br s), 5.87 (1H, s), 6.78-7.00 (3H, m), 7.26 (2H, d, J=8.9 Hz), 7.43 (2H, d, J=8.9 Hz), 8.32 (1H, s).

Example 327

Preparation of 4-[(3,5-difluorobenzyl)amino]-6-{[4-(trifluoromethoxy)phenyl]amino}pyridine-3-carboxyamide

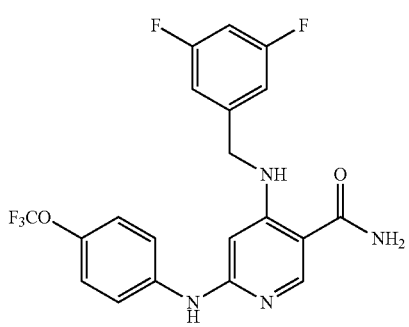 [SMILES: NC(=O)c1cnc(Nc2ccc(OC(F)(F)F)cc2)cc1NCc1cc(F)cc(F)c1]

From 6-chloro-4-[(3,5-difluorobenzyl)amino]pyridine-3-carboxyamide (the compound of Example 20) and 4-(trifluoromethoxy)aniline in a manner similar to Example 193, the title compound was obtained as a white crystalline powder (yield 43%).

m.p. 187-199° C.

$^1$H-NMR (270 MHz, DMSO-d6) δ: 4.44 (2H, d, J=6.3 Hz), 5.78 (1H, s), 6.96-7.23 (6H, m), 7.60 (2H, dd, J=6.9, 2.0 Hz), 8.39 (1H, s), 9.02-9.08 (2H, m).

Example 328

Preparation of 4-[(3,5-difluorobenzyl)amino]-6-[(4-sulfamoylphenyl)amino]pyridine-3-carboxyamide

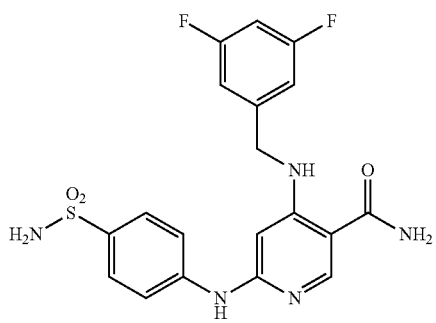 [SMILES: NC(=O)c1cnc(Nc2ccc(S(N)(=O)=O)cc2)cc1NCc1cc(F)cc(F)c1]

From 6-chloro-4-[(3,5-difluorobenzyl)amino]pyridine-3-carboxyamide (the compound of Example 20) and 4-sulfamoylaniline in a manner similar to Example 193, the title compound was obtained as a white crystalline powder (yield 25%).

m.p. 229-232° C.

$^1$H-NMR (400 MHz, CD$_3$OD) δ: 4.47 (2H, s), 5.91 (1H, s), 6.84 (1H, t, J=9.0 Hz), 6.96 (2H, d, J=6.6 Hz), 7.55 (2H, d, J=9.0 Hz), 7.73 (2H, d, J=9.0 Hz), 8.38 (1H, s).

Example 329

Preparation of 4-[(3,5-difluorobenzyl)amino]-6-{[4-(methylsulfamoyl)phenyl]amino}pyridine-3-carboxyamide

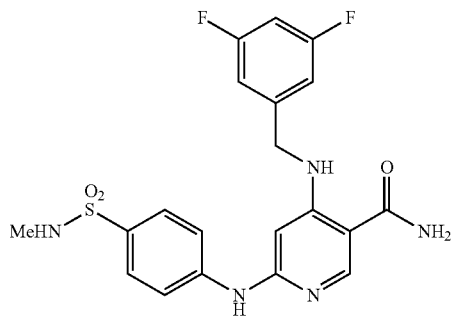 [SMILES: CNS(=O)(=O)c1ccc(Nc2cc(NCc3cc(F)cc(F)c3)c(C(N)=O)cn2)cc1]

From 6-chloro-4-[(3,5-difluorobenzyl)amino]pyridine-3-carboxyamide (the compound of Example 20) and 4-(methylsulfamoyl)aniline in a manner similar to Example 193, the title compound was obtained as a light brown crystalline powder (yield 47%).

m.p. 214-217° C. (dec.)

$^1$H-NMR (270 MHz, DMSO-d6) δ: 2.37 (3H, d, J=5.3 Hz), 4.46 (2H, d, J=5.9 Hz), 5.88 (1H, s), 7.03 (2H, d, J=6.9 Hz), 7.10-7.18 (2H, m), 7.59 (2H, d, J=8.9 Hz), 7.73 (2H, d, J=8.9 Hz), 8.44 (1H, s), 9.03-9.10 (1H, m), 9.37 (1H, s).

Example 330

Preparation of 4-[(3,5-difluorobenzyl)amino]-6-({4-[(2-methoxyethyl)sulfamoyl]phenyl}amino)pyridine-3-carboxyamide

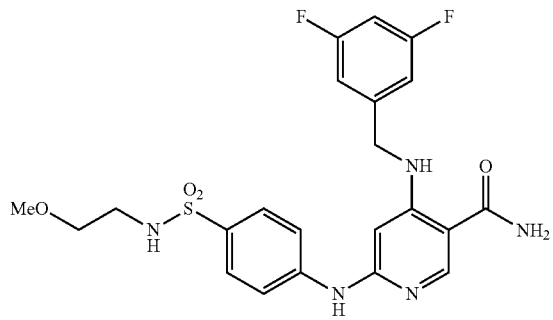 [SMILES: COCCNS(=O)(=O)c1ccc(Nc2cc(NCc3cc(F)cc(F)c3)c(C(N)=O)cn2)cc1]

From 6-chloro-4-[(3,5-difluorobenzyl)amino]pyridine-3-carboxyamide (the compound of Example 20) and 4-[(2-methoxyethyl)sulfamoyl]aniline in a manner similar to Example 193, the title compound was obtained as a white amorphous substance (yield 49%).

$^1$H-NMR (270 MHz, DMSO-d6) δ: 2.85 (2H, td, J=5.9, 5.9 Hz), 3.16 (3H, s), 3.29 (5H, t, J=5.9 Hz), 4.46 (2H, d, J=5.3 Hz), 5.88 (1H, s), 7.02 (2H, d, J=6.3 Hz), 7.13 (1H, t, J=9.2 Hz), 7.44 (1H, t, J=6.3 Hz), 7.61 (2H, d, J=8.9 Hz), 7.72 (2H, d, J=8.9 Hz), 8.44 (1H, s), 9.07 (1H, br s), 9.36 (1H, s).

Example 331

Preparation of 4-[(3,5-difluorobenzyl)amino]-6-{[4-(morpholinosulfonyl)phenyl]amino}pyridine-3-carboxyamide

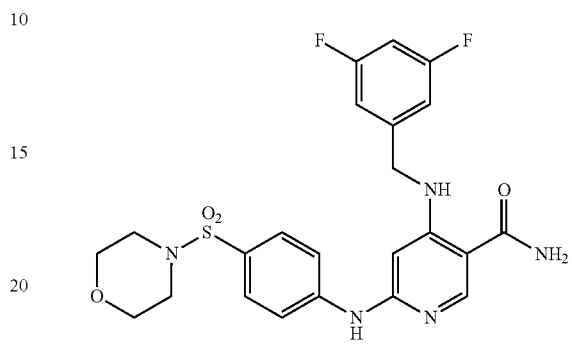

From 6-chloro-4-[(3,5-difluorobenzyl)amino]pyridine-3-carboxyamide (the compound of Example 20) and 4-(morpholinosulfonyl)aniline in a manner similar to Example 193, the title compound was obtained as a light yellow amorphous substance (yield 30%).

$^1$H-NMR (270 MHz, CDCl$_3$) δ: 2.95-3.04 (4H, m), 3.72-3.80 (4H, m), 4.41 (2H, d, J=5.8 Hz), 5.79 (2H, br s), 5.84 (1H, s), 6.77 (1H, t, J=8.6 Hz), 6.86 (2H, d, J=5.3 Hz), 6.98 (1H, s), 7.28 (2H, d, J=8.6 Hz), 7.58 (2H, d, J=8.6 Hz), 8.30 (1H, s), 9.06 (1H, t, J=5.6 Hz).

Example 332

Preparation of 6-[(4-carboxyphenyl)amino]-4-[(3,5-difluorobenzyl)amino]pyridine-3-carboxyamide

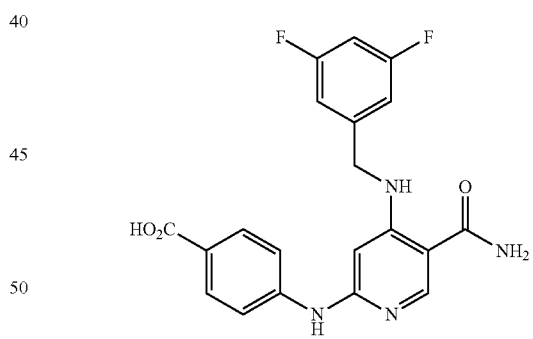

302 mg of 4-[(3,5-difluorobenzyl)amino]-6-[(4-ethoxycarbonylphenyl)amino]pyridine-3-carboxyamide (the compound of Example 321) was dissolved in 13 mL of ethanol, to which 2.5 mL of 2 mol/L sodium hydroxide in water was added, and stirred at 50° C. for 4 hours. After cooling, the reaction mixture was neutralized by adding 1 mol/L hydrochloric acid in water, extracted with chloroform, and dried on anhydrous sodium sulfate. The solvent was evaporated to obtain 90 mg (yield 32%) of the title compound as a light brown solid.

$^1$H-NMR (270 MHz, DMSO-d6) δ: 4.46 (2H, d, J=6.3 Hz), 5.89 (1H, s), 6.98-7.20 (3H, m), 7.63 (2H, d, J=8.9 Hz), 7.79 (2H, d, J=8.9 Hz), 8.45 (1H, s), 9.07 (1H, t, J=6.4 Hz), 9.32 (1H, brs).

Example 333

Preparation of 4-[(3,5-difluorobenzyl)amino]-N-ethyl-6-[(4-morpholinophenyl)amino]pyridine-3-carboxyamide

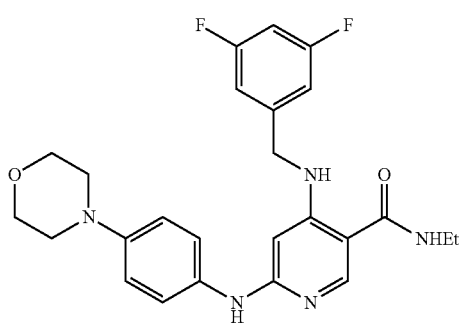

From 4,6-dichloropyridine-3-carboxylic acid ethylester synthesized according to the method described in US2006/0217417 and 3,5-difluorobenzylamine in a manner similar to Example 1, 6-chloro-4-[(3,5-difluorobenzyl)amino]pyridine-3-carboxylic acid ethyl ester was obtained as a light brown crystalline powder (yield 82%).

$^1$H-NMR (400 MHz, CDCl$_3$) δ: 1.39 (3H, t, J=7.2 Hz), 3.13-3.17 (4H, m), 3.85-3.91 (4H, m), 4.29 (2H, d, J=6.1 Hz), 4.32 (2H, q, J=7.2 Hz), 5.58 (1H, s), 6.45 (1H, s), 6.70-6.64 (5H, m), 6.90 (2H, d, J=8.8 Hz), 8.52 (1H, t, J=6.1 Hz), 8.63 (1H, s).

Then, from 6-chloro-4-[(3,5-difluorobenzyl)amino]pyridine-3-carboxylic acid ethyl ester and 4-morpholinoaniline in a manner similar to Example 46, 4-[(3,5-difluorobenzyl)amino]-6-[(4-morpholinophenyl)amino]pyridine-3-carboxylic acid ethylester was obtained as light yellow needle crystals (yield 80%).

$^1$H-NMR (400 MHz, CDCl$_3$) δ: 1.39 (3H, t, J=7.2 Hz), 3.13-3.17 (4H, m), 3.85-3.91 (4H, m), 4.29 (2H, d, J=6.1 Hz), 4.32 (2H, q, J=7.2 Hz), 5.58 (1H, s), 6.45 (1H, s), 6.70-6.64 (5H, m), 6.90 (2H, d, J=8.8 Hz), 8.52 (1H, t, J=6.1 Hz), 8.63 (1H, s).

2.99 g of 4-[(3,5-difluorobenzyl)amino]-6-[(4-morpholinophenyl)amino]pyridine-3-carboxylic acid ethyl ester was dissolved in 30 mL of methanol, to which 12 mL of 4 mol/L sodium hydroxide in water was added at room temperature, and stirred at 80° C. for 1.5 hour. After cooling, methanol was evaporated, weakly acidified (about pH 4) by adding 6 mol/L hydrochloric acid in water under ice cooling, the deposited crystals were filtered, and washed with water and methanol. After air-drying, they were dried under reduced pressure (60-70° C., for 3 hours) to obtain 2.72 g (yield 97%) of 4-[(3,5-difluorobenzyl)amino]-6-[(4-morpholinophenyl)amino]pyridine-3-carboxylic acid as a light reddish purple crystalline powder.

$^1$H-NMR (400 MHz, DMSO-d6) δ: 2.98-3.05 (4H, m), 3.70-3.76 (4H, m), 4.44 (2H, d, J=5.6 Hz), 5.65 (1H, s), 6.81 (2H, d, J=9.0 Hz), 7.00 (2H, d, J=9.0 Hz), 7.10-7.18 (3H, m), 8.44 (1H, s), 8.49 (1H, brs), 8.77 (1H, brs), 12.42 (1H, br).

100 mg of 4-[(3,5-difluorobenzyl)amino]-6-[(4-morpholinophenyl)amino]pyridine-3-carboxylic acid was dissolved in 15 mL of dimethyl sulfoxide, to which 65.3 mg of 1-ethyl-3-(3-dimethylaminopropyl)carbodiimide hydrochloride and 52.2 mg of 1-hydroxybenzotriazole monohydrate were added at room temperature, and stirred at the same temperature for 2 hours. After the reaction was over, 2 mL of 2 mol/L ethylamine-THF solution was added, stirred overnight at room temperature. Then water was added, extracted with chloroform, the extract was washed with saturated saline, and dried on anhydrous sodium sulfate. The solvent was evaporated, and the residue was purified by silica gel thin layer chromatography (chloroform:methanol=10:1) to obtain 13.9 mg (13%) of the title compound as a light brown solid.

$^1$H-NMR (400 MHz, CDCl$_3$) δ: 1.26 (3H, t, J=7.2 Hz), 3.10-3.14 (4H, m), 3.45 (2H, qd, J=7.3, 1.7 Hz), 3.85-3.91 (4H, m), 4.25 (2H, d, J=5.8 Hz), 5.60 (1H, s), 6.07 (1H, brs), 6.59 (1H, brs), 6.69-6.84 (5H, m), 6.89 (2H, d, J=9.0 Hz), 8.14 (1H, s), 8.90 (1H, t, J=5.8 Hz).

Example 334

Preparation of 4-[(3,5-difluorobenzyl)amino]-N,N-diethyl-6-[(4-morpholinophenyl)amino]pyridine-3-carboxyamide

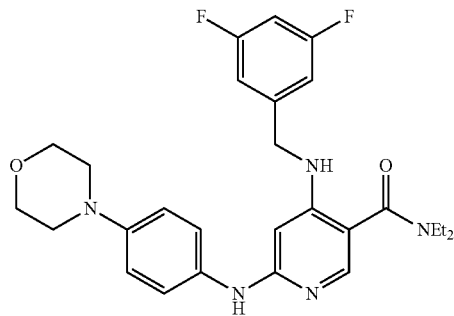

From 4-[(3,5-difluorobenzyl)amino]-6-[(4-morpholinophenyl)amino]pyridine-3-carboxylic acid and diethylamine in a manner similar to Example 333, the title compound was obtained as a gray solid (4 steps, yield 11%).

$^1$H-NMR (400 MHz, CDCl$_3$) δ: 1.25 (6H, t, J=7.1 Hz), 3.11-3.16 (4H, m), 3.52 (4H, q, J=7.1 Hz), 3.85-3.90 (4H, m), 4.23 (2H, d, J=5.6 Hz), 5.68 (1H, s), 6.30 (1H, brs), 6.72 (1H, dddd, J=8.8, 8.8, 2.2, 2.2 Hz), 6.76-6.84 (4H, m), 6.92 (2H, d, J=8.8 Hz), 7.87 (1H, s).

Example 335

Preparation of 4-[(3,5-difluorobenzyl)amino]-6-[(4-morpholinophenyl)amino]pyridine-3-carbohydrazide

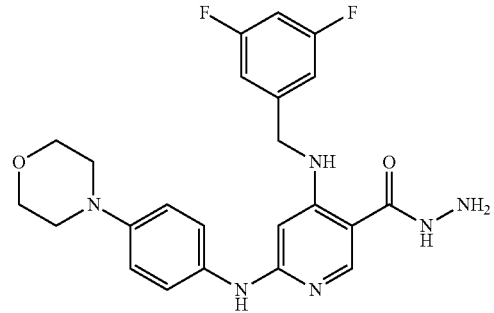 [SMILES: NNC(=O)c1cnc(Nc2ccc(N3CCOCC3)cc2)cc1NCc1cc(F)cc(F)c1]

From 4-[(3,5-difluorobenzyl)amino]-6-[(4-morpholinophenyl)amino]pyridine-3-carboxylic acid and hydrazine

Example 336

Preparation of 4-[(3,5-difluorobenzyl)amino]-N-hydroxy-6-[(4-morpholinophenyl)amino]pyridine-3-carboxyamide

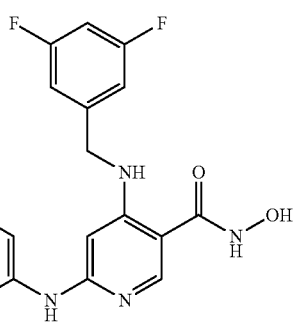

From 4-[(3,5-difluorobenzyl)amino]-6-[(4-morpholinophenyl)amino]pyridine-3-carboxylic acid and hydroxylamine hydrochloride in a manner similar to Example 333, the title compound was obtained as a yellow solid (4 steps, yield 10%).

$^1$H-NMR (400 MHz, CD$_3$OD) δ: 2.95-3.20 (4H, m), 3.78-3.86 (4H, m), 4.99 (2H, s), 6.33 (1H, brs), 6.86-6.98 (5H, m), 7.16 (2H, m), 7.71 (1H, s).

Example 337

Preparation of 4-[(3,5-difluorobenzyl)amino]-N-methoxy-N-methyl-6-[(4-morpholinophenyl)amino]pyridine-3-carboxyamide

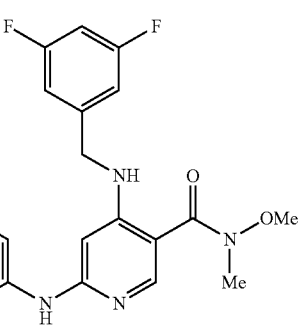

From 4-[(3,5-difluorobenzyl)amino]-6-[(4-morpholinophenyl)amino]pyridine-3-carboxylic acid and N,O-dimethyl hydroxylamine hydrochloride in a manner similar to Example 333, the title compound was obtained as a white crystalline powder (4 steps, yield 52%).

m.p. 162-163° C.

$^1$H-NMR (400 MHz, CDCl$_3$) δ: 3.11-3.17 (4H, m), 3.36 (3H, s), 3.65 (3H, s), 3.85-3.90 (4H, m), 4.24 (2H, d, J=5.6 Hz), 5.65 (1H, s), 6.65 (1H, brs), 6.73 (1H, dddd, J=8.8, 8.8, 2.3, 2.3 Hz), 6.76-6.84 (4H, m), 6.91 (2H, d, J=9.0 Hz), 7.82 (1H, t, J=5.6 Hz), 8.39 (1H, s).

Example 338

Preparation of 4-[(3,5-difluorobenzyl)amino]-N-methoxy-6-[(4-morpholinophenyl)amino]pyridine-3-carboxyamide

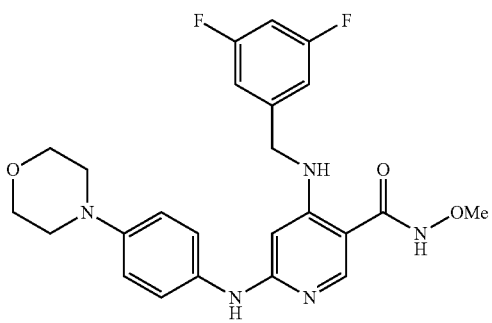 [SMILES: CONC(=O)c1cnc(Nc2ccc(N3CCOCC3)cc2)cc1NCc1cc(F)cc(F)c1]

From 4-[(3,5-difluorobenzyl)amino]-6-[(4-morpholinophenyl)amino]pyridine-3-carboxylic acid and O-methyl hydroxylamine hydrochloride in a manner similar to Example 333, the title compound was obtained as slight yellow needle crystals (4 steps, yield 8%).

m.p. 185-188° C.

IR (ATR): 1628, 1597, 1571, 1549, 1515, 1467, 1452, 1300, 1264, 1235, 1222, 1117 cm$^{-1}$.

$^1$H-NMR (400 MHz, CD$_3$OD) δ: 3.08-3.12 (4H, m), 3.79 (3H, s), 3.82-3.85 (4H, m), 4.37 (2H, s), 5.64 (1H, s), 6.83-6.89 (5H, m), 6.97 (2H, d, J=9.0 Hz), 8.04 (1H, s).

Reference Example 1

Preparation of 2-aminomethyl-1-benzylpyrrolidine

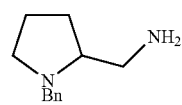

943 mg of 3-hydroxypiperidine was dissolved in 15 mL of toluene, to which, under ice cooling, 1.13 mL of benzaldehyde, 2.97 g of sodium triacetoxyborohydride and 0.3 mL of acetic acid were sequentially added, and stirred at room temperature for 24 hours. To the reaction mixture, saturated sodium bicarbonate was added, extracted with ethyl acetate, the extract was washed with saturated saline, and dried on anhydrous sodium sulfate. The solvent was evaporated, and the residue was purified by silica gel chromatography (chloroform to chloroform:methanol-ammonia=60:1) to obtain 866.3 mg (49%) of 1-benzyl-3-hydroxypiperidine crude product as a colorless oil.

866.3 mg of the 1-benzyl-3-hydroxypiperidine crude product obtained was dissolved in 6 mL of chloroform, to which, under ice cooling, 0.95 mL of triethylamine and 0.42 mL of methanesulfonyl acid chloride were sequentially added, and stirred at the same temperature for 30 minutes. To the reaction mixture, saturated sodium bicarbonate was added, extracted with chloroform, the extract was washed with saturated saline, and dried on anhydrous sodium sulfate. The solvent was evaporated to obtain 1.15 g of methanesulfonic acid (1-benzyl-piperidin-3-yl)methylester crude product as an orange oil. Without further purification, this was used as the feed material for the next reaction.

1.15 g of methanesulfonic acid (1-benzyl-piperidin-3-yl) methylester crude product obtained was dissolved in 3 mL of N,N-dimethylformamide, to which 0.553 g of sodium azide was added, and stirred in an atmosphere of argon gas at 80° C. for 1 hour. To the reaction mixture, water was added, extracted with chloroform, the extract was washed with saturated saline, and dried on anhydrous sodium sulfate. The solvent was evaporated, and the residue was purified by silica gel chromatography (hexane to hexane:ethyl acetate=30:1) to obtain 668.5 mg of 2-azidomethyl-1-benzylpyrrolidine crude product as a colorless oil. Without further purification, this was used as the feed material for the next reaction.

668.5 mg of the 2-azidomethyl-1-benzylpyrrolidine crude product obtained was dissolved in 5 mL of ethanol, to which 160 mg of 10% palladium carbon was added, and stirred at room temperature under an atmosphere of hydrogen gas for 5 hours. The 10% palladium carbon was celite-filtered, and the filtered product was washed with methanol. The solvent was evaporated, and the residue was purified by silica gel chromatography (chloroform to chloroform:methanol=30:1 to chloroform:methanol=15:1) to obtain 539.7 mg of the title compound crude product as a light yellow oil. Without further purification, this was used as the feed material for the next reaction.

Example 339

Preparation of 6-chloro-4-(cyclohexylamino)pyridine-3-carboxyamide

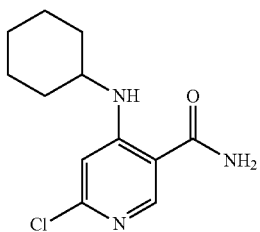 [SMILES: NC(=O)c1cnc(Cl)cc1NC1CCCCC1]

200 mg of 4,6-dichloropyridine-3-carboxyamide synthesized according to the method described in US2006/0217417 was dissolved in 2 mL of ethanol, to which 156 mg of cyclohexylamine and 203 mg of N,N-diisopropylethylamine were added, and heated at reflux for 8 hours. After cooling, the solvent was evaporated, and 10 mL of water was added to the residue, neutralized by adding 2 mol/L hydrochloric acid in water under ice cooling, extracted with chloroform, and the extract was dried on anhydrous sodium sulfate. The solvent was evaporated, and the residue was recrystallized from chloroform-hexane to obtain 243 mg (92%) of the title compound as colorless needle crystals.

$^1$H-NMR (400 MHz, CDCl$_3$) δ: 1.23-1.46 (5H, m), 1.60-1.68 (1H, m), 1.74-1.82 (2H, m), 1.93-2.01 (2H, m), 3.27-3.37 (1H, m), 5.82 (2H, br), 6.53 (1H, s), 8.25 (1H, s), 8.49 (1H, brd, J=6.8 Hz).

Example 340

Preparation of 6-chloro-4-[(2-methylcyclohexyl)amino]pyridine-3-carboxyamide

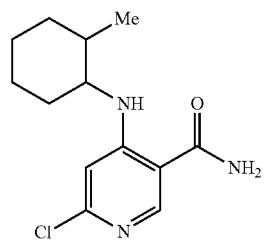 [SMILES: CC1CCCCC1Nc1cc(Cl)ncc1C(N)=O]

From 4,6-dichloropyridine-3-carboxyamide and 2-methylcyclohexylamine in a manner similar to Example 339, the title compound was obtained as a light yellow solid (yield 96%).

$^1$H-NMR (400 MHz, CDCl$_3$) δ: 0.97 (3H, d, J=6.6 Hz), 1.08-2.04 (9H, m), 2.88-2.96 (1H, m), 6.53 (1H, s), 8.23 (1H, s), 8.57 (1H, d, J=7.3 Hz).

Example 341

Preparation of 6-chloro-4-(tricyclo[3.3.1.1$^{3,7}$]deca-2-ylamino)pyridine-3-carboxyamide

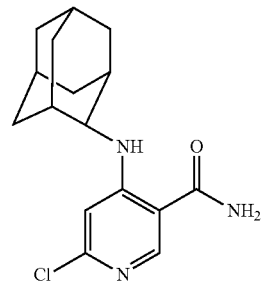 [SMILES: NC(=O)c1cnc(Cl)cc1NC1C2CC3CC(C2)CC1C3]

From 4,6-dichloropyridine-3-carboxyamide and tricyclo[3.3.1.1$^{3,7}$]decane-2-amine in a manner similar to Example 339, the title compound was obtained as a colorless crystalline powder (yield 84%).

Example 342

Preparation of 6-chloro-4-(3,4-dihydro-2H-chromen-4-ylamino)pyridine-3-carboxyamide

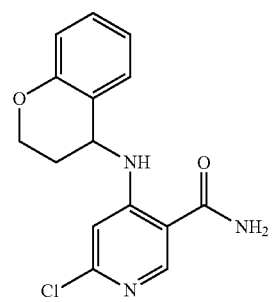 [SMILES: NC(=O)c1cnc(Cl)cc1NC1CCOc2ccccc21]

From 4,6-dichloropyridine-3-carboxyamide and 4-amino-3,4-dihydro-2H-chromene in a manner similar to Example 339, the title compound was obtained as a light yellow crystalline powder (yield 62%).

) δ: 2.18-2.32 (2H, m), 4.16-4.34 (2H, m), 4.65-4.78 (1H, m), 6.73 (1H, s), 6.83-6.94 (2H, m), 7.17-7.25 (2H, m), 8.34 (1)H, s), 8.96 (1H, brd, J=6.9 Hz).

Example 343

Preparation of 6-chloro-4-[(pyridin-3-ylmethyl)amino]pyridine-3-carboxyamide

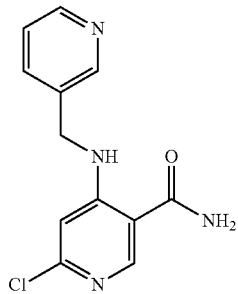 [SMILES: NC(=O)c1cnc(Cl)cc1NCc1cccnc1]

From 4,6-dichloropyridine-3-carboxyamide and 3-aminomethylpyridine in a manner similar to Example 339, the title compound was obtained as a slight yellow crystalline powder (yield 59%).

$^1$H-NMR (400 MHz, CDCl$_3$) δ: 4.46 (2H, d, J=5.8 Hz), 6.51 (1H, s), 7.31 (1H, dd, J=7.8, 4.9) Hz), 7.65 (1H, ddd, J=4.9, 2.2, 1.7 Hz), 8.31 (1H, s), 8.58 (1H, dd, J=4.9, 1.7 Hz), 8.61 (1H, d, J=2.2 Hz), 8.97 (1H, br).

Example 344

Preparation of 6-chloro-4-{[(1-benzylpyrrolidin-2-yl)methyl]amino}pyridine-3-carboxyamide

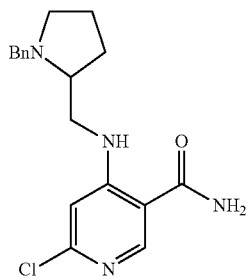 [SMILES: NC(=O)c1cnc(Cl)cc1NCC1CCCN1Cc1ccccc1]

From 4,6-dichloropyridine-3-carboxyamide and 2-aminomethyl-1-benzylpyrrolidine (the compound of Reference Example 1) in a manner similar to Example 339, the crude product of the title compound was obtained as a light yellow solid (100%). This was purified by silica gel column chromatography (chloroform to chloroform:methanol=60:1), and used, without further purification, as the feed material for the next reaction.

Example 345

Preparation of 4-cyclohexylamino-6-[(4-morpholinophenyl)amino]pyridine-3-carboxyamide

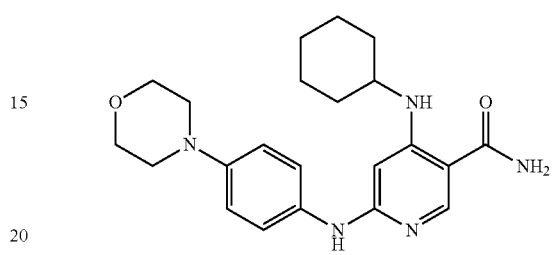

To 60 mg of 6-chloro-4-(cyclohexylamino)pyridine-3-carboxyamide (the compound of Example 339) suspended in 0.5 mL of diphenyl ether, 84 mg of 4-morpholinoaniline and 23 mg of methanesulfonic acid were added, and stirred at 180° C. for 30 minutes. After cooling, the reaction mixture was dissolved in chloroform, washed with saturated sodium bicarbonate in water, and dried on anhydrous sodium sulfate. The solvent was evaporated, and the residue was purified by silica gel column chromatography (chloroform:methanol=40:1 to 20:1) to obtain 77 mg (82%) of the title compound as a light brown crystalline powder.

m.p. 240-243° C. (dec.)

$^1$H-NMR (400 MHz, CDCl$_3$) δ: 1.25-1.39 (5H, m), 1.52-1.61 (1H, m), 1.67-1.77 (2H, m), 1.83-1.92 (2H, m), 3.13-3.23 (5H, m), 3.82-3.90 (4H, m), 5.78 (1H, s), 6.93 (2H, d, J=9.0 Hz), 7.19 (2H, d, J=9.0 Hz), 7.33 (1H, br), 8.45 (1H, s), 8.78 (1H, brd, J=7.8 Hz).

IR (ATR): 1663, 1620, 1599, 1551, 1515, 1416, 1298, 1285, 1227, 1111 cm$^{-1}$.

Example 346

Preparation of 4-cyclohexylamino-6-({4-[4-(methylsulfonyl)piperazin-1-yl]phenyl}amino)pyridine-3-carboxyamide

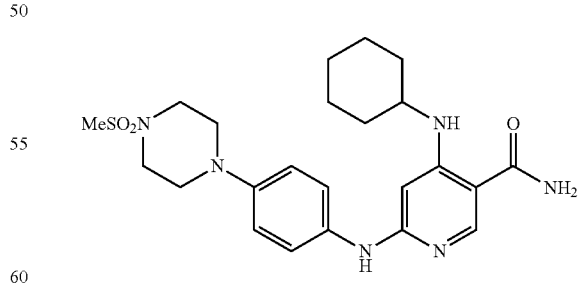

From 6-chloro-4-(cyclohexylamino)pyridine-3-carboxyamide (the compound of Example 339) and 4-(4-methylsulfonylpiperazin-1-yl)aniline in a manner similar to Example 345, the title compound was obtained as colorless needle crystals (yield 96%).

m.p. 235-237° C. (dec.)

¹H-NMR (400 MHz, CDCl₃) δ: 1.24-1.41 (5H, m), 1.53-1.62 (1H, m), 1.67-1.76 (2H, m), 1.82-1.91 (2H, m), 2.85 (3H, s), 3.18 (1H, br), 3.27-3.32 (4H, m), 3.39-3.44 (4H, m), 5.75 (1H, s), 6.96 (2H, d, J=9.0 Hz), 7.20 (2H, d, J=9.0 Hz), 8.07 (1H, br), 8.67 (1H, s), 9.08 (1H, brd, J=7.2 Hz).

IR (ATR):1656, 1620, 1568, 1515, 1413, 1381, 1312, 1298, 1231, 1147 cm⁻¹.

Example 347

Preparation of 4-cyclohexylamino-6-({4-[(methylsulfonyl)amino]phenyl}amino)pyridine-3-carboxyamide

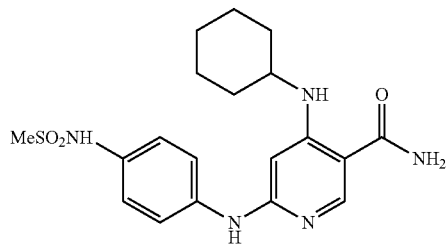

From 6-chloro-4-(cyclohexylamino)pyridine-3-carboxyamide (the compound of Example 339) and 4-[(methylsulfonyl)amino]aniline in a manner similar to Example 345, the title compound was obtained as a light purple crystalline powder (yield 39%).

m.p. 233-236° C.

¹H-NMR (400 MHz, DMSO-d₆) δ: 1.19-1.41 (6H, m), 1.56-1.59 (1H, br), 1.68-1.71 (2H, br), 1.91-1.94 (2H, m), 2.90 (3H, s), 5.92 (1H, s), 7.10 (2H, d, J=8.8 Hz), 7.57 (2H, d, J=8.8 Hz), 8.33 (1H, S), 8.59 (1H, d, J=7.3 Hz), 8.89 (1H, s), 9.33 (1H, s).

Example 348

Preparation of 4-cyclohexylamino-6-[(3,5-difluorophenyl)amino]pyridine-3-carboxyamide

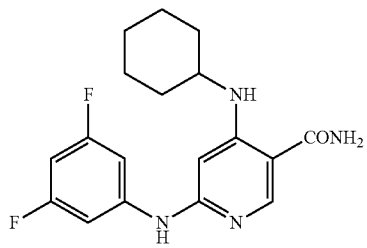 [SMILES: NC(=O)c1cnc(Nc2cc(F)cc(F)c2)cc1NC1CCCCC1]

From 6-chloro-4-(cyclohexylamino)pyridine-3-carboxyamide (the compound of Example 339) and 3,5-difluoroaniline in a manner similar to Example 345, the title compound was obtained as a colorless crystalline powder (yield 56%).

m.p. 194-197° C.

¹H-NMR (400 MHz, CDCl₃) δ: 1.25-1.43 (6H, m), 1.75-1.81 (2H, m), 1.96-2.00 (2H, m), 3.26-3.32 (1H, m), 5.99 (1H, s), 6.45 (1H, dddd, J=2.2, 2.2, 6.8, 6.8 Hz), 6.73 (1H, brs), 6.94 (2H, dd, J=2.2, 9.5 Hz), 8.23 (1H, s), 8.45 (1H, d, J=7.1 Hz).

Example 349

Preparation of 4-[(2-methylcyclohexyl)amino]-6-[(4-morpholinophenyl)amino]pyridine-3-carboxyamide

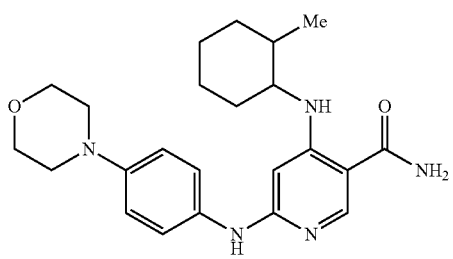 [SMILES: CC1CCCCC1Nc1cc(Nc2ccc(N3CCOCC3)cc2)ncc1C(N)=O]

From 6-chloro-4-[(2-methylcyclohexyl)amino]pyridine-3-carboxyamide (the compound of Example 340) and 4-morpholinoaniline in a manner similar to Example 345, the title compound was obtained as a light yellow crystalline powder (yield 90%).

m.p. 236-239° C.

¹H-NMR (400 MHz, CDCl₃) δ: 0.90 (1.2H, d, J=7.1 Hz), 0.95 (1.8H, d, J=6.6 Hz), 1.03-2.01 (9H, m), 2.74-2.82 (0.6H, m), 3.13-3.16 (4H, m), 3.40-3.45 (0.4H, m), 3.86-3.89 (4H, m), 5.85 (1H, s), 6.35 (1H, s), 6.93 (2H, d, J=9.0 Hz), 7.19 (0.8H, d, J=9.0 Hz), 7.20 (1.2H, d, J=9.0 Hz), 8.16 (0.6H, s), 8.40 (0.4H, s), 8.39 (0.6H, d, J=8.8 Hz), 8.73 (0.4H, d, J=8.8 Hz).

Example 350

Preparation of 6-[(4-morpholinophenyl)amino]-4-(tricyclo[3.3.1.1³,⁷]deca-2-ylamino)pyridine-3-carboxyamide

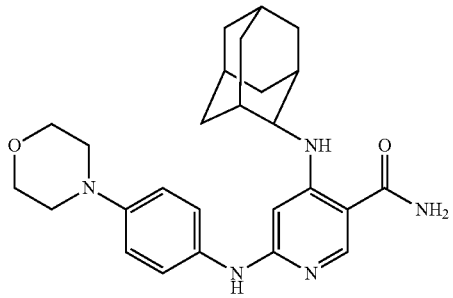 [SMILES: NC(=O)c1cnc(Nc2ccc(N3CCOCC3)cc2)cc1NC1C2CC3CC(C2)CC1C3]

From 6-chloro-4-(tricyclo[3.3.1.1³,⁷]deca-2-ylamino)pyridine-3-carboxyamide (the compound of Example 341) and 4-morpholinoaniline in a manner similar to Example 345, the title compound was obtained as a colorless crystalline powder (yield 90%).

¹H-NMR (400 MHz, CDCl₃) δ: 1.54-1.60 (2H, m), 1.69-1.96 (12H, m), 2.97-3.02 (4H, m), 3.45-3.50 (1H, m), 3.69-3.74 (4H, m), 5.81 (1H, s), 6.85 (2H, d, J=9.0 Hz), 6.91 (1H, br), 7.40 (2H, d, J=9.0 Hz), 7.66 (1H, br), 8.31 (1H, s), 8.61 (1H, s), 9.10 (1H, d, J=7.8 Hz).

Example 351

Preparation of 4-(3,4-dihydro-2H-1-benzopyran-4-ylamino)-6-[(4-morpholinophenyl)amino]pyridine-3-carboxyamide

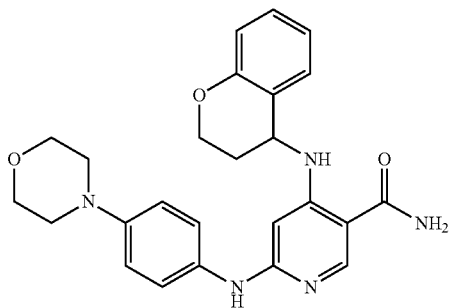 [SMILES: NC(=O)c1cnc(Nc2ccc(N3CCOCC3)cc2)cc1NC1CCOc2ccccc21]

From 6-chloro-4-(3,4-dihydro-2H-1-benzopyran-4-ylamino)pyridine-3-carboxyamide (the compound of Example 342) and 4-morpholinoaniline in a manner similar to Example 345, the title compound was obtained as a brown amorphous substance (yield 60%).

$^1$H-NMR (400 MHz, DMSO-$d_6$) δ: 1.95-2.05 (1H, m), 2.05-2.16 (1H, m), 2.98-3.03 (4H, m), 3.68-3.74 (4H, m), 4.02-4.13 (1H, m), 4.20-4.30 (1H, m), 4.59-4.65 (1H, m), 6.80-6.92 (4H, m), 6.96 (1H, br), 7.16-7.26 (2H, m), 7.42 (2H, d, J=8.8 Hz), 7.73 (1H, br), 8.36 (1H, s), 8.75 (1H, s), 7.42 (1H, brd, J=7.1 Hz).

IR (ATR): 1651, 1597, 1567, 1537, 1513, 1489, 1453, 1410, 1269, 1222, 1118 cm$^{-1}$.

MS: m/z 445(M$^+$, base peak).

Example 352

Preparation of 4-(3,4-dihydro-2H-1-benzopyran-4-ylamino)-6-({4-[4-(propan-2-ylsulfonyl)piperazin-1-yl]phenyl}amino)pyridine-3-carboxyamide

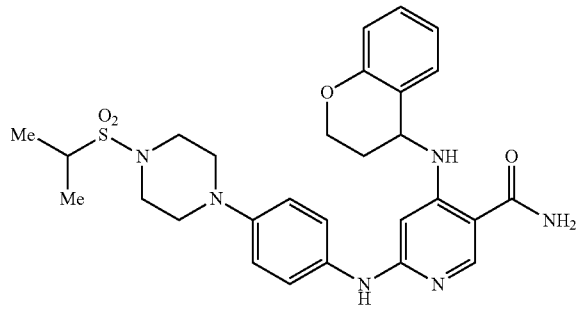 [SMILES: CC(C)S(=O)(=O)N1CCN(c2ccc(Nc3cc(NC4CCOc5ccccc54)c(C(N)=O)cn3)cc2)CC1]

From 6-chloro-4-(3,4-dihydro-2H-1-benzopyran-4-ylamino)pyridine-3-carboxyamide (the compound of Example 342) and 4-[(propan-2-ylsulfonyl)amino]aniline in a manner similar to Example 345, the title compound was obtained as a light yellow amorphous substance (yield 77%).

$^1$H-NMR (400 MHz, CDCl$_3$) δ: 1.38 (6H, d, J=6.8 Hz), 2.02-2.16 (2H, m), 3.14-3.28 (5H, m), 3.47-3.59 (4H, m), 4.14-4.28 (2H, m), 4.50-4.59 (1H, m), 5.59 (2H, br), 5.99 (1H, s), 6.69 (1H, s), 6.80-6.96 (4H, m), 7.14-7.23 (4H, m), 8.23 (1H, s), 8.79 (1H, d, J=7.1 Hz).

Example 353

Preparation of 6-[(4-morpholinophenyl)amino]-4-[(pyridin-3-ylmethyl)amino}pyridine-3-carboxyamide

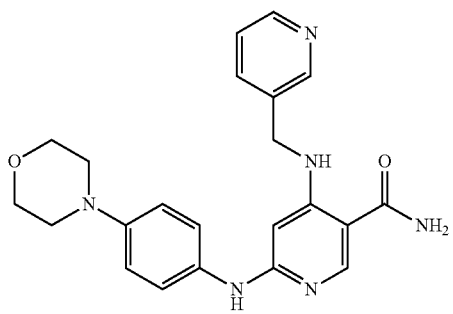 [SMILES: NC(=O)c1cnc(Nc2ccc(N3CCOCC3)cc2)cc1NCc1cccnc1]

From 6-chloro-4-[(pyridin-3-ylmethyl)amino]pyridine-3-carboxyamide (the compound of Example 343) and 4-morpholinoaniline in a manner similar to Example 345, the title compound was obtained as a brown solid (yield 7%).

$^1$H-NMR (400 MHz, CDCl$_3$) δ: 3.11-3.17 (4H, m), 3.85-3.89 (4H, m), 4.32 (2H, d, J=5.9 Hz), 5.68 (2H, s), 5.71 (1H, brs), 6.82 (3H, d, J=9.1 Hz), 6.92 (2H, d, J=9.1 Hz), 7.25-7.29 (1H, m), 7.60 (1H, d, J=7.9 Hz), 8.23 (1H, s), 8.48-8.52 (1H, m), 8.55 (1H, dd, J=4.8, 1.5 Hz), 8.95-9.03 (1H, m).

Example 354

Preparation of 4-[(pyridin-3-ylmethyl)amino}-6-({4-[4-(trifluoroacetyl)piperazin-1-yl]phenyl}amino}pyridine-3-carboxyamide

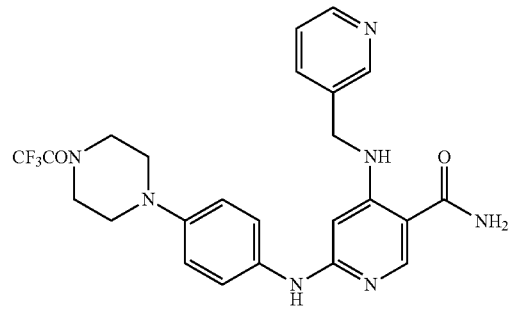

From 6-chloro-4-[(pyridin-3-ylmethyl)amino]pyridine-3-carboxyamide (the compound of Example 43) and 4-[4-(trifluoroacetyl)piperazin-1-yl]aniline in a manner similar to Example 345, the title compound was obtained as a light brown crystalline powder (yield 43%).

$^1$H-NMR (400 MHz, CDCl$_3$) δ: 3.18-3.23 (4H, m), 3.76-3.81 (2H, m), 3.84-3.89 (2H, m), 4.35 (2H, d, J=5.6 Hz), 5.59 (1H, s), 5.69 (2H, br), 6.44 (1H, brs), 6.85 (2H, d, J=9.0 Hz), 6.94 (2H, d, J=9.0 Hz), 7.27-7.30 (1H, m), 7.60-7.64 (1H, m), 8.21 (1H, s), 8.50-8.52 (1H, m), 8.54-8.57 (1H, m), 8.96 (1H, brt, J=5.6 Hz).

Example 355

Preparation of 6-{(4-(piperazin-1-yl)phenyl]amino}-4-[(pyridin-3-ylmethyl)amino}pyridine-3-carboxamide

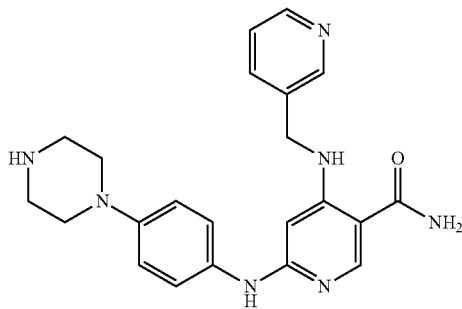 [SMILES: NC(=O)c1cnc(Nc2ccc(N3CCNCC3)cc2)cc1NCc1cccnc1]

66 mg of 4-[(pyridin-3-ylmethyl)amino}-6-({4-[4-(trifluoroacetyl)piperazin-1-yl]phenyl}amino}pyridine-3-carboxamide (the compound of Example 354) was dissolved in 1 mL of methanol, to which 0.5 mL of 1 mol/L sodium hydroxide in water was added at room temperature, and stirred at the same temperature for 20 minutes. To the reaction mixture water was added, extracted with chloroform, and the extract was dried on anhydrous sodium sulfate. The solvent was evaporated, and the residue was purified by silica gel column chromatography (chloroform:ammonia methanol=40:1 to 20:1) to obtain 51 mg (96%) of the title compound as a light brown crystalline powder.

$^1$H-NMR (400 MHz, CDCl$_3$) δ: 3.03-3.07 (4H, m), 3.11-3.15 (4H, m), 4.32 (2H, d, J=9.0 Hz), 5.58 (2H, br), 5.69 (1H, s), 6.47 (1H, brs), 6.85 (2H, d, J=9.0 Hz), 6.92 (2H, d, J=9.0 Hz), 7.25-7.28 (1H, m), 7.57-7.62 (1H, m), 8.20 (1H, s), 8.51-8.52 (1H, m), 8.53-8.56 (1H, m), 8.92 (1H, brt, J=5.6 Hz).

IR (ATR): 1621, 1607, 1572, 1552, 1514, 1459, 1408, 1312, 1300, 1235 cm$^{-1}$.

Example 356

Preparation of 6-({4-[4-(propan-2-yl)piperazin-1-yl]phenyl}amino)-4-[(pyridin-3-ylmethyl)amino]pyridine-3-carboxamide

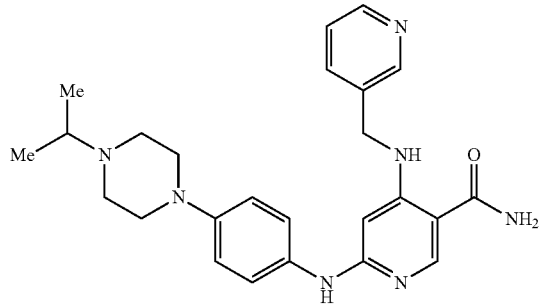 [SMILES: CC(C)N1CCN(c2ccc(Nc3cc(NCc4cccnc4)c(C(N)=O)cn3)cc2)CC1]

From 6-chloro-4-[(pyridin-3-ylmethyl)amino]pyridine-3-carboxamide (the compound of Example 343) and 4-[4-(propan-2-yl)piperazin-1-yl]aniline in a manner similar to Example 345, the title compound was obtained as a light yellow crystalline powder (yield 53%).

$^1$H-NMR (400 MHz, CDCl$_3$) δ: 1.11 (6H, d, J=6.5 Hz), 2.68-2.79 (5H, m), 3.18-3.22 (4H, m), 4.31 (2H, d, J=5.6 Hz), 5.64 (2H, br), 5.68 (1H, s), 6.54 (1H, brs), 6.85 (2H, d, J=8.9 Hz), 6.91 (2H, d, J=8.9 Hz), 7.24-7.28 (1H, m), 7.56-7.61 (1H, m), 8.19 (1H, s), 8.50-8.52 (1H, m), 8.53-8.56 (1H, m), 8.91 (1H, brt, J=5.6 Hz).

IR (ATR): 1649, 1607, 1570, 1542, 1514, 1407, 1292, 1231 cm$^{-1}$.

Example 357

Preparation of 4-{[(1-benzylpyrrolidin-2-yl)methyl]amino}-6-[(4-morpholinophenyl)amino]pyridine-3-carboxamide

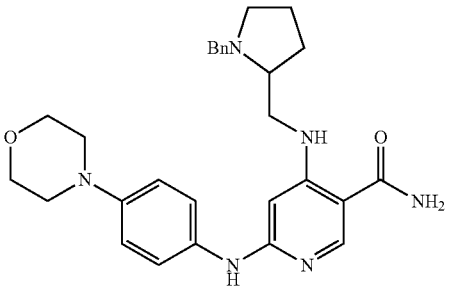

From 6-chloro-4-{[(1-benzylpyrrolidin-2-yl)methyl]amino}pyridine-3-carboxamide (the compound of Example 344) and 4-morpholinoaniline in a manner similar to Example 345, a crude product was obtained as a light yellow amorphous substance (100%). This was purified by silica gel column chromatography (chloroform to chloroform:methanol=60:1 to chloroform:methanol=15:1) to obtain the title compound.

Example 358

Preparation of 6-[(4-morpholinophenyl)amino]-4-[(pyrrolidin-2-ylmethyl)amino]pyridine-3-carboxamide

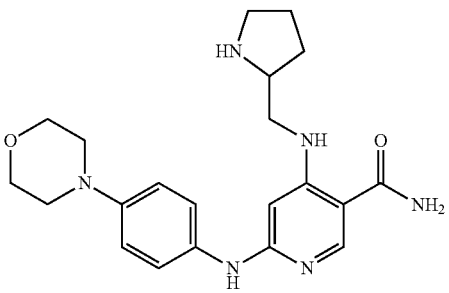 [SMILES: NC(=O)c1cnc(Nc2ccc(N3CCOCC3)cc2)cc1NCC1CCCN1]

143.2 mg of 4-{[(1-benzylpyrrolidin-2-yl)methyl]amino}-6-[(4-morpholinophenyl)amino]pyridine-3-carboxamide crude product (the compound of Example 357) was dissolved in 3 mL of ethanol, to which 103.1 mg of palladium hydroxide (II) and 0.3 mL of 2 mol/L hydrochloric acid in water were sequentially added, and stirred in a sealed tube at 40° C. in a hydrogen atmosphere at an initial pressure of 1 MPa for 12 hours. After cooling, the insoluble substances were filtered with celite, and the solvent was evaporated. The residue was dissolved in chloroform, washed with saturated sodium bicarbonate in water and saturated saline, and dried on anhydrous sodium sulfate. The solvent was evaporated, and the residue was purified by silica gel thin layer chromatography (chloroform:methanol-ammonia=8:1) to obtain 58.1 mg of the title compound as a light yellow crystalline powder.

m.p. 203-206° C.

$^1$H-NMR (400 MHz, CDCl$_3$) δ: 1.40-1.49 (1H, m), 1.60-1.96 (3H, m), 2.88-3.03 (4H, m), 3.14-3.17 (4H, m), 3.32-3.39 (1H, m), 3.86-3.89 (4H, m), 5.83 (1H, s), 6.38 (1H, s), 6.92 (2H, d, J=8.8 Hz), 7.20 (2H, d, J=8.8 Hz), 8.17 (1H, s), 8.51 (1H, t, J=4.2 Hz).

Example 359

Preparation of 4-{[(1-methylpyrrolidin-2-yl)methyl]amino}-6-[(4-morpholinophenyl)amino]pyridine-3-carboxyamide

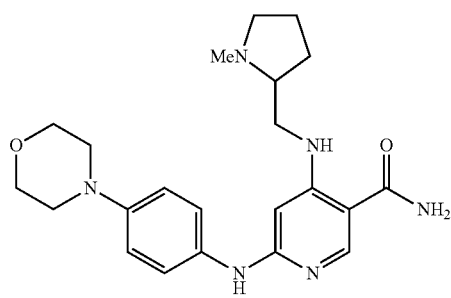

37.9 mg of 6-[(4-morpholinophenyl)amino]-4-[(pyrrolidin-2-ylmethyl)amino]pyridine-3-carboxyamide (the compound of Example 358) was dissolved in 2 mL of methylene chloride, to which, under ice cooling, 19.4 mg of 37% formaldehyde in water, 40.5 mg of sodium triacetoxyborohydride and acetic acid were sequentially added, and stirred at room temperature for 2 hours. To the reaction mixture, saturated sodium bicarbonate in water was added, extracted with chloroform:methanol=10:1, the extract washed with saturated saline, and dried on anhydrous sodium sulfate. The solvent was evaporated, and the residue was recrystallized from chloroform-ether to obtain 27.5 mg (70%) of the title compound as a light yellow crystalline powder.

m.p. 229-233° C.

$^1$H-NMR (400 MHz, CDCl$_3$) δ: 1.61-1.87 (3H, m), 1.92-2.02 (1H, m), 2.22 (1H, ddd, J=7.6, 7.6, 9.5 Hz), 2.32 (3H, s), 2.38-2.46 (1H, m), 2.96 (1H, ddd, J=4.4, 7.1, 11.7 Hz), 3.07-3.16 (6H, m), 3.86-3.89 (4H, m), 5.80 (1H, s), 6.38 (1H, s), 6.92 (2H, d, J=8.8 Hz), 7.20 (2H, d, J=8.8 Hz), 8.16 (1H, s), 8.47-8.49 (1H, m).

Example 360

Preparation of 4-{[(1-acetylpyrrolidin-2-yl)methyl]amino}-6-[(4-morpholinophenyl)amino]pyridine-3-carboxyamide

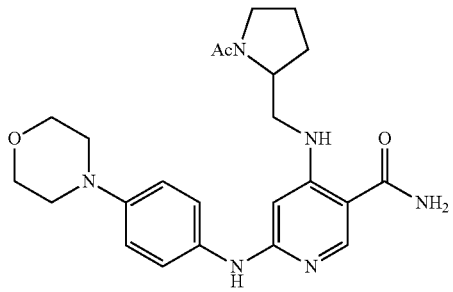

30.3 mg of 6-[(4-morpholinophenyl)amino]-4-[(pyrrolidin-2-ylmethyl)amino]pyridine-3-carboxyamide (the compound of Example 358) was dissolved in 2 mL of methylene chloride, to which 9.4 mg of acetic anhydride and 9.1 mg of pyridine were sequentially added, and stirred at room temperature for 2 hours. To the reaction mixture saturated sodium bicarbonate in water was added, extracted with chloroform:methanol=10:1, the extract was washed with saturated saline, and dried on anhydrous sodium sulfate. The solvent was evaporated, and the residue was purified by silica gel thin layer chromatography (chloroform:ammonia methanol=8:1), recrystallized from chloroform-ether to obtain the title compound (29.3 mg, 87%) as a light yellow crystalline powder.

m.p. 134-138° C.

$^1$H-NMR (400 MHz, DMSO-d$_6$) δ: 1.03-1.27 (2H, m), 1.78-1.95 (5H, m), 3.05-3.54 (8H, m), 3.72-3.75 (4H, m), 4.10-4.14 (1H, m), 5.94 (1H, brs), 6.85-6.91 (2H, m), 7.34-7.36 (2H, m), 8.13-8.29 (2H, m), 8.53-8.59 (1H, m).

Example 361

Preparation of 4-[(cyclohexylmethyl)amino]-6-[(4-morpholinophenyl)amino]pyridine-3-carboxyamide Step 1

6-chloro-4-[(cyclohexylmethyl)amino]pyridine-3-carboxylic acid ethyl ester

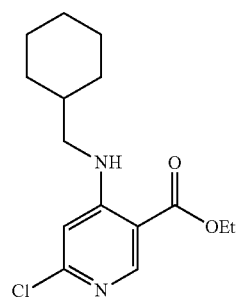 [SMILES: CCOC(=O)c1cnc(Cl)cc1NCC1CCCCC1]

From 4,6-dichloropyridine-3-carboxylic acid ethyl ester synthesized according to the method described in US2006/0217417 and cyclohexylmethylamine in a manner similar to Example 339, the title compound was obtained as a slight yellow oil (yield 85%).

$^1$H-NMR (400 MHz, CDCl$_3$) δ: 0.82-1.05 (2H, m), 1.11-1.33 (3H, m), 1.39 (3H, t, J=7.2 Hz), 1.58-1.85 (6H, m), 3.02 (2H, dd, J=6.6, 5.3 Hz), 4.34 (2H, q, J=7.2 Hz), 6.52 (1H, s), 8.23 (1H, br), 8.66 (1H, s).

Step 2

4-[(cyclohexylmethyl)amino]-6-[(4-morpholinophenyl)amino]pyridine-3-carboxylic acid ethyl ester

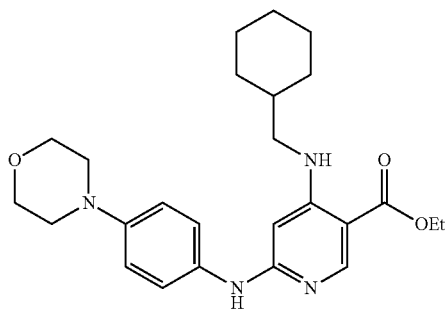 [SMILES: CCOC(=O)c1cnc(Nc2ccc(N3CCOCC3)cc2)cc1NCC1CCCCC1]

From 6-chloro-4-[(cyclohexylmethyl)amino]pyridine-3-carboxylic acid ethyl ester and 4-morpholinoaniline in a manner similar to Example 345, the title compound was obtained as a light brown crystalline powder (yield 64%).

$^1$H-NMR (400 MHz, CDCl$_3$) δ: 0.91-1.03 (2H, m), 1.10-1.31 (3H, m), 1.36 (3H, t, J=7.2 Hz), 1.51-1.63 (1H, m), 1.65-1.81 (5H, m), 2.85-2.89 (2H, m), 3.13-3.17 (4H, m), 3.86-3.89 (4H, m), 4.28 (2H, q, J=7.2 Hz), 5.77 (1H, s), 6.50 (1H, brs), 6.93 (2H, d, J=9.0 Hz), 7.21 (2H, d, J=9.0 Hz), 8.01 (1H, br), 8.60 (1H, s).

Step 3

4-[(cyclohexylmethyl)amino]-6-[(4-morpholinophenyl)amino]pyridine-3-carboxyamide

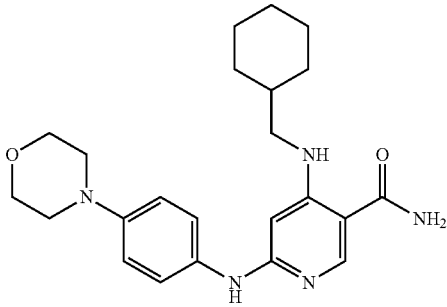 [SMILES: NC(=O)c1cnc(Nc2ccc(N3CCOCC3)cc2)cc1NCC1CCCCC1]

108 mg of 4-[(cyclohexylmethyl)amino]-6-[(4-morpholinophenyl)amino]pyridine-3-carboxylic acid ethyl ester was dissolved in 4 mL of ethanol-tetrahydrofuran (1:1), to which 2 mL of 2 mol/L sodium hydroxide in water was added at room temperature, and stirred while heating at 100° C. for 2 hours. Under ice cooling, hydrochloric acid was added to acidify (about pH 4) the reaction mixture, extracted with chloroform, the extract was washed with water, and dried on anhydrous sodium sulfate. The solvent was evaporated to obtain 108 mg of 4-[(cyclohexylmethyl)amino]-6-[(4-morpholinophenyl)amino]pyridine-3-carboxylic acid as a light brown crystalline powder. This was dissolved in 1 mL of N,N-dimethylformamide, to which 52 mg of 1-ethyl-3-(3-dimethylaminopropyl)carbodiimide hydrochloride and 41 mg of 1-hydroxybenzotriazole monohydrate were added, and stirred at room temperature for 20 minutes. Then 1 mL of 28% ammonia water was added, and stirred at the same temperature for 16 hours. To the reaction mixture 10 mL of water was added, extracted with chloroform, and the extract was dried on anhydrous sodium sulfate. The solvent was evaporated, and the residue was purified by silica gel thin layer chromatography (chloroform:methanol=5:1) to obtain 44 mg (yield 37%) of the title compound as a light yellow crystalline powder.

$^1$H-NMR (400 MHz, CDCl$_3$) δ: 0.90-1.11 (2H, m), 1.19-1.31 (3H, m), 1.51-1.63 (1H, m), 1.63-1.80 (5H, m), 2.83-2.88 (2H, m), 3.13-3.17 (4H, m), 3.88-3.90 (4H, m), 5.76 (2H, br), 5.78 (1H, s), 6.92 (2H, d, J=9.0 Hz), 7.13 (1H, br), 7.20 (2H, d, J=9.0 Hz), 8.21 (1H, s), 8.55 (1H, br).

IR (ATR): 1658, 1617, 1598, 1504, 1414, 1295, 1225, 1116 cm$^{-1}$.

Example 362

Preparation of 4-[(cyclopropylmethyl)amino]-6-[(4-morpholinophenyl)amino]pyridine-3-carboxyamide Step 1

6-chloro-4-[(cyclopropylmethyl)amino]pyridine-3-carboxylic acid ethyl ester

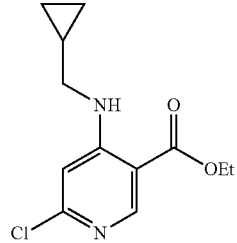 [SMILES: CCOC(=O)c1cnc(Cl)cc1NCC1CC1]

From 4,6-dichloropyridine-3-carboxylic acid ethyl ester synthesized according to the method described in US2006/0217417 and cyclopropylmethylamine in a manner similar to Example 339, the title compound was obtained as a slight yellow crystalline powder (yield 77%).

$^1$H-NMR (400 MHz, CDCl$_3$) δ: 0.27-0.32 (2H, m), 0.61-0.66 (2H, m), 1.08-1.18 (1H, m), 1.40 (3H, t, J=7.2 Hz), 3.05 (2H, dd, J=5.4, 4.9 Hz), 4.35 (2H, q, J=7.2 Hz), 6.52 (1H, s), 8.22 (1H, br), 8.67 (1H, s).

Step 2

4-[(cyclopropylmethyl)amino]-6-[(4-morpholinophenyl)amino]pyridine-3-carboxylic acid ethyl ester

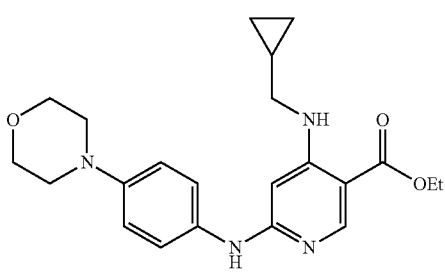 [SMILES: CCOC(=O)c1cnc(Nc2ccc(N3CCOCC3)cc2)cc1NCC1CC1]

From 6-chloro-4-[(cyclopropylmethyl)amino]pyridine-3-carboxylic acid ethyl ester and 4-morpholinoaniline in a manner similar to Example 345, the title compound was obtained as a light brown crystalline powder (yield 84%).

$^1$H-NMR (400 MHz, CDCl$_3$) δ: 0.21-0.26 (2H, m), 0.54-0.59 (2H, m), 1.01-1.12 (1H, m), 1.37 (3H, t, J=7.2 Hz), 2.89 (2H, dd, J=6.8, 4.9 Hz), 3.14-3.18 (4H, m), 3.86-3.89 (4H, m), 4.29 (2H, q, J=7.2 Hz), 6.75 (1H, s), 6.55 (1H, brs), 6.93 (2H, d, J=8.8 Hz), 7.20 (2H, d, J=8.8 Hz), 8.01 (1H, br), 8.61 (1H, s).

Step 3

4-[(cyclopropylmethyl)amino]-6-[(4-morpholinophenyl)amino]pyridine-3-carboxyamide

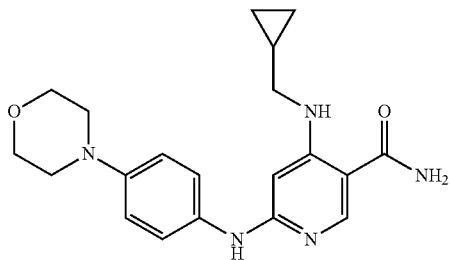 [SMILES: NC(=O)c1cnc(Nc2ccc(N3CCOCC3)cc2)cc1NCC1CC1]

From 4-[(cyclopropylmethyl)amino]-6-[(4-morpholinophenyl)amino]pyridine-3-carboxylic acid ethyl ester in a manner similar to step 3 of Example 361, the title compound was obtained as a light yellow crystalline powder (yield 30%).

$^1$H-NMR (400 MHz, CDCl$_3$) δ: 0.20-0.25 (2H, m), 0.54-0.59 (2H, m), 0.99-1.10 (1H, m), 2.01 (2H, dd, J=6.8, 4.9 Hz), 3.14-3.18 (4H, m), 3.86-3.90 (4H, m), 5.76 (1H, s), 6.12 (2H, br), 6.93 (2H, d, J=9.0 Hz), 7.21 (2H, d, J=9.0 Hz), 7.89 (1H, br), 8.37 (1H, s), 8.73 (1H, brt, J=4.9 Hz).
IR (ATR): 1650, 1613, 1571, 1414, 1271, 1244, 1228, 1116 cm$^{-1}$.

Example 363

Preparation of 6-[(4-morpholinophenyl)amino]-4-[(pyridin-2-ylmethyl)amino]pyridine-3-carboxyamide Step 1

6-chloro-4-[(pyridin-2-ylmethyl)amino]pyridine-3-carboxylic acid ethyl ester

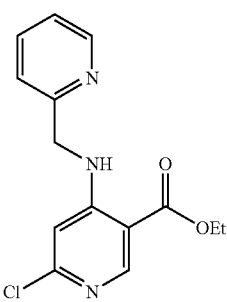 [SMILES: CCOC(=O)c1cnc(Cl)cc1NCc1ccccn1]

From 4,6-dichloropyridine-3-carboxylic acid ethyl ester synthesized according to the method described in US2006/0217417 and 2-(aminomethyl)pyridine in a manner similar to Example 339, the title compound was obtained as a colorless crystalline powder (yield 71%).

$^1$H-NMR (400 MHz, CDCl$_3$) δ: 1.41 (3H, t, J=7.2 Hz), 4.39 (2H, q, J=7.2 Hz), 4.55 (2H, d, J=5.1 Hz), 6.57 (1H, s), 7.22-7.29 (2H, m), 7.69 (1H, ddd, J=7.7, 7.7, 1.7 Hz), 8.65 (1H, ddd, J=4.9, 1.7, 0.8 Hz), 8.71 (1H, s), 9.07 (1H, br).

Step 2

6-[(4-morpholinophenyl)amino]-4-[(pyridin-2-ylmethyl)amino]pyridine-3-carboxylic acid ethyl ester From 6-chloro-4-[(pyridin-2-ylmethyl)amino]pyridine-3-carboxylic acid ethyl ester and 4-morpholinoaniline in a manner similar to Example 345, the title compound was obtained as a light brown crystalline powder (yield 97%).

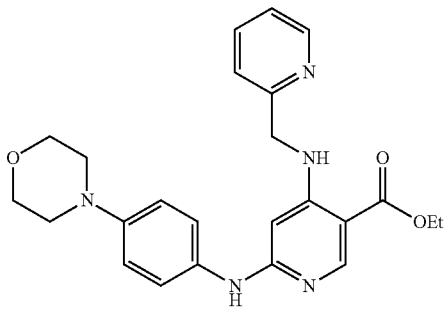 [SMILES: CCOC(=O)c1cnc(Nc2ccc(N3CCOCC3)cc2)cc1NCc1ccccn1]

$^1$H-NMR (400 MHz, CDCl$_3$) δ: 1.39 (3H, t, J=7.2 Hz), 3.12-3.15 (4H, m), 3.86-3.89 (4H, m), 4.33 (2H, q, J=7.2 Hz), 4.44 (2H, d, J=5.3 Hz), 5.74 (1H, s), 5.59 (1H, brs), 6.83 (2H, d, J=8.8 Hz), 7.03 (2H, d, J=8.8 Hz), 7.18-7.22 (1H, m), 7.26-7.28 (1H, m), 7.66 (1H, ddd, J=7.7, 7.7, 1.7 Hz), 8.57-8.60 (1H, m), 8.65 (1H, s), 8.73 (1H, brt, J=5.3 Hz).

Step 3

6-[(4-morpholinophenyl)amino]-4-[(pyridin-2-ylmethyl)amino]pyridine-3-carboxyamide

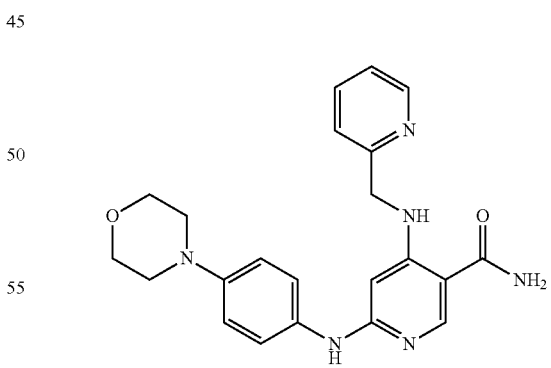

From 6-[(4-morpholinophenyl)amino]-4-[(pyridin-2-ylmethyl)amino]pyridine-3-carboxylic acid ethyl ester in a manner similar to step 3 of Example 361, the title compound was obtained as a light yellow crystalline powder (yield 16%).

$^1$H-NMR (400 MHz, CDCl$_3$) δ: 3.12-3.15 (4H, m), 3.86-3.89 (4H, m), 4.44 (2H, d, J=5.6 Hz), 5.63 (2H, br), 5.75 (1H, s), 6.68 (1H, br), 6.82 (2H, d, J=9.0 Hz), 7.02 (2H, d, J=9.0 Hz), 7.19 (1H, ddd, J=7.6, 4.6, 1.8 Hz), 7.27-7.30 (1H, m), 7.65 (1H, ddd, J=7.6, 7.6, 2.0 Hz), 8.21 (1H, s), 8.57 (1H, Ddd, J=4.6, 2.0, 1.8 Hz), 9.14 (1H, brt, J=5.6 Hz).

IR (ATR): 1625, 1602, 1568, 1546, 1515, 1450, 1411, 1300, 1117 cm$^{-1}$.

Example 364

Preparation of 6-(5-chloro-1H-benzimidazol-1-yl)-4-[(3,5-difluorobenzyl)amino]pyridine-3-carboxyamide and 6-(6-chloro-1H-benzimidazol-1-yl)-4-[(3,5-difluorobenzyl)amino]pyridine-3-carboxyamide

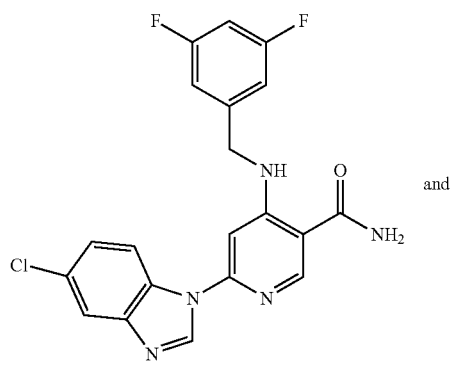

and

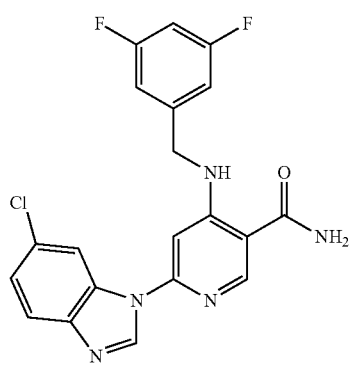

50 mg of 5-chlorobenzimidazole was dissolved in 1.5 mL of N,N-dimethylformamide, to which, under ice cooling, 18 mg of sodium hydride (oily, 50%) was added, and stirred at room temperature in an argon atmosphere for 1 hour. Then, 89 mg of 6-chloro-4-[(3,5-difluorobenzyl)amino]pyridine-3-carboxyamide (the compound of Example 20) was added, and heated at reflux for 14 hours. After cooling, water was added to the reaction mixture, extracted with ethyl acetate, the extract was washed with saturated saline, and dried on anhydrous sodium sulfate. The solvent was evaporated, and the residue was purified by silica gel column chromatography (chloroform:methanol:ammonia water=20:1:0.1 to hexane:acetone=1:1) to obtain 41 mg (yield 41%) of a mixture of the title compound ($^1$H-NMR integral ratio 1:1) as a white solid.

$^1$H-NMR (270 MHz, DMSO-d$_6$) δ: 4.67 (2H, s), 6.96 (1H, d, J=10.6 Hz), 7.05-7.25 (3H, m), 7.29-7.38 (1H, m), 7.53-7.69 (2H, m), 7.76 (0.5H, d, J=8.6 Hz), 7.81-7.85 (0.5H, m), 7.95 (0.5H, d, J=8.6 Hz), 8.08-8.13 (0.5H, m), 8.13-8.23 (0.5H, m), 8.30 (0.5H, d, J=8.9 Hz), 8.69 (1H, d, J=7.3 Hz), 8.97 (1H, s), 9.35 (1H, t, J=6.3 Hz).

Example 365

Preparation of 6-(1H-benzimidazol-1-yl)-4-[(3,5-difluorobenzyl)amino]pyridine-3-carboxyamide

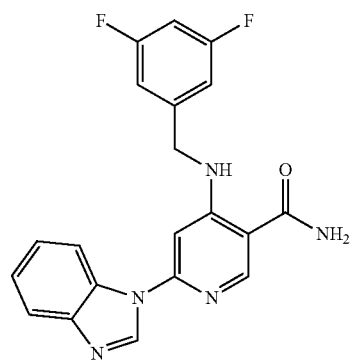 [SMILES: NC(=O)c1cnc(-n2cnc3ccccc32)cc1NCc1cc(F)cc(F)c1]

Step 1

6-[(2-aminophenyl)amino]-4-[(3,5-difluorobenzyl)amino]pyridine-3-carboxyamide

To 89 mg of 6-chloro-4-[(3,5-difluorobenzyl)amino]pyridine-3-carboxyamide (the compound of Example 20) suspended in 3 mL of diphenylether, 65 mg of 1,2-phenylenediamine and 144 mg of methanesulfonic acid were added, and stirred in a nitrogen atmosphere at 180° C. for 30 minutes. After cooling, chloroform was added to the reaction mixture to dissolve the deposit, washed with saturated sodium bicarbonate, and dried on anhydrous sodium sulfate. The solvent was evaporated, and the residue was purified by silica gel column chromatography (chloroform:methanol:ammonia water=10:1:0.1) to obtain 18 mg (yield 17%) of the title compound as a light brown powder.

$^1$H-NMR (270 MHz, DMSO-d$_6$) δ: 4.31 (2H, d, J=5.8 Hz), 5.52 (1H, s), 6.42 (1H, t, J=7.6 Hz), 6.66-6.72 (1H, m), 6.79-6.94 (4H, m), 7.02-7.16 (1H, m), 7.85 (1H, s), 8.30 (1H, s), 9.06 (1H, t, J=5.8 Hz).

Step 2

6-(1H-benzimidazol-1-yl)-4-[(3,5-difluorobenzyl)amino]pyridine-3-carboxyamide 9 mg of 6-[(2-aminophenyl)amino]-4-[(3,5-difluorobenzyl)amino]pyridine-3-carboxyamide (the compound of step 1 of Example 365) was suspended in 0.2 ml of methanol, to which 0.2 mL of trimethyl orthoformate and a catalytic amount of p-toluenesulfonic acid monohydrate were added at room temperature, and stirred at the same temperature for 4 hours. The solvent was evaporated, saturated sodium bicarbonate was added to the residue, extracted with chloroform, the extract was washed with water, and dried on anhydrous sodium sulfate. The solvent was evaporated to obtain 9 mg (yield 94%) of the title compound as a light brown solid.

$^1$H-NMR (400 MHz, CDCl$_3$) δ: 4.54 (2H, d, J=5.6 Hz), 6.54 (1H, s), 6.75-6.97 (3H, m), 7.26-7.36 (2H, m), 7.83 (1H, d, J=7.6 Hz), 8.53 (2H, d, J=2.0 Hz), 9.29 (1H, br s).

Example 366

Preparation of 6-(6-cyano-1H-benzimidazol-1-yl)-4-[(3,5-difluorobenzyl)amino]pyridine-3-carboxyamide

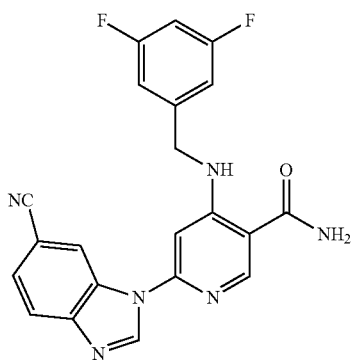 [SMILES: N#Cc1ccc2ncn(-c3cc(NCc4cc(F)cc(F)c4)c(C(N)=O)cn3)c2c1]

Step 1

6-[(2-amino-4-cyanophenyl)amino]-4-[(3,5-difluorobenzyl)amino]pyridine-3-carboxyamide and 6-[(2-amino-5-cyanophenyl)amino]-4-[(3,5-difluorobenzyl)amino]pyridine-3-carboxyamide From 6-chloro-4-[(3,5-difluorobenzyl)amino]pyridine-3-carboxyamide (the compound of Example 20) and 4-cyano-1,2-phenylenediamine in a manner similar to step 1 of Example 365, a mixture of 6-[(2-amino-4-cyanophenyl)amino]-4-[(3,5-difluorobenzyl)amino]pyridine-3-carboxyamide and 6-[(2-amino-5-cyanophenyl)amino]-4-[(3,5-difluorobenzyl)amino]pyridine-3-carboxyamide ($^1$H-NMR integral ratio 1:6) was obtained as a light yellow oil (yield 7%).

6-[(2-amino-4-cyanophenyl)amino]-4-[(3,5-difluorobenzyl)amino]pyridine-3-carboxyamide $^1$H-NMR (270 MHz, CD$_3$OD) δ: 4.38 (2H, br s), 5.62 (1H, s), 6.74-6.90 (6H, m), 7.05 (1H, d, J=1.6 Hz), 7.13 (1H, d, J=8.2 Hz), 8.27 (1H, s).

6-[(2-amino-5-cyanophenyl)amino]-4-[(3,5-difluorobenzyl)amino]pyridine-3-carboxyamide $^1$H-NMR (270 MHz, CD$_3$OD) δ: 4.33 (2H, s), 5.37 (1H, s), 6.73-6.89 (6H, m), 7.26 (1H, s), 7.28 (1H, d, J=5.9 Hz), 8.24 (1H, s).

Step 2

6-(6-cyano-1H-benzimidazol-1-yl)-4-[(3,5-difluorobenzyl)amino]pyridine-3-carboxyamide From the mixture of 6-[(2-amino-4-cyanophenyl)amino]-4-[(3,5-difluorobenzyl)amino]pyridine-3-carboxyamide and 6-[(2-amino-5-cyanophenyl)amino]-4-[(3,5-difluorobenzyl)amino]pyridine-3-carboxyamide in a manner similar to step 2 of Example 365, the title compound was obtained as a yellow solid (yield 45%).

$^1$H-NMR (270 MHz, DMSO-d$_6$) δ: 4.69 (2H, d, J=6.3 Hz), 6.98-7.20 (4H, m), 7.61 (1H, br s), 7.73 (1H, d, J=8.2 Hz), 7.94 (1H, d, J=8.2 Hz), 8.20 (1H, br s), 8.58 (1H, s), 8.72 (1H, s), 9.20 (1H, s), 9.36 (1H, t, J=6.1 Hz).

Example 367

Preparation of 6-(5-cyano-1H-benzimidazol-1-yl)-4-[(3,5-difluorobenzyl)amino]pyridine-3-carboxyamide

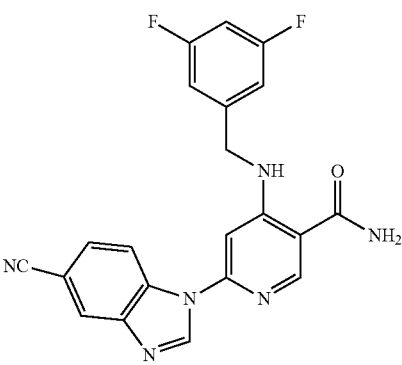 [SMILES: N#Cc1ccc2c(c1)ncn2-c1cc(NCc2cc(F)cc(F)c2)c(C(N)=O)cn1]

Step 1

6-[(2-amino-4-cyanophenyl)amino]-4-[(3,5-difluorobenzyl)amino]pyridine-3-carboxyamide and 6-[(2-amino-5-cyanophenyl)amino]-4-[(3,5-difluorobenzyl)amino]pyridine-3-carboxyamide 89 mg of 6-chloro-4-[(3,5-difluorobenzyl)amino]pyridine-3-carboxyamide (the compound of Example 20), 12 mg of [1,1'-bis(diphenylphosphino)ferrocene]dichloropalladium (II).dichloromethane adduct, 25 mg of 1,1'-bis(diphenylphosphino)ferrocene and 35 mg of sodium tert-butoxide were added to 1 mL of 1,4-dioxane. In an argon atmosphere, 80 mg of 4-cyano-1,2-phenylenediamine was added, and stirred using a microwave reaction apparatus at 100° C. for 1 hour. After cooling, the solvent was evaporated, and the residue was purified by silica gel thin layer chromatography (chloroform:methanol=10:1) to obtain 32 mg (yield 27%) of a mixture of 6-[(2-amino-4-cyanophenyl)amino]-4-[(3,5-difluorobenzyl)amino]pyridine-3-carboxyamide and 6-[(2-amino-5-cyanophenyl)amino]-4-[(3,5-difluorobenzyl)amino]pyridine-3-carboxyamide ($^1$H-NMR integral ratio 3:1) as a light yellow oil.

Step 2

6-(5-cyano-1H-benzimidazol-1-yl)-4-[(3,5-difluorobenzyl)amino]pyridine-3-carboxyamide From the mixture of 6-[(2-amino-4-cyanophenyl)amino]-4-[(3,5-difluorobenzyl)amino]pyridine-3-carboxyamide and 6-[(2-amino-5-cyanophenyl)amino]-4-[(3,5-difluorobenzyl)amino]pyridine-3-carboxyamide ($^1$H-NMR integral ratio 3:1) and trimethyl orthoformate in a manner similar to step 2 of Example 365, the title compound was obtained as a white solid (yield 45%).

$^1$H-NMR (270 MHz, DMSO-d$_6$) δ: 4.68 (2H, d, J=5.9 Hz), 7.01 (1H, s), 7.08-7.24 (3H, m), 7.61 (1H, br s), 7.70 (1H, d, J=8.6 Hz), 8.14 (1H, d, J=8.6 Hz), 8.21 (1H, br s), 8.34 (1H, s), 8.69 (1H, s), 9.12 (1H, s), 9.37 (1H, t, J=6.1 Hz).

Example 368

Preparation of 4-[(3,5-difluorobenzyl)amino]-6-(6-morpholino-1H-benzimidazol-1-yl)pyridine-3-carboxyamide

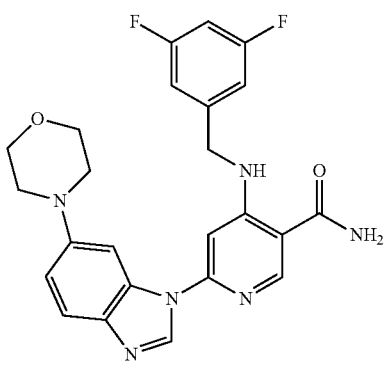 [SMILES: NC(=O)c1cnc(-n2cnc3ccc(N4CCOCC4)cc32)cc1NCc1cc(F)cc(F)c1]

Step 1

6-[(5-morpholino-2-nitrophenol)amino]-4-[(3,5-difluorobenzyl)amino]pyridine-3-carboxyamide 89 mg of 6-chloro-4-[(3,5-difluorobenzyl)amino]pyridine-3-carboxyamide (the compound of Example 20), 12 mg of [1,1'-bis(diphenylphosphino)ferrocene]dichloropalladium (II).methylene chloride adduct, 25 mg of 1,1'-bis(diphenylphosphino)ferrocene and 35 mg of sodium tert-butoxide were added to 1 mL of 1,4-dioxane. In an argon atmosphere, 134 mg of 5-morpholino-2-nitroaniline was added, and stirred using a microwave reaction apparatus at 100° C. for 1 hour. After cooling, the solvent was evaporated, and the residue was purified by silica gel thin layer chromatography (chloroform:methanol=20:1) to obtain 80 mg (yield 55%) of the title compound as a yellow solid.

$^1$H-NMR (270 MHz, DMSO-d$_6$) δ: 3.35-3.42 (4H, m), 3.68-3.77 (4H, m), 4.51 (2H, d, J=5.6 Hz), 6.19-6.33 (1H, m), 6.68 (1H, d, J=7.6 Hz), 6.96-7.21 (4H, m), 7.22-7.37 (1H, m), 7.97-8.05 (1H, m), 8.09-8.16 (1H, m), 8.45-8.56 (1H, m), 9.10 (1H, t, J=5.6 Hz), 10.16 (1H, s).

Step 2

6-[(2-amino-5-morpholinophenyl)amino]-4-[(3,5-difluorobenzyl)amino]pyridine-3-carboxyamide 33 mg of 6-[(5-morpholino-2-nitrophenol)amino]-4-[(3,5-difluorobenzyl)amino]pyridine-3-carboxyamide was dissolved in 3 mL of ethanol, to which 10% palladium carbon was added, and stirred in a hydrogen atmosphere at room temperature for 1.5 hour. The 10% palladium carbon was filtered off, the solvent was evaporated, and the residue was purified by silica gel thin layer chromatography (chloroform:methanol:ammonia water=20:1:0.1) to obtain 10 mg of the title compound crude product as a brown oil.

MS: m/z 454 (M$^+$).

Step 3

4-[(3,5-difluorobenzyl)amino]-6-(6-morpholino-1H-benzimidazol-1-yl)pyridine-3-carboxyamide From 6-[(2-amino-5-morpholinophenyl)amino]-4-[(3,5-difluorobenzyl)amino]pyridine-3-carboxyamide and trimethyl orthoformate in a manner similar to step 2 of Example 365, the title compound was obtained as a light brown solid (2 steps, yield 26%).

$^1$H-NMR (270 MHz, CDCl$_3$) δ: 3.05-3.15 (4H, m), 3.81-3.92 (4H, m), 4.55 (2H, d, J=5.9 Hz), 5.94 (1H, br s), 6.52 (1H, s), 6.75 (1H, t, J=8.7 Hz), 6.88 (2H, d, J=5.9 Hz), 7.02 (1H, dd, J=8.9, 2.3 Hz), 7.40 (1H, d, J=2.3 Hz), 7.70 (1H, d, J=8.9 Hz), 8.26 (1H, s), 8.57 (1H, s), 9.26 (1H, t, J=5.9 Hz).

Example 369

Preparation of 4-[(3,5-difluorobenzyl)amino]-6-(5-morpholino-1H-benzimidazol-1-yl)pyridine-3-carboxyamide and 4-[(3,5-difluorobenzyl)amino]-6-(6-morpholino-1H-benzimidazol-1-yl)pyridine-3-carboxyamide

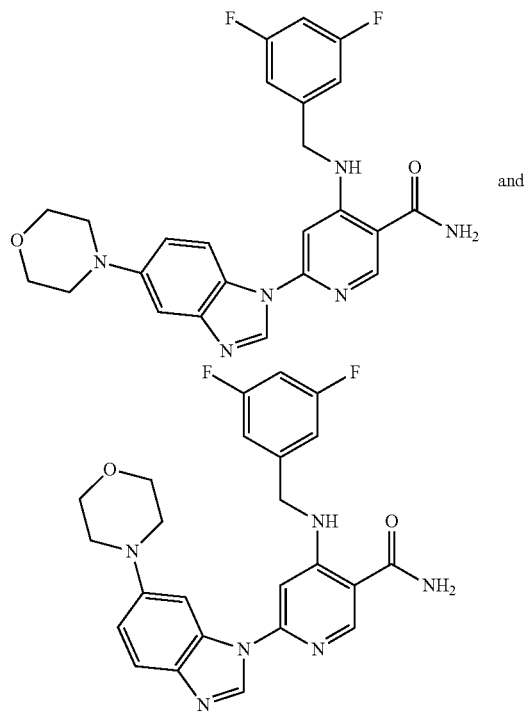

Step 1

6-[(2-amino-4-morpholinophenyl)amino]-4-[(3,5-difluorobenzyl)amino]pyridine-3-carboxyamide and 6-[(2-amino-5-morpholinophenyl)amino]-4-[(3,5-difluorobenzyl)amino]pyridine-3-carboxyamide From 6-chloro-4-[(3,5-difluorobenzyl)amino]pyridine-3-carboxyamide (the compound of Example 20) and 4-morpholino-1,2-phenylenediamine in a manner similar to step 1 of Example 365, a mixture of 6-[(2-amino-4-cyanophenyl)amino]-4-[(3,5-difluorobenzyl)amino]pyridine-3-carboxyamide and 6-[(2-amino-5-cyanophenyl)amino]-4-[(3,5-difluorobenzyl)amino]pyridine-3-carboxyamide (¹H-NMR integral ratio 1:1) was obtained as a red oil (yield 17%).
MS: m/z 454 (M⁺).

Step 2

4-[(3,5-difluorobenzyl)amino]-6-(5-morpholino-1H-benzimidazol-1-yl)pyridine-3-carboxyamide and
4-[(3,5-difluorobenzyl)amino]-6-(6-morpholino-1H-benzimidazol-1-yl)pyridine-3-carboxyamide From the mixture of 6-[(2-amino-4-morpholinophenyl)amino]-4-[(3,5-difluorobenzyl)amino]pyridine-3-carboxyamide and 6-[(2-amino-5-morpholinophenyl)amino]-4-[(3,5-difluorobenzyl)amino]pyridine-3-carboxyamide (¹H-NMR integral ratio 1:1) and trimethyl orthoformate in a manner similar to step 2 of Example 365, a mixture of the title compound (¹H-NMR integral ratio 1:1) was obtained as a light brown solid (yield 28%).
¹H-NMR (270 MHz, CDCl₃) δ: 3.03-3.22 (4H, m), 3.79-3.97 (4H, m), 4.54 (2H, d, J=5.6 Hz), 5.92 (1H, br s), 6.48 (0.5H, s), 6.52 (0.5H, s), 6.64-7.07 (5H, m), 7.19 (0.5H, d, J=9.2 Hz), 7.30 (0.5H, s), 7.39 (0.5H, s), 7.69 (0.5H, d, J=8.9 Hz), 8.25 (0.5H, s), 8.49 (0.5H, s), 8.51 (0.5H, s), 8.57 (0.5H, s), 9.26 (1H, br s).

Example 370

Preparation of 4-[(3,5-difluorobenzyl)amino]-6-{1-[(4-methylphenyl)sulfonyl}-1H-pyrrolo[2,3-b]pyridin-3-yl}pyridine-3-carboxyamide

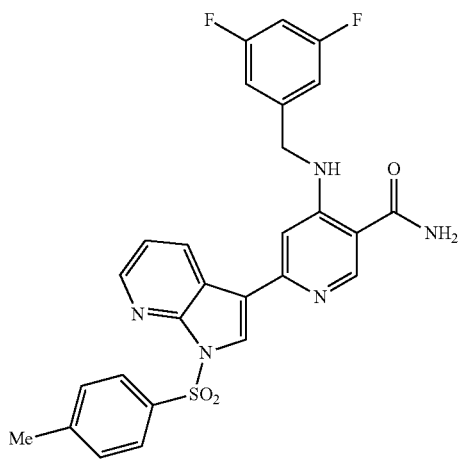 [SMILES: Cc1ccc(S(=O)(=O)n2cc(-c3cc(NCc4cc(F)cc(F)c4)c(C(N)=O)cn3)c3cccnc32)cc1]

26 mg of 6-chloro-4-[(3,5-difluorobenzyl)amino]pyridine-3-carboxyamide (the compound of Example 20) was dissolved in 0.5 mL of tetrahydrofuran, to which 33 mg of 1-[(4-methylphenyl)sulfonyl]-1H-pyrrolo[2,3-b]pyridin-3-boronic acid, 10 mg of tetrakis(triphenylphosphine) palladium (0), and 0.5 mL of 2 mol/L sodium carbonate in water were added, and stirred at 80° C. for 14 hours. To the reaction mixture, water was added, extracted with chloroform, the extract was washed with water, and dried on anhydrous sodium sulfate. The solvent was evaporated, and the residue was purified by silica gel thin layer chromatography (chloroform:methanol=20:1) to obtain 25 mg (yield 54%) of the title compound as a white solid.
¹H-NMR (270 MHz, CDCl₃) δ: 2.37 (3H, s), 4.54 (2H, d, J=6.3 Hz), 6.70 (1H, s), 6.72-6.81 (1H, m), 6.90-6.95 (2H, m), 7.18 (1H, dd, J=8.0, 4.9 Hz), 7.26 (2H, d, J=7.9 Hz), 8.09 (2H, d, J=8.6 Hz), 8.13 (1H, dd, J=8.0, 1.5 Hz), 8.17 (1H, s), 8.44 (1H, dd, J=4.9, 1.5 Hz), 8.60 (1H, s), 9.05 (1H, br s).

Example 371

Preparation of 4-[(3,5-difluorobenzyl)amino]-6-(1H-pyrrolo[2,3-b]pyridin-3-yl)pyridine-3-carboxyamide

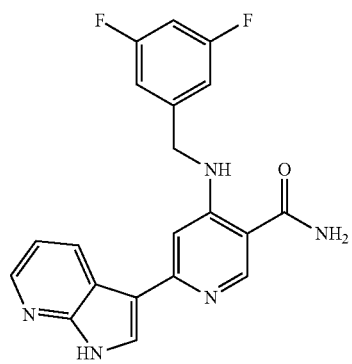 [SMILES: NC(=O)c1cnc(-c2c[nH]c3ncccc23)cc1NCc1cc(F)cc(F)c1]

10 mg of 4-[(3,5-difluorobenzyl)amino]-6-{1-[(4-methylphenyl)sulfonyl]-1H-pyrrolo[2,3-b]pyridin-3-yl}pyridine-3-carboxyamide (the compound of Example 370) was dissolved in 0.5 mL of methanol, to which 0.5 mL of 6 mol/L sodium hydroxide in water was added, and stirred at room temperature for 4 hours. Under ice cooling, hydrochloric acid was added to acidify (about pH 1) the reaction mixture, and washed with chloroform. The aqueous layer was basified (about pH 8) with saturated sodium bicarbonate in water, extracted with chloroform, the extract was washed with water, and dried on anhydrous sodium sulfate. The solvent was evaporated to obtain 2.9 mg (yield 41%) of the title compound as a white solid.
¹H-NMR (270 MHz, DMSO-d₆) δ: 4.64-4.73 (2H, m), 6.94 (1H, s), 7.10-7.18 (5H, m), 8.17-8.22 (1H, m), 8.25-8.30 (1H, m), 8.66 (1H, s).

Example 372

Preparation of 4-benzylamino-6-(pyridin-4-ylamino)pyridine-3-carboxyamide

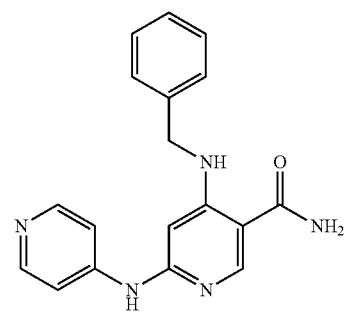 [SMILES: NC(=O)c1cnc(Nc2ccncc2)cc1NCc1ccccc1]

25 mg of 4-benzylamino-6-chloropyridine-3-carboxyamide (the compound of Example 1) was dissolved in 0.5 ml of toluene, to which 13.5 mg of 4-aminopyridine, 2 mg of palladium (II) acetate, 248 mg of potassium carbonate and 11 mg of 2,2'-bis(diphenylphosphino)-1,1'-binaphthyl were added, and stirred at 100° C. for 28 hours. After cooling, the insoluble substances were filtered off, the filtered product was washed with toluene, combined with the filtrate, and the solvent was evaporated. The residue obtained was purified by silica gel column chromatography (chloroform:methanol=10:1) to obtain 4.8 mg (yield 16%) of the title compound as a slight yellow crystalline powder.

$^1$H-NMR (400 MHz, CD$_3$OD) δ: 4.45 (2H, s), 6.05 (1H, s), 7.23-7.36 (5H, m), 7.45 (2H, d, J=5.2 Hz), 8.17 (2H, d, J=5.4 Hz), 8.42 (1H, s).

Example 373

Preparation of 4-benzylamino-6-[(6-morpholinopyridin-3-yl)amino]pyridine-3-carboxyamide

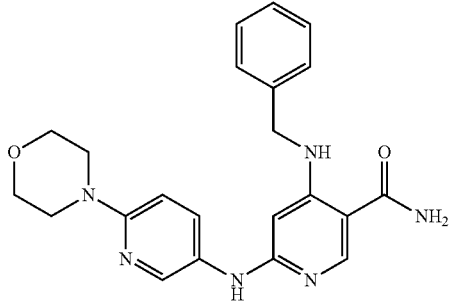 [SMILES: NC(=O)c1cnc(Nc2ccc(N3CCOCC3)nc2)cc1NCc1ccccc1]

Step 1

6-chloro-4-(trifluoroacetyl)aminopyridine-3-carboxylic acid ethyl ester 300 mg of 4-amino-6-chloropyridine-3-carboxylic acid ethyl ester was dissolved in 5 mL of methylene chloride, to which 178 mg of pyridine and 378 mg of trifluoroacetic acid anhydride were added, and stirred at room temperature for 1 hours. Furthermore, 178 mg of pyridine and 378 mg of trifluoroacetic acid anhydride were added, and stirred at room temperature for 1 hour. To the reaction mixture water was added, extracted with ethyl acetate, the extract was washed with saturated saline, and dried on anhydrous sodium sulfate. The solvent was evaporated, and the residue was purified by silica gel chromatography (hexane:ethyl acetate=6:1) to obtain 292 mg (yield 66%) of the title compound as a white solid.

$^1$H-NMR (400 MHz, CDCl$_3$) δ: 1.46 (3H, t, J=7.2 Hz), 4.49 (2H, q, J=7.2 Hz), 8.63 (1H, s), 9.03 (1H, s), 12.38 (1H, brs).

Step 2

6-[4-methoxybenzyl-(6-morpholinopyridin-3-yl)amino]-4-[(trifluoroacetyl)amino]pyridine-3-carboxylic acid ethyl ester 21.8 mg of 6-chloro-4-(trifluoroacetyl)aminopyridine-3-carboxylic acid ethyl ester and 22 mg of 3-(4-methoxybenzyl)amino-6-morpholinopyridine were dissolved in 1 mL of toluene, to which 1.7 mg of palladium (II) acetate, 9.2 mg of 2,2'-bis (diphenylphosphino)-1,1'-binaphthyl and 202 mg of sodium carbonate were added, and stirred overnight at 100° C. After cooling, water was added to the reaction mixture, extracted with chloroform, the extract was washed with saturated saline, and dried on anhydrous sodium sulfate. The solvent was evaporated, and the residue was purified by silica gel thin layer chromatography (hexane:ethyl acetate=1:1) to obtain 5.7 mg (ylod 14%) of the title compound as a light yellow solid.

$^1$H-NMR (400 MHz, CDCl$_3$) δ: 1.40 (3H, t, J=7.2 Hz), 3.50-3.55 (4H, m), 3.77 (3H, s), 3.81-3.85 (4H, m), 4.38 (2H, q, J=7.2 Hz), 5.13 (1H, s), 6.62 (1H, d, J=9.0 Hz), 6.79 (2H, d, J=8.6 Hz), 7.17 (2H, d, J=8.8 Hz), 7.20 (1H, dd, J=8.8, 2.7 Hz), 7.47 (1H, s), 7.97 (1H, d, J=2.7 Hz), 8.92 (1H, s), 12.36 (1H, s).

Step 3

4-amino-6-[4-methoxybenzyl-(6-morpholinopyridin-3-yl)amino]pyridine-3-carboxylic acid ethyl ester 51 mg of 6-[4-methoxybenzyl-(6-morpholinopyridin-3-yl)amino]-4-[(trifluoroacetyl)amino]pyridine-3-carboxylic acid ethyl ester was dissolved in 5 mL of methanol, to which 3 mL of 2 mol/L potassium carbonate in water was added, and stirred at room temperature for 4 hours. To the reaction mixture water was added, extracted with ethyl acetate, the extract was washed with saturated saline, and dried on anhydrous sodium sulfate. The solvent was evaporated to obtain 42 mg (yield 100%) of the title compound as a light yellow solid.

$^1$H-NMR (400 MHz, CDCl$_3$) δ: 1.36 (3H, t, J=7.1 Hz), 3.46-3.52 (4H, m), 3.77 (3H, s), 3.80-3.84 (4H, m), 4.29 (2H, q, J=7.1 Hz), 5.09 (2H, s), 5.29 (1H, s), 5.76 (1H, brs), 6.60 (1H, d, J=9.0 Hz), 6.78 (2H, d, J=8.6 Hz), 7.16 (2H, d, J=8.6 Hz), 7.19 (1H, dd, J=9.0, 2.7 Hz), 7.96 (1H, d, J=2.4 Hz), 8.72 (1H, s).

Step 4

4-benzylamino-6-[4-methoxybenzyl-(6-morpholinopyridin-3-yl)amino]pyridine-3-carboxylic acid ethyl ester 47 mg of 4-amino-6-[4-methoxybenzyl-(6-morpholinopyridin-3-yl)amino]pyridine-3-carboxylic acid ethyl ester was dissolved in 2 mL of tetrahydrofuran, to which 21.5 mg of benzaldehyde, 3.1 mg of dibutyltin dichloride and 16.4 mg of phenylsilane were added, and stirred at room temperature for 3 days. For every 24 hours in the meantime, 21.5 mg of benzaldehyde, 3.1 mg of dibutyltin dichloride and 16.4 mg of phenylsilane were each added twice. To the reaction mixture water was added, extracted with chloroform, the extract was washed with saturated saline, and dried on anhydrous sodium sulfate. The solvent was evaporated, and the residue was purified by silica gel thin layer chromatography (hexane:ethyl acetate=1:1) and silica gel thin layer chromatography (chloroform:methanol=20:1) to obtain 3.0 mg of the title compound crude product containing impurities as a light yellow oil. Without further purification, this was used in the next reaction as it was.

Step 5

4-benzylamino-6-[4-methoxybenzyl-(6-morpholinopyridin-3-yl)amino]pyridine-3-carboxylic acid 3.0 mg of 4-benzylamino-6-[4-methoxybenzyl-(6-morpholinopyridin-3-yl)amino]pyridine-3-carboxylic acid ethylester was dissolved in 1 mL of ethanol, to which 1 mL of 2 mol/L sodium hydroxide in water was added, and stirred at 80° C. for 1 hour. After cooling, hydrochloric acid was added to neutralize the reaction mixture. It was extracted with chloroform, the extract was washed with saturated saline, and dried on anhydrous sodium sulfate. The solvent was evaporated to obtain 3.4 mg of the title compound containing impurities as a brown oil. Without further purification, this was used in the next reaction as it was.

Step 6

4-benzylamino-6-[4-methoxybenzyl-(6-morpholinopyridin-3-yl)amino]pyridine-3-carboxyamide 3.4 mg of 4-benzylamino-6-[4-methoxybenzyl-(6-morpholinopyridin-3-yl)amino]pyridine-3-carboxylic acid was dissolved in 1 mL of dichloromethane, to which 1.9 mg of 1-ethyl-3-(3-dimethylaminopropyl)carbodiimide hydrochloride and 1.5 mg of 1-hydroxybenzotriazole monohydrate were added, and stirred at room temperature for 30 minutes. Then, 1 mL of 28% ammonia water was added, and stirred at the same temperature for 3 hours. To the reaction mixture water was added, extracted with chloroform, the extract was washed with saturated saline, and dried on anhydrous sodium sulfate. The solvent was evaporated to obtain 3.0 mg of the title compound containing impurities as a brown solid. Without further purification, this was used in the next reaction as it was.

Step 7

4-benzylamino-6-[(6-morpholinopyridin-3-yl)amino]pyridine-3-carboxyamide 3.0 mg of 4-benzylamino-6-[4-methoxybenzyl-(6-morpholinopyridin-3-yl)amino]pyridine-3-carboxyamide was dissolved in 0.5 mL of methylene chloride, to which 0.5 mg of trifluoroacetic acid was added, stirred at room temperature for 4 hours, and further heated at reflux at 70° C. for 8 hours. After cooling, the solvent was evaporated, saturated sodium bicarbonate in water was added to the residue, extracted with chloroform, the extract was washed with saturated saline, and dried on anhydrous sodium sulfate. The solvent was evaporated, and the residue was purified by silica gel thin layer chromatography (chloroform:methanol=10:1) and silica gel thin layer chromatography (chloroform:ammonium-saturated methanol=10:1) to obtain 1.2 mg (4 steps, yield 3%) of the title compound as a light brown solid.

$^1$H-NMR (400 MHz, CDCl$_3$) δ: 3.46-3.51 (4H, m), 3.83-3.88 (4H, m), 4.29 (2H, d, J=5.4 Hz), 5.56 (2H, brs), 5.58 (1H, s), 6.42 (1H, brs), 6.53 (1H, d, J=9.0 Hz), 7.22-7.35 (6H, m), 8.03 (1H, d, J=2.4 Hz), 8.18 (1H, s), 8.87 (1H, brs).

Biological Experiment Example 1

JAK3 Kinase Assay

Recombinant human JAK3 enzyme (JAK3 kinase region; Ala795-Ser1124) was purchased from Carna Biosciences, Inc.

The reaction was conducted in a kinase buffer (reaction volume: a total of 50 µl) containing 8 mM MOPS (pH 7.0), 0.2 mM EDTA, a test compound solution prepared to each concentration and 0.5 µg/ml JAK3 enzyme using a 96-well polystyrene plate (clear-bottom white-wall). The concentration of each test compound was adjusted to 0.1 µM or 1 µM. The substrate concentration in this assay was 100 µm ATP and 100 µg/mL poly(Glu)-4-Tyr (molecular weight: 5,000-20,000 Da; Sigma). After incubating them at room temperature for 2 hours, 50 µl of Kinase-Glo Luminescent Kinase Assay reagent (Promega) was added to each well, and further incubated at room temperature for 10 minutes. Using a chemiluminescence microplate reader MicroLumat LB96P (Berthold), chemiluminescence intensity was measured to quantitate the amount of ATP remaining after reaction. From the amount of ATP consumed in the phosphorylation reaction, the inhibition rate (%) of JAK3 kinase activity was determined.

Table 1

A to D show the inhibitory effect of test compounds at 0.1 µM in terms of inhibition rate (%). Table 1-E and F show the inhibitory effect of test compounds at 1 µM in terms of inhibition rate (%). As can be seen from the Tables, it was confirmed that the pyridine-3-carboxyamide derivative of the present invention has a highly potent JAK3 kinase inhibitory activity.

TABLE 1-A

| Test compound | Inhibition rate (%) |
| --- | --- |
| Example 46 | 19 |
| Example 52 | 72 |
| Example 57 | 89 |
| Example 59 | 76 |
| Example 60 | 65 |
| Example 65 | 79 |
| Example 70 | 75 |
| Example 71 | 70 |
| Example 72 | 65 |
| Example 73 | 56 |
| Example 76 | 63 |
| Example 77 | 55 |
| Example 80 | 79 |
| Example 81 | 72 |
| Example 90 | 77 |
| Example 91 | 92 |
| Example 93 | 86 |
| Example 94 | 96 |
| Example 96 | 74 |
| Example 99 | 80 |
| Example 100 | 69 |
| Example 102 | 53 |
| Example 115 | 70 |
| Example 125 | 61 |
| Example 126 | 60 |
| Example 127 | 81 |

TABLE 1-B

| Example 128 | 92 |
| --- | --- |
| Example 131 | 91 |
| Example 134 | 83 |
| Example 136 | 80 |
| Example 140 | 62 |
| Example 141 | 83 |
| Example 142 | 66 |
| Example 143 | 88 |
| Example 144 | 61 |
| Example 145 | 63 |
| Example 146 | 78 |
| Example 147 | 58 |
| Example 150 | 66 |
| Example 151 | 69 |
| Example 153 | 94 |
| Example 155 | 59 |
| Example 157 | 79 |
| Example 159 | 100 |
| Example 160 | 66 |
| Example 162 | 72 |
| Example 163 | 77 |
| Example 164 | 78 |
| Example 165 | 54 |
| Example 170 | 68 |

TABLE 1-B-continued

| Example 172 | 59 |
|---|---|
| Example 174 | 58 |
| Example 176 | 86 |
| Example 177 | 84 |
| Example 178 | 90 |
| Example 179 | 78 |
| Example 180 | 63 |
| Example 185 | 87 |
| Example 186 | 93 |
| Example 187 | 85 |
| Example 188 | 89 |
| Example 190 | 89 |

TABLE 1-C

| Example 191 | 63 |
|---|---|
| Example 192 | 89 |
| Example 201 | 60 |
| Example 202 | 88 |
| Example 205 | 98 |
| Example 219 | 65 |
| Example 221 | 78 |
| Example 222 | 78 |
| Example 223 | 81 |
| Example 224 | 68 |
| Example 225 | 74 |
| Example 226 | 61 |
| Example 233 | 74 |
| Example 234 | 72 |
| Example 235 | 82 |
| Example 236 | 83 |
| Example 237 | 78 |
| Example 238 | 100 |
| Example 239 | 57 |
| Example 240 | 85 |
| Example 241 | 70 |
| Example 242 | 77 |
| Example 244 | 59 |
| Example 245 | 62 |
| Example 248 | 88 |
| Example 249 | 81 |
| Example 251 | 88 |
| Example 255-1 | 74 |
| Example 256 | 77 |
| Example 258 | 60 |
| Example 259 | 67 |
| Example 262 | 78 |
| Example 263 | 98 |
| Example 264 | 92 |
| Example 265 | 74 |
| Example 266 | 77 |

TABLE 1-D

| Example 267 | 72 |
|---|---|
| Example 268 | 65 |
| Example 274 | 79 |
| Example 275 | 96 |
| Example 276 | 68 |
| Example 277 | 70 |
| Example 279 | 59 |
| Example 282 | 89 |
| Example 283 | 79 |
| Example 284 | 63 |
| Example 285-1 | 64 |
| Example 289 | 74 |
| Example 290 | 71 |
| Example 291 | 79 |
| Example 292 | 84 |
| Example 293 | 61 |
| Example 298 | 69 |
| Example 300 | 90 |
| Example 301 | 92 |
| Example 302 | 90 |
| Example 304 | 78 |

TABLE 1-D-continued

| Example 305 | 77 |
|---|---|
| Example 307 | 71 |
| Example 314 | 60 |
| Example 315 | 60 |
| Example 316 | 61 |
| Example 317 | 62 |
| Example 318 | 83 |
| Example 323 | 65 |
| Example 326 | 71 |
| Example 328 | 70 |
| Example 330 | 59 |
| Example 332 | 69 |

TABLE 1-E

| Test compound | Inhibition rate (%) |
|---|---|
| Example 345 | 79 |
| Example 346 | 72 |
| Example 347 | 68 |
| Example 349 | 90 |
| Example 351 | 45 |
| Example 353 | 65 |
| Example 355 | 92 |
| Example 356 | 92 |
| Example 359 | 61 |
| Example 360 | 57 |
| Example 361 | 83 |
| Example 362 | 40 |
| Example 363 | 67 |

TABLE 1-F

| Test compound | Inhibition rate (%) |
|---|---|
| Example 364 | 9 |
| Example 365 | 62 |
| Example 366 | 9 |
| Example 370 | 13 |
| Example 371 | 42 |
| Example 372 | 31 |
| Example 373 | 81 |

From the foregoing, it was confirmed that the pyridine-3-carboxyamide derivative of the present invention has a highly potent JAK3 kinase inhibitory activity.

The invention claimed is:

1. A pyridine-3-carboxyamide derivative represented by the general formula (1):

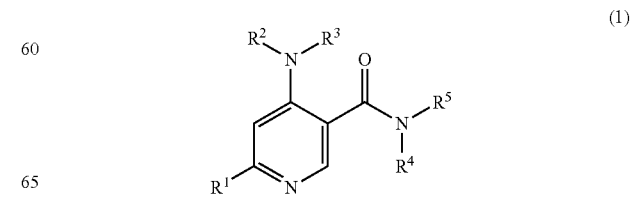

wherein
R¹ is a group selected from one of the following formulas i to iv:

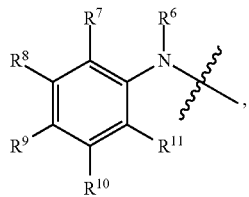
i

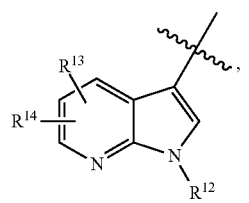
ii

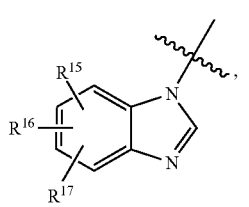
iii

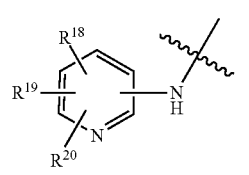
iv wherein
$R^6$ is selected from the group consisting of a hydrogen atom, a $C_{1-6}$ alkyl group and an optionally substituted acyl group, $R^7$, $R^8$, $R^9$, $R^{10}$ and $R^{11}$, which may be the same or different, are selected from the group consisting of a hydrogen atom, a halogen atom, an optionally substituted $C_{1-6}$ alkyl group, a cyano group, an optionally substituted $C_{3-8}$ cycloalkyl group, a $C_{1-6}$ alkoxycarbonyl group, an optionally substituted $C_{1-6}$ alkylcarbonyl group, a $C_{3-8}$ cycloalkylcarbonyl group, a carbamoyl group, a carboxyl group, a $C_{1-6}$ alkylthio group, a $C_{1-6}$ alkylsulfinyl group, a $C_{1-6}$ alkylsulfonyl group, a (5-11-membered heterocyclic)-sulfonyl group, an optionally substituted 5-11-membered heterocyclic group, an optionally substituted sulfamoyl group, —O—$R^{21}$ (wherein $R^{21}$ represents a hydrogen atom, an optionally substituted $C_{1-6}$ alkyl group or a piperazinyl group that may be substituted with a $C_{1-6}$ alkyl group), —$NR^{22}R^{23}$ (wherein $R^{22}$ and $R^{23}$, which may be the same or different, represent a hydrogen atom, an optionally substituted $C_{1-6}$ alkyl group, an optionally substituted $C_{1-6}$ alkylsulfonyl group, a $C_{2-6}$ alkenylsulfonyl group or an optionally substituted 5-11-membered heterocyclic group) and —$NR^{24}COR^{25}$ (wherein $R^{24}$ represents a hydrogen atom or a $C_{1-6}$ alkyl group, and $R^{25}$ represents an amino group, a mono($C_{1-6}$ alkyl)amino group, a di($C_{1-6}$ alkyl) amino group or an optionally substituted 5-11-membered heterocyclic group), $R^{12}$ represents a hydrogen atom or a sulfonyl group, and
$R^{13}$, $R^{14}$, $R^{15}$, $R^{16}$, $R^{17}$, $R^{18}$, $R^{19}$ and $R^{20}$, which may be the same or different, represent a hydrogen atom, a halogen atom, a cyano group or a morpholino group, R² represents a group selected from one of the following formulas v to x:

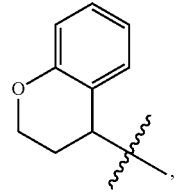
v

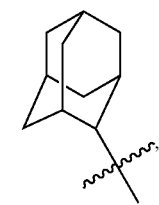
vi

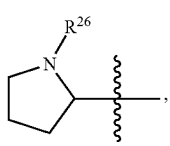
vii

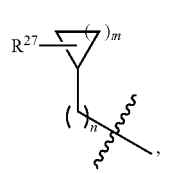
viii

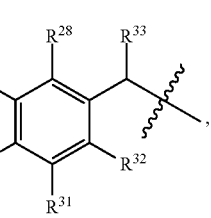
ix

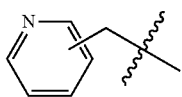
x $R^{26}$ represents a hydrogen atom, a $C_{1-6}$ alkyl group, a $C_{6-10}$ aryl $C_{1-6}$ alkyl group or a $C_{1-6}$ alkylcarbonyl group,
$R^{27}$ represents a hydrogen atom or a $C_{1-6}$ alkyl group,
$R^{28}$, $R^{29}$, $R^{30}$, $R^{31}$ and $R^{32}$, which may be the same or different, are selected from the group consisting of a hydrogen atom, a halogen atom, a $C_{1-6}$ alkyl group, a halo $C_{1-6}$ alkyl group, a $C_{1-6}$ alkoxy group, a carboxyl group, a $C_{1-6}$ alkoxycarbonyl group, a carbamoyl group, a nitro group, a piperazinyl group that may be substituted with a $C_{1-6}$ alkyl group, an amino group, a mono ($C_{1-6}$ alkyl)amino group, a di($C_{1-6}$ alkyl)amino group, a $C_{1-6}$ alkylcarbonylamino group, —$N(R^{34})SO_2R^{35}$ (wherein $R^{34}$ represents a hydrogen atom or a $C_{1-6}$ alkyl group and $R^{35}$ represents a $C_{1-6}$ alkyl group or a $C_{2-6}$ alkenyl group) and —$SO_2NR^{36}R^{37}$ (wherein $R^{36}$ and $R^{37}$, which may be the same or different, represent a hydrogen atom or a $C_{1-6}$ alkyl group), or $R^{28}$ and $R^{29}$ or $R^{29}$ and $R^{30}$ may together form a benzene ring, $R^{33}$ represents a hydrogen atom or a $C_{1-6}$ alkyl group, m represents an integer of 1 to 6, n represents 0 or 1, $R^3$ represents a hydrogen atom or a $C_{1-6}$ alkyl group and $R^4$ and $R^5$, which may be the same or different, are selected from the group consisting of a hydrogen atom, a $C_{1-6}$ alkyl group, a $C_{1-6}$ alkoxy group, an amino group and a hydroxy group], or its salt or a hydrate thereof.

2. The pyridine-3-carboxyamide derivative according to claim 1, wherein $R^{28}$, $R^{29}$, $R^{30}$, $R^{31}$ and $R^{32}$, which may be the same or different, are selected from the group consisting of a hydrogen atom, a halogen atom, a $C_{1-6}$ alkyl group, a halo $C_{1-6}$ alkyl group, a $C_{1-6}$ alkoxy group, a carboxyl group, a $C_{1-6}$ alkoxycarbonyl group, a carbamoyl group, a nitro group, a piperazinyl group that may be substituted with a $C_{1-6}$ alkyl group, —N($R^{34}$)SO$_2R^{35}$ (wherein $R^{34}$ and $R^{35}$ represent the same groups as described above) and —SO$_2$NR$^{36}R^{37}$ (wherein $R^{36}$ and $R^{37}$ represent the same groups as described above), or $R^{28}$ and $R^{29}$ or $R^{29}$ and $R^{30}$ may together form a benzene ring, or its salt or a hydrate thereof.

3. The pyridine-3-carboxyamide derivative according to claim 1, wherein the optionally substituted 5-11-membered heterocyclic group in $R^7$, $R^8$, $R^9$, $R^{10}$ and $R^{11}$ is selected from the group consisting of an optionally substituted morpholinyl group, an optionally substituted piperazinyl group, an optionally substituted piperidinyl group, an optionally substituted hexahydro-1H-1,4-diazepinyl group, an optionally substituted pyrrolidinyl group, an optionally substituted 1,1-dioxoisothiazolidinyl group, an optionally substituted oxolanyl group and an optionally substituted pyrrolidinyl group, or its salt or a hydrate thereof.

4. The pyridine-3-carboxyamide derivative according to claim 1, wherein the compound represented by the general formula (1) is, 4-(benzylamino)-6-({4-[(1-methylpiperidin-4-yl)oxy]phenyl}amino)pyridine-3-carboxyamide, 4-(benzylamino)-6-({4-[4-(2-hydroxyethyl)piperidino]phenyl}amino)pyridine-3-carboxyamide, 4-(benzylamino)-6-[(4-{4-[2-(diethylamino)ethyl]piperidino}phenyl)amino]pyridine-3-carboxyamide, 4-(benzylamino)-6-({4-[4-(2-cyanoethyl)piperidino]phenyl}amino)pyridine-3-carboxyamide, 6-[(4-aminophenyl)amino]-4-(benzylamino)pyridine-3-carboxyamide, 4-(benzylamino)-6-({4-[(2-morpholinoethyl)amino]phenyl}amino)pyridine-3-carboxyamide, 4-(benzylamino)-6-({4-[methyl(2-morpholinoethyl)amino]phenyl}amino)pyridine-3-carboxyamide, 4-(benzylamino)-6-[(4-morpholinophenyl)amino]pyridine-3-carboxyamide, 4-[(2-methoxybenzyl)amino]-6-[(4-morpholinophenyl)amino]pyridine-3-carboxyamide, 4-[(2-methylbenzyl)amino]-6-[(4-morpholinophenyl)amino]pyridine-3-carboxyamide, 4-[(3-methylbenzyl)amino]-6-[(4-morpholinophenyl)amino]pyridine-3-carboxyamide, 4-[(2-chlorobenzyl)amino]-6-[(4-morpholinophenyl)amino]pyridine-3-carboxyamide, 4-[(3-chlorobenzyl)amino]-6-[(4-morpholinophenyl)amino]pyridine-3-carboxyamide, 4-[(2,3-difluorobenzyl)amino]-6-[(4-morpholinophenyl)amino]pyridine-3-carboxyamide, 4-[(2,5-difluorobenzyl)amino]-6-[(4-morpholinophenyl)amino]pyridine-3-carboxyamide, 4-[(2,6-difluorobenzyl)amino]-6-[(4-morpholinophenyl)amino]pyridine-3-carboxyamide, 6-[(4-morpholinophenyl)amino]-4-{[3-fluoro-5-(trifluoromethyl)benzyl]amino}pyridine-3-carboxyamide, 4-[(5-fluoro-2-methoxybenzyl)amino]-6-[4(4-morpholinophenyl)amino]pyridine-3-carboxyamide, 4-[(3-fluoro-2-methylbenzyl)amino]-6-[(4-morpholinophenyl)amino]pyridine-3-carboxyamide, 6-[(4-morpholinophenyl)amino]-4-[(3-nitrobenzyl)amino]pyridine-3-carboxyamide, 4-[(3-carbamoylbenzyl)amino]-6-[(4-morpholinophenyl)amino]pyridine-3-carboxyamide, 6-[(3-cyano-4-morpholinophenyl)amino]-4-[(3,5-difluorobenzyl)amino]pyridine-3-carboxyamide, 4-[(3,5-difluorobenzyl)amino]-6-[(3-methyl-4-morpholinophenyl)amino]pyridine-3-carboxyamide, 6-[(3-chloro-4-morpholinophenyl)amino]-4-[(3,5-difluorobenzyl)amino]pyridine-3-carboxyamide, 4-[(3,5-difluorobenzyl)amino]-6-[(3-methoxy-4-morpholinophenyl)amino]pyridine-3-carboxyamide, 4-[(3,5-difluorobenzyl)amino]-6-[(3-morpholinophenyl)amino]pyridine-3-carboxyamide, 4-(benzylamino)-6-({4-[(3S)-3-methylmorpholino]phenyl}amino)pyridine-3-carboxyamide, 4-[(2,3-difluorobenzyl)amino]-6-({4-[(3R,5S)-3,5-dimethylpiperazin-1-yl]phenyl}amino)pyridine-3-carboxyamide, 4-[(3,5-difluorobenzyl)amino]-6-({4-[(3R,5S)-3,5-dimethylpiperazin-1-yl]phenyl}amino)pyridine-3-carboxyamide, 4-[(2,5-difluorobenzyl)amino]-6-({4-[(3R,5S)-3,5-dimethylpiperazin-1-yl]phenyl}amino)pyridine-3-carboxyamide, 4-[(3,5-difluorobenzyl)amino]-6-({3-[(3R,5S)-3,5-dimethylpiperazin-1-yl]phenyl}amino)pyridine-3-carboxyamide, 4-(benzyl amino)-6-{[4-(4-methylpiperazin-1-yl)phenyl]amino}pyridine-3-carboxyamide, 4-(benzylamino)-6-({4-[4-(propan-2-yl)piperazin-1-yl]phenyl}amino)pyridine-3-carboxyamide, 4-[(2-methoxybenzyl)amino]-6-({4-[4-(propan-2-yl)piperazin-1-yl]phenyl}amino)pyridine-3-carboxyamide, 4-[(2,3-difluorobenzyl)amino]-6-({4-[4-(propan-2-yl)piperazin-1-yl]phenyl}amino)pyridine-3-carboxyamide, 4-[(3,5-difluorobenzyl)amino]-6-({4-[4-(propan-2-yl)piperazin-1-yl]phenyl}amino)pyridine-3-carboxyamide, 4-[(3,5-difluorobenzyl)amino]-6-({3-[4-(propan-2-yl)piperazin-1-yl]phenyl}amino)pyridine-3-carboxyamide, 4-[(3,5-difluorobenzyl)amino]-6-{[4-({2-[(methylsulfonyl)amino]ethyl}amino)phenyl]amino}pyridine-3-carboxyamide, 4-[(3-nitrobenzyl)amino]-6-({4-[(methyl sulfonyl)amino]phenyl}amino)pyridine-3-carboxyamide, 4-[(3,5-difluorobenzyl)amino]-6-({4-[(propylsulfonyl)amino]phenyl}amino)pyridine-3-carboxyamide, 4-(benzylamino)-6-({4-[(propan-2-ylsulfonyl)amino]phenyl}amino)pyridine-3-carboxyamide, 4-[(3,5-difluorobenzyl)amino]-6-({3-[(methylsulfonyl)amino]phenyl}amino)pyridine-3-carboxyamide, 4-[(3,5-difluorobenzyl)amino]-6-({3-[(propan-2-ylsulfonyl)amino]phenyl}amino)pyridine-3-carboxyamide, 4-[(3,5-difluorobenzyl)amino]-6-({4-[4-(propan-2-ylsulfonyl)piperazin-1-yl]phenyl}amino)pyridine-3-carboxyamide,
4-[(2,6-difluorobenzyl)amino]-6-({4-[4-(propan-2-ylsulfonyl)piperazin-1-yl]phenyl}amino)pyridine-3-carboxyamide,
4-[(3,5-difluorobenzyl)amino]-6-({3-[4-(propan-2-ylsulfonyl)piperazin-1-yl]phenyl}amino)pyridine-3-carboxyamide,
4-(benzylamino)-6-[(4-{4-[(2-hydroxyethyl)carbamoyl]piperidino}phenyl)amino]pyridine-3-carboxyamide,
4-[(2,3-difluorobenzyl)amino]-6-({4-[4-(2-hydroxyethyl)piperidino]phenyl}amino)pyridine-3-carboxyamide,
6-({4-[4-(2-hydroxyethyl)piperidino]phenyl}amino)-4-[(3-nitrobenzyl)amino]pyridine-3-carboxyamide,
4-[(2-methylbenzyl)amino]-6-{[4-(4-hydroxypiperidino)phenyl]amino}pyridine-3-carboxyamide,
4-[(2-chlorobenzyl)amino]-6-{[4-(4-hydroxypiperidino)phenyl]amino}pyridine-3-carboxyamide,
4-[(2,3-difluorobenzyl)amino]-6-{[4-(4-hydroxypiperidino)phenyl]amino}pyridine-3-carboxyamide,
4-[(2,5-difluorobenzyl)amino]-6-{[4-(4-hydroxypiperidino)phenyl]amino}pyridine-3-carboxyamide,
4-[(3,5-difluorobenzyl)amino]-6-{[4-(4-methoxypiperidino)phenyl]amino}pyridine-3-carboxyamide,
4-[(3,5-difluorobenzyl)amino]-6-{[4-(4-hydroxypiperidino)phenyl]amino}pyridine-3-carboxyamide,
4-[(3,5-difluorobenzyl)amino]-6-{[4-(4-oxopiperidino)phenyl]amino}pyridine-3-carboxyamide,
6-{[4-(3-aminopropyl)phenyl]amino}-4-[(3,5-difluorobenzyl)amino]pyridine-3-carboxyamide,
4-[(3,5-difluorobenzyl)amino]-6-[(4-{3-[(methanesulfonyl)amino]propyl}phenyl)amino]pyridine-3-carboxyamide,
4-(benzylamino)-6-{[4-piperazin-1-yl]phenyl}amino)pyridine-3-carboxyamide,
4-[(3,5-difluorobenzyl)amino]-6-{[4-(piperazin-1-yl)phenyl]amino}pyridine-3-carboxyamide,
4-[(2,5-difluorobenzyl)amino]-6-{[4-(piperazin-1-yl)phenyl]amino}pyridine-3-carboxyamide,
4-[(2,6-difluorobenzyl)amino]-6-{[4-(piperazin-1-yl)phenyl]amino}pyridine-3-carboxyamide,
4-[(3-nitrobenzyl)amino]-6-{[4-(piperazin-1-yl)phenyl]amino}pyridine-3-carboxyamide,
4-[(3,5-difluorobenzyl)amino]-6-{[3-(piperazin-1-yl)phenyl]amino}pyridine-3-carboxyamide,
4-(benzylamino)-6-{[4-(1,4-diazepan-1-yl)phenyl]amino}pyridine-3-carboxyamide,
4-[(3,5-difluorobenzyl)amino]-6-({4-[(2-methoxyethyl)amino]phenyl}amino)pyridine-3-carboxyamide,
4-[(3,5-difluorobenzyl)amino]-6-({4-[(2-hydroxyethyl)amino]phenyl}amino)pyridine-3-carboxyamide,
6-[(4-{4-[2-(diethylamino)ethyl]piperazin-1-yl}phenyl)amino]-4-[(3-nitrobenzyl)amino]pyridine-3-carboxyamide,
4-(benzylamino)-6-[(4-{4-[2-(diethylamino)ethyl]piperazin-1-yl}phenyl)amino]pyridine-3-carboxyamide,
6-[(4-{4-[2-(diethylamino)ethyl]piperazin-1-yl}phenyl)amino]-4-[(2,3-difluorobenzyl)amino]pyridine-3-carboxyamide,
6-[(3-{4-[2-(diethylamino)ethyl]piperazin-1-yl}phenyl)amino]-4-[(3,5-difluorobenzyl)amino]pyridine-3-carboxyamide,
6-({4-{4-(2-cyanoethyl)piperazin-1-yl]phenyl}amino)-4-[(3,5-difluorobenzyl)amino]pyridine-3-carboxyamide,
4-(benzyl)-6-({4-[4-(2-cyanoethyl)piperazin-1-yl]phenyl}amino)pyridine-3-carboxyamide,
6-({4-{4-(3-cyanopropyl)piperazin-1-yl]phenyl}amino)-4-[(3-nitrobenzyl)amino]pyridine-3-carboxyamide,
4-(benzylamino)-6-{[4-(4-methyl-1,4-diazepan-1-yl)phenyl]amino}pyridine-3-carboxyamide,
4-(benzylamino)-6-({4-[4-(2-hydroxyethyl)-1,4-diazepan-1-yl]phenyl}amino)pyridine-3-carboxyamide,
6-({4-[4-(2-aminoethyl)piperazin-1-yl]phenyl}amino)-4-[(3,5-difluorobenzyl)amino]pyridine-3-carboxyamide,
4-[(3,5-difluorobenzyl)amino]-6-{[4-(4-{2-[(methylsulfonyl)amino]ethyl}piperazin-1-yl)phenyl]amino}pyridine-3-carboxyamide,
4-[(3,5-difluorobenzyl)amino]-6-[(4-{4-[2-(methylamino)ethyl]piperazin-1-yl}phenyl)amino]pyridine-3-carboxyamide,
6-{[4-(4-acetylpiperazin-1-yl)phenyl]amino}-4-(benzylamino)pyridine-3-carboxyamide,
6-{[4-(4-acetyl-1,4-diazepan-1-yl)phenyl]amino}-4-(benzylamino)pyridine-3-carboxyamide,
4-(benzylamino)-6-{[4-(4-butanoylpiperazin-1-yl)phenyl]amino}pyridine-3-carboxyamide,
4-(benzylamino)-6-({4-[4-(2-methylpropanoyl)piperazin-1-yl]phenyl}amino)pyridine-3-carboxyamide,
4-(benzylamino)-6-({4-[4-(cyanoacetyl)piperazin-1-yl]phenyl}amino)pyridine-3-carboxyamide,
6-({4-[4-(cyanoacetyl)piperazin-1-yl]phenyl}amino)-4-[(2,5-difluorobenzyl)amino]pyridine-3-carboxyamide,
6-({4-[4-(cyanoacetyl)piperazin-1-yl]phenyl}amino)-4-[(2,6-difluorobenzyl)amino]pyridine-3-carboxyamide,
6-({3-[4-(cyanoacetyl)piperazin-1-yl]phenyl}amino)-4-[(3,5-difluorobenzyl)amino]pyridine-3-carboxyamide,
4-(benzylamino)-6-({4-[4-(cyanoacetyl)-1,4-diazepan-1-yl]phenyl}amino)pyridine-3-carboxyamide,
4-(benzylamino)-6-({4-[4-(N,N-diethylglycyl)piperazin-1-yl]phenyl}amino)pyridine-3-carboxyamide,
6-({4-[4-(N,N-diethylglycyl)piperazin-1-yl]phenyl}amino)-4-[(3-nitrobenzyl)amino]pyridine-3-carboxyamide,
4-(benzylamino)-6-({4-[1-(N,N-diethylglycyl)piperidin-4-yl]phenyl}amino)pyridine-3-carboxyamide,
4-(benzylamino)-6-({4-[(diethylcarbamoyl)amino]phenyl}amino)pyridine-3-carboxyamide,
4-(benzylamino)-6-({4-[(4-diethylcarbamoyl)piperazin-1-yl]phenyl}amino)pyridine-3-carboxyamide,
4-(benzylamino)-6-[(4-{[4-(propan-2-yl)carbamoyl]piperazin-1-yl}phenyl)amino]pyridine-3-carboxyamide,
4-[(3-nitrobenzyl)amino]-6-{[(4-[4-(propan-2-yl)carbamoyl]piperazin-1-yl}phenyl)amino]pyridine-3-carboxyamide,
4-(benzylamino)-6-({4-[4-(morpholinocarbonyl)piperazin-1-yl]phenyl}amino)pyridine-3-carboxyamide,
4-(benzylamino)-6-{[4-(piperidin-4-ylamino)phenyl]amino}pyridine-3-carboxyamide,
4-(benzylamino)-6-[(4-{1-(diethylcarbamoyl)piperidin-4-yl]amino}phenyl)amino]pyridine-3-carboxyamide,
4-(benzylamino)-6-[(4-{[1-(propan-2-ylcarbamoyl)piperidin-4-yl]amino}phenyl)amino]pyridine-3-carboxyamide,
4-[(2,3-difluorobenzyl)amino]-6-({4-[4-(methylsulfonyl)piperazin-1-yl]phenyl}amino)pyridine-3-carboxyamide,
4-[(3,5-difluorobenzyl)amino]-6-({4-[4-(methylsulfonyl)piperazin-1-yl]phenyl}amino)pyridine-3-carboxyamide,
4-(benzylamino)-6-({4-[4-(methylsulfonyl)-1,4-diazepan-1-yl]phenyl}amino)pyridine-3-carboxyamide,
4-(benzylamino)-6-({-4-[bis(methylsulfonyl)amino]phenyl}amino)pyridine-3-carboxyamide, 4-(benzylamino)-6-({4-[(methylsulfonyl)amino]
phenyl}amino)pyridine-3-carboxyamide,
4-[(3,5-difluorobenzyl)amino]-6-({4-[(propan-2-ylsulfo-
nyl)amino]phenyl}amino)pyridine-3-carboxyamide,
6-{[4-({[2-(diethylamino)ethyl]sulfonyl}amino)phenyl]
amino}-4-[(3,5-difluorobenzyl)amino]pyridine-3-car-
boxyamide,
6-[(4-{[(2-aminoethyl)sulfonyl]amino}phenyl)amino]-4-
[(3,5-difluorobenzyl)amino]pyridine-3-carboxyamide,
4-(benzylamino)-6-{{-4-(1,1-dioxo-1,2-thiazolidin-2-yl)
phenyl]amino}pyridine-3-carboxyamide,
4-(benzylamino)-6-({4-[(piperidin-4-ylcarbonyl)amino]
phenyl}amino)pyridine-3-carboxyamide,
4-[(3,5-difluorobenzyl)amino]-6-({4-[(piperidin-4-ylcar-
bonyl)amino]phenyl}amino)pyridine-3-carboxyamide,
4-(benzylamino)-6-{[4-(L-prolylamino)phenyl]
amino}pyridine-3-carboxyamide,
4-[(3,5-difluorobenzyl)amino]-6-{[4-(L-prolylamino)
phenyl]amino}pyridine-3-carboxyamide,
4-(benzylamino)-6-{[4-(morpholin-4-ylmethyl)phenyl]
amino}pyridine-3-carboxyamide,
6-[(4-acetylphenyl)amino]-4-[(3,5-difluorobenzyl)
amino]pyridine-3-carboxyamide,
4-[(3,5-difluorobenzyl)amino]-6-{[(4-trifluoroacetyl)
phenyl]amino}pyridine-3-carboxyamide,
4-[(3,5-difluorobenzyl)amino]-6-({4-[(2-methoxyethyl)
sulfamoyl]phenyl}amino)pyridine-3-carboxyamide,
6-[(4-carboxyphenyl)amino]-4-[(3,5-difluorobenzyl)
amino]pyridine-3-carboxyamide,
4-cyclohexylamino-6-[(4-morpholinophenyl)amino]pyri-
dine-3-carboxyamide,
4-cyclohexylamino-6-({4-[4-(methylsulfonyl)piperazin-
1-yl]phenyl}amino)pyridine-3-carboxyamide,
4-cyclohexylamino-6-({4-[(methylsulfonyl)amino]
phenyl}amino)pyridine-3-carboxyamide,
4-cyclohexylamino-6-[(3,5-difluorophenyl)amino]pyri-
dine-3-carboxyamide,
4-[(2-methylcyclohexyl)amino]-6-[(4-morpholinophenyl)
amino]pyridine-3-carboxyamide,
6-[(4-morpholinophenyl)amino]-4-(tricyclo[3.3.1.1$^{3,7}$]
deca-2-ylamino)pyridine-3-carboxyamide,
4-(3,4-dihydro-2H-1-benzopyran-4-ylamino)-6-[(4-mor-
pholinophenyl)amino]pyridine-3-carboxyamide,
4-(3,4-dihydro-2H-1-benzopyran-4-ylamino)-6-({4-[4-
(propan-2-ylsulfonyl)piperazin-1-yl]phenyl}amino)
pyridine-3-carboxyamide,
6-[(4-morpholinophenyl)amino]-4-[(pyridin-3-ylmethyl)
amino]pyridine-3-carboxyamide,
4-[(pyridin-3-ylmethyl)amino]-6-({4-[4-(trifluoroacetyl)
piperazin-1-yl]phenyl}amino)pyridine-3-carboxya-
mide,
6-{[4-(piperazin-1-yl)phenyl]amino}-4-[(pyridin-3-ylm-
ethyl)amino]pyridine-3-carboxyamide,
6-({4-[4-(propan-2-yl)piperazin-1-yl]phenyl}amino)-4-
[(pyridin-3-ylmethyl)amino]pyridine-3-carboxyamide,
4-{[(1-benzylpyrrolidin-2-yl)methyl]amino}-6-[(4-mor-
pholinophenyl)amino]pyridine-3-carboxyamide,
6-[(4-morpholinophenyl)amino]-4-[(pyrrolidin-2-ylm-
ethyl)amino]pyridine-3-carboxyamide,
4-{[(1-methylpyrrolidin-2-yl)methyl]amino}-6-[(4-mor-
pholinophenyl)amino]pyridine-3-carboxyamide,
4-{[(1-acetylpyrrolidin-2-yl)methyl]amino}-6-[(4-mor-
pholinophenyl)amino]pyridine-3-carboxyamide,
4-[(cyclohexylmethyl)amino]-6-[(4-morpholinophenyl)
amino]pyridine-3-carboxyamide,
4-[(cyclopropylmethyl)amino]-6-[(4-morpholinophenyl)
amino]pyridine-3-carboxyamide,
6-[(4-morpholinophenyl)amino]-4-[(pyridin-2-ylmethyl)
amino]pyridine-3-carboxyamide,
6-(5-chloro-1H-benzimidazol-1-yl)-4-[(3,5-difluoroben-
zyl)amino]pyridine-3-carboxyamide,
6-(6-chloro-1H-benzimidazol-1-yl)-4-[(3,5-difluoroben-
zyl)amino]pyridine-3-carboxyamide,
6-(1H-benzimidazol-1-yl)-4-[(3,5-difluorobenzyl)amino]
pyridine-3-carboxyamide,
6-(6-cyano-1H-benzimidazol-1-yl)-4-[(3,5-difluoroben-
zyl)amino]pyridine-3-carboxyamide,
6-(5-cyano-1H-benzimidazol-1-yl)-4-[(3,5-difluoroben-
zyl)amino]pyridine-3-carboxyamide,
4-[(3,5-difluorobenzyl)amino]-6-(6-morpholino-1H-ben-
zimidazol-1-yl)pyridine-3-carboxyamide,
4-[(3,5-difluorobenzyl)amino]-6-(5-morpholino-1H-ben-
zimidazol-1-yl)pyridine-3-carboxyamide,
4-[(3,5-difluorobenzyl)amino]-6-{1-[(4-methylphenyl)
sulfonyl]-1H-pyloro[2.3-b]pyridin-3-yl}pyridine-3-
carboxyamide,
4-[(3,5-difluorobenzyl)amino]-6-(1H-pyloro[2,3-b]pyri-
din-3-yl)pyridine-3-carboxyamide,
4-benzylamino-6-(pyridin-4-ylamino)pyridine-3-car-
boxyamide, or
4-benzylamino-6-[(6-morpholinopyridin-3-yl)amino]py-
ridine-3-carboxyamide,
or its salt or a hydrate thereof.

5. A JAK3 inhibitor comprising, as an active ingredient, the pyridine-3-carboxyamide derivative according to claim 1 or its salt or a hydrate thereof.

6. A pharmaceutical composition comprising the pyridine-3-carboxyamide derivative according to claim 1 or its salt or a hydrate thereof and a pharmaceutically acceptable carrier.

* * * * *